US012686690B2

(12) United States Patent
Armacost et al.

(10) Patent No.: US 12,686,690 B2
(45) Date of Patent: Jul. 21, 2026

(54) MACROCYCLIC UREA OREXIN RECEPTOR AGONISTS

(71) Applicant: Merck Sharp & Dohme LLC, Rahway, NJ (US)

(72) Inventors: Kira A. Armacost, Doylestown, PA (US); Maria Irina Chiriac, Hatfield, PA (US); Danielle M. Hurzy, Garnet Valley, PA (US); Jeffrey C. Kern, Gilbertsville, PA (US); Jian Liu, Edison, NJ (US); Peter J. Manley, Harleysville, PA (US); Vanessa L. Rada, Glenside, PA (US); Michael T. Rudd, Collegeville, PA (US); Craig A. Stump, Pottstown, PA (US); Zhe Wu, Blue Bell, PA (US); Dong Xiao, Warren, NJ (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 470 days.

(21) Appl. No.: 18/250,267

(22) PCT Filed: Oct. 28, 2021

(86) PCT No.: PCT/US2021/056947
§ 371 (c)(1),
(2) Date: Apr. 24, 2023

(87) PCT Pub. No.: WO2022/094012
PCT Pub. Date: May 5, 2022

(65) Prior Publication Data

US 2023/0391795 A1 Dec. 7, 2023

Related U.S. Application Data

(60) Provisional application No. 63/271,907, filed on Oct. 26, 2021, provisional application No. 63/108,526, filed on Nov. 2, 2020.

(51) Int. Cl.

| | |
|---|---|
| *C07D 471/18* | (2006.01) |
| *A61K 31/439* | (2006.01) |
| *A61K 31/4995* | (2006.01) |
| *A61K 31/504* | (2006.01) |
| *A61K 31/53* | (2006.01) |
| *A61P 25/00* | (2006.01) |
| *C07D 471/22* | (2006.01) |
| *C07D 487/18* | (2006.01) |
| *C07D 487/22* | (2006.01) |
| *C07D 498/18* | (2006.01) |
| *C07D 498/22* | (2006.01) |
| *C07D 513/22* | (2006.01) |

(52) U.S. Cl.
CPC ......... *C07D 498/18* (2013.01); *C07D 498/22* (2013.01); *C07D 513/22* (2013.01)

(58) Field of Classification Search
CPC .. C07D 471/18; C07D 471/22; C07D 487/18; C07D 487/22; C07D 498/18; C07D 498/22; C07D 513/22; A61K 31/4995; A61K 31/53; A61K 31/439; A61K 31/504; A61P 25/00
See application file for complete search history.

(56) References Cited

U.S. PATENT DOCUMENTS

| | | | |
|---|---|---|---|
| 7,803,810 B2 | 9/2010 | Ramsbeck et al. |
| 10,064,861 B2 | 9/2018 | Jorand-lebrun et al. |
| 10,174,000 B2 | 1/2019 | Lee et al. |
| 2020/0039989 A1 | 2/2020 | Hulme et al. |

FOREIGN PATENT DOCUMENTS

| | | | |
|---|---|---|---|
| CN | 102272103 A | 12/2011 |
| JP | 2010533702 A | 10/2010 |
| JP | 2011513224 A | 4/2011 |
| WO | 2009010804 A1 | 1/2009 |
| WO | 2009108507 A1 | 9/2009 |
| WO | 2010051236 A1 | 5/2010 |
| WO | 2011076744 A1 | 6/2011 |
| WO | 2019053617 A1 | 3/2019 |
| WO | 2020151738 A1 | 7/2020 |
| WO | 2020158958 A1 | 8/2020 |
| WO | 2020167701 A1 | 8/2020 |

OTHER PUBLICATIONS

Chemelli, Richard M. et al., Narcolepsy in orexin Knockout Mice: Molecular Genetics of Sleep Regulation, Cell, 1999, 437-451, 98.
Harris, Glenda C. et al., Arousal and reward: a dichotomy in orexin function, Trends in Neurosciences, 2006, 571-577, 29(10).
Peyron, Christelle et al., Neurons Containing Hypocretin (Orexin) Project to Multiple Neuronal Systems, The Journal of Neuroscience, 1998, 9996-100150, 18(23).
Sakurai, Takeshi et al., Orexins and Orexin Receptors: A Family of Hypothalamic Neuropeptides and G Protein-Coupled Receptors that Regulate Feeding Behavior, Cell, 1998, 573-585, 92.
European Search Report, Application No. 21887481.6 dated Sep. 17, 2024, 7 pages.
Russian Search Report, Application No. 2023114437 dated Apr. 16, 2025, 2 pages.

*Primary Examiner* — Brenda L Coleman
(74) *Attorney, Agent, or Firm* — Patricia A. Shatynski; John C. Todaro

(57) ABSTRACT

The present invention is directed to macrocyclic urea compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

14 Claims, No Drawings

MACROCYCLIC UREA OREXIN RECEPTOR AGONISTS

CROSS-REFERENCE TO RELATED APPLICATIONS

This application is a National Stage application of International Patent Application No. PCT/US2021/056947, filed Oct. 28, 2021, which claims priority to U.S. Provisional Patent Application Nos. 63/108,526, filed Nov. 2, 2020 and 63/271,907, filed Oct. 26, 2021.

BACKGROUND OF THE INVENTION

The orexins (hypocretins) comprise two neuropeptides produced in the hypothalamus: orexin A (OX-A) (a 33 amino acid peptide) and the orexin B (OX-B) (a 28 amino acid peptide) (Sakurai T. et al., Cell, 1998, 92, 573-585). Orexins regulate states of sleep and wakefulness opening potentially novel therapeutic approaches for narcolepsy, idiopathic hypersomnia, excessive daytime sleepiness, shift work disorder, obstructive sleep apnea and insomnia (Chemelli R. M. et al., Cell, 1999, 98, 437-451). Orexins are found to stimulate food consumption in rats suggesting a physiological role for these peptides as mediators in the central feedback mechanism that regulates feeding behavior (Sakurai T. et al., Cell, 1998, 92, 573-585). Orexins have also been indicated as playing a role in arousal, emotion, energy homeostasis, reward, learning and memory (Peyron, et al., Journal Neurosci., 1998, 18(23):9996-100150, Harris, et al., Trends Neurosci., 2006, 29 (10), 571-577). Two orexin receptors have been cloned and characterized in mammals. They belong to the super family of G-protein coupled receptors (Sakurai T. et al., Cell, 1998, 92, 573-585): the orexin-1 receptor (OX or OX1R) is partially selective for OX-A and the orexin-2 receptor (OX2 or OX2R) is capable of binding OX-A as well as OX-B with similar affinity. The physiological actions in which orexins are presumed to participate are thought to be expressed via one or both of OX1 receptor and OX2 receptor as the two subtypes of orexin receptors.

SUMMARY OF THE INVENTION

The present invention is directed to macrocyclic urea compounds which are agonists of orexin receptors. The present invention is also directed to uses of the compounds described herein in the potential treatment or prevention of neurological and psychiatric disorders and diseases in which orexin receptors are involved. The present invention is also directed to compositions comprising these compounds. The present invention is also directed to uses of these compositions in the potential prevention or treatment of such diseases in which orexin receptors are involved.

DETAILED DESCRIPTION OF THE INVENTION

The present invention is directed to compounds of the formula I:

I

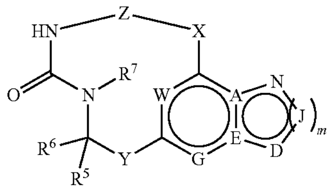

wherein:

A is N or $C(R^8)_n$;
D is N or $C(R^8)_n$;
E is N or $C(R^8)_n$;
G is N or $C(R^8)_n$;
J is N or $C(R^8)_n$;
W is N or $C(R^8)_n$;
when J is N, m is 1 but when J is $C(R^8)_n$, m is 1 or 2;
n is 0 or 1;
X is —O— or $—CH_2—$;
Y is phenyl, pyridyl, pyrazinyl, pyrazolyl, pyridazinyl, pyrimidinyl, pyridofuranyl, oxazolyl, thiazolyl, which is unsubstituted or substituted with one to three groups selected from $R^4$;
Z is;

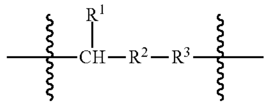

;

R is independently selected from H or $C_{1-6}$alkyl;
$R^1$ is selected from:
(1) hydrogen,
(2) CN,
(3) $—C(O)NR_2—$,
(4) $—CH_2OCH_2CF_3—$,
(5) $—CH_2OCH_2CHCF_2—$,
(6) $C_{1-6}$alkyl, which is unsubstituted or substituted with one to three substituents independently selected from
a. $C_{1-6}$alkyl,
b. halogen,
c. hydroxyl,
d. $—O—C_{1-6}$alkyl which is unsubstituted or substituted with one to three substituents selected from halogen, or $C_{3-6}$cycloalkyl which is unsubstituted or substituted with halogen, $C_{1-6}$alkyl, or $C_{1-6}$alkylfluoro,
e. $C_{3-6}$cycloalkyl, which is unsubstituted or substituted with one to three of $R^4$,
f. Heteroaryl, unsubstituted or substituted with one to three of $R^4$,
g. Heterocyclyl, unsubstituted or substituted with one to three of $R^4$,
h. CN, and
i. $S(O)_2R$;
$R^2$ is selected from
1) linear or branched $C_{1-10}$alkyl or $C_{4-8}$alkenyl,
2) $—(CR_2)_{1-6}—O—(CR_2)_{1-6}—$;
3) $—(CR_2)_{1-6}—N(R^9)—(CR_2)_{1-6}—$, wherein $R^9$ is hydrogen or $—C_{1-6}$alkyl, where the $—C_{1-6}$alkyl is unsubstituted or substituted with halogen,
4) $—(CR_2)_{1-6}C_{3-6}$cycloalkyl-$(CR_2)_{1-6}—$, where the $—C_{3-6}$cycloalkyl is unsubstituted or substituted with $—C_{1-6}$alkyl or halogen, and 5) piperidinyl, pyrrolidinyl, oxaxolyl, oxadiazolyl or thiazolyl ring, which is unsubstituted or substituted with —$C_{1-6}$alkyl or halogen;

$R^3$ is selected from a direct bond, —S—, —NR—, —O—$C_{1-6}$alkyl-, —S—$C_{1-6}$alkyl-, and —$S(O)_2$—$C_{1-6}$alkyl-;

$R^4$ is selected from:
(1) hydrogen,
(2) hydroxyl,
(3) halogen,
(4) —$C_{1-6}$alkyl, which is unsubstituted or substituted with one to six fluoro,
(5) —O—$C_{1-6}$alkyl, which is unsubstituted or substituted with one to six fluoro, and
(6) $C_{3-6}$cycloalkyl;

$R^5$ and $R^6$ are independently selected from:
(1) hydrogen, and
(2) —$C_{1-6}$alkyl, where the alkyl is unsubstituted or substituted with one to six substituents independently selected from halogen,
or $R^5$ and $R^6$ and the carbon atom to which they are attached may be joined together to form a —$C_{3-6}$cycloalkyl group;

$R^7$ is selected from:
(1) hydrogen,
(2) —$C_{1-6}$alkyl, where the alkyl is unsubstituted or substituted with one to six substituents independently selected from halogen, and
(3) —$C_{3-6}$cycloalkyl, where the —$C_{3-6}$cycloalkyl is unsubstituted or substituted with —$C_{1-6}$alkyl or halogen;

$R^8$ is selected from:
(1) hydrogen,
(2) halogen, and
(3) —$C_{1-6}$alkyl, where the alkyl is unsubstituted or substituted with one to six substituents independently selected from halogen;

or a pharmaceutically acceptable salt thereof.

An embodiment of the present invention includes compounds of the formula I':

I'

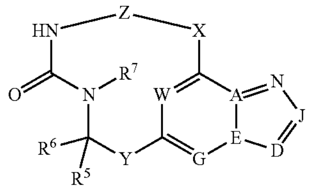

wherein:
A is N or C;
D is N or $C(R^8)_n$;
E is N or $C(R^8)_n$;
G is N or $C(R^8)_n$;
J is N or $C(R^8)_n$;
W is N or $C(R^8)_n$;
with the proviso that one, two, three or four of A, D, E, G, J and W are N, and the remainder of A, D, E, G, J and W are other than N;
n is 0 or 1;
X is —O— or —$CH_2$—;
Y is phenyl, pyridyl, pyrazinyl, pyridazinyl, pyrimidinyl, pyridofuranyl, oxazolyl, thiazolyl, which is unsubstituted or substituted with one to three groups selected from $R^4$;

Z is;

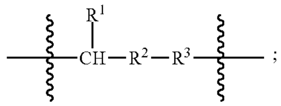

R is independently selected from H or $C_{1-6}$alkyl;

$R^1$ is selected from:
(1) hydrogen,
(2) CN,
(3) —$C(O)NR_2$,
(4) —$CH_2OCH_2CF_3$—,
(5) —$CH_2OCH_2CHCF_2$—,
(6) —$C_{1-6}$alkyl, which is unsubstituted or substituted with one to three substituents independently selected from
a. $C_{1-6}$alkyl,
b. halogen,
c. hydroxyl,
d. —O—$C_{1-6}$alkyl which is unsubstituted or substituted with one to three substituents selected from halogen, or $C_{3-6}$cycloalkyl which is unsubstituted or substituted with halogen, $C_{1-6}$alkyl, or $C_{1-6}$alkylfluoro,
e. —$C_{3-6}$cycloalkyl, which is unsubstituted or substituted with one to three of $R^4$,
f. Heteroaryl, unsubstituted or substituted with one to three of $R^4$,
g. Heterocyclyl, unsubstituted or substituted with one to three of $R^4$,
h. CN, and
i. —$S(O)_2R$;

$R^2$ is selected from
1) linear or branched $C_{1-10}$alkyl or $C_{4-8}$alkenyl,
2) —$(CR_2)_{1-6}$—O—$(CR_2)_{1-6}$—,
3) —$(CR_2)_{1-6}$—$N(R^9)$—$(CR_2)_{1-6}$—, wherein $R^9$ is hydrogen or —$C_{1-6}$alkyl, where the —$C_{1-6}$alkyl is unsubstituted or substituted with halogen,
4) —$(CR_2)_{1-6}C_{3-6}$cycloalkyl-$(CR_2)_{1-6}$, where the —$C_{3-6}$cycloalkyl is unsubstituted or substituted with —$C_{1-6}$alkyl or halogen, and
5) piperidinyl, pyrrolidinyl, oxaxolyl, oxadiazolyl or thiazolyl ring, which is unsubstituted or substituted with —$C_{1-6}$alkyl or halogen;

$R^3$ is selected from a direct bond, —O—$C_{1-6}$alkyl-, —S—$C_{1-6}$alky-1, and —$S(O)_2$—$C_{1-6}$alkyl-;

$R^4$ is selected from:
(1) hydrogen,
(2) hydroxyl,
(3) fluoro,
(4) —$C_{1-6}$alkyl, which is unsubstituted or substituted with one to six fluoro, and
(5) —O—$C_{1-6}$alkyl, which is unsubstituted or substituted with one to six fluoro;

$R^5$ and $R^6$ are independently selected from:
(1) hydrogen, and
(2) —$C_{1-6}$alkyl, where the alkyl is unsubstituted or substituted with one to six substituents independently selected from halogen,
or $R^5$ and $R^6$ and the carbon atom to which they are attached may be joined together to form a —$C_{3-6}$cycloalkyl group;

$R^7$ is selected from:

(1) —$C_{1-6}$alkyl, where the alkyl is unsubstituted or substituted with one to six substituents independently selected from halogen, and (2) —$C_{3-6}$cycloalkyl, where the —$C_{3-6}$cycloalkyl is unsubstituted or substituted with —$C_{1-6}$alkyl or halogen;

$R^8$ is selected from:

(1) hydrogen, (2) halogen, and (3) —$C_{1-6}$alkyl, where the alkyl is unsubstituted or substituted with one to six substituents independently selected from halogen;

or a pharmaceutically acceptable salt thereof.

In an embodiment of the present invention, Y is selected from phenyl, pyridyl, pyridazinyl, and pyrimidinyl, which is unsubstituted or substituted with one to three groups selected from $R^4$.

An embodiment of the present invention includes compounds of the formula Ia:

Ia

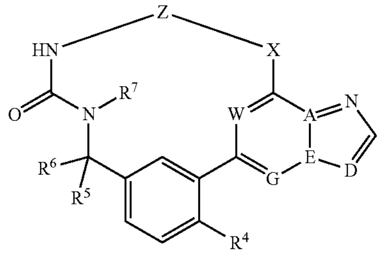

wherein

Z is a linear or branched $C_{3-10}$alkyl or $C_{4-8}$alkenyl, which is unsubstituted or substituted with one to six subsituents selected from:

(1) hydroxyl, (2) halogen, (3) $C_{1-6}$alkyl, which is unsubstituted or substituted with one to six subsituents selected from halogen, tetrahydrofuranyl, —O—$C_{1-6}$alkyl which is unsubstituted or substituted with one to three subsituents selected from halogen, or $C_{3-6}$cycloalkyl which is unsubstituted or substituted with one to three subsituents selected from halogen, $C_{1-6}$alkyl, or $C_{1-6}$alkylfluoro, (4) $C_{3-6}$cycloalkyl, which is unsubstituted or substituted with one to three subsituents selected from halogen, $C_{1-6}$alkyl, or $C_{1-6}$alkylfluoro, (5) —O—$C_{1-6}$alkyl, which is unsubstituted or substituted with one to three halogen, (6) tetrahydrofuranyl, (7) tetrahydropyranyl, (8) isoxazolyl, and (9) thiazolyl;

and which optionally may contain within the $C_{3-10}$alkyl, a group selected from:

(1) —O—, (2) —N($R^9$)—, wherein $R^9$ is hydrogen or —$C_{1-6}$alkyl, where the —$C_{1-6}$alkyl is unsubstituted or substituted with halogen, (3) —$C_{3-6}$cycloalkyl, where the —$C_{3-6}$cycloalkyl is unsubstituted or substituted with —$C_{1-6}$alkyl or halogen, and (4) a piperidinyl, pyrrolidinyl, oxaxolyl, oxadiazolyl or thiazolyl ring, which is unsubstituted or substituted with —$C_{1-6}$alkyl or halogen;

and all other substituents A, D, E, G, W, X, $R^4$, $R^5$, $R^6$ and $R^7$ are defined herein; or a pharmaceutically acceptable salt thereof.

An embodiment of the present invention includes compounds of the formula Ia':

Ia'

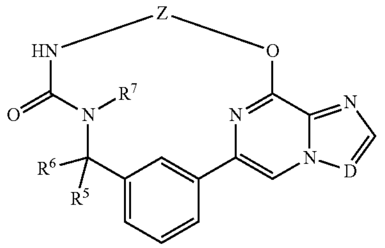

wherein D, Z, $R^4$, $R^5$, $R^6$ and $R^7$ are defined herein; or a pharmaceutically acceptable salt thereof.

An embodiment of the present invention includes compounds of the formula Ia":

Ia"

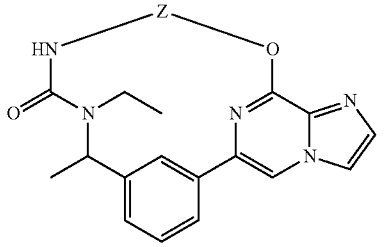

wherein Z is defined herein; or a pharmaceutically acceptable salt thereof.

An embodiment of the present invention includes compounds of the formula Ib:

Ib

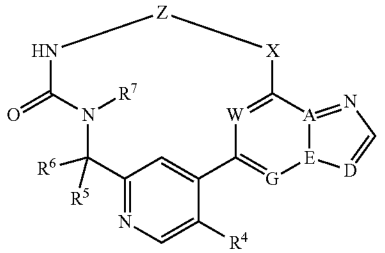

wherein A, D, E, G, W, X, Z, $R^4$, $R^5$, $R^6$ and $R^7$ are defined herein; or a pharmaceutically acceptable salt thereof.

An embodiment of the present invention includes compounds of the formula Ib':

Ib′

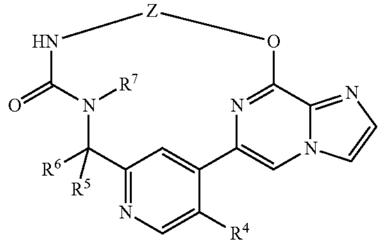

wherein Z, $R^4$, $R^5$, $R^6$ and $R^7$ are defined herein; or a pharmaceutically acceptable salt thereof.

An embodiment of the present invention includes compounds of the formula Ib":

Ib″

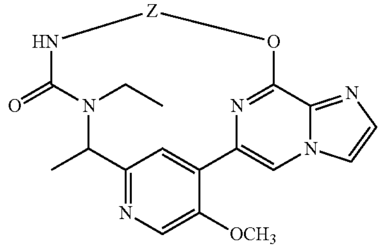

wherein Z is defined herein; or a pharmaceutically acceptable salt thereof.

An embodiment of the present invention includes compounds wherein the group:

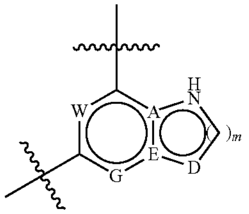

is selected from:

A is N or C;

D is N or $C(R^8)_n$;

E is N or C;

G is N or $C(R^8)_n$;

J is N or $C(R^8)_n$;

W is N or $C(R^8)_n$; and when J is N, m is 1 but when J is $C(R^8)_n$, m is 1 or 2.

An embodiment of the present invention includes compounds wherein the group:

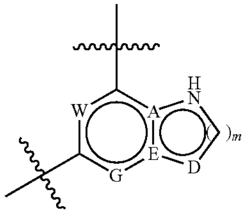

is selected from:

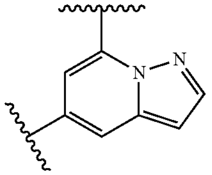,
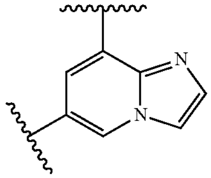,
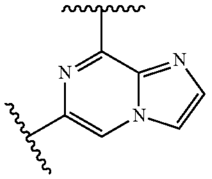,
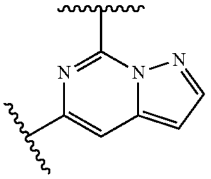,
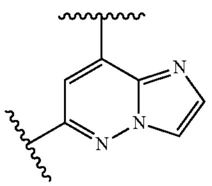,
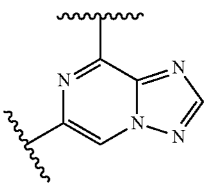,
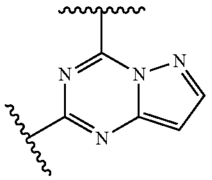,
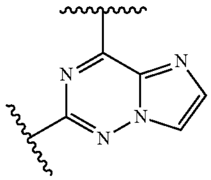,
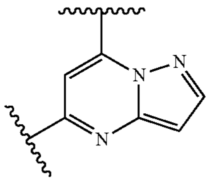,
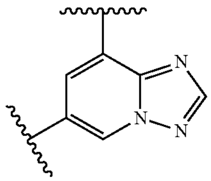,
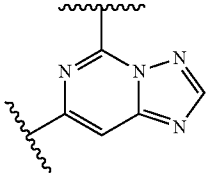,
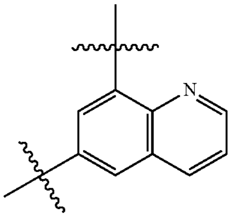, and
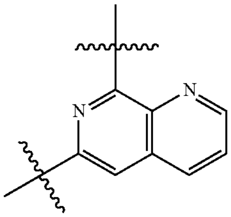.

An embodiment of the present invention includes compounds of Formula I, wherein the group:

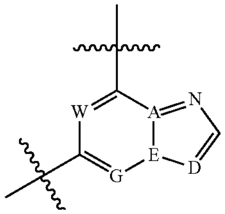

is selected from:

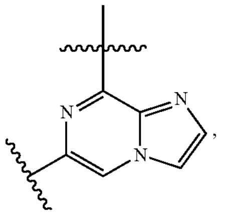, 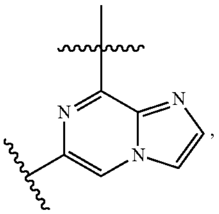,

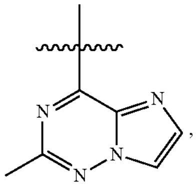, and 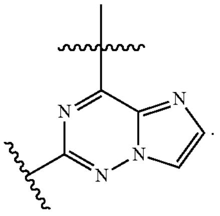.

An embodiment of the present invention includes compounds wherein X is —O—. An embodiment of the present invention includes compounds wherein X is —$CH_2$.

An embodiment of the present invention includes compounds wherein Y is selected from:

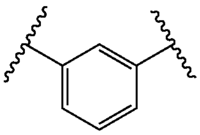, 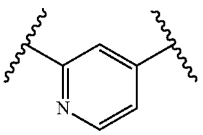,

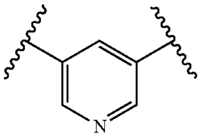, 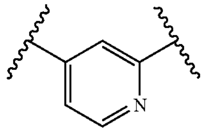,

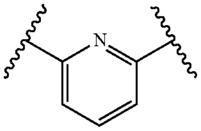, 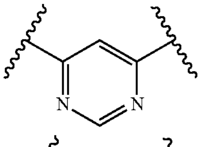,

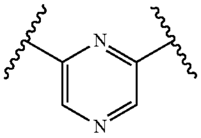, 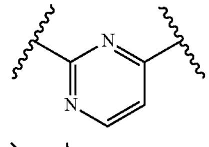,

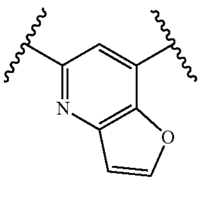, 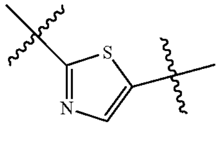,

-continued

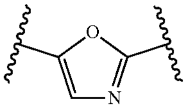, 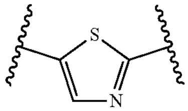,

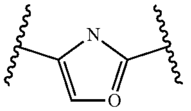, 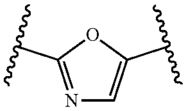,

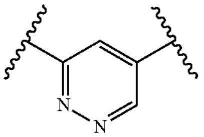, and 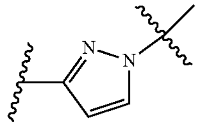.

In an embodiment of the present invention, Y is selected from phenyl, pyridyl, pyridazinyl, and pyrimidinyl, which is unsubstituted or substituted with one to three groups selected from $R^4$. In an embodiment of the present invention, Y is selected from pyridyl, pyridazinyl, and pyrimidinyl, which is unsubstituted or substituted with one to three groups selected from $R^4$. An embodiment of the present invention includes compounds wherein Y is phenyl, pyridyl, pyrazinyl, or pyrimidinyl. An embodiment of the present invention includes compounds wherein Y is phenyl or pyridyl. In an embodiment, Y is phenyl. In an embodiment of the present invention, Y is pyridyl.

An embodiment of the present invention includes compounds wherein Z is

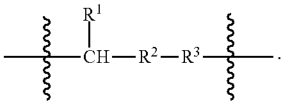.

In an embodiment of the present invention, R1 is selected from (1) hydrogen,
(2) CN,
(3) —C(O)$NR_2$,
(4) $CH_2OCH_2CF_3$
(5) $CH_2OCH_2CHCF_2$,
(6) $C_{1-6}$alkyl, which is unsubstituted or substituted with one to three substituents independently selected from
  a. $C_{1-6}$alkyl,
  b. halogen,
  c. hydroxyl,
  d. —O—$C_{1-6}$alkyl which is unsubstituted or substituted with one to three substituents selected from halogen, or $C_{3-6}$cycloalkyl which is unsubstituted or substituted with halogen, $C_{1-6}$alkyl, or $C_{1-6}$alkylfluoro,
  e. $C_{3-6}$cycloalkyl, which is unsubstituted or substituted with one to three of $R^4$,
  f. Heteroaryl, unsubstituted or substituted with one to three of $R^4$,
  g. Heterocyclyl, unsubstituted or substituted with one to three of $R^4$,
  h. CN, and
  i. $S(O)_2R$.

In an embodiment of the present invention, $R^1$ is selected from hydrogen, —C(O)$NR_2$, $CH_2OCH_2CF_3$, $CH_2OCH_2CHCF_2$, and —$C_{1-6}$alkyl, wherein said alkyl is unsubstituted or substituted with one to three substituents independently selected from $C_{1-6}$alkyl, halogen, hydroxyl, CN, $C_{3-6}$cycloalkyl, which is unsubstituted or substituted with one to three of $R^4$, and —O—$C_{1-6}$alkyl which is unsubstituted or substituted with one to three substituents selected from halogen, or $C_{3-6}$cycloalkyl which is unsubstituted or substituted with halogen, $C_{1-6}$alkyl, or $C_{1-6}$alkylfluoro. In an embodiment of the present invention, $R^1$ is selected from hydrogen, —C(O)$NR_2$, $CH_2OCH_2CF_3$, $CH_2OCH_2CHCF_2$, and —$C_{1-6}$alkyl, wherein said alkyl is unsubstituted or substituted with one to three substituents independently selected from $C_{1-6}$alkyl, halogen, CN, and $C_{3-6}$cycloalkyl, which is unsubstituted or substituted with one to three of $R^4$.

In an embodiment of the present invention, $R^2$ is selected from 1) linear or branched $C_{1-10}$alkyl or $C_{4-8}$alkenyl,
2) $(CR_2)_{1-6}$—O—$(CR_2)_{1-6}$—;
3) $(CR_2)_{1-6}$—N($R^9$)—$(CR_2)_{1-6}$—, wherein $R^9$ is hydrogen or —$C_{1-6}$alkyl, where the —$C_{1-6}$alkyl is unsubstituted or substituted with halogen,
4) —$(CR_2)_{1-6}C_{3-6}$cycloalkyl-$(CR_2)_{1-6}$, where the —$C_{3-6}$cycloalkyl is unsubstituted or substituted with —$C_{1-6}$alkyl or halogen, and
5) piperidinyl, pyrrolidinyl, oxaxolyl, oxadiazolyl or thiazolyl ring, which is unsubstituted or substituted with —$C_{1-6}$alkyl or halogen.

In an embodiment of the present invention, $R^2$ is selected from linear or branched $C_{1-10}$ alkyl or $C_{4-8}$alkenyl, —$(CR_2)_{1-6}$—O—$(CR_2)_{1-6}$—, —$(CR_2)_{1-6}$—N($R^9$)—$(CR_2)_{1-6}$—, wherein $R^9$ is hydrogen or —$C_{1-6}$alkyl, and —$(CR_2)_{1-6}C_{3-6}$cycloalkyl-$(CR_2)_{1-6}$, where the —$C_{3-6}$cycloalkyl is unsubstituted or substituted with —$C_{1-6}$alkyl or halogen. In an embodiment of the present invention, $R^2$ is selected from linear or branched $C_{1-10}$alkyl or $C_{4-8}$alkenyl, and —$(CR_2)_{1-6}$—O—$(CR_2)_{1-6}$—. In an embodiment, $R^2$ is selected from linear or branched $C_{1-10}$alkyl and —$(CR_2)_{1-6}$—O—$(CR_2)_{1-6}$—.

In an embodiment of the present invention, $R^3$ is selected from a direct bond, —S—, —NR—, —O—$C_{1-6}$alkyl, —S—$C_{1-6}$alkyl, and —$S(O)_2$—$C_{1-6}$alkyl. In an embodiment of the present invention, $R^3$ is selected from a direct bond and —O—$C_{1-6}$alkyl. In an embodiment of the present invention, $R^3$ is a direct bond.

An embodiment of the present invention includes compounds wherein Z is a linear or branched $C_{3-8}$alkyl or $C_{4-8}$alkenyl, which is unsubstituted or substituted with a subsituent selected from:

(1) fluoro,
(2) $C_{1-6}$alkyl, which is unsubstituted or substituted with tetrahydrofuranyl, tetrahydropyranyl, one to six fluoro, or $C_{3-6}$cycloalkyl which is unsubstituted or substituted with $C_{1-6}$alkyl, $C_{1-6}$alkylfluoro, or one to six fluoro,
(3) $C_{3-6}$cycloalkyl, which is unsubstituted or substituted with $C_{1-6}$alkyl, $C_{1-6}$ alkylfluoro, or one to six fluoro, and
(4) —O—$C_{1-6}$alkyl, which is unsubstituted or substituted with one to six fluoro, and which optionally may contain within the $C_{3-8}$alkyl, a group selected from: (1) —O—,
(2) —N($R^9$)—, wherein $R^9$ is hydrogen or —$C_{1-6}$alkyl, where the —$C_{1-6}$alkyl is unsubstituted or substituted with halogen,
(3) —$C_{3-6}$cycloalkyl group, where the —$C_{3-6}$cycloalkyl is unsubstituted or substituted with —$C_{1-6}$alkyl or halogen, and
(4) a piperidinyl, pyrrolidinyl, oxaxolyl, oxadiazolyl or thiazolyl ring, which is unsubstituted or substituted with —$C_{1-6}$alkyl or halogen.

An embodiment of the present invention includes compounds wherein Z is a linear or branched $C_{3-8}$alkyl or $C_{4-8}$alkenyl, which is unsubstituted or substituted with a subsituent selected from:

(1) fluoro,
(2) $C_{1-6}$alkyl, which is unsubstituted or substituted with $C_{3-6}$cycloalkyl, or one to six fluoro,
(3) $C_{3-6}$cycloalkyl, which is unsubstituted or substituted with $C_{1-6}$alkyl, $C_{1-6}$ alkylfluoro, or one to six fluoro, and
(4) —O—$C_{1-6}$alkyl, which is unsubstituted or substituted with one to six fluoro, and which optionally may contain within the $C_{3-8}$alkyl, a group selected from:
(1) —O—,
(2) —N($R^9$)—, wherein $R^9$ is hydrogen or —$C_{1-6}$alkyl, where the —$C_{1-6}$alkyl is unsubstituted or substituted with halogen, and
(3) —$C_{3-6}$cycloalkyl group, where the —$C_{3-6}$cycloalkyl is unsubstituted or substituted with —$C_{1-6}$alkyl or halogen.

An embodiment of the present invention includes compounds wherein Z is linear or branched $C_{3-8}$alkyl, which is unsubstituted or substituted with a subsituent selected from:

(1) fluoro,
(2) $C_{1-6}$alkyl, which is unsubstituted or substituted with one to six fluoro, and which optionally may contain within the $C_{3-8}$alkyl, a group selected from:
(1) —O—,
(2) —N($R^9$)—, wherein $R^9$ is hydrogen or —$C_{1-6}$alkyl, where the —$C_{1-6}$alkyl is unsubstituted or substituted with halogen.

An embodiment of the present invention includes compounds wherein Z is selected from:

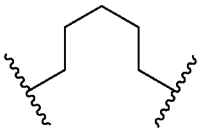 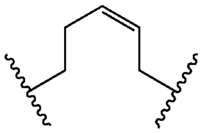

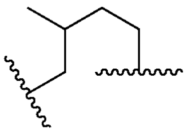 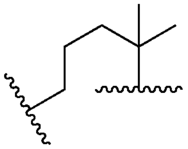

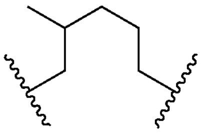 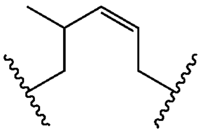

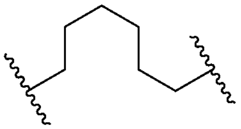 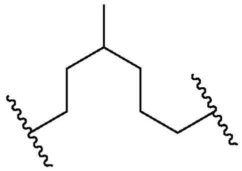

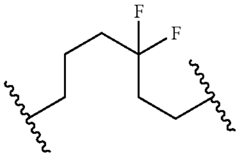 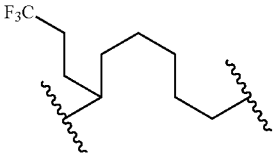

-continued

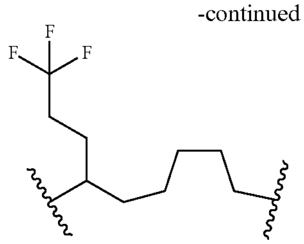

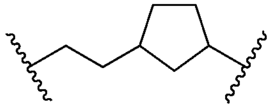

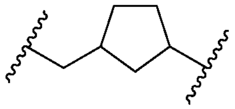

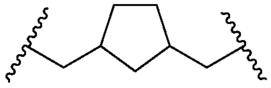

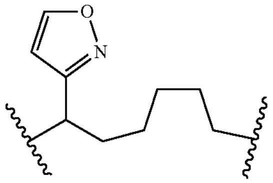

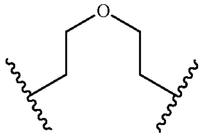

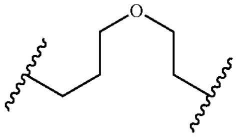

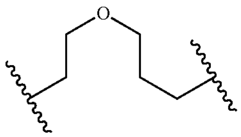

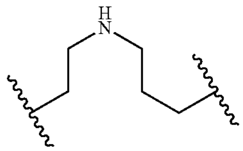

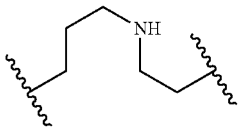

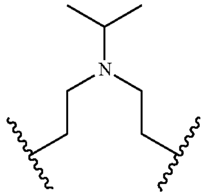

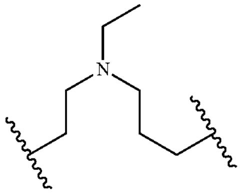

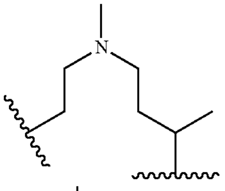

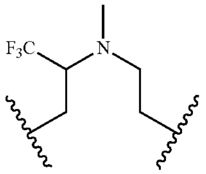

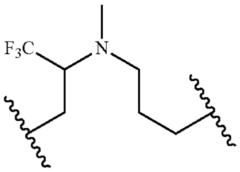

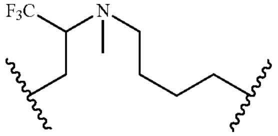

-continued

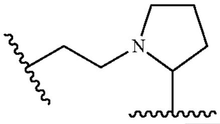

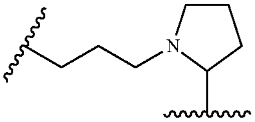

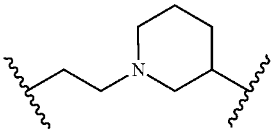

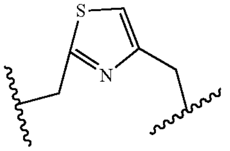

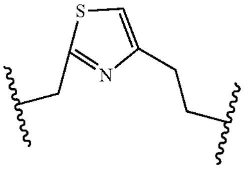

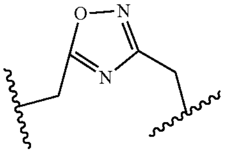

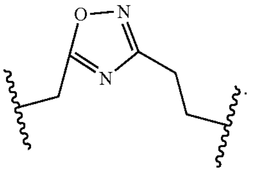

An embodiment of the present invention includes compounds wherein $R^4$ is selected from:

(1) H, (2) $C_{1-6}$alkyl, (3) Halogen, (4) —O—$C_{1-6}$alkyl, and (5) $C_{3-6}$cycloalkyl.

An embodiment of the present invention includes compounds where $R^4$ is selected from hydrogen, methyl, F, Cl, —$OCH_3$, and $C_{3-6}$cycloalkyl. An embodiment of the present invention includes compounds wherein $R^4$ is hydrogen. An embodiment of the present invention includes compounds wherein $R^4$ is methyl. An embodiment of the present invention includes compounds wherein $R^4$ is —$OCH_3$.

An embodiment of the present invention includes compounds wherein $R^5$ and $R^6$ are independently selected from:

(1) hydrogen, and (2) —$C_{1-6}$alkyl, where the alkyl is unsubstituted or substituted with one to six substituents independently selected from fluoro.

An embodiment of the present invention includes compounds wherein $R^5$ is hydrogen and $R^6$ is hydrogen. An embodiment of the present invention includes compounds wherein $R^5$ is hydrogen and $R^6$ is methyl. An embodiment of the present invention includes compounds wherein $R^5$ is hydrogen and $R^6$ is trifluoromethyl.

An embodiment of the present invention includes compounds wherein $R^7$ is selected from:

(1) hydrogen, (2) —$C_{1-6}$alkyl, and (3) —$C_{3-6}$cycloalkyl.

An embodiment of the present invention includes compounds wherein $R^7$ is selected from hydrogen, methyl and ethyl. An embodiment of the present invention includes compounds wherein $R^7$ is ethyl.

An embodiment of the present invention includes compounds wherein $R^8$ is hydrogen. An embodiment of the present invention includes compounds wherein $R^8$ is methyl.

Certain embodiments of the present invention include a compound which is selected from the group consisting of the subject compounds of the Examples herein or a pharmaceutically acceptable salt thereof.

Certain embodiments of the present invention include a compound which is selected from:

(10R,E)-9-ethyl-10-methyl-3-oxa-7,9-diaza-2(6,8)-imidazo[1,2-a]pyrazina-1(1,3)-benzena-4(1,3)-cyclopentanacyclodecaphan-8-one;

(12R)-13-ethyl-12-methyl-12,13,16,17,19,20-hexahydro-6,22-(azeno)-11,7-(metheno)imidazo[1,2-o][1,18,4,6,15]dioxatriazacycloicosin-14(15H)-one;

(12R)-13-ethyl-12-methyl-18-(propan-2-yl)-12,13,15,16,17,18,19,20-octahydro-14H-6,22-(azeno)-11,7-(metheno)imidazo[1,2-r][1,4,7,9,18]oxatetraazacycloicosin-14-one;

(12R)-13-ethyl-12-methyl-12,13,15,16,17,18,21,22,22a,23-decahydro-14H,20H-6,25-(azeno)-11,7-(metheno)imidazo[1,2-s]pyrrolo[2,1-c][1,4,8,10,19]oxatetraazacyclohenicosin-14-one;

(7R)-8-ethyl-7-methyl-18-oxa-8,10,13,21,24,26-hexaazapentacyclo-[17.6.1.1-2,6~0.1~13,17~0.0~20,24~]octacosa-1(25),2(28),3,5,19(26),20,22-heptaen-9-one;

(12R)-13-ethyl-8-methoxy-12-methyl-16-(3,3,3-trifluoropropyl)-12,13,15,16,17,18,20,21-octahydro-14H-6,23-(azeno)-11,7-(metheno)imidazo[2,1-f][1,4,7,13,16,18]dioxatetraazacyclohenicosin-14-one;

(12R)-13-ethyl-8-methoxy-12-methyl-16-(3,3,3-trifluoropropyl)-12,13,15,16,17,18,20,21-octahydro-14H-6,23-(azeno)-11,7-(metheno)imidazo[2,1-f][1,4,7,13,16,18]dioxatetraazacyclohenicosin-14-one;

(12R)-13-ethyl-8-methoxy-12-methyl-12,13,15,16,17,18,20,21-octahydro-14H-6,23-(azeno)-11,7-(metheno)imidazo[2,1-f][1,4,7,13,16,18]dioxatetraazacyclohenicosin-14-one;

(12R)-13-ethyl-8-methoxy-12-methyl-12,13,16,17,20,21-hexahydro-19H-6,23-(azeno)-11,7-(metheno)imidazo[1,2-o][1,18,4,6,9,15]dioxatetraazacyclohenicosin-14(15H)-one;

(12R)-13-ethyl-8-methoxy-12,16-dimethyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12,16-dimethyl-12,13,16,17,18,19,20,21-octahydro-6,23-(azeno)-11,7-(metheno)imidazo[2,1-c][1,4,10,13,15]oxatetraazacyclohenicosin-14(15H)-one;

(R,E)-4-ethyl-3-methyl-13-oxa-4,6,9-triaza-1(6,8)-imidazo[1,2-a]pyrazina-2(1,3)-benzenacyclotridecaphan-5-one;

(12R)-13-ethyl-12-methyl-12,13,16,17,18,19,20,21-octahydro-6,23-(azeno)-11,7-(metheno)imidazo[1,2-s][1,4,8,10,19]oxatetraazacyclohenicosin-14(15H)-one;

(12R)-13-ethyl-12-methyl-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12,19,19-trimethyl-12,13,15,16,17,18,19,20-octahydro-14H-6,22-(azeno)-11,7-(metheno)imidazo[2,1-c][1,4,13,15]oxatriazacycloicosin-14-one;

(12R)-13-ethyl-12-methyl-12,13,15,16,17,18,20,21-octahydro-14H-6,23-(azeno)-11,7-(metheno)imidazo[2,1-f][1,4,7,16,18]dioxatriazacyclohenicosin-14-one;

(12R)-13,18-diethyl-12-methyl-12,13,16,17,18,19,20,21-octahydro-6,23-(azeno)-11,7-(metheno)imidazo[2,1-c][1,4,13,15,18]oxatetraazacyclohenicosin-14(15H)-one;

(12R)-13-ethyl-12,18,21-trimethyl-12,13,16,17,18,19,20,21-octahydro-6,23-(azeno)-11,7-(metheno)imidazo[2,1-c][1,4,13,15,18]oxatetraazacyclohenicosin-14(15H)-one;

(12R)-13-ethyl-12-methyl-12,13,16,17,20,21-hexahydro-19H-6,23-(azeno)-11,7-(metheno)imidazo[1,2-o][1,18,4,6,15]dioxatriazacyclohenicosin-14(15H)-one;

(12R)-13-ethyl-12,16-dimethyl-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12-methyl-16-(1,3-thiazol-4-yl)-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12-methyl-16-(1,3-thiazol-4-yl)-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12-methyl-16-(1,2-oxazol-3-yl)-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-8-methoxy-12-methyl-16-(3,3,3-trifluoropropyl)-12,13,16,17,20,21-hexahydro-19H-6,23-(azeno)-11,7-(metheno)imidazo[1,2-o][1,18,4,6,9,15]dioxatetraazacyclohenicosin-14(15H)-one;

(12R)-13-ethyl-8-methoxy-12-methyl-16-(3,3,3-trifluoropropyl)-12,13,16,17,20,21-hexahydro-19H-6,23-(azeno)-11,7-(metheno)imidazo[1,2-o][1,18,4,6,9,15]dioxatetraazacyclohenicosin-14(15H)-one;

(R,27E,62Z)-10-ethyl-11-methyl-3-oxa-8,10-diaza-6(4,2)-thiazola-2(6,8)-imidazo[1,2-a]pyrazina-1(1,3)-benzenacycloundecaphan-9-one;

(R,27E,54Z)-10-ethyl-11-methyl-3-oxa-8,10-diaza-5(3,5)-oxadiazola-2(6,8)-imidazo[1,2-a]pyrazina-1(1,3)-benzenacycloundecaphan-9-one;

(3R,E)-4-ethyl-3,9-dimethyl-8-(trifluoromethyl)-12-oxa-4,6,9-triaza-1(6,8)-imidazo[1,2-a]pyrazina-2(1,3)-benzenacyclododecaphan-5-one;

(3R,E)-4-ethyl-3,9-dimethyl-8-(trifluoromethyl)-13-oxa-4,6,9-triaza-1(6,8)-imidazo[1,2-a]pyrazina-2(1,3)-benzenacyclotridecaphan-5-one;

(3R,7R,E)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-5-one;

(3R,7R,E)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-5-one;

(12S,16R)-13-ethyl-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12R,16R)-13-ethyl-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12S,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

($1^7$E,3R,7S,9Z)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-9-en-5-one;

(3R,7R,E)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-5-one;

(16S,18Z)-13-ethyl-8-methoxy-12-(trifluoromethyl)-16-(3,3,3-trifluoropropyl)-12,13,15,16,17,20-hexahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-12-(trifluoromethyl)-16-(3,3,3-trifluoropropyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-12-(trifluoromethyl)-16-(3,3,3-trifluoropropyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

13-ethyl-8-methoxy-12-(trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-2-methyl-12-(trifluoromethyl)-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(16R)-13-ethyl-8-methoxy-2-methyl-12-(trifluoromethyl)-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(16R)-13-ethyl-8-methoxy-12,16-bis(trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-16-(2,2,2-trifluoroethyl)-12-(trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-12,16-bis(trifluoromethyl)-12,13,15,16,17,18,19,20-octahydro-14H-6,22-(azeno)-11,7-(metheno)imidazo[2,1-c][1,4,10,13,15]oxatetraazacycloicosin-14-one;

(16R)-13-ethyl-8-methoxy-12,16-bis(trifluoromethyl)-12,13,15,16,17,18,19,20-octahydro-14H-6,22-(azeno)-11,7-(metheno)imidazo[2,1-c][1,4,10,13,15]oxatetraazacycloicosin-14-one;

(12S,16R)-13-ethyl-8-methoxy-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriazacycloicosin-14-one;

(12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriazacycloicosin-14-one;

(12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriazacycloicosin-14-one;

(12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(16R)-13-ethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(3R,7R,E)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-5-one;

(3R,7R,E)-4-ethyl-22-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-5-one;

(3R,E)-4-ethyl-3,9-dimethyl-7-(3,3,3-trifluoropropyl)-12-oxa-4,6-diaza-1(6,8)-imidazo[1,2-a]pyrazina-2(1,3)-benzenacyclododecaphan-5-one;

(12R)-13-ethyl-12-methyl-12,13,15,16,17,18,19,20-octahydro-14H-6,22-(azeno)-11,7-(metheno)imidazo[2,1-c][1,4,13,15]oxatriazacycloicosin-14-one;

(7R)-8-ethyl-14,14-difluoro-3-methoxy-7-methyl-11-(3,3,3-trifluoropropyl)-17-oxa-5,8,10,20,23,25-hexazatetracyclo[16.6.1.12,6,019,23]hexacosa-1(24),2(26),3,5,18(25),19,21-heptaen-9-one;

(7R)-8-ethyl-14,14-difluoro-3-methoxy-7-methyl-11-(3,3,3-trifluoropropyl)-17-oxa-5,8,10,20,23,25-hexazatetracyclo[116.6.1.12,6,019,23]hexacosa-1(24),2(26),3,5,18(25),19,21-heptaen-9-one;

(7R)-8-ethyl-14,14-difluoro-3-methoxy-7-methyl-11-(3,3,3-trifluoropropyl)-17-oxa-5,8,10,20,23,25-hexazatetracyclo[116.6.1.12,6,019,23]hexacosa-1(24),2(26),3,5,18(25),19,21-heptaen-9-one;

(3R,7R,E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-5-one;

(16R)-13-ethyl-8-methoxy-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one;

(12R)-13,16-diethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13,16-diethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(2-methylpropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(2-methylpropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-propyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-propyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopropylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopropylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(2-methoxyethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(2-methoxyethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-cyclopropyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-cyclopropyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(methoxymethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(methoxymethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-[(2,2-difluorocyclopropyl)methyl]-13-ethyl-8-methoxy-12-methyl-12,13,16,17,18,19, 20,21-octahydro-6,23-(azeno)-11,7-(metheno)imidazo[2,1-c][1,4,10,13,15]oxatetraazacyclo henicosin-14(15H)-one;

(12R)-16-[(2,2-difluorocyclopropyl)methyl]-13-ethyl-8-methoxy-12-methyl-12,13,16,17,18, 19,20,21-octahydro-6,23-(azeno)-11,7-(metheno)imidazo[2,1-c][1,4,10,13,15]oxatetraazacyclo henicosin-14(15H)-one;

(12R)-16-[(2,2-difluorocyclopropyl)methyl]-13-ethyl-8-methoxy-12-methyl-12,13,16,17,18,19, 20,21-octahydro-6,23-(azeno)-11,7-(metheno)imidazo[2,1-c][1,4,10,13,15]oxatetraaza cyclohenicosin-14(15H)-one;

(12R)-16-[(2,2-difluorocyclopropyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(3-methoxypropyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(3-methoxypropyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclobutylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclobutylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(ethoxymethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(ethoxymethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-tert-butyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-tert-butyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(2-ethylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(2-ethylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopentylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopentylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-{[1-(trifluoromethyl)cyclopropyl]methyl}-12,13,16,17,18,19,20,21-octahydro-6,23-(azeno)-11,7-(metheno)imidazo[2,1c][1,4,10,13,15]oxatetraazacyclohenicosin-14(15H)-one;

(12R)-13-ethyl-8-methoxy-12-methyl-16-{[1-(trifluoromethyl)cyclopropyl]methyl}-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-[(oxolan-3-yl)methyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-[(oxolan-3-yl)methyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(oxan-4-yl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(oxan-4-yl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-[(3,3-difluorocyclobutyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-[(3,3-difluorocyclobutyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-{[1-(difluoromethyl)cyclopropyl]methyl}-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-{[1-(difluoromethyl)cyclopropyl]methyl}-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluoro-3-methylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluoro-3-methylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluorobutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluorobutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-[2-(trifluoromethoxy)ethyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-[2-(trifluoromethoxy)ethyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(9R,E)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-11-one;

(10R)-7-ethyl-6,19-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,19-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,20-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,20-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(12R,16R)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-13-ethyl-8,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-7-methoxy-11-methyl-15-(3,3,3-trifluoropropyl)-11,12,15,16,17,18,19,20-octahydro-10,6-(azeno)-5,22-(metheno)pyrazolo[1,5-c][1,3,9,13,15]oxatetraazacyclohenicosin-13(14H)-one;

(15R)-12-ethyl-7-methoxy-11-methyl-15-(3,3,3-trifluoropropyl)-11,12,15,16,17,18,19,20-octahydro-10,6-(azeno)-5,22-(metheno)pyrazolo[1,5-c][1,3,9,13,15]oxatetraazacyclohenicosin-13(14H)-one;

(12R,16R)-13-ethyl-8-methoxy-12-methyl-16-(3,3,3-trifluoropropyl)-12,13,15,16,17,18,19,20,21,22-decahydro-14H-6,23-(azeno)-11,7-(metheno)imidazo[1,2-1][1,3,6,12]tetraazacyclohenicosin-14-one;

(12R,16R)-13-ethyl-8-methoxy-12-methyl-16-(3,3,3-trifluoropropyl)-12,13,16,17,18,19,20,21-octahydro-6,23-(azeno)-11,7-(metheno)[1,2,4]triazolo[5,1-c][1,4,10,13,15]oxatetraazacyclohenicosin-14(15H)-one;

(12R,16R)-16-(3,3-difluorobutyl)-13-ethyl-8-methoxy-12-methyl-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-16-(3,3-difluorobutyl)-13-ethyl-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8-methoxy-5,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,13,15]oxatetraazacyclohenicosin-14(15H)-one;

(15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c]1[1,3,10,13,15]oxatetraazacyclohenicosin-13(14H)-one;

(15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c]1[1,3,10,13,15]oxatetraazacyclohenicosin-13(14H)-one;

(12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,5,9,13,15]oxapentaazacyclohenicosin-14(15H)-one;

(16R)-13-ethyl-12-methyl-16-(3,3,3-trifluoropropyl)-12,13,16,17,18,19,20,21-octahydro-6,23:11,7-di(azeno)imidazo[2,1-c][1,4,13,15]oxatriazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,9,13,15]oxatetraazacyclohenicosin-14(15H)-one;

(16R)-13-ethyl-10,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(16R)-13-ethyl-10,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12S,16R)-13-ethyl-8,12-dimethyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(12R,16R)-13-ethyl-8,12-dimethyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(15R)-12-ethyl-11-methyl-15-(3,3,3-trifluoropropyl)-11,12,15,16,17,18,19,20-octahydro-6,22-(azeno)-7,10-epithio-imidazo[2,1-c][1,4,8,12,14]oxatetraazacycloicosin-13(14H)-one;

(15R)-12-ethyl-1i-methyl-15-(3,3,3-trifluoropropyl)-11,12,15,16,17,18,19,20-octahydro-6,22-(azeno)-7,10-epithio-imidazo[2,1-c][1,4,8,12,14]oxatetraazacycloicosin-13(14H)-one;

(15R)-12-ethyl-11-methyl-15-(3,3,3-trifluoropropyl)-11,12,15,16,17,18,19,20-octahydro-6,22-(azeno)-7,10-epithio-imidazo[2,1-c][1,4,9,12,14]oxatetraazacycloicosin-13(14H)-one;

(16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacyclohenicosin-14(15H)-one;

(16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,13,15]oxatriazacyclohenicosin-14(15H)-one;

(11R,15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,5,10,13,15]oxapentaazacyclohenicosin-13(14H)-one;

(12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,5,9,13,15]oxapentaazacyclohenicosin-14(15H)-one;

(11R,15R)-12-ethyl-7-methoxy-11-methyl-15-(3,3,3-trifluoropropyl)-11,12,15,16,17,18,19,20-octahydro-5,22:10,6-di(metheno)pyrazolo[1,5-c][1,3,5,10,13,15]oxapentaazacyclohenicosin-13(14H)-one;

(12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,5,10,13,15]oxapentaazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,10,13,15]oxapentaazacyclohenicosin-14(15H)-one;

(12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-1i-methyl-15-(3,3,3-trifluoropropyl)-11,12,15,16,17,18,19,20-octahydro-6,22-(azeno)-7,10-epoxy-imidazo[2,1-c][1,4,8,12,14]oxatetraazacycloicosin-13(14H)-one;

(15R)-12-ethyl-11-methyl-15-(3,3,3-trifluoropropyl)-11,12,15,16,17,18,19,20-octahydro-6,22-(azeno)-7,10-epoxy-imidazo[2,1-c][1,4,8,12,14]oxatetraazacycloicosin-13(14H)-one;

(15R)-12-ethyl-11-methyl-15-(3,3,3-trifluoropropyl)-11,12,15,16,17,18,19,20-octahydro-6,22:10,7-di(azeno)imidazo[2,1-c][1,8,4,12,14]dioxatriazacycloicosin-13(14H)-one;

(15R)-12-ethyl-11-methyl-15-(3,3,3-trifluoropropyl)-11,12,15,16,17,18,19,20-octahydro-6,22:10,7-di(azeno)imidazo[2,1-c][1,8,4,12,14]dioxatriazacycloicosin-13(14H)-one;

(12R,16R)-13-ethyl-8-methoxy-12-methyl-16-(3,3,3-trifluoropropyl)-12,13,15,16,17,18,19,20,21,22-decahydro-14H-11,7-(azeno)-6,23-(metheno)imidazo[1,2-1][1,3,12]triazacyclohenicosin-14-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-11-methyl-15-(3,3,3-trifluoropropyl)-11,12,15,16,17,18,19,20-octahydro-6,22-(azeno)-7,10-epoxy-imidazo[2,1-c][1,4,9,12,14]oxatetraazacycloicosin-13(14H)-one;

(3R,7R,E)-4-ethyl-25-methoxy-3-methyl-7-(3,3,3-trifluoropropyl)-14-oxa-4,6-diaza-1(6,8)-imidazo[1,2-a]pyrazina-2(4,2)-pyridinacyclotetradecaphan-5-one;

(3R,7R,E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,7R,E)-4-ethyl-25-methoxy-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(12S,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16S)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23-(azeno)-11,7-(metheno)imidazo[2,1-c][1,4,9,10,13,15]oxapentaazacyclohenicosin-14(15H)-one;

(12S,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;
(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;
(16R)-13-ethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;
(3R,E)-7-(2,2-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one;
(3R,7R,E)-4-ethyl-25-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one;
(R,E)-7-(3,3-difluorobutyl)-4-ethyl-22-methoxy-13-oxa-4,6-diaza-1(2,4)-imidazo[2,1-f][1,2,4]triazina-2(3,5)-pyridinacyclotridecaphan-5-one;
(3R,7R,E)-4-ethyl-7-(fluoromethyl)-25-methoxy-3-methyl-13-oxa-4,6-diaza-1(6,8)-imidazo[1,2-a]pyrazina-2(4,2)-pyridinacyclotridecaphan-5-one;
(3R,7S,E)-7-(3,3-difluoropropyl)-4-ethyl-25-fluoro-3-methyl-10,13-dioxa-4,6-diaza-1(2,4)-imidazo[2,1-f][1,2,4]triazina-2(4,2)-pyridinacyclotridecaphan-5-one;
(3R,7R,E)-25-chloro-7-(3,3-difluoropropyl)-4-ethyl-3-methyl-13-oxa-4,6-diaza-1(6,8)-[1,2,4]triazolo[1,5-a]pyrazina-2(4,2)-pyridinacyclotridecaphan-5-one;
(3R,7S,E)-7-(3,3-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-3-methyl-7-((R)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-3-methyl-7-((S)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-3-methyl-7-((R)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-3-methyl-7-((S)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one;
(3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one;
(3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one 10,10-dioxide;
(3R,7S,E)-4-ethyl-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;
(3R,7R,E)-4-ethyl-10-hydroxy-22,3-dimethyl-7-(3,3,3-trifluoropropyl)-13-oxa-4,6-diaza-1(6,8)-imidazo[1,2-a]pyrazina-2(3,5)-pyridinacyclotridecaphan-5-one;
(3R,7R,Z)-4-ethyl-23-methoxy-3-methyl-7-(3,3,3-trifluoropropyl)-4,6-diaza-1(6,8)-imidazo[1,2-a]pyridina-2(2,6)-pyridinacyclododecaphan-5-one;
(3R,7R,E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclotridecaphan-5-one;
(3R,7R,E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-5-one;
(3R,7S,E)-4-ethyl-8,8-difluoro-25-methoxy-3,7-dimethyl-13-oxa-4,6-diaza-1(6,8)-imidazo[1,2-a]pyrazina-2(4,2)-pyridinacyclotridecaphan-5-one;
(3R,7R,E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-5-one;
(R,E)-4-ethyl-3,3-dimethyl-7-(3,3,3-trifluoropropyl)-13-oxa-4,6-diaza-1(6,8)-imidazo[1,2-a]pyrazina-2(4,2)-pyridinacyclotridecaphan-5-one;
(3R,7R,E)-4-ethyl-25-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-5-one;
(3R,E)-4-ethyl-25-methoxy-3-methyl-12-oxa-4,6-diaza-1(6,8)-imidazo[1,2-a]pyrazina-2(4,2)-pyridina-7(1,2)-cyclopropanacyclododecaphan-5-one;
(3R,7R,E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-5-one;
(3R,7R,E)-4-ethyl-25-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-5-one;
(3R,7S,E)-7-(3,3-difluorobutyl)-4-ethyl-22-methoxy-3-methyl-10,13-dioxa-4,6-diaza-1(6,8)-[1,2,4]triazolo[1,5-a]pyrazina-2(3,5)-pyridinacyclotridecaphan-5-one;
(3R,7R,E)-4-ethyl-25-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-5-one;
(3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyridina-2(4,2)-pyridinacyclotridecaphan-5-one;
(3R,7R,E)-7-(2,2-difluoropropyl)-4-ethyl-25-methoxy-3-methyl-13-oxa-4,6-diaza-1(6,8)-imidazo[1,2-a]pyrazina-2(4,2)-pyridinacyclotridecaphan-5-one;
(3R,7R,E)-4-ethyl-25-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-5-one;
(3R,7S,E)-7-(3,3-difluorobutyl)-4-ethyl-25,3-dimethyl-9,13-dioxa-4,6-diaza-1(6,8)-[1,2,4]triazolo[1,5-a]pyrazina-2(4,2)-pyridinacyclotridecaphan-5-one;
(3R,7R,E)-4-ethyl-25-methoxy-3-methyl-7-(2-(methylsulfonyl)ethyl)-13-oxa-4,6-diaza-1(6,8)-[1,2,4]triazolo[1,5-a]pyrazina-2(4,2)-pyridinacyclotridecaphan-5-one;
(3R,7S,E)-7-(3,3-difluorobutyl)-4-ethyl-25-methoxy-3-methyl-10,13-dioxa-4,6-diaza-1(2,4)-imidazo[2,1-f][1,2,4]triazina-2(4,2)-pyridinacyclotridecaphan-5-one;
(3R,7R,E)-4-ethyl-3-methyl-7-(3,3,3-trifluoropropyl)-13-oxa-4,6-diaza-1(5,7)-pyrazolo[1,5-a]pyridina-2(4,2)-pyridinacyclotridecaphan-5-one;
(3R,7R)-4-ethyl-25-methoxy-3-methyl-7-(3,3,3-trifluoropropyl)-13-oxa-4,6-diaza-1(6,8)-quinolina-2(4,2)-pyridinacyclotridecaphan-5-one;
(3R,7R,E)-3,4-dimethyl-7-(3,3,3-trifluoropropyl)-13-oxa-4,6-diaza-1(6,8)-imidazo[1,2-a]pyrazina-2(4,2)-pyridinacyclotridecaphan-5-one;
(3R,7R,E)-4-ethyl-3-methyl-7-(3,3,3-trifluoropropyl)-13-oxa-4,6-diaza-1(6,8)-imidazo[1,2-a]pyrazina-2(5,3)-pyridazinacyclotridecaphan-5-one;

(3R,7R,E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-5-one;

(3R,7S,E)-4-ethyl-3-methyl-7-(3,3,3-trifluoropropyl)-10,13-dioxa-4,6-diaza-1(6,8)-imidazo[1,2-a]pyrazina-2(2,4)-pyridinacyclotridecaphan-5-one;

(3R,7R)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-5-one;

(3R,7S,E)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-9-en-5-one;

(3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;

(3R,7S,E)-4-ethyl-25-methoxy-3-methyl-7-(3,3,3-trifluoropropyl)-10,13-dioxa-4,6-diaza-1(5,7)-pyrazolo[1,5-c]pyrimidina-2(4,2)-pyridinacyclotridecaphan-5-one;

(3R,7R,E)-4-ethyl-25-methoxy-12,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one;

(3R,7S,E)-7-(3,3-difluorobutyl)-4-ethyl-25-methoxy-3-methyl-10,13-dioxa-4,6-diaza-1(5,7)-pyrazolo[1,5-c]pyrimidina-2(4,2)-pyridinacyclotridecaphan-5-one;

(3R,7R,E)-4-ethyl-25-methoxy-13,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one;

(3R,E)-7-(3,3-difluorobutyl)-4-ethyl-25-methoxy-3-methyl-10,13-dioxa-4,6-diaza-1(7,5)-[1,2,4]triazolo[1,5-c]pyrimidina-2(4,2)-pyridinacyclotridecaphan-5-one;

(3R,7S,E)-7-(3,3-difluorobutyl)-4-ethyl-25-methoxy-3-methyl-9,13-dioxa-4,6-diaza-1(5,7)-pyrazolo[1,5-c]pyrimidina-2(4,2)-pyridinacyclotridecaphan-5-one;

(3R,7S,E)-7-(3,3-difluorobutyl)-4-ethyl-25-methoxy-3-methyl-9,13-dioxa-4,6-diaza-1(5,7)-pyrazolo[1,5-c]pyrimidina-2(4,2)-pyridinacyclotridecaphan-5-one;

(3R,7R,E)-7-(3,3-difluorobutyl)-4-ethyl-25-methoxy-15,3-dimethyl-13-oxa-4,6-diaza-1(6,8)-[1,2,4]triazolo[1,5-a]pyrazina-2(4,2)-pyridinacyclotridecaphan-5-one;

(3R,7S,E)-4-ethyl-25-methoxy-3-methyl-7-(3,3,3trifluoropropyl)-9,13-dioxa-4,6-diaza-1(6,8)-[1,2,4]triazolo[4,3-a]pyrazina-2(4,2)-pyridinacyclotridecaphan-5-one;

(3R,7S,E)-4-ethyl-25-methoxy-3-methyl-7-(3,3,3-trifluoropropyl)-9,13-dioxa-4,6-diaza-1(6,8)-[1,2,4]triazolo[1,5-a]pyrazina-2(4,2)-pyridinacyclotridecaphan-5-one;

(3R,7S,E)-4-ethyl-23-fluoro-3-methyl-7-(3,3,3trifluoropropyl)-9,13-dioxa-4,6-diaza-1(6,8)-[1,2,4]triazolo[1,5-a]pyrazina-2(4,2)-pyridinacyclotridecaphan-5-one;

(3R,7R,E)-7-(3,3-difluorobutyl)-4-ethyl-25-methoxy-3-methyl-13-oxa-4,6-diaza-1(7,5)-[1,2,4]triazolo[1,5-c]pyrimidina-2(4,2)-pyridinacyclotridecaphan-5-one;

(R,E)-4-ethyl-25-methoxy-3-methyl-14-oxa-4,6-diaza-1(6,8)-imidazo[1,2-a]pyrazina-2(4,2)-pyridinacyclotetradecaphan-5-one;

(R,E)-4-ethyl-25-methoxy-3-methyl-11-oxa-4,6-diaza-1(6,8)-imidazo[1,2-a]pyrazina-2(4,2)-pyridinacycloundecaphan-5-one;

(7S,E)-4-ethyl-23-fluoro-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-3-methyl-10,13-dioxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-3-methyl-10,13-dioxa-4,6-diaza-1(5,7)-pyrazolo[1,5-c]pyrimidina-2(4,2)-pyridinacyclotridecaphan-5-one;

(3R,E)-7-(2-(difluoromethoxy)ethyl)-4-ethyl-25-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-7-((1-fluorocyclopropyl)methyl)-25-methoxy-3-methyl-13-oxa-4,6-diaza-1(6,8)-imidazo[1,2-a]pyrazina-2(4,2)-pyridinacyclotridecaphan-5-one;

(3R,E)-7-(4,4-difluorobutyl)-4-ethyl-25-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-7-(isopropoxymethyl)-25-methoxy-3-methyl-13-oxa-4,6-diaza-1(6,8)-imidazo[1,2-a]pyrazina-2(4,2)-pyridinacyclotridecaphan-5-one;

(3R,E)-7-(2,2-difluoroethyl)-4-ethyl-25-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(2,2,3,3-tetrafluoropropyl)-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-((2,2,2-trifluoroethoxy)methyl)-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(tetrahydrofuran-3-yl)-13-oxa-4,6-diaza-1(6,8)-imidazo[1,2-a]pyrazina-2(4,2)-pyridinacyclotridecaphan-5-one;

(3R,E)-7-((2,2-difluoroethoxy)methyl)-4-ethyl-25-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-25-methoxy-7-(1-methoxyethyl)-3-methyl-13-oxa-4,6-diaza-1(6,8)-imidazo[1,2-a]pyrazina-2(4,2)-pyridinacyclotridecaphan-5-one;

(3R,E)-7-(2,2-difluorocyclopropyl)-4-ethyl-25-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(tetrahydrofuran-2-yl)-13-oxa-4,6-diaza-1(6,8)-imidazo[1,2-a]pyrazina-2(4,2)-pyridinacyclotridecaphan-5-one;

2-((3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-yl)acetonitrile;

(3R,E)-7-(3,3-difluorocyclobutyl)-4-ethyl-25-methoxy-3-methyl-13-oxa-4,6-diaza-1(6,8)-imidazo[1,2-a]pyrazina-2(4,2)-pyridinacyclotridecaphan-5-one;

3-((3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-yl)propanenitrile;

(3R,E)-25-cyclopropyl-7-(3,3-difluoropropyl)-4-ethyl-3-methyl-13-oxa-4,6-diaza-1(6,8)-imidazo[1,2-a]pyrazina-2(4,2)-pyridinacyclotridecaphan-5-one;

(3R,E)-25-chloro-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,E)-4-ethyl-25-fluoro-7-(methoxymethyl)-3-methyl-13-oxa-4,6-diaza-1(6,8)-imidazo[1,2-a]pyrazina-2(4,2)-pyridinacyclotridecaphan-5-one;

(3R,E)-7-(3,3-difluorobutyl)-4-ethyl-25-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(3,3-difluoropropyl)-4-ethyl-25,3-dimethyl-13-oxa-4,6-diaza-1(6,8)-[1,2,4]triazolo[1,5-a]pyrazina-2(4,2)-pyridinacyclotridecaphan-5-one;

(3R,E)-7-(3,3-difluoropropyl)-4-ethyl-25-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(bicyclo[1.1.1]pentan-1-ylmethyl)-4-ethyl-25-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(3,3-difluoropropyl)-4-ethyl-25-fluoro-3-methyl-13-oxa-4,6-diaza-1(6,8)-imidazo[1,2-b]pyridazina-2(4,2)-pyridinacyclotridecaphan-5-one;

(3R,E)-4-cyclopropyl-7-(3,3-difluoropropyl)-25-fluoro-3-methyl-13-oxa-4,6-diaza-1(2,4)-imidazo[2,1-f][1,2,4]triazina-2(4,2)-pyridinacyclotridecaphan-5-one;

(3R,E)-4-ethyl-25-methoxy-3-methyl-7-((1-methylcyclopropyl)methyl)-13-oxa-4,6-diaza-1(2,4)-imidazo[2,1-f][1,2,4]triazina-2(4,2)-pyridinacyclotridecaphan-5-one;

(3R,E)-7-(2,2-difluoropropyl)-4-ethyl-25-methoxy-3-methyl-13-oxa-4,6-diaza-1(2,4)-imidazo[2,1-f][1,2,4]triazina-2(4,2)-pyridinacyclotridecaphan-5-one;

(3S,E)-7-(3,3-difluoropropyl)-4-ethyl-25-methoxy-3-(trifluoromethyl)-13-oxa-4,6-diaza-1(6,8)-imidazo[1,2-a]pyrazina-2(4,2)-pyridinacyclotridecaphan-5-one;

(9R,13R,E)-14-Cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-11-one;

(16E,22E,7R)-25-cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-5-one;

(9R,13R,E)-14-Cyclopropyl-12-ethyl-13-methyl-9-(3,3,3-trifluoropropyl)-3-oxa-10,12-diaza-1(5,2)-oxazola-2(6,8)-imidazo[1,2-a]pyrazinacyclotridecaphan-11-one;

(3R,E)-4-ethyl-25-methoxy-3-methyl-$7^4$-(trifluoromethyl)-11-oxa-4,6-diaza-1(6,8)-imidazo[1,2-a]pyrazina-2(4,2)-pyridina-7(3,1)-pyrrolidinacycloundecaphan-5-one;

(3R,E)-4-ethyl-$7^4$,$7^4$-difluoro-3-methyl-11-oxa-4,6-diaza-1(6,8)-imidazo[1,2-a]pyrazina-7(3,1)-pyrrolidina-2(1,3)-benzenacycloundecaphan-5-one;

(3R,E)-4-ethyl-25-methoxy-3-methyl-$7^4$-(trifluoromethyl)-12-oxa-4,6-diaza-1(6,8)-imidazo[1,2-a]pyrazina-2(4,2)-pyridina-7(3,1)-pyrrolidinacyclododecaphan-5-one;

(3R,E)-4-ethyl-22-methoxy-3-methyl-7-(2-methylthiazol-4-yl)-13-oxa-4,6-diaza-1(6,8)-imidazo[1,2-a]pyrazina-2(3,5)-pyridinacyclotridecaphan-5-one;

(3R,E)-4-ethyl-25-methoxy-3-methyl-7-(2-methylthiazol-5-yl)-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(1-methyl-1H-tetrazol-5-yl)-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(4-methylthiazol-2-yl)-13-oxa-4,6-diaza-1(6,8)-imidazo[1,2-a]pyrazina-2(4,2)-pyridinacyclotridecaphan-5-one;

(3R,E)-4-ethyl-25-methoxy-3-methyl-7-(1-methyl-TH-1,2,4-triazol-5-yl)-13-oxa-4,6-diaza-1(6,8)-imidazo[1,2-a]pyrazina-2(4,2)-pyridinacyclotridecaphan-5-one;

($1^7$E,3R,8E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one;

(3R,7S,E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-5-one;

(3'R,7'S,7'E,8'E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphanen]-8'-en-5'-one;

(3'R,7'S,E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphan]-5'-one;

(3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-carbonitrile; and (3R,E)-4-ethyl-25-fluoro-3-methyl-5-oxo-13-oxa-4,6-diaza-1(6,8)-imidazo[1,2-a]pyrazina-2(4,2)-pyridinacyclotridecaphane-7-carboxamide;

or a pharmaceutically acceptable salt thereof.

Certain embodiments of the present invention include a compound which is selected from Example Numbers: 110, 125, 129, 136, 142, 164, 165, 169, 174 and 179 or a pharmaceutically acceptable salt thereof. In an embodiment of the present invention, the compounds comprise Example Numbers: 110, 136, 164, and 179 or a pharmaceutically acceptable salt thereof.

Alternate embodiments of the present invention may also exclude any of the compounds which are recited in the list above.

It is understood that reference to "Formula I" also encompasses compounds of Formula I', Formula Ia, Formula Ia', Formula Ia", Formula Ib, Formula Ib', and Formula Ib", unless indicated otherwise.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Likewise, the present invention includes tautomeric forms of the compounds disclosed herein. Formula I shows the structure of the class of compounds without specific stereochemistry. At least some of the chemical names of compounds of the invention as set forth in this application may have been generated on an automated basis by use of commercially available chemical naming software programs, and have not been independently verified.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. Absolute stereochemistry may also be elucidated through other techniques known in the art, such as cryogenic electron microscopy. Relative stereochemistry may be determined using nuclear magnetic resonance with methods known in the art. Stereochemistry may be assigned by analogy to a set of isomers based on their relative biological activity following the same trend established by a similar stereochemically defined group of isomers. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Compounds of the present invention may also be separated by supercritical fluid chromatography (SFC) or reverse-phase HPLC or silica gel chromotography. Isomers are named according to the order they came off the column (first, second, etc eluting or alternatively with "A" and "B" or "a" and "b" being the first, second, etc eluting isomers) with examples named as example #A and example #B, etc according to the order eluting from the purification system. One with skill in the art would understand that sometimes the peaks may contain more than a single isomer and when cut in half or fractionated further result in multiple fractions of one peak and may not represent single isomers.

Furthermore, some separations required multiple rounds of purifications by the same method of purification and/or an alternative purification system. Additionally, a mixture may be a mixture of 2 to 8 stereoisomers. Alternatively, any enantiomer of a compound may be obtained by stereoselective synthesis using optically pure starting materials or reagents of known configuration by methods well known in the art.

As appreciated by those of skill in the art, halogen or halo as used herein are intended to include fluoro, chloro, bromo and iodo. Similarly, $C_{1-6}$, as in $C_{1-6}$alkyl is defined to identify the group as having 1, 2, 3, 4, 5 or 6 carbons in a linear or branched arrangement, such that $C_{1-6}$alkyl specifically includes methyl, ethyl, n-propyl, iso-propyl, n-butyl, iso-butyl, tert-butyl, pentyl, isopentyl, neopentyl, sec-pentyl, hexyl, and the like. A group which is designated as being independently substituted with substituents may be independently substituted with multiple numbers of such substituents.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature. Such compounds are identical to those disclosed herein, but for the fact that one or more atoms are replaced by an atom having an atomic mass or mass number different from the atomic mass or mass number usually found in nature. Examples of isotopes suitable for inclusion in the compounds of the invention include isotopes of hydrogen such as $^{2}H$ and $^{3}H$, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$. Certain isotopically-labelled compounds of Formula I, for example those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection. Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. An embodiment of the present invention includes compounds that are substituted with a positron emitting isotope. An embodiment of the present invention includes compounds that are substituted with a $^{11}C$ isotope. An embodiment of the present invention includes compounds that are substituted with an $1^{8}F$ isotope. In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature.

The present invention is meant to include all suitable isotopic variations of the compounds of the invention. For example, different isotopic forms of hydrogen (H) include protium ($^{1}H$) and deuterium ($^{2}H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Those skilled in the art will recognize those instances in which the compounds of the invention may form salts. In such instances, another embodiment provides pharmaceutically acceptable salts of the compounds of the invention. Thus, reference to a compound of the invention herein is understood to include reference to salts thereof, unless otherwise indicated. The term "pharmaceutically acceptable salts" refers to salts prepared from pharmaceutically acceptable non-toxic bases or acids including inorganic or organic bases and inorganic or organic acids. In addition, when a compound of the invention contains both a basic moiety, such as, but not limited to a pyridine or imidazole, and an acidic moiety, such as, but not limited to a carboxylic acid, zwitterions ("inner salts") may be formed and are included within the present invention. Salts derived from inorganic bases include aluminum, ammonium, calcium, copper, ferric, ferrous, lithium, magnesium, manganic salts, manganous, potassium, sodium, zinc, and the like. Particular embodiments include the ammonium, calcium, magnesium, potassium, and sodium salts. Salts in the solid form may exist in more than one crystal structure, and may also be in the form of hydrates or solvates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particular embodiments include the citric, hydrobromic, hydrochloric, maleic, phosphoric, sulfuric, fumaric, and tartaric acids. It will be understood that, as used herein, references to the compounds of Formula I are meant to also include the pharmaceutically acceptable salts. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplifying the invention is the use of the compounds disclosed in the Examples and herein. Specific compounds within the present invention include a compound which is selected from the compounds disclosed in the following Examples and pharmaceutically acceptable salts thereof and individual enantiomers or diastereomers thereof.

The present invention is also directed to the use of the compounds disclosed herein as agonists of orexin receptor activity. The subject compounds and pharmaceutically acceptable salts thereof are useful in a method of agonizing orexin receptor activity in a subject such as a mammal comprising the administration of an amount of the compound. In addition to primates, especially humans, a variety of other mammals may be administered with a compound of the present invention. The present invention is directed to a compound of the present invention or a pharmaceutically acceptable salt thereof that could be useful in therapy. The present invention may further be directed to a use of a compound of the present invention or a pharmaceutically acceptable salt thereof for the manufacture of a medicament for agonizing orexin receptor activity or treating the disorders and diseases noted herein in humans and animals.

A subject administered with a compound of the present invention, or a pharmaceutically acceptable salt thereof, is generally a mammal, such as a human being, male or female. The amount of compound administered to the subject is an amount sufficient to agonize the orexin receptor in the subject. In an embodiment, the amount of compound can be an "effective amount", wherein the subject compound is administered in an amount that will elicit the biological or medical response of a tissue, system, animal or human that is being sought by the researcher, veterinarian, medical doctor or other clinician. An effective amount does not necessarily include considerations of toxicity and safety related to the administration of the compound. It is recognized that one skilled in the art may affect neurological and psychiatric disorders associated with orexin receptor activation by treating a subject presently afflicted with the disorders, or by prophylactically treating a subject likely to be afflicted with the disorders, with an effective amount of a compound of the present invention. As used herein, the terms "treatment" and "treating" refer to all processes wherein there may be a slowing, interrupting, arresting, controlling, or stopping of the progression of the neurological and psychiatric disorders described herein, but does not necessarily indicate a total elimination of all disorder symptoms, as well as the prophylactic therapy of the mentioned conditions, particularly in a subject that is predisposed to such disease or disorder. The terms "administration of" and or "administering a" compound should be understood to mean providing a compound of the invention or a prodrug of a compound of the invention to to the subject.

The term "composition" as used herein is intended to encompass a product comprising the specified ingredients in the specified amounts, as well as any product which results, directly or indirectly, from combination of the specified ingredients in the specified amounts. Such term is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The utility of the compounds in accordance with the present invention as orexin receptor OX1R and/or OX2R agonists may be readily determined without undue experimentation by methodology well known in the art. Both the OX1R and/or OX2R G-coupled protein receptors (GPCRs) couple through the Guq signaling pathway, which ultimately promotes calcium mobilization via inositol triphosphate (IP3) production. The half-life of IP-3 is relatively short, being rapidly metabolized to inositol monophosphate (IP-1), which can be readily detected using a commercially available assay kit (IP-One; Cisbio; cat #621PAPEC) coupled with a cell line expressing the target receptor(s) of interest. The utility of the compounds in accordance with the present invention as orexin receptor OX1R and/or OX2R agonists may be determined utilizing this assay.

In a typical experiment, the OX1 and OX2 receptor agonist activity is determined in accordance with the following general experimental method. Chinese hamster ovary (CHO) cells expressing human OX1R and/or the human OX2R were grown in Iscove's modified DMEM containing glutaMAX™, 1% G418, 100 U/mL penicillin, 100 μg/mL streptomycin and 10% heat-inactivated qualified fetal bovine serum (FBS). The OX2R cells were seeded at 10,000 cells/well/50 μL and the OX1R cells were seeded at 20,000 cells/well/50 μL into 384-well white tissue culture plates (Greiner; cat #781080). All cell/media reagents were from GIBCO-Invitrogen Corp. The seeded cell plate(s) were incubated at 37° C. with 5% $CO_2$ and 85% humidity for 20-24 hours. On the day of the assay, assay-ready compound plates were prepared using an acoustic liquid handler (ECHO; Labcyte), which dispensed sufficient volume of test compound stock (10 mM in DMSO) or 100% DMSO to prepare 10 point, 1/2-log dilutions in a final volume of 202.5 nL/well in all test wells of a 384-well diamond plate (Labcyte). Following completion of assay-ready plates, importantly, the next three steps were performed with minimal delay: 1) 20 μl of 1× stimulation buffer was added to the compound plate using a Multidrop Combi (small cassette, Thermo Fisher Scientific cat #24073290); 2) culture medium was removed from the cell plate using the Bluewasher plate washer (gentle spin; BlueCatBio); 3) 14 μl of compound/stimulation buffer mixture was added to the cell plate using a Bravo liquid handler (Agilent) prior to incubating cell plates at 37° C. with 5% $CO_2$ and 85% humidity for 1 or 2 hours (OX1R and OX2R, respectively). During this incubation, IP-one detection reagents were prepared (38:1:1 lysis buffer:D2:AB-cryptate reagents). Six μL of mixed detection reagents were added to the cell plate using a Multidrop Combi (small cassette, Thermo Fisher Scientific cat #24073290) and incubated 60 minutes at room temperature in the dark. Fluorescence signal was detected using an Envision plate reader (Perkin Elmer) [LANCE/DELFIA Dual Enh (Em: APC 665; Ex: Cy5 620)].

For each compound, data were fit to a four parameter logistic fit (ActivityBase software) and the $EC_{50}$ was reported as the inflection point of the resulting curve. Percent effect for each test compound was determined as the percentage of sample raw value/mean max effect, where the mean max effect was derived from the mean raw value of 32 control wells per assay plate (using Orexin A (cat #003-30)

at 1 μM for human OX1R and a reference compound at 1 uM with 100% activity previously established by comparison to Orexin A for human OX2R). The intrinsic orexin receptor agonist activity of a compound which may be used in the present invention may be determined by these assays.

All of the final compounds of the following examples had activity in agonizing the human orexin-2 receptor in the aforementioned IPOne assay with an $EC_{50}$ of about 0.01 nM to 5000 nM. Additional data is provided in the following Examples. Such a result is indicative of the intrinsic activity of the compounds in use as agonists of orexin-1 receptor and/or the orexin-2 receptor. In general, one of ordinary skill in the art would appreciate that a substance is considered to effectively agonize the orexin receptor if it has an $EC_{50}$ in the IPOne assay of less than about 50 μM, or more specifically less than about 1000 nM.

The orexin receptors have been implicated in a wide range of biological functions. This has suggested a potential role for these receptors in a variety of disease processes in humans or other species. The compounds of the present invention could therefore potentially have utility in treating, preventing, ameliorating, controlling or reducing the risk of a variety of disorders associated with orexin receptors, including one or more of the following conditions or diseases: narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, wakefulness, nocturnal myoclonus, disturbances of consciousness, such as coma, REM sleep interruptions, jet-lag, excessive daytime sleepiness, shift workers' sleep disturbances, dyssomnias, sleep disorders, sleep disturbances, hypersomnia associated with depression, emotional/mood disorders, Alzheimer's disease or cognitive impairment, Parkinson's disease, Guillain-Barre syndrome, Kleine Levin syndrome, and sleep disorders which accompany aging; Alzheimer's sundowning; conditions associated with circadian rhythmicity as well as mental and physical disorders associated with travel across time zones and with rotating shift-work schedules; fibromyalgia; cardiac failure; diseases related to bone loss; sepsis; syndromes which are manifested by non-restorative sleep and muscle pain or sleep apnea which is associated with respiratory disturbances during sleep; conditions which result from a diminished quality of sleep; and other diseases related to general orexin system dysfunction.

Thus, in certain embodiments the present invention may provide methods for: treating or controlling narcolepsy, narcolepsy syndrome accompanied by narcolepsy-like symptoms, cataplexy in narcolepsy, excessive daytime sleepiness (EDS) in narcolepsy, hypersomnia, idiopathic hypersomnia, repeatability hypersomnia, intrinsic hypersomnia, hypersomnia accompanied by daytime hypersomnia, interrupted sleep, sleep apnea, disturbances of consciousness, REM sleep interruptions, jet-lag, shift workers' sleep disturbances, dyssomnias, night terror, insomnias associated with depression, emotional/mood disorders, Alzheimer's disease or cognitive impairment; treating or controlling sleep disturbances associated with diseases such as neurological disorders including neuropathic pain and restless leg syndrome; treating or controlling addiction disorders; treating or controlling psychoactive substance use and abuse; enhancing cognition; increasing memory retention; treating or controlling obesity; treating or controlling diabetes and appetite, taste, eating, or drinking disorders; treating or controlling insulin resistance syndrome; treating or controlling hypothalamic diseases; treating or controlling depression; treating, controlling, ameliorating or reducing the risk of epilepsy, including absence epilepsy; treating or controlling pain, including neuropathic pain; treating or controlling Parkinson's disease; treating or controlling Guillain-Barre syndrome; treating or controlling Klein Levin syndrome; treating or controlling psychosis; treating or controlling dysthymic, mood, psychotic and anxiety disorders; treating side effects or complications due to anesthesia; reversal of anesthesia; reversal of anesthesia following surgery; treating or controlling depression, including major depression and major depression disorder; treating or controlling bipolar disorder; or treating, controlling, ameliorating or reducing the risk of schizophrenia, in a mammalian subject which comprises administering to the subject a compound of the present invention.

The compounds of the present invention may also potentially have utility in treating, preventing, ameliorating, controlling or reducing the risk of a variety of other disorders associated with orexin receptors, including one or more of the following conditions or diseases including enhancing sleep quality, improving sleep quality, increasing sleep efficiency, augmenting sleep maintenance; increasing the value which is calculated from the time that a subject sleeps divided by the time that a subject is attempting to sleep; improving sleep initiation; decreasing sleep latency or onset (the time it takes to fall asleep); decreasing difficulties in falling asleep; increasing sleep continuity; decreasing the number of awakenings during sleep; decreasing intermittent wakings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; decreasing nocturnal arousals, especially early morning awakenings; increasing daytime alertness; reducing daytime drowsiness; treating or reducing excessive daytime sleepiness; increasing satisfaction with the intensity of sleep; increasing sleep maintenance; idiopathic insomnia; sleep problems; insomnia; night terror, insomnias associated with depression, emotional/mood disorders, Alzheimer's disease or cognitive impairment, as well as sleep walking and enuresis, and sleep disorders which accompany aging; Alzheimer's sundowning; conditions associated with circadian rhythmicity as well as mental and physical disorders associated with travel across time zones and with rotating shift-work schedules, conditions due to drugs which cause reductions in REM sleep as a side effect; fibromyalgia; syndromes which are manifested by non-restorative sleep and muscle pain or sleep apnea which is associated with respiratory disturbances during sleep; conditions which result from a diminished quality of sleep; increasing learning; augmenting memory; increasing retention of memory; eating disorders associated with excessive food intake and complications associated therewith, compulsive eating disorders, obesity (due to any cause, whether genetic or environmental), obesity-related disorders overeating, anorexia, bulimia, cachexia, dysregulated appetite control, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, lung disease, abnormal heart rhythms and arrythmias, myocardial infarction, congestive heart failure, coronary heart disease, acute and congestive heart failure; hypotension; hypertension; urinary retention; osteoporosis; angina pectoris; myocardinal infarction; ischemic or haemorrhagic stroke; subarachnoid haemorrhage; ulcers; allergies; benign prostatic hypertrophy; chronic renal failure; renal disease; impaired glucose tolerance; sudden death, polycystic ovary disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia, metabolic syndrome, also known as syndrome X, insulin resistance syndrome, reproductive hormone abnormalities, sexual and reproductive dysfunction, such as impaired fertility, infertility, hypogonadism in males and hirsutism in females, fetal defects associated with maternal obesity, gastrointestinal motility disorders, intestinal motility dyskinesias, obesity-related gastro-esophageal reflux, hypothalmic diseases, hypophysis diseases, respiratory disorders, such as obesity-hypoventilation syndrome (Pickwickian syndrome), breathlessness, cardiovascular disorders, inflammation, such as systemic inflammation of the vasculature, arteriosclerosis, hypercholesterolemia, hyperuricaemia, lower back pain, gallbladder disease, gout, kidney cancer, increased anesthetic risk, reducing the risk of secondary outcomes of obesity, such as reducing the risk of left ventricular hypertrophy; diseases or disorders where abnormal oscillatory activity occurs in the brain, including depression, migraine, neuropathic pain, Parkinson's disease, psychosis and schizophrenia, as well as diseases or disorders where there is abnormal coupling of activity, particularly through the thalamus; enhancing cognitive function, including cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders; treating or controlling Guillain-Barre syndrome; treating or controlling Klein Levin syndrome; treating or controlling psychosis; treating or controlling dysthymic, mood, psychotic and anxiety disorders; treating complications due to anesthesia; enhancing memory; increasing memory retention; increasing immune response; increasing immune function; hot flashes; night sweats; extending life span; schizophrenia; muscle-related disorders that are controlled by the excitation/relaxation rhythms imposed by the neural system such as cardiac rhythm and other disorders of the cardiovascular system; conditions related to proliferation of cells such as vasodilation or vasorestriction and blood pressure; cancer; cardiac arrhythmia; hypertension; congestive heart failure; conditions of the genital/urinary system; disorders of sexual function and fertility; adequacy of renal function; responsivity to anesthetics; mood disorders, such as depression or more particularly depressive disorders, for example, single episodic or recurrent major depressive disorders and dysthymic disorders, or bipolar disorders, for example, bipolar I disorder, bipolar II disorder and cyclothymic disorder, mood disorders due to a general medical condition, and substance-induced mood disorders; affective neurosis; depressive neurosis; anxiety neurosis; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; acute neurological and psychiatric disorders such as cerebral deficits subsequent to cardiac bypass surgery and grafting, stroke, ischemic stroke, cerebral ischemia, spinal cord trauma, head trauma, perinatal hypoxia, cardiac arrest, hypoglycemic neuronal damage; Huntington's Chorea; Huntington's disease and Tourette syndrome; Cushing's syndrome/disease; basophile adenoma; prolactinoma; hyperprolactinemia; hypophysis tumor/adenoma; hypothalamic diseases; inflammatory bowel disease; gastric diskinesia; gastric ulcers; Froehlich's syndrome; adrenohypophysis disease; hypophysis disease; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth deficiency; dwarfism; gigantism; acromegaly; amyotrophic lateral sclerosis; multiple sclerosis; ocular damage; retinopathy; cognitive disorders; idiopathic and drug-induced Parkinson's disease; muscular spasms and disorders associated with muscular spasticity including tremors, epilepsy, convulsions, seizure disorders, absence seisures, complex partial and generalized seizures; Lennox-Gastaut syndrome; cognitive disorders including dementia (associated with Alzheimer's disease, ischemia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline; schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced psychotic disorder; dissociative disorders including multiple personality syndromes and psychogenic amnesias; substance-related disorders, substance use, substance abuse, substance seeking, substance reinstatement, all types of psychological and physical addictions and addictive behaviors, reward-related behaviors (including substance-induced delirium, persisting dementia, persisting amnestic disorder, psychotic disorder or anxiety disorder; tolerance, addictive feeding, addictive feeding behaviors, binge/purge feeding behaviors, dependence, withdrawal or relapse from substances including alcohol, amphetamines, *cannabis*, cocaine, hallucinogens, inhalants, morphine, nicotine, opioids, phencyclidine, sedatives, hypnotics or anxiolytics); appetite, taste, eating or drinking disorders; movement disorders, including akinesias and akinetic-rigid syndromes (including Parkinson's disease, drug-induced parkinsonism, postencephalitic parkinsonism, progressive supranuclear palsy, multiple system atrophy, corticobasal degeneration, parkinsonism-ALS dementia complex and basal ganglia calcification), chronic fatigue syndrome, fatigue, including Parkinson's fatigue, multiple sclerosis fatigue, fatigue caused by a sleep disorder or a circadian rhythm disorder, medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, and dyskinesias [including tremor (such as rest tremor, essential tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics), restless leg syndrome and dystonia (including generalised dystonia such as iodiopathic dystonia, drug-induced dystonia, symptomatic dystonia and paroxymal dystonia, and focal dystonia such as blepharospasm, oromandibular dystonia, spasmodic dysphonia, spasmodic torticollis, axial dystonia, dystonic writer's cramp and hemiplegic dystonia); neurodegenerative disorders including nosological entities such as disinhibition-dementia-parkinsonism-amyotrophy complex; pallido-ponto-nigral degeneration; epilepsy; seizure disorders; attention deficit/hyperactivity disorder (ADHD); conduct disorder; migraine (including migraine headache); headache; hyperalgesia; pain; enhanced or exaggerated sensitivity to pain such as hyperalgesia, causalgia, and allodynia; acute pain; burn pain; atypical facial pain; neuropathic pain; back pain; complex regional pain syndrome I and II; arthritic pain; sports injury pain; pain related to infection e.g. HIV, post-chemotherapy pain; post-stroke pain; post-operative pain; neuralgia; emesis, nausea, vomiting; gastric dyskinesia; gastric ulcers; Kallman's syndrome (anosmia); asthma; cancer; conditions associated with visceral pain such as irritable bowel syndrome, and angina; eating disorders; urinary incontinence; substance tolerance, substance withdrawal (including, substances such as opiates, nicotine, tobacco products, alcohol, benzodiazepines, cocaine, sedatives, hypnotics, etc.); psychosis; schizophrenia; anxiety (including generalized anxiety disorder, panic disorder, and obsessive compulsive disorder); mood disorders (including depression, mania, bipolar disorders); trigeminal neuralgia; hearing loss; tinnitus; neuronal damage including ocular damage; retinopathy; macular degeneration of the eye; emesis; brain edema; pain, including acute and chronic pain states, severe pain, intractable pain, inflammatory pain, neuropathic pain, post-traumatic pain, bone and joint pain (osteoarthritis), repetitive motion pain, dental pain, cancer pain, myofascial pain (muscular injury, fibromyalgia), perioperative pain (general surgery, gynecological), chronic pain, neuropathic pain, post-traumatic pain, trigeminal neuralgia, migraine and migraine headache and other diseases related to general orexin system dysfunction.

The subject compounds could further be of potential use in a method for the prevention, treatment, control, amelioration, or reduction of risk of the diseases, disorders and conditions noted herein. The dosage of active ingredient in the compositions of this invention may be varied, however, it is necessary that the amount of the active ingredient be such that a suitable dosage form is obtained. The active ingredient may be administered to subjects (animals and human) in need of such treatment in dosages that will provide optimal pharmaceutical efficacy. The selected dosage depends upon the desired therapeutic effect, on the route of administration, and on the duration of the treatment. The dose will vary from subject to subject depending upon the nature and severity of disease, the subject's weight, special diets then being followed by a subject, concurrent medication, and other factors which those skilled in the art will recognize.

Generally, dosage levels of between 0.0001 to 100 mg/kg. of body weight daily are administered to the subject, e.g., humans, adolescent humans and elderly humans, to obtain effective agonism of orexin receptors. The dosage range will generally be about 0.5 mg to 10.0 g. per subject per day which may be administered in single or multiple doses. In one embodiment, the dosage range will be about 0.5 mg to 500 mg per subject per day; in another embodiment about 0.5 mg to 200 mg per subject per day; and in yet another embodiment about 5 mg to 50 mg per subject per day. Pharmaceutical compositions of the present invention may be provided in a solid dosage formulation such as comprising about 0.5 mg to 500 mg active ingredient, or comprising about 1 mg to 250 mg active ingredient. The pharmaceutical composition may be provided in a solid dosage formulation comprising about 1 mg, 5 mg, 10 mg, 25 mg, 30 mg, 50 mg, 80 mg, 100 mg, 200 mg or 250 mg active ingredient. For oral administration, the compositions may be provided in the form of tablets containing 1.0 to 1000 milligrams of the active ingredient, such as 1, 5, 10, 15, 20, 25, 50, 75, 100, 150, 200, 250, 300, 400, 500, 600, 750, 800, 900, and 1000 milligrams of the active ingredient for the symptomatic adjustment of the dosage to the subject to be treated. The compounds may be administered on a regimen of 1 to 4 times per day, such as once or twice per day. The compounds may be administered once or multiple times during the day. The compounds may be administered upon awakeing or otherwise in the morning, or during waking hours. For example, the compounds may be administered about 1 hour after awakening, about 30 minutes after awakening or immediately after awakening.

The compounds of the present invention may be used in combination with one or more other drugs in the treatment, prevention, control, amelioration, or reduction of risk of diseases or conditions for which compounds of the present invention or the other drugs may have utility, where the combination of the drugs together are safer or more effective than either drug alone. Such other drug(s) may be administered, by a route and in an amount commonly used therefor, contemporaneously or sequentially with a compound of the present invention. When a compound of the present invention is used contemporaneously with one or more other drugs, a pharmaceutical composition in unit dosage form containing such other drugs and the compound of the present invention is contemplated. However, the combination therapy may also include therapies in which the compound of the present invention and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of the present invention. The above combinations include combinations of a compound of the present invention not only with one other active compound, but also with two or more other active compounds.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, such as about 200:1 to about 1:200. Combinations of a compound of the present invention and other active ingredients will generally also be within the aforementioned range, but in each case, an effective dose of each active ingredient should be used. In such combinations the compound of the present invention and other active agents may be administered separately or in conjunction. In addition, the administration of one element may be prior to, concurrent to, or subsequent to the administration of other agent(s).

The compounds of the present invention may be administered in combination with compounds which are known in the art to be useful for treating or controlling narcolepsy, including e.g., methylphenidate, amphetamine, pemoline, phenelzine, protriptyline, gamma-hydroxybutyric acid, sodium oxybate, or other oxybate salts, modafinil, armodafinil, caffeine, and salts thereof, and combinations thereof, and the like, The compounds of the present invention may be administered in combination with compounds which are known in the art to be useful for preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, orexin antagonists, other orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, ornortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with other compounds which are known in the art, either administered separately or in the same pharmaceutical compositions, including, but are not limited to: insulin sensitizers including (i) PPARy antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like); (iii) biguanides such as metformin and phenformin; (b) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-$NH_2$); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) α-glucosidase inhibitors, such as acarbose, adiposine; camiglibose; emiglitate; miglitol; voglibose; pradimicin-Q; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (ii) bile acid absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and (acyl CoA: cholesterol acyltransferase (ACAT)) inhibitors such as avasimibe, and melinamide, (v) anti-oxidants, such as probucol, (vi) vitamin E, and (vii) thyromimetics; (f) PPARα agonists such as beclofibrate, benzafibrate, ciprofibrate, clofibrate, etofibrate, fenofibrate, and gemfibrozil; and other fibric acid derivatives, such as Atromid®, Lopid® and Tricor®, and the like, and PPARα agonists as described in WO 97/36579; (g) PPARδ agonists, such as those disclosed in WO97/28149; (h) PPAR α/δ agonists, such as muraglitazar, and the compounds disclosed in U.S. Pat. No. 6,414, 002; (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-163,255, and such as those disclosed in U.S. Pat. Nos. 5,536,716, and 6,358,951, U.S. Patent Application Nos. 2002/049196 and 2002/022637, and PCT Application Nos. WO 01/56592 and WO 02/32888; (2) protein tyrosine phosphatase-1B (PTP-1B) inhibitors; (3) cannabinoid receptor ligands, such as cannabinoid CBi receptor antagonists or inverse agonists, such as rimonabant, taranabant, AMT-251, and SR-14778 and SR 141716A (Sanofi Synthelabo), SLV-319 (Solvay), BAY 65-2520 (Bayer) and those disclosed in U.S. Pat. Nos. 5,532,237, 4,973,587, 5,013,837, 5,081,122, 5,112,820, 5,292,736, 5,624,941, 6,028,084, PCT Application Nos. WO 96/33159, WO 98/33765, WO98/43636, WO98/43635, WO 01/09120, WO98/31227, WO98/41519, WO98/37061, WO00/10967, WO00/10968, WO97/29079, WO99/02499, WO 01/58869, WO 01/64632, WO 01/64633, WO 01/64634, WO02/076949, WO 03/007887, WO 04/048317, and WO 05/000809; (4) anti-obesity serotonergic agents, such as fenfluramine, dexfenfluramine, phentermine, and sibutramine; (5) 03-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate, and those disclosed in PCT Application No. WO 01/77094; (7) neuropeptide Y1 antagonists, such as BIBP3226, J-115814, BIBO 3304, LY-357897, CP-671906, GI-264879A, and those disclosed in U.S. Pat. No. 6,001, 836, and PCT Patent Publication Nos. WO 96/14307, WO 01/23387, WO 99/51600, WO 01/85690, WO 01/85098, WO 01/85173, and WO 01/89528; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104, and those disclosed in U.S. Pat. Nos. 6,057,335; 6,043,246; 6,140,354; 6,166,038; 6,180,653; 6,191,160; 6,313,298; 6,335,345; 6,337,332; 6,326,375; 6,329,395; 6,340,683; 6,388,077; 6,462,053; 6,649,624; and 6,723,847, European Patent Nos. EP-01010691, and EP-01044970; and PCT International Patent Publication Nos. WO 97/19682, WO 97/20820, WO 97/20821, WO 97/20822, WO 97/20823, WO 98/24768; WO 98/25907; WO 98/25908; WO 98/27063, WO 98/47505; WO 98/40356; WO 99/15516; WO 99/27965; WO 00/64880, WO 00/68197, WO 00/69849, WO 01/09120, WO 01/14376; WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/22592, WO 0248152, and WO 02/49648; WO 02/094825; WO 03/014083; WO 03/10191; WO 03/092889; WO 04/002986; and WO 04/031175; (9) melanin-concentrating hormone (MCH) receptor antagonists, such as those disclosed in WO 01/21577 and WO 01/21169; (10) melanin-concentrating hormone 1 receptor (MCH1R) antagonists, such as T-226296 (Takeda), and those disclosed in PCT Patent Application Nos. WO 01/82925, WO 01/87834, WO 02/051809, WO 02/06245, WO 02/076929, WO 02/076947, WO 02/04433, WO 02/51809, WO 02/083134, WO 02/094799, WO 03/004027; (11) melanin-concentrating hormone 2 receptor (MCH2R) agonist/antagonists; (12) orexin receptor antagonists, such as SB-334867-A, and those disclosed in patent publications herein; (13) serotonin reuptake inhibitors such as fluoxetine, paroxetine, and sertraline; (14) melanocortin agonists, such as Melanotan II; (15) Mc4r (melanocortin 4 receptor) agonists, such as CHIR86036 (Chiron), ME-10142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-1065, and those disclosed in U.S. Pat. No. 3,914,250, and PCT Application Nos. WO 02/36596, WO 02/48124, WO 02/10169, WO 01/66548, WO 02/44152, WO 02/51844, WO 02/40456, and WO 02/40457; (18) galanin antagonists; (19) CCK agonists; (20) CCK-A (cholecystokinin-A) agonists, such as AR-R 15849, GI 181771, JMV-180, A-71378, A-71623 and SR14613, and those described in U.S. Pat. No. 5,739,106; (21) GLP-1 agonists; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, GT2394 (Gliatech), and O-[3-(1H-imidazol-4-yl)propanol]-carbamates; (25) β-hydroxy steroid dehydrogenase-1 inhibitors (β-HSD-1); (26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists, such as those disclosed in PCT Application Nos. WO 01/87335, and WO 02/08250; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, beta-Ala11,Phe13,Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as GI-181771 (Glaxo-SmithKline), SR146131 (Sanofi Synthelabo), butabindide, PD170,292, and PD 149164 (Pfizer); (34) CNTF derivatives, such as axokine (Regeneron); (35) monoamine reuptake inhibitors, such as sibutramine; (36) UCP-1 (uncoupling protein-1), 2, or 3 activators, such as phytanic acid, 4-[(E)-2-(5,6,7,8-tetrahydro-5,5,8,8-tetramethyl-2-napthalenyl)-1-propenyl] benzoic acid (TTNPB), retinoic acid; (37) thyroid hormone R agonists, such as KB-2611 (KaroBioBMS); (38) FAS (fatty acid synthase) inhibitors, such as Cerulenin and C75; (39) DGAT1 (diacylglycerol acyltransferase 1) inhibitors; (40) DGAT2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del Mar-Grasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, P93/01, TSL 225, TMC-2A/2B/2C, FE 999011, P9310/K364, VIP 0177, SDZ 274-444, sitagliptin; and the compounds disclosed in U.S. Pat. No. 6,699,871, WO 03/004498; WO 03/004496; EP 1 258 476; WO 02/083128; WO 02/062764; WO 03/000250; WO 03/002530; WO 03/002531; WO 03/002553; WO 03/002593; WO 03/000180; and WO 03/000181; (46) dicarboxylate transporter inhibitors; (47) glucose transporter inhibitors; (48) phosphate transporter inhibitors; (49) Metformin (Glucophage®); (50) Topiramate (Topimax®); (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999)); (51) Neuropeptide Y2 (NPY2) receptor agonists such NPY3-36, N acetyl [Leu(28,31)]NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381; (55) Neuropeptide Y1 (NPY1) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 110 HSD-1 (11-beta hydroxy steroid dehydrogenase type 1) inhibitors such as BVT 3498, BVT 2733, and those disclosed in WO 01/90091, WO 01/90090, WO 01/90092, U.S. Pat. No. 6,730,690 and US 2004-0133011; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70)N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) phenmetrazine; (86) picilorex; (87) phytopharm 57; and (88) zonisamide., (89) neuromedin U and analogs or derivatives thereof, (90) oxyntomodulin and analogs or derivatives thereof, and (91) Neurokinin-1 receptor antagonists (NK-1 antagonists) such as the compounds disclosed in: U.S. Pat. Nos. 5,162,339, 5,232,929, 5,242,930, 5,373,003, 5,387,595, 5,459,270, 5,494,926, 5,496,833, and 5,637,699.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-$HT_{1A}$ agonists or antagonists, especially 5-$HT_{1A}$ partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; citalopram, duloxetine, fluoxetine, fluvoxamine, paroxetine and sertraline; isocarboxazid, phenelzine, tranylcypromine and selegiline; moclobemide: venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors, such as verubecestat; gamma-secretase inhibitors; growth hormone secretagogues; recombinant growth hormone; HMG-CoA reductase inhibitors; NSAID's including ibuprofen; vitamin E; anti-amyloid antibodies; CB-1 receptor antagonists or CB-1 receptor inverse agonists; antibiotics such as doxycycline and rifampin; N-methyl-D-aspartate (NMDA) receptor antagonists, such as memantine; cholinesterase inhibitors such as galantamine, rivastigmine, donepezil, and tacrine; growth hormone secretagogues such as ibutamoren, ibutamoren mesylate, and capromorelin; histamine H3 antagonists; AMPA agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chlordiazepoxide, clomipramine, clonazepam, cloperidone, clorazepate, clorethate, clozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine, thiothixene or trifluoperazine.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone.

In another embodiment, the subject compound may be employed in combination with a nicotine agonist or a nicotine receptor partial agonist such as varenicline, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin® and Concerta®), atomoxetine (e.g., Strattera®), a monoamine oxidase inhibitor (MAOI), amphetamines (e.g., Adderall®)) and anti-obesity agents, such as apo-B/MTP inhibitors, 11Beta-hydroxy steroid dehydrogenase-1 (11Beta-HSD type 1) inhibitors, peptide YY3-36 or analogs thereof, MCR-4 agonists, CCK-A agonists, monoamine reuptake inhibitors, sympathomimetic agents, β3 adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists), thyromimetic agents, dehydroepiandrosterone or analogs thereof, glucocorticoid receptor antagonists, orexin receptor antagonists, such as suvorexant, other orexin agonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and pharmaceutically acceptable salts thereof.

In another embodiment, the subject compound may be employed in combination with an agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentermine, phenylpropanolamine, picilorex and sibutramine; selective serotonin reuptake inhibitor (SSRI); halogenated amphetamine derivatives, including chlorphentermine, cloforex, clortermine, dexfenfluramine, fenfluramine, picilorex and sibutramine; and pharmaceutically acceptable salts thereof.

In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-1 inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention may be effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term “composition” is intended to encompass a product comprising the specified ingredients in the specified amounts, as well as any product which results, directly or indirectly, from combination of the specified ingredients in the specified amounts.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil. Aqueous suspensions contain the active materials in admixture with excipients suitable for the manufacture of aqueous suspensions. Oily suspensions may be formulated by suspending the active ingredient in a suitable oil. Oil-in-water emulsions may also be employed. Dispersible powders and granules suitable for preparation of an aqueous suspension by the addition of water provide the active ingredient in admixture with a dispersing or wetting agent, suspending agent and one or more preservatives. Pharmaceutical compositions of the present compounds may be in the form of a sterile injectable aqueous or oleagenous suspension. The compounds of the present invention may also be administered in the form of suppositories for rectal administration. For topical use, creams, ointments, jellies, solutions or suspensions, etc., containing the compounds of the present invention may be employed. The compounds of the present invention may also be formulated for administered by inhalation. The compounds of the present invention may also be administered by a transdermal patch by methods known in the art.

Several methods for preparing the compounds of this invention are illustrated in the following Schemes and Examples. Starting materials are made according to procedures known in the art or as illustrated herein. The following abbreviations are used herein or are otherwise known in the art: Me: methyl; Et: ethyl; t-Bu: tert-butyl; Ar: aryl; Ph: phenyl; BINAP: 2,2'-bis(diphenylphosphino)-1,1'-binaphthyl; Bn: benzyl; Ac: acetyl; AcCl: acetyl chloride; AcOH: acetic acid; ACN: acetonitrile; $B_2Pin_2$: bis(pinacolato)diboron; BPin: pinacolato boron; BAST: bis(2-methoxyethyl) aminosulfur trifluoride; Bn: benzyl; BnOH: benzyl alcohol; Boc: tert-butyloxy carbonyl; $Boc_2O$, Boc anhydride: di-tert-butyl decarbonate; BSA: bovine serum albumin; CbzCl: benzylchloroformate; CDI: carbonyl diimidazole; DAST: (diethylamino)sulfur trifluoride; DCM ($CH_2Cl_2$): dichloromethane; DCE: dichloroethane; DDQ: 2,3-dichloro-5,6-dicyano-1,4-benzoquinone; DEAD: diethylazodicarboxylate; DIBAL-H: diisobutylaluminium hydride; DIPEA: N,N-diisopropylethylamine; DMA, DMAc: dimethylacetamide; DMAP: 4-dimethylaminopyridine; DMF: N,N-dimethylformamide; DMP: Dess Martin periodinane; DMSO: dimethylsulfoxide; DPPA: diphenylphosphoryl azide; dppf: 1,1'-Fferrocenediyl-bis(diphenylphosphine); DMSO: dimethylsulfoxide; Grubbs II: benzylidene-[1,3-bis(2,4,6-trimethylphenyl)imidazolidin-2-ylidene]-dichlororuthenium,tricyclohexylphosphane; EDC: N-(3-Dimethylaminopropyl)-N'-ethylcarbodiimide; $Et_3N$: triethylamine; EtOAc: ethyl acetate; EtOH: ethanol; HCl: hydrogen chloride; Hoveyda-Grubbs II: [1,3-bis(2,4,6-trimethylphenyl)imidazolidin-2-ylidene]-dichloro-[(2-propan-2-yloxyphenyl)methylidene] ruthenium; HOAt: 1-hydroxy-7-aza-benzotriazole; HOBT: hydroxybenzotriazole hydrate; HPLC: high performance liquid chromatography; Hunig's base, DIEA: N,N-diisopropylethylamine; Grubbs II catalyst: (1,3-bis(2,4,6-trimethylphenyl)-2imidazolidinylidene)dichloro-(phenylmethylene)(tricyclohexylpho sphine)ruthenium; HATU: 1-[bis (dimethylamino)-methylene]-1H-1,2,3-triazolo[4,5-b]

pyridinium 3-oxid hexafluorophosphate, N-[(dimethylamino)-1H-1,2,3-triazolo-[4,5-b]pyridin-1-yl-methylene]-N-methylmethanaminium hexafluorophosphate N-oxide; Hoveyda Grubbs II catalyst: (1,3-bis-(2,4,6-trimethylphenyl)-2-imidazolidinylidene)dichloro(o-isopropoxyphenylmethylene) ruthenium, Dichloro[1,3-bis(2,4,6-trimethylphenyl)-2-imidazolidinylidene](2-isopropoxyphenylmethylene)ruthenium(II); IBX: 2-iodoxybenzoic acid; IPA, iPrOH: isopropyl alcohol; LC-MS: liquid chromatography mass spectroscopy; LDA: lithium diisoproylamide; LiHMDS: lithium hexamethyldisilazide; mCPBA: meta-chloro perbenzoic acid; MeOH: methanol; $MgSO_4$: magnesium sulfate; Ms: methanesulfonyl; MTBE: methyl tert-butyl ether; $NaHCO_3$: sodium bicarbonate; NaOH: sodium hydroxide; $nBu_3SnCl$: tributyltin chloride; n-BuLi: n-butyl lithium; NMM: N-methylmorpholine; NMR: nuclear magnetic resonance; Oxone: potassium peroxymonosulfate; $PCy_3Pd$ G2: chloro[(tricyclohexylphosphine)-2-(2'-aminobiphenyl)]-palladium(II); $Pd(dppf)Cl_2$: [1,1'-bis(diphenylphosphino)ferrocene]-dichloropalladium (II); $Pd(PPh_3)_2Cl_2$: bis(triphenylphosphine)-palladium(II) dichloride; $Pd(PPh_3)_4$: tetrakis(triphenyl-phosphine)palladium(O); $Pd_2dba_3$: tris(dibenzylideneacetone) dipalladium (O); PPTS: pyridinium p-toluenesulfonate; $PtO_2$: platinum oxide; PyClu: 1-(chloro-1-pyrrolidinylmethylene)-pyrrolidinium hexafluorophosphate; rt: room temperature; $SOCl_2$: thionyl chloride; T3P: 2,4,6-tripropyl-1,3,5,2,4,6-trioxatriphosphorinane-2,4,6-trioxide; TBAF: tetrabutyl ammonium fluoride; TBDPSCl: tert-butyl(chloro)diphenyl-silane; TBSCl: tert-butyldimethylsilyl chloride; t-Bu: tert-butyl; TEA, $Et_3N$: triethylamine; TEMPO: 2,2,6,6-tetramethyl-1-piperidinyloxy; THF: tetrahydrofuran; TFA: trifluoracetic acid; TLC: thin layer chromatography; TMSCl: trimethylsilyl chloride; TsCl: p-toluenesulfonyl chloride; XPhos Pd G2: chloro(2-dicyclohexylphosphino-2',4',6'-triisopropyl-1,1'-biphenyl)[2-(2'-amino-1,1'-biphenyl)]-palladium(II); XPhos Pd G3: (2-dicyclohexylphosphino-2',4',6'-triisopropyl-1,1'-biphenyl)[2-(2'-amino-1,1'-biphenyl)]palladium(II) methanesulfonate; X-Phos: 2-(dicyclohexyl-phosphino)-2',4',6'-triisopropylbiphenyl.

The compounds of the present invention can be prepared in a variety of fashions. In some cases the final product may be further modified, for example, by manipulation of substituents. These manipulations may include, but are not limited to, reduction, oxidation, alkylation, acylation, and hydrolysis reactions which are commonly known to those skilled in the art. In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

Starting materials are made according to procedures known in the art or as illustrated herein.

Intermediate A5

(S)-7,7,7-Trifluorohept-1-En-4-Amine (A5)

SCHEME A1

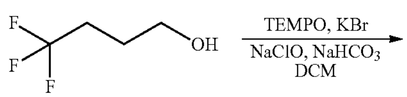

A1

-continued

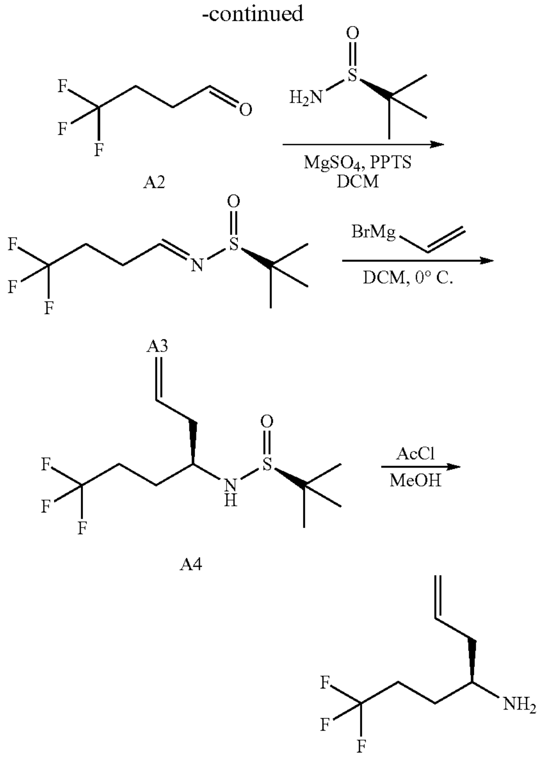

A2

A3

A4

A5

Step 1: 4,4,4-trifluorobutanal (A2)

A solution of 4,4,4-trifluorobutan-1-ol (A1, 10 g, 78 mmol) in DCM (77 mL) was cooled to 0° C. TEMPO (0.183 g, 1.171 mmol) and KBr (1.394 g, 11.71 mmol) (1.394 g in 30 mL of water) were added to the solution and the temperature was maintained at 0° C. Sodium hypochlorite (10%, 100 mL, 78 mmol) was dropwise added to the reaction mixture at 0° C. and the reaction was buffered to pH=8.5 using sat. aq. $NaHCO_3$. The reaction mixture was stirred at 0° C. for 3 h, then stirred at 10° C. for 10 h. The organic phase was separated, and the aqueous layer was extracted with DCE (200 mL). The combined organic layers were dried ($Na_2SO_4$) and filtered to give a solution of 4,4,4-trifluorobutanal (A2) in DCM (77 mL) and DCE (200 mL), which was carried forward without purification. $^1$H NMR (400 MHz, $CDCl_3$) δ 9.73 (s, 1H), 2.72 (t, J=7.6 Hz, 2H), 2.49-2.33 (m, 2H).

Step 2: (S, E)-2-methyl-N-(4,4,4-trifluorobutylidene)propane-2-sulfinamide (A3)

To a solution of 4,4,4-trifluorobutanal (A2, 9.8 g, 78 mmol) in DCM (77 mL) and DCE (200 mL) were added (S)-2-methylpropane-2-sulfinamide (12.25 g, 101 mmol), PPTS (1.563 g, 6.22 mmol) and $MgSO_4$ (24.33 g, 202 mmol). The reaction mixture was stirred at 80° C. for 14 h. LC-MS showed formation of the desired product mass. The reaction mixture was filtered. The filtrate was concentrated and purified by flash silica chromatography (7.7% EtOAc in petroleum ether) to give (S, E)-2-methyl-N-(4,4,4-trifluorobutylidene)propane-2-sulfinamide (A3). $^1$H NMR (400 MHz, $CDCl_3$) δ 8.10 (br d, J=2.9 Hz, 1H), 2.85-2.71 (m, 2H), 2.58-2.38 (m, 2H), 1.18 (s, 9H).

Step 3: (S)-2-methyl-N—((S)-7,7,7-trifluorohept-1-en-4-yl)propane-2-sulfinamide (A4)

To a solution of (S,E)-2-methyl-N-(4,4,4-trifluorobutylidene)propane-2-sulfinamide (A3, 5 g, 21.81 mmol) in DCM (100 mL) was added allylmagnesium bromide (109 mL, 109 mmol) (1.0 M in $Et_2O$) at 0° C. The reaction was stirred at 0° C. for 3 h. LCMS showed complete conversion. The reaction was poured into sat. aq. $NH_4Cl$ (150 mL) and extracted with DCM (3×100 mL). The combined organic layers were washed with brine (100 mL), dried ($Na_2SO_4$), filtered and concentrated. The crude material was purified by flash silica chromatography (0-19% EtOAc in petroleum ether gradient) to give (S)-2-methyl-N—((S)-7,7,7-trifluorohept-1-en-4-yl)propane-2-sulfinamide (A4). $^1$H NMR (400 MHz, $CDCl_3$) δ 5.75 (tdd, J=7.2, 10.2, 17.0 Hz, 1H), 5.23-5.10 (m, 2H), 3.36 (qd, J=6.3, 12.5 Hz, 1H), 3.21 (br d, J=6.4 Hz, 1H), 2.42-2.33 (m, 2H), 2.27-2.03 (m, 2H), 1.90-1.75 (m, 1H), 1.73-1.57 (m, 1H), 1.21-1.15 (m, 9H).

Step 4: (S)-7,7,7-trifluorohept-1-en-4-amine (A5)

To a solution of (S)-2-methyl-N—((S)-7,7,7-trifluorohept-1-en-4-yl)propane-2-sulfinamide (A4, 5 g, 18.43 mmol) in MeOH (100 mL) was added acetyl chloride (2.89 g, 36.9 mmol) and the reaction was stirred at 20° C. for 2 h. LCMS showed complete conversion. The reaction was concentrated to give the crude product. To the crude product was added water (100 mL) and the aqueous layer was extracted with EtOAc (3x30 mL) to remove impurities. The water layer was freeze-dried to afford (S)-7,7,7-trifluorohept-1-en-4-amine (A5) as an HCl salt. $^1$H NMR (400 MHz, $CD_3OD$) δ 5.82 (tdd, J=7.3, 10.0, 17.2 Hz, 1H), 5.35-5.23 (m, 2H), 3.37 (quin, J=6.5 Hz, 1H), 2.57-2.28 (m, 4H), 1.99-1.82 (m, 2H).

Intermediate A8

SCHEME A2

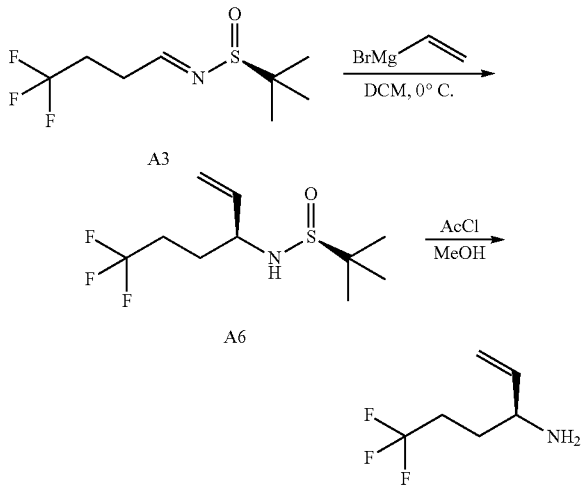

A3

A6

A8

Step 1: (S)-2-methyl-N—((S)-6,6,6-trifluorohex-1-en-3-yl)propane-2-sulfinamide (A6)

To a solution of (S,E)-2-methyl-N-(4,4,4-trifluorobutylidene)propane-2-sulfinamide (A3, 4 g, 17.45 mmol) in DCM (80 mL) was added vinylmagnesium bromide (34.9 mL, 34.9 mmol) at 0° C. The reaction was stirred at 0-15° C. for 5 h. TLC showed complete conversion. The reaction was poured into sat. aq. $NH_4Cl$ (100 mL) and extracted with DCM (3×100 mL). The combined organic layers were dried ($Na_2SO_4$), filtered and concentrated. The crude material was purified and separated from its diastereomer by flash silica chromatography (25% ethyl acetate in petroleum ether) to give (S)-2-methyl-N—((S)-6,6,6-trifluorohex-1-en-3-yl)propane-2-sulfinamide (A6, more polar diastereomer on TLC). A6: $^1$H NMR (400 MHz, $CDCl_3$) δ 5.85-5.73 (m, 1H), 5.33-5.17 (m, 2H), 3.80 (quin, J=6.4 Hz, 1H), 3.20-3.10 (m, 1H), 2.20-2.03 (m, 2H), 1.92-1.76 (m, 2H), 1.22-1.09 (m, 9H).

Step 2: (S)-6,6,6-trifluorohex-1-en-3-amine (A8)

(S)-6,6,6-trifluorohex-1-en-3-amine (A8) HCl salt was prepared in an analogous manner of that described in Step 4 of Scheme A1 for Intermediate A5 from the appropriate sulfinamide. A8: $^1$H NMR (400 MHz, $CD_3OD$) δ 5.88-5.77 (m, 1H), 5.55-5.46 (m, 2H), 3.86-3.76 (m, 1H), 2.35-2.18 (m, 2H), 2.10-1.99 (m, 1H), 1.95-1.81 (m, 1H).

Intermediates A14-A17

Intermediates A14-A17 were prepared in an analogous manner of that described in Scheme A1 for Intermediate A5 from the appropriate sulfinamides (A10-A13) described below.

A10

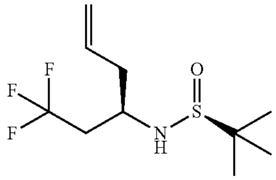

(S)-2-methyl-N—((R)-1,1,1-trifluorohex-5-en-3-yl)propane-2-sulfinamide (A10)

(S)-2-methyl-N—((R)-1,1,1-trifluorohex-5-en-3-yl)propane-2-sulfinamide (A10) was obtained in an analogous manner of that described in Scheme A1 for (S)-2-methyl-N—((S)-7,7,7-trifluorohept-1-en-4-yl)propane-2-sulfinamide (A4) starting with 3,3,3-trifluoropropanal instead of 4,4,4-trifluorobutanal (A2). LC-MS: 258.4 (M+1). $^1$H NMR: (500 MHz, $CDCl_3$ δ 5.71 (ddt, J=17.4, 10.3, 7.2 Hz, 1H), 5.30-4.97 (m, 2H), 3.63 (p, J=6.6 Hz, 1H), 3.42 (d, J=7.4 Hz, 1H), 2.45 (t, J=6.6 Hz, 2H), 2.25 (tdd, J=10.7, 6.0, 4.7 Hz, 2H).

A11

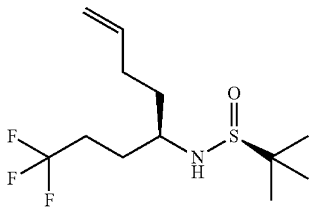

(S)-2-methyl-N—((R)-1,1,1-trifluorooct-7-en-4-yl) propane-2-sulfinamide (1A11)

(S)-2-methyl-N—((R)-1,1,1-trifluorooct-7-en-4-yl)propane-2-sulfinamide (All) was obtained in an analogous manner of that described in Scheme A1 for (S)-2-methyl-N—((S)-7,7,7-trifluorohept-1-en-4-yl)propane-2-sulfinamide (A4) using but-3-en-1-ylmagnesium bromide instead of allylmagnesium bromide. LC-MS: 286.3 (M+1). $^1$H NMR: (500 MHz, $CDCl_3$) δ 5.69 (ddt, J=16.9, 10.2, 6.6 Hz, 1H), 5.02-4.92 (m, 1H), 4.89 (d, J=10.2 Hz, 1H), 3.19 (d, J=8.9 Hz, 2H), 2.16-1.96 (m, 4H), 1.84-1.69 (m, 1H), 1.65 (dt, J=13.8, 7.0 Hz, 1H), 1.61-1.48 (m, 2H), 1.11 (s, 9H).

A12

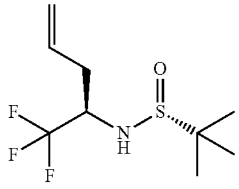

(R)-2-methyl-N—((R)-1,1,1-trifluoropent-4-en-2-yl) propane-2-sulfinamide (A12)

(R)-2-methyl-N—((R)-1,1,1-trifluoropent-4-en-2-yl)propane-2-sulfinamide (A12) was obtained in an analogous manner of that described in Scheme A1 for (S)-2-methyl-N—((S)-7,7,7-trifluorohept-1-en-4-yl)propane-2-sulfinamide (A4) using (R,E)-2-methyl-N-(2,2,2-trifluoroethylidene)propane-2-sulfinamide instead of (S,E)-2-methyl-N-(4,4,4-trifluorobutylidene)propane-2-sulfinamide (A3). LC-MS: 244.2 (M+1).

A13

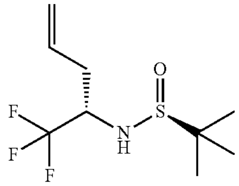

(S)-2-methyl-N—((R)-1,1,1-trifluoropent-4-en-2-yl) propane-2-sulfinamide (A13)

(S)-2-methyl-N—((R)-1,1,1-trifluoropent-4-en-2-yl)propane-2-sulfinamide (A13) was obtained in an analogous manner of that described in Scheme A1 for (S)-2-methyl-N—((S)-7,7,7-trifluorohept-1-en-4-yl)propane-2-sulfinamide (A4) using (S,E)-2-methyl-N-(2,2,2-trifluoroethylidene)propane-2-sulfinamide instead of (S,E)-2-methyl-N-(4,4,4-trifluorobutylidene)propane-2-sulfinamide (A3). LC-MS: 244.2 (M+1).

SCHEME A3

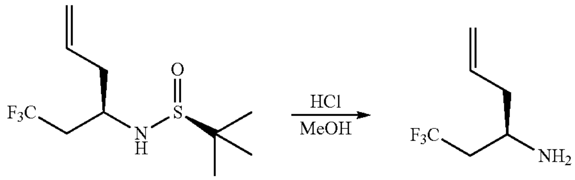

A10

A14

Step 1: (R)-1,1,1-trifluorohex-5-en-3-amine (A14)

(S)-2-methyl-N—((R)-1,1,1-trifluorohex-5-en-3-yl)propane-2-sulfinamide (A10, 272 mg, 1.057 mmol) was dissolved in MeOH (5.3 mL) and HCl (264 μL, 1.057 mmol) (4M in dioxane) was added. The reaction was allowed to stir at ambient temperature for 45 min. LCMS analysis showed complete conversion. The reaction was concentrated, dissolved in dichloromethane and concentrated twice to afford (R)-1,1,1-trifluorohex-5-en-3-amine (A14) as an HCl salt, which was carried forward without purification. LC-MS: 154.1 (M+1).

The following Intermediates from Table A1 were obtained as HCl salts by deprotection of the corresponding sulfinamides in an analogous manner of that described in Scheme A3 for Intermediate A14.

TABLE A1

| Sulfinamide | Intermediate | Observed LC-MS (M + 1) |
|---|---|---|
| 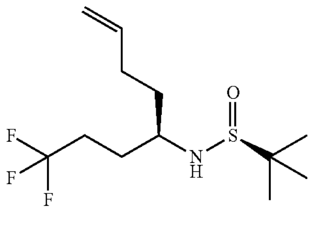 A11 | 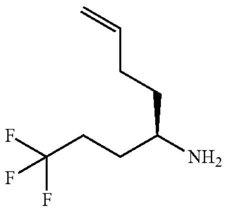 A15 | 182.1 |

TABLE A1-continued
| Sulfinamide | Intermediate | Observed LC-MS (M + 1) |
|---|---|---|
| 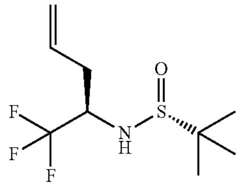 A12 | 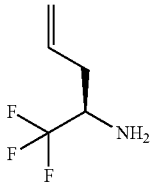 A16 | 140.1 |
| 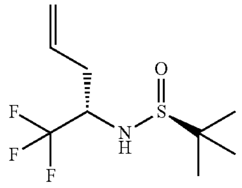 A13 | 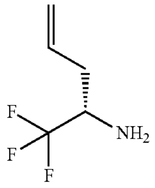 A17 | 140.1 |
| 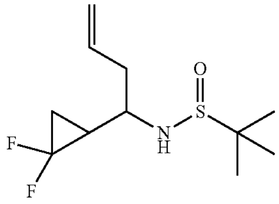 A147 | 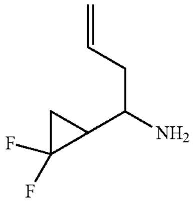 A148 | 148.1 |
| 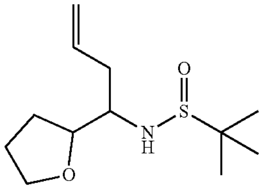 A149 | 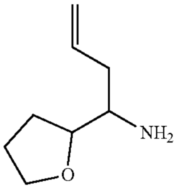 A150 | 142.1 |
| 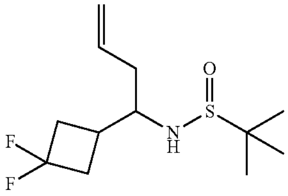 A151 | 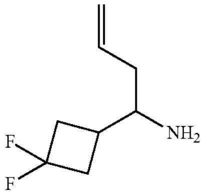 A152 | 162.1 |

Intermediate A21

(S)-7,7-difluorooct-1-en-4-amine (A21)

SCHEME A4

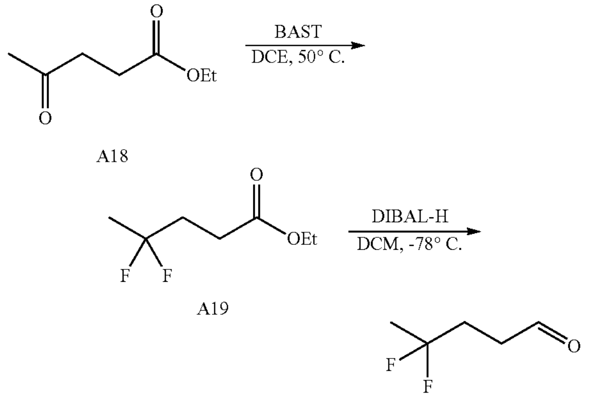

A18

A19

A20

Step 1: ethyl 4-oxopentanoate (A19)

To a solution of ethyl 4-oxopentanoate (A18, 10 g, 69.4 mmol) in DCM (75 mL) was added BAST (38.4 mL, 208 mmol) and the reaction was heated at 50° C. for 48 h. TLC showed consumption of the starting material and formation of new spot. The reaction was poured into water (100 mL), and extracted with EtOAc (3×100 mL). The combined organic layers were washed with brine (150 mL), dried ($Na_2SO_4$), filtered and concentrated. The crude material was purified by flash silica chromatography (0-20% EtOAc in petroleum ether gradient) to give afford ethyl 4,4-difluoropentanoate (A19). $^1$H NMR: (400 MHz, $CDCl_3$) δ 4.23-4.07 (m, 2H), 2.59-2.48 (m, 2H), 2.28-2.15 (m, 2H), 1.69-1.56 (m, 3H), 1.33-1.17 (m, 3H).

Step 2: 4,4-difluoropentanal (1.20)

To a solution of ethyl 4,4-difluoropentanoate (A19, 3.6 g, 21.67 mmol) in DCM (36 mL) was added DIBAL-H (26.0 mL, 26.0 mmol) (1M in toluene) at −78° C., and the resulting mixture was stirred at −78° C. under nitrogen for 30 min. TLC showed consumption of starting material and formation of a new spot. The reaction was poured into water (30 mL), extracted with DCE (3×10 mL). The combined organic layers were washed with brine (20 mL), dried ($Na_2SO_4$), and filtered to give a solution of 4,4-difluoropentanal (A20), which was carried forward to the next step without purification.

Steps 3 and 4: (S)-7,7-difluorooct-1-en-4-amine (A21)

Intermediate A21 was obtained as an HCl salt in an analogous manner of that described in Scheme A1 for (S)-7,7,7-trifluorohept-1-en-4-amine (A5) starting with 4,4-difluoropentanal (A20) instead of 4,4,4-trifluorobutanal (A2).

$^1$H NMR: (400 MHz, $CDCl_3$) δ 5.90-5.74 (m, 1H), 5.33-5.18 (m, 2H), 3.33 (br d, J=4.7 Hz, 1H), 2.60-2.45 (m, 2H), 2.18-1.89 (m, 4H), 1.61 (t, J=18.4 Hz, 3H).

Intermediate A24

7,7,7-trifluoro-3-methylhept-1-en-4-amine (A24)

SCHEME A5

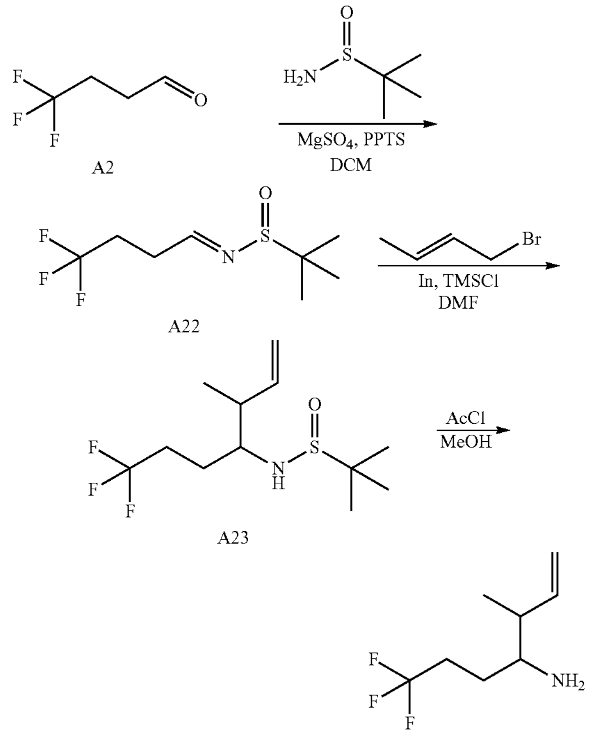

A2

A22

A23

A24

Step 1: (E)-2-methyl-N-(4,4,4-trifluorobutlidene) propane-2-sulfinamide (A22)

To a solution of 4,4,4-trifluorobutanal (A2, 4.92 g, 39.0 mmol) in DCM (65 mL) were added DCE (60 mL), 2-methylpropane-2-sulfinamide (5.68 g, 46.8 mmol), PPTS (0.785 g, 3.12 mmol) and $MgSO_4$ (11.74 g, 98 mmol). The reaction mixture was stirred at 80° C. for 12 h. LCMS showed formation of the desired product mass. The reaction was filtered, concentrated and purified by flash silica chromatography (25% EtOAc in petroleum ether) to give (E)-2-methyl-N-(4,4,4-trifluorobutylidene)propane-2-sulfinamide (A22). LC-MS: 230.0 (M+1). $^1$H NMR: (400 MHz, $CDCl_3$ δ 8.10 (br s, 1H), 2.77 (td, J=3.8, 7.6 Hz, 2H), 2.58-2.30 (m, 2H), 1.33-1.16 (m, 9H).

Step 2: 2-methyl-N-(7,7,7-trifluoro-3-methylhept-1-en-4-yl)propane-2-sulfinamide (A23)

To a solution of (E)-2-methyl-N-(4,4,4-trifluorobutylidene)propane-2-sulfinamide (A22, 2 g, 8.72 mmol) in DMF (20 mL) was added (E)-1-bromobut-2-ene (1.531 g, 11.34 mmol). The solution was cooled at 0° C., then indium (1.302 g, 11.34 mmol) and TMS-Cl (0.112 mL, 0.872 mmol) were added to the above solution. The reaction was warmed slowly at 20° C. for 5 h. LCMS formation of the desired product mass. The reaction was quenched with sat. aq. $NH_4Cl$ (100 mL) and extracted with EtOAc (3×50 mL). The combined organic layers were washed with brine (50 mL), dried ($Na_2SO_4$), filtered and concentrated. The crude material was purified by flash silica chromatography (10% EtOAc in petroleum ether) to give 2-methyl-N-(7,7,7-trifluoro-3-methylhept-1-en-4-yl)propane-2-sulfinamide (A23). LC-MS: 286.1 (M+1). $^1$H NMR: (400 MHz, $CDCl_3$) δ 5.78-5.60 (m, 1H), 5.30-5.04 (m, 2H), 3.44-3.34 (m, 1H), 3.23-3.11 (m, 1H), 2.69 (qd, J=6.9, 13.4 Hz, 1H), 2.28-2.21 (m, 1H), 2.19-1.99 (m, 1H), 1.94-1.80 (m, 1H), 1.74-1.59 (m, 1H), 1.55-1.37 (m, 1H), 1.30-1.19 (m, 9H), 1.12-1.04 (m, 3H).

Step 3: 7,7,7-trifluoro-3-methylhept-1-en-4-amine (A24)

To a solution of 2-methyl-N-(7,7,7-trifluoro-3-methylhept-1-en-4-yl)propane-2-sulfinamide (A23, 1.3 g, 4.56 mmol) in MeOH (10 mL) was added acetyl chloride (0.972 mL, 13.67 mmol) and the reaction was stirred at 25° C. for 2 h. LCMS showed formation of the desired product mass. The reaction was concentrated to give 7,7,7-trifluoro-3-methylhept-1-en-4-amine (A24) as an HCl salt, which was used in next step without purification. LC-MS: 182.2 (M+1).

Intermediate A31

2-methyl-N-(1,1,1-trifluoro-8-hydroxy-6-methyloctan-4-yl)propane-2-sulfinamide (A31)

SCHEME A6

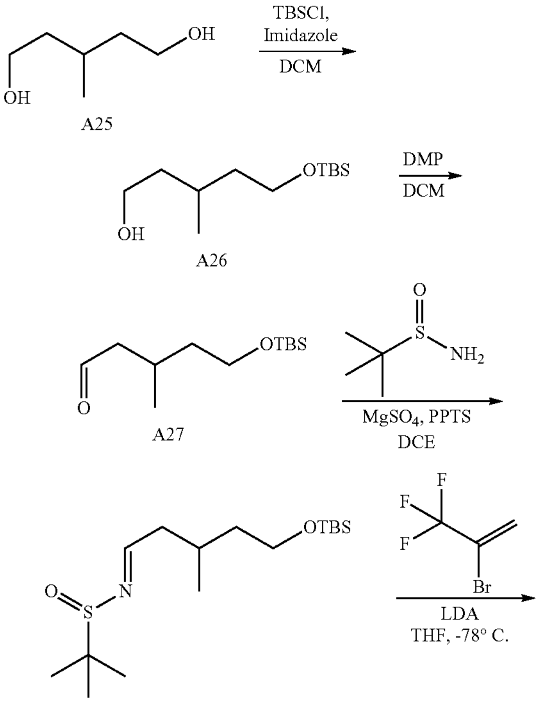

A25

A26

A27

A28

-continued

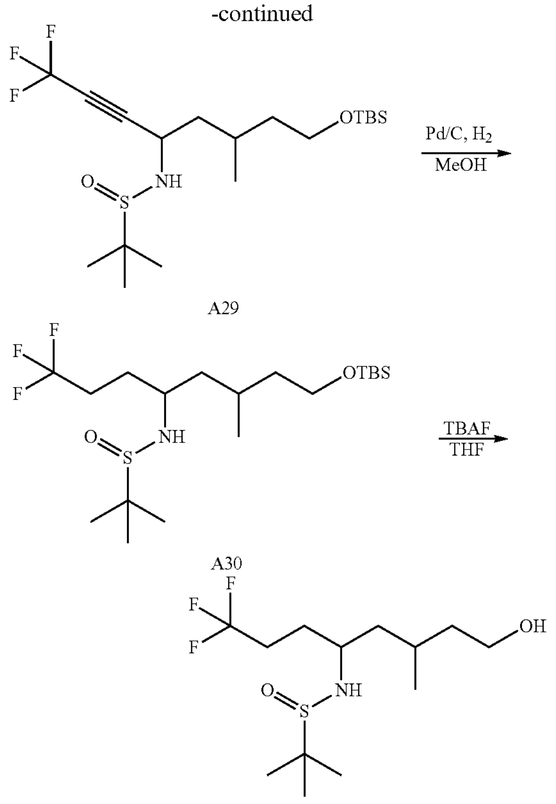

A29

A30

A31

Step 1: 5-((tert-butyldimethylsilvl)oxy)-3-methylpentan-1-ol (A26)

To a solution of 3-methylpentane-1,5-diol (A25, 10 g, 85 mmol) and imidazole (11.52 g, 169 mmol) in anhydrous DCM (100 mL) was added TBSCl (10.20 g, 67.7 mmol) at 0° C. The reaction was warmed from 0° C. to 20° C. over 15 h. TLC showed the formation of new spots. The reaction was poured into water (100 mL) and extracted with EtOAc (3×50 mL). The combined organic layers were washed with brine (50 mL), dried ($Na_2SO_4$), filtered and concentrated. The crude material was purified by flash silica chromatography (15% EtOAc in petroleum ether gradient) to give 5-((tert-butyldimethylsilyl)oxy)-3-methylpentan-1-ol (A26).

Step 2: 5-((tert-butyldimethylsilvl)oxy)-3-methylpentanal (A27)

To a solution of 5-((tert-butyldimethylsilyl)oxy)-3-methylpentan-1-ol (A26, 4 g, 17.21 mmol) in anhydrous DCM (40 mL) was added DMP (8.76 g, 20.65 mmol) at 0° C., and the reaction was stirred at 10° C. for 5 h. TLC showed the formation of new spots. The reaction was filtered and concentrated. The crude material was purified by flash silica chromatography (11% EtOAc in petroleum ether) to give 5-((tert-butyldimethylsilyl)oxy)-3-methylpentanal (A27).

Step 3: (E)-N-(5-((tert-butyldimethylsilvl)oxy)-3-methylpentylidene)-2-methylpropane-2-sulfinamide (A28)

To a solution of 5-((tert-butyldimethylsilyl)oxy)-3-methylpentanal (A27, 3 g, 13.02 mmol) in DCE (30 mL) was added 2-methylpropane-2-sulfinamide (1.894 g, 15.62 mmol), pyridine 4-methylbenzenesulfonate (0.327 g, 1.302 mmol) and magnesium sulfate (3.92 g, 32.5 mmol). The reaction was stirred at 10° C. for 14 h. LCMS showed formation of the desired product mass. The reaction was filtered. The crude material was purified by flash silica chromatography (12% EtOAc in petroleum ether) to give (E)-N-(5-((tert-butyldimethylsilyl)oxy)-3-methylpentylidene)-2-methylpropane-2-sulfinamide (A28). LC-MS: 334.3 (M+1).

Step 4: N-(8-((tert-butyldimethylsilvl)oxy)-1,1,1-trifluoro-6-methyloct-2-yn-4-yl)-2-methylpropane-2-sulfinamide (A29)

A solution of butyllithium (7.19 mL, 17.99 mmol) (2.5 M in hexane) was added to diisopropylamine (1.820 g, 17.99 mmol) in THF (20 mL) at −78° C. The reaction was stirred at −78° C. for 30 min. 2-bromo-3,3,3-trifluoroprop-1-ene (1.573 g, 8.99 mmol) was added slowly at −78° C. The reaction was stirred at −78° C. for 30 min. (E)-N-(5-((tert-butyldimethylsilyl)oxy)-3-methylpentylidene)-2-methylpropane-2-sulfinamide (A28, 2 g, 6.00 mmol) was added to the solution and the reaction was warmed from −78° C. to 0° C. over 3 h. LCMS showed formation of the desired product mass. The reaction mixture was poured into water (100 mL) and extracted with EtOAc (3x30 mL). The combined organic layers were dried ($Na_2SO_4$), filtered and concentrated. The crude material was purified by flash silica chromatography (15% EtOAc in petroleum ether) to give N-(8-((tert-butyldimethylsilyl)oxy)-1,1,1-trifluoro-6-methyloct-2-yn-4-yl)-2-methylpropane-2-sulfinamide (A29). LC-MS: 428.2 (M+1).

Step 5: N-(8-((tert-butyldimethylsilvl)oxy)-1,1,1-trifluoro-6-methyloctan-4-yl)-2-methylpropane-2-sulfinamide (A30)

To a solution of N-(8-((tert-butyldimethylsilyl)oxy)-1,1,1-trifluoro-6-methyloct-2-yn-4-yl)-2-methylpropane-2-sulfinamide (A29, 1.4 g, 3.27 mmol) in MeOH (20 mL) was added Pd-C(300 mg, 0.282 mmol) (10% on C) and the reaction was stirred at 30° C. under H2 (40 psi) for 3 h. LCMS showed complete conversion. The reaction mixture was filtered and concentrated to give N-(8-((tert-butyldimethylsilyl)oxy)-1,1,1-trifluoro-6-methyloctan-4-yl)-2-methylpropane-2-sulfinamide (A30). LC-MS: 432.3 (M+1).

Step 6: 2-methyl-N-(1,1,1-trifluoro-8-hydroxy-6-methyloctan-4-yl)propane-2-sulfinamide (A31)

To a solution of N-(8-((tert-butyldimethylsilyl)oxy)-1,1,1-trifluoro-6-methyloctan-4-yl)-2-methylpropane-2-sulfinamide (A30, 900 mg, 2.085 mmol) in THF (10 mL) was added TBAF (4.17 mL, 4.17 mmol) (1 M in THF) at 10° C. and the reaction was stirred at 10° C. for 2 h. LCMS showed formation of the desired product mass. The reaction was poured into sat. aq. $NH_4Cl$ (100 mL) and extracted with EtOAc (3x30 mL). The combined organic layers were dried ($Na_2SO_4$), filtered and concentrated. The crude material was purified by flash silica chromatography (100% EtOAc) to give 2-methyl-N-(1,1,1-trifluoro-8-hydroxy-6-methyloctan-4-yl)propane-2-sulfinamide (A31). LC-MS: 318.2 (M+1).

Intermediate A39

1-(2-((tert-butyldimethylsilvl)oxy)ethoxy)-6,6,6-trifluorohexan-3-amine (A39)

SCHEME A7

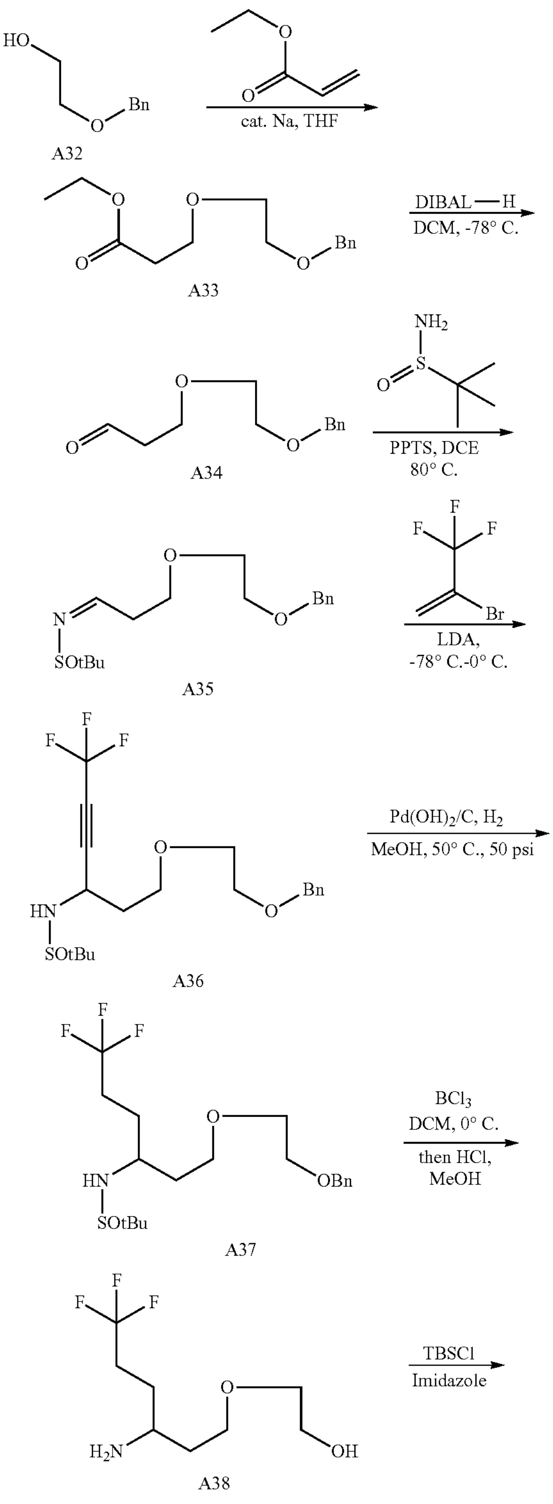

-continued

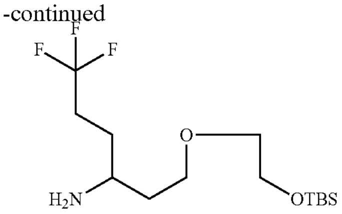

A39

Step 1: ethyl 3-(2-(benzyloxy)ethoxy)propanoate (A33)

To a solution of 2-(benzyloxy)ethan-1-ol (A32, 10 g, 65.7 mmol) and ethyl acrylate (5.92 g, 59.1 mmol) in THF (200 mL) was added sodium (0.151 g, 6.57 mmol) at 20° C. and the reaction was allowed to stir at 20° C. for 16 h. TLC showed consumption of the starting material and formation of new spots. The reaction was quenched with water (100 mL), extracted with EtOAc (3×100 mL). The combined organic layers were dried ($Na_2SO_4$), filtered and concentrated. The crude material was purified by flash silica chromatography (40% EtOAc in petroleum ether) to give ethyl 3-(2-(benzyloxy)ethoxy)propanoate (A33). $^1H$ NMR: (500 MHz, $CDCl_3$) δ 7.29-7.14 (m, 5H), 4.55-4.40 (m, 2H), 4.10-3.93 (m, 2H), 3.69 (t, J=6.5 Hz, 2H), 3.59-3.48 (m, 4H), 2.52 (t, J=6.5 Hz, 2H), 1.17 (t, J=7.1 Hz, 3H).

Step 2: 3-(2-(benzyloxy)ethoxy)propanal (A34)

To a solution of 3-(2-(benzyloxy)ethoxy)propanoate (A33, 4.3 g, 17.04 mmol) in DCM (60 mL) cooled to −78° C., was added DIBAL-H (20.45 mL, 20.45 mmol) (1.0 M in toluene) slowly. The reaction was allowed to stir at −78° C. for 1 h. TLC showed consumption of the starting material. The solution was quenched with sat. aq. $NH_4Cl$ (50 mL) and extracted with EtOAc (3×50 mL). The combined organic layers were washed with brine (50 mL), dried ($Na_2SO_4$), filtered and concentrated. The crude material was purified by flash silica chromatography (40% EtOAc in petroleum ether) to give 3-(2-(benzyloxy)ethoxy)propanal (A34).

Step 3: (Z)-N-(3-(2-(benzyloxy)ethoxy)propylidene)-2-methylpropane-2-sulfinamide (A35)

To a solution of 3-(2-(benzyloxy)ethoxy)propanal (A34, 2.4 g, 11.52 mmol) in DCE (40 mL) were added 2-methylpropane-2-sulfinamide (1.816 g, 14.98 mmol), PPTS (0.290 g, 1.152 mmol) and $MgSO_4$ (4.16 g, 34.6 mmol). The reaction mixture was stirred at 80° C. for 8 h. TLC showed consumption of the starting material and formation of a new spot. The reaction was poured into water (30 mL) and extracted with DCM (3×30 mL). The combined organic layers were dried ($Na_2SO_4$), filtered and concentrated. The crude material was purified by flash silica chromatography (50% EtOAc in petroleum ether) to give (Z)-N-(3-(2-(benzyloxy)ethoxy)propylidene)-2-methylpropane-2-sulfinamide (A35).

Step 4: N-(1-(2-(benzyloxy)ethoxy)-6,6,6-trifluorohex-4-yn-3-yl)-2-methylpropane-2-sulfinamide (A36)

To a solution of diisopropylamine (3.64 mL, 25.9 mmol) in THF (40 mL) was added butyllithium (10.02 mL, 25.04 mmol) at −78° C. The mixture was stirred at −78° C. for 30 min. 2-bromo-3,3,3-trifluoroprop-1-ene (2.191 g, 12.52 mmol) was added slowly at −78° C. The mixture was stirred at −78° C. for 30 min. (Z)-N-(3-(2-(benzyloxy)ethoxy)propylidene)-2-methylpropane-2-sulfinamide (A35, 2.6 g, 8.35 mmol) was added to the above solution and the reaction was stirred at −78° C. for 1 h and then warmed to 20° C. and stirred for 15 min. TLC showed consumption of starting material and formation of new spots. The reaction was poured into water (10 mL), extracted with EtOAc (3×30 mL). The combined organic layers were dried ($Na_2SO_4$), filtered and concentrated. The crude material was purified by flash silica chromatography (50% EtOAc in petroleum ether) to give N-(1-(2-(benzyloxy)ethoxy)-6,6,6-trifluorohex-4-yn-3-yl)-2-methylpropane-2-sulfinamide (A36).

Step 5: N-(1-(2-(benzyloxy)ethoxy)-6,6,6-trifluorohexan-3-yl)-2-methylpropane-2-sulfinamide (A37)

To a solution of N-(1-(2-(benzyloxy)ethoxy)-6,6,6-trifluorohex-4-yn-3-yl)-2-methylpropane-2-sulfinamide (A36, 1.7 g, 4.19 mmol) in MeOH (40 mL) was added $Pd(OH)_2$ (1.178 g, 8.39 mmol) (10% on C) and the reaction was stirred at 30° C. for 16 h under H2 (50 psi). LCMS showed formation of the desired product mass. The reaction was filtered and concentrated to give N-(1-(2-(benzyloxy)ethoxy)-6,6,6-trifluorohexan-3-yl)-2-methylpropane-2-sulfinamide (A37).

Step 6: 2-((3-amino-6,6,6-trifluorohexyl)oxy)ethan-1-ol (A38)

To a solution of N-(1-(2-(benzyloxy)ethoxy)-6,6,6-trifluorohexan-3-yl)-2-methylpropane-2-sulfinamide (A37, 900 mg, 2.198 mmol) in DCM (20 mL) was added boron trichloride (2.116 mL, 13.19 mmol) and the solution was stirred at 20° C. for 3 h. LCMS showed formation of the desired product mass. The reaction was quenched with MeOH (5 mL). HCl (10 mL) (4M in MeOH) was added and the reaction was stirred at 20° C. for 2 h. The mixture was concentrated to give 2-((3-amino-6,6,6-trifluorohexyl)oxy)ethan-1-ol (A38) as an HCl salt.

Step 7: 1-(2-((tert-butyldimethylsilyl)oxy)ethoxy)-6,6,6-trifluorohexan-3-amine (A39)

To a solution of 2-((3-amino-6,6,6-trifluorohexyl)oxy)ethan-1-ol (A38, 260 mg, 1.208 mmol) in DCM (15 mL) was added imidazole (329 mg, 4.83 mmol) and TBS-Cl(364 mg, 2.416 mmol) at 20° C. The reaction was stirred at 20° C. for 10 h. The reaction was poured into water (10 mL) and extracted with EtOAc (3×20 mL). The combined organic layers were dried ($Na_2SO_4$), filtered and concentrated. The crude material was purified by preparative TLC (100% EtOAc) to give 1-(2-((tert-butyldimethylsilyl)oxy)ethoxy)-6,6,6-trifluorohexan-3-amine (A39). $^1H$ NMR (400 MHz, $CDCl_3$) δ 3.72-3.70 (m, 2H), 3.58-3.50 (m, 2H), 3.48-3.40 (m, 2H), 2.90 (brs, 1H), 2.30-2.03 (m, 2H), 1.72-1.63 (m, 2H), 1.62-1.45 (m, 2H), 0.83 (s, 9H), 0.00 (s, 6H).

Intermediate A49

6-amino-6-(isoxazol-3-yl)hexan-1-ol (A49)

SCHEME A8

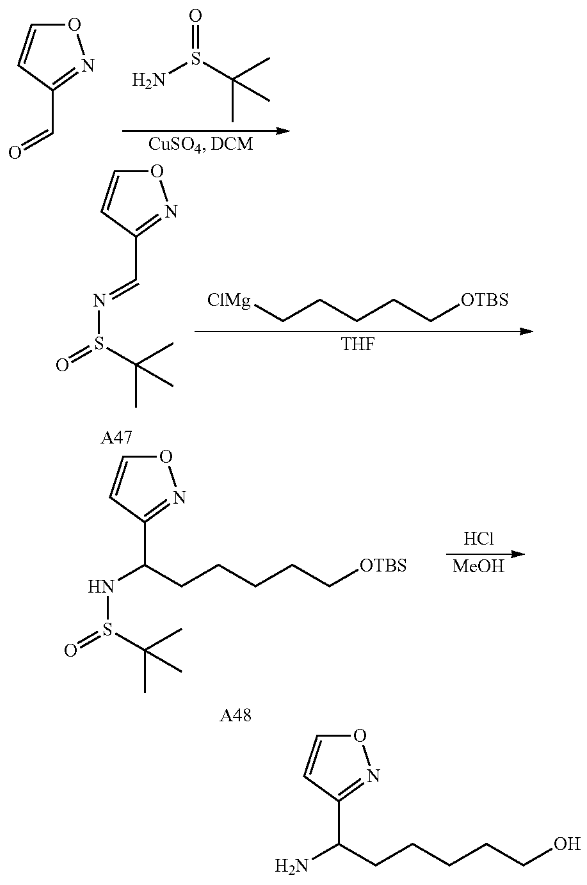

A47

A48

A49

Step 1: (E)-N-(isoxazol-3-ylmethylene)-2-methylpropane-2-sulfinamide (A47)

Isoxazole-3-carbaldehyde (A46, 0.250 g, 2.58 mmol) was dissolved in DCM (5.15 mL) and treated with 2-methylpropane-2-sulfonamide (0.389 g, 2.83 mmol) and copper (II) sulfate (0.904 g, 5.67 mmol). The reaction was stirred at ambient temperature for 18 h. The reaction was filtered over a bed of Celite and concentrated. The crude material was purified by flash silica chromatography (0-50% EtOAc: EtOH 3:1 mix in hexanes) to afford (E)-N-(isoxazol-3-ylmethylene)-2-methylpropane-2-sulfinamide (A47). LC-MS: 201.1 (M+1).

Step 2: N-(6-((tert-butyldimethylsilyl)oxy)-1-(isoxazol-3-yl)hexyl)-2-methylpropane-2-sulfinamide (A48)

(E)-N-(isoxazol-3-ylmethylene)-2-methylpropane-2-sulfinamide (A47, 0.361 g, 1.803 mmol) was dissolved in THF (9 mL) and cooled to 0° C. The solution was treated with 5-(tert-butyldimethylsiloxy)pentylmagnesium chloride (0.5 M in THF) (6.49 mL, 3.24 mmol) and stirred for 90 min. The reaction was quenched with sat. aq. $NH_4Cl$, and extracted with EtOAc. The combined organic layers were washed with water, dried ($Na_2SO_4$), filtered and concentrated. The crude material was purified by flash silica chromatography (0-60% EtOAc in hexanes gradient) to afford N-(6-((tert-butyldimethylsilyl)oxy)-1-(isoxazol-3-yl)hexyl)-2-methylpropane-2-sulfinamide (A48). LC-MS: 403.4 (M+1).

Step 3: 6-amino-6-(isoxazol-3-yl)hexan-1-ol (A49)

N-(6-((tert-butyldimethylsilyl)oxy)-1-(isoxazol-3-yl)hexyl)-2-methylpropane-2-sulfinamide (A48, 130 mg, 0.323 mmol) was dissolved in MeOH (3.3 mL) and treated with HCl (4.0 M in dioxane) (161 μL, 0.646 mmol). The reaction was stirred at ambient temperature for 1 h. The reaction was concentrated to afford 6-amino-6-(isoxazol-3-yl)hexan-1-ol (A49) as an HCl salt, which carried forward without purification. LC-MS: 185.2 (M+1).

Intermediate A51

The following Intermediates from Table A2 were obtained from the appropriate aldehydes in an analogous manner to that used in Scheme A8 to access Intermediate A49.

TABLE A2

| Aldehyde | Intermediate | Observed LCMS (M + 1) |
|---|---|---|
| 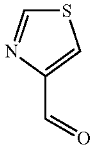 A50 | 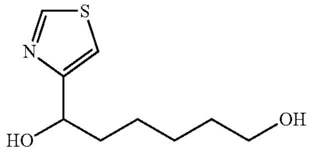 A51 | 201.2 |

Intermediate A53 ethyl 2-(2-((((4-nitrophenoxy)carbonyl)amino)methyl)thiazol-4-yl)acetate (A53)

SCHEME A9

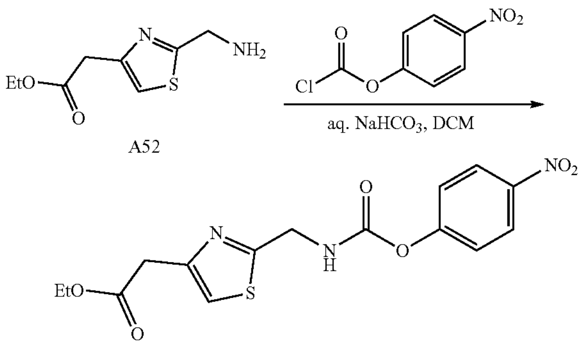

A52

A53

Ethyl 2-[2-(aminomethyl)-1,3-thiazol-4-yl]acetate dihydrochloride (A52, 100 mg, 0.366 mmol) was dissolved in DCM (1830 μL) and treated with sat. aq. $NaHCO_3$(1830 μL) followed by 4-nitrophenyl chloroformate (89 mg, 0.439 mmol) and the reaction was stirred at ambient temperature for 2 h. The reaction was diluted with DCM, washed with sat. aq. $NaHCO_3$, dried by filtering through a hydrophobic frit and concentrated to give ethyl 2-(2-((((4-nitrophenoxy) carbonyl)amino)methyl)thiazol-4-yl)acetate (A53), which was carried forward without purification. LC-MS: 366.2 (M+1).

Intermediates A55 and A57

The following intermediates in Table A3 were synthesized in an analogous manner of that described in Scheme A9 and used to synthesize Intermediate A53 using the appropriate amines.

TABLE A3

| Amine | Intermediate | Observed LCMS (M + 1) |
|---|---|---|
| 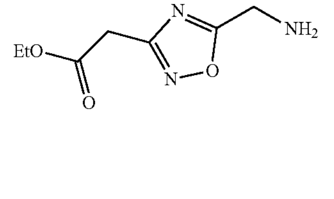 A54 | 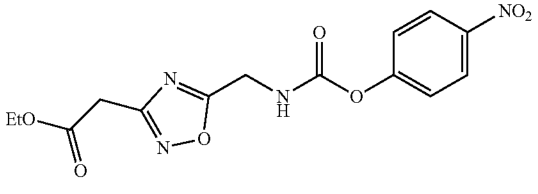 A55 | 351.2 |
| 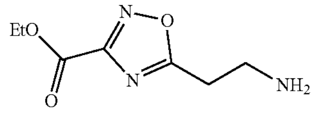 A56 | 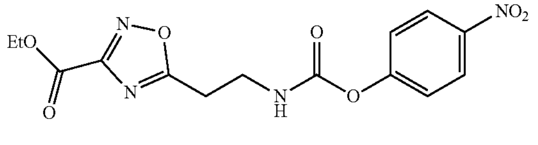 A57 | 351.3 |

Intermediate A60 tert-butyl (2-aminoethyl)(3-((tert-butyldimethylsilvl) oxy)propyl)carbamate (A60)

SCHEME A10

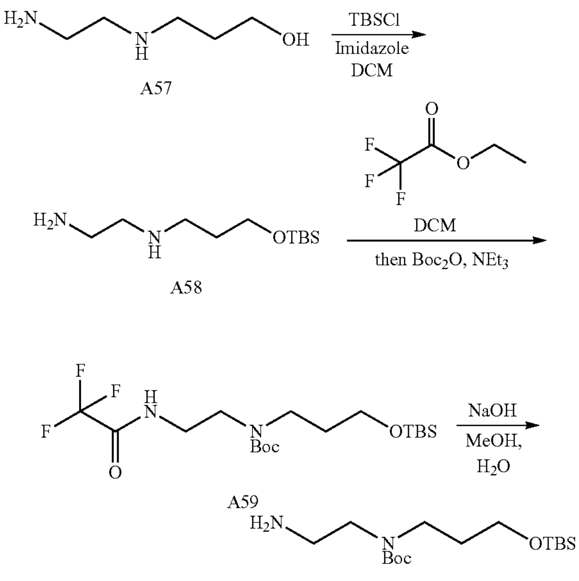

A57

A58

A59

A60

Step 1: N1-(3-((tert-butyldimethylsilvl)oxy)propyl) ethane-1,2-diamine (A58)

N-(3-hydroxypropyl)ethylenediamine (A57, 150 mg, 1.269 mmol) was dissolved in DCM (6 mL). Imidazole (104 mg, 1.523 mmol) was added and the reaction was stirred at ambient temperature for 10 min. TBSCl (230 mg, 1.523 mmol) was added and the reaction was allowed to stir for 16 h. The reaction was quenched with water (5 mL) and extracted with DCM (3×5 mL). The combined organic layers were dried ($Na_2SO_4$), filtered and concentrated to yield N1-(3-((tert-butyldimethylsilyl)oxy)propyl)ethane-1, 2-diamine (A58) which was carried forward without purification.

Step 2: tert-butyl(3-((tert-butyldimethylsilyl)oxy) propyl)(2-(2,2,2-trifluoroacetamido)ethyl)carbamate (A59)

N1-(3-((tert-butyldimethylsilyl)oxy)propyl)ethane-1,2-diamine (A58, 228 mg, 0.981 mmol) was dissolved in DCM (5 mL) and cooled to 0° C. Ethyl trifluoroacetate (129 μL, 1.079 mmol) was added slowly to the reaction. The reaction was stirred for 15 min at 0° C. and then continued stirring at ambient temperature for 1 h. To this mixture, Boc anhydride (273 μL, 1.177 mmol) was added followed by triethylamine (273 μL, 1.962 mmol) and the reaction was allowed to continue stirring for 1 h. The reaction was washed with water (5 mL) and the organic layer was dried ($Na_2SO_4$), filtered and concentrated to afford tert-butyl(3-((tert-butyldimethylsilyl)oxy)propyl)(2-(2,2,2-trifluoroacetamido)ethyl) carbamate (A59) which was carried forward without purification. LC-MS: 429.2 (M+1).

Step 3: tert-butyl (2-aminoethyl)(3-((tert-butyldimethylsilyl)oxy)propyl)carbamate (A60)

tert-butyl (3-((tert-butyldimethylsilyl)oxy)propyl)(2-(2,2,2-trifluoroacetamido)ethyl)carbamate (A59, 413 mg, 0.964 mmol) was dissolved in MeOH (3.2 mL) and water (1.6 mL) and treated with sodium hydroxide (281 mg, 7.03 mmol). The reaction mixture was stirred at ambient temperature for 16 h. The reaction was then concentrated. The crude material was dissolved in water (5 mL) and extracted with DCM (3×5 mL). The combined organic layers were dried ($Na_2SO_4$), filtered and concentrated to afford tert-butyl (2-aminoethyl) (3-((tert-butyldimethylsilyl)oxy)propyl)carbamate (A60) which was carried forward without purification. LC-MS: 333.2 (M+1).

Intermediate A62

The following Intermediates in Table A4 were synthesized in an analogous manner of that described in Scheme A10 and used to synthesize Intermediate A60 using the appropriate amino alcohols.

TABLE A4

| Amino alcohol | Intermediate | Observed LCMS M + 1) |
|---|---|---|
| 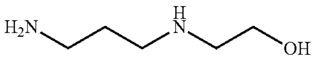 A61 | 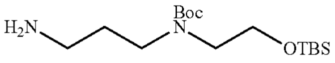 A62 | 333.3 |

Intermediate A64

2-(3-((tert-butyldimethylsilvl)oxy)cyclopentyl)ethan-1-amine (A64)

SCHEME A11

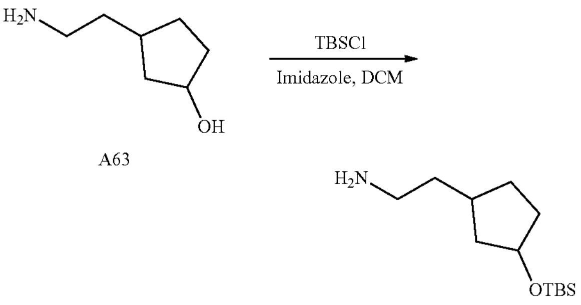

A63

A64

3-(2-aminoethyl)cyclopentan-1-ol (A63, 200 mg, 1.548 mmol) was dissolved in DCM (6 mL). Imidazole (126 mg, 1.858 mmol) was added and the reaction was stirred at ambient temperature for 10 min. TBSCI (280 mg, 1.858 mmol) was added and the reaction was allowed to stir for 16 h. The reaction was quenched with water (5 mL) and extracted with DCM (3×5 mL). The combined organic layers were dried ($Na_2SO_4$), filtered and concentrated to yield 2-(3-((tert-butyldimethylsilyl)oxy)cyclopentyl)ethan-1-amine (A64) which was carried forward without purification. LC-MS: 244.2 (M+1).

Intermediates A66, A68, A70 and A72

The following intermediates in Table A5 were synthesized in an analogous manner of that described in Scheme A11 and used to synthesize Intermediate A64 using the appropriate amino alcohols.

TABLE A5

| Aminoalcohol | Intermediate | Observed LCMS (M + 1) |
|---|---|---|
| 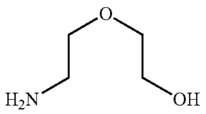 A65 | 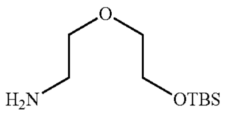 A66 | 220.1 |

TABLE A5-continued
| Aminoalcohol | Intermediate | Observed LCMS (M + 1) |
|---|---|---|
| 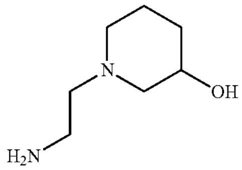 A67 | 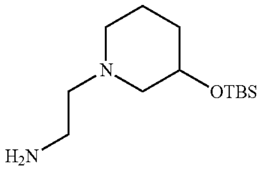 A68 | 259.2 |
| 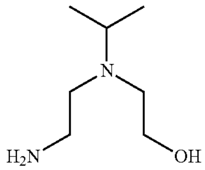 A69 | 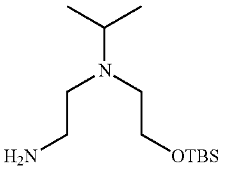 A70 | 261.3 |
| 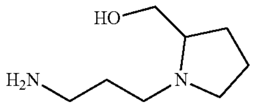 A71 | 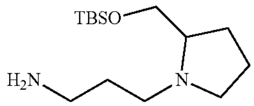 A72 | 273.3 |
| 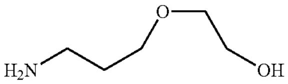 A127 | 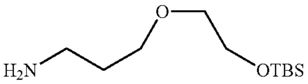 A128 | 234.2 |
| 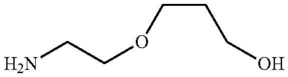 A129 | 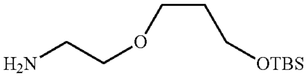 A130 | 234.2 |
| 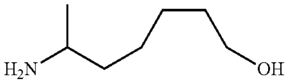 A131 | 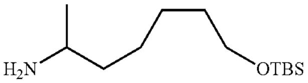 A132 | 246.3 |

Intermediate A79 tert-butyl (1,1,1,7,7-pentafluoro-9-hydroxynonan-4-yl)carbamate (A79)

SCHEME A12

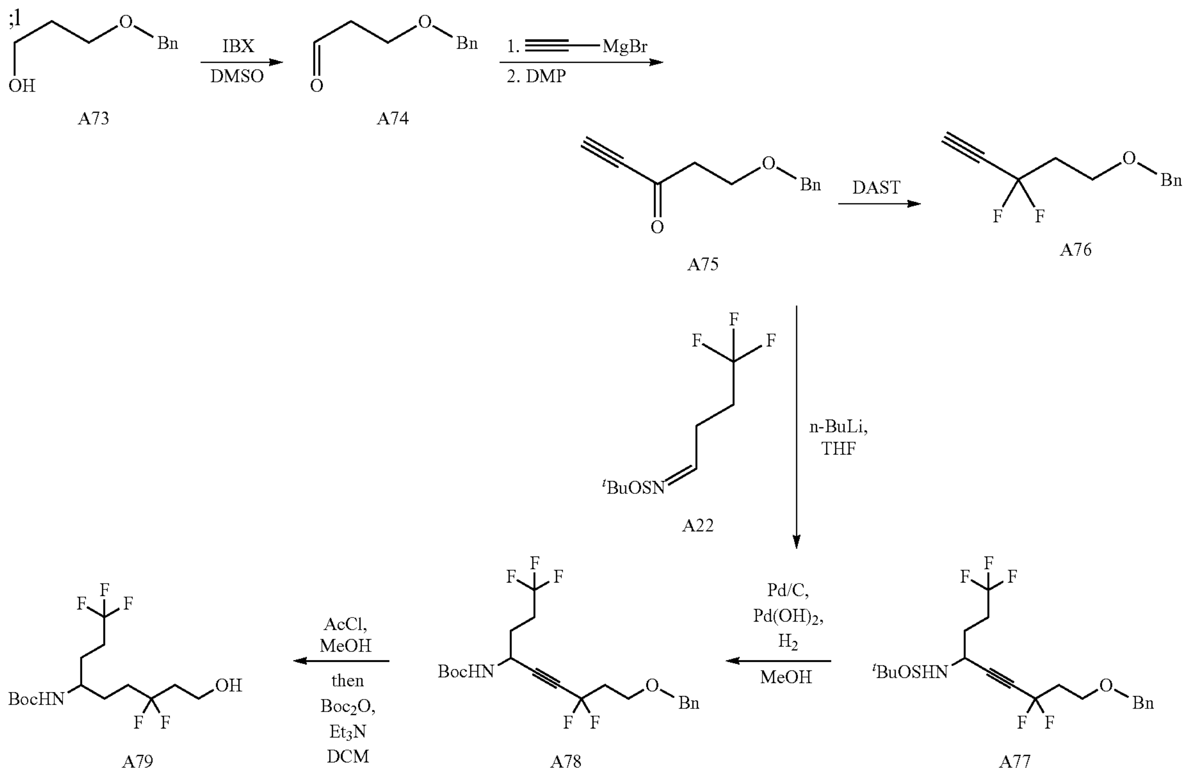

Step 1: 3-(benzyloxy)propanal (A74)

To a solution of 3-(benzyloxy)propan-1-ol (A73, 1 g, 6.02 mmol) in DMSO (10 mL) was added IBX (2.53 g, 9.02 mmol). The reaction was stirred at 20° C. for 12 h. TLC showed consumption of starting material and formation of a new spot. The reaction was poured into water (50 mL), filtered and extracted with EtOAc (3x30 mL). The combined organic layers were dried ($Na_2SO_4$), filtered and concentrated to afford 3-(benzyloxy)propanal (A74), which was carried forward without purification.

Step 2: 5-(benzyloxy)pent-1-yn-3-one (A75)

To a solution of 3-(benzyloxy)propanal (A74, 4.5 g, 27.4 mmol) in THF (50 mL) was added ethynylmagnesium bromide (82 mL, 41.1 mmol) at −78° C. The reaction was stirred at −78° C. for 12 h. The reaction was poured into water (250 mL), filtered and extracted with EtOAc (3x100 mL). The combined organic layers were dried ($Na_2SO_4$), filtered and concentrated. The crude material was purified by flash silica chromatography (0-110% EtOAc in petroleum ether gradient) to afford 5-(benzyloxy)pent-1-yn-3-ol.

To a solution of 5-(benzyloxy) pent-1-yn-3-ol (2.8 g, 14.72 mmol) in anhydrous DCM (45 mL) was added DMP (9.36 g, 22.08 mmol) at 0° C. The reaction was stirred at 20° C. for 2 h. LCMS showed formation of the desired product mass. The reaction was quenched with sat. aq. $NaHCO_3$(25 mL) and sat. aq. $Na_2SO_3$ (25 mL) and extracted with DCM (3x20 mL). The combined organic layers were dried ($Na_2SO_4$), filtered and concentrated. The crude material was purified by flash silica chromatography (0-60% EtOAc in petroleum ether) to afford 5-(benzyloxy)pent-1-yn-3-one (A75). LC-MS: 189.3 (M+H).

Step 3: (((3,3-difluoropent-4-yn-1-yl)oxy)methyl)benzene (A76)

To a solution of 5-(benzyloxy)pent-1-yn-3-one (A75, 2.55 g, 13.55 mmol) in DCM cooled to 0° C. was added DAST (26 mL, 197 mmol). The reaction was heated to 40° C. for 6 h. TLC showed formation of a new spot. The reaction was poured into water (100 mL) and extracted with DCM (3x25 mL). The combined organic layers were washed with brine (30 mL), dried ($Na_2SO_4$), filtered and concentrated. The crude material was purified flash silica chromatography (0-40% EtOAc in petroleum ether gradient) to give (((3,3-difluoropent-4-yn-1-yl)oxy)methyl)benzene (A76). $^1H$ NMR (400 MHz, $CDCl_3$) δ 7.38-7.24 (m, 5H), 4.55-4.48 (m, 2H), 3.72 (t, J=6.97 Hz, 2H), 2.77 (t, J=5.14 Hz, 1H), 2.48-2.22 (m, 2H).

Step 4: N-(9-(benzyloxy)-1,1,1,7,7-pentafluoronon-5-yn-4-yl)-2-methylpropane-2-sulfinamide (A77)

To a solution of (((3,3-difluoropent-4-yn-1-yl)oxy) methyl)benzene (A76, 1.3 g, 6.18 mmol) in THF (20 mL) was added nBuLi (2.474 mL, 6.18 mmol) (2.5 M in hexanes) at −78° C. and the reaction was stirred for 30 min. A solution of (Z)-2-methyl-N-(4,4,4-trifluorobutylidene)propane-2-sulfinamide (A22, 1.418 g, 6.18 mmol) in THF (12 mL) was added and the reaction was stirred at −78° C. for 4 h. LCMS showed the formation of the desired product mass. The reaction mixture was poured into water (30 mL) and extracted with EtOAc (3x20 mL). The combined organic layers were washed with brine (30 mL), dried ($Na_2SO_4$), filtered and concentrated. The crude material was purified by flash silica chromatography (0-30% EtOAc in petroleum ether gradient) to afford N-(9-(benzyloxy)-1,1,1,7,7-pentafluoronon-5-yn-4-yl)-2-methylpropane-2-sulfinamide (A77). LC-MS: 440.2 (M+1).

Step 5: tert-butyl (9-(benzyloxy)-1,1,1,7,7-pentafluoronon-5-yn-4-yl)carbamate (A78)

To a solution of N-(9-(benzyloxy)-1,1,1,7,7-pentafluoronon-5-yn-4-yl)-2-methylpropane-2-sulfinamide (A77, 100 mg, 0.228 mmol) in MeOH (2 mL) was added acetyl chloride (89 mg, 1.138 mmol) and the reaction was stirred at 0° C. for 30 min. LCMS showed the formation of the desired product mass. The reaction was concentrated to afford 9-(benzyloxy)-1,1,1,7,7-pentafluoronon-5-yn-4-amine as an HCl salt, which was carried forward without purification. LC-MS: 336.2 (M+1).

To a solution of 9-(benzyloxy)-1,1,1,7,7-pentafluoronon-5-yn-4-amine (70 mg, 0.209 mmol) in DCM (2 mL) were added triethylamine (0.087 mL, 0.626 mmol) and Boc anhydride (0.058 mL, 0.251 mmol). The reaction was stirred at ambient temperature for 5 h. LCMS showed formation of the desired product mass. The reaction was poured into water (10 mL) and extracted with DCM (3×15 mL). The combined organic layers were washed with brine (10 mL), dried ($Na_2SO_4$), filtered and concentrated. The crude material was concentrated and purified by preparative TLC (1:3 EtOAc in petroleum ether) to give tert-butyl (9-(benzyloxy)-1,1,1,7,7-pentafluoronon-5-yn-4-yl)carbamate (A78). LC-MS: 336.2 (M+1-Boc).

Step 6: tert-butyl (1,1,1,7,7-pentafluoro-9-hydroxynonan-4-yl)carbamate (A79)

To a solution of tert-butyl (9-(benzyloxy)-1,1,1,7,7-pentafluoronon-5-yn-4-yl)carbamate (A78, 60 mg, 0.138 mmol) in MeOH (4 mL) were added $Pd(OH)_2$ (97 mg, 0.069 mmol) (10% on C) and Pd (73.3 mg, 0.069 mmol) (10% on C) and the reaction was at stirred at 30° C. under H2 (50 psi) for 12 h. LCMS showed formation of the desired product mass. The reaction was filtered and concentrated to afford tert-butyl (1,1,1,7,7-pentafluoro-9-hydroxynonan-4-yl)carbamate (A79). LC-MS: 250.3 (M+1-Boc).

Intermediate A86

3-((2-amino-5,5,5-trifluoropentyl)oxy)propan-1-ol (A86)

SCHEME A13

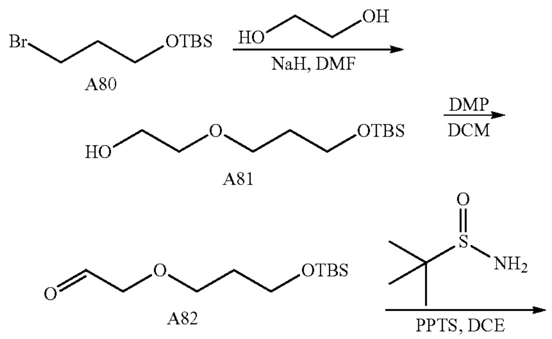

A80

A81

A82

-continued

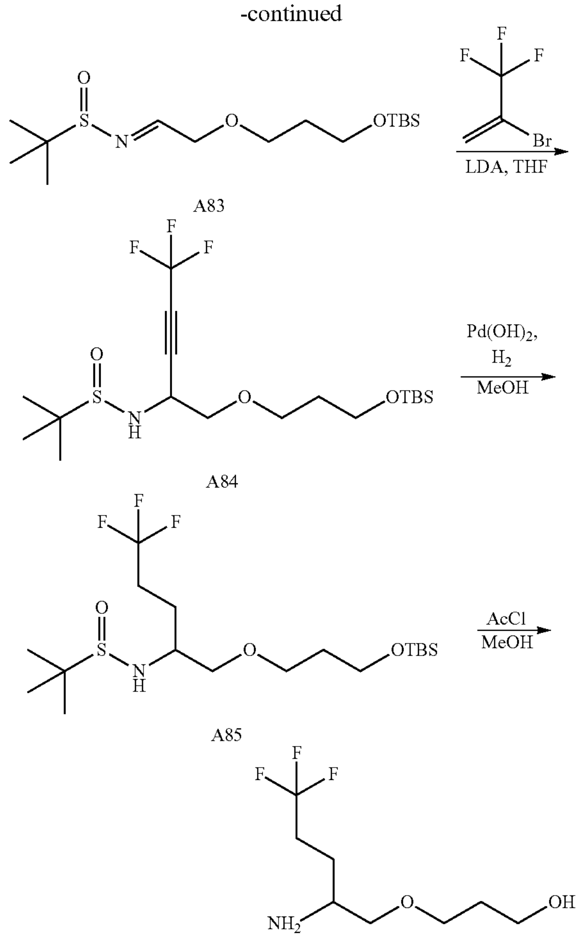

A83

A84

A85

A86

Step 1: 2-(3-((tert-butyldimethylsilyl)oxy)propoxy)ethan-1-ol (A81)

To a solution of ethylene glycol (22.01 mL, 395 mmol) in DMF (100 mL) was added sodium hydride (4.74 g, 118 mmol) (60% in mineral oil) at 0° C. and the reaction was stirred at 0° C. for 30 min. (3-bromopropoxy)(tert-butyl)dimethylsilane (A80, 10 g, 39.5 mmol) was then added to the reaction. TLC showed formation of new spots. The reaction was poured into water (100 mL) and extracted with EtOAc (3×100 mL). The combined organic layers were washed with brine (2×100 mL), dried ($Na_2SO_4$), filtered and concentrated. The crude material was purified by flash silica chromatography (20% EtOAc in petroleum ether) to give 2-(3-((tert-butyldimethylsilyl)oxy)propoxy)ethan-1-ol (A81).

Step 2: 2-(3-((tert-butyldimethylsilyl)oxy)propoxy)acetaldehyde (A82)

To a solution of 2-(3-((tert-butyldimethylsilyl)oxy)propoxy)ethan-1-ol (A81, 1 g, 4.27 mmol) in DCM (20 mL) was added DMP (2.71 g, 6.40 mmol) at 0° C. The reaction was stirred at ambient temperature for 16 h. TLC showed formation of a new spot. The reaction was quenched with sat. aq. $NaHCO_3$ (100 mL) and extracted with DCM (3×20 mL). The combined organic layers were washed with sat. aq. $Na_2SO_3$ (100 mL) and brine (50 mL), dried ($Na_2SO_4$), filtered and concentrated. The crude material was purified by flash silica chromatography (20% EtOAc in petroleum ether) to give 2-(3-((tert-butyldimethylsilyl)oxy)propoxy)acetaldehyde (A82).

Step 3: (E)-N-(2-(3-((tert-butyldimethylsilyl)oxy)propoxy)ethylidene)-2-methylpropane-2-sulfinamide (A83)

To a solution of 2-(3-((tert-butyldimethylsilyl)oxy)propoxy)acetaldehyde (A82, 470 mg, 2.022 mmol) in DCE (10 mL) were added 2-methylpropane-2-sulfinamide (368 mg, 3.03 mmol), PPTS (25.4 mg, 0.101 mmol) and $MgSO_4$ (974 mg, 8.09 mmol). The reaction was stirred at 80° C. for 16 h. TLC showed formation of a new spot. The reaction was filtered and concentrated. The crude material was purified by flash silica chromatography (30% EtOAc in petroleum ether) to afford (E)-N-(2-(3-((tert-butyldimethylsilyl)oxy)propoxy)ethylidene)-2-methylpropane-2-sulfinamide (A83).

Step 4: N-(1-(3-((tert-butyldimethylsilyl)oxy)propoxy)-5,5,5-trifluoropent-3-yn-2-yl)-2-methylpropane-2-sulfinamide (A84)

To a solution of LDA (1.430 mL, 2.86 mmol) (2 M in hexane) in THF (2 mL) was added 2-bromo-3,3,3-trifluoroprop-1-ene (375 mg, 2.146 mmol) in THF (2 mL) at −78° C. The reaction was stirred at −78° C. for 30 min. (E)-N-(2-(3-((tert-butyldimethylsilyl)oxy)propoxy)-ethylidene)-2-methylpropane-2-sulfinamide (A83, 480 mg, 1.430 mmol) was added slowly at −78° C. The reaction was stirred at −78° C. for 30 min and then warmed to 20° C. and stirred for 30 min. TLC showed the formation of new spots. The reaction was poured into sat. aq. $NH_4Cl$ (2 mL) and extracted with EtOAc (3×5 mL). The combined organic layers were dried ($Na_2SO_4$), filtered and concentrated. The crude material was purified by flash silica gel chromatography (20% EtOAc in petroleum ether) to give N-(1-(3-((tert-butyldimethylsilyl)oxy)propoxy)-5,5,5-trifluoropent-3-yn-2-yl)-2-methylpropane-2-sulfinamide (A84).

LC-MS: 430.2 (M+1).

Step 5: N-(1-(3-((tert-butyldimethylsilyl)oxy)propoxy)-5,5,5-trifluoropentan-2-yl)-2-methylpropane-2-sulfinamide (A85)

To a solution of N-(1-(3-((tert-butyldimethylsilyl)oxy)propoxy)-5,5,5-trifluoropent-3-yn-2-yl)-2-methylpropane-2-sulfinamide (A84, 240 mg, 0.559 mmol) in MeOH (5 mL) was added $Pd(OH)_2$ (100 mg, 0.071 mmol) (10% on C). The reaction was stirred at ambient temperature under $H_2$ (15 psi) for 16 h. TLC showed formation of a new spot. The reaction was filtered and concentrated. The crude material was purified by preparative TLC (1:3 EtOAC in petroleum ether) to give N-(1-(3-((tert-butyldimethylsilyl)oxy)propoxy)-5,5,5-trifluoropentan-2-yl)-2-methylpropane-2-sulfinamide (A85).

Step 6: 3-((2-amino-5,5,5-trifluoropentyl)oxy)propan-1-ol (A86)

To a solution of N-(1-(3-((tert-butyldimethylsilyl)oxy)propoxy)-5,5,5-trifluoropentan-2-yl)-2-methylpropane-2-sulfinamide (A85, 120 mg, 0.277 mmol) in MeOH (2 mL) was added acetyl chloride (43.4 mg, 0.553 mmol). The reaction was stirred at 0° C. for 30 min. LCMS showed the formation of the desired product mass. The mixture was concentrated to give 3-((2-amino-5,5,5-trifluoropentyl)oxy)propan-1-ol (A86) as an HCl salt, which was carried forward without purification.

LC-MS: 216.1 (M+1).

Intermediate A91

$N^2$-(2-((tert-butyldiphenylsilyl)oxy)ethyl)-3,3,3-trifluoro-$N^2$-methylpropane-1,2-diamine (A91)

SCHEME A14

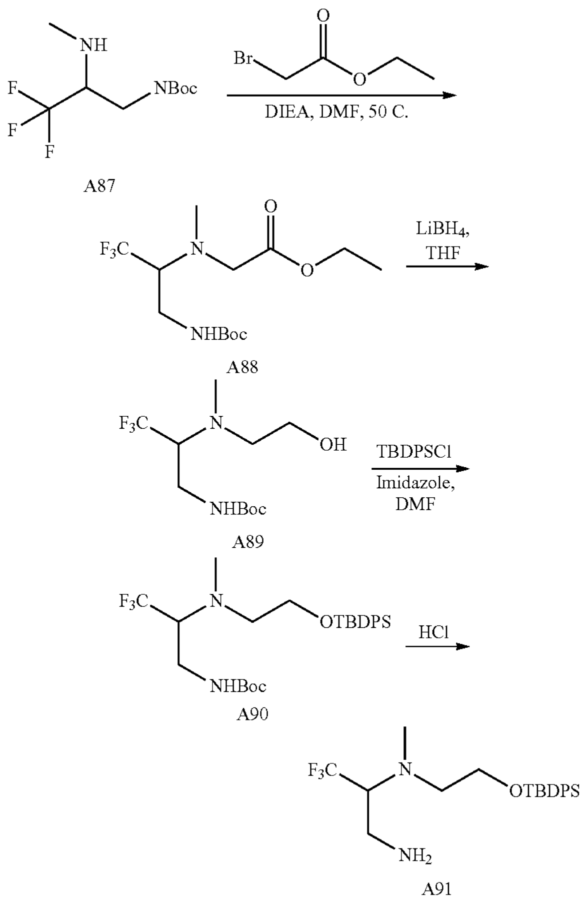

Step 1: ethyl N-(3-((tert-butoxycarbonyl)amino)-1,1,1-trifluoropropan-2-yl)-N-methylglycinate (A88)

A sealable vial was charged with tert-butyl (3,3,3-trifluoro-2-(methylamino)-propyl)carbamate (A87, 0.3 g, 1.238 mmol) which was dissolved in DMF (6.19 mL) and treated with ethyl bromoacetate (0.411 mL, 3.72 mmol) followed by DIEA (0.865 mL, 4.95 mmol). The vial was capped, and the reaction contents were heated to 50° C. for 18 h. The reaction was then diluted with EtOAc, washed with sat. aq. $NaHCO_3$, dried ($Na_2SO_4$), filtered and concentrated. The crude material was purified by flash silica chromatography (0-20% EtOAc:EtOH 3:1 mix in hexanes gradient) to afford ethyl N-(3-((tert-butoxycarbonyl)amino)-1,1,1-trifluoropropan-2-yl)-N-methylglycinate (A88). LC-MS: 329.3 (M+1).

Step 2: tert-butyl (3,3,3-trifluoro-2-((2-hydroxyethyl)(methyl)amino)propyl)carbamate (A89)

Ethyl N-(3-((tert-butoxycarbonyl)amino)-1,1,1-trifluoropropan-2-yl)-N-methylglycinate (A88, 276 mg, 0.841 mmol) was dissolved in THF (5604 μL) and treated with lithium borohydride (841 μL, 1.681 mmol) (2.0 M in THF) and the reaction was stirred at ambient temperature for 90 min. The reaction was then diluted with DCM, washed with sat. aq. $NH_4Cl$, dried ($Na_2SO_4$), filtered and concentrated to afford tert-butyl (3,3,3-trifluoro-2-((2-hydroxyethyl)(methyl)amino)propyl)carbamate (A89), which was carried forward without purification. LC-MS: 287.2 (M+1).

Step 3: tert-butyl (2-((2-((tert-butyldiphenylsilyl)oxy)ethyl)(methyl)amino)-3,3,3-trifluoropropyl)carbamate (A90)

Tert-butyl (3,3,3-trifluoro-2-((2-hydroxyethyl)(methyl)amino)propyl)carbamate (A89, 159 mg, 0.555 mmol) was dissolved in DMF (617 μL) and treated with tert-butylchlorodiphenylsilane (173 μL, 0.666 mmol) and imidazole (76 mg, 1.111 mmol). The reaction was stirred at ambient temperature for 18 h. The reaction was then diluted with EtOAc, washed with water followed by sat. brine, dried ($Na_2SO_4$), filtered and concentrated. The crude material was purified by flash silica chromatography (0-10% EtOAc in hexanes gradient) to afford tert-butyl (2-((2-((tert-butyldiphenylsilyl)oxy)ethyl)(methyl)amino)-3,3,3-trifluoropropyl)carbamate (A90). LC-MS: 525.4 (M+1).

Step 4: $N^2$-(2-((tert-butyldiphenylsilyl)oxy)ethyl)-3,3,3-trifluoro-$N^2$-methylpropane-1,2-diamine (A91)

A flask was charged with the tert-butyl (2-((2-((tert-butyldiphenylsilyl)oxy)-ethyl)(methyl)amino)-3,3,3-trifluoropropyl)carbamate (A90, 204 mg, 0.389 mmol) and HCl (972 μL, 3.89 mmol) (4 M in dioxane) was added. The reaction was stirred at ambient temperature for 1 h. The reaction was concentrated to afford $N^2$-(2-((tert-butyldiphenylsilyl)oxy)ethyl)-3,3,3-trifluoro-$N^2$-methylpropane-1,2-diamine (A91) as an HCl salt, which was carried forward without purification. LC-MS: 425.3 (M+1).

Intermediate A97

4-nitrophenyl (2-((3-((tert-butyldiphenylsilyl)oxy)propyl)(methyl)amino)-3,3,3-trifluoropropyl)carbamate (A97)

SCHEME A15

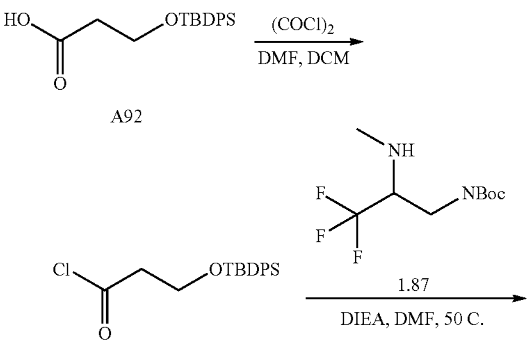

A92

A93

-continued

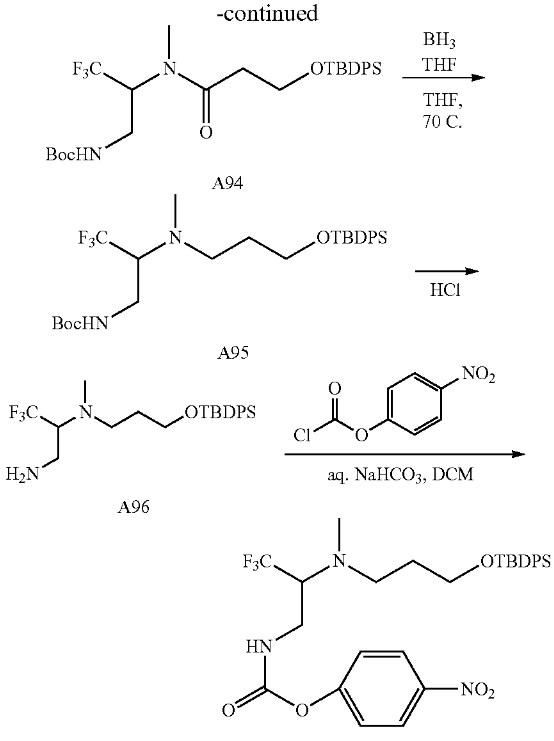

A94

A95

A96

A97

Step 1: 3-((tert-butyldiphenylsilyl)oxy)propanoyl chloride (A93)

3-((tert-butyldiphenylsilyl)oxy)propanoic acid (A92, 0.5 g, 1.522 mmol) was dissolved in DCM (7.61 mL) and the solution was cooled to 0° C. The solution was treated with oxalyl chloride (1.522 mL, 3.04 mmol) (2.0 M in DCM) and DMF (0.012 mL, 0.152 mmol) and allowed to stir for 90 min at 0° C. The reaction was concentrated to afford 3-((tert-butyldiphenylsilyl)oxy)propanoyl chloride (A93), which was carried forward without purification.

Step 2: tert-butyl (2-(3-((tert-butyldiphenylsilyl)oxy)-N-methylpropanamido)-3,3,3-trifluoropropyl)carbamate (A94)

Tert-butyl N-[3,3,3-trifluoro-2-(methylamino)propyl]carbamate (A87, 250 mg, 1.032 mmol) was dissolved in DMF (5160 μL) and treated with 3-((tert-butyldiphenylsilyl)-oxy)propanoyl chloride (A93) (526 mg, 1.517 mmol) and DIEA (541 μL, 3.10 mmol). The reaction was heated to 50° C. and stirred for 18 h. The reaction was diluted with DCM, washed with sat. aq. $NaHCO_3$, dried by filtering through a hydrophobic frit and concentrated. The crude material was purified by flash silica chromatography (0-50% EtOAc:EtOH 3:1 mix in hexanes gradient) to afford tert-butyl (2-(3-((tert-butyldiphenylsilyl)oxy)-N-methylpropanamido)-3,3,3-trifluoropropyl)carbamate (A94).

LC-MS: 553.2 (M+1).

Step 3: tert-butyl (2-((3-((tert-butyldiphenylsilyl)oxy)propyl)(methyl)amino)-3,3,3-trifluoropropyl)carbamate (A95)

Tert-butyl (2-(3-((tert-butyldiphenylsilyl)oxy)-N-methylpropanamido)-3,3,3-trifluoropropyl)carbamate (A94, 570 mg, 1.031 mmol) was dissolved in THF (5 mL) and treated with borane-tetrahydrofuran complex (3094 μL, 3.09 mmol) (1.0 M in THF). The reaction was heated to 70° C. for 18 h. The reaction was diluted with DCM, washed with 2 M NaOH, dried ($Na_2SO_4$), filtered and concentrated. The crude material was purified by flash silica chromatography (0-50% EtOAc:EtOH 3:1 mix in hexanes gradient) to afford tert-butyl (2-((3-((tert-butyldiphenylsilyl)oxy)propyl)(methyl)amino)-3,3,3-trifluoropropyl)carbamate (A95). LC-MS: 539.5 (M+1).

Step 4: $N^2$-(3-((tert-butyldiphenylsilyl)oxy)propyl)-3,3,3-trifluoro-$N^2$-methylpropane-1,2-diamine (A96)

Tert-butyl (2-((3-((tert-butyldiphenylsilyl)oxy)propyl)(methyl)amino)-3,3,3-trifluoropropyl)carbamate (A95) (50 mg, 0.093 mmol) was treated with HCl (232 μL, 0.928 mmol) (4 M in dioxane) and the reaction was stirred at ambient temperature for 90 min. The reaction was concentrated under vacuum to afford $N^2$-(3-((tert-butyldiphenylsilyl)oxy)propyl)-3,3,3-trifluoro-$N^2$-methylpropane-1,2-diamine (A96) as an HCl salt, which was carried forward without purification. LC-MS: 439.4 (M+1).

Step 5: 4-nitrophenyl (2-((3-((tert-butyldiphenylsilyl)oxy)propyl)(methyl)amino)-3,3,3-trifluoropropyl) carbamate (A97)

$N^2$-(3-((tert-butyldiphenylsilyl)oxy)propyl)-3,3,3-trifluoro-$N^2$-methylpropane-1,2-diamine (A96) (47.5 mg, 0.093 mmol) was dissolved in DCM (464 μL) and treated with 4-nitrophenyl chloroformate (23 mg, 0.111 mmol) and sat. aq. $NaHCO_3$(464 μL). The reaction was stirred at ambient temperature for 1 h. The reaction was then diluted with DCM, washed with water, dried by filtering through a hydrophobic frit and concentrated to afford 4-nitrophenyl (2-((3-((tert-butyldiphenylsilyl)oxy)propyl)(methyl)amino)-3,3,3-trifluoropropyl)carbamate (A97), which was carried forward without purification. LC-MS: 604.5 (M+1).

Intermediate A100

1-((R)-1-(4-(8-(but-3-en-1-yloxy)imidazo[1,2-a]pyrazin-6-yl)-5-methoxypyridin-2-yl)ethyl)-1-ethyl-3-(6-methylhept-1-en-4-yl)urea (A100)

SCHEME A16

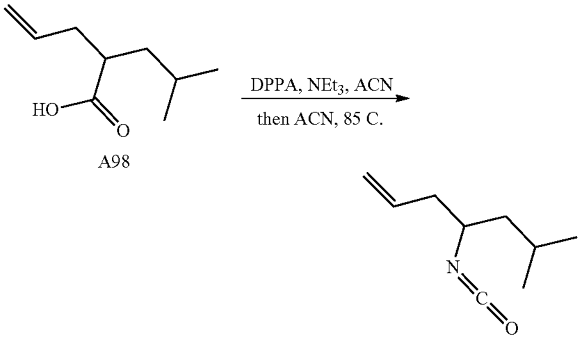

A98

A99

-continued

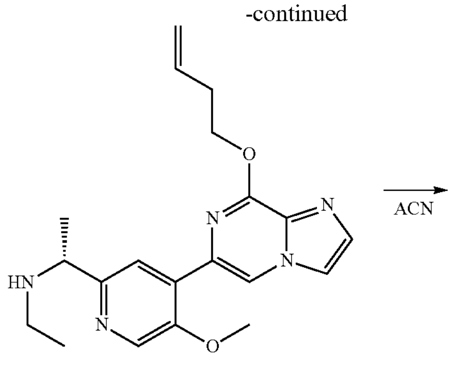

C74

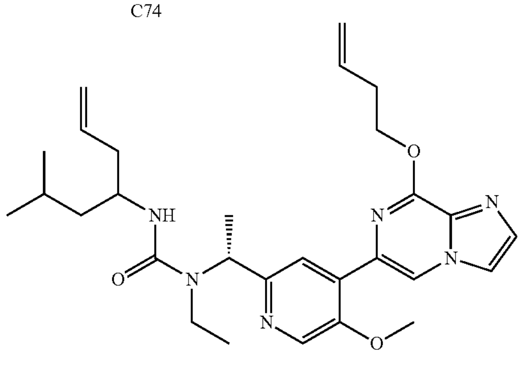

A100

Step 1: 4-isocyanato-6-methylhept-1-ene (A99)

2-isobutylpent-4-enoic acid (A98, 200 mg, 1.28 mmol) was dissolved in ACN (4.3 mL) under nitrogen and triethylamine (357 μL, 2.56 mmol) was added. DPPA (303 μL, 1.41 mmol) was added dropwise and the reaction was allowed to stir at ambient temperature for 1 h. The reaction was concentrated and filtered through a silica plug with 10% EtOAc in hexanes. The filtrate was concentrated, dissolved in ACN (5 mL) and heated to 85° C. for 4 h. The resulting solution of 4-isocyanato-6-methylhept-1-ene (A99) was carried forward without purification.

Step 2: 1-((R)-1-(4-(8-(but-3-en-1-yloxy)imidazo[1,2-a]pyrazin-6-yl)-5-methoxypyridin-2-yl)ethyl)-1-ethyl-3-(6-methylhept-1-en-4-yl)urea (A100)

To a solution of crude 4-isocyanato-6-methylhept-1-ene (A99, 120 mg, 0.78 mmol) in ACN (4 mL) was added (R)-1-(4-(8-(but-3-en-1-yloxy)imidazo[1,2-a]pyrazin-6-yl)-5-methoxypyridin-2-yl)-N-ethylethan-1-amine (C74, 60 mg, 0.163 mmol) and the reaction was stirred at ambient temperature for 15 min. The reaction was then concentrated and the crude material was purified by flash silica chromatography (50-100% EtOAc in hexanes gradient) to afford 1-((R)-1-(4-(8-(but-3-en-1-yloxy)imidazo[1,2-a]pyrazin-6-yl)-5-methoxypyridin-2-yl)ethyl)-1-ethyl-3-(6-methylhept-1-en-4-yl)urea (A100). LC-MS: 521.3 (M+1).

Intermediates A101-A103

The following intermediates in Table A6 were synthesized in an analogous manner of that described in general Scheme A16 and used to synthesize Intermediate A100 using the appropriate commercial acids.

TABLE A6

| Intermediate | Observed LC-MS (M + 1) |
|---|---|
| 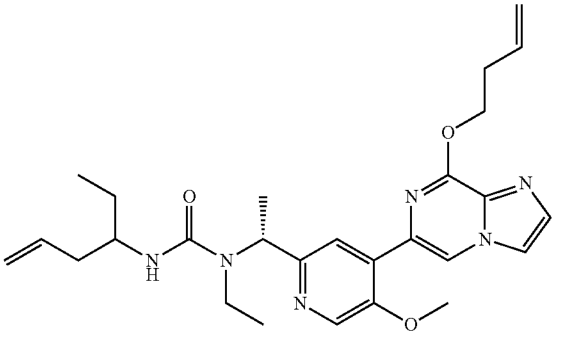 A101 | 493.3 |
| 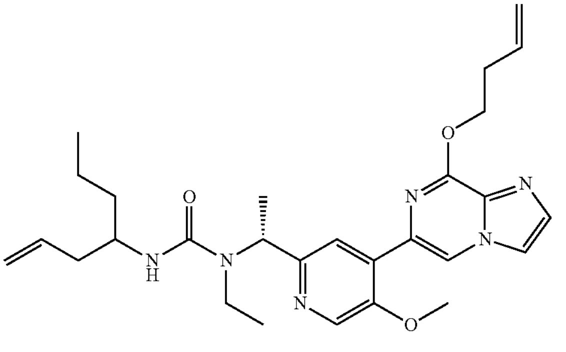 A102 | 507.3 |
| 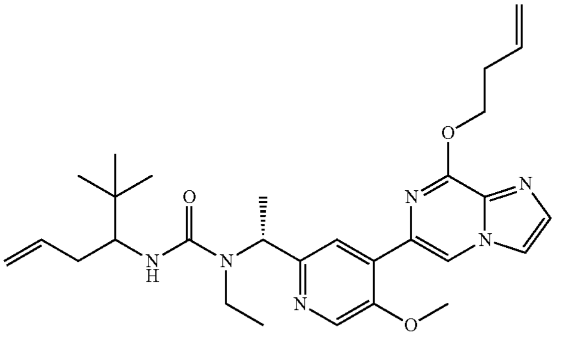 A103 | 521.4 |

Intermediates A106-A108

SCHEME A17

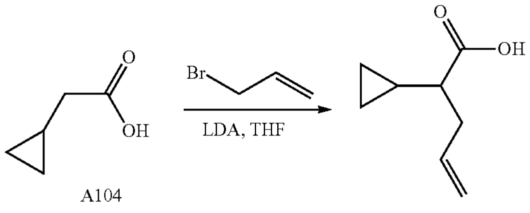

A104 A105

2-cyclopropylpent-4-enoic acid (A105)

2-cyclopropylacetic acid (A104, 0.45 mL, 4.63 mmol) was dissolved in THF (14 mL) under nitrogen and the solution was cooled to 0° C. LDA (4.86 mL, 9.72 mmol) (2 M in THF) was added dropwise and the reaction was stirred at 0° C. for 1 h. Allyl bromide (0.4 mL, 4.63 mmol) was added dropwise and the reaction was allowed to stir for 1 h. The reaction was quenched with 1N aq. HCl (20 mL) and extracted with EtOAc. The combined organic layers were dried ($Na_2SO_4$) and concentrated to afford 2-cyclopropyl-pent-4-enoic acid (A105) which was carried forward without purification.

The following intermediates in Table A7 were synthesized in an analogous manner of that described in Scheme A17 for acid A105 by allylation of the appropriate commercial acids, followed by isocyanate and urea formation using the listed intermediate C as described in Scheme A16 for Intermediate A100.

TABLE A7
| Intermediate C | Intermediate | Observed LC-MS (M + 1) |
|---|---|---|
| C74 | 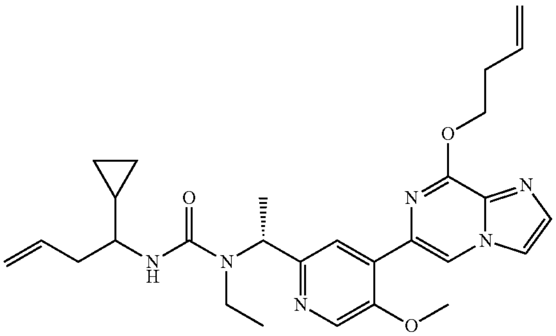 A106 | 505.3 |
| C74 | 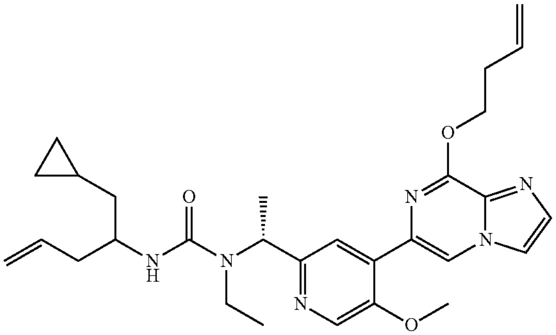 A107 | 519.3 |
| C74 | 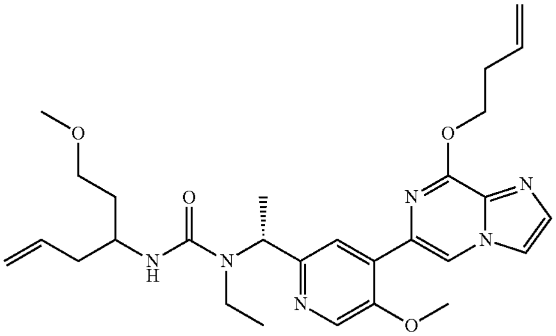 A108 | 523.3 |

TABLE A7-continued
| Intermediate C | Intermediate | Observed LC-MS (M + 1) |
|---|---|---|
| C155 | 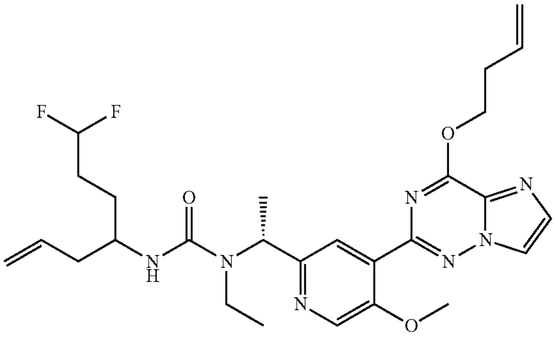<br>A157 | 544.2 |
| C155 | 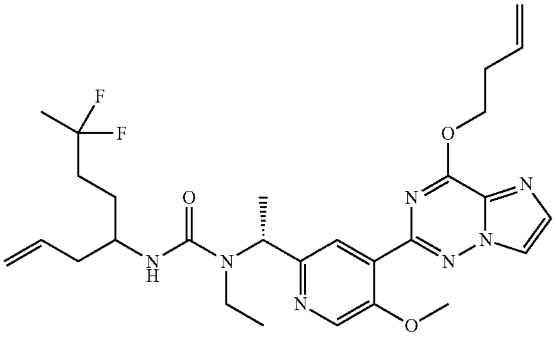 [SMILES: C=CCCOc1nc(-c2cc([C@@H](C)N(CC)C(=O)NC(CC=C)CCC(C)(F)F)ncc2OC)nn2ccnc12]<br>A153 | 558.2 |
| C155 | 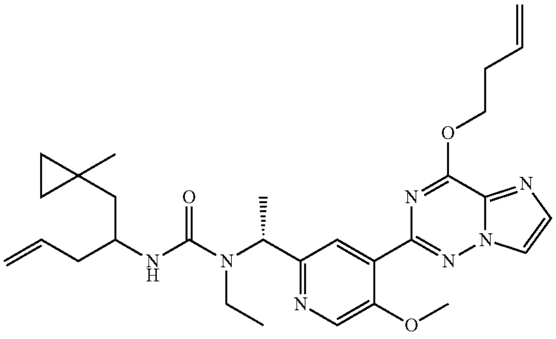 [SMILES: C=CCCOc1nc(-c2cc([C@@H](C)N(CC)C(=O)NC(CC=C)CC3(C)CC3)ncc2OC)nn2ccnc12]<br>A154 | 534.3 |
| C155 | 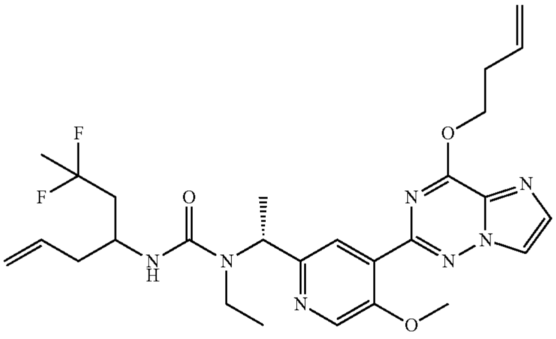 [SMILES: C=CCCOc1nc(-c2cc([C@@H](C)N(CC)C(=O)NC(CC=C)CC(C)(F)F)ncc2OC)nn2ccnc12]<br>A155 | 544.3 |

TABLE A7-continued
| Intermediate C | Intermediate | Observed LC-MS (M + 1) |
| --- | --- | --- |
| C157 | 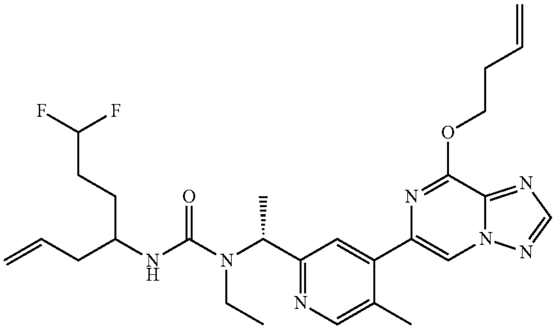 A156 | 528.3 |
| C74 | 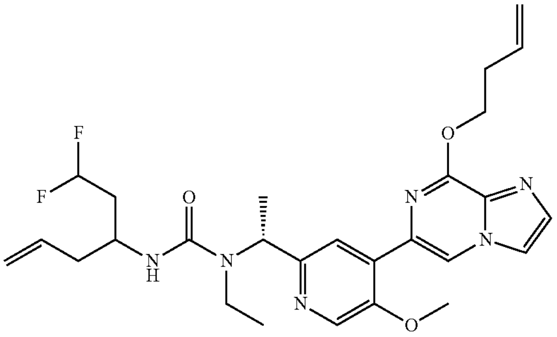 A157 | 529.4 |
| C160 | 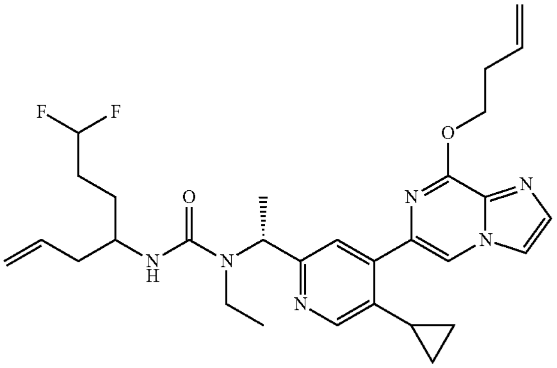 A158 | 553.3 |
| C162 | 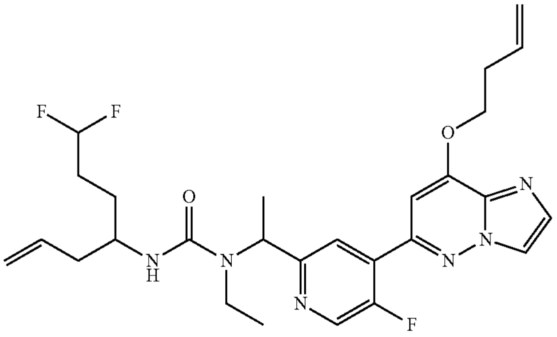 A159 | 531.2 |

TABLE A7-continued

| Intermediate C | Intermediate | Observed LC-MS (M + 1) |
|---|---|---|
| C156 | 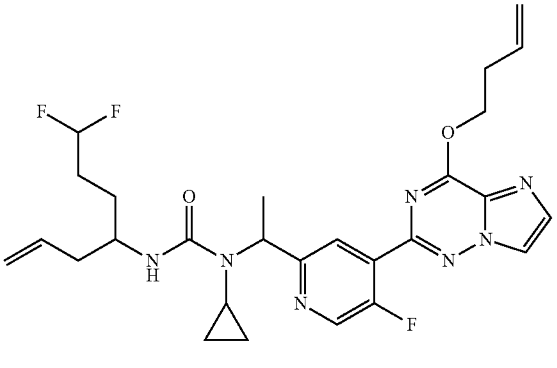 A160 | 544.2 |
| C158 | 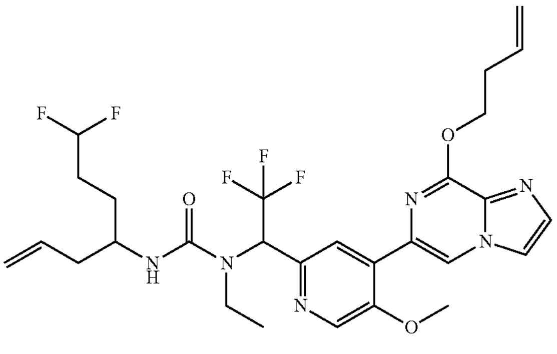 A161 | 597.5 |

Intermediates A111-A125

SCHEME A18

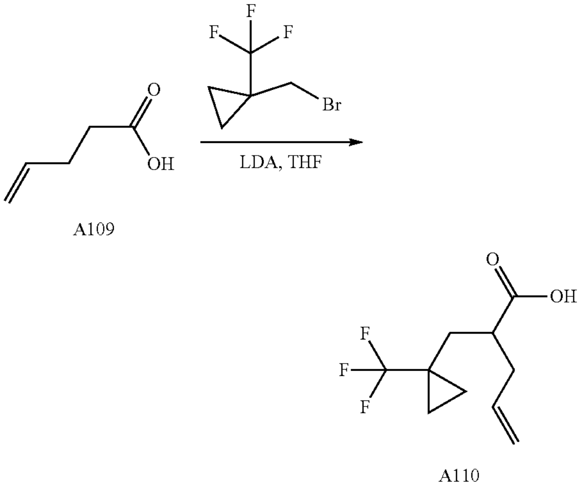

A109

A110

2-((1-(trifluoromethyl)cyclopropyl)methyl)pent-4-enoic acid (A110)

Pent-4-enoic acid (A109, 0.3 mL, 2.94 mmol) was dissolved in THF (10 mL) under nitrogen and the solution was cooled to 0° C. LDA (3.09 mL, 6.17 mmol) (2M) was added dropwise and the reaction was allowed to stir for 1 h. 1-(bromomethyl)-1-(trifluoromethyl)cyclopropane (0.597 g, 2.94 mmol) was added and the reaction was allowed to warm to ambient temperature overnight. The reaction was quenched with TN aq. HCl (15 mL) and extracted with EtOAc. The combined organic layers were dried ($Na_2SO_4$) and concentrated to afford 2-((1-(trifluoromethyl)cyclopropyl)methyl)pent-4-enoic acid (Alto), which was carried forward without purification.

The following intermediates in Table A8 were synthesized in an analogous manner of that described in Scheme A18 for acid A110 by alkylation of pent-4-enoic acid (A109) with the appropriate alkyl chlorides or bromides, followed by isocyanate and urea formation using the listed intermediate C as described in Scheme A16 for Intermediate A100.

TABLE A8
| Intermediate C | Intermediate | Observed LC-MS (M + 1) |
| --- | --- | --- |
| C74 | 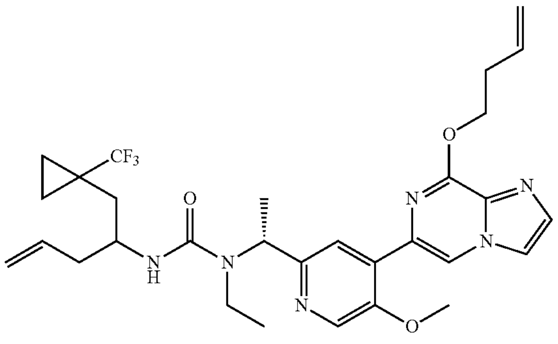 A111 | 587.3 |
| C74 | 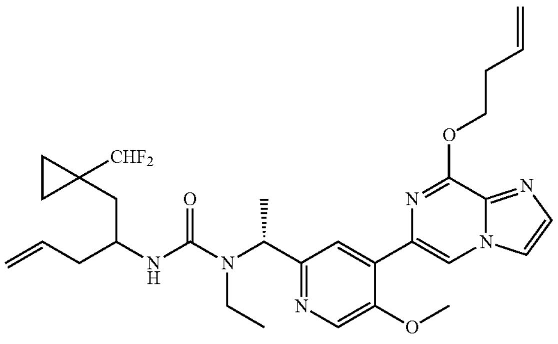 A112 | 569.4 |
| C74 | 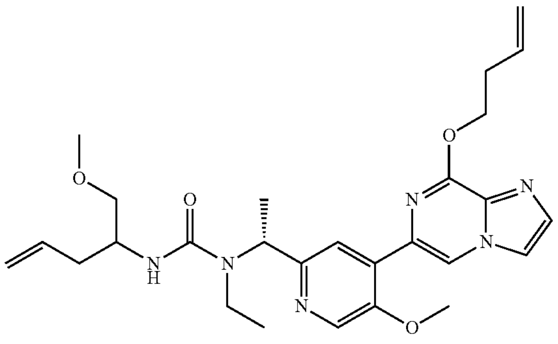 A113 | 509.3 |
| C74 | 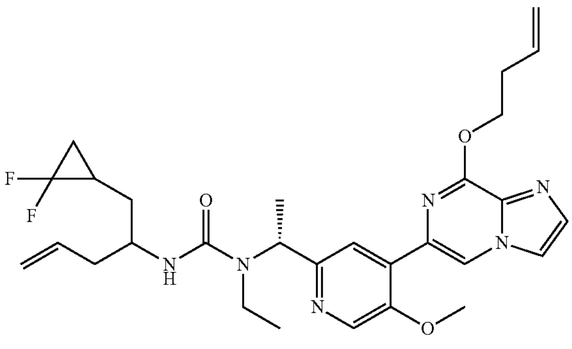 A114 | 555.5 |

TABLE A8-continued
| Intermediate C | Intermediate | Observed LC-MS (M + 1) |
|---|---|---|
| C74 | 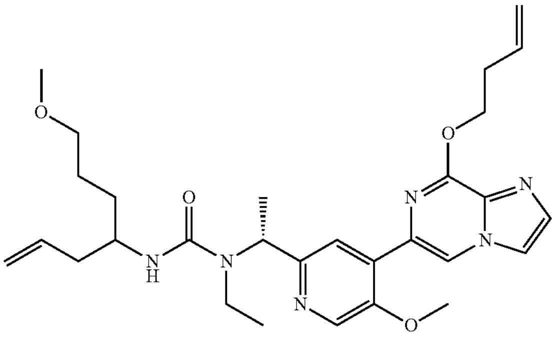 A115 | 537.4 |
| C74 | 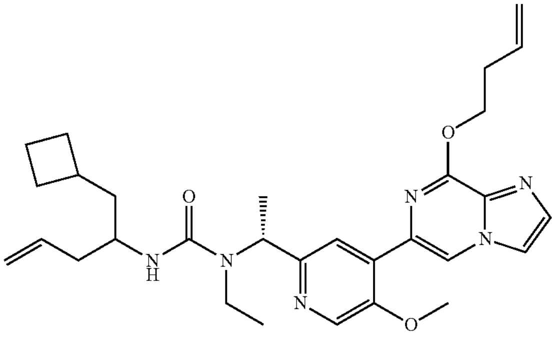 A116 | 533.4 |
| C74 | 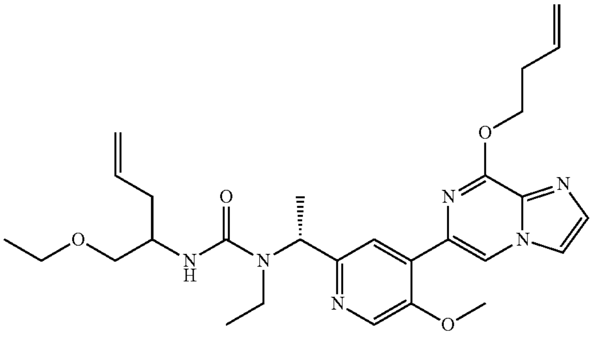 A117 | 523.3 |
| C74 | 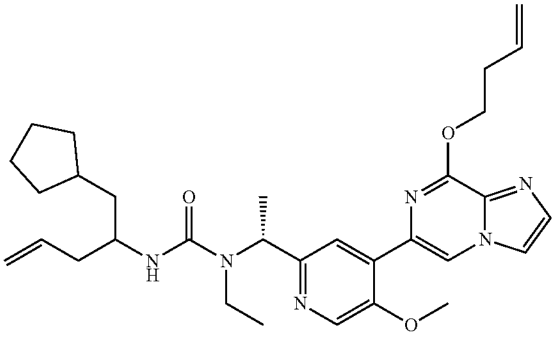 A118 | 547.4 |

TABLE A8-continued
| Intermediate C | Intermediate | Observed LC-MS (M + 1) |
|---|---|---|
| C74 | 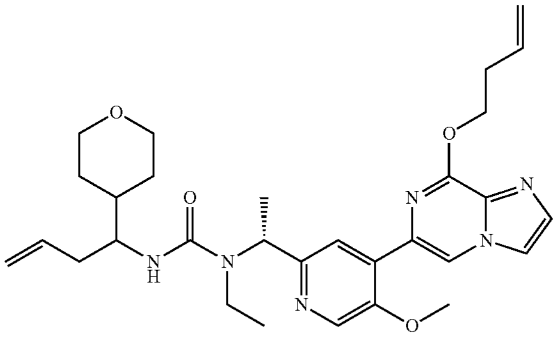 A119 | 549.4 |
| C74 | 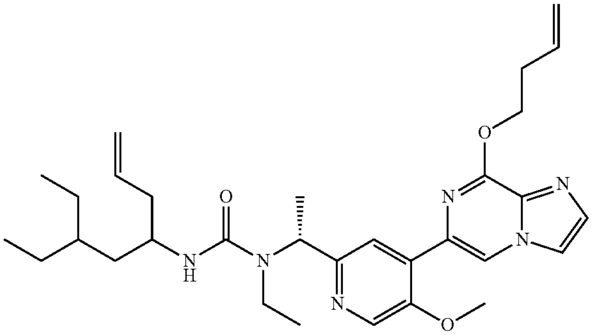 A120 | 549.5 |
| C74 | 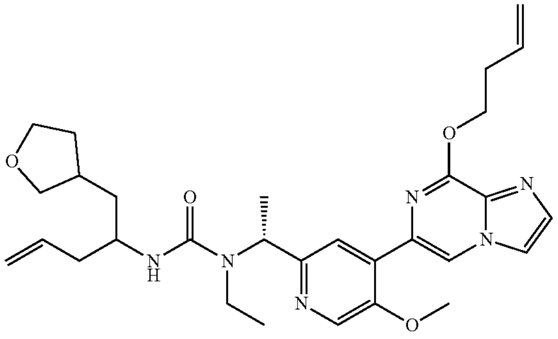 A121 | 549.4 |
| C74 | 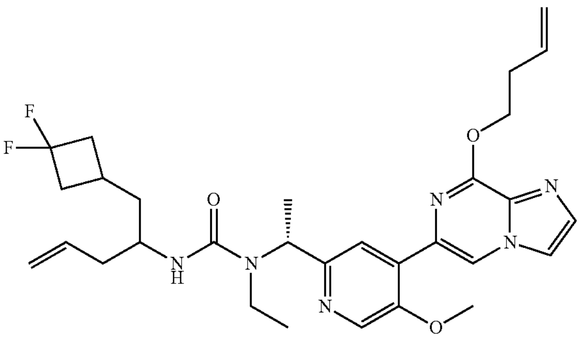 A122 | 569.4 |

TABLE A8-continued
| Intermediate C | Intermediate | Observed LC-MS (M + 1) |
|---|---|---|
| C74 | 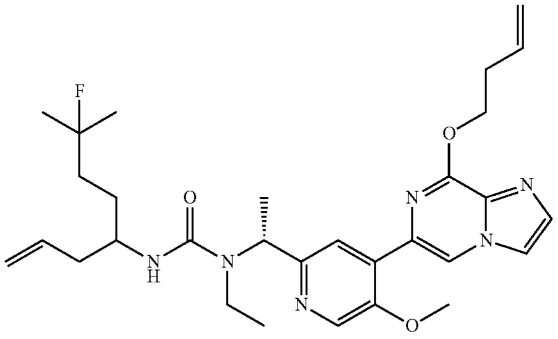 A123 | 553.5 |
| C74 | 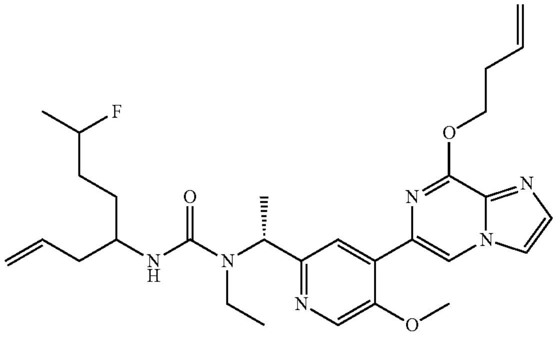 A124 | 539.4 |
| C74 | 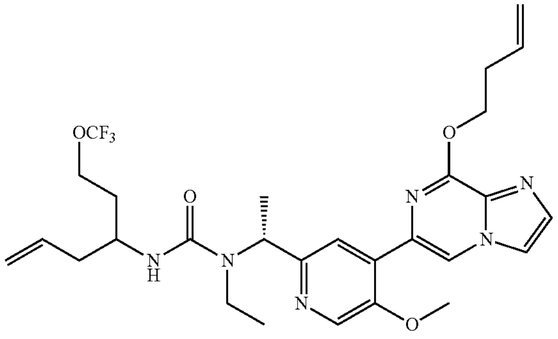 A125 | 577.4 |
| C155 | 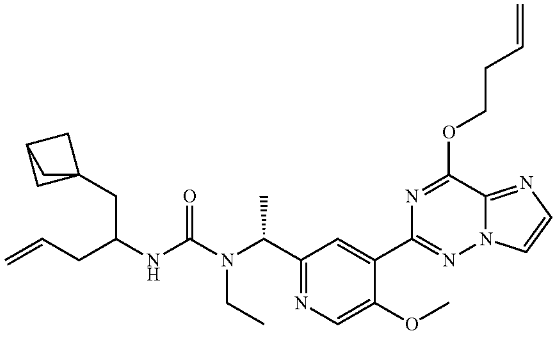 A162 | 546.2 |

TABLE A8-continued
| Intermediate C | Intermediate | Observed LC-MS (M + 1) |
|---|---|---|
| C74 | 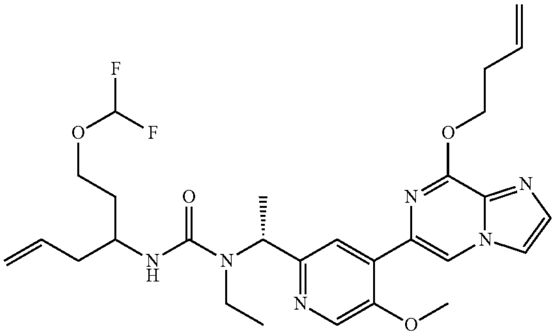 A163 | 559.4 |
| C74 | 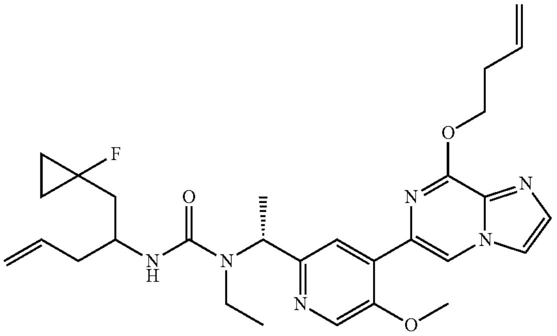 A164 | 537.5 |
| C74 | 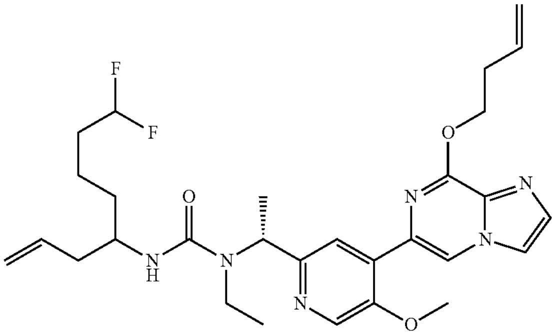 A165 | 557.4 |
| C74 | 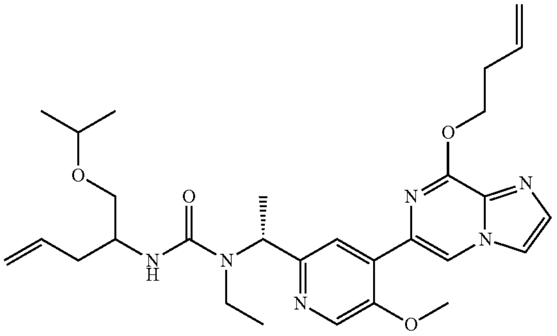 A166 | 537.5 |

TABLE A8-continued
| Intermediate C | Intermediate | Observed LC-MS (M + 1) |
|---|---|---|
| C74 | 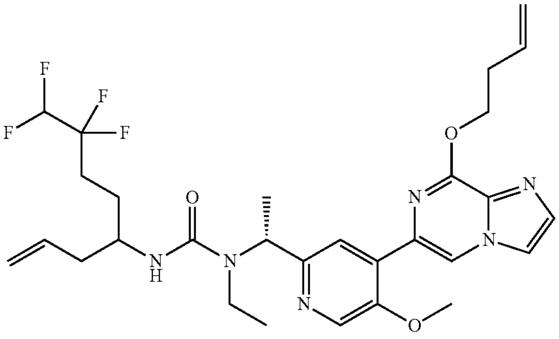 A167 | 593.4 |
| C74 | 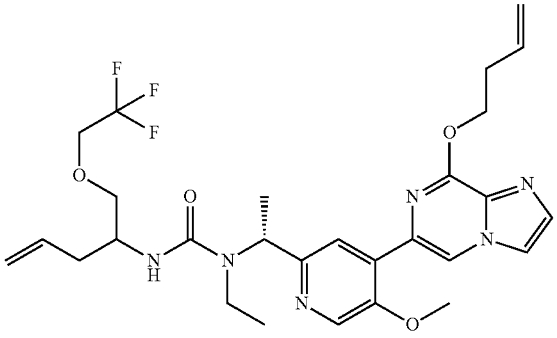 A168 | 577.4 |
| C74 | 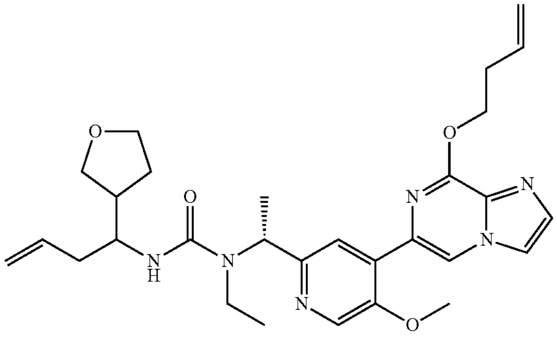 A169 | 535.4 |
| C74 | 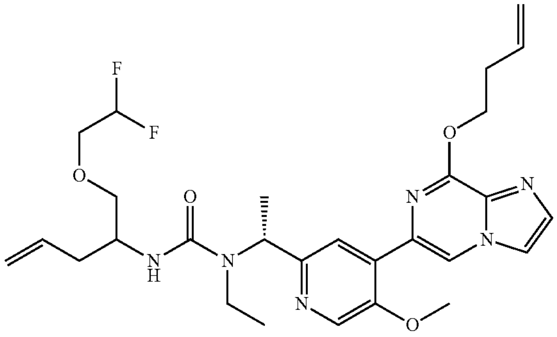 A170 | 559.4 |

TABLE A8-continued
| Intermediate C | Intermediate | Observed LC-MS (M + 1) |
|---|---|---|
| C74 | 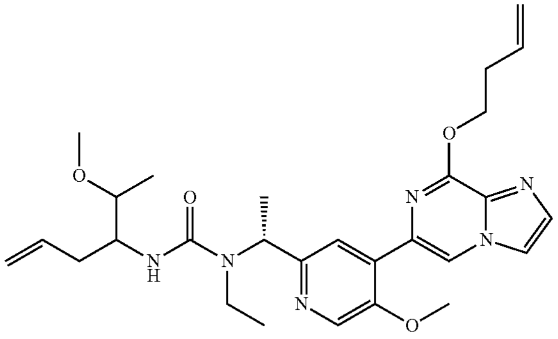 A171 | 523.5 |
| C74 | 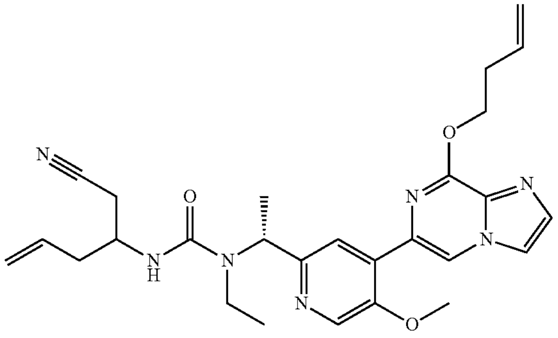 A172 | 504.4 |
| C74 | 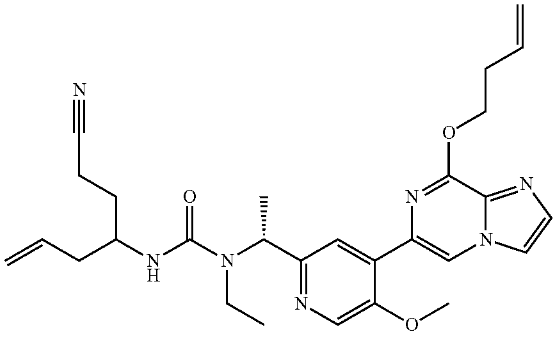 A173 | 518.5 |
| C154 | 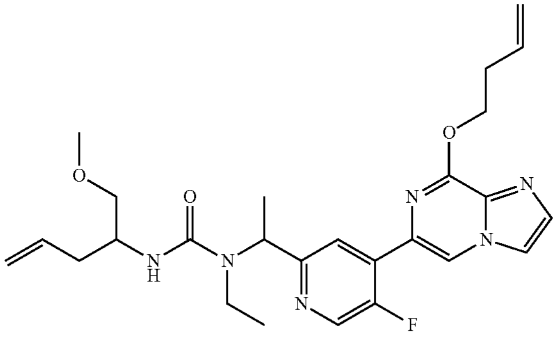 A174 | 497.4 |

Intermediate A126

(S)-7,7,7-trifluoro-4-isocyanatohept-1-ene (A126)

SCHEME A19

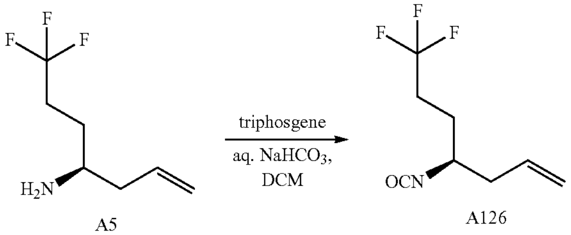

A5 A126

To a solution of (S)-7,7,7-trifluorohept-1-en-4-amine (A5, 500 mg, 2.455 mmol) in DCM (5 mL) and sat. aq. $NaHCO_3$(5 mL) was added triphosgene (240 mg, 0.810 mmol) at 0° C. and the reaction was stirred for 1 h. The reaction was poured into water (20 mL) and extracted with DCM (3×10 mL). The combined organic layers were washed with brine (10 mL), dried ($Na_2SO_4$), filtered and concentrated to afford (S)-7,7,7-trifluoro-4-isocyanatohept-1-ene (A126), which was carried forward without purification.

$^1$H NMR (400 MHz, $CDCl_3$) δ 5.87-5.72 (m, 1H), 5.27-5.16 (m, 2H), 3.60 (tt, J=4.5, 8.6 Hz, 1H), 2.46-2.06 (m, 4H), 1.88-1.61 (m, 2H).

Intermediate A133 tert-butyl (6,6-difluoro-1-(2-hydroxyethoxy)hexan-3-yl)carbamate (A133)

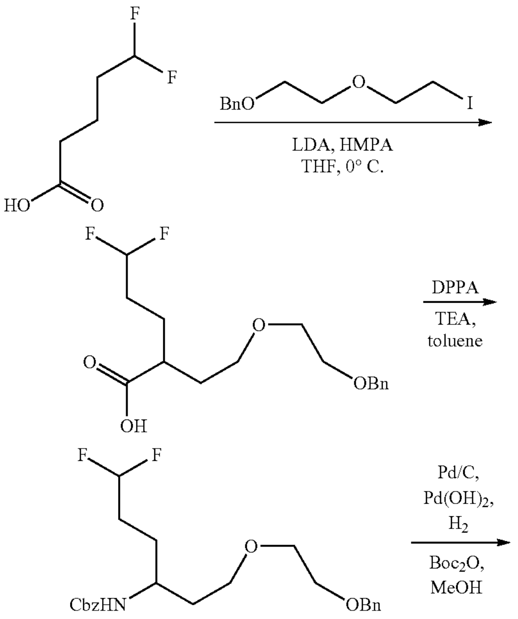

-continued

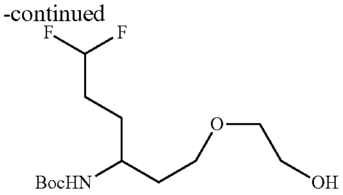

A133

To a solution of 5,5-difluoropentanoic acid (1 g, 7.24 mmol) in THF (25 mL was added LDA (10.86 mL, 21.72 mmol) (2 M in THF) at 0° C. and stirred for 30 mins.

Hexamethylphosphoramide (1.298 g, 7.24 mmol) and ((2-(2-iodoethoxy)ethoxy)methyl)benzene (2.66 g, 8.69 mmol) were added and stirred at 25° C. for 12 hours. The reaction mixture was poured into water (50 mL) and adjusted to pH=4 with 1 N HCl, extracted with EtOAc (30 mL×3). The organic layer was washed with brine (50 mL), dried over $Na_2SO_4$ and filtered. The filtrate was concentrated and purified by flash silica gel chromatography (ISCO®; 12 g SepaFlash® Silica Flash Column, eluent of [0-60]% ethyl acetate/pet. ether gradient) to give 2-(2-(2-(benzyloxy)ethoxy)ethyl)-5,5-difluoropentanoic acid.

To a solution of 2-(2-(2-(benzyloxy)ethoxy)ethyl)-5,5-difluoropentanoic acid (900 mg, 2.84 mmol) and TEA (0.793 mL, 5.69 mmol) in Toluene (10 mL) was added diphenylphosphoryl azide (940 mg, 3.41 mmol). The mixture was stirred at 100° C. for 1 h. Then phenylmethanol (923 mg, 8.53 mmol) was added and stirred at 100° C. for 16 h. LCMS showed the desired product was formed. The mixture was quenched with $H_2O$(20 mL) and extracted with EtOAC (15 mL×3), washed with brine (20 mL), dried over $Na_2SO_4$, filtered and concentrated under reduced pressure. The crude was purified by Flash silica gel chromatography (ISCO®; 4 g SepaFlash® Silica Flash Column, Eluent of 0~20% EtOAc/Pet.ether gradient) to give benzyl (1-(2-(benzyloxy)ethoxy)-6,6-difluorohexan-3-yl)carbamate. LCMS m/z (M+H): 422.2 required, 422.1 found.

To a solution of benzyl (1-(2-(benzyloxy)ethoxy)-6,6-difluorohexan-3-yl)carbamate (1 g, 2.373 mmol) in EtOAc (20 mL) were added BOC-Anhydride (0.606 mL, 2.61 mmol), $Pd(OH)_2$ (0.167 g, 0.237 mmol) and Pd-C(0.252 g, 0.237 mmol). The mixture was stirred at 25° C. under H2 (50 psi) for 12 hours. The reaction mixture was filtered, concentrated and purified by flash silica gel chromatography (ISCO®; 12 g SepaFlash® Silica Flash Column, eluent of [0-50]% ethyl acetate/pet. ether gradient) to give tert-butyl (6,6-difluoro-1-(2-hydroxyethoxy)hexan-3-yl)carbamate. LCMS m/z (M+H): 520.6 required, 520.6 found.

Intermediate A134

7,7-difluoro-4-isocyanatohept-1-ene (A134)

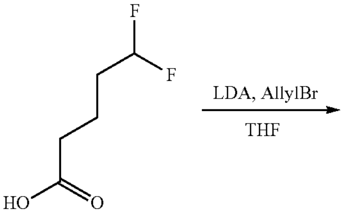

-continued

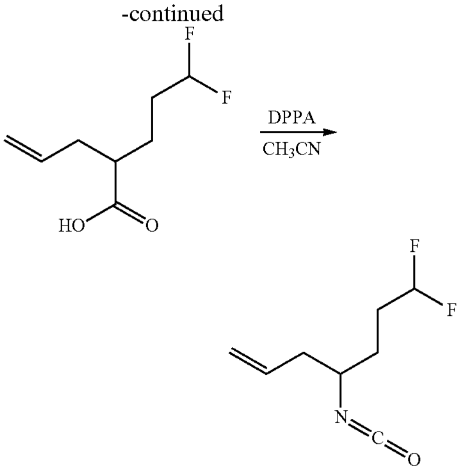

A134

To a solution of 5,5-Difluoropentanoic acid (3 g, 21.72 mmol) in THF (75 mL) was added LDA (32.6 mL, 65.2 mmol) (2 M in THF) at 0° C. and stirred at 0° C. for 1 hour. 3-bromoprop-1-ene (5.26 g, 43.4 mmol) was added and stirred at 25° C. for 2 hours. The reaction mixture was poured into water (100 mL), extracted with EtOAc (50 mL×3). The organic layer was washed with brine (50 mL), dried over $Na_2SO_4$ and filtered. The filtrate was concentrated and purified by flash silica gel chromatography (ISCO®; 4 g SepaFlash® Silica Flash Column, eluent of [0-20]% ethyl acetate/pet. ether gradient) to give 2-(3,3-difluoropropyl)pent-4-enoic acid. $^1H$ NMR (500 MHz, $CDCl_3$) δ 5.97-5.65 (m, 2H), 5.17-5.06 (m, 2H), 2.57-2.37 (m, 2H), 2.35-2.24 (m, 1H), 1.97-1.68 (m, 4H)

To a solution of 2-(3,3-difluoropropyl)pent-4-enoic acid (465 mg, 2.61 mmol) in MeCN (9 mL) were added $Et_3N$ (0.728 mL, 5.22 mmol) and diphenylphosphoryl azide (790 mg, 2.87 mmol). The mixture was stirred at 25° C. for 30 mins. The reaction mixture was concentrated to minimal MeCN and poured into silica plug, the silica plug was washed with 100 mL 10% ethyl acetate/Pet. ether. The filtrate was concentrated and taken up in 9 mL dry acetonitrile under $N_2$ and heated to 85° C. for 1 hr. The mixture of 7,7-difluoro-4-isocyanatohept-1-ene A134 which was used crude directly.

Intermediate A135

2-((3-amino-6,6-difluoroheptyl)oxy)ethan-1-ol (A135)

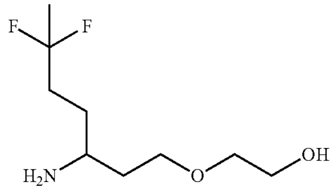

2-((3-amino-6,6-difluoroheptyl)oxy)ethan-1-ol was prepared according to the method described for A133 starting with ethyl 5,5-difluorohexanoate, and not including $Boc_2O$ in the last step. LCMS m/z (M+H): 212.2 required, 212.2 found.

To a solution of ethyl 4-acetylbutyrate (15 g, 95 mmol) in DCM (350 mL) was added Bis(2-methoxyethyl)aminosulfur trifluoride (43.7 mL, 237 mmol). The mixture was stirred at 50° C. for 12 h. The mixture was quenched with $H_2O$(500 mL) and extracted with DCM (300 mL×3), washed with brine (300 mL), dried over $Na_2SO_4$, filtered and concentrated under reduced pressure. The crude was purified by Flash silica gel chromatography (ISCO®; 120 g SepaFlash® Silica Flash Column, Eluent of 10% EtOAc/Pet. ether gradient) to give ethyl 5,5-difluorohexanoate. $^1H$ NMR (400 MHz, $CDCl_3$) δ=4.16-4.06 (m, 2H), 2.33 (br t, J=7.1 Hz, 2H), 1.92-1.52 (m, 7H), 1.27-1.20 (m, 3H)

Intermediate A136 tert-butyl (6,6,6-trifluoro-1-(2-hydroxyethoxy)hexan-3-yl)carbamate (A136)

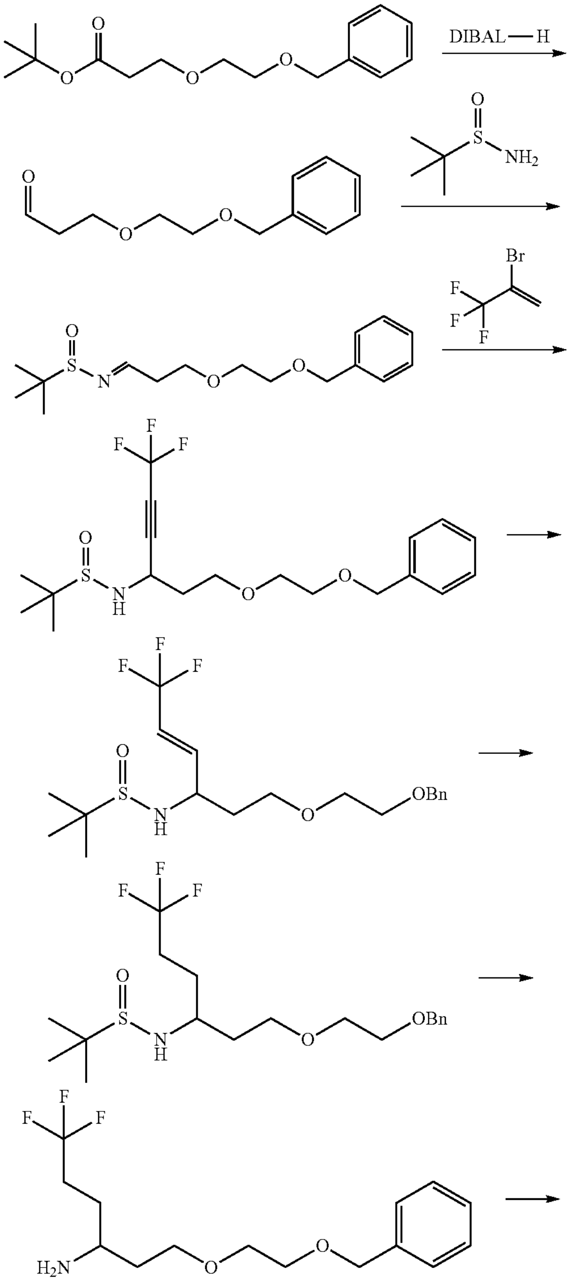

-continued

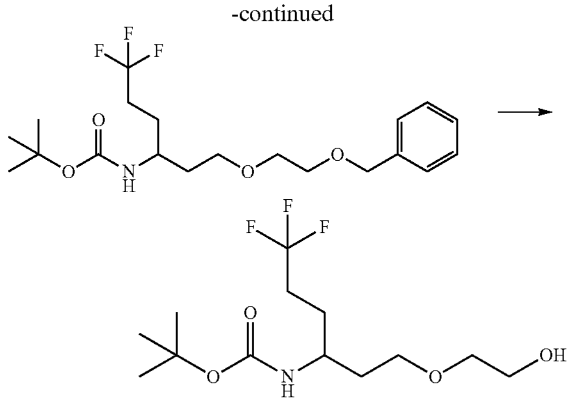

A136

To a solution of tert-butyl 3-(2-(benzyloxy)ethoxy)propanoate (15 g, 53.5 mmol) in DCM (300 ml) was added DIBAL-H (80 ml, 80 mmol) (1M in toluene). The mixture was stirred at −78° C. for 1 h. The reaction mixture was poured into water (600 mL), extracted with EtOAc (300 mL×3). The organic phases was dried over $Na_2SO_4$ and filtered. The filtrate was concentrated to give 3-(2-(benzyloxy)ethoxy)propanal which was used to the next step without further purification. LCMS m/z (M+H): 209.2 required, 209.2 found.

To a solution of 3-(2-(benzyloxy)ethoxy)propanal (13 g, 62.4 mmol) in DCE (300 ml) was added $MgSO_4$ (45.1 g, 375 mmol), 2-methylpropane-2-sulfinamide (9.08 g, 74.9 mmol) and PPTS (1.569 g, 6.24 mmol). The resulting mixture was stirred at 80° C. under N2 protection for 12 h. The reaction mixture was concentrated and purified by flash silica gel chromatography (ISCO®; 120 g SepaFlash® Silica Flash Column, eluent of 60% ethyl acetate/pet. ether gradient) to give (E)-N-(3-(2-(benzyloxy)ethoxy)propylidene)-2-methylpropane-2-sulfinamide. LCMS m/z (M+H): 312.1 required, 312.1 found.

To a solution of 2-bromo-3,3,3-trifluoroprop-1-ene (6.07 g, 34.7 mmol) in THF (200 ml) was added LDA (34.7 ml, 69.4 mmol) (2M in THF) at −78° C. after the reaction mixture was stirred for 30 minutes at −78° C., (E)-N-(3-(2-(benzyloxy)ethoxy)propylidene)-2-methylpropane-2-sulfinamide (9 g, 28.9 mmol) was added, the reaction mixture was continued to stirred at −78° C. for 2 h. The reaction mixture was poured into $NH_4Cl$ (600 mL), extracted with EtOAc (300 mL×3). The organic layer was dried over $Na_2SO_4$ and filtered. The filtrate was concentrated and purified by flash silica gel chromatography (ISCO®; 120 g SepaFlash® Silica Flash Column, eluent of 60% ethyl acetate/pet. ether gradient) to give N-(1-(2-(benzyloxy)ethoxy)-6,6,6-trifluorohex-4-yn-3-yl)-2-methylpropane-2-sulfinamide. LCMS m/z (M+H): 406.1 required, 406.1 found.

To a solution of N-(1-(2-(benzyloxy)ethoxy)-6,6,6-trifluorohex-4-yn-3-yl)-2-methylpropane-2-sulfinamide (6 g, 14.80 mmol) in MeOH (100 ml) were added Pd-C(1.575 g, 1.480 mmol) (10% wt) and dihydroxypalladium (1.039 g, 1.480 mmol) (20% wt). The solution was stirred at 25° C. for 10 h under dihydrogen (excess) 15 psi. The mixture was filtered and concentrated to give (E)-N-(1-(2-(benzyloxy)ethoxy)-6,6,6-trifluorohex-4-en-3-yl)-2-methylpropane-2-sulfinamide which was used to the next step without further purification. LCMS m/z (M+H): 408.1 required, 408.1 found.

To a solution of (E)-N-(1-(2-(benzyloxy)ethoxy)-6,6,6-trifluorohex-4-en-3-yl)-2-methylpropane-2-sulfinamide (5.5 g, 13.50 mmol) in MeOH (80 mL) was added nickel (3.96 g, 67.5 mmol). The solution was stirred at 25° C. for 12 h under dihydrogen (excess) 15 psi. The mixture was filtered and concentrated to give N-(1-(2-(benzyloxy)ethoxy)-6,6,6-trifluorohexan-3-yl)-2-methylpropane-2-sulfinamide which was used to the next step without further purification. LCMS m/z (M+H): 410.1 required, 410.1 found.

To a solution of N-(1-(2-(benzyloxy)ethoxy)-6,6,6-trifluorohexan-3-yl)-2-methylpropane-2-sulfinamide (5.5 g, 13.43 mmol) in MeOH (80 mL) was added AcCl (1.910 mL, 26.9 mmol). The reaction was stirred at 20° C. for 2 h. The mixture was concentrated under reduced pressure and freeze-dried to give 1-(2-(benzyloxy)ethoxy)-6,6,6-trifluorohexan-3-amine which was used to the next step without further purification. LCMS m/z (M+H): 306.1 required, 306.1 found.

To a solution of 1-(2-(benzyloxy)ethoxy)-6,6,6-trifluorohexan-3-amine (4 g, 13.10 mmol) in DCM (80 mL) was added $Et_3N$ (5.48 mL, 39.3 mmol) and BOC-Anhydride (4.56 mL, 19.65 mmol) at 0° C. The reaction was stirred at 0° C. to 25° C. for 12 h. The mixture was quenched with $H_2O$(150 mL) and extracted with DCM (100 mL*3), washed with brine (50 mL), dried over $Na_2SO_4$, filtered and concentrated under reduced pressure. The crude product was purified by Flash silica gel chromatography (ISCO®; 40 g SepaFlash® Silica Flash Column, Eluent of 20% EtOAc/Pet.ether gradient) to give tert-butyl (1-(2-(benzyloxy)ethoxy)-6,6,6-trifluorohexan-3-yl)carbamate. LCMS m/z (M-100+H): 306.1 required, 306.1 found.

To a solution of tert-butyl (1-(2-(benzyloxy)ethoxy)-6,6,6-trifluorohexan-3-yl)carbamate (2 g, 4.93 mmol) in MeOH (50 ml) was added Raney nickel (1.448 g, 24.66 mmol). The solution was stirred at 25° C. for 24 h under H2 at 50 psi. The mixture was filtered and concentrated and the crude was purified by flash silica gel chromatography (ISCO®; 40 g SepaFlash® Silica Flash Column, eluent of 85% ethyl acetate/pet. ether gradient) to give tert-butyl (6,6,6-trifluoro-1-(2-hydroxyethoxy)hexan-3-yl)carbamate A136. LCMS m/z (M-Boc+H): 216.2 required, 216.1 found. $^1$H NMR (400 MHz, CHLOROFORM-d) δ=4.45 (br d, J=9.4 Hz, 1H), 3.89-3.72 (m, 1H), 3.68-3.50 (m, 3H), 3.50-3.36 (m, 3H), 2.74 (br s, 1H), 2.21-1.97 (m, 3H), 1.87-1.61 (m, 3H), 1.57-1.35 (m, 12H), 1.32-1.16 (m, 1H)

Intermediate A137 tert-butyl (6,6-difluoro-1-(2-hydroxyethoxy)heptan-3-yl) carbamate (A137)

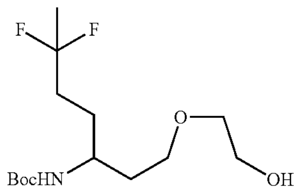 [SMILES: CC(F)(F)CCC(CCOCCO)NC(=O)OC(C)(C)C]

tert-butyl (6,6-difluoro-1-(2-hydroxyethoxy)heptan-3-yl) carbamate was prepared according to the method described for A133 starting with ethyl 5,5-difluorohexanoate. LCMS m/z (M-100+H): 212.2 required, 212.2 found.

Intermediate A138

2-methyl-N-(6,6,6-trifluoro-1-(2-hydroxyethoxy)hexan-3-yl)propane-2-sulfinamide (A138)

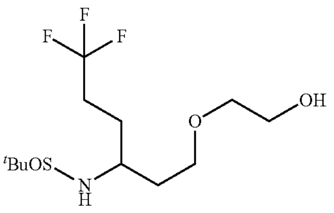

To a solution of N-(1-(2-(benzyloxy)ethoxy)-6,6,6-trifluorohexan-3-yl)-2-methylpropane-2-sulfinamide (100 mg, 0.244 mmol) in DCM (1 ml) was added $BCl_3$ (0.118 ml, 0.733 mmol) and the solution was stirred at 20° C. for 3 h. The mixture was quenched with MeOH (1 mL) and concentrated to give 2-methyl-N-(6,6,6-trifluoro-1-(2-hydroxyethoxy)hexan-3-yl)propane-2-sulfinamide A138. LCMS m/z (M+H): 320.0 required, 320.0 found.

Intermediate A139

(S)-1-(2-((tert-butyldimethylsilyl)oxy)ethoxy)-6,6,6-trifluorohexan-3-amine (A139)

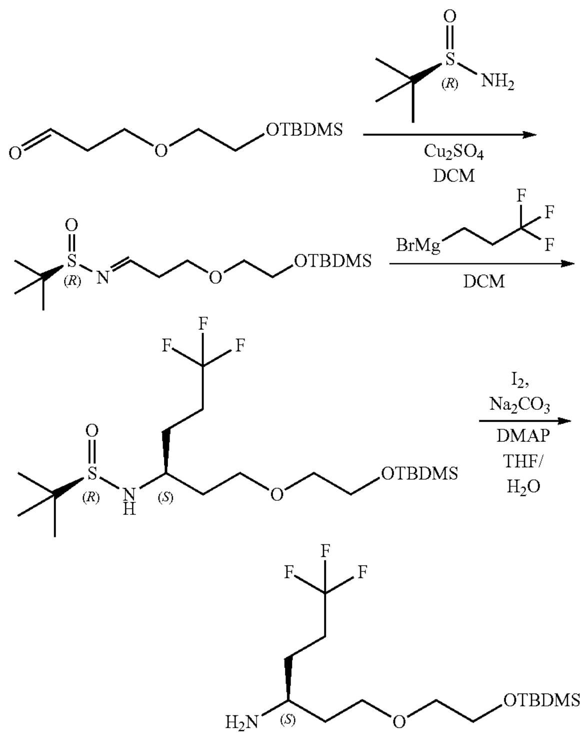

A139

Step 1: (R,E)-N-(3-(2-((tert-butyldimethylsilvl)oxy)ethoxy)propylidene)-2-methylpropane-2-sulfinamide To a solution of 3-(2-((tert-butyldimethylsilyl)oxy)ethoxy)propanal (6.15 g, 26.5 mmol) in dichloromethane (60 mL) were added (R)-2-methylpropane-2-sulfinamide (4.81 g, 39.7 mmol) and copper(II)sulfate (12.7 g, 79.0 mmol). The reaction mixture was stirred at ambient temperature for 48 hours. The reaction was diluted with dichloromethane and filtered through a pad of Celite and concentrated. The crude material was purified by flash silica chromatography (0-25% EtOAc in heptane gradient) to give (R,E)-N-(3-(2-((tert-butyldimethylsilyl)oxy)ethoxy)propylidene)-2-methylpropane-2-sulfinamide.

Step 2: (R)—N—((S)-1-(2-((tert-butyldimethylsilvl)oxy)ethoxy)-6,6,6-trifluorohexan-3-yl)-2-methylpropane-2-sulfinamide To a solution of (R,E)-N-(3-(2-((tert-butyldimethylsilyl)oxy)ethoxy)propylidene)-2-methylpropane-2-sulfinamide (6.45 g, 19.2 mmol) in dichloromethane (100 mL) at 0° C. was slowly added a 0.5M solution of (3,3,3-trifluoropropyl)magnesium bromide in diethyl ether (148 mL, 74.0 mmol). The mixture was stirred at 0° C. for 4 hours and then quenched with saturated aqueous ammonium chloride (300 mL) and extracted with EtOAc (3×100 mL). The combined organic layers were dried ($MgSO_4$), filtered and concentrated. The crude material was purified by flash silica chromatography (0-50% EtOAc in heptane gradient) to give (R)—N—((S)-1-(2-((tert-butyldimethylsilyl)oxy)ethoxy)-6,6,6-trifluorohexan-3-yl)-2-methylpropane-2-sulfinamide.

Step 3: (S)-1-(2-((tert-butyldimethylsilyl)oxy)ethoxy)-6,6,6-trifluorohexan-3-amine (A139)

To a solution of (R)—N—((S)-1-(2-((tert-butyldimethylsilyl)oxy)ethoxy)-6,6,6-trifluorohexan-3-yl)-2-methylpropane-2-sulfinamide (3.50 g, 8.07 mmol) in tetrahydrofuran (80 mL) and water (80 mL) were added sodium carbonate (2.57 g, 24.2 mmol) and DMAP (0.197 g, 1.61 mmol). The reaction mixture was stirred until the solids dissolved and then iodine (5.12 g, 20.2 mmol) was added. The reaction mixture was stirred at ambient temperature for 18 hours. The reaction was quenched by the addition of saturated aqueous sodium thiosulfate (25 mL). The mixture was poured into water (50 mL) and extracted with DCM (3×50 mL). The combined organic layers were dried ($Na_2SO_4$), filtered and concentrated. The crude material was purified by flash silica chromatography (0-100% EtOAc/EtOH 3:1 mix in heptane gradient) to give (S)-1-(2-((tert-butyldimethylsilyl)oxy)ethoxy)-6,6,6-trifluorohexan-3-amine. LC-MS: 330.3 (M+1)

Intermediate A140

6,6-difluorohept-1-en-4-amine (A140)

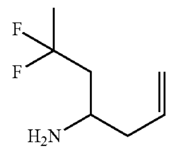

To a solution of LDA (22.57 ml, 45.1 mmol) (2 M in THF) in THF (50 ml) was added ethyl 4,4-difluoropentanoate (5 g, 30.1 mmol) at −78° C. and stirred at −78° C. for 30 mins. 3-bromoprop-1-ene (23.64 ml, 33.1 mmol) was added to the above mixture and stirred at −78° C. to 20° C. for 12 h. The mixture was quenched with $NH_4Cl$ (200 mL) and extracted with EtOAc, washed with brine (50 mL), dried over $Na_2SO_4$, filtered and concentrated under reduced pressure. The crude was purified by prep-TLC (silica, Pet. ether/EtOAc=5:1) to give ethyl 2-(2,2-difluoropropyl)pent-4-enoate. LCMS m/z (M+H): 207.1 required, 207.1 found.

To a solution of ethyl 2-(2,2-difluoropropyl)pent-4-enoate (2.62 g, 12.70 mmol) in EtOH (50 ml) and Water (20.00 ml) was added sodium hydroxide (1.524 g, 38.1 mmol). The reaction was stirred at 20° C. for 12 h. The mixture was quenched with 1M HCl to adjust pH=3 and extracted with EtOAc, washed with brine (50 mL), dried over $Na_2SO_4$, filtered and concentrated under reduced pressure to give 2-(2,2-difluoropropyl)pent-4-enoic acid. LCMS m/z (M+H): 179.1 required, 179.1 found.

To a solution of 2-(2,2-difluoropropyl)pent-4-enoic acid (1.9 g, 10.66 mmol) and triethylamine (2.97 ml, 21.33 mmol) in Toluene (50 ml) was added diphenyl phosphorazidate (3.52 g, 12.80 mmol). The mixture was stirred at 100° C. for 1 h. Then phenylmethanol (3.46 g, 32.0 mmol) was added and stirred at 100° C. for 12 h. The mixture was quenched with $H_2O$(30 mL) and extracted with EtOAc (20 mL*3), washed with brine (30 mL), dried over $Na_2SO_4$, filtered and concentrated under reduced pressure. The crude was purified by Flash silica gel chromatography (ISCO®; 4 g SepaFlash® Silica Flash Column, Eluent of 20% EtOAc/Pet.ether gradient) to give benzyl (6,6-difluorohept-1-en-4-yl)carbamate. LCMS m/z (M+H): 284.1 required, 325.2 found [+MeCN]

A mixture of benzyl (6,6-difluorohept-1-en-4-yl)carbamate (500 mg, 1.765 mmol) and hydrogen chloride (10 mL, 60.0 mmol)(6M in water) was stirred at 100° C. for 16 h. The mixture was concentrated to give 6,6-difluorohept-1-en-4-amine, which was used without further purification. LCMS m/z (M+H): 150.1 required, 150.2 found.

Intermediate A141

2-((3-amino-6,6,6-trifluorohexyl)oxy)ethan-1-ol (A141)

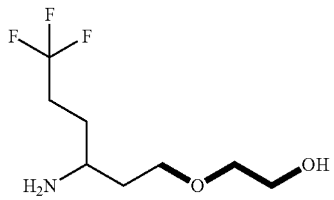

To a solution of tert-butyl (6,6,6-trifluoro-1-(2-hydroxyethoxy)hexan-3-yl)carbamate A136 (500 mg, 1.586 mmol) was added TFA (2 ml) at 0° C. The mixture was stirred at 25° C. for 1 h. The mixture was concentrated under reduced pressure and freeze-dried to give 2-((3-amino-6,6,6-trifluorohexyl)oxy)ethan-1-ol. LCMS m/z (M+H): 216.2 required, 216.1 found.

Intermediate A142

(S)-1-(3-((tert-butyldimethylsilyl)oxy)propoxy)-5,5,5-trifluoropentan-2-amine (A142)

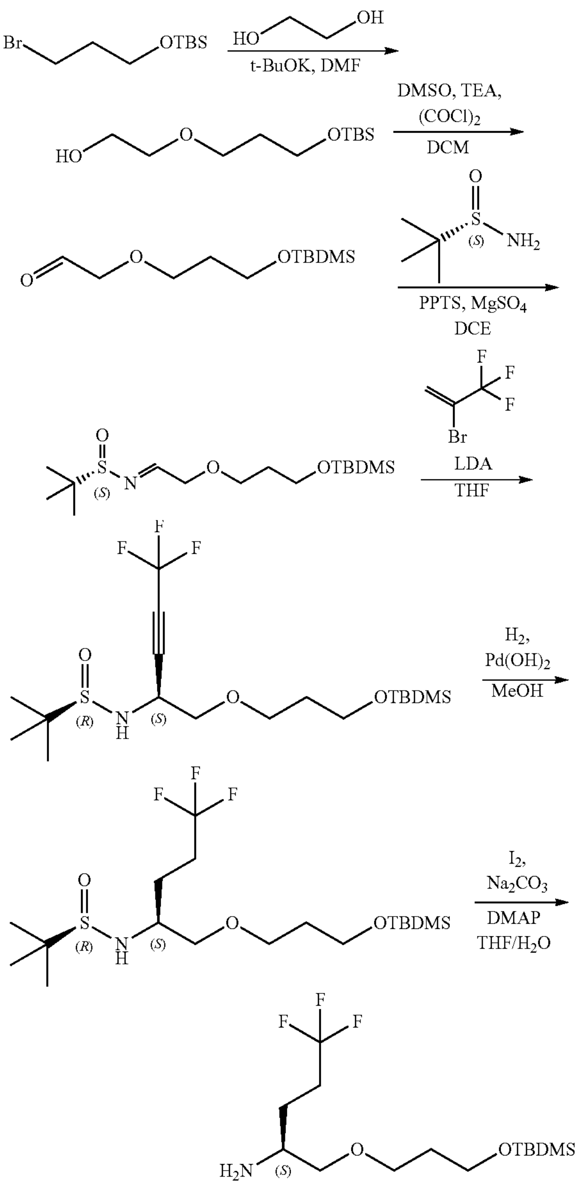

A142

Step 1: 2-(3-((tert-butyldimethylsilyl)oxy)propoxy)ethan-1-ol

To a solution of ethylene glycol (490 g, 7.90 mol) in DMF (2000 mL) at 0° C. was added potassium tert-butoxide (266 g, 2.34 mol). The reaction mixture was stirred at 0° C. for 0.5 hours, then (3-bromopropoxy)(tert-butyl)dimethylsilane (200 g, 790 mmol) was added. The reaction was stirred at 20° C. for 12 hours, then poured onto water (1000 mL) and extracted with MTBE (3×500 mL). The combined organic layers were washed with brine (2×500 mL), dried ($Na_2SO_4$), filtered and concentrated. The crude material was purified by flash silica chromatography (2-50% EtOAc in pet ether gradient). The crude material was purified by flash silica chromatography (0-25% EtOAc in heptane gradient) to give 2-(3-((tert-butyldimethylsilyl)oxy)propoxy)ethan-1-ol. $^1$H NMR: (400 MHz, $CDCl_3$) δ 3.69-3.73 (m, 4H), 3.53-3.59 (m, 4H), 2.00 (s, 1H), 1.75-1.82 (m, 2H), 0.891 (s, 9H), 0.049 (s, 6H).

Step 2: 2-(3-((tert-butyldimethylsilyl)oxy)propoxy) acetaldehyde

To a solution of DMSO (164 g, 2.10 mol) in dichloromethane (1120 mL) was added oxalyl chloride (133 g, 1.05 mol) at −78° C. The reaction mixture was stirred at −78° C. for 1 hour, then 2-(3-((tert-butyldimethylsilyl)oxy) propoxy)ethan-1-ol (112 g, 480 mmol) was added. The reaction was stirred at −78° C. for 2 hours. Triethylamine (242 g, 2.39 mol) was added at −78° C. and then the reaction was warmed to 20° C. for 1 hour. The reaction was poured onto ice water (400 mL) and extracted with PE (3×400 mL). The combined organic layers were washed with brine (2×400 mL), dried ($Na_2SO_4$), filtered and concentrated to give 2-(3-((tert-butyldimethylsilyl)oxy)propoxy)acetaldehyde, which was used without further purification.

Step 3: (S,E)-N-(2-(3-((tert-butyldimethylsilvl)oxy) propoxy)ethylidene)-2-methylpropane-2-sulfinamide To a solution of 2-(3-((tert-butyldimethylsilyl)oxy) propoxy)acetaldehyde (81.0 g, 348 mmol) in dichloroethane (1620 mL) were added (S)-2-methylpropane-2-sulfinamide (63.4 g, 523 mmol), PPTS (4.38 g, 17.4 mmol), and magnesium sulfate (168 g, 1390 mmol). The reaction mixture was stirred at 60° C. for 16 hours. The reaction was filtered and concentrated. The crude material was purified by flash silica chromatography (2-50% EtOAc in pet ether gradient) to give (S,E)-N-(2-(3-((tert-butyldimethylsilyl)oxy) propoxy)ethylidene)-2-methylpropane-2-sulfinamide. $^1$H NMR (400 MHz, $CDCl_3$) δ 8.09 (t, J=3.6 Hz, 1H), 4.34-4.36 (m, 2H), 3.69-3.73 (m, 2H), 3.60-3.64 (m, 2H), 1.79-1.85 (m, 2H), 1.21 (s, 9H), 0.89 (s, 9H), 0.04 (s, 6H).

Step 4: (R)—N—((S)-1-(3-((tert-butyldimethylsilvl) oxy)propoxy)-5,5,5-trifluoropent-3-yn-2-yl)-2-methylpropane-2-sulfinamide To a solution of LDA (2.5M, 41.7 mmol, 104 mmol) in tetrahydrofuran (60 mL) at −78° C. was slowly added a solution of 2-bromo-3,3,3-trifluoroprop-1-ene (10.9 g, 62.6 mmol) tetrahydrofuran (60 mL). The mixture was stirred at −78° C. for 0.5 hours and then (S,E)-N-(2-(3-((tert-butyldimethylsilyl)oxy)propoxy)ethylidene)-2-methylpropane-2-sulfinamide was added over 0.5 hours. The reaction mixture was warmed to 20° C. for 0.5 hours, and then poured into ice water (200 mL) and extracted with EtOAc (3×200 mL). The combined organic layers were dried ($Na_2SO_4$), filtered and concentrated. The crude material was purified by flash silica chromatography (2-50% EtOAc in pet ether gradient) to give (R)—N—((S)-1-(3-((tert-butyldimethylsilyl)oxy) propoxy)-5,5,5-trifluoropent-3-yn-2-yl)-2-methylpropane-2-sulfinamide. $^1$HNMR (400 MHz, $CDCl_3$) δ 4.41 (s, 1H), 3.70-3.87 (m, 1H), 3.58-3.70 (m, 6H), 1.74-1.81 (m, 2H), 1.24 (s, 9H), 0.88 (s, 9H), 0.04 (s, 6H).

Step 5: (R)—N—((S)-1-(3-((tert-butyldimethylsilvl) oxy)propoxy)-5,5,5-trifluoropentan-2-yl)-2-methylpropane-2-sulfinamide To a suspension of 20% palladium hydroxide (6.86 g, 48.9 mmol) in methanol (140 mL) was added (R)—N—((S)-1-(3-((tert-butyldimethylsilyl)oxy)propoxy)-5,5,5-trifluoropent-3-yn-2-yl)-2-methylpropane-2-sulfinamide (7.00 g, 16.0 mmol). The mixture was stirred under a hydrogen atmosphere at 30 psi for 12 hours. The reaction mixture was filtered and concentrated to give (R)—N—((S)-1-(3-((tert-butyldimethylsilyl)oxy)propoxy)-5,5,5-trifluoropentan-2-yl)-2-methylpropane-2-sulfinamide. $^1$H NMR (400 MHz, $CDCl_3$) δ 3.65-3.69 (m, 3H), 3.53-3.57 (m, 4H), 3.39-3.51 (m, 1H), 1.81-1.83 (m, 2H), 1.75-1.80 (m, 4H), 1.22 (s, 9H), 0.88 (s, 9H), 0.04 (s, 6H).

Step 6: (S)-1-(3-((tert-butyldimethylsilyl)oxy) propoxy)-5,5,5-trifluoropentan-2-amine (A142)

To a solution of (R)—N—((S)-1-(3-((tert-butyldimethylsilyl)oxy)propoxy)-5,5,5-trifluoropentan-2-yl)-2-methylpropane-2-sulfinamide (5.15 g, 11.9 mmol) in tetrahydrofuran (60 mL) and water (60 mL) were added sodium carbonate (3.78 g, 35.6 mmol) and DMAP (0.290 g, 2.38 mmol). The reaction mixture was stirred until the solids dissolved and then iodine (7.54 g, 29.7 mmol) was added. The reaction mixture was stirred at ambient temperature for 16 hours. The mixture was poured into saturated aqueous sodium sulfite (50 mL) and extracted with EtOAc (3×50 mL). The combined organic layers were dried ($Na_2SO_4$), filtered and concentrated. The crude material was purified by flash silica chromatography (0-100% EtOAc/EtOH 3:1 mix in hexanes gradient) to give (S)-1-(3-((tert-butyldimethylsilyl)oxy)propoxy)-5,5,5-trifluoropentan-2-amine. LC-MS: 330.3 (M+1).

Intermediate A143

1-(2-((tert-butyldimethylsilyl)oxy)ethoxy)-6,6-difluoroheptan-3-amine (A143)

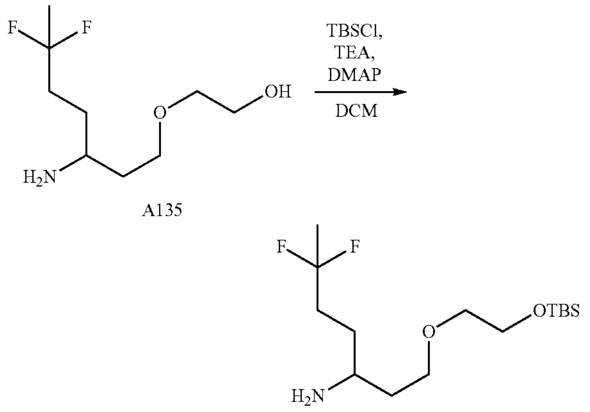

A135

A143

To a solution of 2-((3-amino-6,6-difluoroheptyl)oxy) ethan-1-ol (850 mg, 4.02 mmol) in DCM (20 mL) were added triethylamine (1.68 mL, 12.1 mmol), DMAP (246 mg, 2.01 mmol) and TBS-Cl(1030 mg, 6.84 mmol). The reaction was stirred at 35° C. for 48 hours. The mixture was quenched with $H_2O$(20 mL) and extracted with DCM (20 mL×3), washed with brine (10 mL), dried over $Na_2SO_4$, filtered and concentrated under reduced pressure. The crude was purified by Flash silica gel chromatography (ISCO®; 12 g SepaFlash® Silica Flash Column, (eluent of 100% EtOAc in a pet.ether gradient) to give 1-(2-((tert-butyldimethylsilyl)

oxy)ethoxy)-6,6-difluoroheptan-3-amine (A143). LCMS m/z (M+H): 326.2 required, 326.3 found. $^1$H NMR (400 MHz, $CD_3OD$) δ 3.79-3.74 (m, 2H), 3.66-3.48 (m, 4H), 2.93-2.86 (m, 1H), 2.04-1.80 (m, 2H), 1.76-1.68 (m, 1H), 1.66-1.45 (m, 6H), 0.91 (s, 9H), 0.08 (s, 6H).

Intermediate A144

(S)-1-(3-((tert-butyldimethylsilyl)oxy)propoxy)-5,5-difluorohexan-2-amine (A144)

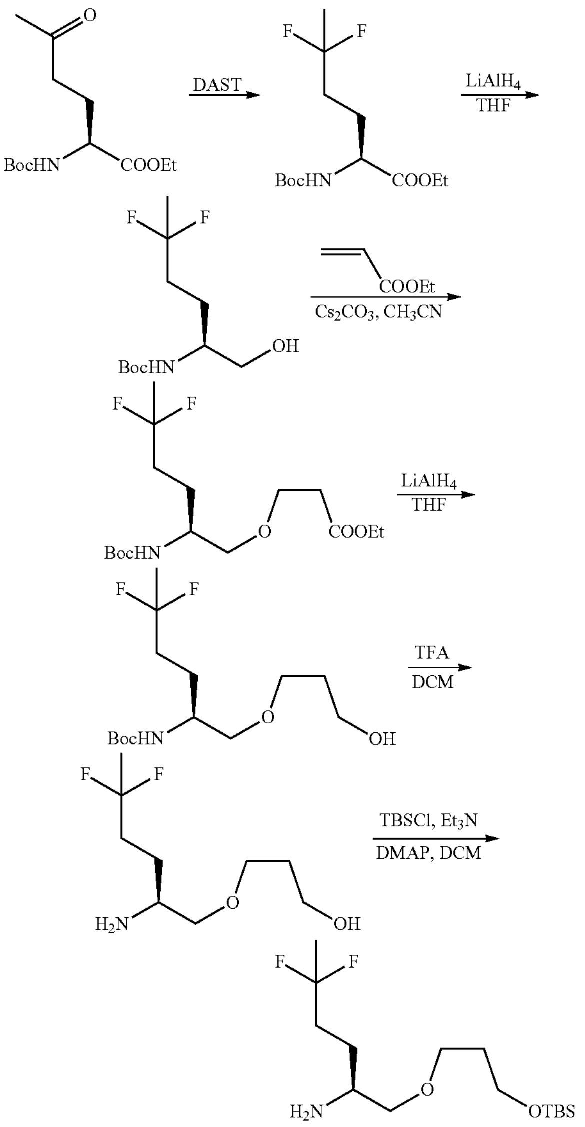

A144

A mixture of ethyl (S)-2-((tert-butoxycarbonyl)amino)-5-oxohexanoate (2.00 g, 7.32 mmol) and DAST (10.0 mL, 76.0 mmol) was stirred at 15° C. for 16 hours. The reaction mixture was poured into saturated aqueous $NaHCO_3$(200 mL), extracted with DCM (3×50 mL), and washed with brine (50 mL). The organic layer was dried over $Na_2SO_4$, filtered and the filtrate was concentrated. The residue was purified by flash silica gel chromatography (ISCO®; 20 g SepaFlash® Silica Flash Column, eluent of 30% ethyl acetate/pet. ether gradient) to give ethyl (S)-2-((tert-butoxycarbonyl)amino)-5,5-difluorohexanoate. LCMS m/z (M+H-Boc): 196.1 required, 196.1 found. $^1$H NMR (400 MHz, $CDCl_3$) δ 8.92 (br s, 1H), 4.46-4.02 (m, 3H), 3.23-2.91 (m, 1H), 2.07-1.80 (m, 3H), 1.60 (br t, J=18.3 Hz, 3H), 1.49-1.44 (s, 9H), 1.30 (br t, J=7.1 Hz, 3H).

To a stirred solution of $LiAlH_4$ (1.00 g, 26.3 mmol) in THF (80 mL) was added ethyl (S)-2-((tert-butoxycarbonyl)amino)-5,5-difluorohexanoate (7.00 g, 23.7 mmol) in THF (20 mL) at 0° C. The reaction was allowed to stir for 1 hour at 0° C. The reaction was diluted with $H_2O$(1 mL), NaOH (15%, 1 mL), $H_2O$(3 mL) and dried over $MgSO_4$, filtered, and the filtrate was concentrated to give tert-butyl (S)-(5,5-difluoro-1-hydroxyhexan-2-yl)carbamate, which was used in the next step directly. LCMS m/z (M+H): 254.1 required, 254.1 found. $^1$H NMR (400 MHz, $CDCl_3$) δ 4.74 (br s, 1H), 3.72-3.54 (m, 3H), 2.35-2.20 (m, 1H), 1.93 (dtd, J=6.6, 9.9, 16.1 Hz, 2H), 1.81-1.70 (m, 1H), 1.66-1.55 (m, 3H), 1.45 (s, 9H).

To a mixture of tert-butyl (S)-(5,5-difluoro-1-hydroxyhexan-2-yl)carbamate (5.50 g, 21.7 mmol) and $Cs_2CO_3$ (14.2 g, 43.4 mmol) in MeCN (60 mL) was added ethyl acrylate (11.8 mL, 109 mmol). The mixture was stirred at 15° C. for 5 hours. $H_2O$(50 mL) was added to the mixture, extracted with EtOAc (50 mL×3). The organic layer was washed with brine (50 mL), dried over $Na_2SO_4$ and filtered. The filtrate was concentrated and purified by flash silica gel chromatography (ISCO®; 80 g SepaFlash® Silica Flash Column, eluent of (0-20% ethyl acetate/pet. ether gradient) to give ethyl (S)-3-((2-((tert-butoxycarbonyl)amino)-5,5-difluorohexyl)oxy)propanoate. LCMS m/z (M+H-Boc): 254.1 required, 254.1 found. $^1$H NMR (400 MHz, $CDCl_3$) δ 4.77 (br s, 1H), 4.21-4.12 (m, 2H), 3.73 (t, J=6.1 Hz, 2H), 3.52-3.39 (m, 2H), 2.57 (t, J=6.2 Hz, 2H), 1.97-1.84 (m, 2H), 1.77-1.63 (m, 2H), 1.60-1.55 (m, 3H), 1.45 (s, 9H), 1.31-1.26 (m, 3H).

To a stirred solution of $LiAlH_4$ (500 mg, 13.2 mmol) in THF (30 mL) was added ethyl (S)-3-((2-((tert-butoxycarbonyl)amino)-5,5-difluorohexyl)oxy)propanoate (3.50 g, 9.90 mmol) in THF (10 mL) at 0° C. The reaction was allowed to stir for 1 hour at 0° C. The reaction was diluted with $H_2O$(0.5 mL), NaOH (15%, 0.5 mL), $H_2O$(1.5 mL) and dried over $MgSO_4$, filtered and the filtrate was concentrated to give tert-butyl (S)-(5,5-difluoro-1-(3-hydroxypropoxy)hexan-2-yl)carbamate, which was used in the next step directly.

To a stirred solution of tert-butyl (S)-(5,5-difluoro-1-(3-hydroxypropoxy)hexan-2-yl)carbamate (2.50 g, 8.03 mmol) in DCM (20 mL) was added TFA (5.00 mL, 8.03 mmol). The reaction was stirred for 1 hour at 15° C. The mixture was concentrated to give (S)-3-((2-amino-5,5-difluorohexyl)oxy)propan-1-ol, which was used in the next step directly. LCMS m/z (M+H): 212.1 required, 212.1 found.

To a solution of (S)-3-((2-amino-5,5-difluorohexyl)oxy)propan-1-ol (1.00 g, 4.73 mmol) in DCM (5 mL) were added TEA (3.30 mL, 23.7 mmol), DMAP (0.145 g, 1.18 mmol) and TBS-Cl(1.07 g, 7.10 mmol). The reaction was stirred at 20° C. for 16 hours. The mixture was quenched with $H_2O$(4 mL) and extracted with DCM (20 mL×3), washed with brine (5 mL), dried over $Na_2SO_4$, filtered and concentrated under reduced pressure. The crude was purified by Flash silica gel chromatography (ISCO®; 20 g SepaFlash® Silica Flash Column, eluent of 10% EtOAc/MeOH gradient) to give (S)-1-(3-((tert-butyldimethylsilyl)oxy)propoxy)-5,5-difluorohexan-2-amine (A144). LCMS m/z (M+H): 326.2 required, 326.3 found. $^1$H NMR (400 MHz, $CD_3OD$) δ 3.74 (t, J=6.1 Hz, 2H), 3.61-3.52 (m, 2H), 3.46 (dd, J=4.3, 9.7 Hz, 1H), 3.37-3.32 (m, 1H), 3.06-2.97 (m, 1H), 2.02-1.88 (m, 2H), 1.83-1.76 (m, 2H), 1.75-1.67 (m, 1H), 1.59 (t, J=18.5 Hz, 4H), 0.91 (s, 9H).

Intermediate A145

((S)-2-methyl-N—((R)-1,1,1-trifluoro-9-hydroxynonan-4-yl)propane-2-sulfinamide (A145)

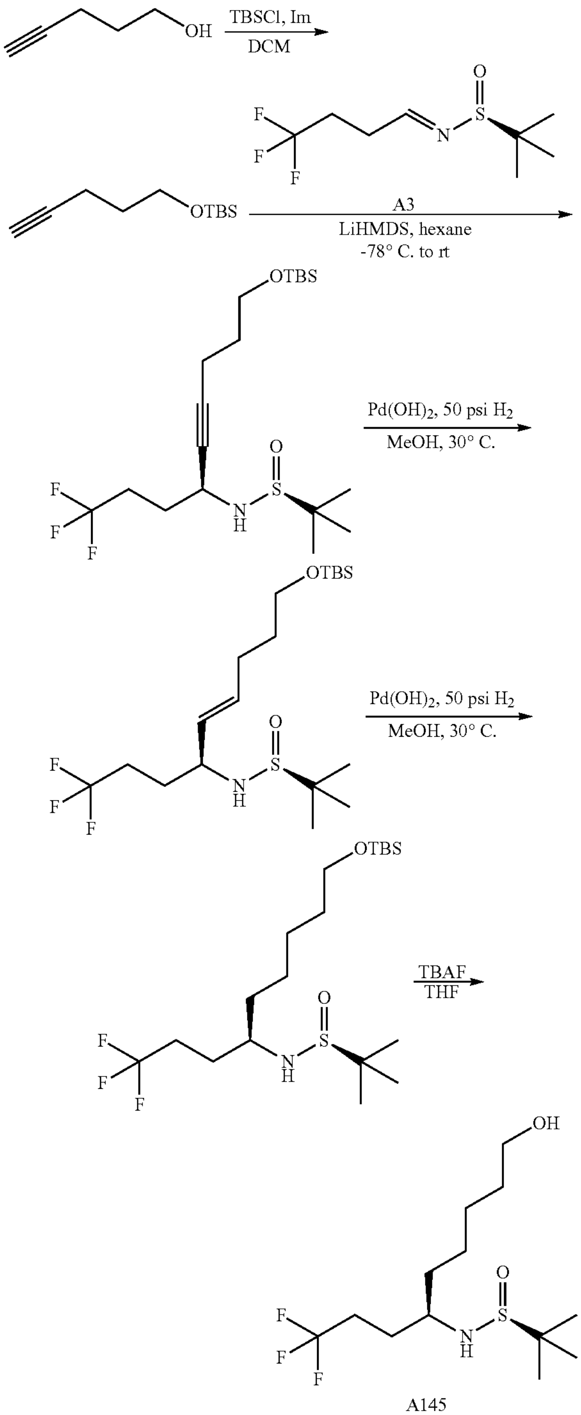

A145

To a solution of pent-4-yn-1-ol (10.0 g, 119 mmol) in DCM (200 mL) were added imidazole (16.19 g, 238 mmol) and tert-butyldimethylchlorosilane (26.9 g, 178 mmol). The mixture was stirred at 20° C. for 2 hours. The reaction mixture was poured into water (300 mL), extracted with DCM (100 mL×3). The combined organic layers were washed with brine (100 mL), dried over $Na_2SO_4$ and filtered. The filtrate was concentrated and purified by flash silica gel chromatography (ISCO®; 80 g SepaFlash® Silica Flash Column, eluent of (0-10% ethyl acetate/pet. ether gradient) to give tert-butyldimethyl(pent-4-yn-1-yloxy)silane. $^1H$ NMR (400 MHz, $CDCl_3$) δ 3.64 (t, J=6.0 Hz, 2H), 2.22 (dt, J=2.7, 7.1 Hz, 2H), 1.87 (t, J=2.7 Hz, 1H), 1.72-1.61 (m, 2H), 0.84 (s, 9H), 0.00 (s, 6H)

To a solution of LiHMDS (52.3 mL, 52.3 mmol) in hexane (160 mL) at −78° C. was added tert-butyldimethyl (pent-4-yn-1-yloxy)silane (10.4 g, 52.3 mmol). The mixture was stirred at 25° C. for 10 minutes, then was added (S,E)-2-methyl-N-(4,4,4-trifluorobutylidene)propane-2-sulfinamide (A3, 6.00 g, 26.2 mmol) in hexane (6 mL) at −78° C. The mixture was stirred at 25° C. for 6 hours. The reaction mixture was poured into saturated aqueous $NH_4Cl$ (200 mL) and extracted with EtOAc (100 mL×3). The combined organic layers were washed with brine (100 mL), dried over $Na_2SO_4$ and filtered. The filtrate was concentrated and purified by flash silica gel chromatography (ISCO®; 40 g SepaFlash® Silica Flash Column, eluent of (0-23% ethyl acetate/pet. ether gradient) to give (S)—N—((S)-9-((tert-butyldimethylsilyl)oxy)-1,1,1-trifluoronon-5-yn-4-yl)-2-methylpropane-2-sulfinamide.

To a solution of (S)—N—((S)-9-((tert-butyldimethylsilyl)oxy)-1,1,1-trifluoronon-5-yn-4-yl)-2-methylpropane-2-sulfinamide (6.00 g, 14.03 mmol) in MeOH (60 mL) was added $Pd(OH)_2$ (1.97 g, 2.81 mmol) and stirred at 30° C. under an atmosphere of H2 (50 psi) for 24 hours. The reaction mixture filtered and concentrated to give (S)—N—((S,E)-9-((tert-butyldimethylsilyl)oxy)-1,1,1-trifluoronon-5-en-4-yl)-2-methylpropane-2-sulfinamide, which was used in next step without purification.

To a solution of (S)—N—((S,E)-9-((tert-butyldimethylsilyl)oxy)-1,1,1-trifluoronon-5-en-4-yl)-2-methylpropane-2-sulfinamide (6.00 g, 14.0 mmol) in MeOH (60 mL) was added $Pd(OH)_2$ (6.86 g, 9.78 mmol) and stirred at 30° C. under an atmosphere of H2 (50 psi) for 24 hours. The reaction mixture was filtered and concentrated and purified by flash silica gel chromatography (ISCO®; 12 g SepaFlash® Silica Flash Column, eluent of (25-30% ethyl acetate/pet. ether gradient) to give (S)—N—((R)-9-((tert-butyldimethylsilyl)oxy)-1,1,1-trifluorononan-4-yl)-2-methylpropane-2-sulfinamide. $^1H$ NMR (400 MHz, $CDCl_3$) δ 3.59 (t, J=6.5 Hz, 2H), 3.37-3.22 (m, 1H), 2.95 (br d, J=6.7 Hz, 1H), 2.29-2.03 (m, 2H), 1.92-1.78 (m, 1H), 1.70-1.61 (m, 2H), 1.52 (qd, J=6.7, 13.3 Hz, 3H), 1.43-1.29 (m, 4H), 1.22 (s, 10H), 0.88 (s, 9H), 0.04 (s, 6H)

To a solution of (S)—N—((R)-9-((tert-butyldimethylsilyl)oxy)-1,1,1-trifluorononan-4-yl)-2-methylpropane-2-sulfinamide (2.50 g, 5.79 mmol) in THF (40 mL) was added TBAF (11.6 mL, 11.6 mmol) (1 M in THF). The mixture was stirred at 25° C. for 12 hours. The reaction mixture was poured into water (50 mL) and extracted with EtOAc (30 mL×3). The organic layer was washed with brine (30 mL), dried over $Na_2SO_4$ and filtered. The filtrate was concentrated and purified by flash silica gel chromatography (ISCO®; 25 g SepaFlash® Silica Flash Column, eluent of (80-90% ethyl acetate/pet. ether gradient) to give (S)-2-methyl-N—((R)-1,1,1-trifluoro-9-hydroxynonan-4-yl)propane-2-sulfinamide (A145). $^1H$ NMR (500 MHz, $CDCl_3$) δ 3.63 (br d, J=4.6 Hz, 2H), 3.35-3.22 (m, 1H), 2.98 (br d, J=6.9 Hz, 1H), 2.28-2.02 (m, 3H), 1.89-1.72 (m, 1H), 1.67-1.54 (m, 4H), 1.50-1.31 (m, 4H), 1.25-1.18 (m, 9H)

Intermediate A146

(R)-10-((tert-butyldimethylsilvl)oxy)-2,2-difluorodecan-5-amine (A146)

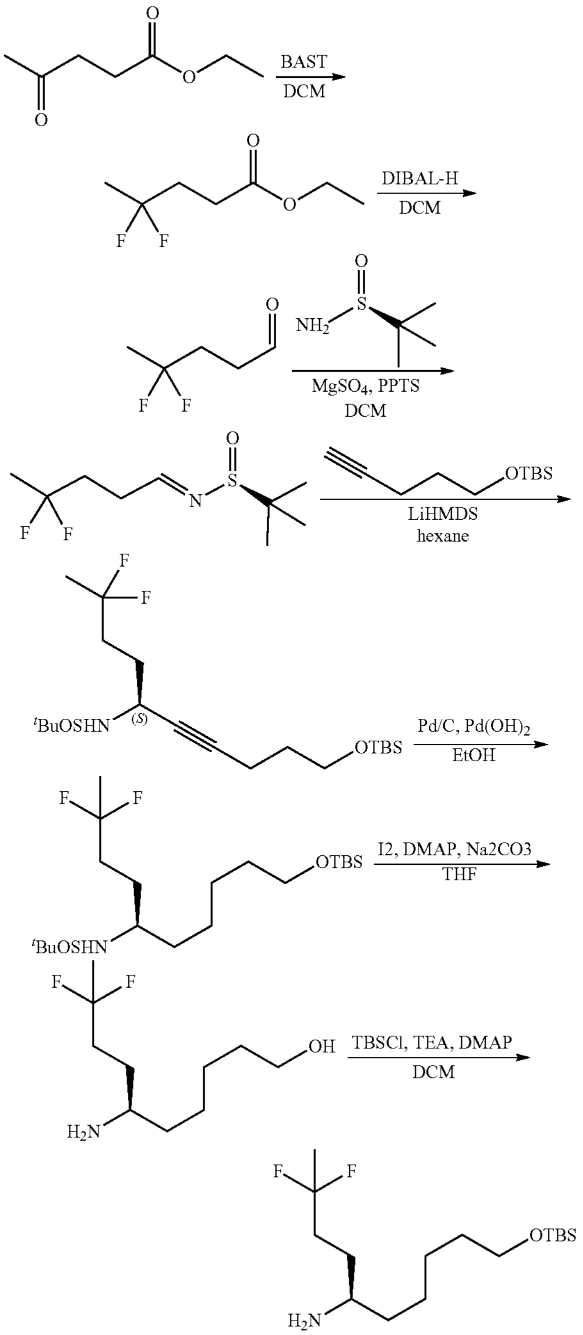

A146

To a solution of ethyl 4-oxopentanoate (20.0 g, 139 mmol) in DCM (250 mL) was added BAST (38.4 mL, 208 mmol) at 20° C. The mixture was stirred at 50° C. under N2 for 24 hours. The mixture was quenched with saturated aqueous $Na_2CO_3$ (100 mL) and extracted with DCM (50 mL×3), washed with brine (50 mL), dried over $Na_2SO_4$, filtered and concentrated under reduced pressure. The crude was purified by Flash silica gel chromatography (ISCO®; 80 g SepaFlash® Silica Flash Column, eluent of 20% EtOAc/Pet.ether gradient) to give ethyl 4,4-difluoropentanoate.

To a solution of ethyl 4,4-difluoropentanoate (5.00 g, 30.1 mmol) in DCM (100 mL) was added DIBAL-H (36.1 mL, 36.1 mmol) at −78° C., and the resulting mixture was stirred at −78° C. under N2 protection for 0.5 hours. The reaction mixture was stirred and added water (3 mL) then added 15% NaOH (3 mL), water (8 mL), $MgSO_4$ and filtered. The filtrate was concentrated to give crude 4,4-difluoropentanal, which was used in the next step directly.

To a solution of 4,4-difluoropentanal (3.67 g, 30.1 mmol) in DCE (50 mL) and DCM (200 mL) was added (S)-2-methylpropane-2-sulfinamide (4.01 g, 33.1 mmol), PPTS (0.755 g, 3.01 mmol), and $MgSO_4$ (10.8 g, 90.0 mmol) at 20° C. The reaction mixture was stirred at 80° C. for 4 hours. The mixture were filtered and concentrated to the crude product. The crude product was purified by flash silica gel chromatography (ISCO®; 40 g SepaFlash® Silica Flash Column, (eluent of 20% EtOAc/Pet.ether gradient) to give (S,E)-N-(4,4-difluoropentylidene)-2-methylpropane-2-sulfinamide. LCMS m/z (M+H): 226.1 required, 225.7 found.

To a solution of lithium bis(trimethylsilyl)amide (44.4 mL, 44.4 mmol) (1M in THF) in hexane (100 mL) was added (S,E)-N-(4,4-difluoropentylidene)-2-methylpropane-2-sulfinamide (8.81 g, 44.4 mmol) at −78° C. The resulting mixture was stirred at 20° C. under $N_2$ protection for 20 minutes, then was added (S,E)-N-(4,4-difluoropentylidene)-2-methylpropane-2-sulfinamide (5.00 g, 22.2 mmol) in hexane (5 mL). The reaction was stirred at 20° C. for 3 hours. The reaction mixture was poured into saturated aqueous $NaHCO_3$(15 mL) and extracted with EtOAc (150 mL×3). The organic layer was washed with brine (10 mL), dried over $Na_2SO_4$ and filtered. The filtrate was concentrated and purified by flash silica gel chromatography (ISCO®; 80 g SepaFlash® Silica Flash Column, eluent of (0-20% ethyl acetate/pet. ether gradient) ($SiO_2$, Pet. ether:EtOAc=5:1) to give N—((S)-10-((tert-butyldimethylsilyl)oxy)-2,2-difluorodec-6-yn-5-yl)-2-methylpropane-2-sulfinamide. LCMS m/z (M+H): 424.2 required, 424.2 found.

To a solution of N—((S)-10-((tert-butyldimethylsilyl)oxy)-2,2-difluorodec-6-yn-5-yl)-2-methylpropane-2-sulfinamide (3.60 g, 8.50 mmol) in ethanol (10 mL) were added a solution of $Pd(OH)_2$ (0.119 g, 0.850 mmol) and 10% Pd-C(0.090 g, 0.850 mmol) in ethanol at 20° C. The resulting mixture was stirred at 20° C. under an atmosphere of H2 for 24 hours. The reaction mixture was filtered and concentrated to give N—((R)-10-((tert-butyldimethylsilyl)oxy)-2,2-difluorodecan-5-yl)-2-methylpropane-2-sulfinamide. LCMS m/z (M+H): 427.9 required, 428.3 found.

To a solution of N—((R)-10-((tert-butyldimethylsilyl)oxy)-2,2-difluorodecan-5-yl)-2-methylpropane-2-sulfinamide (2.70 g, 6.31 mmol) in THF (32 mL) and water (8 mL) were added DMAP (0.154 g, 1.263 mmol) and $Na_2CO_3$ (2.007 g, 18.94 mmol), and the resulting mixture was stirred at 20° C. for 5 minutes, then added 12 (4.01 g, 15.78 mmol), and the mixture was stirred at 20° C. under N2 protection for 24 hours. The reaction mixture was poured into water (10 mL) and extracted with EtOAc (20 mL×3). The organic layer was washed with brine (10 mL), dried over $Na_2SO_4$ and filtered. The filtrate was concentrated and purified by flash silica gel chromatography (ISCO®; 24 g SepaFlash® Silica Flash Column, eluent of (0-30% ethyl acetate/pet.

ether gradient) ($SiO_2$, EtOAc) to give (R)-6-amino-9,9-difluorodecan-1-ol. LCMS m/z (M+H): 324.3 required, 210.1 found.

To a solution of (R)-6-amino-9,9-difluorodecan-1-ol (2.80 g, 9.37 mmol) in DCM (60 mL) were added TBS-Cl(2.54 g, 16.9 mmol), DMAP (0.286 g, 2.34 mmol), and TEA (3.92 mL, 28.1 mmol), and the resulting mixture was stirred at 37° C. under N2 protection for 16 hours. The reaction mixture was poured into water (10 mL) and extracted with EtOAc (20 mL×3). The organic layer was washed with brine (10 mL), dried over $Na_2SO_4$ and filtered. The filtrate was concentrated and purified by flash silica gel chromatography (ISCO®; 40 g SepaFlash® Silica Flash Column, eluent of (0-100% ethyl acetate/pet. ether gradient) ($SiO_2$, EtOAc) to give (R)-10-((tert-butyldimethylsilyl)oxy)-2,2-difluorodecan-5-amine (A146). LCMS m/z (M+H): 324.3 required, 324.3 found. $^1H$ NMR (400 MHz, $CDCl_3$) δ 3.61 (t, J=6.5 Hz, 2H), 2.72 (br d, J=4.7 Hz, 1H), 2.06-1.78 (m, 2H), 1.66-1.23 (m, 13H), 0.90 (s, 9H), 0.07-0.02 (m, 6H)

Intermediate A175

N-(6-((tert-butyldimethylsilyl)oxy)-1-(2-methylthiazol-4-yl)hexyl)-2-methylpropane-2-sulfinamide (A175)

A175

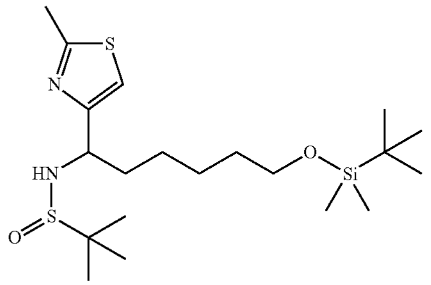

The title compound was prepared from 2-methylthiazole-4-carbaldehyde in an analogous manner to the procedures outlined in steps 1 and 2 in Scheme A8. LC-MS: 433.4 (M+1).

Intermediate A176

4-nitrophenyl (S)-but-3-en-2-ylcarbamate (A176)

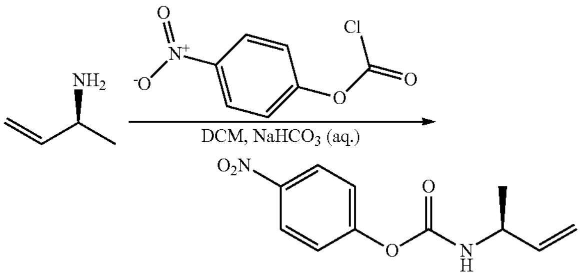

A176

Step 1: 4-nitrophenyl (S)-but-3-en-2-ylcarbamate (A176)

The (S)-but-3-en-2-amine hydrochloride (30 mg, 0.279 mmol) was dissolved in DCM (697 μl) and treated with saturated $NaHCO_3$(697 μl) and 4-nitrophenyl chloroformate (84 mg, 0.418 mmol) and stirred at ambient temperature for 18 h. Work-up involved diluting with $CH_2Cl_2$, washing with sat'd $NaHCO_3$, drying by filtering through a hydrophobic frit and evaporating to give an oil. This was purified via flash silica gel chromatography (0-30% 3:1 EtOAc:EtOH/hexanes) to give 4-nitrophenyl (S)-but-3-en-2-ylcarbamate (A176). LC-MS: 237.9 (M+1).

Intermediate B5

(R)-1-(4-bromo-5-methoxypyridin-2-yl)-N-ethylethan-1-amine (B5)

SCHEME B1

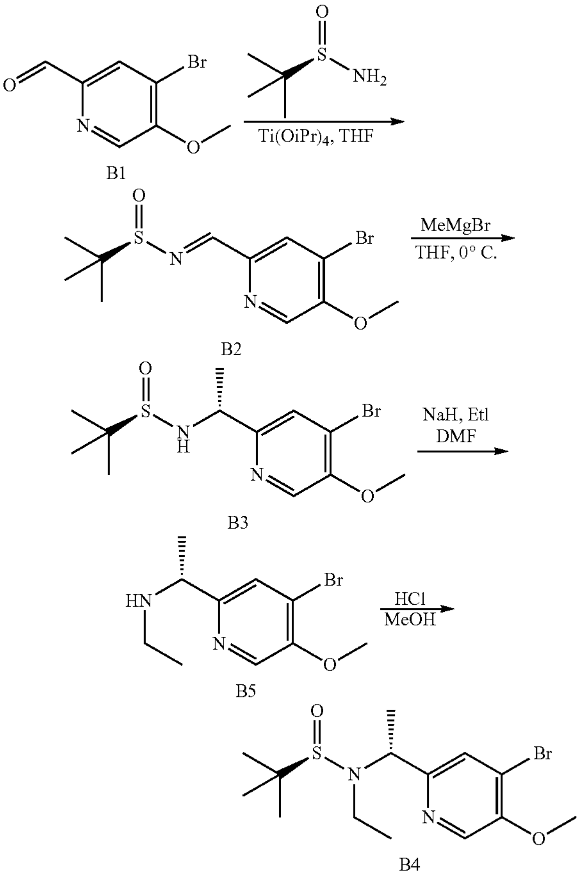

Step 1: (R,E)-N-((4-bromo-5-methoxypyridin-2-yl)methylene)-2-methylpropane-2-sulfinamide To a solution of 4-bromo-5-methoxypicolinaldehyde (B1, 200 mg, 0.926 mmol) and (R)-2-methylpropane-2-sulfinamide (135 mg, 1.111 mmol) in THF (3 mL) was added tetraethoxytitanium (1056 mg, 4.63 mmol). The reaction was stirred at 80° C. for 2 h. LCMS showed formation of the desired product mass. The reaction was poured into brine (3 mL) and extracted with EtOAc (3×5 mL). The combined organic layers were dried ($Na_2SO_4$), filtered and concentrated. The crude material was purified by flash silica chromatography (50% EtOAc in petroleum ether) to give (R,E)-N-((4-bromo-5-methoxypyridin-2-yl)methylene)-2-methylpropane-2-sulfinamide (B2). LC-MS: 319.1, 321.1 (M+1).

Step 2: (R,E)-N-((4-bromo-5-methoxypyridin-2-yl)methylene)-2-methylpropane-2-sulfinamide (B3)

To a solution of (R,E)-N-((4-bromo-5-methoxypyridin-2-yl)methylene)-2-methylpropane-2-sulfinamide (B2, 260 mg, 0.774 mmol) in THF (3 mL) at 0° C. was added methylmagnesium bromide (2.063 mL, 6.19 mmol) (3 M in $Et_2O$). The reaction was stirred at 0° C. under nitrogen for 1 h. LCMS showed formation of the desired product mass. The reaction was quenched with sat. aq. $NH_4Cl$ (2 mL) and extracted with EtOAc (3×5 mL). The combined organic layers were dried ($Na_2SO_4$), filtered and concentrated. The crude material was purified by flash silica chromatography (50% EtOAc in petroleum ether) to give (R,E)-N-((4-bromo-5-methoxypyridin-2-yl)methylene)-2-methylpropane-2-sulfinamide (B3). LC-MS: 335.1, 337.1 (M+1).

Step 3: (R)—N—((R)-1-(4-bromo-5-methoxypyridin-2-yl)ethyl)-N-ethyl-2-methylpropane-2-sulfinamide (B4)

To a solution of (R,E)-N-((4-bromo-5-methoxypyridin-2-yl)methylene)-2-methylpropane-2-sulfinamide (B3, mg, 0.652 mmol) in DMF (3 mL) was added sodium hydride (39.1 mg, 0.978 mmol) (60% in mineral oil) at 0° C. under nitrogen. The reaction was stirred at 0° C. for 30 min. Ethyl iodide (203 mg, 1.303 mmol) was added and the reaction was stirred at 0° C. for 1 h. LCMS showed formation of the desired product mass. The reaction was poured into water (5 mL) and extracted with EtOAc (3×5 mL). The combined organic layers were washed with brine (10 mL), dried ($Na_2SO_4$), filtered and concentrated. The crude material was purified by flash silica chromatography (70% EtOAc in petroleum ether) to give (R)—N—((R)-1-(4-bromo-5-methoxypyridin-2-yl)ethyl)-N-ethyl-2-methylpropane-2-sulfinamide (B4). LC-MS: 363.1, 365.1 (M+1).

Step 4: (R)-1-(4-bromo-5-methoxypyridin-2-yl)-N-ethylethan-1-amine (B5)

(R)—N—((R)-1-(4-bromo-5-methoxypyridin-2-yl)ethyl)-N-ethyl-2-methylpropane-2-sulfinamide (B4, 466 mg, 1.283 mmol) was dissolved MeOH (6413 μL) and HCl (321 μL, 1.283 mmol) (4M in dioxane) was added. The reaction was allowed to stir at ambient temperature for 20 min. LCMS showed formation of the desired product mass. The reaction was concentrated and rotavaped twice with DCM to afford (R)-1-(4-bromo-5-methoxypyridin-2-yl)-N-ethylethan-1-amine (B5) as an HCl salt. LC-MS: 259.2, 261.2 (M+1)

Intermediate B10

(R)-1-(4-bromopyridin-2-yl)-N-ethylethan-1-amine (B10)

SCHEME B2

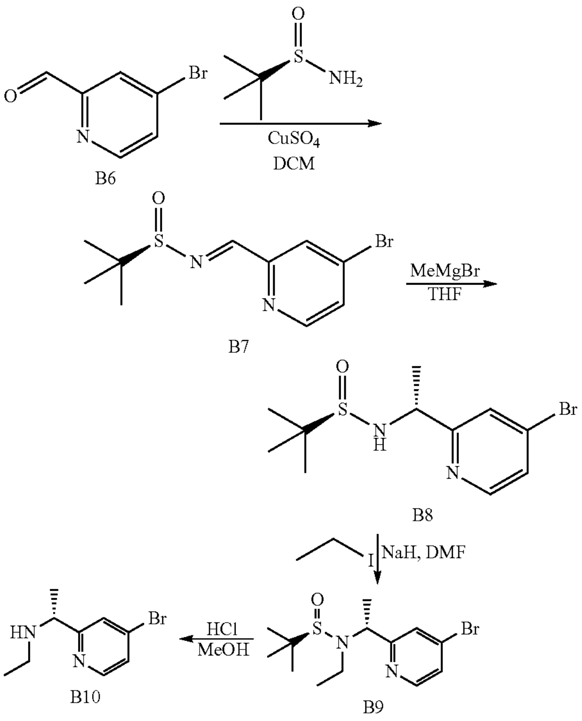

Step 1: (R,E)-N-((4-bromopyridin-2-yl)methylene)-2-methylpropane-2-sulfinamide (B7)

To a solution of 4-bromopicolinaldehyde (B6, 5.18 g, 27.8 mmol) and (R)-2-methylpropane-2-sulfinamide (6.75 g, 55.7 mmol) in DCM (111 mL) at ambient temperature was added copper(II) sulfate (19.56 g, 123 mmol) and the solution was stirred for 68 h. The mixture was filtered through Celite, rinsing with DCM (3×20 mL) and concentrated. The crude material was purified by flash silica chromatography (0-60% EtOAc in Hexanes gradient) to yield (R,E)-N-((4-bromopyridin-2-yl)methylene)-2-methylpropane-2-sulfinamide (B7). LC-MS: 289.1, 291.1 (M+1).

Step 2: (R)—N—((R)-1-(4-bromopyridin-2-yl)ethyl)-2-methylpropane-2-sulfinamide (B8)

To a solution of (R,E)-N-((4-bromopyridin-2-yl)methylene)-2-methylpropane-2-sulfinamide (B7, 7.43 g, 25.7 mmol) in THF (184 mL) at −78° C. was added methylmagnesium bromide (19.18 mL, 57.6 mmol) (3M in THF) dropwise over 20 min and the reaction was stirred for 1.5 h at −78° C. The reaction was quenched by the slow addition of sat. aq. $NH_4Cl$ (50 mL) at −78° C. and then poured into water (100 mL) and extracted with EtOAc (3×60 mL). The combined organic layers were dried ($Na_2SO_4$), filtered and concentrated. The crude material was purified by flash silica chromatography (0-100% EtOAc in hexanes gradient) to yield (R)—N—((R)-1-(4-bromopyridin-2-yl)ethyl)-2-methylpropane-2-sulfinamide (B8). LC-MS: 305.1, 307.1 (M+1).

Step 3: (R)—N—((R)-1-(4-bromopyridin-2-yl) ethyl)-N-ethyl-2-methylpropane-2-sulfinamide (B9)

To a solution of (R)—N—((R)-1-(4-bromopyridin-2-yl) ethyl)-2-methylpropane-2-sulfinamide (B8, 7.07 g, 23.16 mmol) in DMF (93 mL) at 0° C. was added sodium hydride (60% in mineral oil, 1.390 g, 34.7 mmol) and the solution was stirred for 30 min. Ethyl iodide (2.226 mL, 27.8 mmol) was then added and stirring continued for 3 h. The reaction was quenched by the dropwise addition of water (50 mL) and then poured into water (300 mL) and extracted with $Et_{20}$ (3×100 mL). The combined organic layers were dried ($Na_2SO_4$), filtered and concentrated. The crude material was purified by flash silica chromatography (0-60% EtOAc in hexanes gradient) to yield (R)—N—((R)-1-(4-bromopyridin-2-yl)ethyl)-N-ethyl-2-methylpropane-2-sulfinamide (B9). LC-MS: 333.0, 335.0 (M+1).

Step 4: (R)-1-(4-bromopyridin-2-yl)-N-ethylethan-1-amine (B10)

To a solution of (R)—N—((R)-1-(4-bromopyridin-2-yl) ethyl)-N-ethyl-2-methylpropane-2-sulfinamide (B9, 4.37 g, 13.11 mmol) in MeOH (26.2 mL) at 0° C. was added HCl (3.28 mL, 13.11 mmol) (4M in dioxane) and the reaction was stirred for 30 min. The reaction was concentrated and dried under high vacuum to yield (R)-1-(4-bromopyridin-2-yl)-N-ethylethan-1-amine (B10) as an HCl salt. LC-MS: 229.0, 231.0 (M+1).

Intermediates B12, B14 and B16

The following intermediates in Table B1 were synthesized in an analogous manner of that described in Scheme B1 and used to synthesize Intermediate B5 using the appropriate aldehydes.

TABLE B1

| Aldehyde | Intermediate | Observed LCMS (M + 1) |
|---|---|---|
| 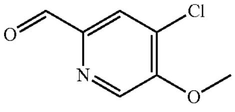 B11 | 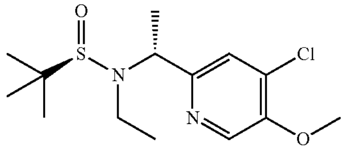 B12 | 319.1 |
| 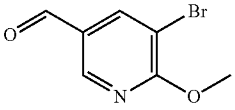 B13 | 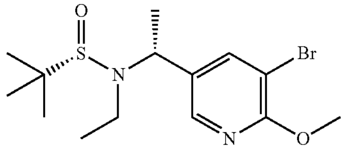 * B14 | 362.9, 364.9 |
| 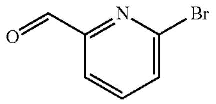 B15 | 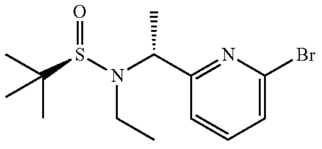 * B16 | 333.2, 335.2 |
| 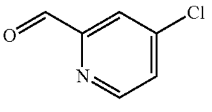 B88 | 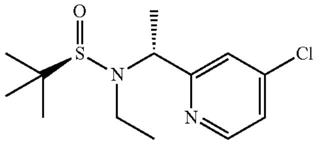 B89 | 260.9 (M + 1 − tBuSOH) |

TABLE B1-continued

| Aldehyde | Intermediate | Observed LCMS (M + 1) |
| --- | --- | --- |
| 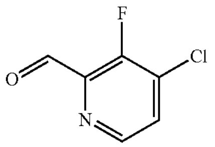 | 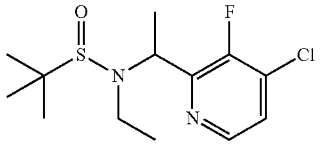 [SMILES: CCN(C(C)c1nccc(Cl)c1F)S(=O)C(C)(C)C]<br>B93 | 263.0 |

* (S)-2-methylpropane-2-sulfinamide was used instead of (R)-2-methylpropane-2-sulfinamide in the synthesis of (S)-N—((R)-1-(5-bromo-6-methoxypyridin-3-yl)ethyl)-N-ethyl-2-methylpropane-2-sulfinamide (B14) and of (R)-N-((R)-1-(6-bromopyridin-2-yl)ethyl)-N-ethyl-2-methylpropane-2-sulfinamide (B89). (RS)-2-methylpropane-2-sulfinamide was used instead of (R)-2-methylpropane-2-sulfinamide in the synthesis of N-(1-(4-chloro-3-fluoropyridin-2-yl)ethyl)-N-ethyl-2-methylpropane-2-sulfinamide (B93)

Intermediate B17

(2-((R)-1-(((R)-tert-butylsulfinyl)(ethyl)amino)ethyl)-5-methoxypyridin-4-yl)boronic acid (B17)

SCHEME B3

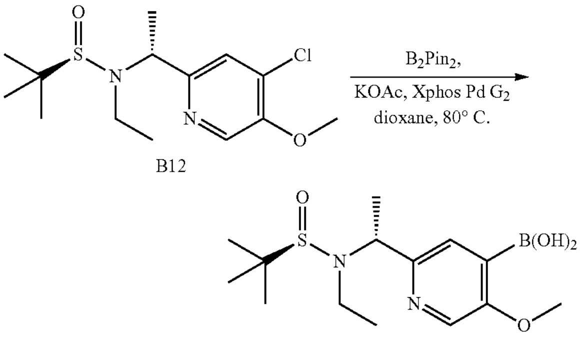

B12

B17

To a mixture of (R)—N—((R)-1-(4-chloro-5-methoxy-pyridin-2-yl)ethyl)-N-ethyl-2-methylpropane-2-sulfinamide (B12, 1 g, 3.14 mmol), 4,4,4',4',5,5,5',5'-octamethyl-2,2'-bi(1,3,2-dioxaborolane) (1.593 g, 6.27 mmol) and potassium acetate (0.923 g, 9.41 mmol) in dioxane (10 mL) was added XPhos Pd G2 (0.123 g, 0.157 mmol), and the reaction was stirred at 80° C. under nitrogen for 16 h. LCMS showed formation of the desired product mass. The reaction was filtered and concentrated to give boronic ester B17, which was carried forward without purification. LC-MS: 329.2 (M+H).

SCHEME B4

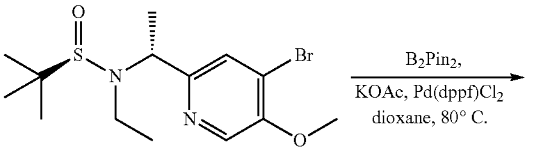

B4

-continued

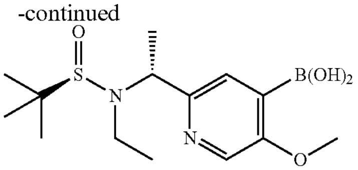

B17

To a mixture of (R)—N—((R)-1-(4-bromo-5-methoxy-pyridin-2-yl)ethyl)-N-ethyl-2-methylpropane-2-sulfinamide (B4, 200 mg, 0.550 mmol), 4,4,4',4',5,5,5',5'-octamethyl-2,2'-bi(1,3,2-dioxaborolane) (280 mg, 1.101 mmol) and potassium acetate (162 mg, 1.651 mmol) in 1,4-dioxane (3 mL) was added $Pd(dppf)Cl_2$ (40.3 mg, 0.055 mmol), and the reaction was stirred at 80° C. under nitrogen for 4 h. LCMS showed formation of the desired product mass. The reaction was filtered and concentrated to give boronic ester B17, which was carried forward without purification. LC-MS: 329.2 (M+1).

Intermediate B18 tert-butyl (R)-(1-(4-bromo-5-methoxypyridin-2-yl)ethyl)(ethyl)carbamate (B18)

SCHEME B5

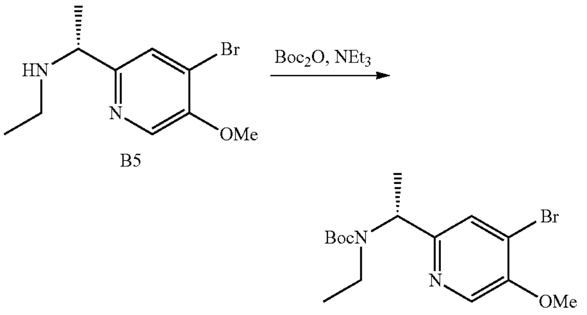

B5

B18

(R)-1-(4-bromo-5-methoxypyridin-2-yl)-N-ethylethan-1-amine (B5, 172 mg, 0.664 mmol) was dissolved in DCM (6637 μL) and Boc anhydride (185 μL, 0.796 mmol) and triethylamine (111 μL, 0.796 mmol) were added. The reaction was allowed to stir at ambient temperature for 18 h. LCMS analysis showed complete conversion. The reaction was quenched with MeOH (3 mL) and concentrated. The crude material was purified by ISCO column chromatography (0-100% EtOAc:EtOH 3:1 mix in hexanes gradient) to afford tert-butyl (R)-(1-(4-bromo-5-methoxypyridin-2-yl)ethyl)(ethyl)carbamate (B18). LC-MS: 359.2, 361.2 (M+1).

Intermediates B19 and B20

B19

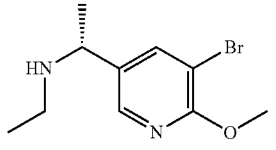

(R)-1-(5-bromo-6-methoxypyridin-3-yl)-N-ethyl-ethan-1-amine (B19)

Intermediate B19 was prepared from intermediate B14 in an analogous manner of that described in Step 4 of Scheme B2 and used to synthesize Intermediate B10. LC-MS: 258.9. 260.9 (M+1). $^1$H NMR: (400 MHz, $CD_3OD$) δ 8.24 (d, J=2.3 Hz, 1H), 8.12 (d, J=2.3 Hz, 1H), 4.42 (q, J=6.7 Hz, 1H), 4.01 (s, 3H), 3.11-3.00 (m, 1H), 2.98-2.81 (m, 1H), 1.67 (d, J=7.0 Hz, 3H), 1.29 (t, J=7.4 Hz, 3H).

The following intermediates in Table B19-1 were synthesized in an analogous manner of that described for Intermediate B19 starting from the appropriate halides.

| Halide | Intermediate | Observed LCMS (M + 1) |
|---|---|---|
| 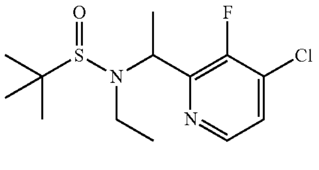 [SMILES: CCN(C(C)c1nccc(Cl)c1F)S(=O)C(C)(C)C] | 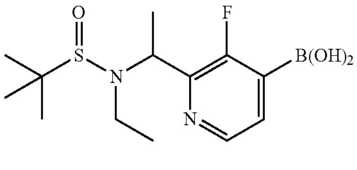 [SMILES: CCN(C(C)c1nccc(B(O)O)c1F)S(=O)C(C)(C)C] | 317.1 |
| B93 | B94 | |

B20

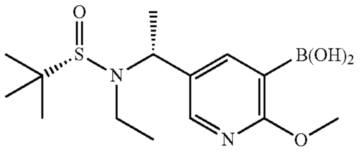

(5-((R)-1-(((S)-tert-butylsulfinyl)(ethyl)amino)ethyl)-2-methoxypyridin-3-yl)boronic acid (B20)

Intermediate B20 was prepared from intermediate B14 in an analogous manner of that described in Scheme B4 and used to synthesize Intermediate B17.

LC-MS: 329.3 (M+1).

Intermediate B27

(R)-1-(2-chloropyridin-4-yl)-N-ethylethan-1-amine (B27)

SCHEME B6

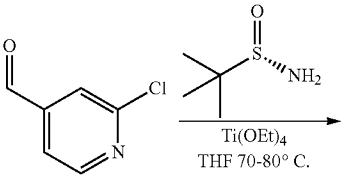

B21

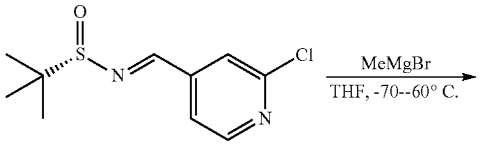

B22

-continued

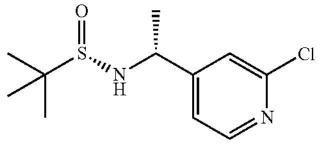

B23

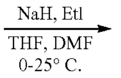

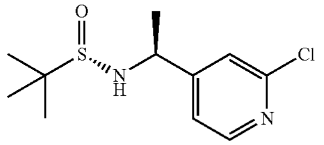

B24

-continued

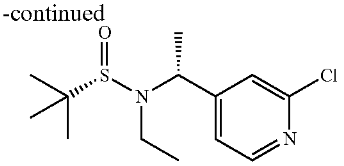

B25

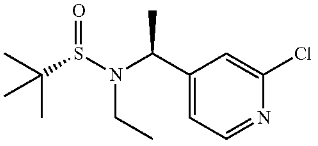

B26

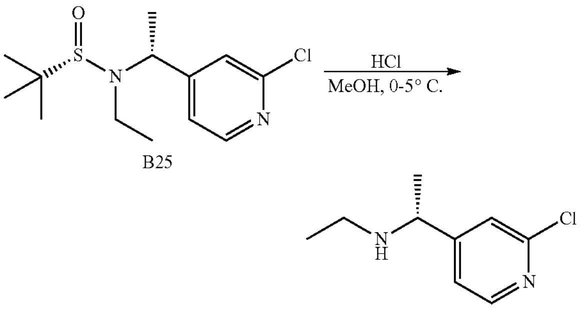

B25

B27

Step 1: (S,E)-N-((2-chloropyridin-4-yl)methylene)-2-methylpropane-2-sulfinamide (B22)

2-chloroisonicotinaldehyde (B21, 160 g, 1.13 mol, 1.0 eq) was dissolved in THF (1.5 L). (S)-2-methylpropane-2-sulfinamide (205 g, 1.70 mol, 1.5 eq) and $Ti(OEt)_4$ (773 g, 3.39 mol, 703 mL, 3.0 eq) were added to the solution. The reaction was purged and degassed with nitrogen and was then heated to 70-80° C. for 1 h. TLC showed the formation of a more polar spot. The reaction was quenched with water (2.0 L) and diluted with EtOAc (2.0 L). The biphasic mixture was extracted with ethyl acetate (3×2.0 L). The organic layers were combined and washed with brine (2.0 L), dried ($Na_2SO_4$) filtered and concentrated. The crude material was purified by flash silica chromatography (1:20 to 1:3 EtOAc in petroleum ether gradient) to afford (S,E)-N-((2-chloropyridin-4-yl)methylene)-2-methylpropane-2-sulfinamide (B22). $^1$H NMR: (400 MHz, $CDCl_3$) δ: 8.56-8.54 (m, 1H), 7.75-7.70 (m, 1H), 7.61-7.59 (m, 1H), 1.62 (s, 9H).

Step 2: (S)—N—((R)-1-(2-chloropyridin-4-yl)ethyl)-2-methylpropane-2-sulfinamide (B23) and (S)—N—((S)-1-(2-chloropyridin-4-yl)ethyl)-2-methylpropane-2-sulfinamide (B24)

(S,E)-N-((2-chloropyridin-4-yl)methylene)-2-methylpropane-2-sulfinamide (B22, 220 g, 899 mmol) was dissolved in THF (2.2 L) and the solution was purged and degassed with nitrogen and then cooled to −70–−60° C. MeMgBr (900 mL, 2.7 mol) (3.0 M in THF) was added dropwise to the reaction at −70–−60° C. The reaction was allowed to stir at −70–−60° C. for 1 h. TLC showed formation of a more polar spot. The reaction was quenched with sat. aq. $NH_4Cl$ (2 L), diluted with EtOAc (2 L) and extracted with EtAOc (3×2 L). The combined organic layers were dried ($Na_2SO_4$), filtered and concentrated. The crude material was purified by flash silica chromatography (1:20 to 1:3 EtOAc in petroleum ether gradient) to afford a mixture of (S)—N—((R)-1-(2-chloropyridin-4-yl)ethyl)-2-methylpropane-2-sulfinamide (B23) and (S)—N—((S)-1-(2-chloropyridin-4-yl)ethyl)-2-methylpropane-2-sulfinamide (B24). $^1$H NMR: (400 MHz, $CDCl_3$) δ: 8.37-8.35 (m, 1H), 7.32-7.30 (m, 1H), 7.23-7.21 (m, 1H), 4.53-4.50 (m, 1H), 3.51-3.38, (m, 1H), 1.53-1.51 (m, 3H), 1.25-1.23 (m, 9H).

Step 3: (S)—N—((R)-1-(2-chloropyridin-4-yl)ethyl)-N-ethyl-2-methylpropane-2-sulfinamide (B25) and (S)—N—((S)-1-(2-chloropyridin-4-yl)ethyl)-N-ethyl-2-methylpropane-2-sulfinamide (B26)

A mixture of (S)—N—((R)-1-(2-chloropyridin-4-yl)ethyl)-2-methylpropane-2-sulfinamide (B23) and (S)—N—((S)-1-(2-chloropyridin-4-yl)ethyl)-2-methylpropane-2-sulfinamide (B24) was dissolved in THF (800 mL) and DMF (80 mL) and the solution was purged and degassed with nitrogen and then cooled to 0-5° C. Sodium hydride (24.5 g, 613 mmol) (60% in mineral oil) was added in 10 portions and the reaction was stirred at 0-5° C. for 30 min. Ethyl iodide (95.7 g, 613 mmol) was added and the reaction was stirred at 15° C.—ambient temperature for 2 h. TLC showed formation of a new spot. The reaction was quenched with water (2 L), diluted with EtOAc (2 L) and extracted with EtOAc(3×2 L). The combined organic layers were washed with brine (2 L), dried ($Na_2SO_4$), filtered and concentrated. The crude material was purified by reverse phase HPLC (35%-55% water in ACN, with 0.1% TFA as modifier) to afford separated (S)—N—((R)-1-(2-chloropyridin-4-yl)ethyl)-N-ethyl-2-methylpropane-2-sulfinamide (B25) and (S)—N—((S)-1-(2-chloropyridin-4-yl)ethyl)-N-ethyl-2-methylpropane-2-sulfinamide (B26). B25: $^1$H NMR (400 MHz, $CDCl_3$) δ: 8.32-8.31 (m, 1H), 7.28-7.27 (m, 1H), 7.21-7.19 (m, 1H), 4.58-4.52 (m, 1H), 3.20-3.14 (m, 1H), 2.91-2.85 (m, 1H), 1.60 (d, J=3.2 Hz, 3H), 1.24 (t, J=7.2 Hz, 3H).1.21 (s, 9H). B26: $^1$H NMR (400 MHz, $CDCl_3$) δ: 8.35-8.33 (m, 1H), 7.43-7.40 (m, 2H), 4.63-4.58 (m, 1H), 3.20-3.13 (m, 1H), 2.63-2.59 (m, 1H), 1.60 (d, J=3.2 Hz, 3H), 1.26 (s, 9H), 1.08 (t, J=7.2 Hz, 3H).

Step 4: (R)-1-(2-chloropyridin-4-yl)-N-ethylethan-1-amine (B27)

(S)—N—((R)-1-(2-chloropyridin-4-yl)ethyl)-N-ethyl-2-methylpropane-2-sulfinamide (B25, 15.0 g, 0.05 mmol) was dissolved in MeOH (50 mL) and the solution was cooled to 0-5° C. HCl (200 mL, 800 mmol) (4M in EtOAc) was added and the reaction was stirred at 0-5° C. for 2 h. TLC showed formation of a more polar spot. The reaction was concentrated. The crude material was slurred with EtOAc (30 mL) at ambient temperature for 2 h. The slurry was filtered to afford (R)-1-(2-chloropyridin-4-yl)-N-ethylethan-1-amine (B27) as an HCl salt. $^1$H NMR: (400 MHz, DMSO-hd6) 6:10.03 (s, 1H), 9.60 (s, 1H), 8.50-8.48 (m, 1H), 7.85-7.83 (m, 1H), 7.72-7.70 (m, 1H), 4.45-4.40 (m, 1H), 2.90-2.86 (m, 1H), 2.72-2.69 (m, 1H), 1.57 (d, J=6.8 Hz, 3H), 1.20 (t, J=7.2 Hz, 3H).

Intermediate B31

(R)—N—((R)-1-(4-chloro-5-methylpyridin-2-yl)ethyl)-N-ethyl-2-methylpropane-2-sulfinamide

SCHEME B7

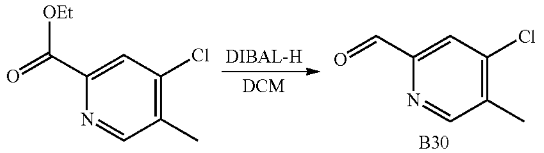

B29

B30

Step 1: 4-chloro-5-methylpicolinaldehyde (B30)

To a solution of ethyl 4-chloro-5-methylpicolinate (B29, 1.2 g, 6.01 mmol) in anhydrous DCM (20 mL) was added DIBAL-H (9.02 mL, 9.02 mmol) (1.0 M in toluene) slowly at −78° C., and the reaction was stirred at −78° C. under nitrogen for 1 h. LCMS showed the formation of the desired product mass. The reaction was poured into water (50 mL) and extracted with DCM (3×20 mL). The combined organic layers were washed with brine (20 mL), dried ($Na_2SO_4$), filtered and concentrated to afford 4-chloro-5-methylpicolinaldehyde (B30), which was carried forward without purification. LC-MS: 156.2 (M+1).

B31

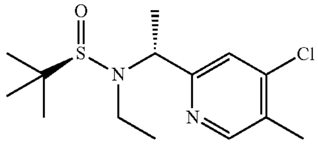

(R)—N—((R)-1-(4-chloro-5-methylpyridin-2-yl)ethyl)-N-ethyl-2-methylpropane-2-sulfinamide (B31)

Intermediate B31 was prepared in an analogous manner of that described in Scheme B1 and used to synthesize Intermediate B4. LC-MS: 303.2 (M+1). $^1$H NMR δ 8.37 (s, 1H), 7.35 (s, 1H), 4.64 (q, J=6.8 Hz, 1H), 3.29-3.17 (m, 1H), 2.93 (qd, J=6.9, 14.3 Hz, 1H), 2.32 (s, 3H), 1.64 (d, J=6.8 Hz, 3H), 1.18-1.09 (m, 12H)

Intermediate B33

1-(6-chloropyrimidin-4-yl)-N-ethylethan-1-amine (B33)

SCHEME B8

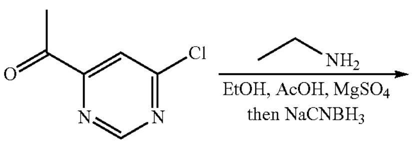

B32

-continued

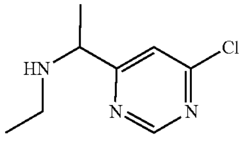

B33

To a solution of 1-(6-chloropyrimidin-4-yl)ethan-1-one (B32, 460 mg, 2.94 mmol) in EtOH (10 mL) was added magnesium sulfate (707 mg, 5.88 mmol), ethylamine (2.0 M in THF, 7.35 mL, 14.69 mmol), and acetic acid (0.673 mL, 11.75 mmol). The reaction was heated to 90° C. for 1 h, then cooled to ambient temperature. Sodium cyanoborohydride (369 mg, 5.88 mmol) was added and the mixture was stirred for 18 h at ambient temperature. The reaction was cooled and poured onto 0.5N aq. NaOH (60 mL) and extracted with DCM (3×30 mL). The combined organic layers were dried ($Na_2SO_4$), filtered and concentrated. The crude product was purified by flash silica chromatography (0-100% EtOAc/EtOH 3:1 mix in hexanes gradient) to yield 1-(6-chloropyrimidin-4-yl)-N-ethylethan-1-amine (B33). LC-MS: 186.1 (M+1).

Intermediate B35

1-(2-chloropyridin-4-yl)-N-ethylethan-1-amine (B35)

SCHEME B9

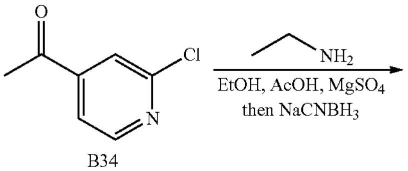

B34

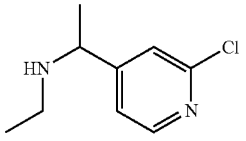

B35

Step 1: 1-(2-chloropyridin-4-yl)-N-ethylethan-1-amine (B35)

A sealable vial was charged with 1-(2-chloropyridin-4-yl)ethan-1-one (B34, 530 mg, 3.41 mmol), which was dissolved in EtOH (20 mL) and treated with magnesium sulfate (820 mg, 6.81 mmol) and ethylamine (8.52 mL, 17.03 mmol) (2.0 M in THF). Acetic acid (0.780 mL, 13.63 mmol) was added, and the reaction was heated to 50° C. and for 1 h. The reaction was cooled to ambient temperature and sodium cyanoborohydride (428 mg, 6.81 mmol) was added and stirring continued for 20 h. The reaction was filtered through a pad of Celite, rinsing with EtOAc (3×20 mL) and concentrated. The crude material was purified by flash silica chromatography (0-15% $NH_4OH$/MeOH 100:1 mix in DCM) to afford 1-(2-chloropyridin-4-yl)-N-ethylethan-1-amine (B35). LC-MS: 185.1 (M+1).

Intermediate B43

(R)-1-(5-chloro-6-methoxypyridazin-3-yl)-N-ethylethan-1-amine (B43)

SCHEME B10

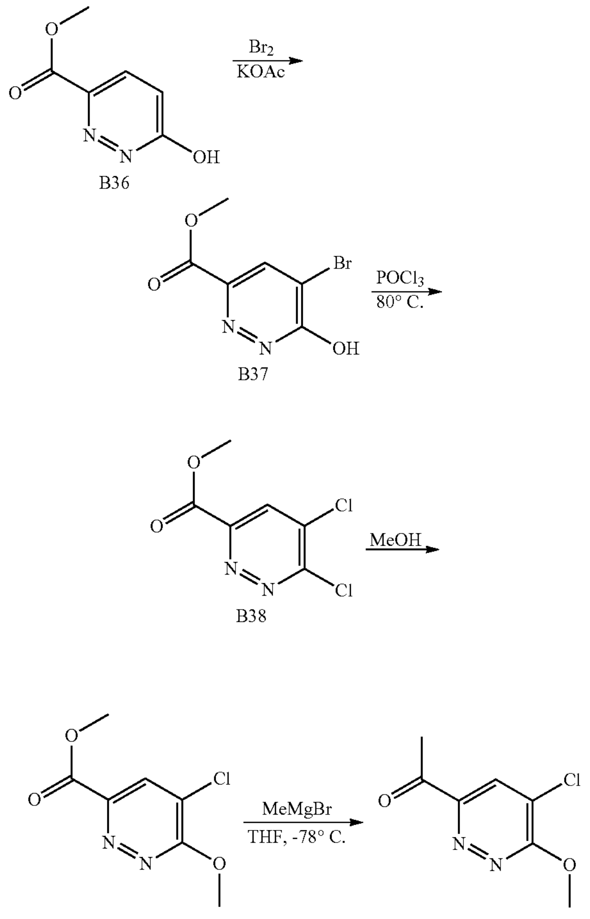

B36 B37 B38 B39 B40

Step 1: methyl 5-bromo-6-hydroxypyridazine-3-carboxylate (B37)

To a solution of methyl 6-hydroxypyridazine-3-carboxylate (B36, 5 g, 162 mmol) in AcOH (250 mL) were added potassium acetate (80 g, 811 mmol) and bromine (104 g, 649 mmol) slowly and the reaction was stirred at 80° C. for 3 h. LCMS showed formation of the desired product mass. The reaction was adjusted to pH=8 with sat. aq. $NaHCO_3$ and extracted with EtOAc (3×200 mL). The combined organic layers were washed with brine (100 mL), dried ($Na_2SO_4$), filtered and concentrated to yield methyl 5-bromo-6-hydroxypyridazine-3-carboxylate (B37), which was carried forward without purification. $^1$H NMR: (400 MHz, $CD_3OD$) δ 8.33 (s, 1H), 3.91 (s, 3H).

Step 2: methyl 5,6-dichloropyridazine-3-carboxylate (B38)

A solution of 5-bromo-6-hydroxypyridazine-3-carboxylate (B37, 15 g, 64.4 mmol) in $POCl_3$ (150 mL) was stirred at 110° C. for 3 h. LCMS showed complete conversion. The reaction was concentrated to give methyl 5,6-dichloropyridazine-3-carboxylate (B38), which was carried forward without purification.

Step 3: methyl 5-chloro-6-methoxypyridazine-3-carboxylate (B39)

A solution of methyl 5,6-dichloropyridazine-3-carboxylate (B38, 30 g, 145 mmol) in MeOH (300 mL) was stirred at 20° C. for 3 h. LCMS showed complete conversion. The reaction was concentrated and dissolved in water (500 mL). Sat. aq. $NaHCO_3$ was added to adjust to pH=8 and the reaction was extracted with EtOAc (3×200 mL). The combined organic layers were washed with brine (100 mL), dried ($Na_2SO_4$), filtered and concentrated. The crude material was purified by flash silica chromatography (0-20% EtOAc in petroleum ether gradient) to give methyl 5-chloro-6-methoxypyridazine-3-carboxylate (B39). $^1$H NMR: (400 MHz, $CDCl_3$) δ 8.16 (s, 1H), 4.30 (s, 3H), 4.04 (s, 3H).

Step 4. 1-(5-chloro-6-methoxypyridazin-3-yl)ethan-1-one (B40)

To a solution of methyl 5-chloro-6-methoxypyridazine-3-carboxylate (B39, 4 g, 19.74 mmol) in THF (40 mL) was added methylmagnesium bromide (13.16 mL, 39.5 mmol) at −78° C. and the reaction was stirred at −78° C. for 4 h. LCMS showed formation of the desired product mass. The reaction mixture was poured into water (50 mL) and extracted with EtOAc (3×30 mL). The combined organic layers were washed with brine (30 mL), dried ($Na_2SO_4$), filtered and concentrated. The crude material was purified by flash silica chromatography (0-16% EtOAc in petroleum ether gradient) to afford 1-(5-chloro-6-methoxypyridazin-3-yl)ethan-1-one (B40).

1-(5-chloro-6-methoxypyridazin-3-yl)-N-ethylethan-1-amine (B41)

Intermediate B41 was prepared in an analogous manner of that described in Scheme B8 and used to synthesize Intermediate B33. $^1$H NMR: (500 MHz, $CDCl_3$) δ 7.58 (s, 1H), 4.25-4.15 (m, 3H), 4.14-4.04 (m, 1H), 2.60 (qd, J=7.1, 11.4 Hz, 1H), 2.46 (qd, J=7.2, 11.3 Hz, 1H), 1.40 (d, J=6.7 Hz, 3H), 1.08 (t, J=7.1 Hz, 3H)

(R)-1-(5-chloro-6-methoxypyridazin-3-yl)-N-ethyl-ethan-1-amine (B43)

The 2 enantiomers of 1-(5-chloro-6-methoxypyridazin-3-yl)-N-ethylethan-1-amine (B41) were separated by chiral SFC separation (Daicel Chiralpack AY-H column, 20% EtOH, 80% $CO_2$ with 0.1% $NH_3H_2O$ as additive) to (R)-1-(5-chloro-6-methoxypyridazin-3-yl)-N-ethylethan-1-amine (B43) and its enantiomer. $^1$H NMR (400 MHz, $CD_3OD$) δ 7.83 (s, 1H), 4.14 (s, 3H), 4.03 (q, J=6.8 Hz, 1H), 2.51 (qd, J=7.2, 11.5 Hz, 1H), 2.38 (qd, J=7.2, 11.4 Hz, 1H), 1.38 (d, J=6.8 Hz, 3H), 1.07 (t, J=7.1 Hz, 3H).

Intermediate B48

1-(4-chloro-5-methoxypyrimidin-2-yl)-N-ethylethan-1-amine (B48)

SCHEME B11

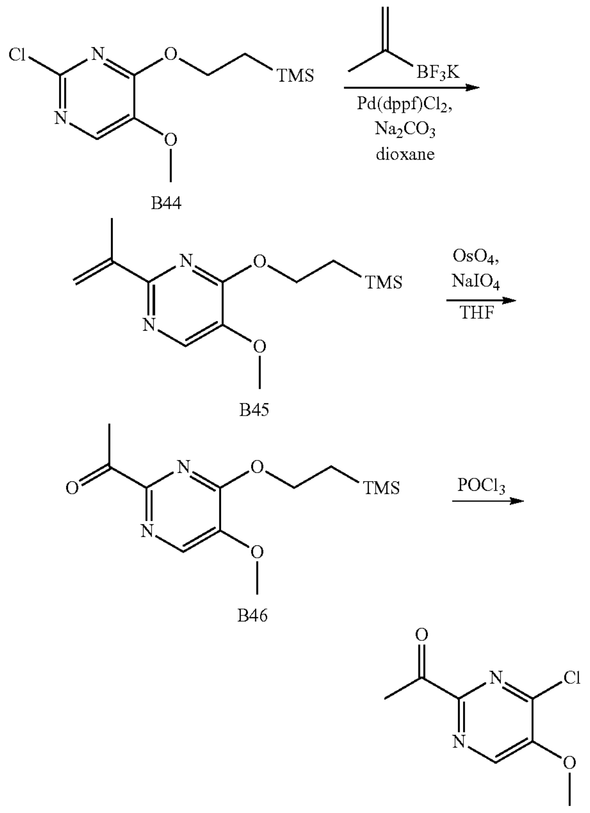

B44

B45

B46

B47

Step 1: 5-methoxy-2-(prop-1-en-2-yl)-4-(2-(trimethylsilyl)ethoxy)pyrimidine (B45)

A solution of 2-chloro-5-methoxy-4-(2-(trimethylsilyl)ethoxy)pyrimidine (B44, 1.7 g, 6.52 mmol), potassium isopropenyltrifluoroborate (1.061 g, 7.17 mmol) and $Na_2CO_3$ (1.382 g, 13.04 mmol) in 1,4-dioxane (30 mL) and water (10 mL) was purged with nitrogen at ambient temperature and $Pd(dppf)Cl_2$ (0.266 g, 0.326 mmol) was added. The reaction was heated at 90° C. for 10 h under nitrogen. TLC showed almost complete conversion to the desired product mass. The reaction was cooled, diluted with water and extracted with EtOAc (5×10 mL). The combined organic layers were dried ($Na_2SO_4$), filtered and concentrated. The crude material was purified by flash silica chromatography (10% EtOAc in petroleum ether) to give 5-methoxy-2-(prop-1-en-2-yl)-4-(2-(trimethylsilyl)ethoxy)pyrimidine (B45). LC-MS: m/z (M+H): 267.1 found, 267.1 required.

Step 2: 1-(5-methoxy-4-(2-(trimethylsilyl)ethoxy)pyrimidin-2-yl)ethan-1-one (B46)

To a solution of 5-methoxy-2-(prop-1-en-2-yl)-4-(2-(trimethylsilyl)ethoxy)-pyrimidine (B45, 3.2 g, 12.01 mmol) in THF (50 mL) was added osmium(VIII) oxide (0.15 g, 0.601 mmol) (1% aqueous solution) at 0° C. and the reaction was stirred for 30 min. Sodium periodate (10.28 g, 48.0 mmol) was then added and the reaction was stirred at 20° C. for 12 h. LCMS analysis showed the formation of the desired product mass. The reaction mixture was poured into water (30 mL) and extracted with EtOAc (3×20 mL). The combined organic layers were washed with sat. aq. $Na_2SO_3$ (20 mL) and brine (20 mL), dried ($Na_2SO_4$), filtered and concentrated. The crude material was purified by flash silica chromatography (30% EtOAc in petroleum ether) to give 1-(5-methoxy-4-(2-(trimethylsilyl)ethoxy)pyrimidin-2-yl)ethan-1-one.

Step 3: 1-(4-chloro-5-methoxypyrimidin-2-yl)ethan-1-one (B47)

To 1-(5-methoxy-4-(2-(trimethylsilyl)ethoxy)pyrimidin-2-yl)ethan-1-one (B46, 2 g, 7.45 mmol) was added phosphoryl trichloride (12.57 g, 82 mmol) under nitrogen. The reaction was stirred at 80° C. reflux for 3 h. TLC showed consumption of the starting material and formation of a new spot. The reaction was concentrated. The residue was poured into water (150 mL). neutralized with $Na_2CO_3$ and extracted with EtOAc (3×20 mL). The combined organic layers were dried ($Na_2SO_4$), filtered and concentrated. The crude material was purified by flash silica chromatography (55% EtOAc in petroleum ether) to afford 1-(4-chloro-5-methoxypyrimidin-2-yl)ethan-1-one (B47). LC-MS: 186.9 (M+1).

1-(4-chloro-5-methoxypyrimidin-2-yl)-N-ethylethan-1-amine (B48)

Intermediate B48 was prepared in an analogous manner of that described in Scheme B8 and used to synthesize Intermediate B33. LC-MS: 216.1 (M+1).

Intermediate B51

1-(6-chloro-2-methylpyrimidin-4-yl)-N-ethylethan-1-amine (B51)

SCHEME B12

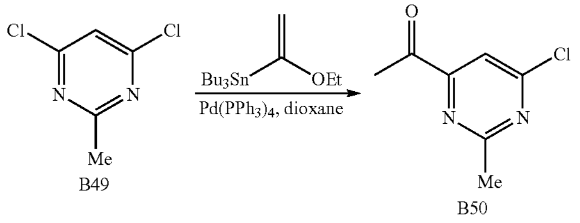

B49

B50

Step 1: 1-(6-chloro-2-methylpyrimidin-4-yl)ethan-1-one (B50)

A solution of 4,6-dichloro-2-methylpyrimidine (B49, 606 mg, 3.72 mmol) in dioxane (33 mL) was degassed with nitrogen. Tributyl(1-ethoxyvinyl)tin (1.884 mL, 5.58 mmol) and tetrakis(triphenylphosphine)palladium(0) (430 mg, 0.372 mmol) were added and the reaction was heated at 100° C. for 3 h. The reaction was cooled to ambient temperature and 10% aq. HCl (1 mL) was added and stirring continued for 1 h. The reaction was poured into sat. aq. $NaHCO_3$(30 mL) and extracted with EtOAc (3×30 mL). The combined organic layers were dried ($Na_2SO_4$), filtered and concentrated. The crude material was purified by flash silica chromatography (0-100% EtOAc/EtOH 3:1 mix in hexanes gradient). The desired were combined to afford 1-(6-chloro-2-methylpyrimidin-4-yl)ethan-1-one (B50). LC-MS: 171.0 (M+1).

B51

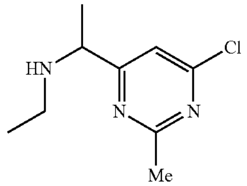

1-(6-chloro-2-methylpyrimidin-4-yl)-N-ethylethan-1-amine (B51)

Intermediate B51 was prepared in an analogous manner of that described in Scheme B8 and used to synthesize Intermediate B33. LC-MS: 200.1 (M+1).

Intermediate B53

The following intermediates in Table B2 were synthesized in an analogous manner of that described in Schemes B12 and B8 and used to synthesize Intermediate B51 starting from the appropriate halides.

TABLE B2

| Halide | Intermediate | Observed LCMS (M + 1) |
| --- | --- | --- |
| 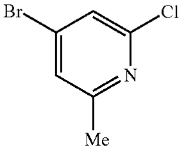 B52 | 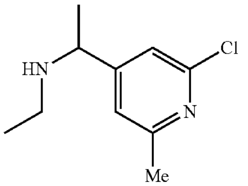 B53 | 199.1 |

Intermediate B58

(R)—N—((R)-1-(6-bromo-5-methoxypyridin-2-yl)ethyl)-N-ethyl-2-methylpropane-2-sulfinamide (B58)

SCHEME B13

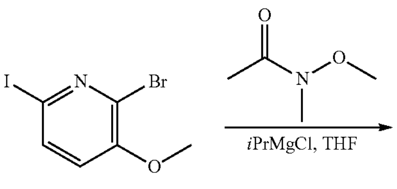

B54

-continued

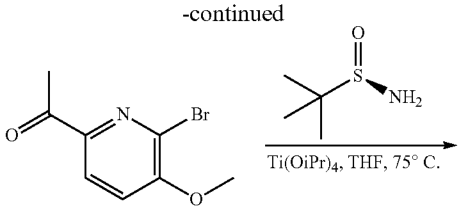

B55

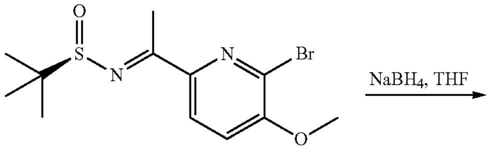

B56

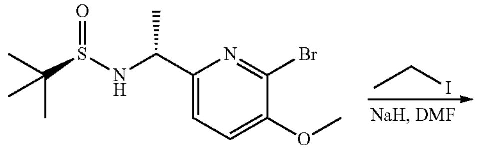

B57

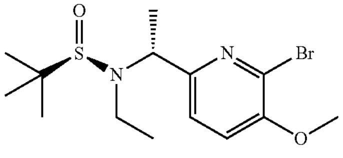

B58

Step 1: 1-(6-bromo-5-methoxypyridin-2-yl)ethan-1-one (B55)

To a solution of 2-bromo-6-iodo-3-methoxypyridine (B54, 3 g, 9.56 mmol) in THF (30 mL) cooled to 0° C. were added N-methoxy-N-methylacetamide (1.084 g, 10.51 mmol), then isopropylmagnesium chloride (7.17 mL, 14.33 mmol). The solution was stirred at 0° C. to 20° C. for 3 h. TLC showed complete conversion. The reaction was poured into water (100 mL) and extracted with EtOAc (3×30 mL). The combined organic layers were washed with brine (50 mL), dried ($Na_2SO_4$), filtered and concentrated. The crude material was purified by flash silica chromatography (0-25% EtOAc in petroleum ether gradient) to afford 1-(6-bromo-5-methoxypyridin-2-yl)ethan-1-one (B55).

Step 2: (R,E)-N-(1-(6-bromo-5-methoxypyridin-2-yl)ethylidene)-2-methylpropane-2-sulfinamide To a solution of 1-(6-bromo-5-methoxypyridin-2-yl)ethan-1-one (B55, 1.5 g, 6.52 mmol) in THF (30 mL) were added (R)-2-methylpropane-2-sulfinamide (1.580 g, 13.04 mmol) and tetraisopropoxytitanium (11.12 g, 39.1 mmol). The reaction was stirred at 75° C. for 5 h. TLC showed complete conversion. The reaction was poured into brine (100 mL) and the layers were separated after filtering the solid formed. The organic layer was dried ($Na_2SO_4$), filtered and concentrated. The crude material was purified by flash silica chromatography (20-50% EtOAc in petroleum ether gradient) to afford (R,E)-N-(1-(6-bromo-5-methoxypyridin-2-yl)ethylidene)-2-methylpropane-2-sulfinamide (B56).

Step 3: (R)—N—((R)-1-(6-bromo-5-methoxypyridin-2-yl)ethyl)-2-methylpropane-2-sulfinamide To a solution of (R,E)-N-(1-(6-bromo-5-methoxypyridin-2-yl)ethylidene)-2-methylpropane-2-sulfinamide (B56, 1.3 g, 3.90 mmol) in THF (20 mL) was added $NaBH_4$ (0.443 g, 11.70 mmol) at −10° C., and the reaction was stirred at −10° C. under nitrogen for 5 h. LCMS showed complete conversion. The reaction was poured into water (100 mL) and extracted with EtOAc (3×100 mL). The combined organic layers were washed with brine (100 mL), dried ($Na_2SO_4$), filtered and concentrated. The crude material was purified by flash silica chromatography (0-30% EtOAc in petroleum ether gradient) to afford (R)—N—((R)-1-(6-bromo-5-methoxypyridin-2-yl)ethyl)-2-methylpropane-2-sulfinamide (B57). LC-MS: 335.3. 337.3 (M+1).

Step 4: (R)—N—((R)-1-(6-bromo-5-methoxypyridin-2-yl)ethyl)-N-ethyl-2-methylpropane-2-sulfinamide To a solution of (R)—N—((R)-1-(6-bromo-5-methoxypyridin-2-yl)ethyl)-2-methylpropane-2-sulfinamide (B57, 0.8 g, 2.386 mmol) in DMF (50 mL) was added sodium hydride (260 mg, 6.50 mmol) at 0° C. under nitrogen. The reaction was stirred at 0° C. for 30 min. Iodoethane (744 mg, 4.77 mmol) was added and the reaction was stirred at ambient temperature for 1 h. LCMS showed formation of the desired product mass. The reaction was poured into water (20 mL) and extracted with EtOAc (3×20 mL). The combined organic layers were washed with brine (50 mL), dried ($Na_2SO_4$), filtered and concentrated. The crude material was purified by flash silica chromatography (30-70% EtOAc in petroleum ether gradient) to afford (R)—N—((R)-1-(6-bromo-5-methoxypyridin-2-yl)ethyl)-N-ethyl-2-methylpropane-2-sulfinamide (B58). LC-MS: 364.5. 366.5 (M+1).

Intermediate B61

(R)—N—((R)-1-(5-bromo-6-methylpyridin-3-yl)ethyl)-N-ethyl-2-methylpropane-2-sulfinamide

SCHEME B14

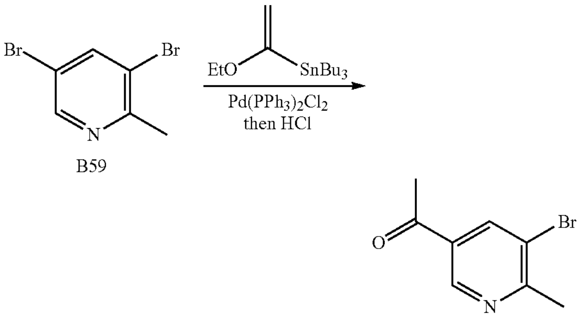

B59

B60

Step 1: 1-(5-bromo-6-methylpyridin-3-yl)ethan-1-one (B60)

To a solution of 3,5-dibromo-2-methylpyridine (B59, 20 g, 80 mmol) in dioxane (200 mL) were added tributyl (1-ethoxyvinyl)stannane (25.9 g, 71.7 mmol) and bis (triphenylphosphine)-palladium (II) dichloride (2.80 g, 3.99 mmol). The reaction was stirred at 100° C. for 10 h. LCMS showed complete conversion. The reaction was cooled to 20° C. and HCl (100 mL) (4M in dioxane) was added and the reaction was stirred for 1 h. LCMS showed formation of the desired product mass. The reaction was poured into 10% aq. KF (300 mL) and extracted with EtOAc (3×200 mL). The combined organic layers were washed with brine (200 mL), dried ($Na_2SO_4$), filtered and concentrated. The crude material was purified by flash silica chromatography (54% EtOAc in petroleum ether) to give 1-(5-bromo-6-methylpyridin-3-yl)ethan-1-one (B60). LC-MS: 214.1, 216.1 (M+1). $^1$H NMR: (400 MHz, $CDCl_3$) δ 8.92 (d, J=1.7 Hz, 1H), 8.31 (d, J=2.0 Hz, 1H), 2.87-2.64 (m, 3H), 2.60-2.53 (m, 3H)

B61

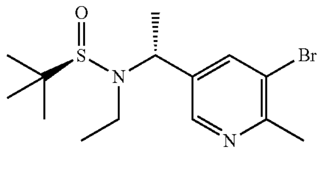

(R)—N—((R)-1-(5-bromo-6-methylpyridin-3-yl)ethyl)-N-ethyl-2-methylpropane-2-sulfinamide Intermediate B61 was prepared in an analogous manner of that described in the last 3 Steps of Scheme B13 and used to synthesize Intermediate B58. In step 3, DIBAL-H was used instead of $NaHB_4$. LC-MS: 347.1, 349.1 (M+1). $^1$H NMR: (400 MHz, $CDCl_3$) δ 8.41 (d, J=1.7 Hz, 1H), 7.77 (d, J=1.7 Hz, 1H), 4.53 (br d, J=6.4 Hz, 1H), 3.23 (qd, J=7.3, 14.7 Hz, 1H), 2.93-2.74 (m, 1H), 2.63 (s, 3H), 1.68-1.56 (m, 3H), 1.33-1.13 (m, 3H), 1.09-1.01 (m, 9H)

Intermediate B65 tert-butyl ethyl(3-(4,4,5,5-tetramethyl-1,3,2-dioxaborolan-2-yl)benzyl)carbamate (B65)

SCHEME B15

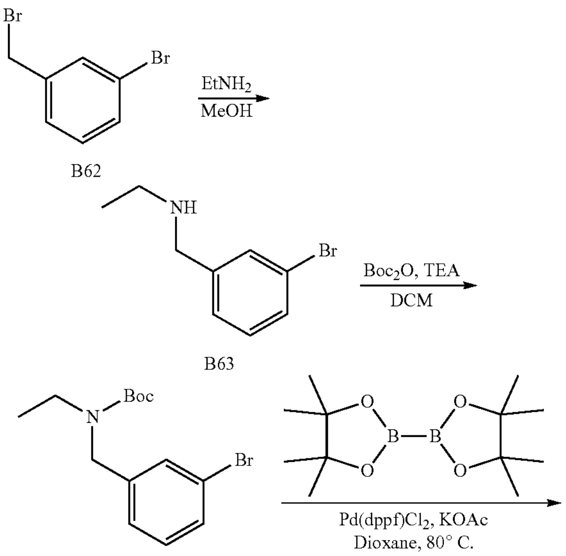

B62

B63

B64

-continued

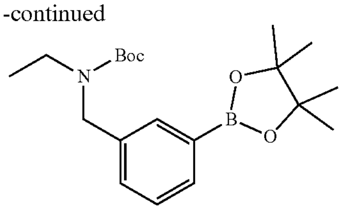

B65

Step 1: N-(3-bromobenzyl)ethanamine (B63)

To a solution of 1-bromo-3-(bromomethyl)benzene (B62, 10 g, 40.0 mmol) in MeOH (100 mL) was added ethanamine (18.04 g, 400 mmol) and the reaction was stirred at ambient temperature for 4 h. TLC showed formation of a new spot. The reaction was concentrated to afford N-(3-bromobenzyl) ethanamine (B63), which was carried forward without purification.

Step 2: tert-butyl (3-bromobenzyl)(ethyl)carbamate (B64)

To a solution of N-(3-bromobenzyl)ethanamine (B63, 8.57 g, 40.0 mmol) in DCM (100 mL) were added TEA (16.74 mL, 120 mmol) and Boc anhydride (17.5 g, 80 mmol). The reaction was stirred at ambient temperature for 16 h. LCMS showed formation of the desired product mass. The reaction was poured into water (200 mL) and extracted with DCM (3×50 mL). The combined organic layers were washed with brine (100 mL), dried ($Na_2SO_4$), filtered and concentrated. The crude material was purified by flash silica chromatography (0-10% EtOAc in petroleum ether gradient) to give tert-butyl (3-bromobenzyl)(ethyl)carbamate (B64). LC-MS: 258.1, 260.1 (M+1-tBu). $^1H$ NMR: (400 MHz, $CDCl_3$) δ 7.37-7.10 (m, 4H), 4.37 (br s, 2H), 3.38-3.06 (m, 2H), 1.49-1.40 (m, 9H), 1.14-1.00 (m, 3H).

Step 3: tert-butyl ethyl(3-(4,4,5,5-tetramethyl-1,3,2-dioxaborolan-2-yl)benzyl)carbamate (B65)

To a solution of tert-butyl (3-bromobenzyl)(ethyl)carbamate (B64, 2 g, 6.37 mmol) in dioxane (35 mL) were added 4,4,4',4',5,5,5',5'-octamethyl-2,2'-bi (1,3,2-dioxaborolane) (2.10 g, 8.27 mmol), KOAc (1.25 g, 12.74 mmol) and $PdCl_2$(dppf) (0.466 g, 0.637 mmol). The reaction was stirred at 80° C. for 5 h under nitrogen. LCMS showed formation of the desired product mass. The resulting solution of tert-butyl ethyl(3-(4,4,5,5-tetramethyl-1,3,2-dioxaborolan-2-yl)benzyl)carbamate (B65) was carried forward without purification. LC-MS: 306.2 found (M+1-tBu).

Intermediates B69-B71 and B73

SCHEME B16

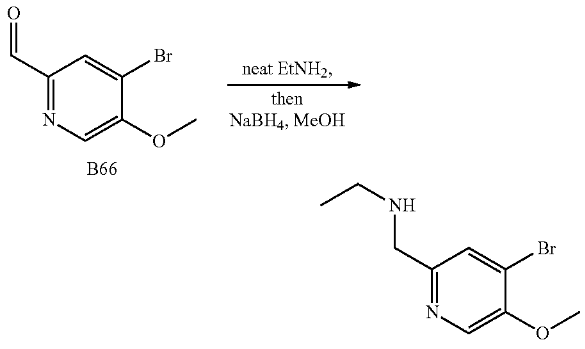

B66

B67

Step 1: N-((4-bromo-5-methoxypyridin-2-yl)methyl) ethanamine (B67)

A solution of 4-bromo-5-methoxypicolinaldehyde (B66, 100 mg, 0.463 mmol) in ethanamine (209 mg, 4.63 mmol) was stirred for 2 h at 20° C. The reaction was concentrated in vacuo. The residue was dissolved in MeOH (1 mL) and sodium borohydride (35.0 mg, 0.926 mmol) was added at 0° C. The reaction was stirred at 0° C. and then allowed to warm to 20° C. for 1 h. LCMS showed formation of the desired product mass. The reaction was quenched with HCl (4M in dioxane) to adjust the pH to 7. The resulting solution of N-((4-bromo-5-methoxypyridin-2-yl)methyl)ethanamine (B67) was carried forward without purification.

The following intermediates in Table B3 were synthesized in an analogous manner of that described in Scheme B15 and used to synthesize Intermediate B65 starting from the appropriate halides.

TABLE B3

| Halide | Intermediate | Observed LCMS (M + 1) |
| --- | --- | --- |
| 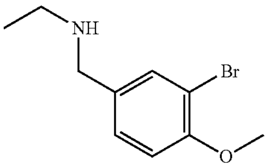 B68 | 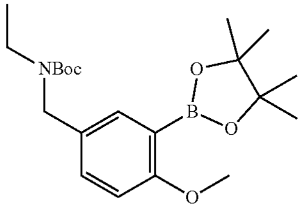 B69 | 336.2 (M + 1 − tBu) |

TABLE B3-continued

| Halide | Intermediate | Observed LCMS (M + 1) |
|---|---|---|
| 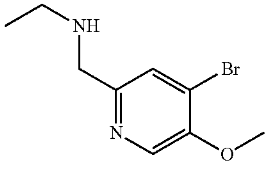 B67 | 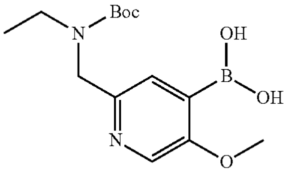 B70 | 311.1 |
| 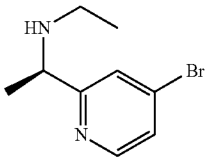 B10 | 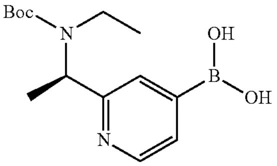 B71 | 295.3 |
| 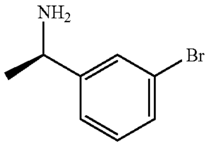 B72 | 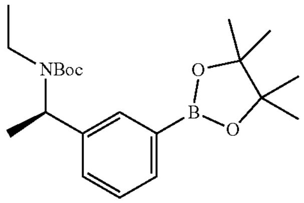 * B73 | 320.2 (M + 1 − tBu) |
| 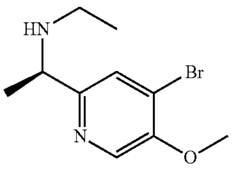 B5 | 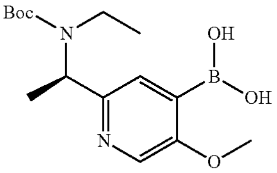 B3-1 | 325.1 |

* Between Boc protection and borylation, the conversion of (R)-1-(3-bromophenyl)ethan-1-amine (B72) to boronic acid B73 included a N alkylation with iodoethane as described for the conversion of Intermediate B57 to Intermediate B58 in Step 4 of Scheme B13.

Intermediate B76

1-(4-chloro-5-methoxypyridin-2-yl)-N-ethyl-2,2,2-trifluoroethan-1-amine (B76)

SCHEME B17

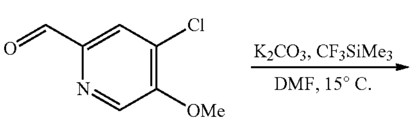

B11

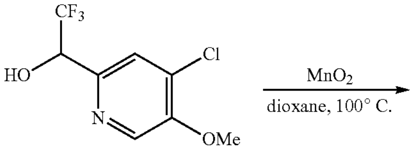

B74

-continued

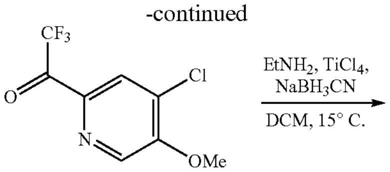

B75

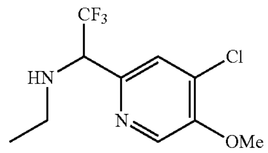

B76

Step 1: 1-(4-chloro-5-methoxypyridin-2-yl)-2,2,2-trifluoroethan-1-ol (B74)

4-chloro-5-methoxypicolinaldehyde (B11, 140 g, 816 mmol), $CF_3SiMe_3$ (232 g, 1.63 mol) and K2C03 (45.1 g, 326 mmol) were combined in DMF (1.00 L) at 15° C. The reaction was stirred at 15 C for 12 h. TLC showed complete conversion. The reaction was poured into 1M aq. HCl (1 L) and stirred at 15° C. for another 15 min. The pH was then adjusted to 7-8 using solid $NaHCO_3$. The reaction was extracted with EtOAc (3×500 mL). The combined organic layers were dried ($Na_2SO_4$) and concentrated to afford 1-(4-chloro-5-methoxypyridin-2-yl)-2,2,2-trifluoroethan-1-ol (B74) which was carried forward without purification. $^1$H-NMR: (400 MHz, $CDCl_3$) (8.27 (s, 1H), 7.45 (s, 1H), 5.08 (s, 1H), 4.95 (s, 1H), 4.04 (s, 3H)

Step 2: 1-(4-chloro-5-methoxypyridin-2-yl)-2,2,2-trifluoroethan-1-one (B75)

1-(4-chloro-5-methoxypyridin-2-yl)-2,2,2-trifluoroethan-1-ol (B74, 179 g, 741 mmol) and $MnO_2$ (258 g, 2.96 mol) were combined in dioxane (1.1 L) at 15° C. The reaction was heated to 100° C. for 12 h. LCMS showed complete conversion. The reaction was filtered through Celite and rinsed with EtOAc (3 L). The filtrate was concentrated to afford 1-(4-chloro-5-methoxypyridin-2-yl)-2,2,2-trifluoroethan-1-one (B75), which was carried forward without purification. $^1$H-NMR: (400 MHz, $CDCl_3$) δ 8.43 (s, 1H), 8.20 (s, 1H), 4.12 (s, 3H)

Step 3: 1-(4-chloro-5-methoxypyridin-2-yl)-N-ethyl-2,2,2-trifluoroethan-1-amine (B76)

1-(4-chloro-5-methoxypyridin-2-yl)-2,2,2-trifluoroethan-1-one (B75, 126 g, 526 mmol), $EtNH_2$ (119 g, 2.63 mol, 172 mL, 5.00 eq) and $TiCl_4$ (200 g, 1.05 mol, 2.00 eq) were combined in DCM (760 mL) at 15° C. The reaction was stirred at 15° C. for 12 h. $NaBH_3CN$ (99.2 g, 1.58 mol) was added to the reaction in portions and the reaction was stirred at 15° C. for another 2 h. TLC showed complete conversion. The reaction was poured into MeOH (550 mL) and stirred at 15° C. for 30 min. The pH was then adjusted to 10 with 5M aq. NaOH solution. The reaction was then filtered through Celite, rinsed with DCM (2 L) and concentrated. The crude material was purified by flash silica chromatography (3-100% EtOAc in petroleum ether) to afford 1-(4-chloro-5-methoxypyridin-2-yl)-N-ethyl-2,2,2-trifluoroethan-1-amine (B76). $^1$H NMR: (400 MHz, $CDCl_3$) δ 8.29 (s, 1H), 7.44 (s, 1H), 4.18 (q, J=14.4 Hz, 1H), 4.03 (s, 3H), 2.61-2.65 (m, 2H), 1.12 (t, J=7.2 Hz, 3H)

Intermediate B80

1-(2-Chlorothiazol-5-yl)-N-ethylethan-1-amine (B80)

SCHEME B18

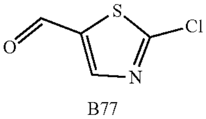

B77

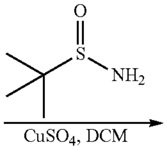

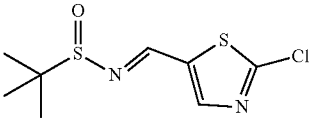

B78

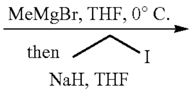

-continued

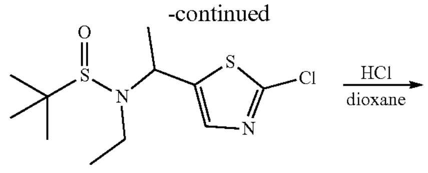

B79

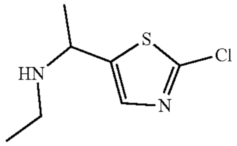

B80

Step 1: (E)-N-((2-Chlorothiazol-5-yl)methylene)-2-methylpropane-2-sulfinamide (B78)

2-Chlorothiazole-5-carbaldehyde (B77, 250 mg, 1.694 mmol), 2-methylpropane-2-sulfinamide (411 mg, 3.39 mmol), and $CuSO_4$ (1190 mg, 7.45 mmol) were combined in DCM (8 mL) and the reaction was stirred at ambient temperature overnight. The reaction was then diluted with DCM and filtered through a pad of Celite washing with DCM. The filtrate was concentrated. The crude material was purified by flash silica chromatography (0-25% EtOAc in heptane gradient) to afford (E)-N-((2-Chlorothiazol-5-yl)methylene)-2-methylpropane-2-sulfinamide (B78). LC-MS: 250.9 (M+1). $^1$H-NMR: (500 MHz, $CDCl_3$) δ 8.65 (s, 1H), 7.93 (s, 1H), 1.24 (s, 9H).

Step 2: N-(1-(2-Chlorothiazol-5-yl)ethyl)-N-ethyl-2-methylpropane-2-sulfinamide (B79)

A solution of (E)-N-((2-chlorothiazol-5-yl)methylene)-2-methylpropane-2-sulfinamide (B78, 103 mg, 0.411 mmol) in THF (2 mL) was cooled to 0° C. To this was added MeMgBr (0.21 mL, 0.630 mmol) (3M in $Et_2O$) slowly and the reaction was allowed to stir at 0° C. for 1 h. The reaction was quenched with sat. aq. $NH_4Cl$ then warmed to ambient temperature. The resulting mixture was diluted with $H_2O$then extracted with EtOAc. The combined organic layers were dried ($MgSO_4$), filtered and concentrated to afford N-(1-(2-chlorothiazol-5-yl)ethyl)-2-methylpropane-2-sulfinamide which was carried forward without purification. Crude N-(1-(2-chlorothiazol-5-yl)ethyl)-2-methylpropane-2-sulfinamide (110 mg, 0.411 mmol) was taken up in THF (2 mL). To this was added NaH (32.9 mg, 0.822 mmol) (60% mineral oil) at ambient temperature. After gas evolution had ceased iodoethane (0.13 mL, 1.609 mmol) was added and stirring was continued at ambient temperature overnight. The reaction was quenched with sat. aq. $NH_4Cl$ then diluted with $H_2O$then extracted with EtOAc. The combined organic layers were dried ($MgSO_4$), filtered and concentrated. The crude material was purified by flash silica chromatography (0-100% EtOAc in heptane gradient) to afford N-(1-(2-Chlorothiazol-5-yl)ethyl)-N-ethyl-2-methylpropane-2-sulfinamide (B79). LC-MS: 295.0 (M+1).

Step 3: 1-(2-Chlorothiazol-5-yl)-N-ethylethan-1-amine (B80)

N-(1-(2-Chlorothiazol-5-yl)ethyl)-N-ethyl-2-methylpropane-2-sulfinamide (B79, 61 mg, 0.207 mmol) was taken up in HCl (1.5 mL) (4M in dioxane) and the reaction was stirred at ambient temperature for 1 h. The reaction was concentrated to afford 1-(2-Chlorothiazol-5-yl)-N-ethylethan-1-amine (B80) which was carried forward without purification. LC-MS: 191.0 (M+1).

Intermediate B84

1-(5-Chlorothiazol-2-yl)-N-ethylethan-1-amine (B84)

SCHEME B19

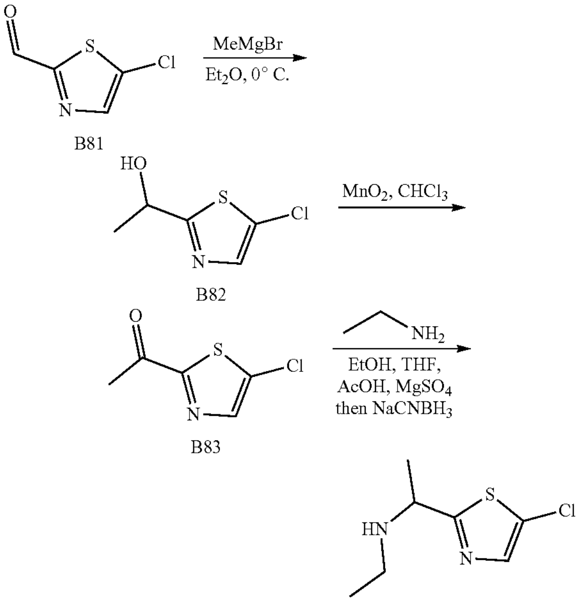

B81

B82

B83

B84

Step 1: 1-(5-Chlorothiazol-2-yl)ethan-1-ol (B82)

To a solution of 5-chlorothiazole-2-carbaldehyde (B81, 250 mg, 1.694 mmol) in THF (8 mL) was added MeMgBr (0.85 mL, 2.55 mmol) (3M in $Et_2O$) slowly at 0° C. The reaction was stirred at 0° C. for 1 h. The reaction was quenched with sat. aq. $NH_4Cl$ then warmed to ambient temperature, diluted with $H_2O$and extracted with EtOAc. The combined organic layers were dried ($MgSO_4$) filtered and concentrated to afford 1-(5-Chlorothiazol-2-yl)ethan-1-ol (B82) which was carried forward without purification. LC-MS: 163.9 (M+1).

Step 2: 1-(5-Chlorothiazol-2-yl)ethan-1-one (B83)

1-(5-chlorothiazol-2-yl)ethan-1-ol (B82, 0.277 g, 1.694 mmol) was dissolved in $CHCl_3$ (8 mL) and $MnO_2$ (0.74 g, 8.51 mmol) was added. The reaction was heated to reflux overnight. The reaction was cooled to ambient temperature, diluted with $CHCl_3$ and filtered through Celite washing with $CHCl_3$. The filtrate was concentrated to afford 1-(5-Chlorothiazol-2-yl)ethan-1-one (B83), which was carried forward without purification.

Step 3: 1-(5-Chlorothiazol-2-yl)-N-ethylethan-1-amine (B84)

To a solution of 1-(5-chlorothiazol-2-yl)ethan-1-one (B83, 218 mg, 1.349 mmol) in EtOH (7 mL) in a microwave vial was added 2M ethanamine (3.4 mL, 6.80 mmol) in THF, AcOH (0.39 mL, 6.81 mmol), $MgSO_4$ (325 mg, 2.70 mmol), then $NaBH_3CN$ (170 mg, 2.70 mmol). The vial was sealed then heated to 80° C. by conventional heating overnight. The reaction was cooled to ambient temperature then diluted with EtOH and filtered through Celite washing with EtOH. The filtrate was concentrated. The crude material taken up in 20 mL 1:1 DCM:TEA then concentrated. This material was then was purified by flash silica chromatography (0-100% EtOAc:EtOH 3:1 mix in heptane gradient) to give mixed fractions. The fractions containing product were pooled then concentrated. The crude material was purified by reverse phase HPLC (5-50% ACN in water, with 0.1% TFA as modifier) to afford 1-(5-Chlorothiazol-2-yl)-N-ethylethan-1-amine (B84). LC-MS: 191.0 (M+1). $^1$H-NMR: (500 MHz, $CDCl_3$) δ 7.62 (s, 1H), 4.65 (q, J=6.9 Hz, 1H), 3.10 (qt, J=7.4, 3.8 Hz, 2H), 1.78 (d, J=6.9 Hz, 3H), 1.34 (t, J=7.3 Hz, 3H).

Intermediate B87

1-(6-chloropyrimidin-4-yl)ethan-1-one (B87)

SCHEME B20

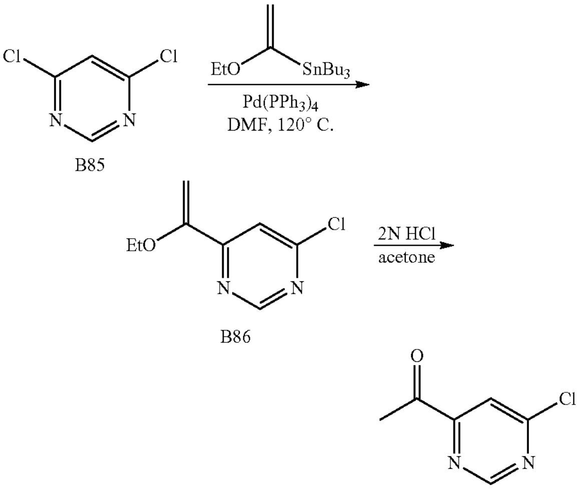

B85

B86

B87

Step 1: 4-chloro-6-(1-ethoxyvinyl)pyrimidine (B86)

To a solution of 4,6-dichloropyrimidine (B85, 10 g, 67.1 mmol) in DMF (100 mL) were added tributyl(1-ethoxyvinyl)stannane (24.24 g, 67.1 mmol) and $Pd(Ph_3P)_4$ (7.76 g, 6.71 mmol). The mixture was stirred at 120° C. for 12 h. TLC showed formation of new spots. The reaction was poured into water (200 mL) and extracted with EtOAc (3×100 mL). The combined organic layers were washed with brine (50 mL), dried ($Na_2SO_4$), filtered and concentrated. The crude material was purified by flash silica chromatography (0-4% EtOAc in petroleum ether gradient) to afford 4-chloro-6-(1-ethoxyvinyl)pyrimidine (B86). $^1$H NMR: (400 MHz, $CDCl_3$) δ 8.88 (s, 1H), 7.65 (s, 1H), 5.70 (d, J=2.3 Hz, 1H), 4.56 (d, J=2.0 Hz, 1H), 3.96 (q, J=7.0 Hz, 2H), 1.44 (t, J=7.0 Hz, 3H).

Step 2: 1-(6-chloropyrimidin-4-yl)ethan-1-one (B87)

To a solution of 4-chloro-6-(1-ethoxyvinyl)pyrimidine (B86, 3.5 g, 18.96 mmol) in acetone (40 mL) was added HCl (56.9 mL, 114 mmol) (2M in HCl) and the reaction was stirred at 20° C. for 3 h. TLC showed complete conversion. The reaction mixture was poured into sat. aq. $NaHCO_3$(100 mL) and extracted with EtOAc (3×50 mL). The combined organic layers were washed with brine (50 mL), dried ($Na_2SO_4$), filtered and concentrated. The filtrate was concentrated and purified by flash silica chromatography (0-3% EtOAc in petroleum ether gradient) to afford 1-(6-chloropyrimidin-4-yl)ethan-1-one (B87). $^1H$ NMR (400 MHz, $CDCl_3$) δ 9.18 (d, J=0.8 Hz, 1H), 7.92 (d, J=0.8 Hz, 1H), 2.72 (s, 3H).

Intermediate B88

(R)-(2-(1-((tert-butoxycarbonyl)(ethyl)amino)ethyl)-5-fluoropyridin-4-yl)boronic acid (B88)

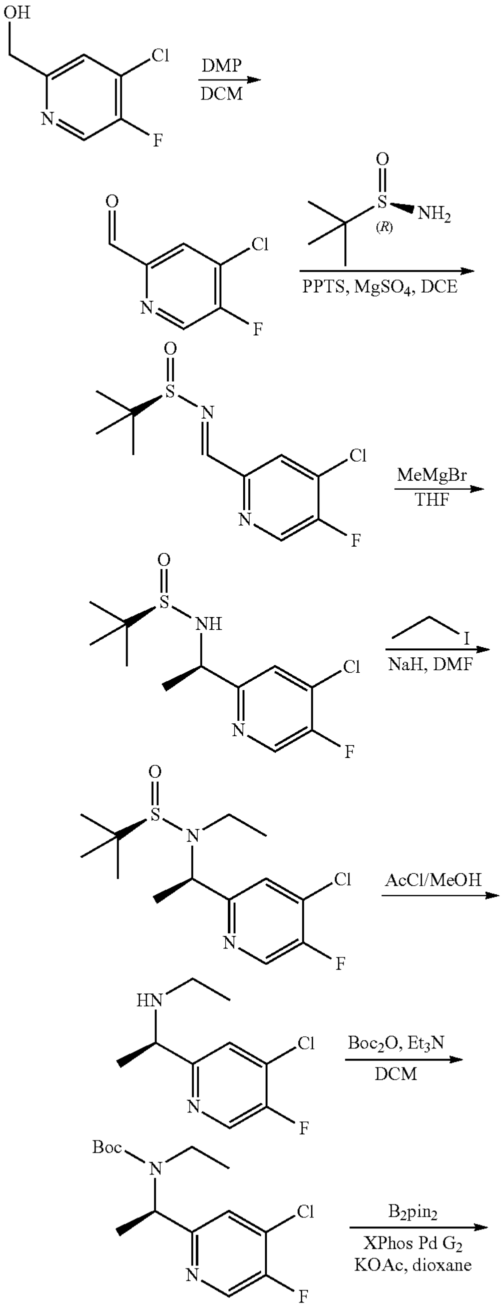

-continued

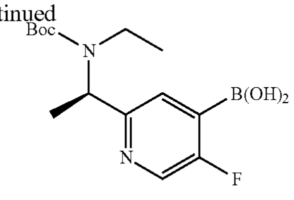

B88

To a solution of (4-chloro-5-fluoropyridin-2-yl)methanol (2 g, 12.38 mmol) in DCM (50 mL) was added Dess-Martin periodinane (5.78 g, 13.62 mmol) at 0° C. The mixture was stirred at 0° C. to 20° C. for 3 h. The mixture was quenched with $NaHCO_3$(30 mL) and $H_2O$ (50 mL) and filtered, Then extracted with DCM (50 mL×3), washed with brine (50 mL), dried over $Na_2SO_4$, filtered and concentrated under reduced pressure. The crude was purified by Flash silica gel chromatography (ISCO®; 20 g SepaFlash® Silica Flash Column, Eluent of 5% EtOAc/Pet. ether gradient) to give 4-chloro-5-fluoropicolinaldehyde. LCMS m/z (M+H): 160.0 required, 160.1 found.

To a solution of 4-chloro-5-fluoropicolinaldehyde (1.7 g, 10.66 mmol) in DCE (50 mL) was added $MgSO_4$ (7.69 g, 63.9 mmol), (R)-2-methylpropane-2-sulfinamide (1.550 g, 12.79 mmol) and PPTS (0.268 g, 1.066 mmol). The resulting mixture was stirred at 80° C. under N2 protection for 12 h. The reaction mixture was concentrated and purified by flash silica gel chromatography (ISCO®; 20 g SepaFlash® Silica Flash Column, eluent of 50% ethyl acetate/pet. ether gradient) to give (R,E)-N-((4-chloro-5-fluoropyridin-2-yl)methylene)-2-methylpropane-2-sulfinamide. LCMS m/z (M+H): 263.0 required, 263.0 found. $^1H$ NMR 5044576-0127-1 (400 MHz, $CDCl_3$) δ 8.55 (d, J=15.9 Hz, 2H), 8.05 (d, J=6.0 Hz, 1H), 1.28-1.16 (m, 9H)

To a solution of (R,E)-N-((4-chloro-5-fluoropyridin-2-yl)methylene)-2-methylpropane-2-sulfinamide (1.95 g, 7.42 mmol) in THF (50 mL) was added methylmagnesium bromide (9.90 mL, 29.7 mmol) (3M in $Et_2O$). The mixture was stirred at 0° C. under N2 protection for 2 h. The reaction mixture was poured into $NH_4Cl$ (100 mL), extracted with EtOAc (50 mL×3), dried over $Na_2SO_4$ and filtered. The filtrate was concentrated and purified Flash silica gel chromatography (ISCO®; 40 g SepaFlash® Silica Flash Column, Eluent of 60% EtOAc/Pet.ether gradient) to give (R)—N—((R)-1-(4-chloro-5-fluoropyridin-2-yl)ethyl)-2-methylpropane-2-sulfinamide. LCMS m/z (M+H): 279.1 required, 279.1 found.

To a solution of (R)—N—((R)-1-(4-chloro-5-fluoropyridin-2-yl)ethyl)-2-methylpropane-2-sulfinamide (1.7 g, 6.10 mmol) in DMF (50 mL) was added NaH (0.488 g, 12.20 mmol) (60% wt) at 0° C. under N2. The mixture was stirred at 0° C. for 30 min., iodoethane (0.976 mL, 12.20 mmol) was added and stirred at 0° C. for 2 h. The reaction mixture was poured into water (150 mL), extracted with EtOAc (100 mL×3). The combined organic layers were washed with brine (100 mL), dried over $Na_2SO_4$ and filtered. The filtrate was concentrated and purified by Flash silica gel chromatography (ISCO®; 40 g SepaFlash® Silica Flash Column, Eluent of 60% EtOAc/Pet.ether gradient) to give (R)—N—((R)-1-(4-chloro-5-fluoropyridin-2-yl)ethyl)-N-ethyl-2-methylpropane-2-sulfinamide. LCMS m/z (M+H): 307.1 required, 307.0 found.

To a solution of (R)—N—((R)-1-(4-chloro-5-fluoropyridin-2-yl)ethyl)-N-ethyl-2-methylpropane-2-sulfinamide (1.6 g, 5.21 mmol) in MeOH (40 mL) was added AcCl (0.742 mL, 10.43 mmol) at 0° C. The reaction was stirred at 0° C. to 25° C. for 2 h. $Et_3N$ was added to adjust pH to between 7-8, then the reaction mixture was concentrated under reduced pressure to give (R)-1-(4-chloro-5-fluoropyridin-2-yl)-N-ethylethan-1-amine, which was used to the next step without further purification. LCMS m/z (M+H): 203.1 required, 203.0 found.

To a solution of (R)-1-(4-chloro-5-fluoropyridin-2-yl)-N-ethylethan-1-amine (1 g, 4.93 mmol) in DCM (40 mL) was added $Et_3N$ (2.063 mL, 14.80 mmol) and Boc-Anhydride (1.719 mL, 7.40 mmol) at 0° C. The reaction was stirred at 0° C. to 25° C. for 14 h. The mixture was quenched with $H_2O$(100 mL) and extracted with DCM (50 mL×3), washed with brine (30 mL), dried over $Na_2SO_4$, filtered and concentrated under reduced pressure. The filtrate was concentrated and purified by flash silica gel chromatography (ISCO®; 20 g SepaFlash® Silica Flash Column, eluent of 10% ethyl acetate/pet. ether gradient) to give tert-butyl (R)-(1-(4-chloro-5-fluoropyridin-2-yl)ethyl)(ethyl)carbamate. LCMS m/z (M+H): 303.1 required, 303.0 found.

To a solution of tert-butyl (R)-(1-(4-chloro-5-fluoropyridin-2-yl)ethyl)(ethyl)carbamate (300 mg, 0.991 mmol) in Dioxane (5 mL) were added 4,4,4',4',5,5,5',5'-octamethyl-2,2'-bi(1,3,2-dioxaborolane) (327 mg, 1.288 mmol), potassium acetate (292 mg, 2.97 mmol), chloro(2-dicyclohexylphosphino-2',4',6'-triisopropyl-1,1'-biphenyl)[2-(2'-amino-1,1'-biphenyl)]palladium(ii) (78 mg, 0.099 mmol). The resulting mixture was stirred at 80° C. under N2 protection for 12 h. The resulting crude mixture of (R)-(2-(1-((tert-butoxycarbonyl)(ethyl)amino)ethyl)-5-fluoropyridin-4-yl)boronic acid (B88) in dioxane was used as is without further purification. LCMS m/z (M+H): 313.2 required, 313.1 found.

Intermediate B89

(R)-(2-(1-((tert-butoxycarbonyl)(ethyl)amino)ethyl)pyridin-4-yl)boronic acid (B89)

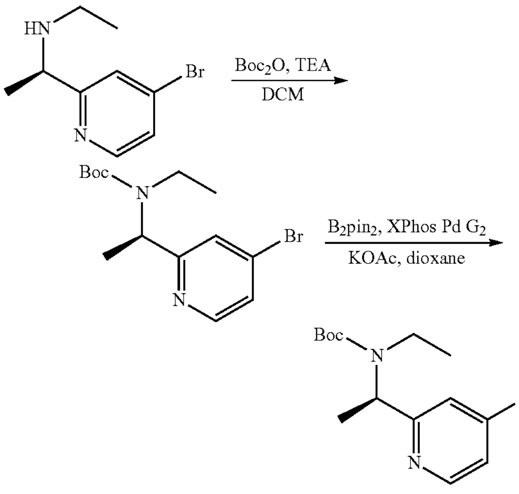

B89

To a solution of R-1-(4-bromopyridin-2-yl)-N-ethylethan-1-amine B10 (3.44 g, 15.01 mmol) in DCM (50 mL) were added $Et_3N$ (6.28 mL, 45.0 mmol) and Boc-Anhydride (5.23 mL, 22.52 mmol) at 0° C. The reaction was stirred at 0° C. to 25° C. for 12 h. The mixture was quenched with $H_2O$(50 mL) and extracted with DCM (50 mL×3), washed with brine (50 mL), dried over $Na_2SO_4$, filtered and concentrated under reduced pressure. The crude product was purified by Flash silica gel chromatography (ISCO®; 40 g SepaFlash® Silica Flash Column, Eluent of 6% EtOAc/Pet.ether gradient) to give tert-butyl (R)-(1-(4-bromopyridin-2-yl)ethyl)(ethyl)carbamate. LCMS m/z (M-100+H): 329.1 required, 329.0 found.

To a solution of tert-butyl (R)-(1-(4-bromopyridin-2-yl)ethyl)(ethyl)carbamate (3 g, 9.11 mmol) in Dioxane (60 mL) were added 4,4,4',4',5,5,5',5'-octamethyl-2,2'-bi(1,3,2-dioxaborolane) (3.47 g, 13.67 mmol), potassium acetate (2.68 g, 27.3 mmol), chloro(2-dicyclohexylphosphino-2',4',6'-triisopropyl-1,1'-biphenyl)[2-(2'-amino-1,1'-biphenyl)]palladium(ii) (0.358 g, 0.456 mmol). The resulting mixture was stirred at 80° C. under N2 protection for 12 h. The mixture was filtered and concentrated under reduced pressure to give (R)-(2-(1-((tert-butoxycarbonyl)(ethyl)amino)ethyl)pyridin-4-yl)boronic acid B89 which was used without further purification. LCMS m/z (M+H): 295.2 required, 295.1 found.

Intermediate B91 tert-butyl (1-(2-bromopyridin-4-yl)ethyl)(ethyl)carbamate (B91)

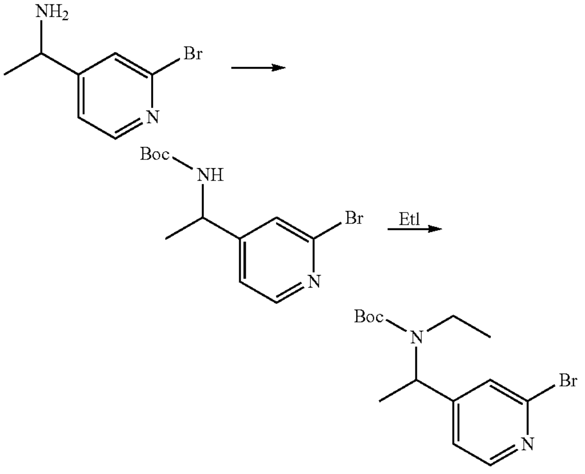

B91

To a mixture of 1-(2-bromopyridin-4-yl)ethan-1-amine (4 g, 0.00 mmol), TEA (4.87 ml, 34.9 mmol) and BOC-Anhydride (8.11 ml, 34.9 mmol) in MeCN (100 ml) under N2 protection, DMAP (0.213 g, 1.746 mmol) was added, and the resulting mixture was stirred at 25° C. for 10 h. The reaction mixture was concentrated and quenched with water (10 mL), then extracted with EtOAc (10 mL×3), washed with brine (10 mL). The organic layer dried over $Na_2SO_4$, filtered and the filtrate was concentrated. The residue was purified by Flash silica gel chromatography (ISCO®; 25 g SepaFlash® Silica Flash Column, Eluent of 15% EtOAc/Pet.ether) to tert-butyl (1-(2-bromopyridin-4-yl)ethyl)carbamate. LRMS m/z (M+H): 329.2 required, 329.2 found.

To a solution of tert-butyl (1-(2-bromopyridin-4-yl)ethyl)carbamate (9.12 g, 30.3 mmol) in DMF (150 ml) was added NaH (2.422 g, 60.6 mmol) at 0° C., then the mixture was stirred at 0° C. under N2 for 30 min. Then iodoethane (9.45 g, 60.6 mmol) was added to the mixture and the mixture was stirred at 20° C. for 1 h. The reaction mixture was poured into water (150 mL), extracted with EtOAc (200 mL×3).The organic layer was washed with brine (100 mL), dried over $Na_2SO_4$ and filtered. The filtrate was concentrated and purified Flash silica gel chromatography (ISCO®; 120 g SepaFlash® Silica Flash Column, Eluent of 15-30% EtOAc/Pet.ether gradient) to give tert-butyl (1-(2-bromopyridin-4-yl)ethyl)(ethyl)carbamate (B91). LCMS m/z (M+H+2): 331.0 required, 330.7 found.

Intermediate B92

2-chloro-3-fluoro-4-iodo-5-methoxypyridine (B92)

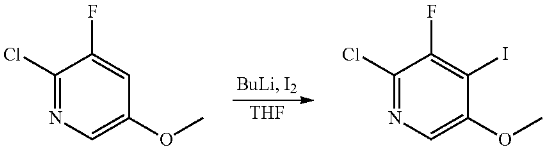

B92

To a solution of 2-chloro-3-fluoro-5-methoxypyridine (2.65 g, 16.4 mmol) in tetrahydrofuran (50 mL) at −78° C. was added 2.5M butyllithium (7.22 mL, 18.0 mmol) dropwise and the solution was stirred at −78° C. for 1 hour. Iodine (4.62 g, 18.2 mmol) was added in batches and the solution warmed to ambient temperature over 2 hours. The mixture was quenched by the slow addition of saturated aqueous sodium bisulfite (50 mL) and extracted with EtOAc (3×30 mL). The combined organics were dried ($Na_2SO_4$), filtered, and concentrated to yield 2-chloro-3-fluoro-4-iodo-5-methoxypyridine (B92). LC-MS: 288.0 (M+1).

Intermediate B95 tert-butyl (1-(4-chloro-5-fluoropyridin-2-yl)ethyl)(ethyl)carbamate

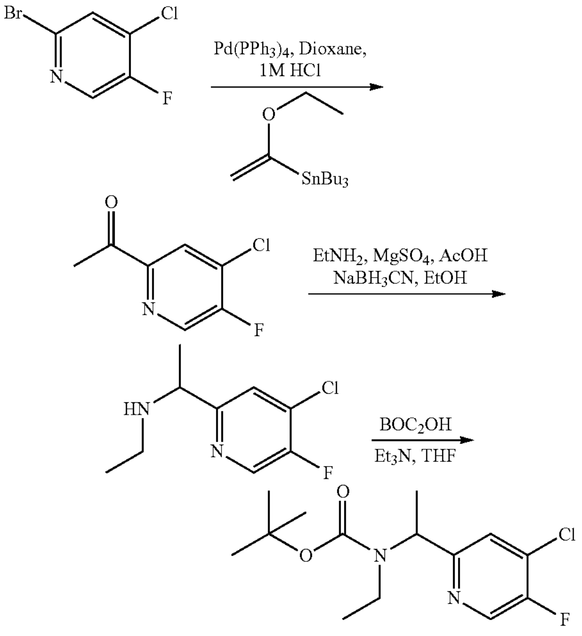

B95

Step 1: 1-(4-chloro-5-fluoropyridin-2-yl)ethan-1-one

In an analogous manner to C152, 2-bromo-4-chloro-5-fluoropyridine and tributyl (1-ethoxyvinyl)stannane were used to prepare 1-(4-chloro-5-fluoropyridin-2-yl)ethan-1-one. LC-MS: 174.0

Step 2: 1-(4-chloro-5-fluoropyridin-2-yl)-N-ethyl-ethan-1-amine

In an analogous manner to C153, 1-(4-chloro-5-fluoropyridin-2-yl)ethan-1-one and ethanamine were used to prepare 1-(4-chloro-5-fluoropyridin-2-yl)-N-ethylethan-1-amine. LC-MS: 203.0

Step 3: tert-butyl (1-(4-chloro-5-fluoropyridin-2-yl)ethyl)(ethyl)carbamate (B95)

To a stirred solution of 1-(4-chloro-5-fluoropyridin-2-yl)-N-ethylethan-1-amine (2.20 g, 10.89 mmol), and triethylamine (3.0 mL, 21.78 mmol) in THF (27 mL) was added BOC-anhydride (2.61 g, 11.98 mmol) and the resulting solution was stirred at room temperature. Additional BOC-anhydride added as necessary until reaction complete by LCMS. The mixture was diluted with water and extracted several times with ethyl acetate. The combined organic layers were concentrated. The crude material was purified by flash silica chromatography (0-20% EtOAc in hexanes) to give tert-butyl (1-(4-chloro-5-fluoropyridin-2-yl)ethyl)(ethyl)carbamate (B95). LC-MS: 303.1

4-chloro-5-fluoropicolinaldehyde (B96)

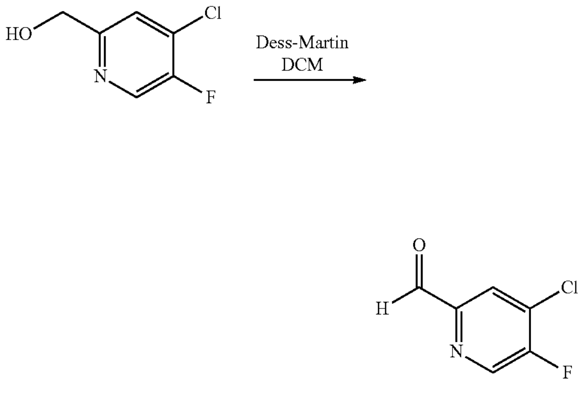

B96

To a solution of (4-chloro-5-fluoropyridin-2-yl)methanol (B5, 1.00 g, 6.19 mmol) in Dichloromethane (20 mL) at room temperature was added Dess-Martin periodinate (2.63 g, 6.19 mmol) portionwise and the reaction was stirred for 20 min. Saturated sodium thiosulfate solution and saturation sodium bicarbonate solution were added and stirred for 10 minutes. The reaction extracted with DCM several times and the combined organic layers were concentrated. The crude material was purified by flash silica chromatography (0-20% EtOAc in hexanes) to give 4-chloro-5-fluoropicolinaldehyde (B96). LC-MS: 178.1 (M+1+18).

Intermediate B98 tert-butyl (1-(4-chloro-5-fluoropyridin-2-yl)ethyl)(cyclopropyl)carbamate)

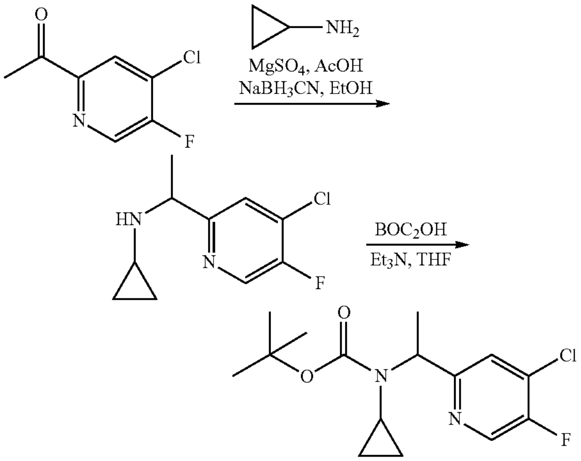

B98

Step 1: N-(1-(4-chloro-5-fluoropyridin-2-yl)ethyl)cyclopropanamine

In an analogous manner to C153, 1-(4-chloro-5-fluoro-pyridin-2-yl)ethan-1-one and cyclopropylamine were used to prepare N-(1-(4-chloro-5-fluoropyridin-2-yl)ethyl)cyclo-propanamine. LC-MS: 215.0

Step 2: tert-butyl (1-(4-chloro-5-fluoropyridin-2-yl)ethyl)(cyclopropyl)carbamate (B98)

In an analogous manner to B95, N-(1-(4-chloro-5-fluoro-pyridin-2-yl)ethyl)cyclopropanamine and Boc-anhydride were used to prepare tert-butyl (1-(4-chloro-5-fluoropyridin-2-yl)ethyl)(cyclopropyl)carbamate_(B98). LC-MS: 315.1

Intermediate C6

(R)-1-(5-(8-(but-3-en-1-yloxy)-5-methylimidazo[1,2-a]pyrazin-6-yl)-6-methoxypyridin-3-yl)-N-ethyl-ethan-1-amine (C6)

SCHEME C1

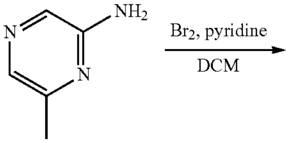

C1

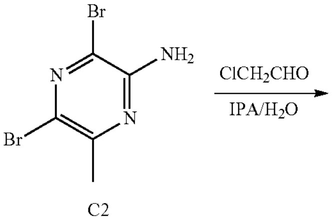

C2

-continued

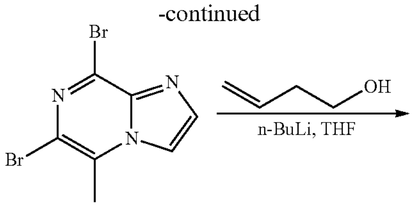

C3

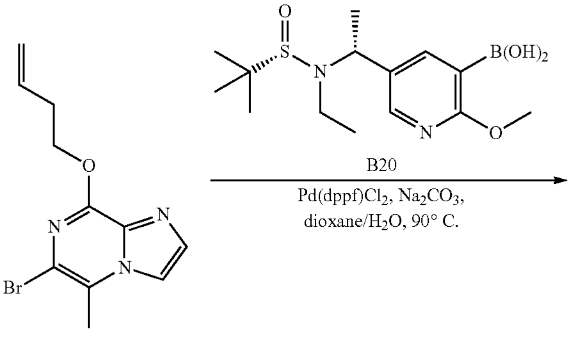

C4

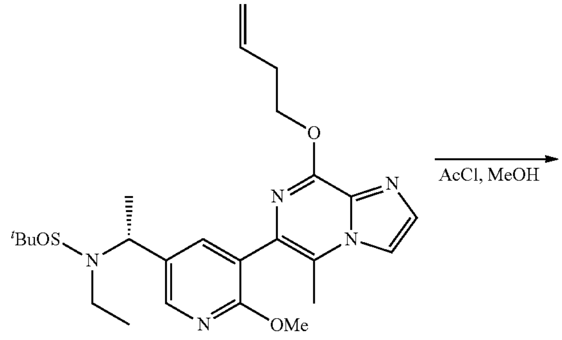

C5

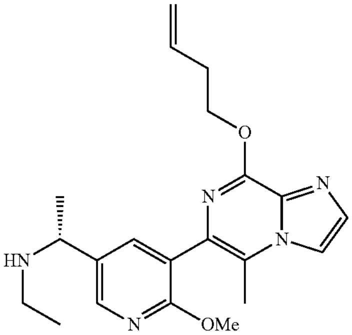

C6

Step 1: 3,5-dibromo-6-methylpyrazin-2-amine (C2)

To a solution of 6-methylpyrazin-2-amine (C1, 1 g, 9.16 mmol) and pyridine (1.853 mL, 22.91 mmol) in DCM (20 mL) was added $Br_2$ (1.180 mL, 22.91 mmol) dropwise. The reaction was stirred at ambient temperature for 15 h. LCMS showed formation of the desired product mass. The reaction was poured into sat. aq. $NaHCO_3$ to pH 7 and extracted with DCM (3×10 mL). The combined organic layers were washed with brine (10 mL), dried ($Na_2SO_4$), filtered and concentrated to give 3,5-dibromo-6-methylpyrazin-2-amine (C2), which was carried forward without purification. LC-MS: 268.0 (M+1).

Step 2: 6,8-dibromo-5-methylimidazo[1,2-a]pyrazine (C3)

To a solution of 3,5-dibromo-6-methylpyrazin-2-amine (C2, 4 g, 14.99 mmol) in water (40 mL) and IPA (8 mL) was added 2-chloroacetaldehyde (5.88 g, 30.0 mmol) and the reaction was stirred at 110° C. for 3 h. LCMS showed formation of the desired product mass. The reaction was poured into water (10 mL) and adjusted to pH 8 with $Na_2CO_3$. The mixture was extracted with EtOAc (3×10 mL). The combined organic layers were washed with brine (10 mL), dried ($Na_2SO_4$), filtered and concentrated to give 6,8-dibromo-5-methylimidazo[1,2-a]pyrazine (C3) which was carried forward without purification. LC-MS: 292.1 (M+1). $^1$H-NMR (400 MHz, $CDCl_3$) δ ppm 8.31 (dd, J=4.70, 1.57 Hz, 1H), 7.93 (dd, J=8.41, 1.37 Hz, 1H), 3.06 (s, 3H).

Step 3: 6-bromo-8-(but-3-en-1-yloxy)-5-methylimidazo[1,2-a]pyrazine (C4)

To a solution of but-3-en-1-ol (0.595 g, 8.25 mmol) in THF (10 mL) was added butyllithium (3.30 mL, 8.25 mmol) (2.5 M in hexanes) at −78° C. and the reaction was stirred at −78° C. for 30 min. 6,8-dibromo-5-methylimidazo[1,2-a]pyrazine (C3, 1.5 g, 4.12 mmol) in THF (10 mL) was added and the reaction was stirred at 80° C. for 12 h. LCMS showed formation of the desired product mass. The reaction was quenched with sat. aq. $NH_4Cl$ (10 mL) and extracted with EtOAc (3×10 mL). The combined organic layers were dried ($Na_2SO_4$), filtered and concentrated. The crude material was purified by flash silica chromatography (35% EtOAc in petroleum ether) to give 6-bromo-8-(but-3-en-1-yloxy)-5-methylimidazo[1,2-a]pyrazine (C4). LC-MS: 282.2, 284.2 (M+1). $^1$H-NMR: (400 MHz, $CDCl_3$) δ 7.71 (d, J=0.78 Hz, 1H), 7.55 (d, J 1.17 Hz, 1H), 6.00-5.89 (m, 1H), 5.21 (dd, J=17.22, 1.57 Hz, 1H), 5.12 (d, J=10.17 Hz, 1H), 4.58 (t, J=7.04 Hz, 2H), 2.72-2.67 (m, 2H), 2.66 (s, 3H).

Step 4: N—((R)-1-(5-(8-(but-3-en-1-yloxy)-5-methylimidazo[1,2-a]pyrazin-6-yl)-6-methoxypyridin-3-yl)ethyl)-N-ethyl-2-methylpropane-2-sulfinamide (C5)

To a mixture of 6-bromo-8-(but-3-en-1-yloxy)-5-methylimidazo[1,2-a]pyrazine (C4, 186 mg, 0.658 mmol), (5-((R)-1-(((S)-tert-butylsulfinyl)(ethyl)amino)ethyl)-2-methoxypyridin-3-yl)boronic acid (B20, 180 mg, 0.548 mmol) and $Na_2CO_3$ (174 mg, 1.645 mmol) in dioxane (10 mL) and water (2 mL) was added Pd(dppf)$Cl_2$ (20.06 mg, 0.027 mmol). The reaction was stirred at 90° C. under nitrogen for 16 h. LCMS showed formation of the desired product mass. The reaction was quenched with water (10 mL) and extracted with EtOAc (3×10 mL). The combined organic layers were washed with brine (10 mL), dried ($Na_2SO_4$), filtered and concentrated. The crude material was purified by preparative TLC (50% EtOAc in petroleum ether) to afford N—((R)-1-(5-(8-(but-3-en-1-yloxy)-5-methylimidazo[1,2-a]pyrazin-6-yl)-6-methoxypyridin-3-yl)ethyl)-N-ethyl-2-methylpropane-2-sulfinamide (C5). LC-MS: 486.3 (M+1).

Step 5: (R)-1-(5-(8-(but-3-en-1-yloxy)-5-methylimidazo[1,2-a]pyrazin-6-yl)-6-methoxypyridin-3-yl)-N-ethylethan-1-amine (C6)

To a solution of N—((R)-1-(5-(8-(but-3-en-1-yloxy)-5-methylimidazo[1,2-a]pyrazin-6-yl)-6-methoxypyridin-3-yl)

ethyl)-N-ethyl-2-methylpropane-2-sulfinamide (C5, 150 mg, 0.278 mmol) in MeOH (2 mL) was added acetyl chloride (0.059 mL, 0.834 mmol) at 0° C. The reaction was stirred at 20° C. for 2 h. LCMS showed formation of the desired product mass. The reaction was quenched with sat. aq. $NaHCO_3$ to pH 7-8. The reaction was concentrated to afford (R)-1-(5-(8-(but-3-en-1-yloxy)-5-methylimidazo[1,2-a]pyrazin-6-yl)-6-methoxypyridin-3-yl)-N-ethylethan-1-amine (C6) as an HCl salt, which was carried forward without purification. LC-MS: 382.3 (M+H=1).

Intermediates C15-C18 C20 and C21

SCHEME C2

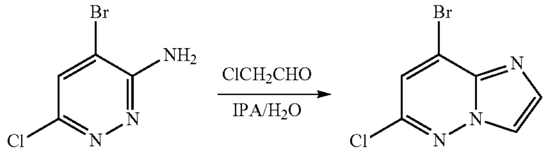

C7

C8

Step 1: 8-bromo-6-chloroimidazo[1,2-b]pyridazine (C8)

To a solution of 4-bromo-6-chloropyridazin-3-amine (C7, 1 g, 4.80 mmol) in water (10 mL) and 2-propanol (3 mL) was added 2-chloroacetaldehyde (1.883 g, 9.59 mmol) (40% in water) and the reaction was stirred at 110° C. for 15 h. LCMS showed formation of the desired product mass. The reaction was poured into water (20 mL), and $Na_2CO_3$ was added to adjust the pH to 8. The mixture was filtered to afford 8-bromo-6-chloroimidazo[1,2-b]pyridazine (C8), which was carried forward without purification. LC-MS: 232.1, 234.1 (M+1).

SCHEME C3

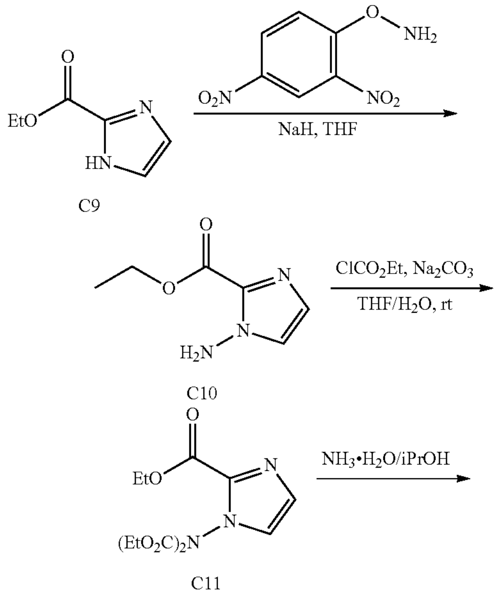

C9

C10

C11

-continued

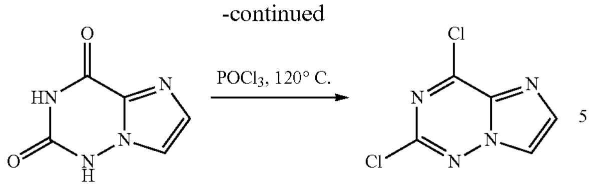

C12 C13

Step 1: Ethyl 1-amino-1H-imidazole-2-carboxylate (C10)

To a solution of ethyl 1H-imidazole-2-carboxylate (C9, 20 g, 143 mmol) in THF (300 mL) was added NaH (6.85 g, 171 mmol) (60% in mineral oil) at 0° C., and the reaction was stirred at ambient temperature for 1 h. O-(2,4-dinitrophenyl)hydroxylamine (39.8 g, 200 mmol) was then added and the reaction was stirred at ambient temperature for 16 h. LCMS showed formation of the desired product mass. The reaction was poured into water (300 mL) and extracted with EtOAc (5×200 mL). The combined organic layers were washed with sat. aq. $NaHCO_3$(400 mL) and brine (400 mL), dried $Na_2SO_4$), filtered and concentrated. The crude material was purified by flash silica chromatography (0-100% EtOAc in petroleum ether gradient) to afford ethyl 1-amino-1H-imidazole-2-carboxylate (C10). LC-MS: 156.1 (M+1).

Step 2: Ester C11

To a solution of ethyl 1-amino-1H-imidazole-2-carboxylate (C10, 12 g, 77 mmol) in THF (150 mL) and water (150 mL) were added ethyl carbonochloridate (37.8 g, 348 mmol) and $Na_2CO_3$ (57.4 g, 541 mmol) at 20° C. The reaction was stirred at 20° C. for 2 h. LCMS showed formation of the desired product mass. The reaction was poured into water (300 mL) and extracted with EtOAc (3×300 mL). The combined organic layers were washed with brine (500 mL), dried ($Na_2SO_4$), filtered and concentrated. The crude material was purified by flash silica chromatography (50% EtOAc in petroleum ether) to give ester C11. LC-MS: 300.0 (M+1). $^1$H NMR: (500 MHz, $CDCl_3$) δ 7.19 (d, J=1.2 Hz, 1H), 7.09 (d, J=1.2 Hz, 1H), 4.41-4.25 (m, 6H), 1.37 (t, J=7.1 Hz, 3H), 1.27-1.20 (m, 6H).

Step 3: Imidazo[2,1-f][1,2,4]triazine-2,4(1H,3H)-dione (C12)

To a solution of ester C11 (6 g, 20.05 mmol) in iPrOH (36 mL) was added ammonia hydrate (96 mL, 20.05 mmol), and the reaction was stirred in a sealed tube at 120° C. for 8 h. LCMS showed formation of the desired product mass. The reaction was concentrated and the crude material was washed with MeOH: $Et_{20}$ (1:10, 60 mL) and filtered to afford imidazo[2,1-f][1,2,4]triazine-2,4(1H,3H)-dione (C12), which was carried forward without purification. LC-MS: 153.0 (M+1).

Step 4: 2,4-dichloroimidazo[2,1-f][1,2,4]triazine (C13)

To a solution of imidazo[2,1-f][1,2,4]triazine-2,4(1H, 3H)-dione (C12, 3.4 g, 22.35 mmol) in $POCl_3$ (28 mL) was added triethylamine hydrochloride (6.15 g, 44.7 mmol), and the reaction was stirred at 120° C. for 16 h. LCMS showed formation of the desired product mass. The reaction was concentrated, and the crude material was poured into ice water (30 mL) and neutralized with sat. aq. $NaHCO_3$(50 mL) and extracted with EtOAc (3×30 mL). The combined organic layers were washed with brine (20 mL), dried ($Na_2SO_4$), filtered and concentrated. The crude material was purified by flash silica chromatography (23% EtOAc in petroleum ether) to afford 2,4-dichloroimidazo[2,1-f][1,2,4] triazine (C13). LC-MS: 189.1 (M+1). $^1$H NMR: (400 MHz, $CDCl_3$) δ 8.07 (s, 1H) 7.98 (s, 1H).

SCHEME C4

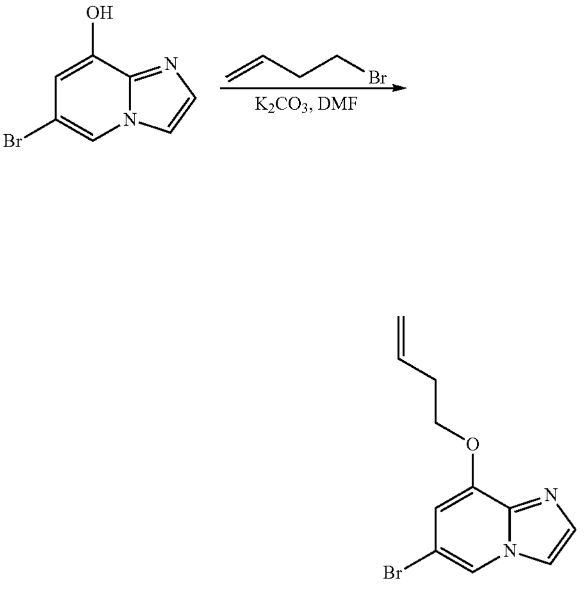

C14

To a solution of 6-bromoimidazo[1,2-a]pyridin-8-ol (2 g, 9.39 mmol) in DMF (20 ml) was added 4-bromobut-1-ene (1.267 g, 9.39 mmol) and K2C03 (2.59 g, 18.78 mmol). The reaction was stirred at 80° C. for 12 h. LCMS showed complete conversion. The reaction was poured into water (50 mL), extracted with EtOAc (3×30 mL). The combined organic layers were washed with brine (50 mL), dried ($Na_2SO_4$), filtered and concentrated. The crude material was purified by flash silica chromatography (0-50% EtOAc in petroleum ether gradient) to give 6-bromo-8-(but-3-en-1-yloxy)imidazo[1,2-a]pyridine (C14). LC-MS: 268.9 (M+1).

The following intermediates in Table C1 were synthesized in an analogous manner of that described in Schemes C1 and used to synthesize Intermediate C6 using the appropriate halides and cores. For Intermediates C15 and C16, K2C03 was used instead of $Na_2CO_3$ in Step 4. For Intermediates C18 and C20, XPhos G2 Pd and K2C03 were used in Step 4.

TABLE C1
| Halide | Core | Intermediate | Observed LCMS (M + 1) |
|---|---|---|---|
| 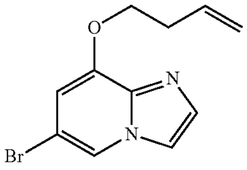 C14 | 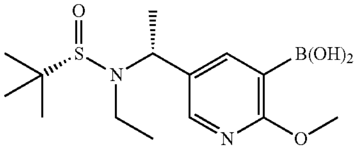 B20 | 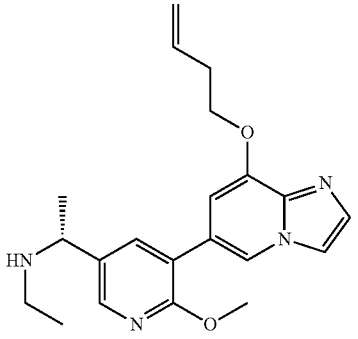 C15 | 367.4 |
| 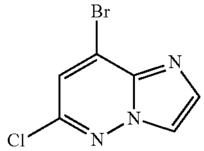 C8 | 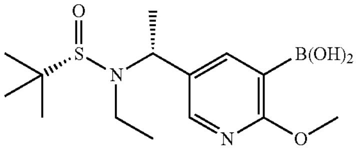 B20 | 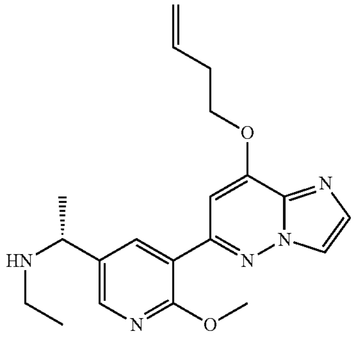 C16 | 368.2 |
| 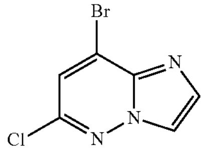 C8 | 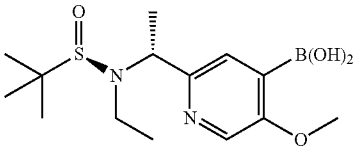 B17 | 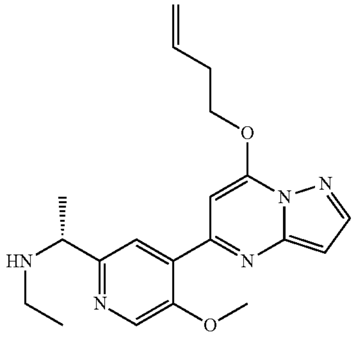 C17 | 368.2 |
| 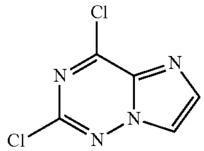 C13 | 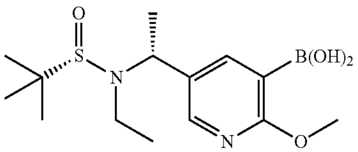 B20 | 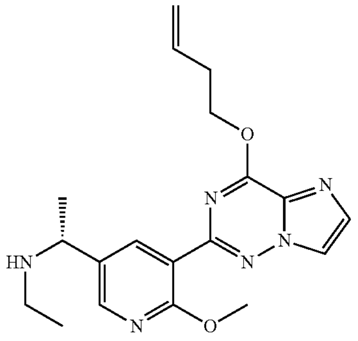 C18 | 369.2 |

TABLE C1-continued

| Halide | Core | Intermediate | Observed LCMS (M + 1) |
|---|---|---|---|
| 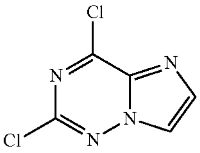 C13 | 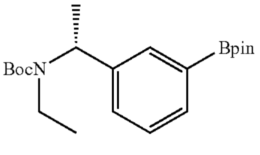 B73 | 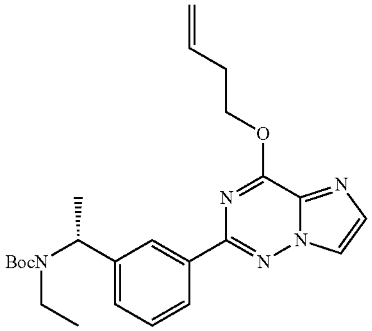 * C19 | 438.6 |

* For Intermediate C19, the last step was replaced with that in Scheme C5 to lead to Intermediate C20.

SCHEME C5

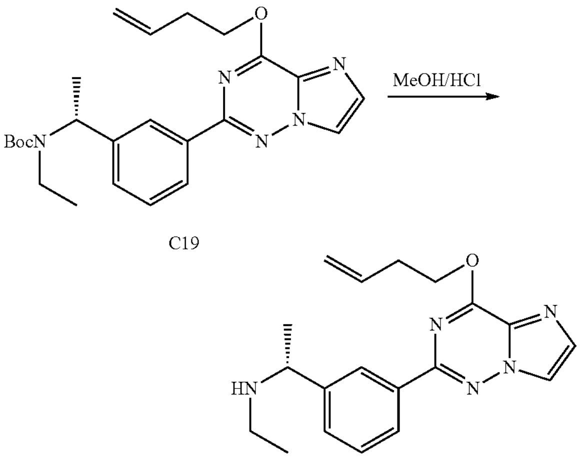

Step 1: (R)-1-(3-(4-(but-3-en-1-yloxy)imidazo[2,1-f][1,2,4]triazin-2-yl)phenyl)-N-ethylethan-1-amine (C20)

A solution of tert-butyl (R)-(1-(3-(4-(but-3-en-1-yloxy) imidazo[2,1-f][1,2,4]triazin-2-yl)phenyl)ethyl)(ethyl)carbamate (C19, 350 mg, 0.800 mmol) in MeOH (2 mL) and HCl (2 mL) (4M in MeOH) was stirred at 0° C. for 1 h. LCMS showed the formation of the desired product mass. The reaction was adjusted to pH 8 to using $NaHCO_3$. The reaction was filtered and concentrated (R)-1-(3-(4-(but-3-en-1-yloxy)imidazo[2,1-f][1,2,4]triazin-2-yl)phenyl)-N-ethylethan-1-amine (C20). LC-MS: 338.3 (M+1).

The following intermediates in Table C2 were synthesized in an analogous manner of that described in Schemes C1 and C4 and used to synthesize Intermediate C20 using the appropriate halides and cores. For Intermediate C21, XPhos Pd G2 and $K2CO_3$ were used in the Suzuki coupling.

TABLE C2

| Halide | Core | Intermediate | Observed LCMS (M + 1) |
|---|---|---|---|
| 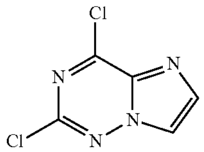 C13 | 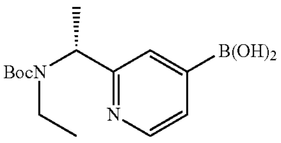 B71 | 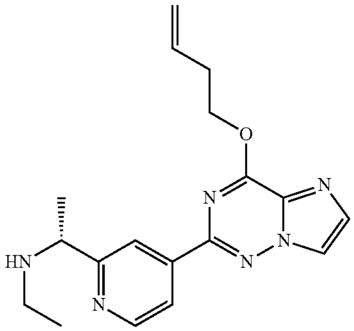 C21 | 339.4 |

Intermediate C33

(5-(1-((Tert-butoxycarbonyl)(ethyl)amino)ethyl)furo[3,2-b]pyridin-7-yl)boronic acid (C33)

SCHEME C6

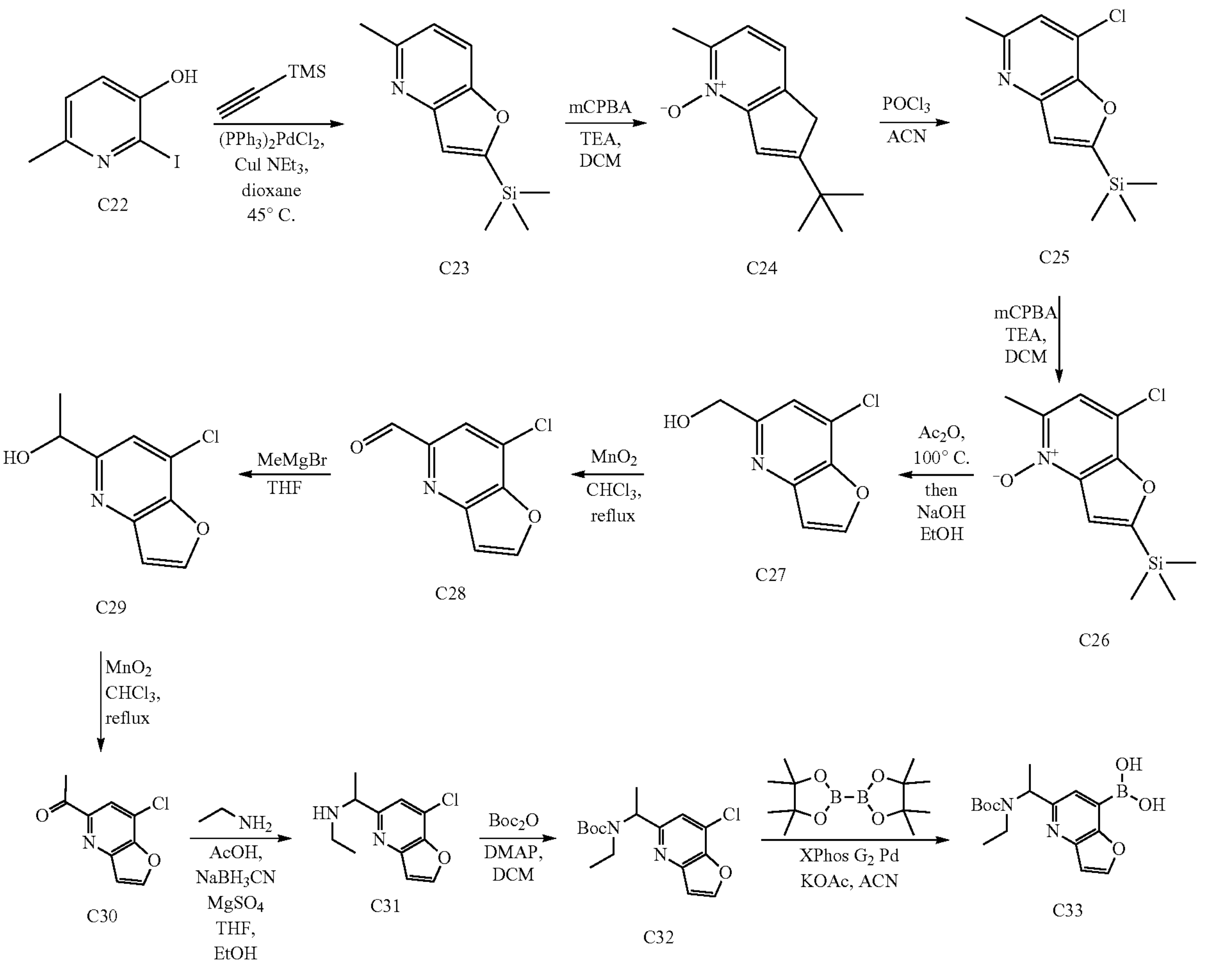

C22, C23, C24, C25, C26, C27, C28, C29, C30, C31, C32, C33

Step 1: 5-Methyl-2-(trimethylsilyl)furo[3,2-b]pyridine (C23)

A solution of 2-iodo-6-methylpyridin-3-ol (C22, 3.1 g, 13.19 mmol) in a mixture of 1,4-dioxane (30 mL) and TEA (30 mL) was degassed with nitrogen. Ethynyltrimethylsilane (2.4 mL, 17.10 mmol), $(PPh_3)_2PdCl_2$ (0.463 g, 0.660 mmol), and CuI (0.126 g, 0.660 mmol) were added. The reaction was degassed with nitrogen then heated to 45° C. overnight. The reaction was then cooled to ambient temperature and diluted with EtOAc. The mixture was filtered through a pad of Celite washing with EtOAc then the filtrate was concentrated. The crude material was purified by flash silica chromatography (0-15% EtOAc in heptane gradient) to give 5-methyl-2-(trimethylsilyl)-furo[3,2-b]pyridine (C23). LC-MS: 206.1 (M+1). $^1$H NMR (500 MHz, $CDCl_3$) δ 7.63 (d, J=8.4 Hz, 1H), 7.06 (d, J=0.9 Hz, 1H), 7.04 (d, J=8.4 Hz, 1H), 2.65 (s, 3H), 0.36 (s, 9H).

Step 2: 5-Methyl-2-(trimethylsilyl)furo[3,2-b]pyridine 4-oxide (C24)

To a solution of 5-methyl-2-(trimethylsilyl)furo[3,2-b]pyridine (C23, 2.63 g, 12.81 mmol) in DCM (60 mL) was added mCPBA (2.98 g, 17.29 mmol) at ambient temperature. After 4 h, $NEt_3$ (5.4 mL, 38.7 mmol) was added. After 5 min the reaction was concentrated. The crude material was purified by flash silica chromatography (0-100% EtOAc: EtOH 3:1 mix in heptane gradient) to give the 5-methyl-2-(trimethylsilyl)furo[3,2-b]pyridine 4-oxide (C24). LC-MS: 222.1 (M+1). $^1$H NMR (500 MHz, $CDCl_3$) δ 7.39 (s, 1H), 7.38 (d, J=8.7 Hz, 1H), 7.13 (d, J=8.4 Hz, 1H), 2.63 (s, 3H), 0.37 (s, 9H).

Step 3: 7-Chloro-5-methyl-2-(trimethylsilyl)furo[3,2-b]pyridine (C25)

To a solution of 5-methyl-2-(trimethylsilyl)furo[3,2-b]pyridine 4-oxide (C24, 2.975 g, 13.44 mmol) in ACN (60 mL) was added $POCl_3$ (3.8 mL, 40.8 mmol) then the reaction was heated to reflux overnight. The reaction was then cooled to ambient temperature and quenched by slow addition of sat. aq. $NaHCO_3$. After the quench was complete the mixture was diluted with sat. aq. $NaHCO_3$ then extracted with DCM. The combined organic layers were dried ($MgSO_4$) and filtered through a short plug of silica gel washing with DCM. The filtrate was concentrated to give 7-chloro-5-methyl-2-(trimethylsilyl)furo[3,2-b]pyridine (C25). LC-MS: 240.1 (M+1).

Step 4: 7-Chloro-5-methyl-2-(trimethylsilyl)furo[3,2-b]pyridine 4-oxide (C26)

To a solution of crude 7-chloro-5-methyl-2-(trimethylsilyl)furo[3,2-b]pyridine (C25, 2.58 g, 10.76 mmol) in DCM (50 mL) was added mCPBA (2.51 g, 14.55 mmol) at ambient temperature. After 2 h, $NEt_3$ (4.50 mL, 32.3 mmol) was added. After 5 min the reaction was concentrated. The crude material was purified by flash silica chromatography (0-100% EtOAc:EtOH 3:1 mix in heptane gradient) to give 7-Chloro-5-methyl-2-(trimethylsilyl)furo[3,2-b]pyridine 4-oxide (C26). LC-MS 256.0 (M+1).

Step 5: (7-Chlorofuro[3,2-b]pyridin-5-yl)methanol (C27)

7-Chloro-5-methyl-2-(trimethylsilyl)furo[3,2-b]pyridine 4-oxide (C26, 2.39 g, 9.34 mmol) was taken up in $Ac_2O$ (45 mL) and the reaction was heated to 100° C. After 90 min the reaction was cooled to ambient temperature then concentrated. The residue was taken up in heptane then concentrated (2 x) to give a crude material which was taken up in EtOH (45 mL). To this was added 2M aq. NaOH (14.1 mL, 28.2 mmol) at ambient temperature. After 90 min the reaction was concentrated. The residue was taken up in sat. aq. $NH_4Cl$ and extracted with EtOAc. The combined organic layers were dried ($MgSO_4$), filtered and concentrated. The crude material was purified by flash silica chromatography (0-100% EtOAc in heptane gradient) to give (7-chlorofuro[3,2-b]pyridin-5-yl)methanol (C27). LC-MS: 183.9 (M+1). $^1$H-NMR (500 MHz, $CDCl_3$) δ 7.91 (d, J=2.3 Hz, 1H), 7.27 (s, 1H), 7.00 (d, J=2.3 Hz, 1H), 4.85 (d, J=5.1 Hz, 2H), 3.47 (t, J=5.3 Hz, 1H).

Step 6: 7-Chlorofuro[3,2-b]pyridine-5-carbaldehyde (C28)

To a solution of (7-chlorofuro[3,2-b]pyridin-5-yl)methanol (C27, 1.32 g, 7.19 mmol) in $CHCl_3$ (35 mL) was added $MnO_2$ (3.13 g, 35.9 mmol) and the reaction was heated to reflux overnight. The reaction was then cooled to ambient temperature and filtered through a pad of Celite washing with $CHCl_3$. The filtrate was concentrated to afford 7-Chlorofuro[3,2-b]pyridine-5-carbaldehyde (C28) which was carried forward without purification. LC-MS: 182.0 (M+1).

Step 7: 1-(7-Chlorofuro[3,2-b]pyridin-5-yl)ethan-1-ol (C29)

A solution of crude 7-chlorofuro[3,2-b]pyridine-5-carbaldehyde (C28, 1.11 g, 6.11 mmol) in THF (30 mL) was cooled to 0° C. To this was added MeMgBr (2.65 mL, 7.95 mmol) (3M in $Et_2O$) slowly. After 30 min the reaction was warmed to ambient temperature then diluted with sat. aq. $NH_4Cl$ and extracted with EtOAc. The combined organic layers were dried ($MgSO_4$), filtered and concentrated to give 1-(7-chlorofuro[3,2-b]pyridin-5-yl)ethan-1-ol (C29) which was carried forward without purification. LC-MS: 198.0 (M+1).

Step 8: 1-(7-Chlorofuro[3,2-b]pyridin-5-yl)ethan-1-one (C30)

To a solution of crude 1-(7-chlorofuro[3,2-b]pyridin-5-yl)ethan-1-ol (C29, 1.2 g, 6.07 mmol) in $CHCl_3$ (30 mL) was added $MnO_2$ (2.64 g, 30.4 mmol) then the reaction was heated to reflux overnight. The reaction was then cooled to ambient temperature and filtered through a pad of Celite washing with $CHCl_3$. The filtrate was concentrated to give 1-(7-chlorofuro[3,2-b]pyridin-5-yl)ethan-1-one (C30) which was carried forward without purification. LC-MS: 196.0 (M+1).

Step 9: 1-(7-Chlorofuro[3,2-b]pyridin-5-yl)-N-ethyl-ethan-1-amine (C31)

Crude 1-(7-chlorofuro[3,2-b]pyridin-5-yl)ethan-1-one (C30, 1.07 g, 5.47 mmol) was taken up in EtOH (40 mL) then transferred to a glass pressure vessel. To this was added ethanamine (13.7 mL, 27.4 mmol) (2M in THF), AcOH (1.6 mL, 27.9 mmol), $MgSO_4$ (1.32 g, 10.97 mmol), then $NaBH_3CN$ (0.69 g, 10.98 mmol). The vessel was sealed then heated to 80° C. overnight. The reaction was cooled to ambient temperature then diluted with EtOH, filtered through a pad of Celite washing with EtOH and the filtrate was concentrated. The residue was taken up in $H_2O$then the pH was adjusted to 9 using 2M aq. NaOH. The resulting mixture was extracted with DCM. The combined organic layers were dried ($Na_2SO_4$), filtered and concentrated to give 1-(7-chlorofuro[3,2-b]pyridin-5-yl)-N-ethylethan-1-amine (C31) which was carried forward without purification. LC-MS: 225.1 (M+1).

Step 10: Tert-butyl (1-(7-chlorofuro[3,2-b]pyridin-5-yl)ethyl)(ethyl)carbamate (C32)

1-(7-chlorofuro[3,2-b]pyridin-5-yl)-N-ethylethan-1-amine (C31, 1.275 g, 5.67 mmol) was taken up in DCM (30 mL) then Boc anhydride (1.61 g, 7.38 mmol) was added at ambient temperature. After 90 min Boc anhydride (1.61 g, 7.38 mmol) was added and stirring continued at ambient temperature. After 90 min a small chip of DMAP was added and stirring was continued at ambient temperature for 18 h. The reaction was concentrated. The crude material was purified by flash silica chromatography (0-25% EtOAc in heptane gradient) to give tert-butyl (1-(7-chlorofuro[3,2-b]pyridin-5-yl)ethyl)(ethyl)carbamate (C32). LC-MS: 325.1 (M+1) $^1$H-NMR (500 MHz, $CDCl_3$) δ 7.88 (d, J=2.2 Hz, 1H), 7.29 (s, 1H), 7.01 (d, J=2.2 Hz, 1H), 5.53 (bs, 1H), 3.17 (bs, 2H), 1.65 (d, J=7.1 Hz, 3H), 1.46 (s, 9H), 1.02 (bs, 3H).

Step 11: (5-(1-((Tert-butoxycarbonyl)(ethyl)amino)ethyl)furo[3,2-b]pyridin-7-yl)boronic acid (C33)

Tert-butyl (1-(7-chlorofuro[3,2-b]pyridin-5-yl)ethyl)(ethyl)carbamate (C32, 200 mg, 0.616 mmol), bis(pinacolato)diboron (235 mg, 0.924 mmol), KOAc (181 mg, 1.847 mmol), and X-Phos G2 Pd (24 mg, 0.031 mmol) were combined in a microwave vial. The vial was sealed then degassed with nitrogen. To this was added degassed dioxane (5 mL). The gas inlet was removed then the reaction was heated to 100° C. by conventional heating overnight. The reaction was then cooled to ambient temperature and diluted with EtOAc and filtered through a pad of Celite washing with EtOAc. The filtrate was concentrated. The crude material was purified by preparative reverse phase HPLC (5-95% ACN in water, with 0.1% TFA as modifier) to afford (5-(1-((Tert-butoxycarbonyl)(ethyl)amino)ethyl)furo[3,2-b]pyridin-7-yl)boronic acid (C33).

LC-MS: 335.1 (M+1).

Intermediate C37

(8-(but-3-en-1-yloxy)imidazo[1,2-a]pyrazin-6-yl)boronic acid (C37)

SCHEME C7

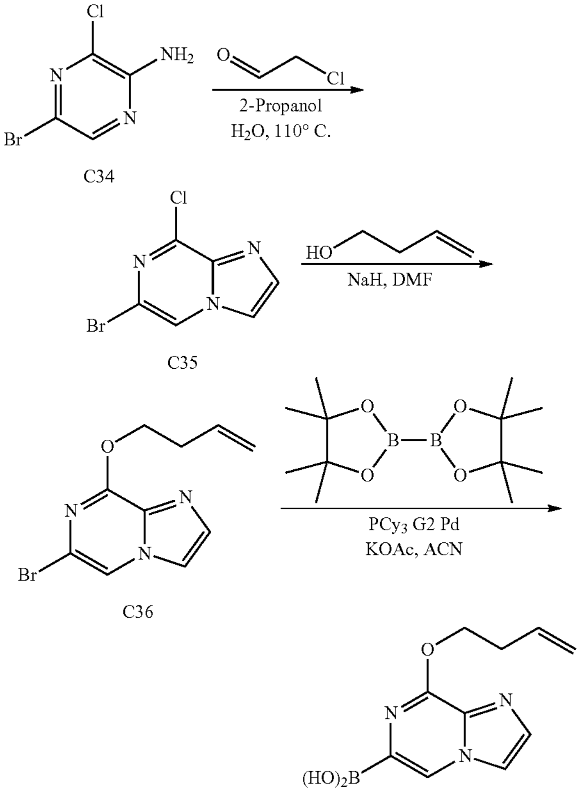

C34 C35 C36 C37

Step 1: 6-bromo-8-chloroimidazo[1,2-a]pyrazine (C35)

To a solution of 5-bromo-3-chloropyrazin-2-amine (C34, 10 g, 48.0 mmol) in water (100 mL) and 2-propanol (20 mL) was added 2-chloroacetaldehyde (37.7 g, 192 mmol) (40% by weight) and the reaction was stirred at 110° C. for 15 h. LCMS showed formation of the desired product mass. The reaction was neutralized with sat. aq. $NaHCO_3$ to pH 8 and extracted with EtOAc (3×100 mL). The combined organic layers were washed with brine (100 mL), dried ($Na_2SO_4$), filtered and concentrated. The crude material was purified by flash silica gel chromatography (50% EtOAc in petroleum ether) to give 6-bromo-8-chloroimidazo[1,2-a]pyrazine (C35). LC-MS: 233.7, 235.7 (M+1). $^1H$ NMR: (400 MHz, $CD_3OD$) δ 8.78 (s, 1H), 8.11 (d, J=1.0 Hz, 1H), 7.84 (d, J=1.0 Hz, 1H).

Step 2: 6-bromo-8-(but-3-en-1-yloxy)imidazo[1,2-a]pyrazine (C36)

But-3-en-1-ol (5.62 mL, 65.3 mmol) was dissolved in DMF (150 mL) and sodium hydride (2.61 g, 65.3 mmol) (60% in mineral oil) was added. The reaction was allowed to stir at 0° C. for 30 min. 6-Bromo-8-chloroimidazo[1,2-a]pyrazine (C35, 10.12 g, 43.5 mmol) in DMF (50 mL) was added to the reaction over 2 min. The reaction was allowed to continue stirring at 0° C. for 1 h. The reaction was quenched with the dropwise addition of water (50 mL). The mixture was then poured into water (600 mL) and the resulting precipitate was filtered. The solid was washed with water (2×50 mL) and dried to yield 6-bromo-8-(but-3-en-1-yloxy)imidazo[1,2-a]pyrazine (C36). LC-MS 268.0, 270.0 (M+1).

Step 3: (8-(but-3-en-1-yloxy)imidazo[1,2-a]pyrazin-6-yl)boronic acid (C37)

6-Bromo-8-(but-3-en-1-yloxy)imidazo[1,2-a]pyrazine (C36, 5.75 g, 21.45 mmol), 4,4,4',4',5,5,5',5'-octamethyl-2,2'-bi(1,3,2-dioxaborolane) (10.89 g, 42.9 mmol), and potassium acetate (8.42 g, 86 mmol) were combined in ACN (214 mL) and the solution was degassed with nitrogen. $PCy_3Pd$ G2 (2.53 g, 4.29 mmol) was added and the reaction was sealed and heated to 90° C. for 2 h. The reaction was filtered through Celite, washed with EtOAc (3×20 mL) and concentrated. To the resulting crude material was added ACN (50 mL), the resulting precipitate was filtered, and the filtrate was concentrated and dried under vacuum to yield (8-(but-3-en-1-yloxy)imidazo[1,2-a]pyrazin-6-yl)boronic acid (C37), which was carried forward without purification. LC-MS: 234.1 (M+1).

Intermediate C39

1-(7-(8-(but-3-en-1-yloxy)imidazo[1,2-a]pyrazin-6-yl)furo[3,2-b]pyridin-5-yl)-N-ethylethan-1-amine (C39)

SCHEME C8

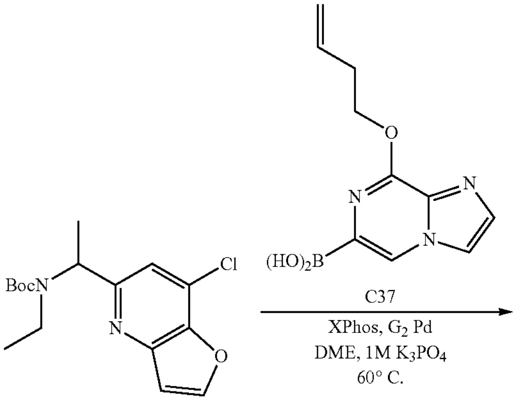

C32

-continued

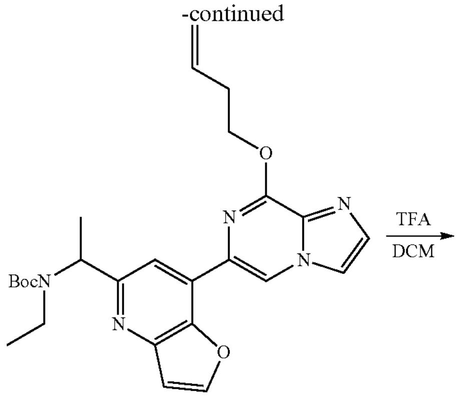

C38

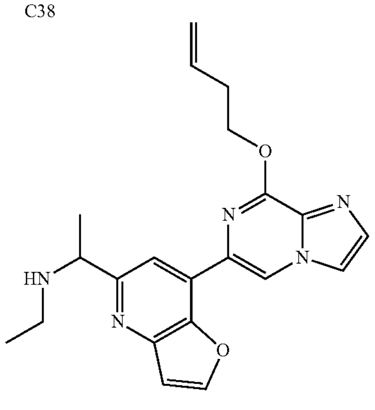

C39

Step 1: Tert-butyl (1-(7-(8-(but-3-en-1-yloxy)imidazo[1,2-a]pyrazin-6-yl)furo[3,2-b]pyridin-5-yl)ethyl)(ethyl)carbamate (C38)

Tert-butyl (1-(7-chlorofuro[3,2-b]pyridin-5-yl)ethyl)(ethyl)carbamate (C32, 50 mg, 0.154 mmol) and crude (8-(but-3-en-1-yloxy)imidazo[1,2-a]pyrazin-6-yl)boronic acid (C37, 161 mg, 0.693 mmol) were combined in a screw cap vial with a septum cap. To this was added DME (1 mL) and 1M aq. $K_3PO_4$ (0.46 mL, 0.460 mmol). The mixture was degassed with nitrogen and XPhos G2 Pd (12 mg, 0.015 mmol) was added. The gas inlet was removed then the reaction was heated to 60° C. After 1 h the reaction was cooled to ambient temperature, diluted with EtOAc, then filtered through a pad of Celite washing with EtOAc. The filtrate was concentrated. The crude material was purified by flash silica chromatography (0-100% EtOAc in heptane gradient) to give material which required additional purification. This material was purified by preparative reversed-phase HPLC (5-95% ACN in water, with 0.1% TFA as modifier) to afford tert-butyl (1-(7-(8-(but-3-en-1-yloxy)imidazo[1,2-a]pyrazin-6-yl)furo[3,2-b]pyridin-5-yl)ethyl)(ethyl)-carbamate (C38). LC-MS: 478.2 (M+1) $^1$H-NMR: (500 MHz, $CDCl_3$) δ 9.27 (s, 1H), 8.51 (s, 1H), 8.26 (d, J=2.1 Hz, 1H), 7.98 (s, 2H), 7.46 (s, 1H), 5.96 (ddt, J=17.0, 10.2, 6.8 Hz, 1H), 5.40 (q, J=7.2 Hz, 1H), 5.26 (dd, J=17.2, 1.5 Hz, 1H), 5.17 (dd, J=10.3, 1.3 Hz, 1H), 4.77 (dt, J=13.4, 6.6 Hz, 2H), 3.44 (m, 2H), 2.73 (q, J=6.7 Hz, 2H), 1.88 (d, J=7.1 Hz, 3H), 1.44-1.37 (m, 9H), 1.24 (t, J=7.0 Hz, 3H).

Step 2: 1-(7-(8-(But-3-en-1-yloxy)imidazo[1,2-a]pyrazin-6-yl)furo[3,2-b]pyridin-5-yl)-N-ethylethan-1-amine (C39)

Tert-butyl (1-(7-(8-(but-3-en-1-yloxy)imidazo[1,2-a]pyrazin-6-yl)furo[3,2-b]pyridin-5-yl)ethyl)(ethyl)carbamate, TFA (C38, 38 mg, 0.064 mmol) was taken up in DCM (1 mL). To this was added TFA (1 mL) at ambient temperature. After 1 h the reaction was concentrated. The residue was taken up in 1:1 DCM:heptane and concentrated (2 x) to afford 1-(7-(8-(but-3-en-1-yloxy)imidazo[1,2-a]pyrazin-6-yl)furo[3,2-b]pyridin-5-yl)-N-ethylethan-1-amine (C39) as a TFA salt which was carried forward without purification. LC-MS: 378.2 (M+1).

Intermediates C45 and C46

SCHEME C9

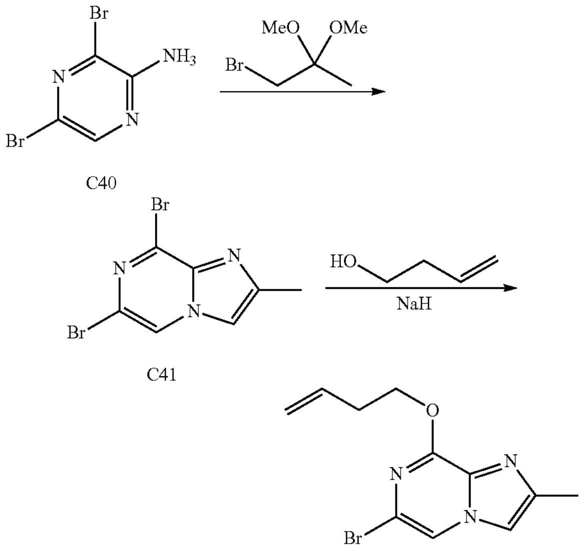

C40

C41

C42

Step 1: 6,8-Dibromo-2-methylimidazo[1,2-a]pyrazine (C41)

3,5-Dibromopyrazin-2-amine (C40, 1.2 g, 4.75 mmol) and PPTS (0.119 g, 0.475 mmol) were combined in 2-propanol (10 mL). To this was added 1-bromo-2,2-dimethoxypropane (0.97 mL, 7.15 mmol) then the mixture was heated to 70° C. overnight. The reaction was cooled to ambient temperature then diluted with $NEt_3$ and concentrated. The crude material was purified by flash silica chromatography (0-50% EtOAc in heptane gradient) to give the 6,8-dibromo-2-methylimidazo[1,2-a]pyrazine (C41). LC-MS: 291.9 (M+1).

Step 2: 6-Bromo-8-(but-3-en-1-yloxy)-2-methylimidazo[1,2-a]pyrazine (C42)

NaH (52 mg, 1.300 mmol) (60% in mineral oil) was taken up in 3 mL DMF. To this was added but-3-en-1-ol (0.115 mL, 1.340 mmol) dropwise at ambient temperature. After 30 min a solution of 6,8-dibromo-2-methylimidazo[1,2-a]pyrazine (C41, 250 mg, 0.859 mmol) in DMF (1 mL) was added and stirring continued at ambient temperature overnight. The reaction was diluted with water and extracted with EtOAc. The combined organic layers were washed with water and brine, dried ($MgSO_4$), filtered, and concentrated. The crude material was purified by flash silica chromatography (0-100% EtOAc in heptane gradient) to afford 6-Bromo-8-(but-3-en-1-yloxy)-2-methylimidazo[1,2-a] pyrazine (C42). LC-MS: 283.9. 285.9 (M+1). $^1$H-NMR: (500 MHz, $CDCl_3$) δ 7.79 (s, 1H), 7.33 (s, 1H), 5.92 (ddt, J=17.1, 10.3, 6.8 Hz, 1H), 5.19 (dq, J=17.2, 1.6 Hz, 1H), 5.11 (dq, J=10.3, 1.2 Hz, 1H), 4.58 (t, J=7.1 Hz, 2H), 2.68 (qt, J=7.1, 1.3 Hz, 2H), 2.47 (d, J=0.7 Hz, 3H).

The following Intermediates in Table C3 were synthesized in an analogous manner of that described in Scheme C9 and used to synthesize halide C42 using the appropriate dihalides.

TABLE C3

| Dihalide | Intermediate | Observed LCMS (M + 1) |
|---|---|---|
| 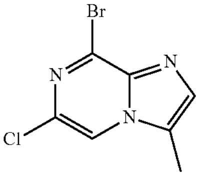 C43 | 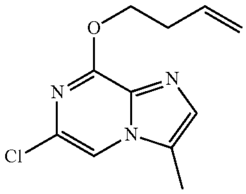 C44 | 238.0 |
| 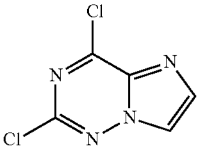 C13 | 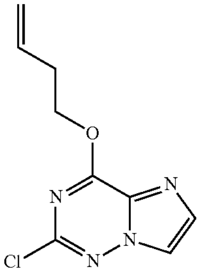 C140 | 225.0 |

The following intermediates in Table C4 were synthesized in an analogous manner of that described in Scheme C8 and used to synthesize Intermediate C39 using the appropriate halides and cores. The halide and boronic acid functionalities were switched in the Suzuki coupling partners, but the reaction conditions were analogous.

TABLE C4

| Halide | Core | Intermediate | Observed LCMS (M + 1) |
|---|---|---|---|
| 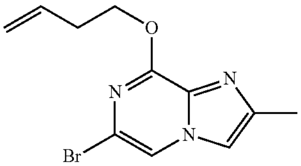 C42 | 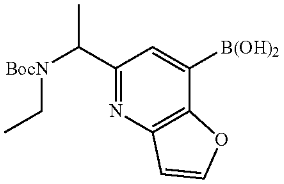 C33 | 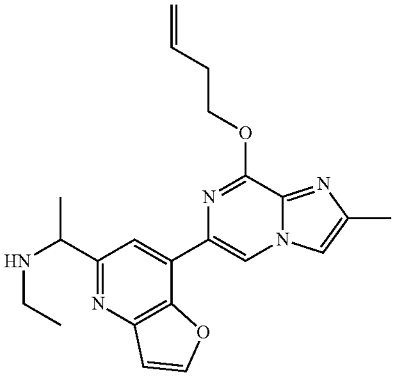 C45 | 392.2 |

TABLE C4-continued

| Halide | Core | Intermediate | Observed LCMS (M + 1) |
| --- | --- | --- | --- |
| 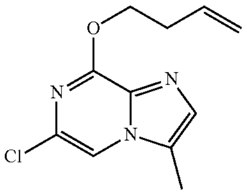 C44 | 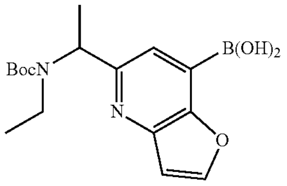 C33 | 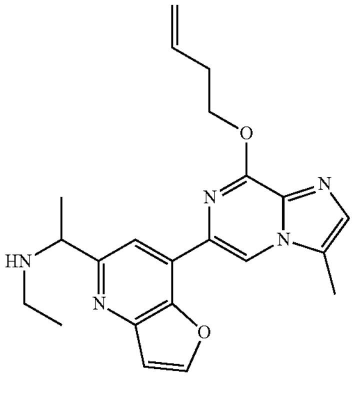 C46 | 392.2 |

Intermediate C48

(R)-1-(4-(8-chloroimidazo[1,2-a]pyrazin-6-yl)-5-methoxypyridin-2-yl)-N-ethylethan-1-amine (C48)

SCHEME C10

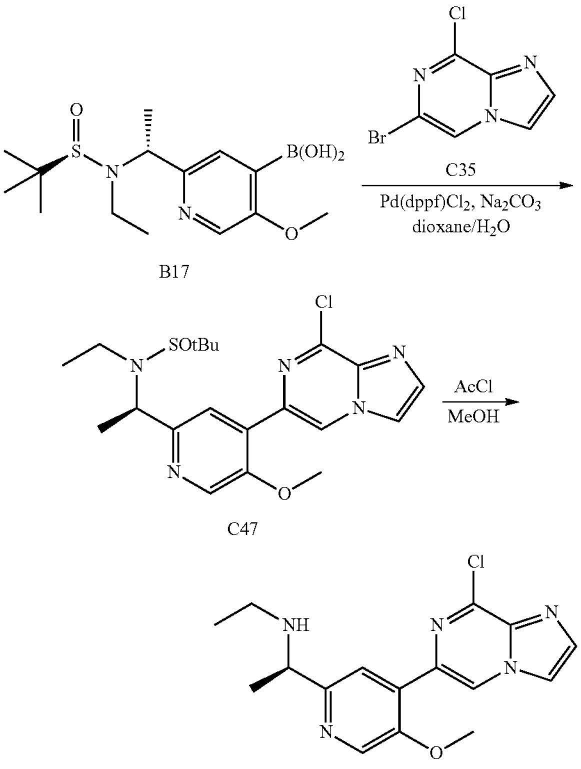

Step 1: N—((R)-1-(4-(8-chloroimidazo[1,2-a]pyrazin-6-yl)-5-methoxypyridin-2-yl)ethyl)-N-ethyl-2-methylpropane-2-sulfiamide (C47)

To a solution of (2-((R)-1-(((R)-tert-butylsulfinyl)(ethyl)amino)ethyl)-5-methoxypyridin-4-yl)boronic acid (B17, 950 mg, 2.89 mmol) in dioxane (10 mL) and water (2 mL) were added 6-bromo-8-chloroimidazo[1,2-a]pyrazine (C35, 1009 mg, 4.34 mmol), $Na_2CO_3$ (920 mg, 8.68 mmol) and $Pd(dppf)Cl_2$ (106 mg, 0.145 mmol). The reaction was stirred at 90° C. for 2 h. TLC showed formation of new spots. The reaction was poured into water (20 mL) and extracted with EtOAc (3×10 mL). The combined organic layers were washed with brine (10 mL), dried ($Na_2SO_4$), filtered and concentrated. The crude material was purified by flash silica chromatography (100% EtOAc) to give N—((R)-1-(4-(8-chloroimidazo[1,2-a]pyrazin-6-yl)-5-methoxypyridin-2-yl)ethyl)-N-ethyl-2-methylpropane-2-sulfinamide (C47).

Step 2: (R)-1-(4-(8-chloroimidazo[1,2-a]pyrazin-6-yl)-5-methoxypyridin-2-yl)-N-ethylethan-1-amine (C48)

To a solution of N—((R)-1-(4-(8-chloroimidazo[1,2-a]pyrazin-6-yl)-5-methoxypyridin-2-yl)ethyl)-N-ethyl-2-methylpropane-2-sulfinamide (C47, 100 mg, 0.229 mmol) in MeOH (2 mL) was added acetyl chloride (36.0 mg, 0.459 mmol). The reaction was stirred at 0° C. for 30 min. LCMS showed formation of the desired product mass. The reaction was concentrated to afford (R)-1-(4-(8-chloroimidazo[1,2-a]pyrazin-6-yl)-5-methoxypyridin-2-yl)-N-ethylethan-1-amine (C48) as an HCl salt, which was carried forward without purification. LC-MS: 332.1 (M+1).

Intermediates C50 and C52

SCHEME C11

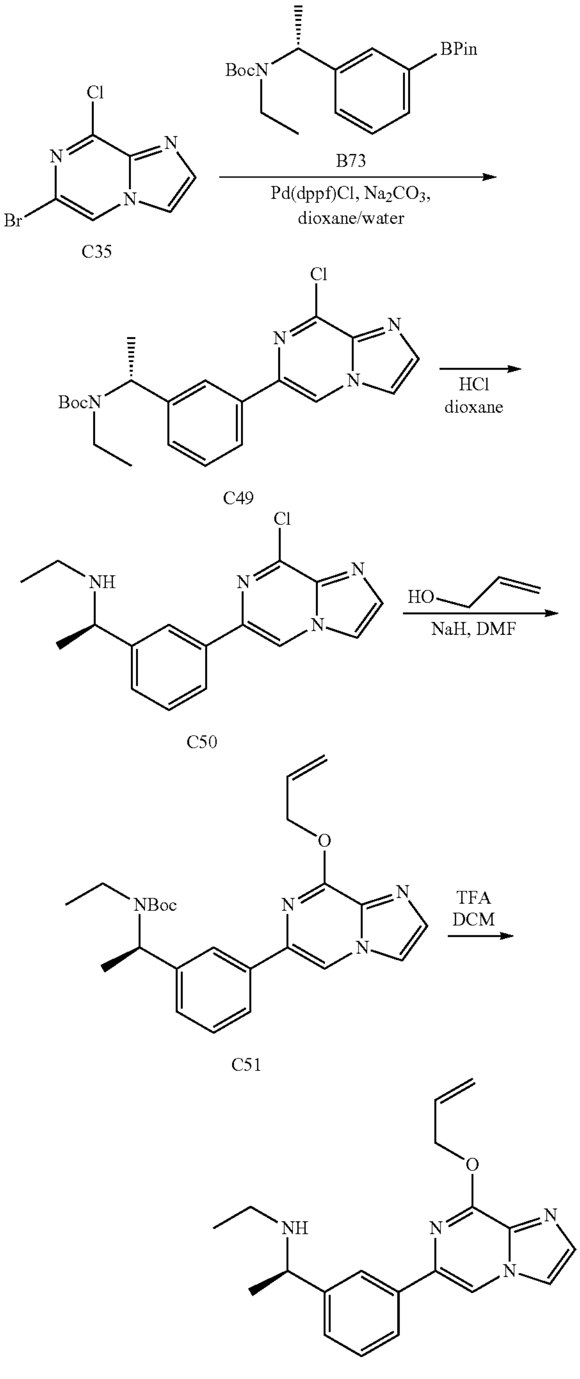

C35 C49 C50 C51 C52

Step 1: tert-butyl (R)-(1-(3-(8-chloroimidazo[1,2-a]pyrazin-6-yl)phenyl)ethyl)(ethyl)carbamate (C49)

To a solution of 6-bromo-8-chloroimidazo[1,2-a]pyrazine (C35, 0.818 g, 3.52 mmol) in dioxane (20 mL) and water (5 mL) was added (R)-tert-butyl ethyl(1-(3-(4,4,5,5-tetramethyl-1,3,2-dioxaborolan-2-yl)phenyl)ethyl)carbamate (B73, 1.1 g, 2.93 mmol), $Na_2CO_3$ (0.621 g, 5.86 mmol) and $PdCl_2$(dppf) (0.214 g, 0.293 mmol). The reaction was stirred at 90° C. for 2 h. LCMS showed formation of the desired product mass. The reaction was poured into water (100 mL) and extracted with EtOAc (3×50 mL). The combined organic layers were washed with brine (100 mL) and dried ($Na_2SO_4$), filtered and concentrated. The crude material was purified by flash silica chromatography (30% EtOAc in petroleum ether) to give tert-butyl (R)-(1-(3-(8-chloroimidazo[1,2-a]pyrazin-6-yl)phenyl)ethyl)(ethyl)carbamate (C49). LC-MS: 401.0 (M+1).

Step 2: (R)-1-(3-(8-chloroimidazo[1,2-a]pyrazin-6-yl)phenyl)-N-ethylethan-1-amine (C50)

Tert-butyl (R)-(1-(3-(8-chloroimidazo[1,2-a]pyrazin-6-yl)phenyl)ethyl)(ethyl)-carbamate (C49, 297 mg, 0.741 mmol) was treated with HCl (926 μL, 3.70 mmol) (4M in dioxane) and the reaction was stirred at ambient temperature for 15 min. LCMS showed formation of the desired product mass. The reaction was concentrated to afford (R)-1-(3-(8-chloroimidazo[1,2-a]pyrazin-6-yl)phenyl)-N-ethylethan-1-amine (C50), which was carried forward without purification. LC-MS: 301.2 (M+1).

Step 3: tert-butyl (R)-(1-(3-(8-(allyloxy)imidazo[1,2-a]pyrazin-6-yl)phenyl)ethyl)(ethyl) carbamate (C51)

To a solution of prop-2-en-1-ol (304 mg, 5.24 mmol) in DMF (20 mL) was added sodium hydride (126 mg, 5.24 mmol) (60% in mineral oil) at 0° C. and the reaction was stirred at 0° C. for 30 min. Tert-butyl (R)-(1-(3-(8-chloroimidazo[1,2-a]pyrazin-6-yl)phenyl)ethyl)(ethyl)carbamate (C49, 700 mg, 1.746 mmol) was added and the reaction was allowed to continue stirring at 0° C. for 1 h. LCMS showed complete conversion. The reaction was poured into water (100 mL) and extracted with EtOAc (3×50 mL). The organic layers were combined, washed with brine (50 mL), dried ($Na_2SO_4$), filtered and concentrated to afford tert-butyl (R)-(1-(3-(8-(allyloxy)imidazo[1,2-a]pyrazin-6-yl)phenyl)ethyl)(ethyl)carbamate (C51), which was carried forward without purification.

LC-MS: 423.1 (M+1).

Step 4: (R)-1-(3-(8-(allyloxy)imidazo[1,2-a]pyrazin-6-yl)phenyl)-N-ethylethan-1-amine (C52)

To a solution of tert-butyl (R)-(1-(3-(8-(allyloxy)imidazo[1,2-a]pyrazin-6-yl)phenyl)ethyl)(ethyl)carbamate (C51, 680 mg, 1.609 mmol) in DCM (5 mL) was added TFA (5 mL) and the reaction was stirred at ambient temperature for 1 h. LCMS showed complete conversion. The reaction was concentrated to afford (R)-1-(3-(8-(allyloxy)imidazo[1,2-a]pyrazin-6-yl)phenyl)-N-ethylethan-1-amine (C52) as a TFA salt, which was carried forward without purification. LC-MS: 323.1 (M+1).

Intermediates C53-C55

The following intermediates were synthesized in an analogous manner of that described in Scheme C11 and used to synthesize Intermediate C52 using the appropriate boronic acids or esters and halides.

TABLE C5
| Boronic ester/acid | Halide | Intermediates | Observed LCMS (M + 1) |
|---|---|---|---|
| 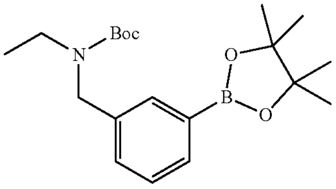 B65 | 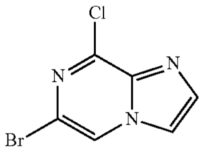 C35 | 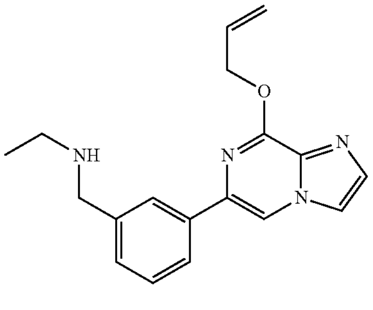 C53 | 309.2 |
| 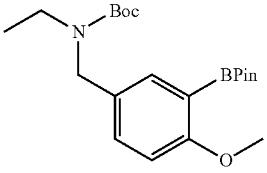 B69 | 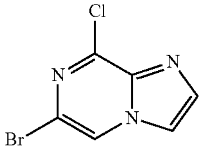 C35 | 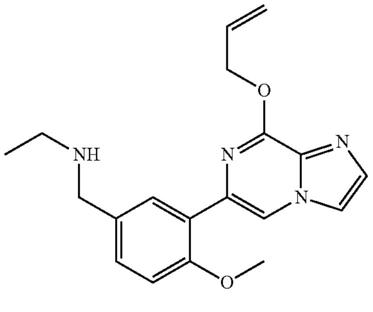 C54 | 339.2 |
| 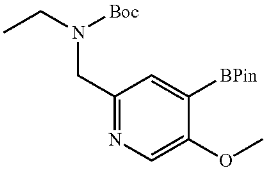 B67 | 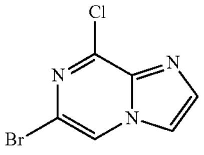 C35 | 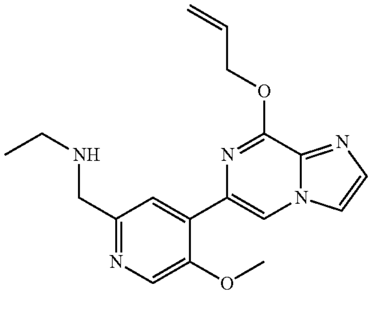 C55 | 340.1 |
Intermediate C59
(R)-1-(4-(4-(but-3-en-1-yloxy)pyrazolo[1,5-a][1.3.5]triazin-2-yl)-5-methoxypyridin-2-yl)-N-ethylethan-1-amine (C59)
SCHEME C12
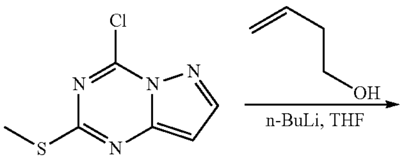
-continued
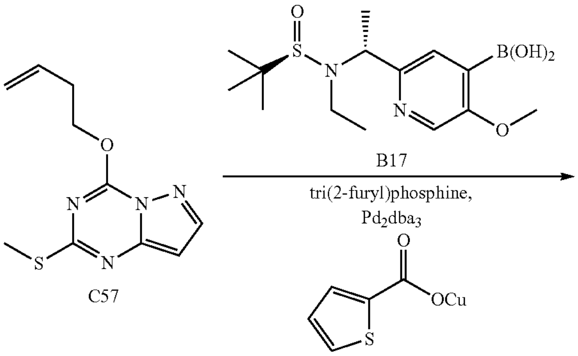

-continued

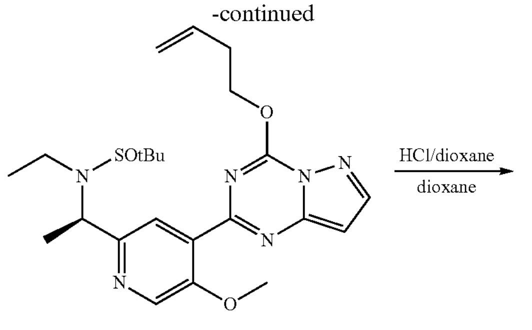

C58

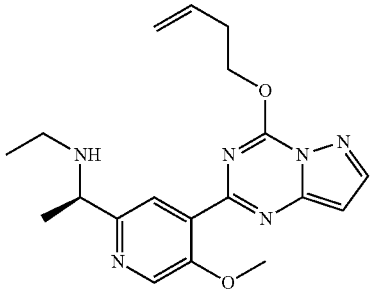

C59

Step 1: 4-(but-3-en-1-yloxy)-2-(methylthio)pyrazolo [1,5-a][1,3,5]triazine (C57)

To a solution of but-3-en-1-ol (0.539 g, 7.48 mmol) in THF (10 mL) was added n-butyllithium (2.99 mL, 7.48 mmol) at −78° C. and the reaction was stirred at −78° C. for 30 min. 4-chloro-2-(methylthio)pyrazolo[1,5-a][1,3,5]triazine (C56, 1 g, 4.98 mmol) in THF (10 mL) was added and the reaction was stirred at 80° C. for 12 h. LCMS showed formation of the desired product mass. The reaction was quenched with water (50 mL) and extracted with EtOAc (3×20 mL). The combined organic layers were dried ($Na_2SO_4$), filtered and concentrated. The crude material was purified by flash silica chromatography (0-27% EtOAc in petroleum ether gradient) to 4-(but-3-en-1-yloxy)-2-(methylthio)pyrazolo[1,5-a][1,3,5]triazine (C57). LC-MS: 237.2 (M+1).

Step 2: N—((R)-1-(4-(4-(but-3-en-1-yloxy)pyrazolo [1,5-a][1,3,5]triazin-2-yl)-5-methoxypyridin-2-yl) ethyl)-N-ethyl-2-methylpropane-2-sulfinamide (C58)

To a solution of (2-((R)-1-(((R)-tert-butylsulfinyl)(ethyl)amino)ethyl)-5-methoxypyridin-4-yl)boronic acid (B17, 222 mg, 0.677 mmol) and 4-(but-3-en-1-yloxy)-2-(methylthio)pyrazolo[1,5-a][1,3,5]triazine (C57, 160 mg, 0.677 mmol) in THF (2 mL) was added copper(i) thiophene-2-carboxylate (258 mg, 1.354 mmol), tri(2-furyl)phosphine (31.4 mg, 0.135 mmol) and tris(dibenzylideneacetone)dipalladium(0) (124 mg, 0.135 mmol) at 10° C. The reaction was stirred for 15 h at 50° C. under nitrogen. LCMS showed formation of the desired product mass. The reaction was poured into water (10 mL) and extracted with EtOAc (3×3 mL). The combined organic layers were dried ($Na_2SO_4$), filtered and concentrated. The crude material was purified by preparative TLC (100% EtOAc) to afford N—((R)-1-(4-(4-(but-3-en-1-yloxy)pyrazolo[1,5-a][1,3,5]triazin-2-yl)-5-methoxypyridin-2-yl)ethyl)-N-ethyl-2-methylpropane-2-sulfinamide (C58). LC-MS: 473.2 (M+1).

Step 3: (R)-1-(4-(4-(but-3-en-1-yloxy)pyrazolo[1,5-a][1,3,5]triazin-2-yl)-5-methoxypyridin-2-yl)-N-ethylethan-1-amine (C59)

To a solution of N—((R)-1-(4-(4-(but-3-en-1-yloxy)pyrazolo[1,5-a][1,3,5]triazin-2-yl)-5-methoxypyridin-2-yl)ethyl)-N-ethyl-2-methylpropane-2-sulfinamide (C58, 40 mg, 0.085 mmol) in dioxane (2 mL) was added HCl (0.2 mL) (4M in dioxane) and the reaction was stirred at 15° C. for 30 min. LCMS showed formation of the desired product mass. The reaction was concentrated to afford (R)-1-(4-(4-(but-3-en-1-yloxy)pyrazolo[1,5-a][1,3,5]triazin-2-yl)-5-methoxypyridin-2-yl)-N-ethylethan-1-amine (C59), which was carried forward without purification. LC-MS: 369.3 (M+1).

Intermediate C65

1-(4-(8-(allyloxy)-[1,2,4]triazolo[1,5-a]pyrazin-6-yl)-5-methoxypyridin-2-yl)-N-ethyl-2,2,2-trifluoroethan-1-amine (C65)

SCHEME C13

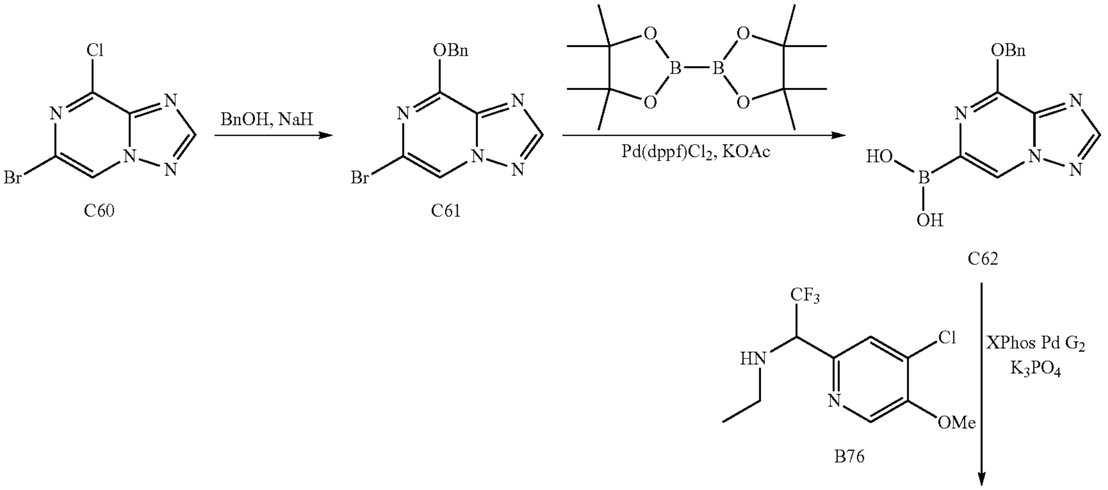

C60 C61 C62 B76

-continued

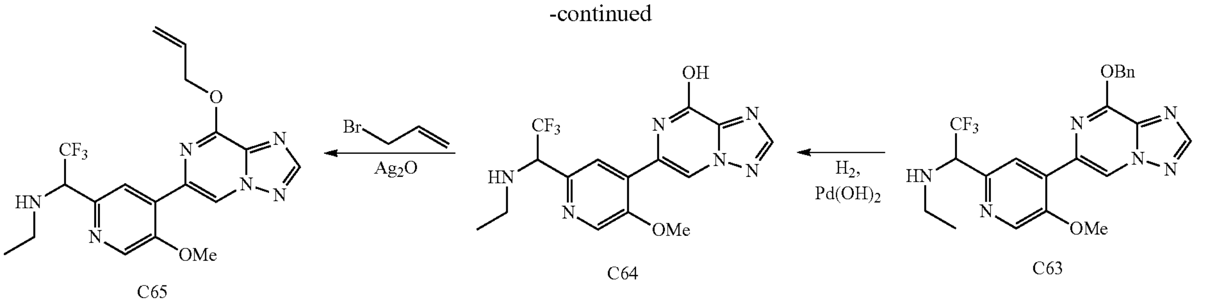

C65 C64 C63

Step 1: 8-(benzyloxy)-6-bromo-[1,2,4]triazolo[1,5-a]pyrazine (C61)

Benzyl alcohol (779 μL, 7.50 mmol) was dissolved in DMF (9519 μL) and sodium hydride (300 mg, 7.50 mmol) (60% in mineral oil) was added. The reaction was allowed to stir at 0° C. for 30 min. 6-bromo-8-chloro-[1,2,4]triazolo[1,5-a]pyrazine (C60, 500 mg, 2.142 mmol) dissolved in DMF (4759 μL) and precooled to 0° C. was added and the reaction was allowed to continue stirring at 0° C. for 1 min. The reaction was quenched with brine (30 mL) and extracted with EtOAC (3×50 mL). LCMS analysis showed formation of the desired product mass. The combined organic fractions were washed with water (2×20 mL), brine (2×20 mL), dried ($MgSO_4$) and concentrated. The crude material was purified by reverse phase preparative HPLC (10-95% ACN:water, 0.1% TFA). The product containing fraction was neutralized with sat. aq. $NaHCO_3$ and extracted with DCM and concentrated to afford 8-(benzyloxy)-6-bromo-[1,2,4]triazolo[1,5-a]pyrazine (C61). LC-MS: 305.2, 307.2 (M+1)

Step 2: (8-(benzyloxy)-[1,2,4]triazolo[1,5-a]pyrazin-6-yl)boronic acid (C62)

8-(benzyloxy)-6-bromo-[1,2,4]triazolo[1,5-a]pyrazine (C61, 400 mg, 1.311 mmol), bis(pinacolato)diboron (419 mg, 1.652 mmol), Pd(dppf)$Cl_2$ (48.0 mg, 0.066 mmol) and potassium acetate (386 mg, 3.93 mmol) were combined. Dioxane (9167 μL) was added and the reaction was degassed with nitrogen for 5 min. The reaction was then sealed and heated to 90° C. for 3 h. LCMS analysis showed complete conversion. The reaction was filtered through Celite and concentrated. The crude material was allowed to dry under vacuum for 5 h to afford (8-(benzyloxy)-[1,2,4]triazolo[1,5-a]pyrazin-6-yl)boronic acid (C62), which was carried forward without purification.

LC-MS: 271.2 (M+1).

Step 3: 6-(2-(1-(ethylamino)-2,2,2-trifluoroethyl)-5-methoxypyridin-4-yl)-[1,2,4]triazolo[1,5-a]pyrazin-8-ol (C63)

1-(4-chloro-5-methoxypyridin-2-yl)-N-ethyl-2,2,2-trifluoroethan-1-amine (B76, 176 mg, 0.656 mmol) was combined with (8-(benzyloxy)-[1,2,4]triazolo[1,5-a]pyrazin-6-yl)boronic acid (C62, 354 mg, 1.312 mmol) and XPhos Pd G2 (51.6 mg, 0.066 mmol). The vial was taken into the glovebox and tripotassium phosphate (2624 μL, 2.62 mmol) (1 M in water) and dioxane (6560 μL) were added. The vial was sealed, removed from the glovebox and heated to 85° C. for 18 h. LCMS analysis showed formation of the desired product mass. The reaction was filtered through Celite and concentrated. The crude material was purified by ISCO column chromatography (0-70% EtOAc:EtOH 3:1 mix in hexanes) to afford 6-(2-(1-(ethylamino)-2,2,2-trifluoroethyl)-5-methoxypyridin-4-yl)-[1,2,4]triazolo[1,5-a]pyrazin-8-ol (C63). LC-MS: 459.4 (M+1).

Step 4: 6-(2-(1-(ethylamino)-2,2,2-trifluoroethyl)-5-methoxypyridin-4-yl)-[1,2,4]triazolo[1,5-a]pyrazin-8-ol (C64)

1-(4-(8-(benzyloxy)-[1,2,4]triazolo[1,5-a]pyrazin-6-yl)-5-methoxypyridin-2-yl)-N-ethyl-2,2,2-trifluoroethan-1-amine (C63, 381 mg, 0.831 mmol) was dissolved in MeOH (4.16E+04 μL) and palladium hydroxide (117 mg, 0.166 mmol) (20% on carbon) was added. The reaction was degassed with hydrogen for 5 min before the exhaust needle was removed and the reaction was run under a balloon of hydrogen for 30 min. LCMS analysis showed formation of the desired product mass. The reaction was filtered through Celite and concentrated to afford 6-(2-(1-(ethylamino)-2,2,2-trifluoroethyl)-5-methoxypyridin-4-yl)-[1,2,4]triazolo[1,5-a]pyrazin-8-ol (C64), which was carried forward without purification. LC-MS: 369.3 (M+1).

Step 5: 1-(4-(8-(allyloxy)-[1,2,4]triazolo[1,5-a]pyrazin-6-yl)-5-methoxypyridin-2-yl)-N-ethyl-2,2,2-trifluoroethan-1-amine (C65)

6-(2-(1-(ethylamino)-2,2,2-trifluoroethyl)-5-methoxypyridin-4-yl)-[1,2,4]triazolo[1,5-a]pyrazin-8-ol (C64, 153 mg, 0.415 mmol) was dissolved in NMP (2769 μL) and allyl bromide (71.9 μL, 0.831 mmol) and silver oxide (193 mg, 0.831 mmol) were added. The vial was sealed, and the reaction was heated in the microwave at 100° C. for 5 min. LCMS analysis showed formation of the desired product mass. The reaction was diluted with DMSO (10 mL), filtered through a syringe filter and purified directly on reverse phase preparative HPLC (10-95% ACN:water, with 0.1% TFA as a modifier). The product containing fractions were neutralized with sat. aq. $NaHCO_3$, extracted with DCM and concentrated to afford 1-(4-(8-(allyloxy)-[1,2,4]triazolo[1,5-a]pyrazin-6-yl)-5-methoxypyridin-2-yl)-N-ethyl-2,2,2-trifluoroethan-1-amine (C65). LC-MS: 409.4 (M+1)

Intermediates C67-C69

The following intermediates in Table C6 were synthesized in an analogous manner of that described in Scheme C13 and used to synthesize Intermediate C65 using the appropriate halides and cores.

TABLE C6

| Halide | Core | Intermediate | Observed LCMS (M + 1) |
|---|---|---|---|
| 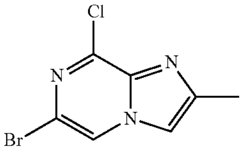 C66 | 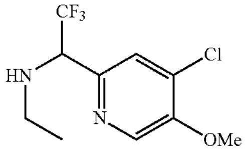 B76 | 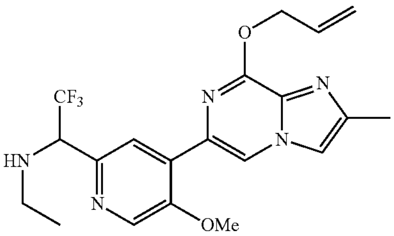 C67 | 422.4 |
| 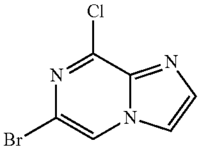 C35 | 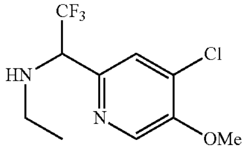 B76 | 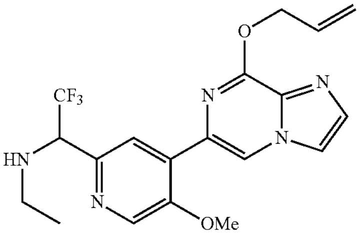 C68 | 408.3 |
| 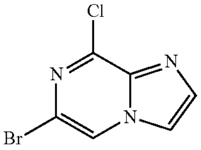 C35 | 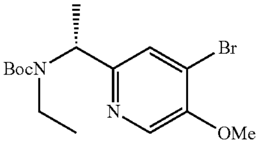 B18 | 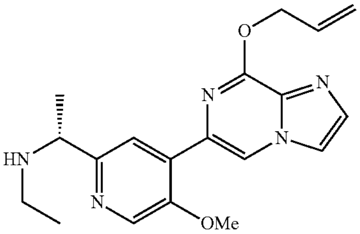 * C69 | 354.4 |

* A final Boc deprotection step analogous to the deprotection leading to Intermediate C20 in Scheme C5 was used in the synthesis of Intermediate C69.

Intermediates C74-C82

SCHEME C14

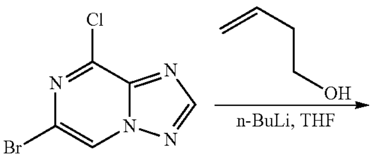

C60

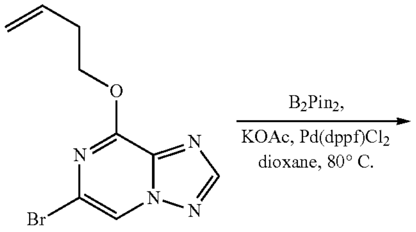

C70

-continued

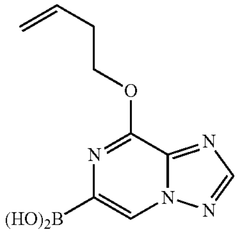

C71

Step 1: 6-bromo-8-(but-3-en-1-yloxy)-[1,2,4]triazolo[1,5-a]pyrazine (C70)

To a solution of but-3-en-1-ol (0.273 mL, 3.21 mmol) in THF (4 mL) was added n-butyllithium (1.199 mL, 3.00 mmol) (2.5 M in hexanes) at −78° C. and the reaction was stirred at −78° C. for 30 min. 6-bromo-8-chloro-[1,2,4]triazolo[1,5-a]pyrazine (C60, 500 mg, 2.142 mmol) in THF (2 mL) was added and the reaction was stirred at 80° C. for 12 h. TLC showed formation of new spots. The reaction was quenched with sat. aq. $NH_4Cl$ (5 mL) and extracted with EtOAc (3×10 mL). The combined organic layers were washed with brine (5 mL), dried ($Na_2SO_4$), filtered and concentrated. The crude material was purified by flash silica chromatography (50% EtOAc in petroleum ether) to afford 6-bromo-8-(but-3-en-1-yloxy)-[1,2,4]triazolo[1,5-a]pyrazine (C70). $^1H$ NMR: (400 MHz, $CDCl_3$) δ 8.53-8.19 (m, 2H), 5.92 (tdd, J=6.7, 10.3, 17.1 Hz, 1H), 5.30-5.09 (m, 2H), 4.71-4.62 (m, 2H), 2.70 (q, J=6.8 Hz, 2H).

Step 2: (8-(but-3-en-1-yloxy)-[1,2,4]triazolo[1,5-a]pyrazin-6-yl)boronic acid (C71)

To a mixture of 6-bromo-8-(but-3-en-1-yloxy)-[1,2,4]triazolo[1,5-a]pyrazine (C70, 380 mg, 1.412 mmol), 4,4,4',4',5,5,5',5'-octamethyl-2,2'-bi(1,3,2-dioxaborolane) (717 mg, 2.82 mmol) and potassium acetate (416 mg, 4.24 mmol) in dioxane (4 mL) was added Pd(dppf)$Cl_2$ (103 mg, 0.141 mmol), and the reaction was stirred at 80° C. under nitrogen for 4 h. LCMS showed formation of the desired product mass. This resulting solution of boronic ester C71 was carried forward without purification. LC-MS: 235.2 (M+1).

The following boronic esters/acids in Table C7 were synthesized in an analogous manner of that described in Scheme C14 and used to synthesize Intermediate C71 from the appropriate halides. For Intermediate C72, XPhos G2 Pd was used instead of Pd(dffp)$Cl_2$.

TABLE C7

| Halide | Boronic acid/ester | Observed LCMS (M + 1) |
|---|---|---|
| 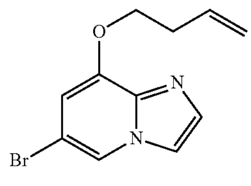 C14 | 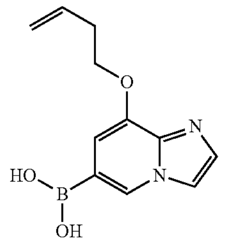 C72 | 233.3 |

SCHEME C15

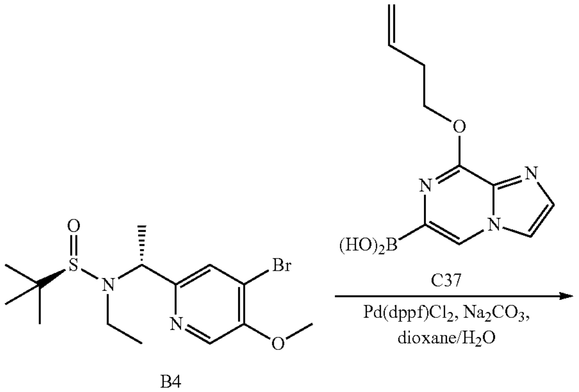

B4 C37

-continued

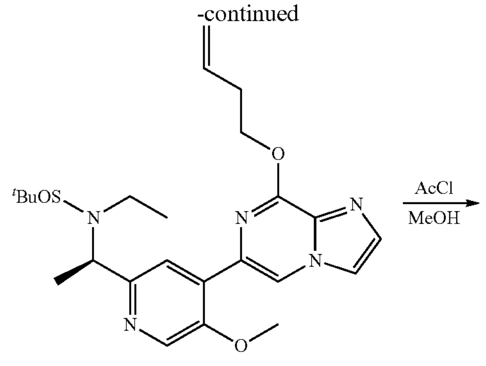

C73

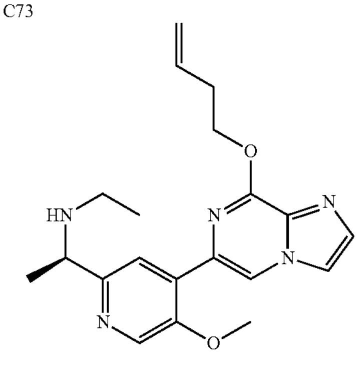

C74

Step 1: N—((R)-1-(4-(8-(but-3-en-1-yloxy)imidazo[1,2-a]pyrazin-6-yl)-5-methoxypyridin-2-yl)ethyl)-N-ethyl-2-methylpropane-2-sulfinamide (C73)

To a solution of (8-(but-3-en-1-yloxy)imidazo[1,2-a]pyrazin-6-yl)boronic acid (C37, 257 mg, 1.101 mmol) in dioxane (3 mL) and water (0.5 mL) were added (R)—N—((R)-1-(4-bromo-5-methoxypyridin-2-yl)ethyl)-N-ethyl-2-methylpropane-2-sulfinamide (B4, 200 mg, 0.550 mmol), $Na_2CO_3$ (175 mg, 1.651 mmol) and Pd(dppf)$Cl_2$ (40.3 mg, 0.055 mmol). The reaction was stirred at 90° C. for 2 h. LCMS showed formation of the desired product mass. The reaction was extracted with EtOAc (3×3 mL), washed with brine (3 mL), dried ($Na_2SO_4$), filtered and concentrated. The crude material was purified by flash silica chromatography (80% EtOAc in petroleum ether) to afford N—((R)-1-(4-(8-(but-3-en-1-yloxy)imidazo[1,2-a]pyrazin-6-yl)-5-methoxypyridin-2-yl)ethyl)-N-ethyl-2-methylpropane-2-sulfinamide (C73). LC-MS: 472.2 (M+1).

Step 2: (R)-1-(4-(8-(but-3-en-1-yloxy)imidazo[1,2-a]pyrazin-6-yl)-5-methoxypyridin-2-yl)-N-ethylethan-1-amine (C74)

To a solution of N—((R)-1-(4-(8-(but-3-en-1-yloxy)imidazo[1,2-a]pyrazin-6-yl)-5-methoxypyridin-2-yl)ethyl)-N-ethyl-2-methylpropane-2-sulfinamide (C73, 100 mg, 0.212 mmol) in MeOH (5 mL) was added acetyl chloride (83 mg, 1.060 mmol), and the reaction was stirred at 0° C. for 30 min. LCMS showed formation of the desired product mass. The reaction was concentrated to)-1-(4-(8-(but-3-en-1-yloxy)imidazo[1,2-a]pyrazin-6-yl)-5-methoxypyridin-2-yl)-N-ethylethan-1-amine (C74) an HCl salt, which was carried forward without purification. LC-MS: 368.2 (M+1).

The following intermediates in Table C8 were synthesized in an analogous manner of that described in Scheme C15 and used to synthesize Intermediate C74 from the appropriate halides and cores. For Intermediates C75, C77 and C82 XPhos Pd G2 and K2C03 were used in Step 1. For Intermediate C76 $K2CO_3$ was used instead of $Na_2CO_3$.
TABLE C8
| Halide | Core | Intermediate | Observed LCMS (M + 1) |
|---|---|---|---|
| 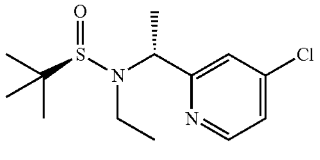 B88 | 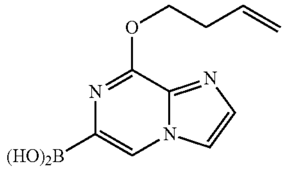 C37 | 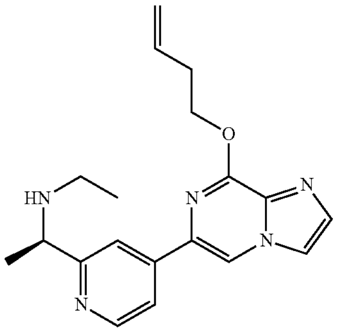 C75 | 338.2 |
| 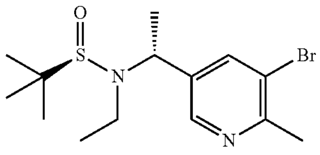 B61 | 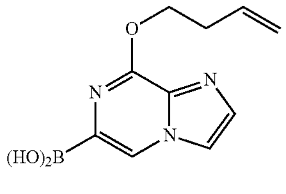 C37 | 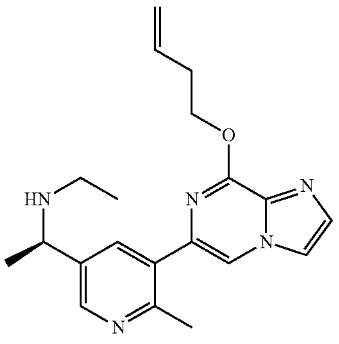 C76 | 352.2 |
| 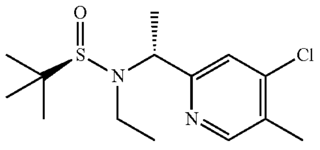 B31 | 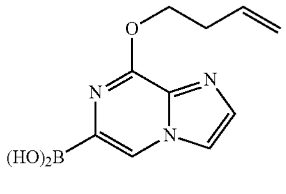 C37 | 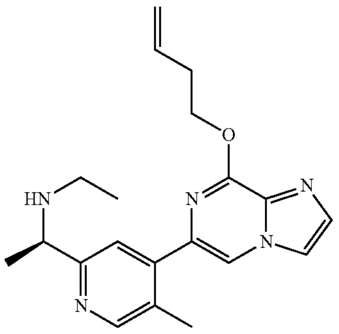 C77 | 352.2 |

TABLE C8-continued
| Halide | Core | Intermediate | Observed LCMS (M + 1) |
|---|---|---|---|
| 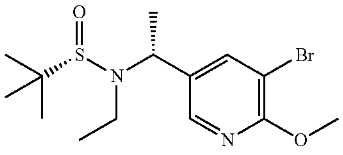 B14 | 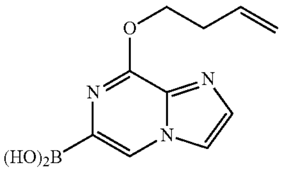 C37 | 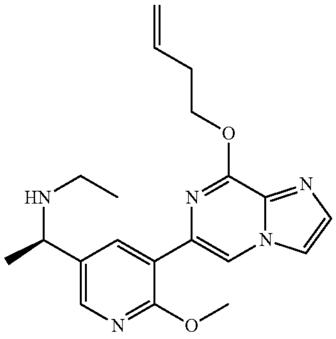 C78 | 368.2 |
| 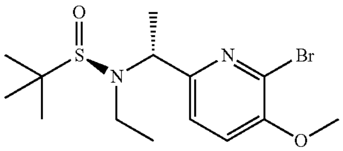 B58 | 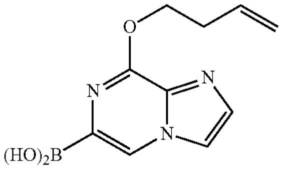 C37 | 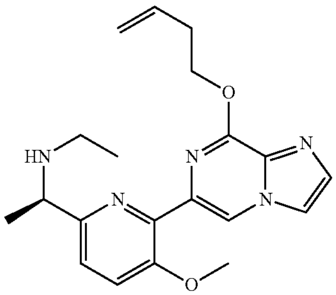 C79 | 368.1 |
| 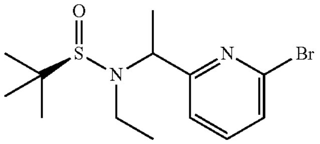 B16 | 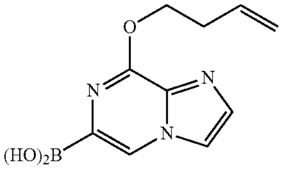 C37 | 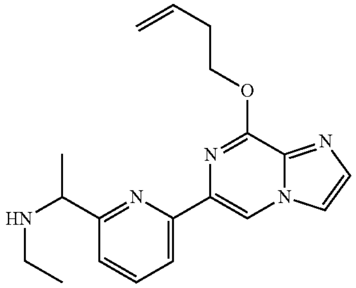 C80 | 338.3 |
| 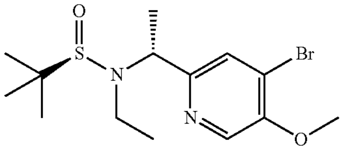 B4 | 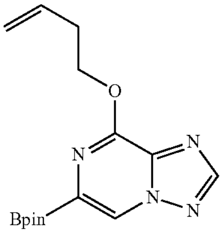 C71 | 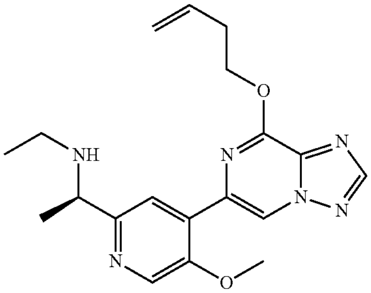 C81 | 369.0 |

TABLE C8-continued

| Halide | Core | Intermediate | Observed LCMS (M + 1) |
|---|---|---|---|
| 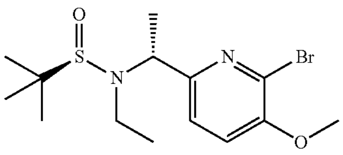 B58 | 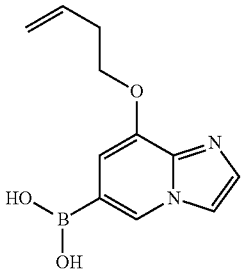 C72 | 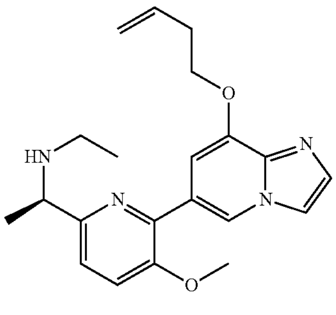 C82 | 367.5 |

Intermediate C88

1-(6-(7-(but-3-en-1-yloxy)pyrazolo[1,5-a]pyridin-5-yl)-5-methoxypyrazin-2-yl)-N-ethylethan-1-amine (C88)

SCHEME C16

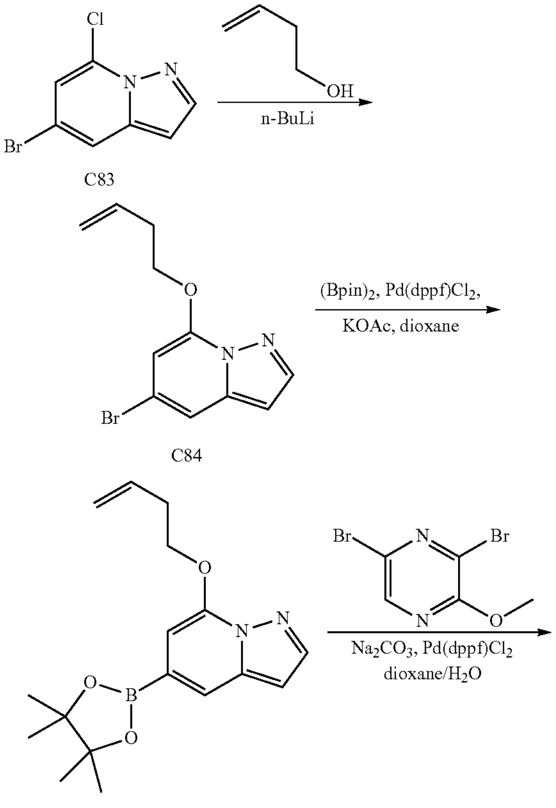

C83

C84

C85

-continued

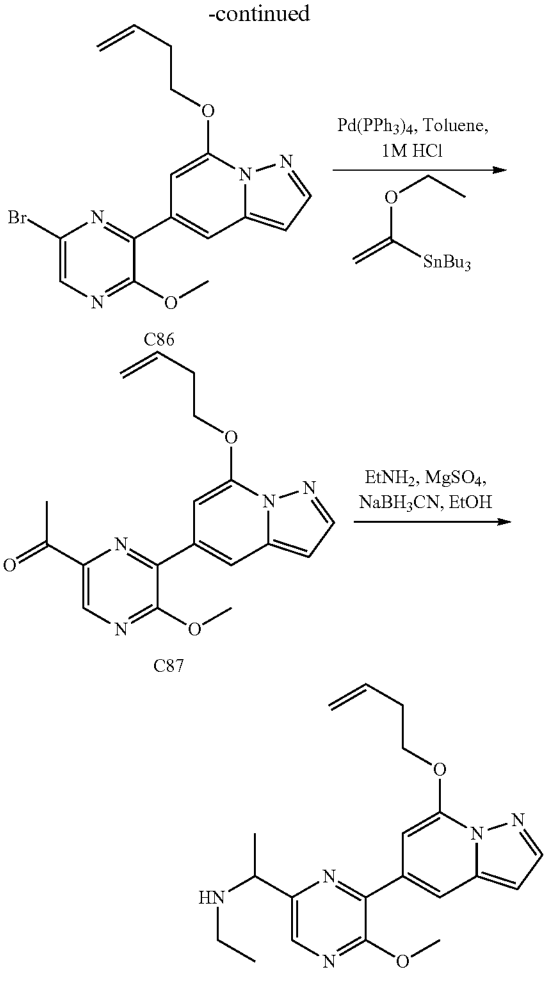

C86

C87

C88

Step 1: 5-bromo-7-(but-3-en-1-yloxy)pyrazolo[1,5-a]pyridine (C84)

To a solution of but-3-en-1-ol (0.860 g, 11.92 mmol) in THF (20 mL) was added n-butyllithium (4.37 mL, 10.93 mmol) (2.5 M in hexane) and then 5-bromo-7-chloropyrazolo[1,5-a]pyridine (C83, 2.3 g, 9.94 mmol) in THF (10 mL) was added at −78° C. and the reaction was stirred at 80° C.

for 15 h. LCMS formation of the desired product mass. The reaction was poured into water (100 mL) and extracted with EtOAc (3×30 mL). The combined organic layers were dried ($Na_2SO_4$), filtered and concentrated. The crude material was purified by flash silica chromatography (0-7% EtOAc in petroleum ether gradient) to give 5-bromo-7-(but-3-en-1-yloxy)pyrazolo[1,5-a]pyridine (C84). LC-MS: 267.1 (M+1).

Step 2: 7-(but-3-en-1-yloxy)-5-(4,4,5,5-tetramethyl-1,3,2-dioxaborolan-2-yl)pyrazolo[1,5-a]pyridine (C85)

To a solution of 5-bromo-7-(but-3-en-1-yloxy)pyrazolo[1,5-a]pyridine (C84, 800 mg, 2.99 mmol) in dioxane (10 mL) were added 4,4,4',4',5,5,5',5'-octamethyl-2,2'-bi (1,3,2-dioxaborolane) (913 mg, 3.59 mmol), potassium acetate (735 mg, 7.49 mmol) and Pd(dppf)$Cl_2$ (219 mg, 0.299 mmol). The reaction was stirred at 80° C. for 15 h. LCMS showed complete conversion. The reaction was filtered to give 7-(but-3-en-1-yloxy)-5-(4,4,5,5-tetramethyl-1,3,2-dioxaborolan-2-yl)pyrazolo[1,5-a]pyridine (C85) in dioxane (10 mL), which was carried forward without purification. LC-MS: 315.2 (M+1).

Step 3: 5-(6-bromo-3-methoxypyrazin-2-yl)-7-(but-3-en-1-yloxy)pyrazolo[1,5-a]pyridine (C86)

To a solution of 7-(but-3-en-1-yloxy)-5-(4,4,5,5-tetramethyl-1,3,2-dioxaborolan-2-yl)pyrazolo[1,5-a]pyridine (C85, 941 mg, 3.00 mmol) in dioxane (20 mL) were added 3,5-dibromo-2-methoxypyrazine (802 mg, 3.00 mmol), $Na_2CO_3$ (635 mg, 5.99 mmol) and Pd(dppf)$Cl_2$ (219 mg, 0.300 mmol). The reaction was stirred at 80° C. for 3 h. LCMS showed formation of the desired product mass. The reaction was poured into water (100 mL) and extracted with EtOAc (3×30 mL). The combined organic phases were washed with brine (100 mL), dried ($Na_2SO_4$), filtered and concentrated. The crude material was purified by flash silica chromatography (25% EtOAc in petroleum ether) to give 5-(6-bromo-3-methoxypyrazin-2-yl)-7-(but-3-en-1-yloxy)pyrazolo[1,5-a]pyridine (C86). LC-MS: 375.1, 377.1 (M+1).

Step 4: 1-(6-(7-(but-3-en-1-yloxy)pyrazolo[1,5-a]pyridin-5-yl)-5-methoxypyrazin-2-yl)ethan-1-one (C87)

To a solution of give 5-(6-bromo-3-methoxypyrazin-2-yl)-7-(but-3-en-1-yloxy)pyrazolo[1,5-a]pyridine (C86, 420 mg, 1.119 mmol) in toluene (5 mL) were added tributyl (1-ethoxyvinyl)stannane (606 mg, 1.679 mmol) and tetrakis (triphenylphosphine)palladium (0) (129 mg, 0.112 mmol). The reaction was stirred at 100° C. for 15 h. The reaction was then cooled down to 20° C. and 1 M aq. HCl (4 mL) was added. The reaction was allowed to stir at 20° C. for another 3 h. LCMS formation of the desired product mass. The reaction was poured into water (20 mL) and the pH was adjusted to 8 using sat. aq. $NaHCO_3$. The mixture was then extracted with EtOAc (3×10 mL). The combined organic layers were washed with brine (20 mL), dried ($Na_2SO_4$), filtered and concentrated. The crude material was purified by flash silica chromatography (33% EtOAc in petroleum ether) to give 1-(6-(7-(but-3-en-1-yloxy)pyrazolo[1,5-a]pyridin-5-yl)-5-methoxypyrazin-2-yl)ethan-1-one (C87). LC-MS: 339.2 (M+1). $^1H$ NMR: (400 MHz, $CDCl_3$) δ 8.81 (s, 1H), 8.26 (d, J=1.6 Hz, 1H), 8.06 (d, J=2.0 Hz, 1H), 7.08 (d, J=1.6 Hz, 1H), 6.70 (d, J=2.3 Hz, 1H), 6.00 (tdd, J=6.7, 10.2, 17.1 Hz, 1H), 5.34-5.11 (m, 2H), 4.47 (t, J=7.0 Hz, 2H), 4.21 (s, 3H), 2.90-2.82 (m, 2H), 2.80-2.71 (m, 3H)

Step 5: 1-(6-(7-(but-3-en-1-yloxy)pyrazolo[1,5-a]pyridin-5-yl)-5-methoxypyrazin-2-yl)-N-ethylethan-1-amine (C88)

To a solution of 1-(6-(7-(but-3-en-1-yloxy)pyrazolo[1,5-a]pyridin-5-yl)-5-methoxypyrazin-2-yl)ethan-1-one (C87, 170 mg, 0.502 mmol) in EtOH (5 mL) were added ethanamine (45.3 mg, 1.005 mmol), AcOH (2.88 μL, 0.050 mmol), $MgSO_4$ (121 mg, 1.005 mmol) and $NaBH_3CN$ (63.1 mg, 1.005 mmol) at 15° C. The reaction was stirred for 2 h at 90° C. LCMS showed formation of the desired product mass. The reaction mixture was filtered and concentrated to afford 1-(6-(7-(but-3-en-1-yloxy)pyrazolo[1,5-a]pyridin-5-yl)-5-methoxypyrazin-2-yl)-N-ethylethan-1-amine (C88), which was carried forward without purification. LC-MS: 368.3 (M+1).

Intermediates C90 and C92

The following intermediates in Table C9 were synthesized in an analogous manner of that described in Scheme C16 (last 3 steps) and used to synthesize Intermediate C88 from the appropriate halides and boronic esters/acids. For Intermediate C90 XPhos Pd G2 was used in the Suzuki coupling. For Intermediate C92 $Pd(PPh_3)_4$ was used in the Suzuki coupling.

TABLE C9

| Halide | Boronic acid | Intermediate | Observed LCMS (M + 1) |
|---|---|---|---|
| 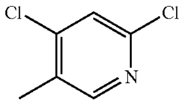 C89 | 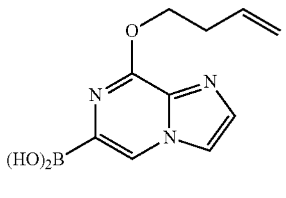 C37 | 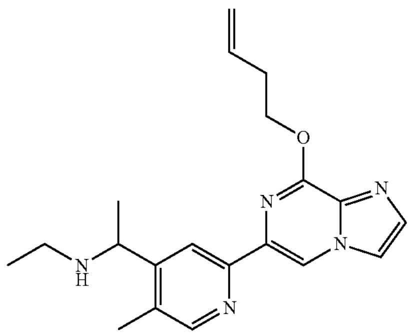 C90 | 352.1 |

TABLE C9-continued

| Halide | Boronic acid | Intermediate | Observed LCMS (M + 1) |
|---|---|---|---|
| 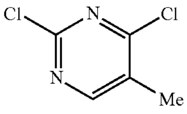 C91 | 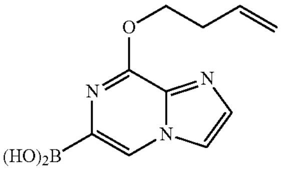 C37 | 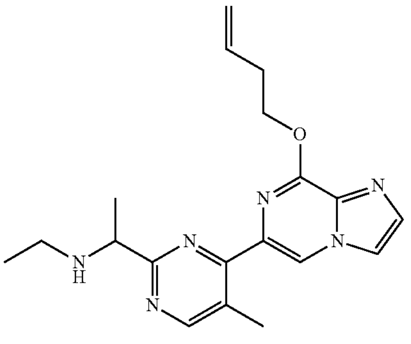 C92 | 353.3 |

Intermediate C95

1-(6-(8-(but-3-en-1-yloxy)imidazo[1,2-a]pyridin-6-yl)pyrimidin-4-yl)-N-ethylethan-1-amine (C95)

SCHEME C17

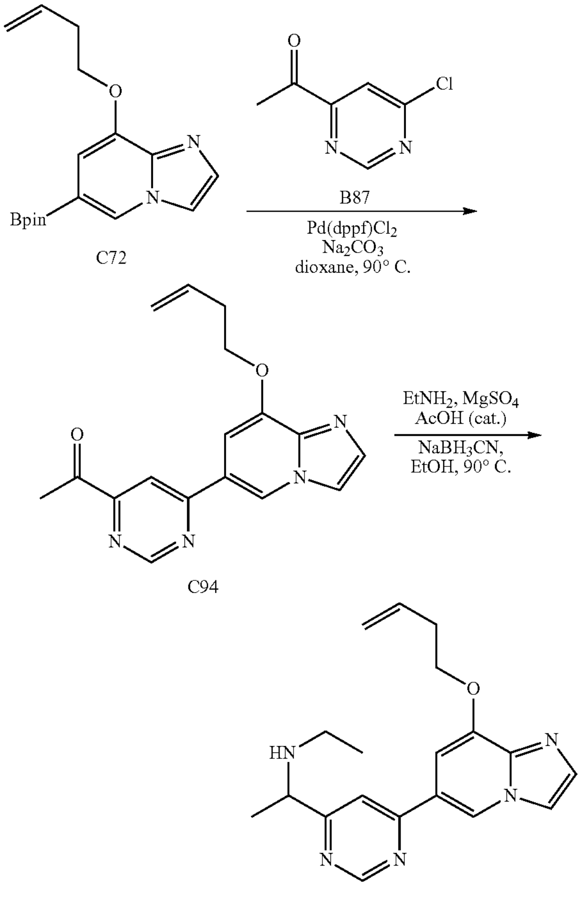

C72 C94 C95

Step 2: 1-(6-(8-(but-3-en-1-yloxy)imidazo[1,2-a]pyridin-6-yl)pyrimidin-4-yl)ethan-1-one (C94)

To a solution of (8-(but-3-en-1-yloxy)imidazo[1,2-a]pyridin-6-yl)boronic acid (C72, 20 mL, 7.40 mmol) (0.37 M in dioxane) were added 1-(6-chloropyrimidin-4-yl)ethan-1-one (B87, 1159 mg, 7.40 mmol), $Na_2CO_3$ (1569 mg, 14.80 mmol) and Pd(dppf)$Cl_2$ (541 mg, 0.740 mmol). The reaction was stirred at 80° C. for 12 h. LCMS showed complete conversion. The reaction was poured into water (50 mL) and extracted with EtOAc (3×30 mL). The combined organic layers were washed with brine (30 mL), dried ($Na_2SO_4$), filtered and concentrated. The crude material was purified by flash silica chromatography (0-100% EtOAc in petroleum ether gradient) to afford 1-(6-(8-(but-3-en-1-yloxy)imidazo[1,2-a]pyridin-6-yl)pyrimidin-4-yl)ethan-1-one (C94).

Step 3: 1-(6-(8-(but-3-en-1-yloxy)imidazo[1,2-a]pyridin-6-yl)pyrimidin-4-yl)-N-ethylethan-1-amine (C95)

To a solution of 1-(6-(8-(but-3-en-1-yloxy)imidazo[1,2-a]pyridin-6-yl)pyrimidin-4-yl)ethan-1-one (C94, 600 mg, 1.946 mmol) in EtOH (10 mL) were added ethanamine (175 mg, 3.89 mmol), acetic acid (11.69 mg, 0.195 mmol), $MgSO_4$ (1171 mg, 9.73 mmol) and $NaBH_3CN$ (245 mg, 3.89 mmol). The reaction was stirred at 90° C. for 2 h. LCMS showed complete conversion. The reaction was filtered and concentrated to give 1-(6-(8-(but-3-en-1-yloxy)imidazo[1,2-a]pyridin-6-yl)pyrimidin-4-yl)-N-ethylethan-1-amine (C95), which was carried forward without purification. LC-MS: 338.4 (M+1).

Intermediate C98

1-(4-(8-(but-3-en-1-yloxy)imidazo[1,2-a]pyrazin-6-yl)-6-methylpyridin-2-yl)-N-ethylethan-1-amine (C98)

SCHEME C18

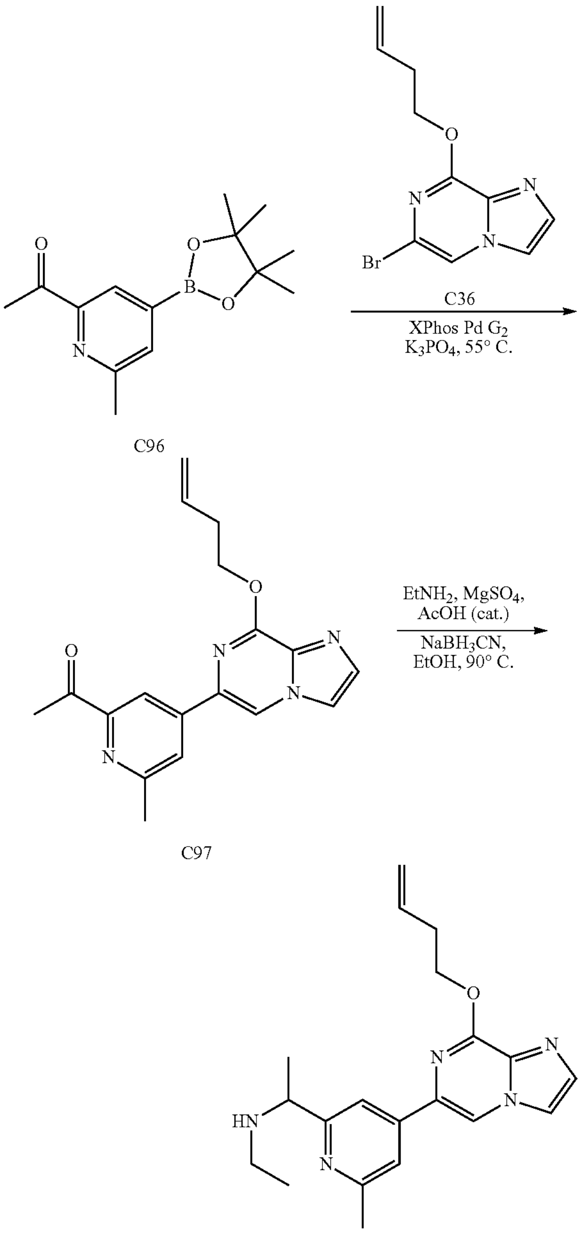

Step 1: 1-(4-(8-(but-3-en-1-yloxy)imidazo[1,2-a]pyrazin-6-yl)-6-methylpyridin-2-yl)ethan-1-one (C97)

A solution of 1-(6-methyl-4-(4,4,5,5-tetramethyl-1,3,2-dioxaborolan-2-yl)pyridin-2-yl)ethan-1-one (C96, 501 mg, 1.919 mmol), 6-bromo-8-(but-3-en-1-yloxy)imidazo[1,2-a]pyrazine (C36, 633 mg, 2.360 mmol), and potassium phosphate (3.84 mL, 3.84 mmol) (1M aq.) in dioxane (19 mL) was degassed with nitrogen. X-Phos Pd G2 (151 mg, 0.192 mmol) was added and the reaction was heated at 55° C. for 1.5 h. The reaction was poured into water (50 mL) and extracted with EtOAc (3×25 mL). The combined organic layers were dried ($Na_2SO_4$), filtered and concentrated. The crude material was purified by flash silica chromatography (0-100% EtOAc:EtOH 3:1 mix in hexanes) to afford 1-(4-(8-(but-3-en-1-yloxy)imidazo[1,2-a]pyrazin-6-yl)-6-methylpyridin-2-yl)ethan-1-one (C97). LC-MS: 323.2 (M+1).

Step 2: 1-(4-(8-(but-3-en-1-yloxy)imidazo[1,2-a]pyrazin-6-yl)-6-methylpyridin-2-yl)-N-ethylethan-1-amine (C98)

1-(4-(8-(but-3-en-1-yloxy)imidazo[1,2-a]pyrazin-6-yl)-6-methylpyridin-2-yl)ethan-1-one (C97, 480 mg, 1.489 mmol) and $MgSO_4$ (358 mg, 2.98 mmol) were combined in EtOH (7445 μL) in a microwave vial. To this were added ethanamine (3722 μL, 7.44 mmol) (2M in THF), AcOH (426 μL, 7.44 mmol), then sodium cyanoborohydride (187 mg, 2.98 mmol). The vial was capped then stirred at ambient temperature for 7 h. Additional sodium cyanoborohydride (40 mg) was added after 3 h. The reaction was filtered through Celite, rinsed with EtOH (2×10 mL), and concentrated. The crude material was purified by flash silica chromatography (0-20% $NH_4OH$/MeOH 100:1 mix in DCM) to afford 1-(4-(8-(but-3-en-1-yloxy)imidazo[1,2-a]pyrazin-6-yl)-6-methylpyridin-2-yl)-N-ethylethan-1-amine (C98). LC-MS: 352.3 (M+1).

Intermediate C110

1-(4-(7-(but-3-en-1-yloxy)pyrazolo[1,5-c]pyrimidin-5-yl)-5-methoxypyridin-2-yl)-N-ethylethan-1-amine (C110)

SCHEME C19

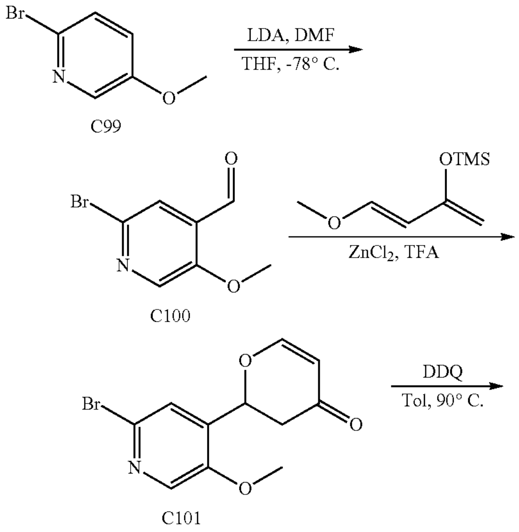

-continued

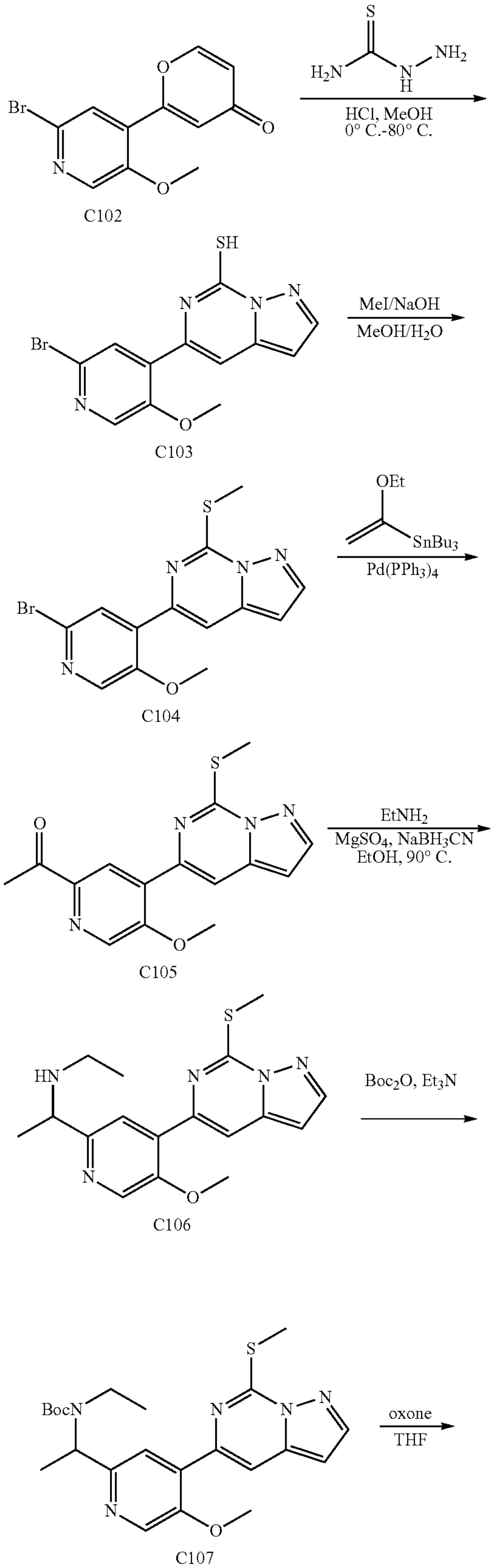

C102

C103

C104

C105

C106

C107

-continued

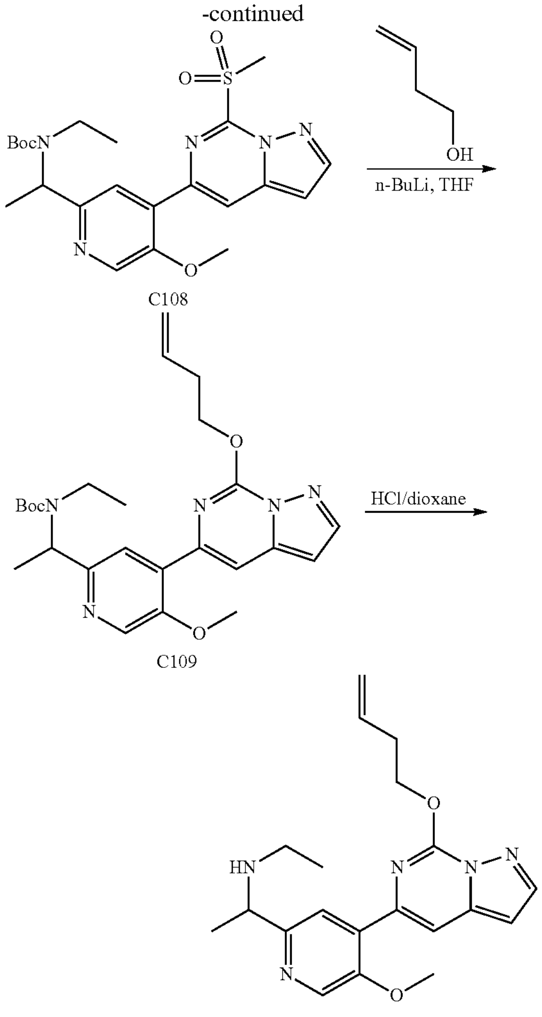

C108

C109

C110

Step 1: 2-bromo-5-methoxyisonicotinaldehyde (C100)

To a solution of 2-bromo-5-methoxypyridine (C99, 24 g, 128 mmol) (20 mL) was added LDA (77 mL, 153 mmol) (2M in THF) at −78° C. and the reaction was stirred at −78° C. for 30 min, and then DMF (10.87 mL, 140 mmol) was added to the above solution at −78° C. The reaction was stirred at −78° C. for 1 h. TLC showed complete conversion. The reaction was quenched with water (300 mL) and extracted with EtOAc (3×100 mL). The combine organic layers were washed with brine (100 mL), dried ($Na_2SO_4$), filtered and concentrated. The crude material was purified by flash silica chromatography (7-10% EtOAc in petroleum ether gradient) to afford 2-bromo-5-methoxyisonicotinaldehyde (C100). $^1H$ NMR: (400 MHz, $CDCl_3$) δ 10.41 (s, 1H), 8.28 (s, 1H), 7.73 (s, 1H), 4.04 (s, 3H).

Step 2: 2-(2-bromo-5-methoxypyridin-4-yl)-2,3-dihydro-4H-pyran-4-one (3.101)

A solution of zinc chloride (1.451 mL, 2.90 mmol) (2 M in 2-Me-THF) was added to a solution of (E)-((4-methoxybuta-1,3-dien-2-yl)oxy)trimethylsilane (29.0 mL, 29.0 mmol) (1 M in toluene) and 2-bromo-5-methoxyisonicotinaldehyde (C100, 8.15 g, 37.7 mmol) at 20° C. After stirring for 1 h, water (25 mL) and TFA (2.5 mL) were added, and the reaction was stirred vigorously for 3 h. TLC showed formation of new spots. The reaction was poured into water (100 mL) and extracted with EtOAc (3×50 mL). The combined organic layers were washed with brine (50 mL), dried ($Na_2SO_4$), filtered and concentrated. The crude material was purified by flash silica chromatography (0-20% EtOAc in petroleum ether gradient) to afford 2-(2-bromo-5-methoxypyridin-4-yl)-2,3-dihydro-4H-pyran-4-one (C101). LC-MS: 284.1. 286.1 (M+1).

Step 3: 2-(2-bromo-5-methoxypyridin-4-yl)-4H-pyran-4-one (C102)

To a solution of 2-(2-bromo-5-methoxypyridin-4-yl)-2,3-dihydro-4H-pyran-4-one (C101, 6 g, 21.12 mmol) in toluene (70 mL) was added DDQ (9.59 g, 42.2 mmol). The reaction was stirred at 90° C. for 12 h. TLC showed consumption of the starting material and formation of new spots. The reaction mixture was poured into DCM (300 mL) and quenched with sat. aq. $NaHCO_3$(100 mL). The organic layer was washed with brine (100 mL), dried ($Na_2SO_4$), filtered and concentrated. The crude material was suspended in petroleum ether (50 mL) and stirred for 30 min. The mixture was filtered to afford 2-(2-bromo-5-methoxypyridin-4-yl)-4H-pyran-4-one (C102). LC-MS: 281.9, 283.9 (M+1).

Step 4: 5-(2-bromo-5-methoxypyridin-4-yl)pyrazolo[1,5-c]pyrimidine-7-thiol (C103)

To a mixture of 2-(2-bromo-5-methoxypyridin-4-yl)-4H-pyran-4-one (C102, 500 mg, 1.772 mmol) and hydrazinecarbothioamide (242 mg, 2.66 mmol) in MeOH (20 mL) was added conc. HCl (0.4 mL) at 0° C. under nitrogen. The reaction was stirred at 0° C. for 15 min, at 20° C. for 15 min and at 80° C. for 2 h. LCMS showed formation of the desired product mass. The resulting solution of 5-(2-bromo-5-methoxypyridin-4-yl)pyrazolo[1,5-c]pyrimidine-7-thiol (C103) was carried forward without purification. LC-MS: 336.9. 338.9 (M+1).

Step 5: 5-(2-bromo-5-methoxypyridin-4-yl)-7-(methylthio)pyrazolo[1,5-c]pyrimidine (C104)

To a mixture of 5-(2-bromo-5-methoxypyridin-4-yl)pyrazolo[1,5-c]pyrimidine-7-thiol (C103, 204 mL, 17.73 mmol) (0.087M in MeOH) and sodium hydroxide (3.55 g, 89 mmol) in $H_2O$(100 mL) was added iodomethane (5.54 mL, 89 mmol) at 0° C. The reaction was stirred at 20° C. for 15 h. LCMS showed formation of the desired product mass. The reaction was poured into water (300 mL), extracted with EtOAc (3×150 mL). The combined organic layers were washed with brine (100 mL), dried ($Na_2SO_4$), filtered and concentrated. The crude material was purified by flash silica chromatography (30% EtOAc in petroleum ether) to afford 5-(2-bromo-5-methoxypyridin-4-yl)-7-(methylthio)pyrazolo[1,5-c]pyrimidine (C104). LC-MS: 351.0, 353.0 (M+1).

Step 6: 1-(5-methoxy-4-(7-(methylthio)pyrazolo[1,5-c]pyrimidin-5-yl)pyridin-2-yl)ethan-1-one To a solution of 5-(2-bromo-5-methoxypyridin-4-yl)-7-(methylthio)pyrazolo[1,5-c]pyrimidine (C104, 1.7 g, 4.84 mmol) in dioxane (20 mL) were added tributyl(1-ethoxyvinyl)-stannane (2.098 g, 5.81 mmol) and $Pd(Ph_3P)_4$ (0.559 g, 0.484 mmol). The reaction mixture was stirred at 110° C. for 12 h. The reaction was cooled to ambient temperature. 1M aq. HCl (5 mL) was added and the reaction was stirred at 20° C. for 3 h. LCMS showed formation of the desired product mass. The reaction was poured into water (30 mL) and extracted with EtOAc (3×20 mL). The combined organic layers were washed with brine (10 mL), dried ($Na_2SO_4$), filtered and concentrated. The crude material was purified by flash silica chromatography (0-22% EtOAc in petroleum ether gradient) to give 1-(5-methoxy-4-(7-(methylthio)pyrazolo[1,5-c]pyrimidin-5-yl)pyridin-2-yl)ethan-1-one (C105). LC-MS: 315.2 (M+1).

Step 7: N-ethyl-1-(5-methoxy-4-(7-(methylthio)pyrazolo[1,5-c]pyrimidin-5-yl)pyridin-2-yl)ethan-1-amine (C106)

To a solution of 1-(5-methoxy-4-(7-(methylthio)pyrazolo[1,5-c]pyrimidin-5-yl)pyridin-2-yl)ethan-1-one (C105, 600 mg, 1.909 mmol) in EtOH (10 mL) were added ethanamine (172 mg, 3.82 mmol), AcOH (0.022 mL, 0.382 mmol), $MgSO_4$ (1149 mg, 9.54 mmol) and $NaBH_3CN$ (240 mg, 3.82 mmol). The reaction was stirred at 90° C. for 5 h. LCMS showed complete conversion. The reaction was poured into water (30 mL) and extracted with EtOAc (3×20 mL). The combined organic layers were washed with brine (10 mL), dried ($Na_2SO_4$), filtered and concentrated to afford N-ethyl-1-(5-methoxy-4-(7-(methylthio)pyrazolo[1,5-c]pyrimidin-5-yl)pyridin-2-yl)ethan-1-amine (C106), which was carried forward without purification. LC-MS: 344.2 (M+1).

Step 8: tert-butyl ethyl(1-(5-methoxy-4-(7-(methylthio)pyrazolo[1,5-c]pyrimidin-5-yl)pyridin-2-yl)ethyl)carbamate (C107)

To a solution of N-ethyl-(5-methoxy-4-(7-(methylthio)pyrazolo[1,5-c]pyrimidin-5-yl)pyridin-2-yl)ethan-1-amine (C106, 650 mg, 1.893 mmol) in DCM (10 mL) were added $Et_3N$ (0.791 mL, 5.68 mmol) and Boc anhydride (0.527 mL, 2.271 mmol). The reaction was stirred at ambient temperature for 15 h. LCMS showed complete conversion. The reaction was poured into water (10 mL) and extracted with DCM (3×20 mL). The combined organic layers were washed with brine (10 mL), dried ($Na_2SO_4$), filtered and concentrated. The crude material was purified by flash silica chromatography (0-35% EtOAc in petroleum ether gradient) to give tert-butyl ethyl(1-(5-methoxy-4-(7-(methylthio)pyrazolo[1,5-c]pyrimidin-5-yl)pyridin-2-yl)ethyl)carbamate (C107). LC-MS: 444.2 (M+1).

Step 9: tert-butyl ethyl(1-(5-methoxy-4-(7-(methylsulfonyl)pyrazolo[1,5-c]pyrimidin-5-yl)pyridin-2-yl)ethyl)carbamate (C108)

To a solution of tert-butyl ethyl(1-(5-methoxy-4-(7-(methylthio)pyrazolo[1,5-c]pyrimidin-5-yl)pyridin-2-yl)ethyl)carbamate (C107, 500 mg, 1.127 mmol) in THF (5 mL) was added oxone monopersulfate (1.386 g, 2.254 mmol) and the reaction was stirred at ambient temperature for 12 h. LCMS showed formation of the desired product. The reaction was filtered and concentrated. The crude material was purified by flash silica chromatography (0-100% EtOAc in petroleum ether gradient) to give tert-butyl ethyl(1-(5-methoxy-4-(7-(methylsulfonyl)pyrazolo[1,5-c]pyrimidin-5-yl)pyridin-2-yl)ethyl)carbamate (C108). LC-MS: 476.2 (M+1).

Step 10: tert-butyl (1-(4-(7-(but-3-en-1-yloxy)pyrazolo[1,5-c]pyrimidin-5-yl)-5-methoxypyridin-2-yl)ethyl)(ethyl)carbamate (C109)

To a solution of but-3-en-1-ol (334 mg, 4.63 mmol) in THF (3 mL) was added n-BuLi (0.370 mL, 0.925 mmol) (2.5M in hexanes) and tert-butyl ethyl(1-(5-methoxy-4-(7-(methylsulfonyl)pyrazolo[1,5-c]pyrimidin-5-yl)pyridin-2-yl)ethyl)carbamate (C108, 220 mg, 0.463 mmol) at 0° C. The reaction was stirred at 0° C. for 1 h. LCMS showed complete conversion. The reaction was poured into water (10 mL) and extracted with EtOAc (3x20 mL). The combined organic layers were washed with brine (10 mL), dried ($Na_2SO_4$), filtered and concentrated to afford tert-butyl (1-(4-(7-(but-3-en-1-yloxy)pyrazolo[1,5-c]pyrimidin-5-yl)-5-methoxypyridin-2-yl)ethyl)(ethyl)carbamate (C109), which was carried forward without purification. LC-MS: 468.2 (M+1).

Step 11: 1-(4-(7-(but-3-en-1-yloxy)pyrazolo[1,5-c]pyrimidin-5-yl)-5-methoxypyridin-2-yl)-N-ethylethan-1-amine (C100)

To a solution of tert-butyl (1-(4-(7-(but-3-en-1-yloxy)pyrazolo[1,5-c]pyrimidin-5-yl)-5-methoxypyridin-2-yl)ethyl)(ethyl)carbamate (C109, 180 mg, 0.385 mmol) in dioxane (2 mL) was added HCl (2 mL) (4M in MeOH) and the reaction was stirred at 20° C. for 2 h. LCMS showed complete conversion. The reaction was concentrated to afford 1-(4-(7-(but-3-en-1-yloxy)pyrazolo[1,5-c]pyrimidin-5-yl)-5-methoxypyridin-2-yl)-N-ethylethan-1-amine (C110) as an HCl salt, which was carried forward without purification. LC-MS: 368.2 (M+1).

Intermediate C112

N-((5-(8-(but-3-en-1-yloxy)imidazo[1,2-a]pyrazin-6-yl)-6-methoxypyridin-3-yl)methyl)ethanamine (C112)

SCHEME C20

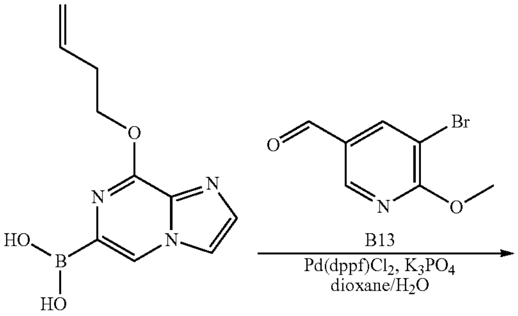

C37

-continued

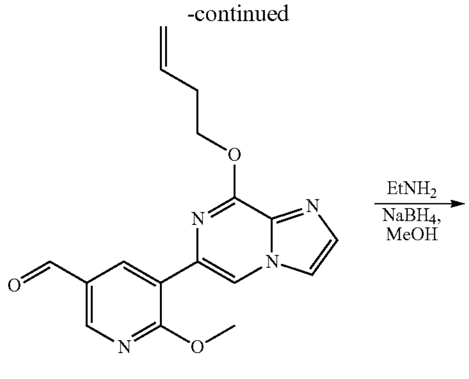

C111

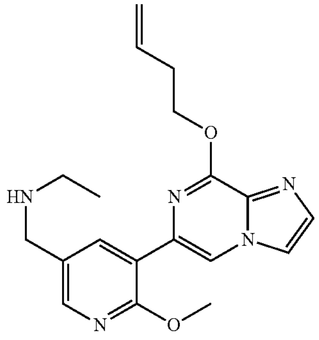

C112

Step 1: 5-(8-(but-3-en-1-yloxy)imidazo[1,2-a]pyrazin-6-yl)-6-methoxynicotinaldehyde (C111)

To a solution of (8-(but-3-en-1-yloxy)imidazo[1,2-a]pyrazin-6-yl)boronic acid (C37, 435 mg, 1.867 mmol) in dioxane (10 mL) and water (2 mL) were added 5-bromo-6-methoxynicotinaldehyde (B13, 403 mg, 1.867 mmol), K2C03 (516 mg, 3.73 mmol) and Pd(dppf)$Cl_2$ (137 mg, 0.187 mmol). The reaction was stirred at 90° C. overnight. LCMS showed formation of the desired product mass. The reaction was poured into water (20 mL) and extracted with EtOAc (3x10 mL). The combined organic layers were washed with brine (20 mL), dried ($Na_2SO_4$), filtered and concentrated. The crude material was purified by flash silica chromatography (70% EtOAc in petroleum ether) to afford 5-(8-(but-3-en-1-yloxy)imidazo[1,2-a]pyrazin-6-yl)-6-methoxynicotinaldehyde (C111). LC-MS: 325.1 (M+1).

Step 2: N-((5-(8-(but-3-en-1-yloxy)imidazo[1,2-a]pyrazin-6-yl)-6-methoxypyridin-3-yl)methyl)ethanamine (C112)

A solution of 5-(8-(but-3-en-1-yloxy)imidazo[1,2-a]pyrazin-6-yl)-6-methoxynicotinaldehyde (C111, 320 mg, 0.987 mmol) in ethanamine (7 mL, 0.987 mmol) was stirred at ambient temperature for 3 h. The reaction was concentrated to give (E)-1-(5-(8-(but-3-en-1-yloxy) imidazo [1,2-a]pyrazin-6-yl)-6-methoxypyridin-3-yl)-N-ethylmethanimine, which was carried forward without purification. To a solution of (E)-1-(5-(8-(but-3-en-1-yloxy) imidazo [1,2-a]pyrazin-6-yl)-6-methoxypyridin-3-yl)-N-ethylmethanimine (347 mg, 0.987 mmol) in MeOH (7 mL) was added $NaBH_4$ (37.4 mg, 0.987 mmol), and the reaction was stirred at ambient temperature for 30 min. LCMS showed formation of the desired product mass. The reaction was diluted with water (20 mL) and extracted EtOAc (3x10 mL). The combined organic layers were washed with brine (20 mL), dried ($Na_2SO_4$), filtered and concentrated to afford N-((5-(8-(but-3-en-1-yloxy)imidazo[1,2-a]pyrazin-6-yl)-6-methoxypyridin-3-yl)methyl)ethanamine (C112), which was carried forward without purification.

LC-MS: 354.2 (M+1).

Intermediate C121

1-(5-(8-(But-3-en-1-yloxy)imidazo[1,2-a]pyrazin-6-yl)oxazol-2-yl)-N-ethylethan-1-amine

SCHEME C21

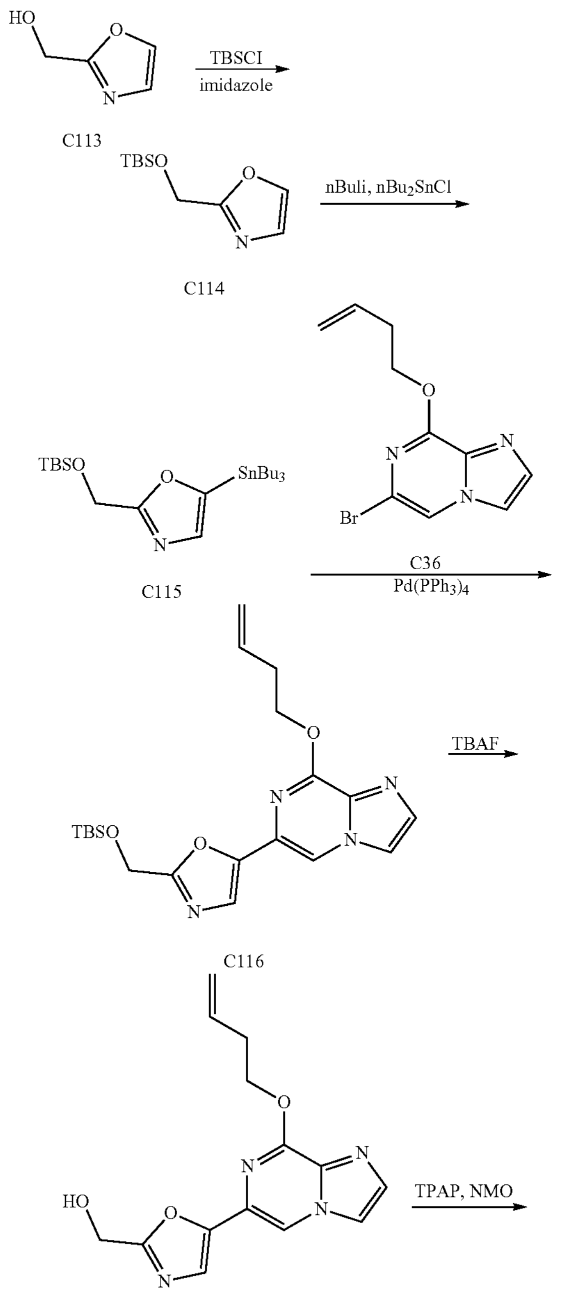

C113

C114

C115

C116

C117

-continued

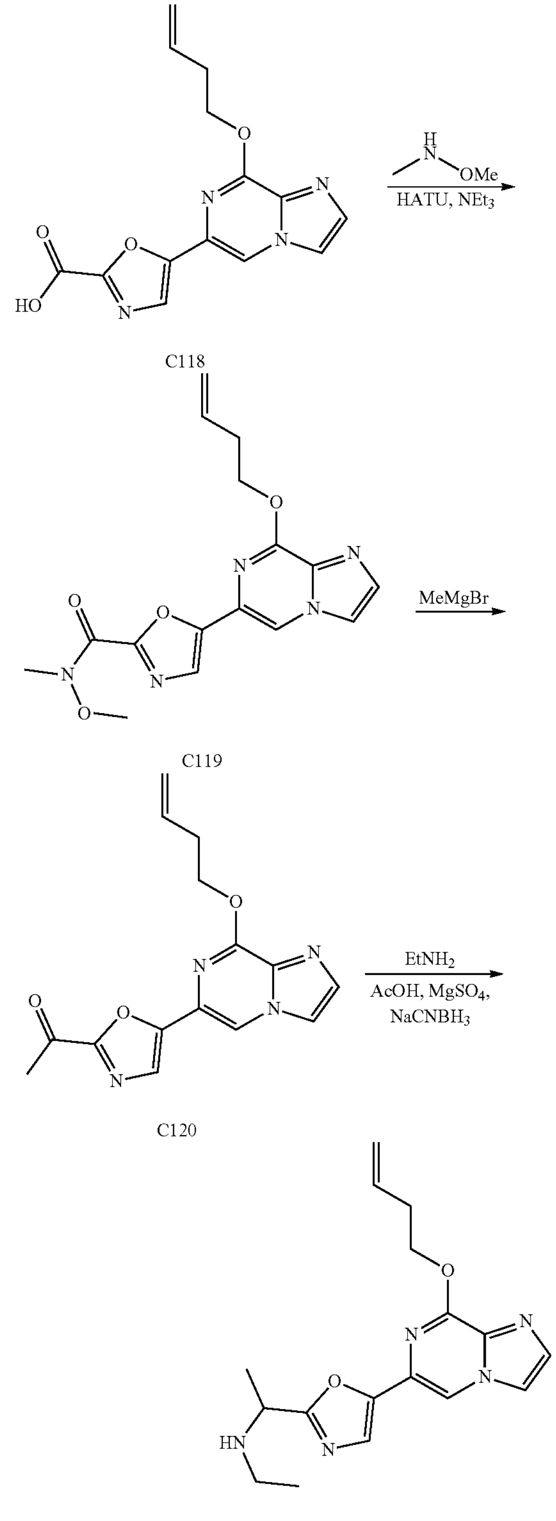

C118

C119

C120

C121

Step 1: 2-(((Tert-butyldimethylsilyl)oxy)methyl)oxazole (C114)

A solution of oxazol-2-ylmethanol (C113, 250 mg, 2.52 mmol) in DCM (5 mL) was cooled to 0° C. To this was added imidazole (258 mg, 3.78 mmol) then a solution of TBSCl (494 mg, 3.28 mmol) in DCM (4 mL). The reaction was allowed to warm as the bath warmed to ambient temperature overnight. The reaction was concentrated. The crude material was purified by flash silica chromatography (0-25% EtOAc in heptane gradient) to afford 2-(((Tert-butyldimethylsilyl)oxy)methyl)oxazole (C114). LC-MS: 214.0 (M+1). $^1$H NMR: (500 MHz, $CDCl_3$) δ 7.63 (s, 1H), 7.08 (s, 1H), 4.76 (s, 2H), 0.91 (d, J=2.7 Hz, 9H), 0.11 (d, J=2.8 Hz, 6H).

Step 2: 2-(((Tert-butyldimethylsilyl)oxy)methyl)-5-(tributylstannyl)oxazole (C115)

A solution of 2-(((tert-butyldimethylsilyl)oxy)methyl) oxazole (C114, 200 mg, 0.937 mmol) in THF (5 mL) was cooled to −78° C. To this was added n-BuLi (0.56 mL, 1.400 mmol) in (2.5M hexanes) and the reaction was allowed to stir at −78° C. for 90 min. n-$Bu_3SnCl$ (0.63 mL, 2.323 mmol) was then added slowly. The reaction was allowed to warm as the bath warmed to ambient temperature overnight. The reaction was diluted with water then extracted with DCM. The combined organic layers were dried ($MgSO_4$), filtered and concentrated. The crude material was purified by flash silica chromatography (0-25% EtOAc in heptane gradient) to afford 2-(((Tert-butyldimethylsilyl)oxy)methyl)-5-(tributylstannyl)oxazole (C115). $^1$H NMR: (500 MHz, $CDCl_3$) δ 7.08 (s, 1H), 4.80 (s, 2H), 1.58-1.44 (m, 6H), 1.33 (h, J=7.3 Hz, 6H), 1.14-1.07 (m, 6H), 0.96-0.86 (m, 18H), 0.09 (s, 6H).

Step 3: 5-(8-(But-3-en-1-yloxy)imidazo[1,2-a]pyrazin-6-yl)-2-(((tert-butyldimethylsilyl)oxy)methyl)oxazole (C116)

6-Bromo-8-(but-3-en-1-yloxy)imidazo[1,2-a]pyrazine (C37, 155 mg, 0.578 mmol), 2-(((tert-butyldimethylsilyl)oxy)methyl)-5-(tributylstannyl)oxazole (C115, 343 mg, 0.683 mmol), and $Pd(Ph_3P)_4$ (34 mg, 0.029 mmol) were combined in a screw cap vial and dioxane (3 mL) was added. Nitrogen was bubbled through the mixture for 1 min. The vial was capped and heated to 100° C. overnight. The reaction was cooled to ambient temperature then concentrated. The crude material was purified by flash silica chromatography (0-50% EtOAc in heptane gradient) to afford 5-(8-(But-3-en-1-yloxy)imidazo[1,2-a]pyrazin-6-yl)-2-(((tert-butyldimethylsilyl)oxy)methyl)oxazole (C116). LC-MS: 401.2 (M+1).

Step 4: (5-(8-(But-3-en-1-yloxy)imidazo[1,2-a]pyrazin-6-yl)oxazol-2-yl)methanol (C117)

To a solution of 5-(8-(but-3-en-1-yloxy)imidazo[1,2-a]pyrazin-6-yl)-2-(((tert-butyldimethylsilyl)oxy)methyl)oxazole (C116, 219 mg, 0.547 mmol) in THF (3 mL) was added TBAF (1.640 mL, 1.640 mmol) (1M in THF) at ambient temperature. After 1 h, five drops of water were added then the reaction was concentrated. The crude material was purified by flash silica chromatography (0-100% EtOAc:EtOH 3:1 mix in heptane gradient) to afford (5-(8-(But-3-en-1-yloxy)imidazo[1,2-a]pyrazin-6-yl)oxazol-2-yl)methanol (C117). LC-MS: 287.1 (M+1).

Step 5: 5-(8-(But-3-en-1-yloxy)imidazo[1,2-a]pyrazin-6-yl)oxazole-2-carboxylic acid (C118)

(5-(8-(But-3-en-1-yloxy)imidazo[1,2-a]pyrazin-6-yl)oxazol-2-yl)methanol (C117, 143 mg, 0.499 mmol) was taken up in ACN (5 mL). To this was added 4-methylmorpholine N-oxide monohydrate (675 mg, 4.99 mmol) then TPAP (18 mg, 0.051 mmol) at ambient temperature. After 3 h the reaction was diluted with sat. aq. $NH_4Cl$ then extracted with EtOAc. The combined organic layers were filtered through a pad of Celite washing with EtOAc then the filtrate was concentrated. The aqueous layer was acidified to pH 4 then extracted again with EtOAc. The combined organic layers were filtered through a pad of Celite washing with EtOAc then the filtrate was concentrated. Product still in aqueous phase. The organic and aqueous phases were concentrated together. The crude material was purified reverse phase HPLC (0-50% ACN in water, with 0.1% TFA as modifier) to afford 5-(8-(But-3-en-1-yloxy)imidazo[1,2-a]pyrazin-6-yl)oxazole-2-carboxylic acid (C118). LC-MS: 301.0 (M+1).

Step 6: 5-(8-(But-3-en-1-yloxy)imidazo[1,2-a]pyrazin-6-yl)-N-methoxy-N-methyloxazole-2-carboxamide (C119)

5-(8-(But-3-en-1-yloxy)imidazo[1,2-a]pyrazin-6-yl)oxazole-2-carboxylic acid (C118, 114 mg, 0.380 mmol), N,O-dimethylhydroxylamine hydrochloride (75 mg, 0.769 mmol), and HATU (289 mg, 0.759 mmol) were combined in DMF (3 mL). TEA (0.22 mL, 1.578 mmol) was added to the reaction at ambient temperature and the reaction was stirred for 2 h. The reaction was then diluted with water then extracted with EtOAc (3 x). The combined organic layers were dried ($MgSO_4$), filtered and concentrated. The crude material was purified by flash silica chromatography (0-100% EtOAc in heptane gradient) to afford 5-(8-(But-3-en-1-yloxy)imidazo[1,2-a]pyrazin-6-yl)-N-methoxy-N-methyloxazole-2-carboxamide (C119). LC-MS: 344.1 (M+1).

Step 7: 1-(5-(8-(But-3-en-1-yloxy)imidazo[1,2-a]pyrazin-6-yl)oxazol-2-yl)ethan-1-one (C120)

A solution of 5-(8-(but-3-en-1-yloxy)imidazo[1,2-a]pyrazin-6-yl)-N-methoxy-N-methyloxazole-2-carboxamide (C119, 150 mg, 0.437 mmol) in THF (3 mL) was cooled to 0° C. To this was added MeMgBr (0.3 mL, 0.900 mmol) (3M in $Et_2O$) slowly. After 1.5 h the reaction was diluted with sat. aq. $NH_4Cl$ then warmed to ambient temperature and extracted with EtOAc. The combined organic layers were dried ($MgSO_4$), filtered and concentrated to afford 1-(5-(8-(But-3-en-1-yloxy)imidazo[1,2-a]pyrazin-6-yl)oxazol-2-yl)ethan-1-one (C120), which was carried forward without purification. LC-MS: 299.1 (M+1).

Step 8: 1-(5-(8-(But-3-en-1-yloxy)imidazo[1,2-a]pyrazin-6-yl)oxazol-2-yl)-N-ethylethan-1-amine (C121)

A solution of crude 1-(5-(8-(but-3-en-1-yloxy)imidazo[1,2-a]pyrazin-6-yl)oxazol-2-yl)ethan-1-one (C120, 91 mg, 0.305 mmol) in EtOH (2 mL) was transferred to a microwave vial. To this was added ethanamine (0.8 mL, 1.600 mmol) (2M in THF), AcOH (0.095 mL, 1.659 mmol), $MgSO_4$ (74 mg, 0.615 mmol), then sodium cyanoborohydride (39 mg, 0.621 mmol). The vial was sealed and heated to 80° C. by conventional heating overnight. The reaction was cooled to ambient temperature then diluted with EtOH and filtered through a pad of Celite washing with EtOH. The filtrate was concentrated. The crude material was purified by preparative reverse phase HPLC (5-50% ACN in water, with 0.1% TFA as modifier) to afford 1-(5-(8-(But-3-en-1-yloxy)

imidazo[1,2-a]pyrazin-6-yl)oxazol-2-yl)-N-ethylethan-1-amine (C121). LC-MS: 328.2 (M+1).

Intermediates C125 and C127

SCHEME C22

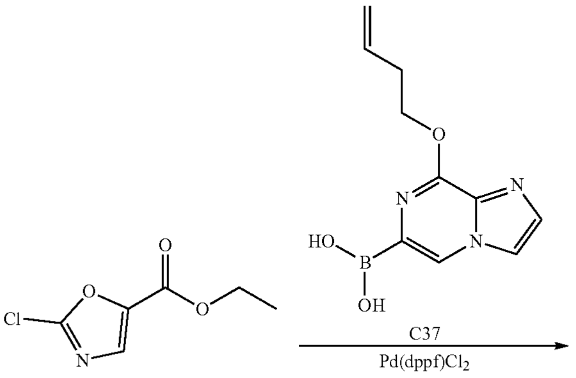

C122

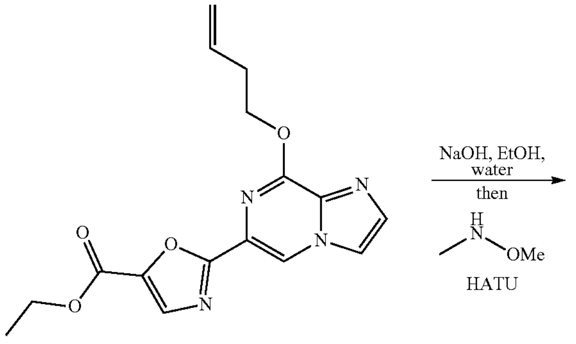

C123

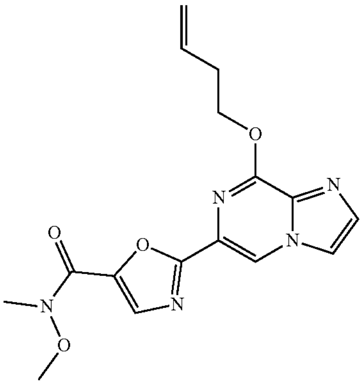

C124

Step 1: Ethyl 2-(8-(but-3-en-1-yloxy)imidazo[1,2-a]pyrazin-6-yl)oxazole-5-carboxylate (C123)

Ethyl 2-chlorooxazole-5-carboxylate (C122, 200 mg, 1.139 mmol), (8-(but-3-en-1-yloxy)imidazo[1,2-a]pyrazin-6-yl)boronic acid, TFA (3.37, 395 mg, 1.139 mmol), and $PdCl_2$(dppf) (83 mg, 0.114 mmol) were combined in a microwave vial. To this was added toluene (5 mL) and 2M aq. $K2CO_3$ (1.8 mL, 3.60 mmol). The vial was sealed then degassed with nitrogen. The gas inlet was removed then the mixture was heated to 90° C. overnight. The reaction was cooled to ambient temperature then diluted with EtOAc and filtered through a pad of Celite washing with EtOAc. The filtrate was concentrated. The crude material was purified by flash silica chromatography (0-100% EtOAc in heptane gradient) to afford ethyl 2-(8-(but-3-en-1-yloxy)imidazo[1,2-a]pyrazin-6-yl)oxazole-5-carboxylate (C123). LC-MS: 329.1 (M+1).

Step 2: 2-(8-(But-3-en-1-yloxy)imidazo[1,2-a]pyrazin-6-yl)-N-methoxy-N-methyloxazole-5-carboxamide (C124)

To a suspension of ethyl 2-(8-(but-3-en-1-yloxy)imidazo[1,2-a]pyrazin-6-yl)oxazole-5-carboxylate (C123, 188 mg, 0.573 mmol) in EtOH (5 mL) was added 2M NaOH (0.86 mL, 1.720 mmol) at ambient temperature. The suspension gradually became a solution over 15 min. After stirring overnight 1M aq. HCl (1.72 mL) was added the reaction was concentrated to give crude 2-(8-(but-3-en-1-yloxy)imidazo[1,2-a]pyrazin-6-yl)oxazole-5-carboxylic acid. LC-MS: 301.0 (M+1).

Crude 2-(8-(but-3-en-1-yloxy)imidazo[1,2-a]pyrazin-6-yl)oxazole-5-carboxylic acid (172 mg, 0.573 mmol) was taken up in DMF (5 mL). To this was added N,O-dimethylhydroxylamine hydrochloride (112 mg, 1.146 mmol), HATU (436 mg, 1.146 mmol), then TEA (0.32 mL, 2.296 mmol) at ambient temperature. After 2 h the reaction was diluted with water and extracted with EtOAc. The combined organic layers were washed with water and brine then dried ($MgSO_4$), filtered and concentrated. The crude material was purified by flash silica chromatography (0-100% EtOAc: EtOH 3:1 mix in heptane) to afford 2-(8-(But-3-en-1-yloxy)imidazo[1,2-a]pyrazin-6-yl)-N-methoxy-N-methyloxazole-5-carboxamide (C124). LC-MS: 344.1 (M+1).

The following intermediates in Table C10 were synthesized in an analogous manner of that described in Scheme C21 and used to synthesize Intermediate C121 from the appropriate Weinreb amides.

TABLE C10
| Weinreb amide | Intermediate | Observed LCMS (M + 1) |
|---|---|---|
| 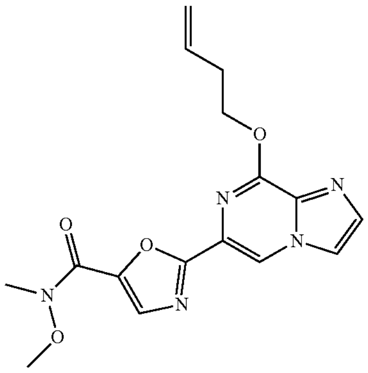 [SMILES: C=CCCOc1nc(-c2ncc(C(=O)N(C)OC)o2)cn2ccnc12]<br>C124 | 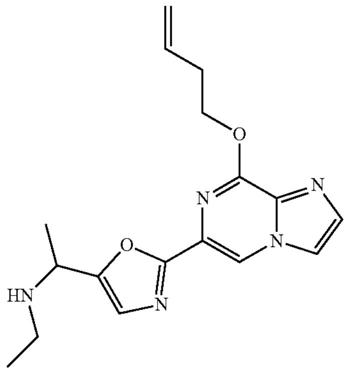 [SMILES: C=CCCOc1nc(-c2ncc(C(C)NCC)o2)cn2ccnc12]<br>C125 | 328.2 |
The following intermediates in Table C11 were synthesized in an analogous manner of that described in Schemes C22 (Steps 1-2) and C21 (last 2 steps) and used to synthesize Intermediate C125 from the appropriate halides.
TABLE C11
| Halide | Intermediate | Observed LCMS (M + 1) |
|---|---|---|
| 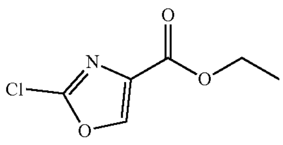<br>C126 | 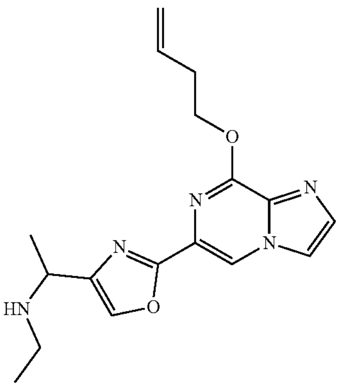<br>C127 | 328.2 |

Intermediate C128

1-(5-(8-(but-3-en-1-yloxy)imidazo[1,2-a]pyrazin-6-yl)thiazol-2-yl)-N-ethylethan-1-amine

SCHEME C23

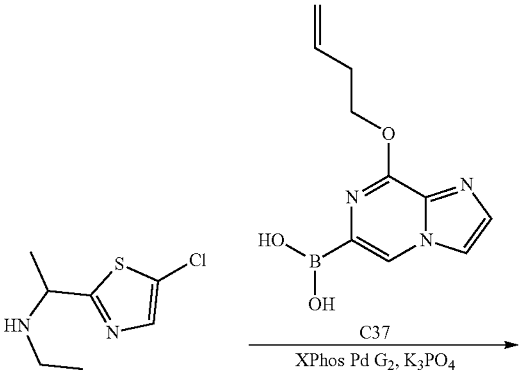

B84

-continued

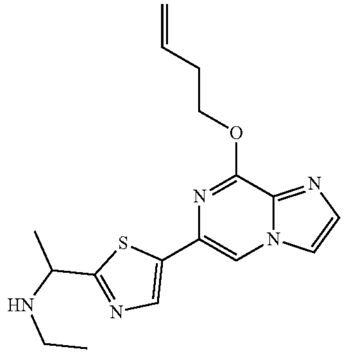

C128

1-(5-chlorothiazol-2-yl)-N-ethylethan-1-amine, TFA (B84, 70 mg, 0.230 mmol), (8-(but-3-en-1-yloxy)imidazo[1,2-a]pyrazin-6-yl)boronic acid, TFA (C37, 159 mg, 0.459 mmol), and $K_3PO_4$ (244 mg, 1.149 mmol) were combined in a screw cap vial. To this were added dioxane (1.5 mL) and water (0.150 mL). Nitrogen was bubbled through the reaction for 1 min and X-Phos Pd G2 (27 mg, 0.034 mmol) was added. The vial was capped then heated to 80° C. overnight. The reaction was cooled to ambient temperature, diluted with EtOAc, filtered through a pad of Celite washing with EtOAc, and concentrated. The crude material was purified by flash silica chromatography (0-100% EtOAc:EtOH 3:1 mix in heptane gradient) to afford 1-(5-(8-(but-3-en-1-yloxy)imidazo[1,2-a]pyrazin-6-yl)thiazol-2-yl)-N-ethylethan-1-amine (C128). LC-MS: 344.2 (M+1).

Intermediate C129

The following Intermediates in Table C12 were synthesized in an analogous manner of that described in Scheme C23 and used to synthesize Intermediate C128 from the appropriate halides.

TABLE C12

| Halide | Intermediate | Observed LCMS (M + 1) |
|---|---|---|
| 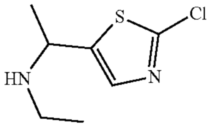 B80 | 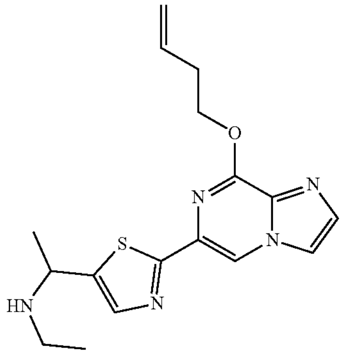 C129 | 344.1 |

Intermediate C134

(R)—N-ethyl-1-(5-methoxy-4-(8-(pent-4-en-1-yl)imidazo[1,2-a]pyrazin-6-yl)pyridin-2-yl)ethan-1-amine (C134)

SCHEME C24

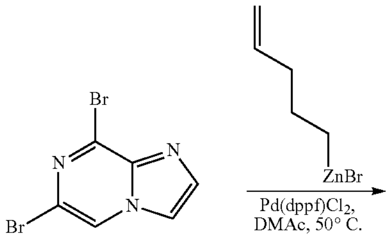

C130

-continued

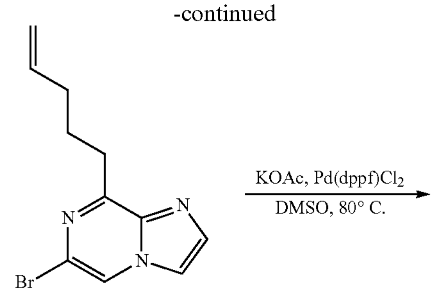

C131

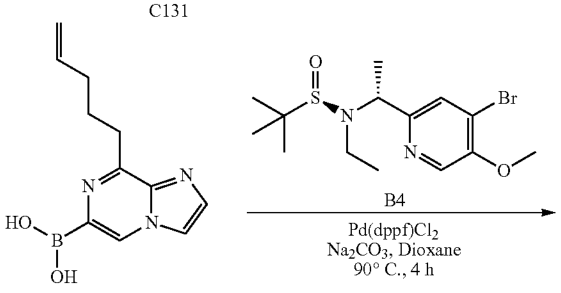

B4

C132

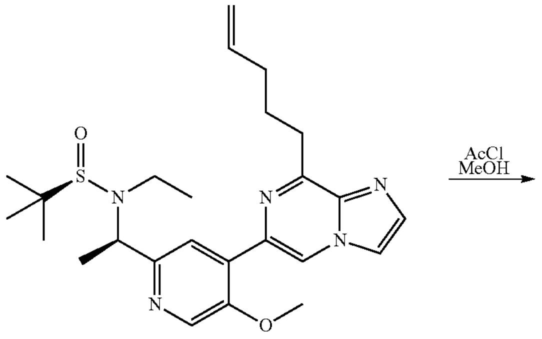

C133

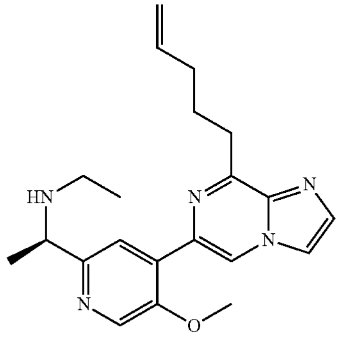

C134

Step 1: 6-bromo-8-(pent-4-en-1-yl)imidazo[1,2-a]pyrazine (C131)

To a solution of 6,8-dibromoimidazo[1,2-a]pyrazine (C130, 2.4 g, 8.67 mmol) in DMA (24 mL) was added pent-4-en-1-ylzinc (II) bromide (17.33 mL, 17.33 mmol) and Pd(dppf)$Cl_2$ (634 mg, 0.867 mmol). The reaction was stirred at 50° C. for 2 h. LCMS showed formation of the desired product mass. The reaction was quenched with water (80 mL) and extracted with EtOAc (3×50 mL). The combined organic layers were dried ($Na_2SO_4$), filtered and concentrated. The crude material was purified by flash silica chromatography (10-50% EtOAc in petroleum ether gradient) to afford 6-bromo-8-(pent-4-en-1-yl)imidazo[1,2-a]pyrazine (C131). LC-MS: 266.1, 268.1 (M+1).

Step 2: (8-(pent-4-en-1-yl)imidazo[1,2-a]pyrazin-6-yl)boronic acid (C132)

To a solution of 6-bromo-8-(pent-4-en-1-yl)imidazo[1,2-a]pyrazine (C131, 500 mg, 1.879 mmol) in DMSO (5 mL) were added 4,4,4',4',5,5,5',5'-octamethyl-2,2'-bi (1,3,2-dioxaborolane) (716 mg, 2.82 mmol), potassium acetate (553 mg, 5.64 mmol) and Pd(dppf)$Cl_2$ (137 mg, 0.188 mmol). The reaction was stirred at 80° C. for 6 h. LCMS showed complete conversion. The solution of (8-(pent-4-en-1-yl)imidazo[1,2-a]pyrazin-6-yl)boronic acid (C132) was carried forward without purification. LC-MS: 232.1 (M+1).

Step 3: (R)—N-ethyl-N—((R)-1-(5-methoxy-4-(8-(pent-4-en-1-yl)imidazo[1,2-a]pyrazin-6-yl)pyridin-2-yl)ethyl)-2-methylpropane-2-sulfinamide (C133)

To a solution of (8-(pent-4-en-1-yl)imidazo[1,2-a]pyrazin-6-yl)boronic acid (C132, 127 mg, 0.550 mmol) in dioxane (3 mL) and water (1 mL) was added (R)—N—((R)-1-(4-bromo-5-methoxypyridin-2-yl)ethyl)-N-ethyl-2-methylpropane-2-sulfinamide (B4, 200 mg, 0.550 mmol), $Na_2CO_3$ (175 mg, 1.651 mmol) and Pd(dppf)$Cl_2$ (40.3 mg, 0.055 mmol). The reaction was stirred at 90° C. for 16 h. LCMS showed formation of the desired product mass. The reaction was poured into water (20 mL) and extracted with EtOAc (3×20 mL). The combined organic layers were washed with brine (20 mL), dried ($Na_2SO_4$), filtered and concentrated. The crude material was purified by flash silica chromatography (60% EtOAc in petroleum ether gradient) to give (R)—N-ethyl-N—((R)-1-(5-methoxy-4-(8-(pent-4-en-1-yl)imidazo[1,2-a]pyrazin-6-yl)pyridin-2-yl)ethyl)-2-methylpropane-2-sulfinamide (C133). LC-MS: 470.2 (M+1).

Step 4: (R)—N-ethyl-1-(5-methoxy-4-(8-(pent-4-en-1-yl)imidazo[1,2-a]pyrazin-6-yl)pyridin-2-yl)ethan-1-amine (C134)

To a solution of (R)—N-ethyl-N—((R)-1-(5-methoxy-4-(8-(pent-4-en-1-yl)imidazo[1,2-a]pyrazin-6-yl)pyridin-2-yl)ethyl)-2-methylpropane-2-sulfinamide (C133, 130 mg, 0.277 mmol) in MeOH (2 mL) was added acetyl chloride (0.079 mL, 1.107 mmol) and the reaction was stirred at ambient temperature for 1 h. LCMS showed formation of the desired product mass. The reaction was concentrated to afford (R)—N-ethyl-1-(5-methoxy-4-(8-(pent-4-en-1-yl)imidazo[1,2-a]pyrazin-6-yl)pyridin-2-yl)ethan-1-amine (C134) as an HCl salt, which was carried forward without purification. LC-MS: 366.2 (M+1).

Intermediate C139

(R)—N-ethyl-1-(5-methoxy-6-(8-(pent-4-en-1-yl)imidazo[1,2-a]pyridin-6-yl)pyridin-2-yl)ethan-1-amine (C139)

SCHEME C25

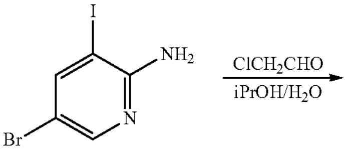

C135

-continued

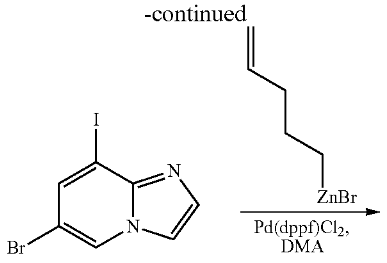

C136

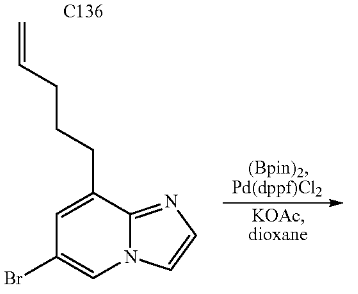

C137

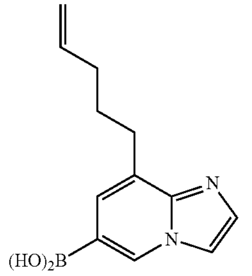

C138

Step 1: 6-bromo-8-iodoimidazo[1,2-a]pyridine (C136)

To a solution of 5-bromo-3-iodopyridin-2-amine (C135, 5 g, 16.73 mmol) in water (60 mL) and 2-propanol (24 mL) was added 2-chloroacetaldehyde (4.14 mL, 25.09 mmol) (40% in water) and the reaction was stirred at 110° C. for 12 h. LCMS showed formation of the desired product mass.

The reaction was poured into water (60 mL), and $Na_2CO_3$ was added to adjust the pH to 8. The reaction was filtered, and the filtrate was extracted with EtOAc (3×25 mL). The combined organic layers were washed with brine (30 mL), dried ($Na_2SO_4$), filtered and concentrated to afford 6-bromo-8-iodoimidazo[1,2-a]pyridine (C136), which was carried forward without purification. LC-MS: 321.3, 323.3 (M+1).

Step 2: 6-bromo-8-(pent-4-en-1-yl)imidazo[1,2-a]pyridine (C137)

To a solution of 6-bromo-8-iodoimidazo[1,2-a]pyridine (C136, 3.8 g, 11.77 mmol) in DMA (84 mL) were added pent-4-en-1-ylzinc(II) bromide (23.53 mL, 23.53 mmol) and $Pd(dppf)Cl_2$ (0.861 g, 1.177 mmol). The reaction was stirred at 50° C. for 4 h. LCMS showed formation of the desired product mass. The reaction was poured into water (30 mL) and extracted with EtOAc (3×20 mL). The combined organic layers were dried ($Na_2SO_4$), filtered and concentrated. The crude material purified by flash silica chromatography (0-30% EtOAc in petroleum ether gradient) to afford 6-bromo-8-(pent-4-en-1-yl)imidazo[1,2-a]pyridine (C137). LC-MS: 264.1, 266.1 (M+H). $^1$H NMR: (400 MHz, $CDCl_3$) δ 8.16-8.11 (m, 1H), 7.59 (s, 1H), 7.52 (s, 1H), 7.02 (s, 1H), 5.84 (tdd, J=6.69, 10.24, 16.96 Hz, 1H), 4.93-5.09 (m, 2H), 3.03-2.95 (m, 2H), 2.17 (q, J=7.17 Hz, 2H), 1.88 (q, J=7.64 Hz, 2H)

Step 3: (8-(pent-4-en-1-yl)imidazo[1,2-a]pyridin-6-yl)boronic acid (C138)

To a solution of 6-bromo-8-(pent-4-en-1-yl)imidazo[1,2-a]pyridine (C137, 100 mg, 0.377 mmol) in dioxane (2 mL) were added 4,4,4',4',5,5,5',5'-octamethyl-2,2'-bi(1,3,2-dioxaborolane) (115 mg, 0.453 mmol), potassium acetate (111 mg, 1.131 mmol) and $Pd(dppf)Cl_2$ (27.6 mg, 0.038 mmol). The reaction was stirred at 85° C. for 12 h. LCMS showed formation of the desired product mass. The solution of boronic acid C138 was carried forward without purification. LC-MS: 231.2 (M+1).

The following intermediates in Table C13 were synthesized in an analogous manner of that described in Scheme C24 and used to synthesize Intermediate C134 from the appropriate boronic esters/acids.

TABLE C13

| Boronic ester/ acid | Core | Intermediate | Observed LCMS (M + 1) |
|---|---|---|---|
| 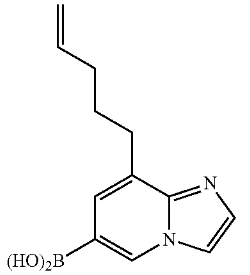 C138 | 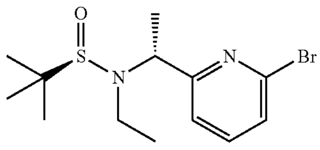 B16 | 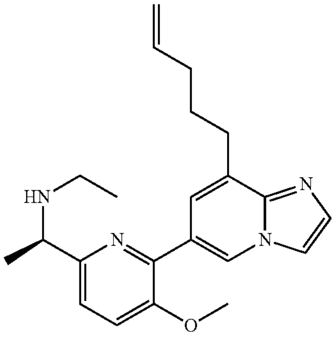 C139 | 365.2 |

Intermediate C141 tert-butyl (R)-(1-(4-(8-chloro-[1,2,4]triazolo[1,5-a]pyrazin-6-yl)-5-methylpyridin-2-yl)ethyl)(ethyl)carbamate (C141)

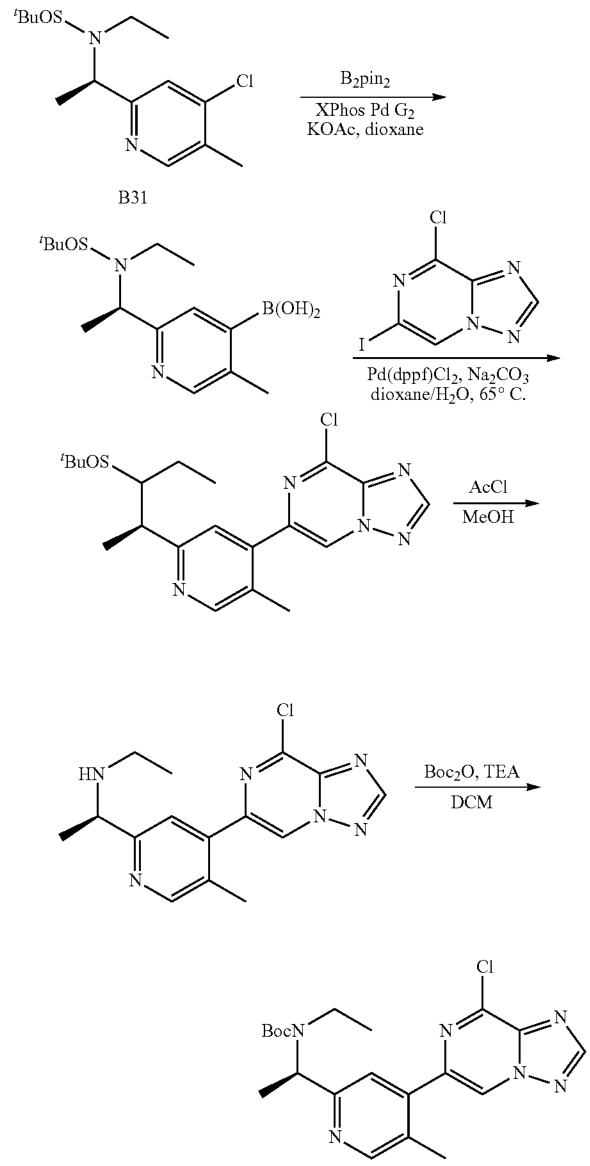

B31

C141

To a solution of B31 (2 g, 6.60 mmol) in Dioxane (20 mL) was added 4,4,4',4',5,5,5',5'-octamethyl-2,2'-bi(1,3,2-dioxaborolane) (2.012 g, 7.92 mmol), potassium acetate (1.296 g, 13.21 mmol) and chloro(2-dicyclohexylphosphino-2',4',6'-triisopropyl-1,1'-biphenyl)[2-(2'-amino-1,1'-biphenyl)]palladium(ii) (0.520 g, 0.660 mmol). The resulting mixture was stirred at 90° C. under N2 protection for 3 h. The mixture of (2-((1R)-1-((tert-butylsulfinyl)(ethyl)amino)ethyl)-5-methylpyridin-4-yl)boronic acid in 20 mL dioxane was used for next steps without purification. LCMS m/z (M+H): 312.2 required, 313.1 found.

To a solution of (2-((1R)-1-((tert-butylsulfinyl)(ethyl)amino)ethyl)-5-methylpyridin-4-yl)boronic acid (20 mL, 6.60 mmol) (0.33 M in Dioxane) was added 8-chloro-6-iodo-[1,2,4]triazolo[1,5-a]pyrazine (1.851 g, 6.60 mmol), $Na_2CO_3$ (1.399 g, 13.20 mmol), $Pd(dppf)Cl_2$ (0.483 g, 0.660 mmol) and Water (4 mL). The resulting mixture was stirred at 65° C. under N2 protection for 4 h. The mixture was poured into water (50 mL), extracted with EtOAc (30 mL*3). The combined organic phases were dried over $Na_2SO_4$, filtered and concentrated. The residue was purified by flash silica gel chromatography (ISCO®; 40 g Sepa-Flash® Silica Flash Column, eluent of 0-100% ethyl acetate/pet. ether gradient) to give N—((R)-1-(4-(8-chloro-[1,2,4]triazolo[1,5-a]pyrazin-6-yl)-5-methylpyridin-2-yl)ethyl)-N-ethyl-2-methylpropane-2-sulfinamide. LCMS m/z (M+H): 420.2 required, 420.8 found.

To a solution of N—((R)-1-(4-(8-chloro-[1,2,4]triazolo[1,5-a]pyrazin-6-yl)-5-methylpyridin-2-yl)ethyl)-N-ethyl-2-methylpropane-2-sulfinamide (500 mg, 1.188 mmol) in MeOH (5 mL) was added AcCl (0.169 mL, 2.376 mmol). The mixture was stirred at 25° C. for 1 h. The reaction mixture was concentrated to give (R)-1-(4-(8-chloro-[1,2,4]triazolo[1,5-a]pyrazin-6-yl)-5-methylpyridin-2-yl)-N-ethylethan-1-amine which was used in next step without purification. LCMS m/z (M+H): 316.7 required, 317.1 found.

To a solution of (R)-1-(4-(8-chloro-[1,2,4]triazolo[1,5-a]pyrazin-6-yl)-5-methylpyridin-2-yl)-N-ethylethan-1-amine (156 mg, 0.492 mmol) in DCM (3 mL) was added TEA (0.343 mL, 2.462 mmol) and $BOC_2O$ (0.229 mL, 0.985 mmol). The mixture was stirred at 30° C. for 16 hours. $H_2O$(5 mL) was added to the mixture, extracted with DCM (10 mL×3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of 100% ethyl acetate) to give tert-butyl (R)-(1-(4-(8-chloro-[1,2,4]triazolo[1,5-a]pyrazin-6-yl)-5-methylpyridin-2-yl)ethyl)(ethyl)carbamate C141. LCMS m/z (M+H): 417.2 required, 417.2 found.

Intermediate C142 tert-butyl (R)-(1-(4-(8-chloro-[1,2,4]triazolo[1,5-a]pyrazin-6-yl)-5-methoxypyridin-2-yl)ethyl)(ethyl)carbamate (C142)

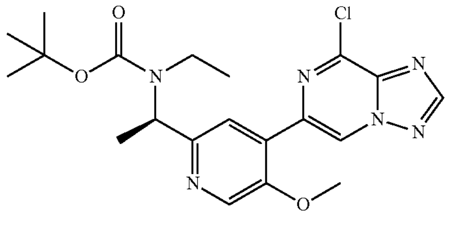 [SMILES: CCN(C(=O)OC(C)(C)C)[C@H](C)c1cc(-c2cn3ncnc3c(Cl)n2)c(OC)cn1]

tert-butyl (R)-(1-(4-(8-chloro-[1,2,4]triazolo[1,5-a]pyrazin-6-yl)-5-methoxypyridin-2-yl)ethyl)(ethyl)carbamate was prepared according to the method described for C141 using B17 and C60. LCMS m/z (M+H): 433.2 required, 433.1 found.

Intermediate C143

(R)-1-(4-(8-chloro-[1,2,4]triazolo[1,5-a]pyrazin-6-yl)-5-methoxypyridin-2-yl)-N-ethylethan-1-amine (C143)

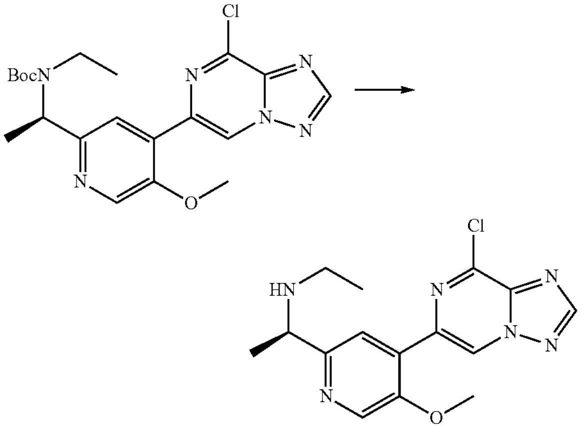

To a solution of tert-butyl (R)-(1-(4-(8-chloro-[1,2,4]triazolo[1,5-a]pyrazin-6-yl)-5-methoxypyridin-2-yl)ethyl)(ethyl)carbamate C142 (130 mg, 0.300 mmol) was added TFA (0.2 ml) at 0° C. The mixture was stirred at 0° C. to 25° C. for 2 h. The mixture was concentrated under reduced pressure and the solvent was removed by lyophilization to give (R)-1-(4-(8-chloro-[1,2,4]triazolo[1,5-a]pyrazin-6-yl)-5-methoxypyridin-2-yl)-N-ethylethan-1-amine C143 which was used to the next step without further purification. LCMS m/z (M+H): 333.1 required, 333.0 found.

Intermediate C144 tert-butyl (R)-(1-(4-(8-chloro-[1,2,4]triazolo[1,5-a]pyrazin-6-yl)pyridin-2-yl)ethyl)(ethyl)carbamate (C144)

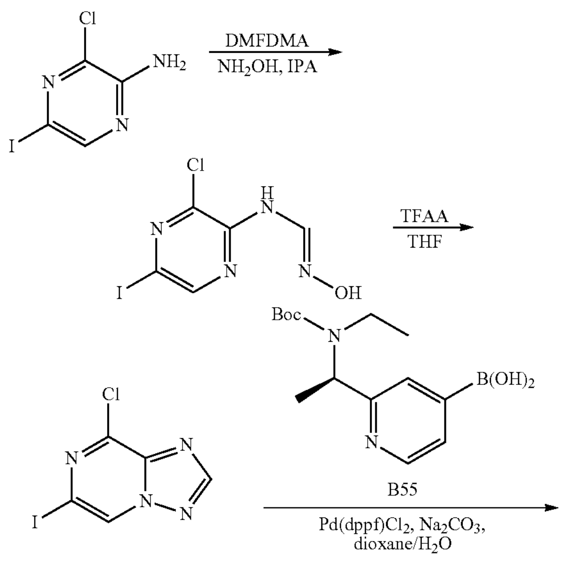

-continued

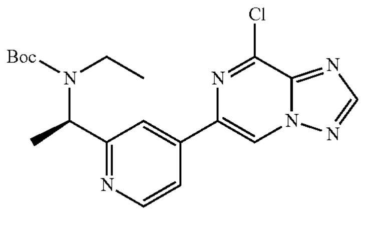

C144

To a solution of 3-chloro-5-iodopyrazin-2-amine (31 g, 121 mmol) in 2-Propanol (400 mL) was added N,N-dimethylformamide dimethyl acetal (20.96 mL, 158 mmol). The mixture was refluxed at 90° C. for 4 h. The reaction mixture was cooled to 50° C. and hydroxylamine hydrochloride (10.96 g, 158 mmol) was added. The reaction mixture was stirred at 50° C. for 12 h. The reaction mixture was concentrated and washed with EtOAc to give (E)-N-(3-chloro-5-iodopyrazin-2-yl)-N'-(trimethylsilyl)formimidamide. LCMS m/z (M+H): 298.9 required, 298.9 found.

To a solution (E)-N-(3-chloro-5-iodopyrazin-2-yl)-N'-(trimethylsilyl)formimidamide (15 g, 50.3 mmol) in THF (200 mL) was added TFAA (8.50 mL, 60.3 mmol) at 0° C. The mixture was stirred at 25° C. for 12 h. The mixture was quenched with $H_2O$(400 mL) and extracted with EtOAc (200 mL×3), washed with brine (200 mL), dried over $Na_2SO_4$, filtered and concentrated under reduced pressure. The crude was purified by Flash silica gel chromatography (ISCO®; 120 g SepaFlash® Silica Flash Column, Eluent of 20% EtOAc/Pet. ether gradient) to give 8-chloro-6-iodo-[1,2,4]triazolo[1,5-a]pyrazine. LCMS m/z (M+H): 280.9 required, 280.9 found.

To a solution of B89 (2.68 g, 9.11 mmol) in Dioxane (60 mL) were added Water (20.00 mL), $Na_2CO_3$ (2.90 g, 27.3 mmol), compound 8-chloro-6-iodo-[1,2,4]triazolo[1,5-a]pyrazine (3.07 g, 10.93 mmol) and $Pd(dppf)Cl_2$ (0.333 g, 0.456 mmol). The mixture was stirred at 80° C. for 12 h. The reaction mixture was poured into $H_2O$(150 mL) and extracted with EtOAc (100 mL×3). The combined organic layers were washed with brine (100 mL), dried over $Na_2SO_4$ and filtered, concentrated in vacuo. The residue was purified by flash silica gel chromatography (ISCO®; 40 g Sepa-Flash® Silica Flash Column, eluent of 85% ethyl acetate/pet. ether gradient) to give tert-butyl (R)-(1-(4-(8-chloro-[1,2,4]triazolo[1,5-a]pyrazin-6-yl)pyridin-2-yl)ethyl)(ethyl)carbamate C144. LCMS m/z (M+H): 403.2 required, 403.1 found.

Intermediate C145

8-(pent-4-en-1-yl)-6-(4,4,5,5-tetramethyl-1,3,2-dioxaborolan-2-yl)imidazo[1,2-a]pyridine

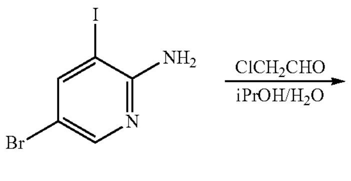

-continued

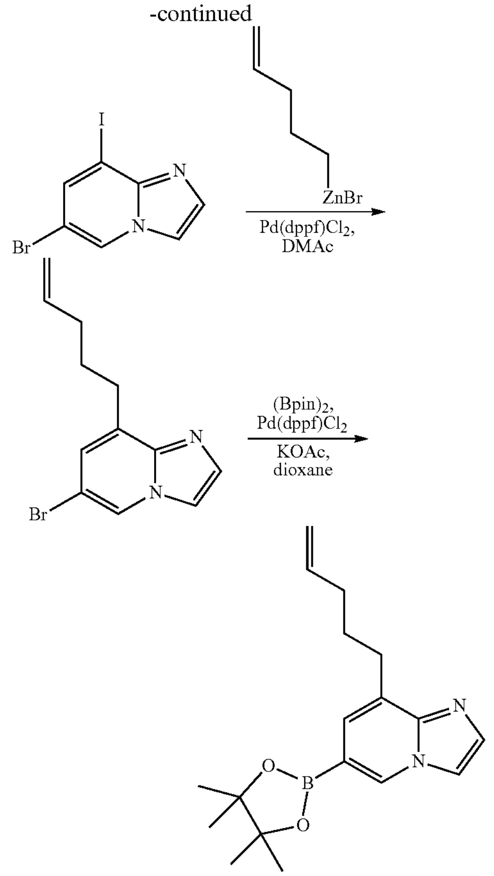

C145

To a solution of 5-bromo-3-iodopyridin-2-amine (5 g, 16.73 mmol) in water (60 mL) and 2-Propanol (24 mL) was added 2-chloroacetaldehyde (4.14 mL, 25.09 mmol) (40% in water) and stirred at 110° C. for 12 hours. Then the reaction was poured into water (60 mL), and then $Na_2CO_3$ was added to adjusted pH=8. The solid was filtered and filtrate was extracted with EtOAc (25 mL×3). The organic layer was washed with brine (30 mL), dried over $Na_2SO_4$, filtered and concentrated to give 6-bromo-8-iodoimidazo[1,2-a]pyridine which was used for next step without purification. LCMS m/z (M+H+2): 325.0 required, 323.3 found.

To a solution of 6-bromo-8-iodoimidazo[1,2-a]pyridine (3.8 g, 11.77 mmol) in DMA (84 mL) were added pent-4-en-1-ylzinc(II) bromide (23.53 mL, 23.53 mmol) and $Pd(dppf)Cl_2$ (0.861 g, 1.177 mmol). The mixture was stirred at 50° C. for 4 h. The mixture was poured into water (30 mL), extracted with EtOAc (20 mL×3). The combined organic phases were dried over $Na_2SO_4$, filtered. The filtrate was concentrated and purified by flash silica gel chromatography (ISCO®; 12 g SepaFlash® Silica Flash Column, eluent of 0-30% ethyl acetate/pet. ether gradient) to give 6-bromo-8-(pent-4-en-1-yl)imidazo[1,2-a]pyridine. LCMS m/z (M+H): 266.1 required, 266.1 found. $^1H$ NMR (400 MHz, $CDCl_3$) δ 8.16-8.11 (m, 1H), 7.59 (s, 1H), 7.52 (s, 1H), 7.02 (s, 1H), 5.84 (tdd, J=6.69, 10.24, 16.96 Hz, 1H), 4.93-5.09 (m, 2H), 3.03-2.95 (m, 2H), 2.17 (q, J=7.17 Hz, 2H), 1.88 (q, J=7.64 Hz, 2H)

To a solution of 6-bromo-8-(pent-4-en-1-yl)imidazo[1,2-a]pyridine (100 mg, 0.377 mmol) in Dioxane (2 mL) were added 4,4,4',4',5,5,5',5'-octamethyl-2,2'-bi(1,3,2-dioxaborolane) (115 mg, 0.453 mmol), potassium acetate (111 mg, 1.131 mmol) and $Pd(dppf)Cl_2$ (27.6 mg, 0.038 mmol). The mixture was stirred at 85° C. for 12 hours. The reaction mixture 8-(pent-4-en-1-yl)-6-(4,4,5,5-tetramethyl-1,3,2-dioxaborolan-2-yl)imidazo[1,2-a]pyridine C145 which was used without purification. LCMS m/z (M+H): 231.2 required, 231.2 found.

Intermediate C146

(R)-1-(4-(8-(but-3-en-1-yloxy)-[1,2,4]triazolo[1,5-a]pyrazin-6-yl)pyridin-2-yl)-N-ethylethan-1-amine (C146)

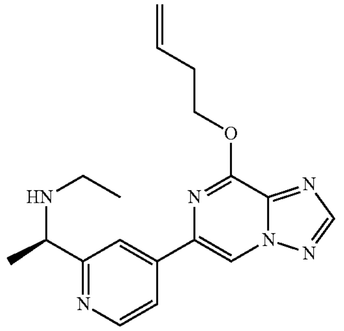

(R)-1-(4-(8-(but-3-en-1-yloxy)-[1,2,4]triazolo[1,5-a]pyrazin-6-yl)pyridin-2-yl)-N-ethylethan-1-amine was prepared according to the procedure used to prepare intermediate C75 using intermediate C71 in place of C37.

Intermediate C146

8-(but-3-en-1-yloxy)-6-chloroimidazo[1,2-b]pyridazine (C146)

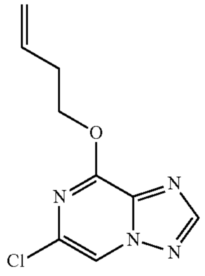

To a solution of 3-buten-1-ol (0.341 g, 4.73 mmol) in DMF (10 mL) was added sodium hydride (0.258 g, 6.45 mmol) (60% wt) at 0° C. and stirred at 0° C. for 30 mins. 8-bromo-6-chloroimidazo[1,2-b]pyridazine (1 g, 4.30 mmol) was added to the above mixture and stirred at 0° C. for 2 h. The mixture was quenched with $H_2O$(50 mL) and extracted with EtOAC (30 mL×3), washed with brine (50 mL), dried over $Na_2SO_4$, filtered and concentrated under reduced pressure. The crude was purified by Flash silica gel chromatography (ISCO®; 25 g SepaFlash® Silica Flash Column, Eluent of 20% EtOAc/Pet.ether gradient) to give 8-(but-3-en-1-yloxy)-6-chloroimidazo[1,2-b]pyridazine. LCMS m/z (M+H): 224.0 required, 224.1 found. $^1H$ NMR (400 MHz, $CDCl_3$) δ 7.81 (d, J=1.0 Hz, 1H), 7.62 (d, J=1.0 Hz, 1H), 6.37 (s, 1H), 5.98-5.79 (m, 1H), 5.25-5.08 (m, 2H), 4.30 (t, J=6.8 Hz, 2H), 2.73-2.67 (m, 2H)

Intermediate C147

(R)—N-ethyl-1-(5-methoxy-4-(7-(methylthio)pyrazolo[1,5-c]pyrimidin-5-yl)pyridin-2-yl)ethan-1-amine (C147)

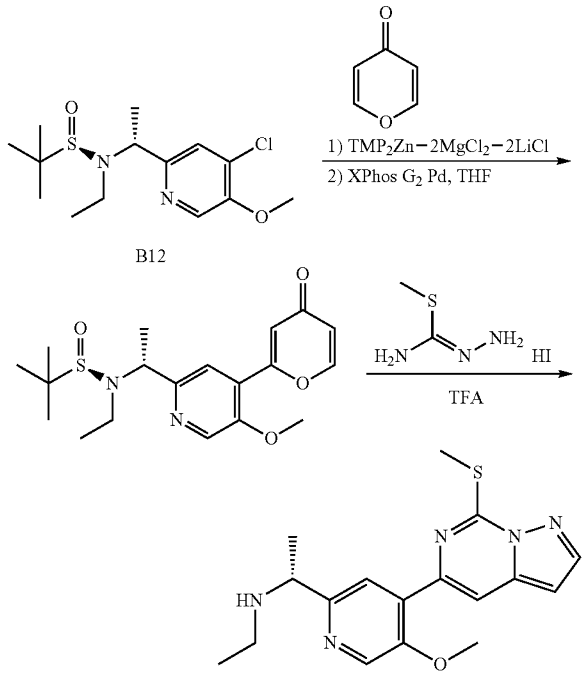

B12

C147

Step 1: (R)—N-ethyl-N—((R)-1-(5-methoxy-4-(4-oxo-4H-pyran-2-yl)pyridin-2-yl)ethyl)-2-methylpropane-2-sulfinamide To a solution of 0.3 M $TMP_2Zn-2MgCl_2-2LiCl$ (1570 mL, 471 mmol) in THF (1000 mL) at 0° C. was added 4H-pyran-4-one (46.2 g, 321 mmol) dropwise and the reaction was stirred at 0° C. for 2 hours. (R)—N—((R)-1-(4-chloro-5-methoxypyridin-2-yl)ethyl)-N-ethyl-2-methylpropane-2-sulfinamide (75.0 g, 235 mmol) in THF (1500 mL) and Xphos G2 Pd (27.3 g, 34.7 mmol) were added and the reaction was stirred at 45° C. for 3 hours. The reaction was cooled to 0° C. and quenched with saturated aqueous ammonium chloride (500 mL) and extracted with EtOAc (3×500 mL). The combined organic layers were washed with brine (500 mL), dried ($MgSO_4$), filtered and concentrated. The crude material was purified by purified by reverse phase HPLC (10-40% ACN in water, with 0.1% TFA as modifier) to yield (R)—N-ethyl-N—((R)-1-(5-methoxy-4-(4-oxo-4H-pyran-2-yl)pyridin-2-yl)ethyl)-2-methylpropane-2-sulfinamide. LC-MS: 379.2 (M+1).

Step 2: (R)—N-ethyl-1-(5-methoxy-4-(7-(methylthio)pyrazolo[1,5-c]pyrimidin-5-yl)pyridin-2-yl)ethan-1-amine (C147)

To a mixture of (R)—N-ethyl-N—((R)-1-(5-methoxy-4-(4-oxo-4H-pyran-2-yl)pyridin-2-yl)ethyl)-2-methylpropane-2-sulfinamide (35.0 g, 92.5 mmol) and methylisothiosemicarbazide hydroiodide (32.3 g, 139 mmol) in 2-propanol (700 mL) was added TFA (24.0 g, 210 mmol). The reaction was heated at 80° C. overnight. The reaction mixture was dissolved with 1:1 acetonitrile:TFA/$H_2O$ and purified by reverse phase HPLC (10-40% ACN in water, with 0.1% TFA as modifier) to yield (R)—N-ethyl-1-(5-methoxy-4-(7-(methylthio)pyrazolo[1,5-c]pyrimidin-5-yl)pyridin-2-yl)ethan-1-amine. LC-MS: 344.1 (M+1). The following Intermediates in Table C14 were synthesized in an analogous manner of that described in C147.

TABLE C14

| Halide | Intermediate | Number | Observed LCMS (M + 1) |
|---|---|---|---|
| 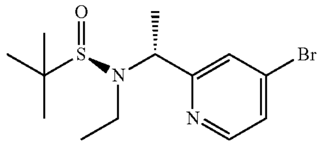 B9 | 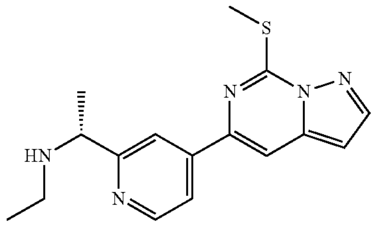 [SMILES: CCN[C@H](C)c1cc(-c2cc3ccnn3c(SC)n2)ccn1] | C151 | 314.2 |

Intermediate C148

(R)—N-ethyl-1-(5-methoxy-4-(5-(methylthio)-[1,2,4]triazolo[1,5-c]pyrimidin-7-yl)pyridin-2-yl)ethan-1-amine dihydrochloride (C148)

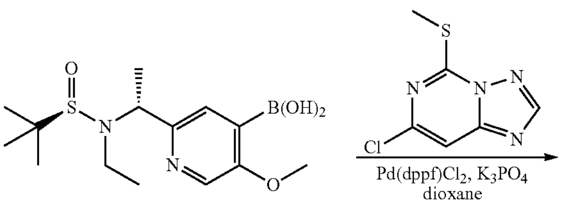

B17

-continued

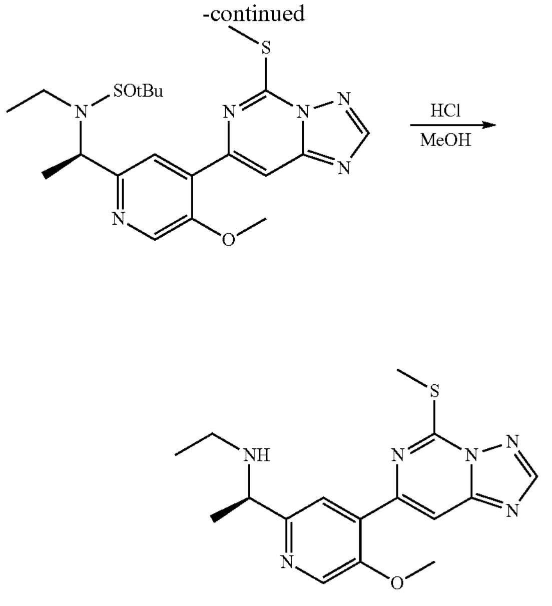

C148

Step 1: (S)—N-ethyl-N—((R)-1-(5-methoxy-4-(5-(methylthio)-[1,2,4]triazolo[1,5-c]pyrimidin-7-yl)pyridin-2-yl)ethyl)-2-methylpropane-2-sulfinamide A solution of (2-((R)-1-(((R)-tert-butylsulfinyl)(ethyl)amino)ethyl)-5-methoxypyridin-4-yl)boronic acid (B17, 696 mg, 2.12 mmol), 7-chloro-5-(methylthio)-[1,2,4]triazolo[1,5-c]pyrimidine (213 mg, 1.06 mmol), 1M $K_3PO_4$ (2.12 mL, 2.12 mmol) and Pd(dppf)$Cl_2$-dichloromethane adduct (173 mg, 0.212 mmol) in dioxane (10.6 mL) was stirred at 90° C. for 18 hours. The reaction was concentrated and the crude material was purified by flash silica chromatography (0-100% EtOAc/EtOH 3:1 mix in hexanes gradient) to give (S)—N-ethyl-N—((R)-1-(5-methoxy-4-(5-(methylthio)-[1,2,4]triazolo[1,5-c]pyrimidin-7-yl)pyridin-2-yl)ethyl)-2-methylpropane-2-sulfinamide. LC-MS: 449.3 (M+1).

Step 2 (R)—N-ethyl-1-(5-methoxy-4-(5-(methylthio)-[1,2,4]triazolo[1,5-c]pyrimidin-7-yl)pyridin-2-yl)ethan-1-amine (C148)

To a solution of (S)—N-ethyl-N—((R)-1-(5-methoxy-4-(5-(methylthio)-[1,2,4]triazolo[1,5-c]pyrimidin-7-yl)pyridin-2-yl)ethyl)-2-methylpropane-2-sulfinamide (131 mg, 0.292 mmol) in dichloromethane (2 mL) was added a solution of 4M HCl (0.365 mL, 1.46 mmol) in dioxane. The reaction was stirred at ambient temperature for 1 hour. The reaction was concentrated to afford (R)—N-ethyl-1-(5-methoxy-4-(5-(methylthio)-[1,2,4]triazolo[1,5-c]pyrimidin-7-yl)pyridin-2-yl)ethan-1-amine (C148) as an HCl salt. LC-MS: 345.2 (M+1).

Intermediate C149

(R)—N-ethyl-1-(5-methoxy-4-(3-methyl-7-(methylthio)pyrazolo[1,5-c]pyrimidin-5-yl)pyridin-2-yl)ethan-1-amine (C149)

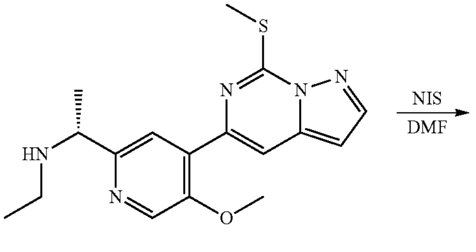

C147

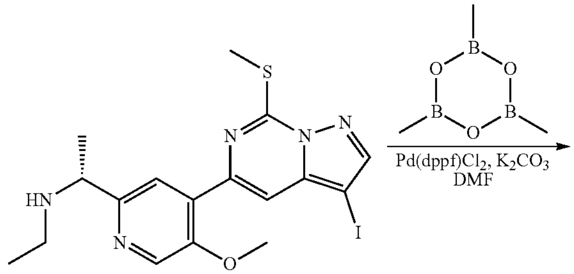

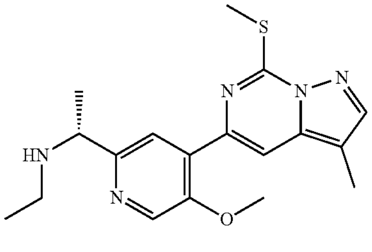

C149

Step 1:R-1-ethyl-1-(4-(3-iodo-7-(methylthio)prazolo[1,5-c]primidin-5-vi-5-methoxypyridin-2-yl)ethan-1-amine N-Iodosuccinimide (221 mg, 0.984 mmol) was added to a solution of (R)—N-ethyl-1-(5-methoxy-4-(7-(methylthio)pyrazolo[1,5-c]pyrimidin-5-yl)pyridin-2-yl)ethan-1-amine (C147, 300 mg, 0.656 mmol) in DMF (3 mL) and the reaction was stirred at ambient temperature for 3 hours. The reaction was quenched with saturated aqueous sodium bisulfite (5 mL) and diethy ether (5 mL) was added. After 15 minutes, the resulting solid was filtered, washed with diethyl ether (3×5 mL), and dried to yield (R)—N-ethyl-1-(4-(3-iodo-7-(methylthio)pyrazolo[1,5-c]pyrimidin-5-yl)-5-methoxypyridin-2-yl)ethan-1-amine. LC-MS: 470.1 (M+1).

Step 2: (R)—N-ethyl-1-(5-methoxy-4-(3-methyl-7-(methylthio)pyrazolo[1,5-c]pyrimidin-5-yl)pyridin-2-yl)ethan-1-amine (C149)

To a solution of (R)—N-ethyl-1-(4-(3-iodo-7-(methylthio)pyrazolo[1,5-c]pyrimidin-5-yl)-5-methoxypyridin-2-yl)ethan-1-amine (238 mg, 0.507 mmol), trimethylboroxine (0.213 mL, 1.52 mmol), and K2C03 (350 mg, 2.54 mmol) in DMF (5.1 mL) was added Pd(dppf)$Cl_2$—dichloromethane adduct (41.4 mg, 0.051 mmol). The reaction was stirred at 100° C. for 23 hours. The reaction was poured into water (30 mL) and extracted with dichloromethane (3×15 mL). The combined organic layers were dried ($Na_2SO_4$), filtered and concentrated. The crude material was purified by flash silica chromatography (0-30% MeOH/$NH_4OH$ 99:1 mix in dichloromethane gradient) to yield (R)—N-ethyl-1-(5-methoxy-4-(3-methyl-7-(methylthio)pyrazolo[1,5-c]pyrimidin-5-yl)pyridin-2-yl)ethan-1-amine. LC-MS: 358.2 (M+1).

Intermediate C150

6,8-dibromo-5-methyl-[1,2,4]triazolo[1,5-a]pyrazine (C150)

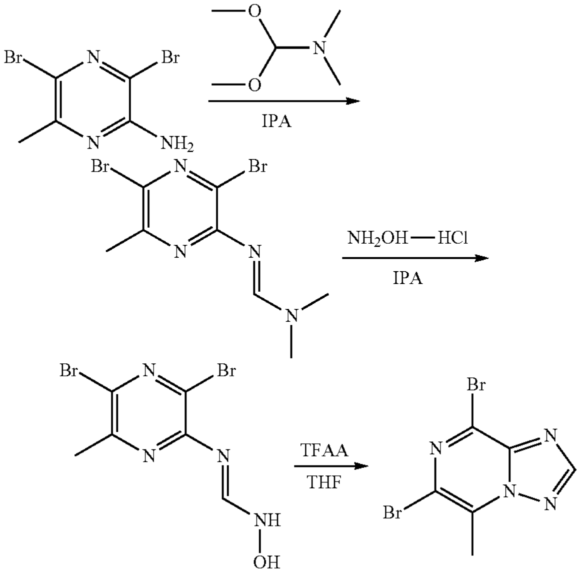

C150

Step 1: (E)-N'-(3,5-dibromo-6-methylpyrazin-2-yl)-N,N-dimethylformimidamide

To a solution of 3,5-dibromo-6-methylpyrazin-2-amine (2.90 g, 10.9 mmol) in 2-propanol (50 mL) was added N,N-dimethylformamide dimethyl acetal (2.91 mL, 21.7 mmol). The reaction was stirred at 120° C. for 16 hours. The reaction mixture was concentrated to give (E)-N'-(3,5-dibromo-6-methylpyrazin-2-yl)-N,N-dimethylformimidamide, which was used without further purification. LC-MS: 323.0 (M+1).

Step 2: (E)-N'-(3,5-dibromo-6-methylpyrazin-2-yl)-N-hydroxyformimidamide

To a solution of (E)-N'-(3,5-dibromo-6-methylpyrazin-2-yl)-N,N-dimethylformimidamide (3.50 g, 10.9 mmol) in 2-propanol (50 mL) was added hydroxylamine hydrochloride (982 mg, 14.1 mmol). The reaction was stirred at 50° C. for 5 hours. The reaction mixture was concentrated to give (E)-N'-(3,5-dibromo-6-methylpyrazin-2-yl)-N-hydroxyformimidamide, which was used without further purification. LC-MS: 311.0 (M+1). 6,8-dibromo-5-methyl-[1,2,4]triazolo[1,5-a]pyrazine (C150)

To a solution of (E)-N'-(3,5-dibromo-6-methylpyrazin-2-yl)-N-hydroxyformimidamide (3.37 g, 10.9 mmol) in tetrahydrofuran (150 mL) at 0° C. was added trifluoroacetic anhydride (10.8 mL, 76.0 mmol) over 30 minutes. The reaction was stirred at ambient temperature for 16 hours. The reaction was poured into water (100 mL) and extracted with EtOAc (3×50 mL). The combined organic layers were washed with saturated aqueous sodium bicarbonate (30 mL), dried ($Na_2SO_4$), filtered, and concentrated. The crude material was purified by flash silica chromatography (0-50% EtOAc in hexanes gradient) to yield 6,8-dibromo-5-methyl-[1,2,4]triazolo[1,5-a]pyrazine, which was used without further purification. LC-MS: 292.9 (M+1).

Intermediate C153

1-(4-(8-(but-3-en-1-yloxy)imidazo[1,2-a]pyrazin-6-yl)-5-chloropyridin-2-yl)-N-ethylethan-1-amine

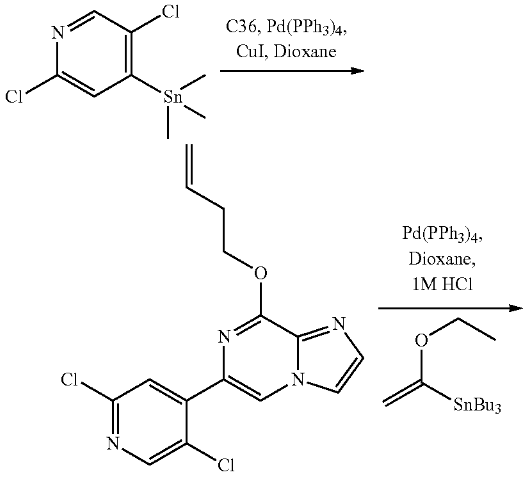

C159

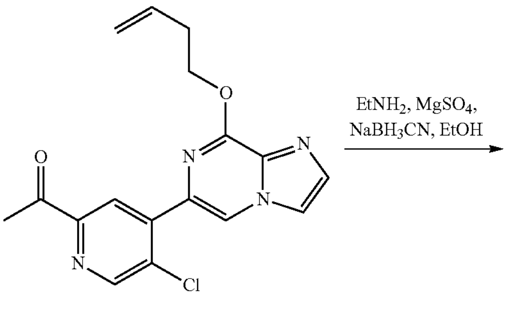

C152

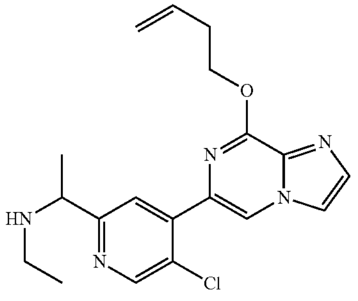

C153

Step 1: 8-(but-3-en-1-yloxy)-6-(2,5-dichloropyridin-4-yl)imidazo[1,2-a]pyrazine (C159)

To a vial containing 6-bromo-8-(but-3-en-1-yloxy)imidazo[1,2-a]pyrazine (C36, 86 mg, 0.322 mmol), 2,5-dichloro-4-(trimethylstannyl)pyridine (100 mg, 0.322 mmol), tetrakis (triphenylphosphine)palladium (0) (37 mg, 0.032 mmol) and CuI (61 mg, 0.322 mmol) under nitrogen was added dioxane (1 mL) and the reaction was stirred at 130° C. for 1 h. The reaction was then cooled, diluted with EtOAC and washed with saturated sodium bicarbonate solution. The mixture was then extracted with EtOAc and the combined organic layers were washed with brine and concentrated. The crude material was purified by flash silica chromatography (0-50% EtOAc in hexanes) to give 8-(but-3-en-1-yloxy)-6-(2,5-dichloropyridin-4-yl)imidazo[1,2-a]pyrazine (C159). LC-MS: 335.1

Step 2: 1-(4-(8-(but-3-en-1-yloxy)imidazo[1,2-a]pyrazin-6-yl)-5-chloropyridin-2-yl)ethan-1-one To a solution of 8-(but-3-en-1-yloxy)-6-(2,5-dichloropyridin-4-yl)imidazo[1,2-a]pyrazine (C159, 1380 mg, 4.12 mmol) in dioxane (10 mL) were added tributyl (1-ethoxyvinyl)stannane (1.46 ml, 4.32 mmol) and tetrakis (triphenylphosphine)palladium (0) (476 mg, 0.412 mmol). The reaction was stirred at 130° C. for 1 h. The reaction was then cooled down to 20° C. and 1 M aq. HCl (5 mL) was added. The reaction was allowed to stir at 20° C. for another 2 h. The reaction was poured into saturated bicarbonate solution. The mixture was then extracted with EtOAc. The combined organic layers were concentrated. The crude material was purified by flash silica chromatography (0-60% EtOAc in hexanes) to give 1-(4-(8-(but-3-en-1-yloxy)imidazo[1,2-a]pyrazin-6-yl)-5-chloropyridin-2-yl)ethan-1-one (C152). LC-MS: 343.2

Step 3: 1-(4-(8-(but-3-en-1-yloxy)imidazo[1,2-a]pyrazin-6-yl)-5-chloropyridin-2-yl)-N-ethylethan-1-amine (C153)

To a solution of 1-(4-(8-(but-3-en-1-yloxy)imidazo[1,2-a]pyrazin-6-yl)-5-chloropyridin-2-yl)ethan-1-one (C152, 150 mg, 0.438 mmol) in EtOH (1.5 mL) were added ethanamine (2M, 0.656 mL, 1.31 mmol), AcOH (5.0 μL, 0.088 mmol), $MgSO_4$ (132 mg, 1.09 mmol) and $NaBH_3CN$ (55 mg, 0.875 mmol) at room temperature. The reaction was stirred overnight at room temperature. The reaction mixture was filtered and concentrated to afford 1-(4-(8-(but-3-en-1-yloxy)imidazo[1,2-a]pyrazin-6-yl)-5-chloropyridin-2-yl)-N-ethylethan-1-amine (C153), which was carried forward without purification. LC-MS: 372.2 (M+1).

Intermediate C160

1-(4-(8-(but-3-en-1-yloxy)imidazo[1,2-a]pyrazin-6-yl)-5-cyclopropylpyridin-2-yl)-N-ethylethan-1-amine

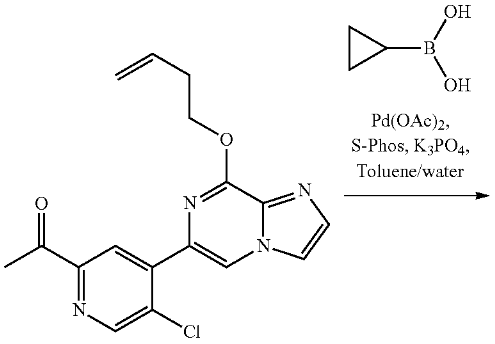

C152

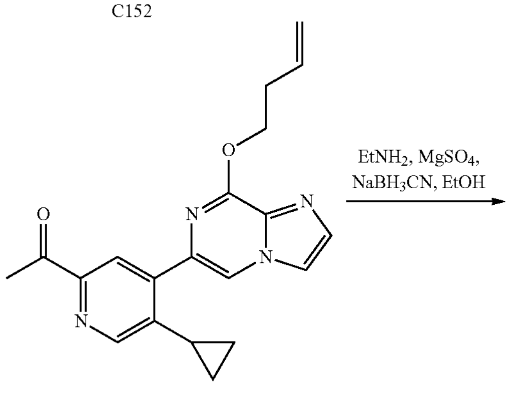

C161

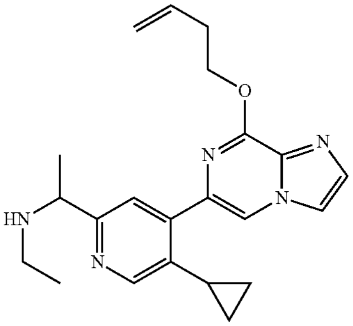

C160

Step 1: 1-(4-(8-(but-3-en-1-yloxy)imidazo[1,2-a]pyrazin-6-yl)-5-cyclopropylpyridin-2-yl)ethan-1-one (C161)

To a vial containing 1-(4-(8-(but-3-en-1-yloxy)imidazo[1,2-a]pyrazin-6-yl)-5-chloropyridin-2-yl)ethan-1-one (C152, 420 mg, 1.225 mmol), $Pd(OAc)_2$ (27 mg, 0.12 mmol), cyclopropyl boronic acid (137 mg, 1.59 mmol), $K_3PO_4$ (910 mg, 4.29 mmol) and S-Phos (101 mg, 0.245 mmol) under nitrogen was added Toluene (3.6 mL) and water (0.4 mL). The resulting mixture was heated to 100° C. overnight. To the mixture was added water and extracted with Ethyl acetate several times. The combined organic layers were combined and concentrated. The crude material was purified by flash silica chromatography (0-60% EtOAc in hexanes) to give 1-(4-(8-(but-3-en-1-yloxy)imidazo[1,2-a]pyrazin-6-yl)-5-cyclopropylpyridin-2-yl)ethan-1-one (C161). LC-MS: 349.2 (M+1).

Step 2: 1-(4-(8-(but-3-en-1-yloxy)imidazo[1,2-a]pyrazin-6-yl)-5-cyclopropylpyridin-2-yl)-N-ethylethan-1-amine (C160)

To a solution of 1-(4-(8-(but-3-en-1-yloxy)imidazo[1,2-a]pyrazin-6-yl)-5-cyclopropylpyridin-2-yl)ethan-1-one (C161, 86 mg, 0.247 mmol) in EtOH (0.8 mL) were added ethanamine (2M, 0.370 mL, 0.741 mmol), AcOH (2.8 μL, 0.049 mmol), $MgSO_4$ (74 mg, 0.617 mmol) and $NaBH_3CN$ (31 mg, 0.494 mmol) at room temperature. The reaction was stirred overnight at room temperature. The reaction mixture was filtered and concentrated to afford 1-(4-(8-(but-3-en-1-yloxy)imidazo[1,2-a]pyrazin-6-yl)-5-cyclopropylpyridin-2-yl)-N-ethylethan-1-amine (C160), which was carried forward without purification. LC-MS: 378.3 (M+1).

Intermediate C162

1-(4-(8-(but-3-en-1-yloxy)imidazo[1,2-b]pyridazin-6-yl)-5-fluoropyridin-2-yl)-N-ethylethan-1-amine

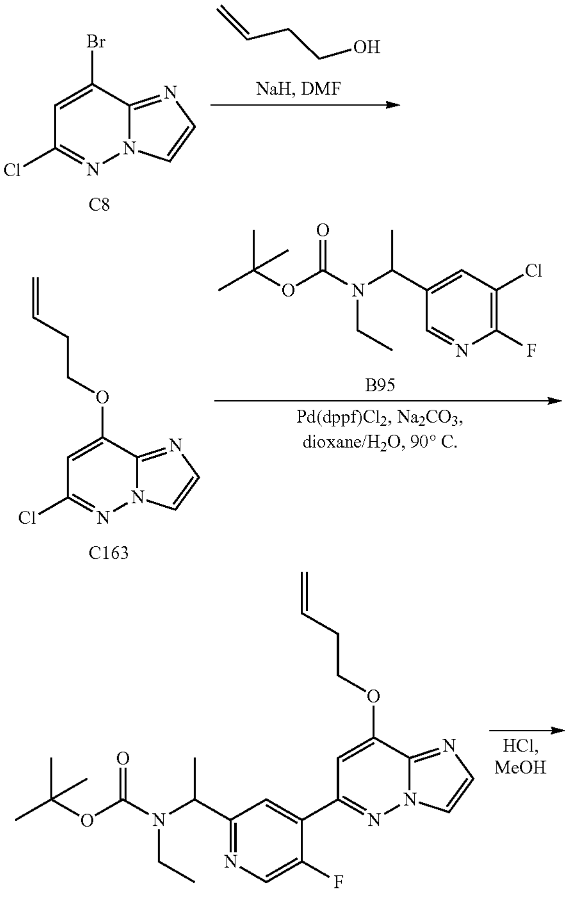

C8

B95

C163

C164

-continued

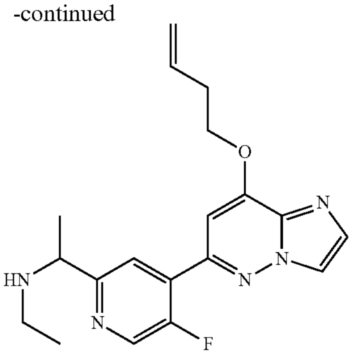

C162

Step 1: 18-(but-3-en-1-yloxy)-6-chloroimidazo[1,2-b]pyridazine (C163)

In an analogous manner to C36, C8 and But-3-en-1-ol were used to prepare 18-(but-3-en-1-yloxy)-6-chloroimidazo[1,2-b]pyridazine (C163). LC-MS: 224.0 (M+1).

Step 2: tert-butyl (1-(4-(8-(but-3-en-1-yloxy)imidazo[1,2-b]pyridazin-6-yl)-5-fluoropyridin-2-yl)ethyl)(ethyl)carbamate (C164)

To a mixture of tert-butyl (1-(4-chloro-5-fluoropyridin-2-yl)ethyl)(ethyl)carbamate (B95, 300 mg, 0.991 mmol), potassium acetate (189 mg, 1.92 mmol), Bis(pinacolato) diboron (293 mg, 1.15 mmol), and $Pd(dppf)Cl_2$ (70.3 mg, 0.096 mmol) in a vial under nitrogen was added dioxane (2.5 mL). The reaction was stirred at 90° C. under nitrogen for 2 h. To this was added 18-(but-3-en-1-yloxy)-6-chloroimidazo[1,2-b]pyridazine (C163, 215 mg, 0.96 mmol) and $Na_2CO_3$ (153 mg, 1.44 mmol) dissolved in water (0.86 mL). The reaction was stirred at 90° C. under nitrogen overnight. The reaction was quenched with water and extracted with EtOAc several times. The combined organic layers were concentrated. The crude material was purified by flash silica chromatography (0-50% EtOAc in hexanes) to give tert-butyl (1-(4-(8-(but-3-en-1-yloxy)imidazo[1,2-b]pyridazin-6-yl)-5-fluoropyridin-2-yl)ethyl)(ethyl)carbamate (C164). LC-MS: 456.1 (M+1).

Step 3: 1-(4-(8-(but-3-en-1-yloxy)imidazo[1,2-b]pyridazin-6-yl)-5-fluoropyridin-2-yl)-N-ethylethan-1-amine (C162)

In an analogous manner to B5, tert-butyl (1-(4-(8-(but-3-en-1-yloxy)imidazo[1,2-b]pyridazin-6-yl)-5-fluoropyridin-2-yl)ethyl)(ethyl)carbamate (C164) and HCl were used to prepare 1-(4-(8-(but-3-en-1-yloxy)imidazo[1,2-b]pyridazin-6-yl)-5-fluoropyridin-2-yl)-N-ethylethan-1-amine (C162). LC-MS: 356.2 (M+1).

The following intermediates were synthesized in an analogous manner of that described for C162 using the appropriate halides and cores.

| Halide | Core | Intermediate | Observed LCMS (M + 1) |
|---|---|---|---|
| 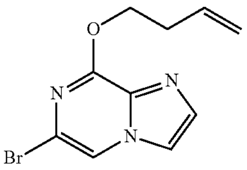 C36 | 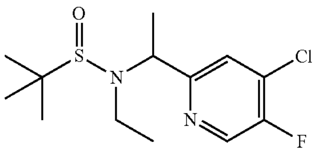 B97 | 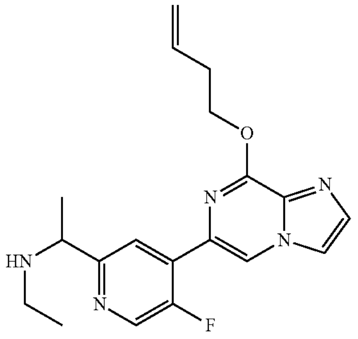 C154 | 356.2 |
| 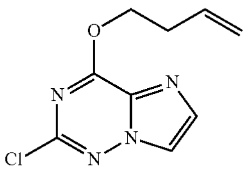 C140 | 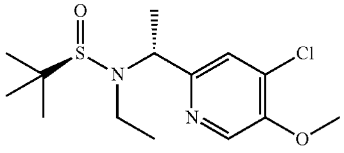 B12 | 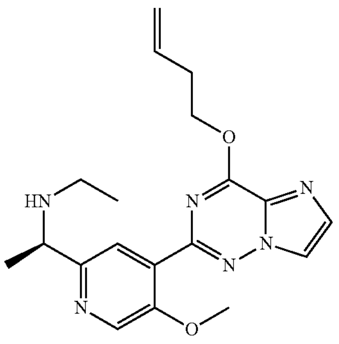 C155 | 369.2 |
| 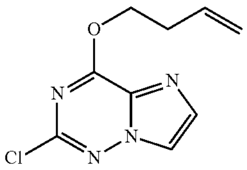 C140 | 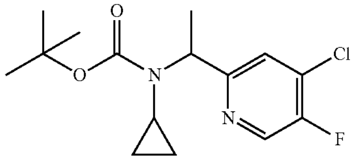 B98 | 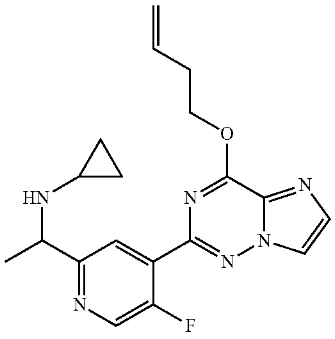 C156 | 369.2 |
| 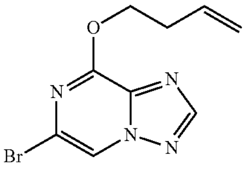 C70 | 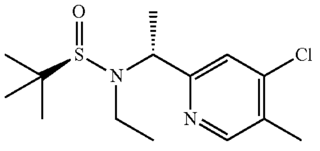 B31 | 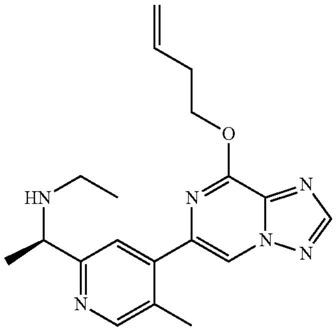 C157 | 353.15 |

-continued

| Halide | Core | Intermediate | Observed LCMS (M + 1) |
|---|---|---|---|
| 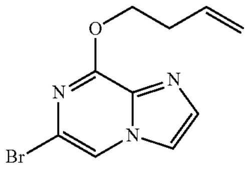 C36 | 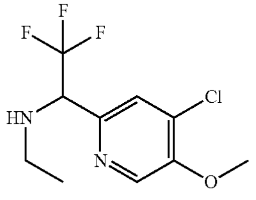 B76 | 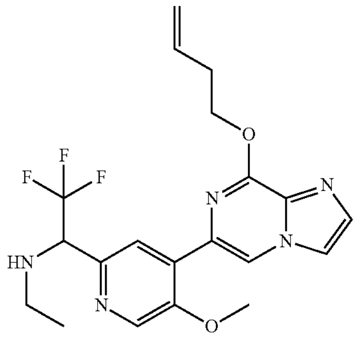 C158 | 422.3 |

Intermediate C166

(R)-1-(5-(8-chloroimidazo[1,2-a]pyrazin-6-yl)-6-methoxypyridin-3-yl)-N-ethylethan-1-amine (C166)

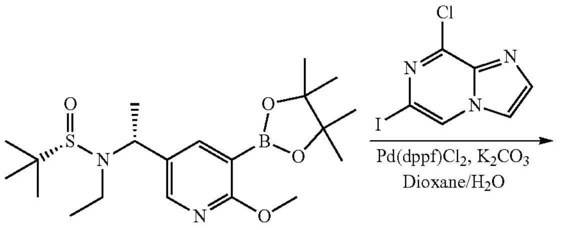

B20

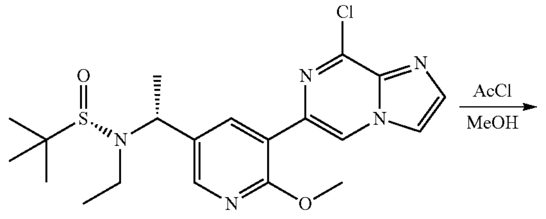

C165

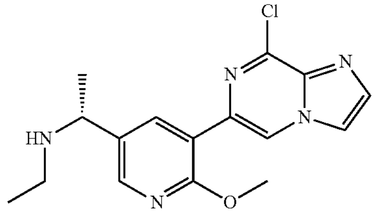

C166

Step 1: (S)—N—((R)-1-(5-(8-chloroimidazo[1,2-a]pyrazin-6-yl)-6-methoxypyridin-3-yl)ethyl)-N-ethyl-2-methylpropane-2-sulfinamide (C165)

To a solution of (5-((R)-1-(((S)-tert-butylsulfinyl)(ethyl)amino)ethyl)-2-methoxypyridin-3-yl)boronic acid (B20, 136 mg, 0.414 mmol) in Dioxane (2 mL) and Water (0.5 mL) were added K2C03 (172 mg, 1.243 mmol), 8-chloro-6-iodoimidazo[1,2-a]pyrazine (127 mg, 0.456 mmol) and Pd(dppf)$Cl_2$ (30.3 mg, 0.041 mmol). The mixture was stirred at 90° C. for 3 hours. The reaction mixture was poured into water (10 mL), extracted with EtOAc (10 mL×3). The organic layer was washed with brine (10 mL), dried over $Na_2SO_4$ and filtered. The filtrate was concentrated and purified by flash silica gel chromatography (eluent of 100% ethyl acetate/pet. ether gradient) to give (S)—N—((R)-1-(5-(8-chloroimidazo[1,2-a]pyrazin-6-yl)-6-methoxypyridin-3-yl)ethyl)-N-ethyl-2-methylpropane-2-sulfinamide (C165). LC-MS: 436.1 (M+H).

Step 2: (R)-1-(5-(8-chloroimidazo[1,2-a]pyrazin-6-yl)-6-methoxypyridin-3-yl)-N-ethylethan-1-amine (C166)

To a solution of (S)—N—((R)-1-(5-(8-chloroimidazo[1,2-a]pyrazin-6-yl)-6-methoxypyridin-3-yl)ethyl)-N-ethyl-2-methylpropane-2-sulfinamide (C165, 240 mg, 0.550 mmol) in MeOH (5 mL) was added acetyl chloride (216 mg, 2.75 mmol), the mixture was stirred at 0° C. for 30 mins. The mixture was concentrated, and the reaction mixture was poured into water (10 mL), extracted with EtOAc (10 mL×3). The organic layer was washed with brine (10 mL), dried over $Na_2SO_4$ and filtered to give R)-1-(5-(8-chloroimidazo[1,2-a]pyrazin-6-yl)-6-methoxypyridin-3-yl)-N-ethylethan-1-amine (C166). LC-MS: 332.1 (M+1). $^1H$ NMR (400 MHz, $CD_3OD$) δ 9.36 (s, 1H), 8.61 (d, J=2.20 Hz, 1H), 8.22 (d, J=0.98 Hz, 1H), 8.16 (d, J 2.45 Hz, 1H), 7.82 (d, J=0.98 Hz, 1H), 4.12 (s, 3H), 4.07-4.00 (m, 1H), 2.73-2.52 (m, 2H), 1.51 (d, J=6.60 Hz, 3H), 1.14 (t, J=7.21 Hz, 3H).

Intermediate C167 tert-butyl (R)-ethyl(1-(5-fluoro-4-(8-((6-hydroxyhexyl)oxy)imidazo[1,2-a]pyrazin-6-yl)pyridin-2-yl)ethyl)carbamate (C167)

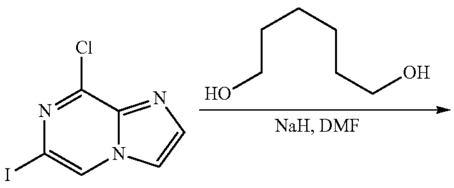

-continued

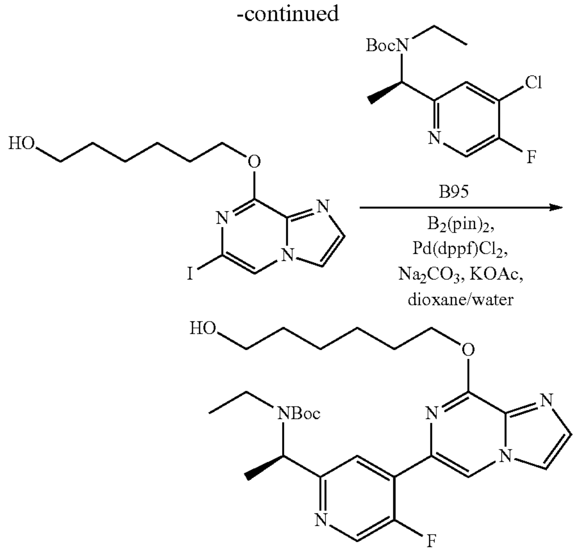

C167

Step 1: 6-((6-iodoimidazo[1,2-a]pyrazin-8-yl)oxy)hexan-1-ol

The 1,6-hexanediol (0.262 ml, 2.147 mmol) was dissolved in DMF (8.95 ml) and treated with sodium hydride (0.072 g, 2.68 mmol) and stirred 5 min at rt and treated with 8-chloro-6-iodoimidazo[1,2-a]pyrazine (0.5 g, 1.789 mmol) and stirred overnight. Work-up involved diluting with water, extracting with 3:1 $HCCl_3$:IPA, drying ($Na_2SO_4$), filtering and concentrated. This was purified via flash silica gel chromatography (0-70% 3:1 EtOAc:EtOH/hexanes) to give 6-((6-iodoimidazo[1,2-a]pyrazin-8-yl)oxy)hexan-1-ol. LC-MS: 362.2 (M+1).

Step 2: tert-butyl (R)-ethyl(1-(5-fluoro-4-(8-((6-hydroxyhexyl)oxy)imidazo[1,2-a]pyrazin-6-yl)pyridin-2-yl)ethyl)carbamate A sealable vial was charged with tert-butyl (R)-(1-(4-chloro-5-fluoropyridin-2-yl)ethyl)(ethyl)carbamate (B95, 110 mg, 0.363 mmol) and bis(pinacolato)diboron (111 mg, 0.436 mmol) which were dissolved in Dioxane (1362 μl) which had been sparged with nitrogen for 10 min. The [1,1'-bis(diphenylphosphino)ferrocene]dichloropalladium (II) (53.2 mg, 0.073 mmol) was and potassium acetate (71.3 mg, 0.727 mmol) were added and the vial was capped and heated to 90° C. and stirred 8 h. To this was added 6-((6-iodoimidazo[1,2-a]pyrazin-8-yl)oxy)hexan-1-ol (131 mg, 0.363 mmol) along with sodium carbonate (57.8 mg, 0.545 mmol) and water (454 μl) which had been sparged with nitrogen for 10 min. The vial was capped and the reaction contents were heated to 90° C. and stirred 4 h. This was diluted with EtOAc, filtered through a SPE cartridge containing celite and concentrated. This was purified via flash silica gel chromatography (0-18% 3:1 EtOAc:EtOH/hexanes) to give tert-butyl (R)-ethyl(1-(5-fluoro-4-(8-((6-hydroxyhexyl)oxy)imidazo[1,2-a]pyrazin-6-yl)pyridin-2-yl)ethyl)carbamate (C167). LC-MS: 502.5 (M+1).

Intermediate C168

4-nitrophenyl (1-cyano-6-((6-(2-((R)-1-(ethylamino)ethyl)-5-fluoropyridin-4-yl)imidazo[1,2-a]pyrazin-8-yl)oxy)hexyl)carbamate (C168)

C168

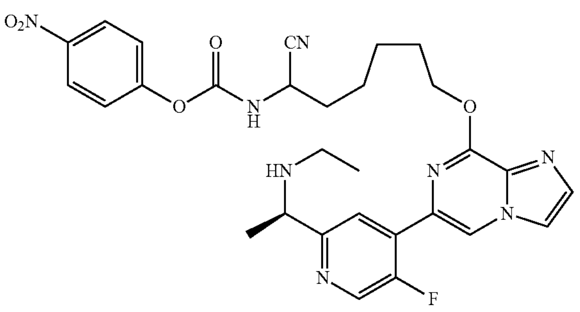

The title compound was prepared from C167 according to the general procedures herein and in an analogous manner of that described in steps 4 through 6 used to synthesize Example 224. LC-MS: 692.6 (M+1).

Example 1

(10R,E)-9-ethyl-10-methyl-3-oxa-7,9-diaza-2(6,8)-imidazo[1,2-a]pyrazina-1(1,3)-benzena-4(1,3)-cyclopentanacyclodecaphan-8-one

SCHEME 1

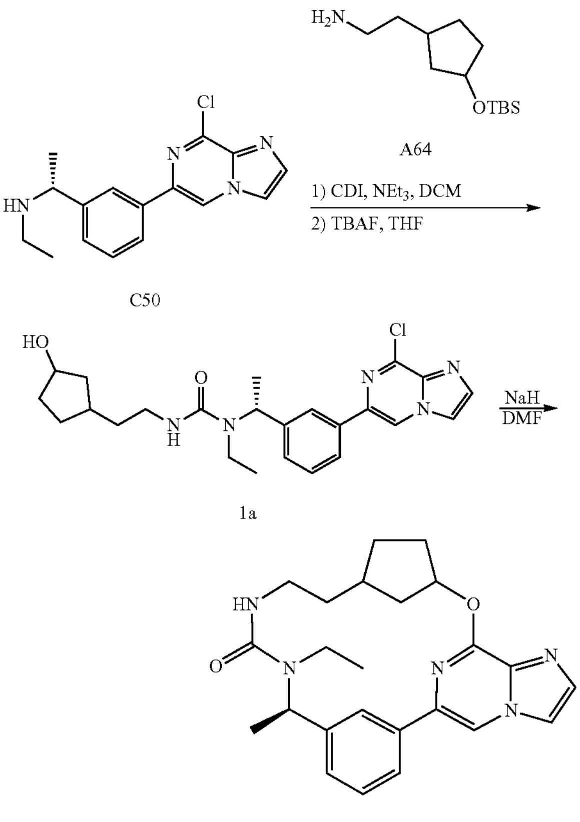

Example 1

Step 1: 1-((R)-1-(3-(8-chloroimidazo[1,2-a]pyrazin-6-yl)phenyl)ethyl)-1-ethyl-3-(2-(3-hydroxycyclopentyl)ethyl)urea (la)

2-(3-((tert-butyldimethylsilyl)oxy)cyclopentyl)ethan-1-amine (A64, 40.4 mg, 0.166 mmol) and triethylamine (40 μL, 0.322 mmol) were combined in DCM (500 μL). CDI (21.56 mg, 0.133 mmol) was added and the reaction was stirred at ambient temperature for 1 h. (R)-1-(3-(8-chloroimidazo[1,2-a]pyrazin-6-yl)phenyl)-N-ethylethan-1-amine (C50, 25 mg, 0.083 mmol) was then added and the reaction was stirred at ambient temperature for 16 h. The reaction was concentrated, dissolved in THF (500 μL), treated with TBAF (150 μL, 0.166 mmol) (1M in THF) and stirred at ambient temperature for an additional 16 h. The reaction was diluted with EtOAc (3 mL), washed with sat. aq. $NH_4Cl$ and water, dried ($Na_2SO_4$), filtered and concentrated. The crude material was purified by reverse phase HPLC (10-50% ACN in water, with 0.1% TFA as modifier) to yield 1-((R)-1-(3-(8-chloroimidazo[1,2-a]pyrazin-6-yl)phenyl)ethyl)-1-ethyl-3-(2-(3-hydroxycyclopentyl)ethyl)urea (la). LC-MS: 456.3 (M+1).

Step 2: (10R,E)-9-ethyl-10-methyl-3-oxa-7,9-diaza-2(6,8)-imidazo[1,2-a]pyrazina-1(1,3)-benzena-4(1,3)-cyclopentanacyclodecaphan-8-one (Example 1)

1-((R)-1-(3-(8-chloroimidazo[1,2-a]pyrazin-6-yl)phenyl)ethyl)-1-ethyl-3-(2-(3-hydroxycyclopentyl)ethyl)urea (la, 9.2 mg, 0.020 mmol) was dissolved in DMF (500 μL) and the solution was cooled to 0° C. Sodium hydride (0.807 mg, 0.020 mmol) (60% in mineral oil) was added and the reaction was stirred at 0° C. for 15 min and then warmed to ambient temperature and stirred for 30 min. The reaction was quenched with a few drops of water and filtered. The crude material was purified by reverse phase HPLC (10-50% ACN in water, with 0.1% TFA as modifier) to yield 2 sets of 2 diastereomers of (10R,E)-9-ethyl-10-methyl-3-oxa-7,9-diaza-2(6,8)-imidazo[1,2-a]pyrazina-1(1,3)-benzena-4(1,3)-cyclopentanacyclodecaphan-8-one (Examples 1A and 1B) whose absolute stereochemistry was not assigned.

Ex. 1A (mixture of 2 diastereomers): LC-MS: 420.5 (M+1).

Ex. 1B (mixture of 2 diastereomers): LC-MS: 420.5 (M+1).

Examples 2-9

The following compound in Table 1 were prepared according to the general procedures herein and in an analogous manner of that described in Scheme 1 and used to synthesize Example 1 using the appropriate intermediates referenced in Table 1. The starting materials were either prepared as described in the intermediates section, commercially available, or prepared from commercially available reagents using conventional reactions well known in the art. For Example 6 Step 1 was run under the same conditions as Step 1 in Scheme 4. For Example 6, the last step was run in THF. The diastereomers were optionally separated by reverse phase HPLC or flash silica chromatography with the more active diastereomer assumed by analogy to be the same relative configuration as Example 111. All examples are single enantiomers unless denoted with * in which case it was obtained as a mixture of isomers.

TABLE 1

| Ex. # | Structure | Name | Exact Mass [M + H]+ | Interm A | Interm C |
|---|---|---|---|---|---|
| 2 | 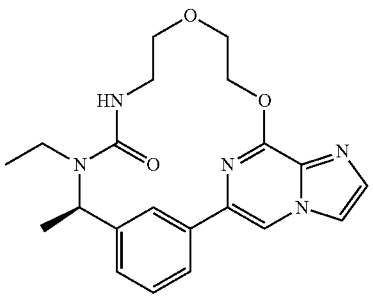 [SMILES: CCN1C(=O)NCCOCCOc2nc(cn3ccnc23)-c2cccc(c2)[C@H]1C] | (12R)-13-ethyl-12-methyl-12,13,16,17,19,20-hexahydro-6,22-(azeno)-11,7-(metheno)imidazo[1,2-o][1,18,4,6,15]dioxatriaza-cycloicosin-14(15H)-one | Calc'd 396.2, found 396.6 | A66 | C50 |
| 3 | 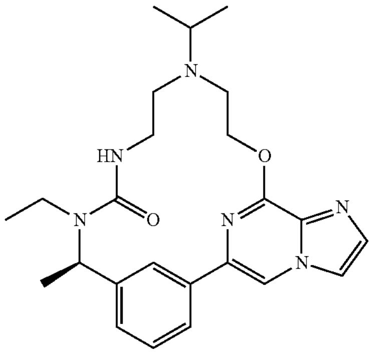 [SMILES: CCN1C(=O)NCCN(C(C)C)CCOc2nc(cn3ccnc23)-c2cccc(c2)[C@H]1C] | (12R)-13-ethyl-12-methyl-18-(propan-2-yl)-12,13,15,16,17,18,19,20-octahydro-14H-6,22-(azeno)-11,7-(metheno)imidazo[1,2-r][1,4,7,9,18]oxatetraaza-cycloicosin-14-one | Calc'd 437.3, found 437.5 | A70 | C50 |

TABLE 1-continued

| Ex. # | Structure | Name | Exact Mass [M + H]+ | Interm A | Interm C |
|---|---|---|---|---|---|
| 4* | 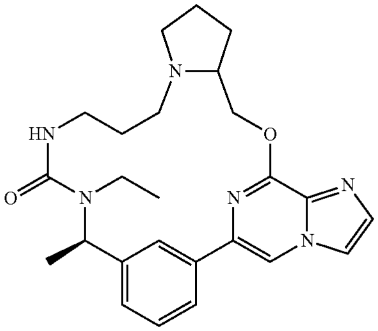 [SMILES: CCN1C(=O)NCCCN2CCCC2COc2nc(cn3ccnc23)-c2cccc(c2)[C@H]1C] | (12R)-13-ethyl-12-methyl-12,13,15,16,17,18,21,22,22a,23-decahydro-14H,20H-6,25-(azeno)-11,7-(metheno)imidazo[1,2-s]pyrrolo[2,1-c][1,4,8,10,19]oxatetraaza-cyclohenicosin-14-one | Calc'd 449.3, found 449.6 | A72 | C50 |
| 5* | 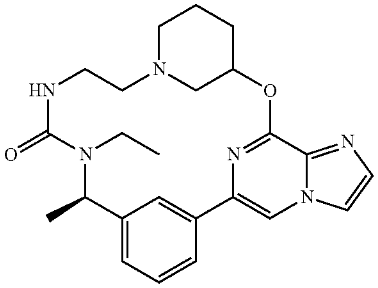 [SMILES: CCN1C(=O)NCCN2CCCC(C2)Oc2nc(cn3ccnc23)-c2cccc(c2)[C@H]1C] | (7R)-8-ethyl-7-methyl-18-oxa-8,10,13,21,24,26-hexaazapentacyclo[17.6.1.1~2,6~.1~13,17~.0~20,24~]octacosa-1(25),2(28),3,5,19(26),20,22-heptaen-9-one (non-preferred name) | Calc'd 435.3, found 435.3 | A68 | C50 |
| 6A | 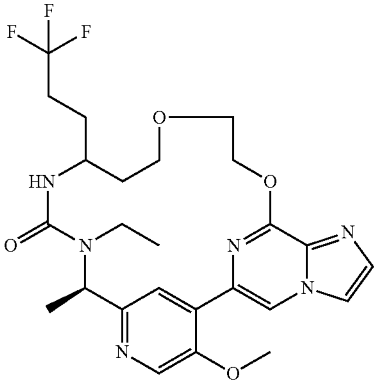 [SMILES: CCN1C(=O)NC(CCC(F)(F)F)CCOCCOc2nc(cn3ccnc23)-c2cc(ncc2OC)[C@H]1C] | (12R)-13-ethyl-8-methoxy-12-methyl-16-(3,3,3-trifluoropropyl)-12,13,15,16,17,18,20,21-octahydro-14H-6,23-(azeno)-11,7-(metheno)imidazo[2,1-f][1,4,7,13,16,18]dioxatetra-azacyclohenicosin-14-one | Calc'd 537.2, found 537.2 | A39 | C48 |
| 6B | 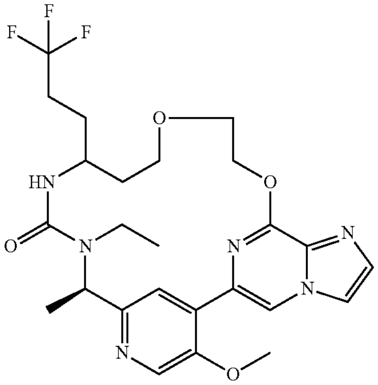 | (12R)-13-ethyl-8-methoxy-12-methyl-16-(3,3,3-trifluoropropyl)-12,13,15,16,17,18,20,21-octahydro-14H-6,23-(azeno)-11,7-(metheno)imidazo[2,1-f][1,4,7,13,16,18]dioxatetra-azacyclohenicosin-14-one | Calc'd 537.2, found 537.2 | A39 | C48 |

TABLE 1-continued

| Ex. # | Structure | Name | Exact Mass [M + H]+ | Interm A | Interm C |
|---|---|---|---|---|---|
| 7 | 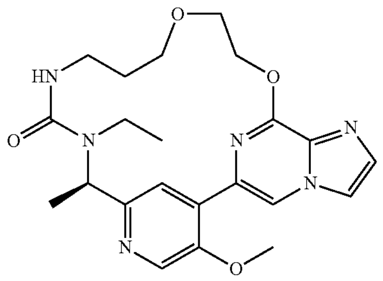 [SMILES: CCN1C(=O)NCCCOCCOc2nc(cn3ccnc23)-c2cc(ncc2OC)[C@H]1C] | (12R)-13-ethyl-8-methoxy-12-methyl-12,13,15,16,17,18,20,21-octahydro-14H-6,23-(azeno)-11,7-(metheno)imidazo[2,1-f][1,4,7,13,16,18]dioxatetra-azacyclohenicosin-14-one | Calc'd 441.2, found 441.6 | A128 | C48 |
| 8 | 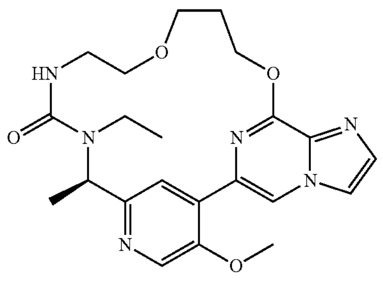 [SMILES: CCN1C(=O)NCCOCCCOc2nc(cn3ccnc23)-c2cc(ncc2OC)[C@H]1C] | (12R)-13-ethyl-8-methoxy-12-methyl-12,13,16,17,20,21-hexahydro-19H-6,23-(azeno)-11,7-(metheno)imidazo[1,2-o][1,18,4,6,9,15]dioxatetra-azacyclohenicosin-14(15H)-one | Calc'd 441.2, found 441.1 | A130 | C48 |
| 9A | 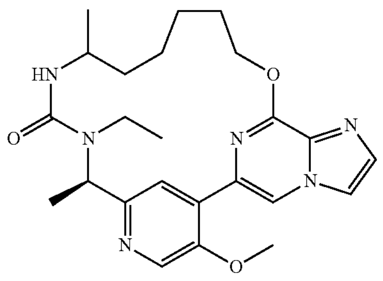 [SMILES: CCN1C(=O)NC(C)CCCCCOc2nc(cn3ccnc23)-c2cc(ncc2OC)[C@H]1C] | (12R)-13-ethyl-8-methoxy-12,16-dimethyl-12,13,16,17,18,19,20,21-octahydro-6,23-(azeno)-11,7-(metheno)imidazo[2,1-c][1,4,10,13,15]oxatetra-azacyclohenicosin-14(15H)-one | Calc'd 453.3, found 453.7 | A132 | C48 |
| 9B | 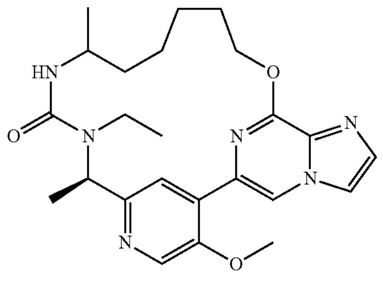 [SMILES: CCN1C(=O)NC(C)CCCCCOc2nc(cn3ccnc23)-c2cc(ncc2OC)[C@H]1C] | (12R)-13-ethyl-8-methoxy-12,16-dimethyl-12,13,16,17,18,19,20,21-octahydro-6,23-(azeno)-11,7-(metheno)imidazo[2,1-c][1,4,10,13,15]oxatetraaza-cyclohenicosin-14(15H)-one | Calc'd 453.3, found 453.8 | A132 | C48 |

Example 10

(R,E)-4-ethyl-3-methyl-13-oxa-4,6,9-triaza-1(6,8)-imidazo[1,2-a]pyrazina-2(1,3)-benzenacyclotridecaphan-5-one (Example 10)

SCHEME 2

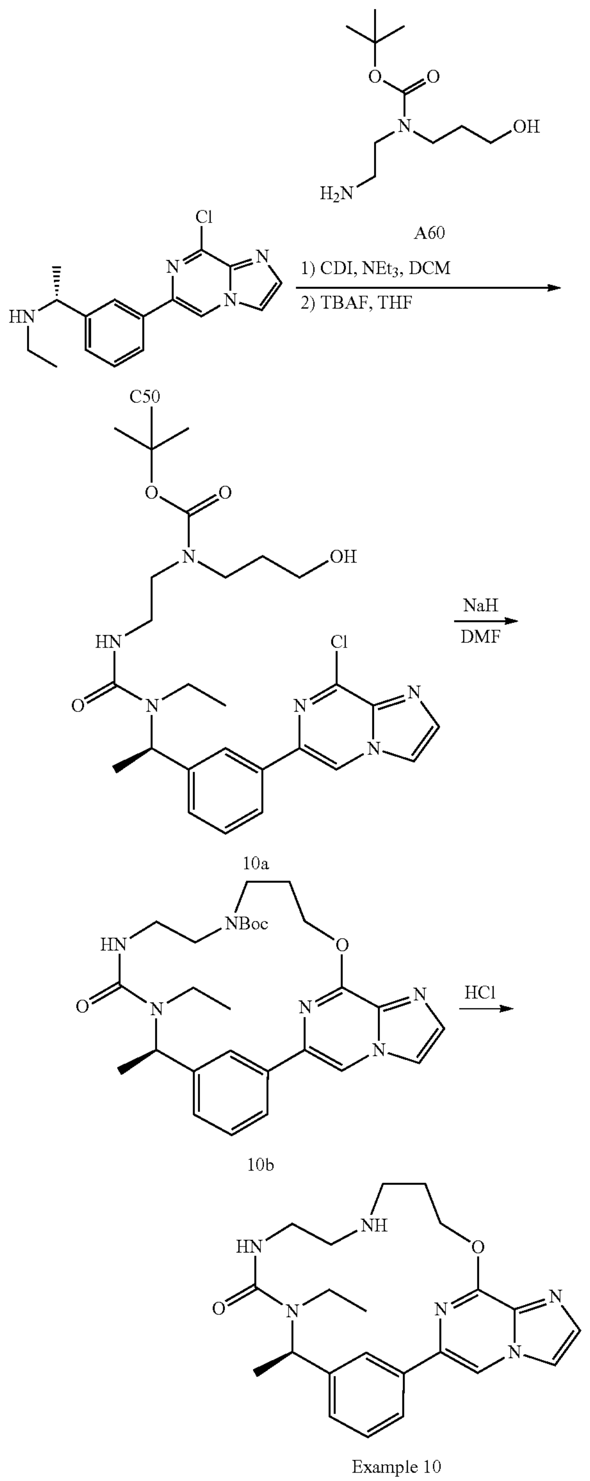

Example 10

Step 1: tert-butyl (R)-(2-(3-(1-(3-(8-chloroimidazo[1,2-a]pyrazin-6-yl)phenyl)ethyl)-3-ethylureido)ethyl)(3-hydroxypropyl)carbamate (10a)

tert-butyl (2-aminoethyl)(3-((tert-butyldimethylsilyl)oxy)propyl)carbamate (A60, 44.2 mg, 0.133 mmol) and triethylamine (37.1 μL, 0.266 mmol) were combined in DCM (332 μL). CDI (21.56 mg, 0.133 mmol) was added and the reaction was stirred at ambient temperature for 1 h. (R)-1-(3-(8-chloroimidazo[1,2-a]pyrazin-6-yl)phenyl)-N-ethylethan-1-amine (C50, 20 mg, 0.066 mmol) was then added and the reaction was stirred at ambient temperature for 16 h. The reaction was concentrated, dissolved in THF (500 μL), treated with TBAF (133 μL, 0.133 mmol) (1.0 M in THF) and stirred at ambient temperature for an additional 16 h. The reaction was diluted with EtOAc (3 mL), washed with sat. aq. $NH_4Cl$ and water, dried ($Na_2SO_4$), filtered and concentrated. The crude material was purified by reverse phase HPLC (10-95% ACN in water, with 0.1% TFA as modifier) to yield tert-butyl (R)-(2-(3-(1-(3-(8-chloroimidazo[1,2-a]pyrazin-6-yl)phenyl)ethyl)-3-ethylureido)ethyl)(3-hydroxypropyl)carbamate (10a). LC-MS: 545.4 (M+1).

Step 2: tert-butyl (R,E)-4-ethyl-3-methyl-5-oxo-13-oxa-4,6,9-triaza-1(6,8)-imidazo[1,2-a]pyrazina-2(1,3)-benzenacyclotridecaphane-9-carboxylate (10b)

tert-butyl (R)-(2-(3-(1-(3-(8-chloroimidazo[1,2-a]pyrazin-6-yl)phenyl)ethyl)-3-ethylureido)ethyl)(3-hydroxypropyl)carbamate (10a, 13.5 mg, 0.025 mmol) was dissolved in DMF (500 μL) and the solution was cooled to 0° C. Sodium hydride (0.991 mg, 0.025 mmol) (60% in mineral oil) was added and the reaction was stirred at 0° C. for 15 min and then warmed to ambient temperature and stirred for 30 min. The reaction was quenched with a few drops of water, extracted with EtOAc, dried ($Na_2SO_4$), filtered and concentrated to afford tert-butyl (R,E)-4-ethyl-3-methyl-5-oxo-13-oxa-4,6,9-triaza-1(6,8)-imidazo[1,2-a]pyrazina-2(1,3)-benzenacyclotridecaphane-9-carboxylate (10b), which was carried forward without purification. LC-MS: 509.4 (M+1).

Step 3: (R,E)-4-ethyl-3-methyl-13-oxa-4,6,9-triaza-1(6,8)-imidazo[1,2-a]pyrazina-2(1,3)-benzenacyclotridecaphan-5-one (Example 10)

tert-butyl (R,E)-4-ethyl-3-methyl-5-oxo-13-oxa-4,6,9-triaza-1(6,8)-imidazo[1,2-a]pyrazina-2(1,3)-benzenacyclotridecaphane-9-carboxylate (10b, 12.6 mg, 0.025 mmol) was dissolved in DCM (124 μL) and treated with HCl (2.034 μL, 0.025 mmol) (4M in dioxane). The reaction was stirred at ambient temperature for 15 min before being concentrated. The crude material was purified by reverse phase HPLC (5-50% ACN in water, with 0.1% TFA as modifier) to yield (R,E)-4-ethyl-3-methyl-13-oxa-4,6,9-triaza-1(6,8)-imidazo[1,2-a]pyrazina-2(1,3)-benzenacyclotridecaphan-5-one as a TFA salt (Example 10).

LC-MS: 409.5 (M+1).

Example 11

The following compound in Table 2 were prepared according to the general procedures herein and in an analogous manner of that described in Scheme 2 and used to synthesize Example 10 using the appropriate intermediates referenced in Table 2. The starting materials were either prepared as described in the intermediates section, commercially available, or prepared from commercially available reagents using conventional reactions well known in the art.

TABLE 2

| Ex. # | Structure | Name | Exact Mass [M + H]+ | Interm A | Interm C |
|---|---|---|---|---|---|
| 11 | 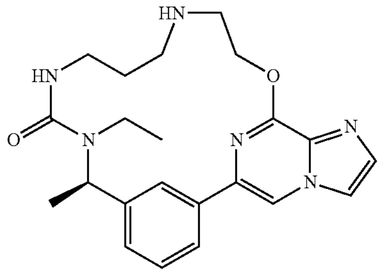 [SMILES: CCN1C(=O)NCCCNCCOc2nc(cn3ccnc23)-c2cccc(c2)[C@H]1C] | (12R)-13-ethyl-12-methyl-12,13,16,17,18,19,20,21-octahydro-6,23-(azeno)-11,7-(metheno)imidazo[1,2-s][1,4,8,10,19]oxatetraazacyclo-henicosin-14(15H)-one | Calc'd 409.2, found 409.4 | A62 | C50 |

Examples 12-21

The following compound in Table 3 were prepared according to the general procedures herein and in an analogous manner of that described in Scheme 1 and used to synthesize Example 1, without the TBS deprotection step if intermediates A were not TBS protected, using the appropriate intermediates referenced in Table 3 or commercially available amino alcohols. The starting materials were either prepared as described in the intermediates section, commercially available, or prepared from commercially available reagents using conventional reactions well known in the art. For Examples 19, 20 and 21, Step 1 was run under the same conditions as Step 1 in Scheme 4. For Examples 19 and 20, the TBS deprotection was done with $NH_4F$ instead of TBAF. The diastereomers were optionally separated by reverse phase HPLC or flash silica chromatography with the more active diastereomer assumed by analogy to be the same relative configuration as Example 111. All examples are single enantiomers unless denoted with * in which case it was obtained as a mixture of isomers.

TABLE 3

| Ex. # | Structure | Name | Exact Mass [M + H]+ | Interm A | Interm C |
|---|---|---|---|---|---|
| 12 | 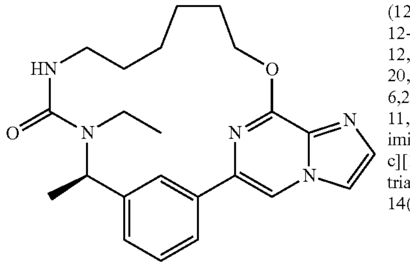 | (12R)-13-ethyl-12-methyl-12,13,16,17,18,19,20,21-octahydro-6,23-(azeno)-11,7-(metheno) imidazo[2,1-c][1,4,13,15]oxa-triazacyclohenicosin-14(15H)-one | Calc'd 408.2, found 408.2 | 6-amino-hexan-1-ol | C50 |
| 13 | 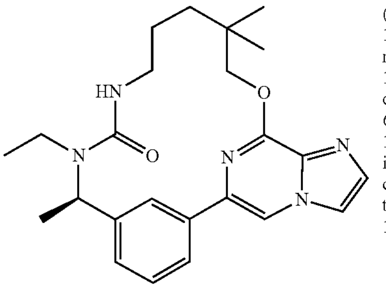 | (12R)-13-ethyl-12,19,19-tri-methyl-12,13,15,16,17,18,19,20-octahydro-14H-6,22-(azeno)-11,7-(metheno) imidazo[2,1-c][1,4,13,15]oxa-triazacycloicosin-14-one | Calc'd 422.3, found 422.2 | 5-amino-2,2-dimethyl-pentan-1-ol | C50 |

TABLE 3-continued

| Ex. # | Structure | Name | Exact Mass [M + H]+ | Interm A | Interm C |
|---|---|---|---|---|---|
| 14 | 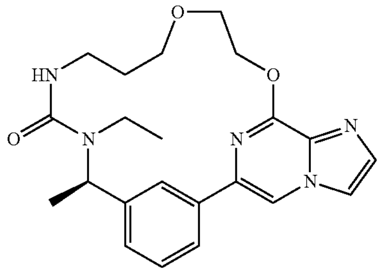 [SMILES: CCN1C(=O)NCCCOCCOc2nc(cn3ccnc23)-c2cccc(c2)[C@H]1C] | (12R)-13-ethyl-12-methyl-12,13,15,16,17,18,20,21-octahydro-14H-6,23-(azeno)-11,7-(metheno)imidazo[2,1-f][1,4,7,16,18]dioxatriaza-cyclohenicosin-14-one | Calc'd 410.2, found 410.7 | 2-(3-amino-propoxy) ethan-1-ol | C50 |
| 15 | 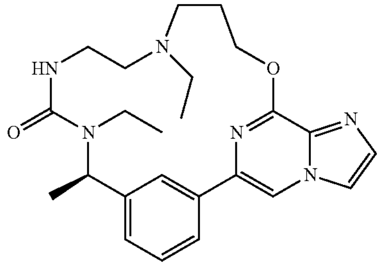 [SMILES: CCN1CCCOc2nc(cn3ccnc23)-c2cccc(c2)[C@@H](C)N(CC)C(=O)NCC1] | (12R)-13,18-diethyl-12-methyl-12,13,16,17,18,19,20,21-octahydro-6,23-(azeno)-11,7-(metheno) imidazo[2,1-c][1,4,13,15,18]oxa-tetraazacyclo-henicosin-14(15H)-one | Calc'd 437.3, found 437.5 | 3-((2-amino-ethyl) (ethyl) amino) propan-1-ol | C50 |
| 16* | 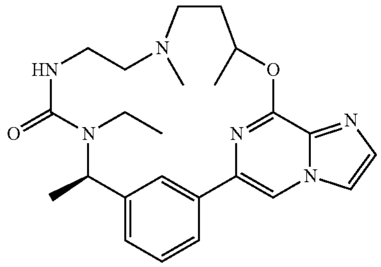 [SMILES: CCN1C(=O)NCCN(C)CCC(C)Oc2nc(cn3ccnc23)-c2cccc(c2)[C@H]1C] | (12R)-13-ethyl-12,18,21-trimethyl-12,13,16,17,18,19,20,21-octahydro-6,23-(azeno)-11,7-(metheno) imidazo[2,1-c][1,4,13,15,18]oxa-tetraazacyclo-henicosin-14(15H)-one | Calc'd 437.3, found 437.5 | 4-((2-amino-ethyl) (methyl) amino) butan-2-ol | C50 |
| 17 | 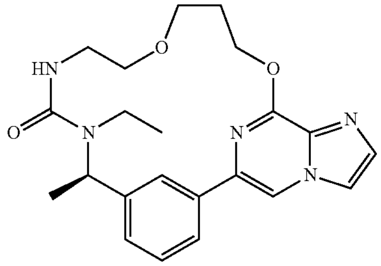 [SMILES: CCN1C(=O)NCCOCCCOc2nc(cn3ccnc23)-c2cccc(c2)[C@H]1C] | (12R)-13-ethyl-12-methyl-12,13,16,17,20,21-hexahydro-19H-6,23-(azeno)-11,7-(metheno) imidazo[1,2-o][1,18,4,6,15]dioxa-triazacyclohenicosin-14(15H)-one | Calc'd 410.2, found 410.3 | 3-(2-amino-ethoxy) propan-1-ol | C50 |
| 18* | 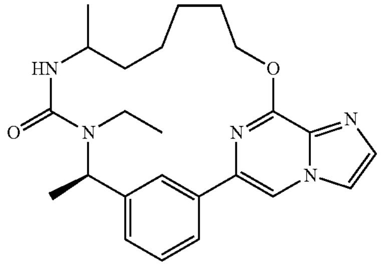 [SMILES: CCN1C(=O)NC(C)CCCCCOc2nc(cn3ccnc23)-c2cccc(c2)[C@H]1C] | (12R)-13-ethyl-12,16-dimethyl-12,13,16,17,18,19,20,21-octahydro-6,23-(azeno)-11,7-(metheno) imidazo[2,1-c][1,4,13,15]oxatriaza-cyclohenicosin-14(15H)-one | Calc'd 422.3, found 422.4 | 6-amino-heptan-1-ol | C50 |

TABLE 3-continued

| Ex. # | Structure | Name | Exact Mass [M + H]+ | Interm A | Interm C |
|---|---|---|---|---|---|
| 19A | 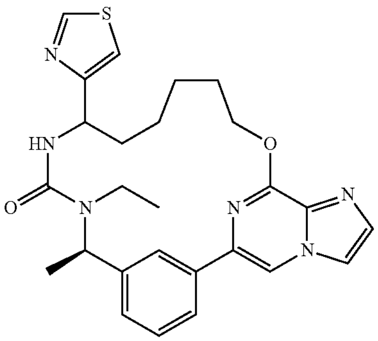 [SMILES: CCN1C(=O)NC(c2cscn2)CCCCCOc2nc(cn3ccnc23)-c2cccc(c2)[C@H]1C] | (12R)-13-ethyl-12-methyl-16-(1,3-thiazol-4-yl)-12,13,16,17,18,19,20,21-octahydro-6,23-(azeno)-11,7-(metheno)imidazo[2,1-c][1,4,13,15]oxa-triazacyclohenicosin-14(15H)-one | Calc'd 491.2, found 491.4 | A51 | C50 |
| 19B | 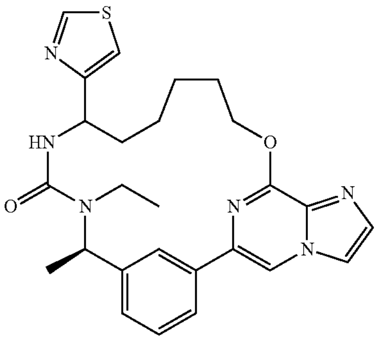 [SMILES: CCN1C(=O)NC(c2cscn2)CCCCCOc2nc(cn3ccnc23)-c2cccc(c2)[C@H]1C] | (12R)-13-ethyl-12-methyl-16-(1,3-thiazol-4-yl)-12,13,16,17,18,19,20,21-octahydro-6,23-(azeno)-11,7-(metheno)imidazo[2,1-c][1,4,13,15]oxa-triazacyclohenicosin-14(15H)-one | Calc'd 491.2, found 491.4 | A51 | C50 |
| 20* | 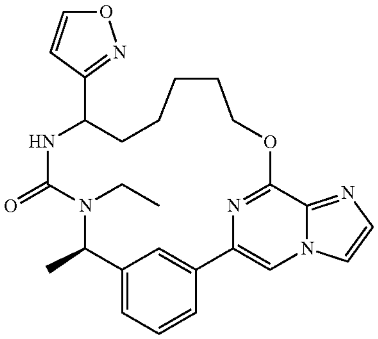 [SMILES: CCN1C(=O)NC(c2ccon2)CCCCCOc2nc(cn3ccnc23)-c2cccc(c2)[C@H]1C] | (12R)-13-ethyl-12-methyl-16-(1,2-oxazol-3-yl)-12,13,16,17,18,19,20,21-octahydro-6,23-(azeno)-11,7-(metheno)imidazo[2,1-c][1,4,13,15]oxa-triazacyclohenicosin-14(15H)-one | Calc'd 475.2, found 475.4 | A49 | C50 |
| 21A | 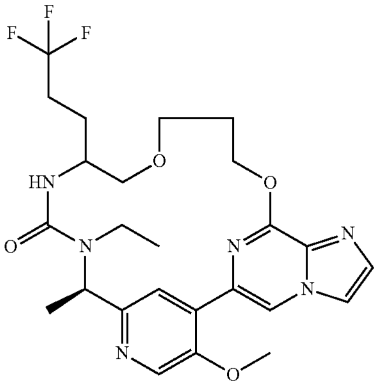 | (12R)-13-ethyl-8-methoxy-12-methyl-16-(3,3,3-trifluoropropyl)-12,13,16,17,20,21-hexahydro-19H-6,23-(azeno)-11,7-(metheno)imidazo[1,2-o][1,18,4,6,9,15]dioxa-tetraazacyclo-henicosin-14(15H)-one | Calc'd 537.2, found 537.3 | A86 | C48 |

TABLE 3-continued
| Ex. # | Structure | Name | Exact Mass [M + H]+ | Interm A | Interm C |
|---|---|---|---|---|---|
| 21B | 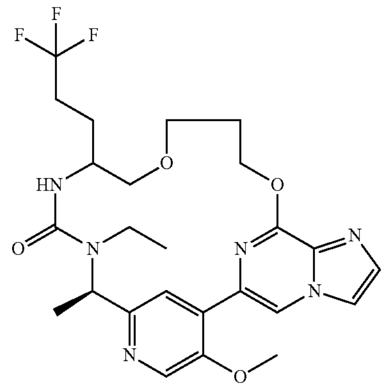 | (12R)-13-ethyl-8-methoxy-12-methyl-16-(3,3,3-trifluoropropyl)-12,13,16,17,20,21-hexahydro-19H-6,23-(azeno)-11,7-(metheno) imidazo[1,2-o][1,18,4,6,9,15] dioxatetraazacyclo-henicosin-14(15H)-one | Calc'd 537.2, found 537.3 | A86 | C48 |
Example 22
(R,2[7]E,6[2]Z)-10-ethyl-1-methyl-3-oxa-8,10-diaza-6(4,2)-thiazola-2(6,8)-imidazo[1,2-a]pyrazina-1(1,3)-benzenacycloundecaphan-9-one (Example 22)
SCHEME 3
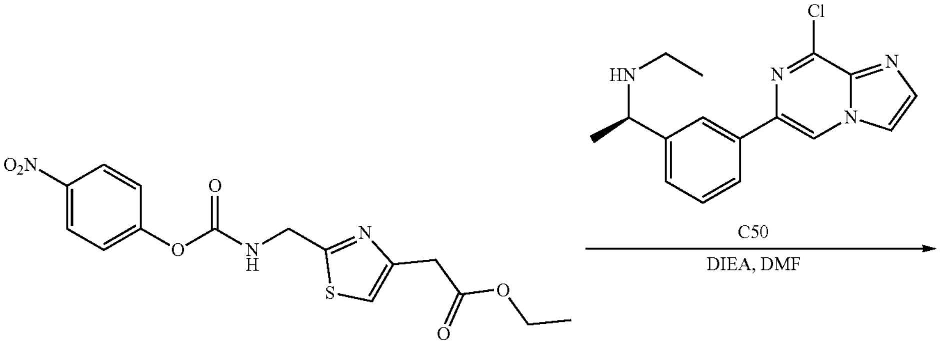
A53
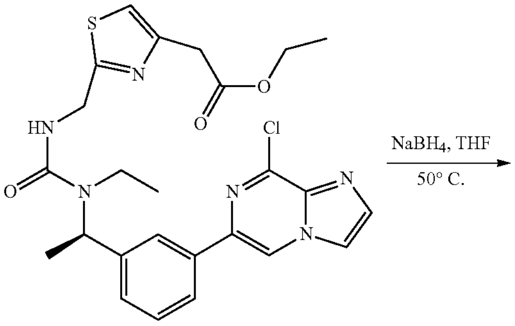
22a -continued

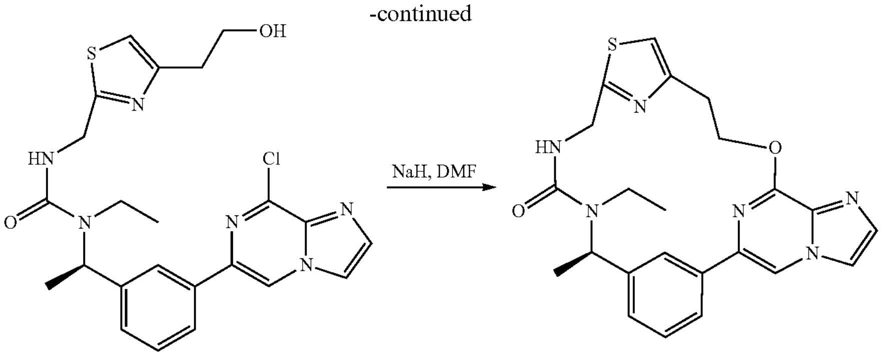

22b

Example 22

Step 1: ethyl (R)-2-(2-((3-(1-(3-(8-chloroimidazo[1,2-a]pyrazin-6-yl)phenvl)ethyl)-3-ethylureido)methyl)thiazol-4-yl)acetate (22a)

(R)-1-(3-(8-chloroimidazo[1,2-a]pyrazin-6-yl)phenyl)-N-ethylethan-1-amine (C50, 20 mg, 0.066 mmol) was dissolved in DMF (332 μL) and treated with ethyl 2-(2-((((4-nitrophenoxy)carbonyl)amino)methyl)thiazol-4-yl)acetate (A53) (29.2 mg, 0.080 mmol) and DIEA (23.23 μL, 0.133 mmol). The reaction was stirred at ambient temperature for 18 h. The reaction was diluted with EtOAc, washed with sat. aq. $NaHCO_3$, dried by filtering through a hydrophobic frit and concentrated. The crude material was purified by flash silica chromatography (0-70% EtOAc:EtOH 3:1 mix in hexanes gradient) to afford ethyl (R)-2-(2-((3-(1-(3-(8-chloroimidazo[1,2-a]pyrazin-6-yl)phenyl)ethyl)-3-ethylureido)methyl)thiazol-4-yl)acetate (22a). LC-MS: 528.4 (M+1).

Step 2: (R)-1-(1-(3-(8-chloroimidazo[1,2-a]pyrazin-6-yl)phenyl)ethyl)-1-ethyl-3-((4-(2-hydroxyethyl)thiazol-2-yl)methyl)urea (22b)

Ethyl (R)-2-(2-((3-(1-(3-(8-chloroimidazo[1,2-a]pyrazin-6-yl)phenyl)ethyl)-3-ethylureido)methyl)thiazol-4-yl)acetate (22a, 26 mg, 0.049 mmol) was dissolved in THF (247 μL) and treated with sodium borohydride (7.47 mg, 0.197 mmol). The reaction was heated to 50° C. for 48 h. The reaction was diluted with DCM, washed with sat. aq. $NaHCO_3$, dried by filtering through a hydrophobic frit and concentrated. The crude material was purified by reverse phase HPLC (13-38% ACN/water, with 0.1% TFA as modifier). The fractions containing product were neutralized with sat. aq. $NaHCO_3$, extracted with DCM and the organic portion was filtered through a hydrophobic frit and concentrated to give (R)-1-(1-(3-(8-chloroimidazo[1,2-a]pyrazin-6-yl)phenyl)ethyl)-1-ethyl-3-((4-(2-hydroxyethyl)thiazol-2-yl)methyl)urea (22b). LC-MS: 486.4 (M+1).

Step 3: (R,27E,$6^2$Z)-10-ethyl-11-methyl-3-oxa-8,10-diaza-6(4,2)-thiazola-2(6,8)-imidazo[1,2-a]pyrazina-1(1,3)-benzenacycloundecaphan-9-one (Example 22)

(R)-1-(1-(3-(8-chloroimidazo[1,2-a]pyrazin-6-yl)phenyl)ethyl)-1-ethyl-3-((4-(2-hydroxyethyl)thiazol-2-yl)methyl)urea (22b) (6.0 mg, 0.012 mmol) was dissolved in DMF (247 μL) and treated with sodium hydride (1.649 mg, 0.062 mmol) (60% in mineral oil) and stirred at ambient temperature for 2 h. The reaction was diluted with EtOAc, washed with water (×3), dried by filtering through a hydrophobic frit and concentrated to afford (R,27E,$6^2$Z)-10-ethyl-11-methyl-3-oxa-8,10-diaza-6(4,2)-thiazola-2(6,8)-imidazo[1,2-a]pyrazina-1(1,3)-benzenacycloundecaphan-9-one (Example 22). LC-MS: 449.3 (M+1).

Examples 23 and 24

The following compound in Table 4 were prepared according to the general procedures herein and in an analogous manner of that described in Scheme 3 and used to synthesize Example 1 using the appropriate intermediates referenced in Table 4. The starting materials were either prepared as described in the intermediates section, commercially available, or prepared from commercially available reagents using conventional reactions well known in the art.

TABLE 4

| Ex. # | Structure | Name | Exact Mass [M + H]+ | Interm A | Interm C |
|---|---|---|---|---|---|
| 23 | 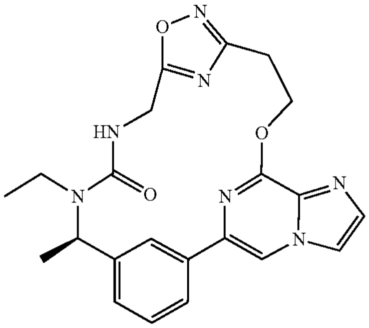 [SMILES: CCN1C(=O)NCc2nc(no2)CCOc2nc(cn3ccnc23)-c2cccc(c2)[C@H]1C] | (R,27E,64Z)-10-ethyl-11-methyl-3-oxa-8,10-diaza-6(3,5)-oxadiazola-2(6,8)-imidazo[1,2-a]pyrazina-1(1,3)-benzenacyclo-undecaphan-9-one | Calc'd 434.2, found 434.4 | A55 | C50 |
| 24 | 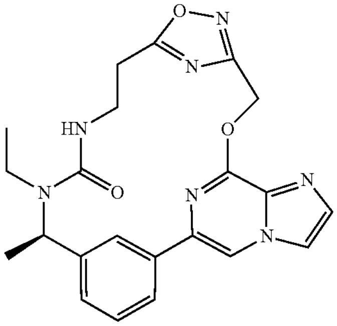 [SMILES: CCN1C(=O)NCCc2nc(no2)COc2nc(cn3ccnc23)-c2cccc(c2)[C@H]1C] | (R,27E,54Z)-10-ethyl-11-methyl-3-oxa-8,10-diaza-5(3,5)-oxadiazola-2(6,8)-imidazo[1,2-a]pyrazina-1(1,3)-benzenacyclo-undecaphan-9-one | Calc'd 434.2, found 434.3 | A57 | C50 |

Example 25

(3R,E)-4-ethyl-3,9-dimethyl-8-(trifluoromethyl)-12-oxa-4,6,9-triaza-1(6,8)-imidazo[1,2-a]pyrazina-2(1.3)-benzenacyclododecaphan-5-one (Example 25)

SCHEME 4

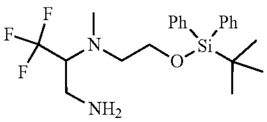

A91

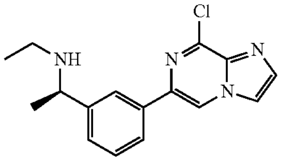

C50 triphosgene, $NaHCO_3$, DCM

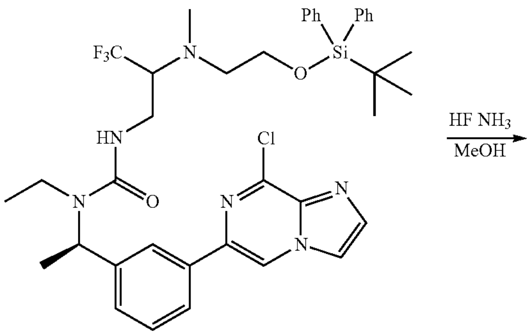

25a

-continued

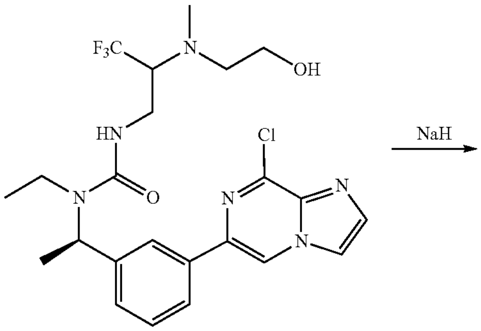

25b

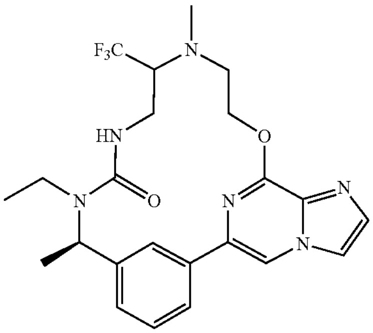

Example 25

Step 1: 3-(2-((2-((tert-butyldiphenylsilyl)oxy)ethyl)(methyl)amino)-3,3,3-trifluoropropyl)-1-((R)-1-(3-(8-chloroimidazo[1,2-a]pyrazin-6-yl)phenyl)ethyl)-1-ethylurea (25a)

N2-(2-((tert-butyldiphenylsilyl)oxy)ethyl)-3,3,3-trifluoro-N2-methylpropane-1,2-diamine HCl salt (A91, 100 mg, 0.201 mmol) was dissolved in DCM (669 μL) and treated with sat. aq. $NaHCO_3$(669 μL) and triphosgene (39.7 mg, 0.134 mmol). The reaction was stirred at ambient temperature for 30 min and was then treated with (R)-1-(3-(8-chloroimidazo[1,2-a]pyrazin-6-yl)phenyl)-N-ethylethan-1-amine HCl salt (C50, 50 mg, 0.134 mmol) and stirred overnight. LCMS showed formation of the desired product mass. The reaction was diluted with DCM, washed with sat. aq. $NaHCO_3$, dried by filtering through a hydrophobic frit and concentrated. The crude material was purified by flash silica chromatography (0-100% EtOAc:EtOH 3:1 mix in hexanes) to afford 3-(2-((2-((tert-butyldiphenylsilyl)oxy)ethyl)(methyl)-amino)-3,3,3-trifluoropropyl)-1-((R)-1-(3-(8-chloroimidazo[1,2-a]pyrazin-6-yl)phenyl)ethyl)-1-ethylurea (25a). LC-MS: 376.7 [(M+2)/2].

Step 2: 1-((R)-1-(3-(8-chloroimidazo[1,2-a]pyrazin-6-yl)phenyl)ethyl)-1-ethyl-3-(3,3,3-trifluoro-2-((2-hydroxyethyl)(methyl)amino)propyl)urea (25b)

3-(2-((2-((tert-butyldiphenylsilyl)oxy)ethyl)(methyl)amino)-3,3,3-trifluoropropyl)-1-((R)-1-(3-(8-chloroimidazo[1,2-a]pyrazin-6-yl)phenyl)ethyl)-1-ethylurea (25a, 12 mg, 0.016 mmol) was dissolved in MeOH (160 μL) and treated with ammonium fluoride (8.87 mg, 0.240 mmol). The reaction was stirred at ambient temperature overnight. LCMS showed formation of the desired product mass. The reaction was diluted with 3:1 $CHCl_3$:isopropanol, washed with sat. aq. $NaHCO_3$, dried by filtering through a hydrophobic frit and concentrated to afford 1-((R)-1-(3-(8-chloroimidazo[1,2-a]pyrazin-6-yl)phenyl)ethyl)-1-ethyl-3-(3,3,3-trifluoro-2-((2-hydroxyethyl)(methyl)amino)propyl)urea (25b) which was carried forward without purification.

LC-MS: 513.3 (M+1).

Step 3: (3R,E)-4-ethyl-3,9-dimethyl-8-(trifluoromethyl)-12-oxa-4,6,9-triaza-1(6,8)-imidazo[1,2-a]pyrazina-2(1,3)-benzenacyclododecaphan-5-one (Example 25)

1-((R)-1-(3-(8-chloroimidazo[1,2-a]pyrazin-6-yl)phenyl)ethyl)-1-ethyl-3-(3,3,3-trifluoro-2-((2-hydroxyethyl)(methyl)amino)propyl)urea (25b, 8.2 mg, 0.016 mmol) was dissolved in DMF (160 μL) and treated with sodium hydride (3.20 mg, 0.080 mmol) (60% in mineral oil). The reaction was stirred at 60° C. for 1 h. LCMS showed formation of the desired product mass. The reaction was diluted with DMSO and purified by reverse phase HPLC (13-38% ACN in water, with 0.1% TFA as modifier). The fractions containing product were treated with sat. aq. $NaHCO_3$, extracted with DCM and the organic portion was filtered through a hydrophobic frit and concentrated to give (3R,E)-4-ethyl-3,9-dimethyl-8-(trifluoromethyl)-12-oxa-4,6,9-triaza-1(6,8)-imidazo[1,2-a]pyrazina-2(1,3)-benzenacyclododecaphan-5-one (Example 25A, 1st eluting diastereomer) and (3R,E)-4-ethyl-3,9-dimethyl-8-(trifluoromethyl)-12-oxa-4,6,9-triaza-1(6,8)-imidazo[1,2-a]pyrazina-2(1,3)-benzenacyclododecaphan-5-one (Example 25B, 2nd eluting diastereomer). Ex. 25A LC-MS: 477.3 (M+1) Ex. 25B LC-MS: 477.3 (M+1)

Example 26

(3R,E)-4-ethyl-3,9-dimethyl-8-(trifluoromethyl)-13-oxa-4,6,9-triaza-1(6,8)-imidazo[1,2-a]pyrazina-2(1,3)-benzenacyclotridecaphan-5-one (Example 26)

SCHEME 5

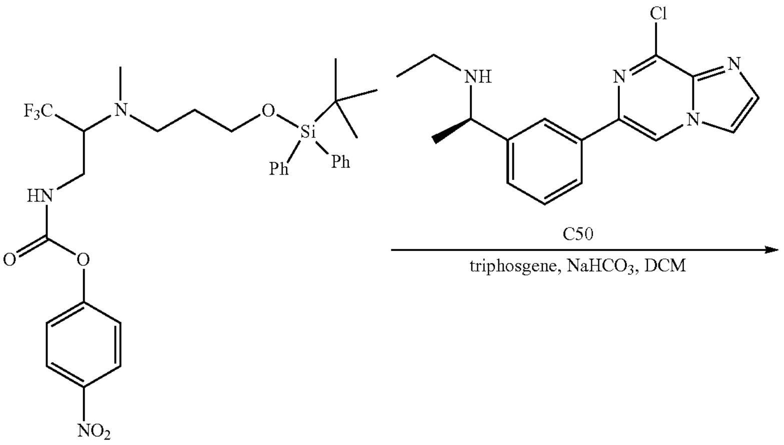

A97

-continued

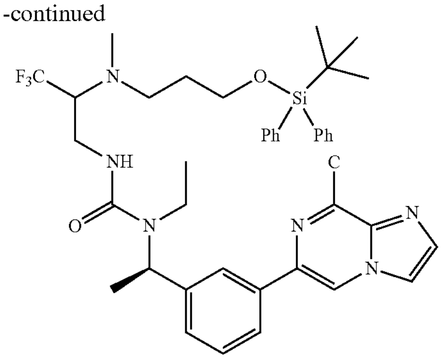

26a

Step 1: 3-(2-((3-((tert-butyldiphenylsilyl)oxy)propyl)(methyl)amino)-3,3,3-trifluoropropyl)-1-((R)-1-(3-(8-chloroimidazo[1,2-a]pyrazin-6-yl)phenyl)ethyl)-1-ethylurea (26a)

(R)-1-(3-(8-chloroimidazo[1,2-a]pyrazin-6-yl)phenyl)-N-ethylethan-1-amine (C50, 20 mg, 0.066 mmol) was dissolved in DMF (332 µL) and treated with 4-nitrophenyl (2-((3-((tert-butyldiphenylsilyl)oxy)propyl)(methyl)amino)-3,3,3-trifluoropropyl)carbamate (A97, 48.2 mg, 0.080 mmol) and DIEA (23.23 µL, 0.133 mmol). The reaction was stirred at ambient temperature overnight. LCMS showed formation of the desired product mass. The reaction was diluted with EtOAc, washed with sat. aq. $NaHCO_3$, dried by filtering through a hydrophobic frit and concentrated. The crude material was purified by flash silica chromatography (0-50% EtOAc:EtOH 3:1 mix in hexanes gradient) to afford 3-(2-((3-((tert-butyldiphenylsilyl)oxy)-propyl)(methyl)amino)-3,3,3-trifluoropropyl)-1-((R)-1-(3-(8-chloroimidazo[1,2-a]pyrazin-6-yl)phenyl)ethyl)-1-ethylurea (26a). LC-MS: 383.4 [(M+2)/2]

Example 26

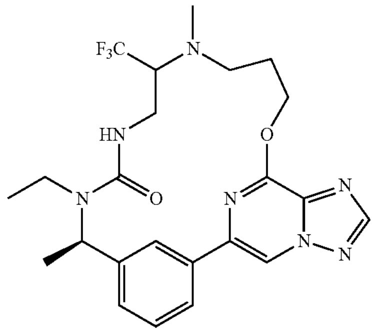

(3R,E)-4-ethyl-3,9-dimethyl-8-(trifluoromethyl)-13-oxa-4,6,9-triaza-1(6,8)-imidazo[1,2-a]pyrazina-2(1,3)-benzenacyclotridecaphan-5-one (Example 26)

Intermediate 26a was elaborated into Example 26 through the same method used to elaborate Intermediate 25a into Example 25. Ex. 26A LC-MS: 491.6 (M+1). Ex. 26B LC-MS: 491.6 (M+1).

Examples 27 and 28
(3R,7R,E)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-5-one (Example 27) and (3R,7R,E)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-5-one (Example 28)
SCHEME 6
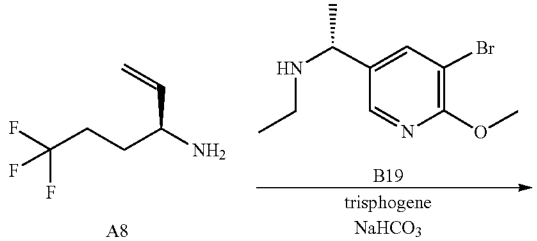
A8
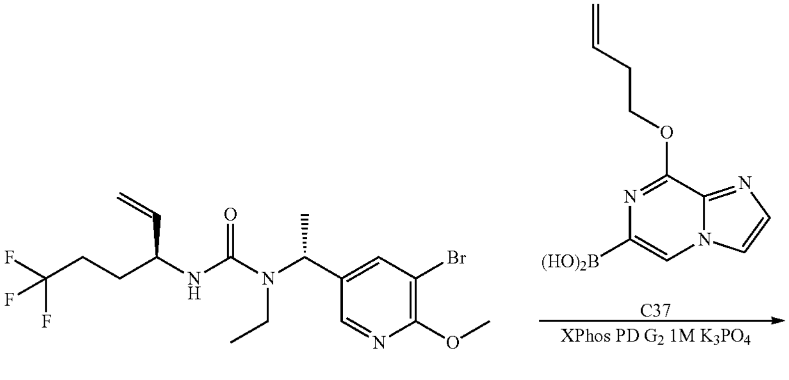
27a
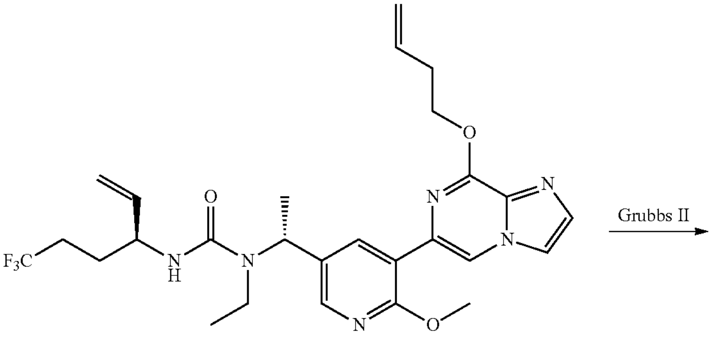
27b -continued

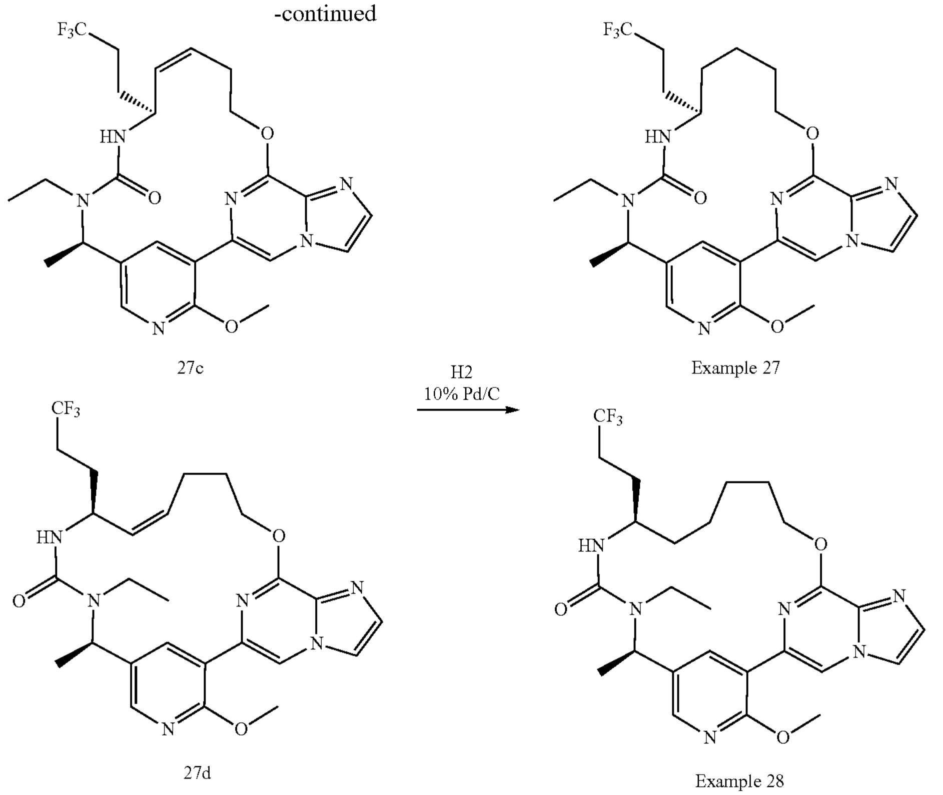

27c

Example 27

27d

Example 28

Step 1: 1-((R)-1-(5-bromo-6-methoxypyridin-3-yl)ethyl)-1-ethyl-3-((S)-6,6,6-trifluorohex-1-en-3-yl)urea (27a)

Triphosgene (91 mg, 0.308 mmol) was added to a solution of (S)-6,6,6-trifluorohex-1-en-3-amine hydrochloride (A8, 192 mg, 1.015 mmol) in DCM (2 mL) and sat. aq. $NaHCO_3$(2 mL) at ambient temperature and the solution was stirred for 1 h. The organic layer was separated, and the aqueous layer was washed with DCM (2×1 mL). The combined organic layers were dried ($Na_2SO_4$), filtered, and then added to (R)-1-(5-bromo-6-methoxypyridin-3-yl)-N-ethylethan-1-amine hydrochloride (B19, 100 mg, 0.338 mmol). The reaction was stirred for 1 h at ambient temperature and was then concentrated to 2 mL and purified by flash silica chromatography (0-50% EtOAc/EtOH 3:1 mix in hexanes gradient) to yield 1-((R)-1-(5-bromo-6-methoxypyridin-3-yl)ethyl)-1-ethyl-3-((S)-6,6,6-trifluorohex-1-en-3-yl)urea (27a). LC-MS: 438.2, 440.2 (M+1).

Step 2: 1-((R)-1-(5-(8-(but-3-en-1-yloxy)imidazo[1,2-a]pyrazin-6-yl)-6-methoxypyridin-3-yl)ethyl)-1-ethyl-3-((S)-6,6,6-trifluorohex-1-en-3-yl)urea (27b)

A solution of 1-((R)-1-(5-bromo-6-methoxypyridin-3-yl)ethyl)-1-ethyl-3-((S)-6,6,6-trifluorohex-1-en-3-yl)urea (27a, 148 mg, 0.338 mmol), (8-(but-3-en-1-yloxy)imidazo[1,2-a]pyrazin-6-yl)boronic acid (C37, 354 mg, 1.520 mmol), and 1 M aq. tripotassium phosphate (675 μL, 0.675 mmol) in dioxane (3377 μL) was degassed with nitrogen. XPhos Pd G2 (26.6 mg, 0.034 mmol) was added and the reaction was heated to 55° C. for 2 h. The reaction mixture was concentrated and purified by flash silica chromatography (0-50% EtOAc/EtOH 3:1 mix in hexanes gradient) to yield the 1-((R)-1-(5-(8-(but-3-en-1-yloxy)imidazo[1,2-a]pyrazin-6-yl)-6-methoxypyridin-3-yl)ethyl)-1-ethyl-3-((S)-6,6,6-trifluorohex-1-en-3-yl)urea (27b). LC-MS: 547.4 (M+1).

Step 3: ($1^7$E,3R,7S,8Z)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-8-en-5-one (27c) and ($1^7$E,3R,7S,8Z)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-8-en-5-one (27d)

Grubbs II catalyst (9.32 mg, 10.98 μmol) was added to a degassed solution of 1-((R)-1-(5-(8-(but-3-en-1-yloxy)imidazo[1,2-a]pyrazin-6-yl)-6-methoxypyridin-3-yl)ethyl)-1-ethyl-3-((S)-6,6,6-trifluorohex-1-en-3-yl)urea (27b, 30 mg, 0.055 mmol) in DCE (2744 μL) and the reaction was stirred at ambient temperature for 30 min and at 45° C. for 3 h. The reaction was quenched by the addition of water (0.1 mL) and concentrated. The crude material was purified by flash silica chromatography (0-100% EtOAc/EtOH 3:1 mix in hexanes gradient) to yield a mixture of ($1^7$E,3R,7S,8Z)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-8-en-5-one (27c) and ($1^7$E,3R,7S,8Z)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-8-en-5-one (27d). 27c LC-MS: 519.3 (M+1) 27d LC-MS: 533.4 (M+1).

Step 4: (3R,7R,E)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-5-one (Example 27) and (3R,7R,E)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-5-one (Example 28)

To a degassed solution of ($1^7$E,3R,7S,8Z)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-8-en-5-one and ($1^7$E,3R,7S,8Z)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-8-en-5-one (27d, 15 mg, 0.029 mmol) and ($1^7$E,3R,7S,8Z)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-8-en-5-one and ($1^7$E,3R,7S,8Z)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-8-en-5-one (27c, 15 mg, 0.029 mmol) in EtOAc (1446 μL) was added Pd (6.16 mg, 5.79 μmol) (10% on C) and the solution was placed under a balloon of hydrogen for 20 h. The reaction mixture was filtered and concentrated through a pad of Celite. The crude material was purified by flash silica chromatography (0 to 100% EtOAc/EtOH 3:1 mix in hexanes gradient) and then further purified by reverse phase HPLC (5-95% ACN in water, with 0.1% TFA as modifier) to yield (3R,7R,E)-4-ethyl-22-methoxy-3-methyl-7-(3,3,3-trifluoropropyl)-12-oxa-4,6-diaza-1(6,8)-imidazo[1,2-a]pyrazina-2(3,5)-pyridinacyclododecaphan-5-one (Example 27) and (3R,7R,E)-4-ethyl-22-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-5-one (Example 28).

Ex. 27: LC-MS: 521.3 (M+1). $^1$H NMR (500 MHz, Methanol-$d_4$) δ 9.14 (s, 1H), 8.44 (d, J=2.3 Hz, 1H), 8.33 (d, J=1.7 Hz, 1H), 8.15 (d, J=1.8 Hz, 1H), 8.04 (d, J=1.7 Hz, 1H), 5.87 (q, J=7.1 Hz, 1H), 4.99-4.90 (m, 1H), 4.65 (ddd, J=11.0, 9.1, 4.7 Hz, 1H), 4.14 (s, 3H), 4.04-4.00 (m, 1H), 3.16 (dq, J=14.0, 7.0 Hz, 1H), 2.95 (dq, J=15.5, 14.6, 8.1 Hz, 1H), 2.33-2.18 (m, 2H), 2.15-2.04 (m, 1H), 1.93-1.54 (m, 1OH), 1.10 (t, J=7.1 Hz, 3H).

Ex. 28: LC-MS: 535.3 (M+1). $^1$H NMR (500 MHz, Methanol-$d_4$) δ 9.27 (s, 1H), 8.60 (d, J=2.3 Hz, 1H), 8.34 (d, J=1.7 Hz, 1H), 8.21 (d, J=2.2 Hz, 1H), 8.02 (d, J=1.6 Hz, 1H), 5.97 (q, J=7.0 Hz, 1H), 5.00 (td, J=11.2, 4.9 Hz, 1H), 4.62 (td, J=11.2, 5.6 Hz, 1H), 4.18 (s, 3H), 4.16-4.07 (m, 1H), 3.16-3.02 (m, 2H), 2.29-2.17 (m, 2H), 2.06-1.84 (m, 2H), 1.82-1.32 (m, 11H), 0.97 (t, J=7.0 Hz, 3H).

Examples 29 and 30

The following compound in Table 5 were prepared according to the general procedures herein and in an analogous manner of that described in Scheme 6 and used to synthesize Example 27 and 28 using the appropriate intermediates referenced in Table 5. The starting materials were either prepared as described in the intermediates section, commercially available, or prepared from commercially available reagents using conventional reactions well known in the art.AcOH (1 equiv) was used as an additive in Step 3. The diastereomers were optionally separated by reverse phase HPLC or flash silica chromatography with the more active diastereomer assumed by analogy to be the same relative configuration as Example 111.

TABLE 5

| Ex. # | Structure | Name | Exact Mass [M + H]+ | Interm A | Interm B | Interm C |
|---|---|---|---|---|---|---|
| 29A | 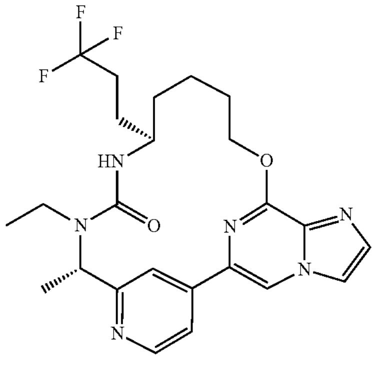 [SMILES: CCN1C(=O)N[C@@H](CCC(F)(F)F)CCCCOc2nc(cn3ccnc23)-c2ccnc(c2)[C@@H]1C] | (12S,16R)-13-ethyl-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one | Calc'd 491.2, found 491.3 | A8 | 1-(4-chloropyridin-2-yl)-N-ethylethan-1-amine | C37 |

TABLE 5-continued

| Ex. # | Structure | Name | Exact Mass [M + H]+ | Interm A | Interm B | Interm C |
|---|---|---|---|---|---|---|
| 29B | 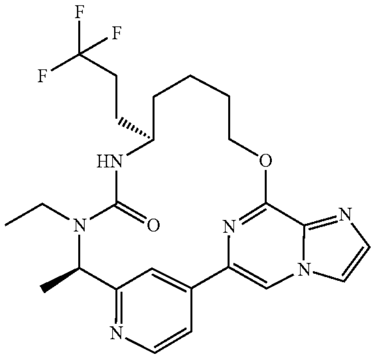 [SMILES: CCN1C(=O)N[C@@H](CCC(F)(F)F)CCCCOc2nc(cn3ccnc23)-c2ccnc(c2)[C@H]1C] | (12R,16R)-13-ethyl-12-methyl-16-(3,3,3-trifluoropropyl)-12,13,15,16,17,18,19,20-octahydro-14H-6,22-(azeno)-11,7-(metheno) imidazo[2,1-c][1,4,10,13,15] oxatetraazacyclo-icosin-14-one | Calc'd 491.2, found 491.3 | A8 | 1-(4-chloro-pyridin-2-yl)-N-ethyl-ethan-1-amine | C37 |
| 30 | 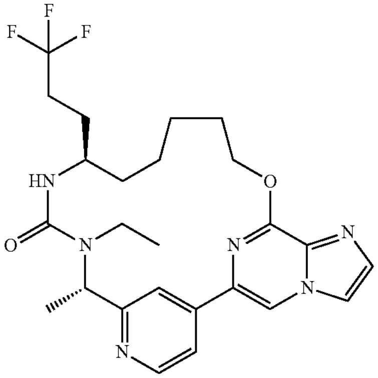 [SMILES: CCN1C(=O)N[C@@H](CCC(F)(F)F)CCCCCOc2nc(cn3ccnc23)-c2ccnc(c2)[C@@H]1C] | (12S,16R)-13-ethyl-12-methyl-16-(3,3,3-trifluoropropyl)-12,13,16,17,18,19,20,21-octa-hydro-6,23-(azeno)-11,7-(metheno)imidazo [2,1-c][1,4,10,13,15]oxatetra-azacyclohenicosin-14(15H)-one | Calc'd 505.3, found 505.3 | A8 | 1-(4-chloro-pyridin-2-yl)-N-ethyl-ethan-1-amine | C37 |

Examples 31 and 32

SCHEME 7

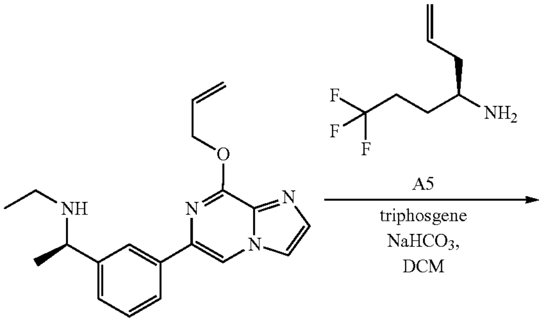

C50

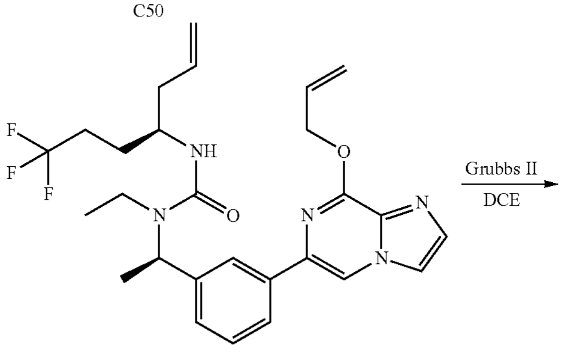

31a

-continued

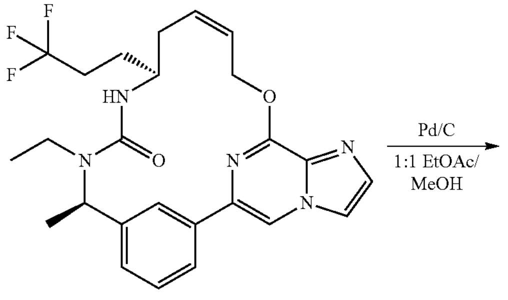

Example 31

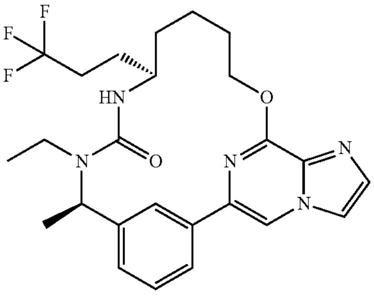

Example 32

Step 1: 1-((R)-1-(3-(8-(allyloxy)imidazo[1,2-a]pyrazin-6-yl)phen. 1)ethyl)-1-ethyl-3-((S)-7,7,7-trifluorohept-1-en-4-yl)urea (31a)

To a solution of (S)-7,7,7-trifluorohept-1-en-4-amine (A5, 36.3 mg, 0.217 mmol) in DCM (2 mL) and sat. aq. $NaHCO_3$ (2 mL) was added triphosgene (21.26 mg, 0.072 mmol) at 0° C., the resulting mixture was stirred at 0° C. for 30 min. (R)-1-(3-(8-(allyloxy)imidazo[1,2-a]pyrazin-6-yl)phenyl)-N-ethylethan-1-amine (C52, 70 mg, 0.217 mmol) was added and the mixture was stirred at 28° C. for 1 h. LCMS showed formation of the desired product mass. The reaction was poured into water (10 mL), extracted with DCM (3×5 mL). The combined organic phases were washed with brine (10 mL), dried ($Na_2SO_4$), filtered and concentrated. The crude material was purified by reverse phase HPLC (20-40% ACN in water, with 0.10% TFA as modifier) to afford 1-((R)-1-(3-(8-(allyloxy)imidazo[1,2-a]pyrazin-6-yl)phenyl)ethyl)-1-ethyl-3-((S)-7,7,7-trifluorohept-1-en-4-yl)urea (31a). LC-MS: 516.1 (M+1).

Step 2: ($1^7$E,3R,7S,9Z)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-9-en-5-one (Example 31)

To a solution of 1-((R)-1-(3-(8-(allyloxy)imidazo[1,2-a]pyrazin-6-yl)phenyl)ethyl)-1-ethyl-3-((S)-7,7,7-trifluorohept-1-en-4-yl)urea (31a, 40 mg, 0.078 mmol) in DCE (4 mL) was added Grubbs II catalyst (13 mg, 0.016 mmol) and the reaction was stirred at 15° C. for 1 h. LCMS showed trace product formation. More Grubbs II catalyst (13.17 mg, 0.016 mmol) was added and the reaction was stirred at 15° C. for 15 h. LCMS showed the formation of the desired product mass. The reaction mixture was concentrated and purified by preparative TLC (100% EtOAc) to afford ($1^7$E,3R,7S,9Z)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-9-en-5-one (Example 31). LC-MS: 488.1 (M+1). $^1$H NMR: (400 MHz, $CD_3OD$) δ 8.73 (s, 1H), 8.19-8.09 (m, 1H), 7.96 (s, 1H), 7.88 (s, 1H), 7.82-7.73 (m, 1H), 7.55-7.37 (m, 2H), 6.25-6.09 (m, 1H), 6.04-5.83 (m, 2H), 5.63-5.44 (m, 1H), 5.03 (br d, J=11.7 Hz, 1H), 4.05 (br s, 1H), 3.13 (dd, J=6.8, 15.8 Hz, 1H), 2.81-2.67 (m, 1H), 2.46 (br s, 1H), 2.33-2.20 (m, 3H), 1.91-1.75 (m, 2H), 1.69-1.60 (m, 3H), 1.13 (t, J=7.2 Hz, 3H).

Step 3: (3R,7R,E)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-5-one (Example 32)

To a solution of ($1^7$E,3R,7S,9Z)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-9-en-5-one (Example 31, 11 mg, 0.023 mmol) in MeOH (1 mL) and EtOAc (1 mL) was added Pd (12.01 mg, 0.011 mmol) (10% on C) and the reaction was stirred at 20° C. under H2 (15 psi) for 1.5 h. LCMS showed complete conversion. The reaction mixture was filtered and purified by reverse phase HPLC (29-59% ACN in water, with 0.1% TFA as modifier) to afford (3R,7R,E)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-5-one (Example 32). LC-MS: 490.2 (M+1). $^1$H NMR: (400 MHz, $CD_3OD$) δ 8.75-8.66 (m, 1H), 8.15 (d, J=1.2 Hz, 1H), 8.02 (s, 1H), 7.91 (d, J=1.6 Hz, 1H), 7.75 (d, J=7.0 Hz, 1H), 7.50-7.41 (m, 2H), 5.89 (br d, J=7.0 Hz, 1H), 4.84 (br d, J=9.8 Hz, 1H), 4.67 (dt, J=5.5, 10.0 Hz, 1H), 4.01 (br s, 1H), 3.26-3.11 (m, 1H), 2.89 (dd, J=7.2, 15.8 Hz, 1H), 2.37-2.17 (m, 2), 2.09 (br s, 1H), 1.95-1.60 (m, 1OH), 1.11 (t, J=7.0 Hz, 3H).

Examples 33-45

The following compound in Table 6 were prepared according to the general procedures herein and in an analogous manner of that described in Scheme 7 and used to synthesize Example 31 and 32 using the appropriate intermediates referenced in Table 6. The starting materials were either prepared as described in the intermediates section, commercially available, or prepared from commercially available reagents using conventional reactions well known in the art. Step 2 for Examples 41 and 42 was run in toluene at 80'° C. The diastereomers were optionally separated by reverse phase HPLC or flash silica chromatography with the more active diastereomer assumed by analogy to be the same relative configuration as Example 111.

TABLE 6

| Ex. # | Structure | Name | Exact Mass [M + H]+ | Interm A | Interm C |
|---|---|---|---|---|---|
| 33 | 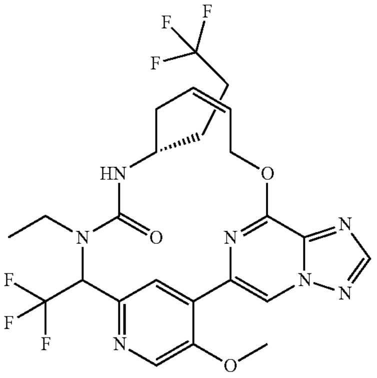 [SMILES: CCN1C(=O)N[C@@H](CCC(F)(F)F)C/C=C\COc2nc(cn3ncnc23)-c2cc(ncc2OC)C1C(F)(F)F] | (16S,18Z)-13-ethyl-8-methoxy-12-(trifluoromethyl)-16-(3,3,3-trifluoropropyl)-12,13,15,16,17,20-hexahydro-14H-6,22-(azeno)-11,7-(metheno)[1,2,4]triazolo[5,1-c][1,4,10,13,15]oxatetra-azacycloicosin-14-one | Calc'd 574.2, found 574.4 | A5 | C65 |

TABLE 6-continued

| Ex. # | Structure | Name | Exact Mass [M + H]+ | Interm A | Interm C |
| --- | --- | --- | --- | --- | --- |
| 34A | 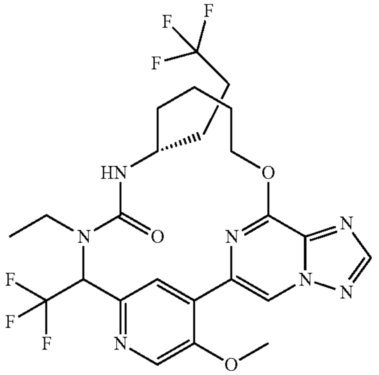 [SMILES: CCN1C(=O)N[C@@H](CCC(F)(F)F)CCCCOc2nc(cn3ncnc23)-c2cc(ncc2OC)C1C(F)(F)F] | (16R)-13-ethyl-8-methoxy-12-(trifluoro-methyl)-16-(3,3,3-trifluoropropyl)-12,13,15,16,17,18,19,20-octahydro-14H-6,22-(azeno)-11,7-(metheno)[1,2,4]triazolo[5,1-c][1,4,10,13,15]oxatetra-azacycloicosin-14-one | Calc'd 576.2, found 576.5 | A5 | C65 |
| 34B | 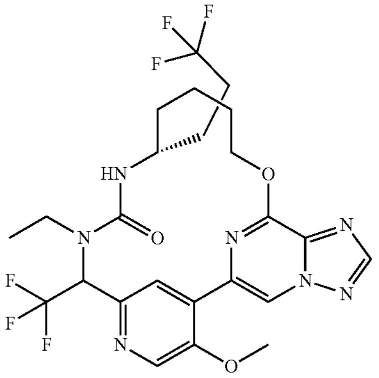 [SMILES: CCN1C(=O)N[C@@H](CCC(F)(F)F)CCCCOc2nc(cn3ncnc23)-c2cc(ncc2OC)C1C(F)(F)F] | (16R)-13-ethyl-8-methoxy-12-(trifluoromethyl)-16-(3,3,3-trifluoropropyl)-12,13,15,16,17,18,19,20-octahydro-14H-6,22-(azeno)-11,7-(metheno)[1,2,4]triazolo[5,1-c][1,4,10,13,15]oxatetra-azacycloicosin-14-one | Calc'd 576.2, found 576.5 | A5 | C65 |
| 35 | 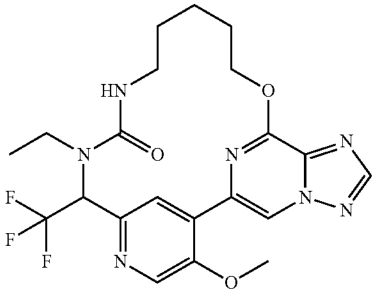 [SMILES: CCN1C(=O)NCCCCCOc2nc(cn3ncnc23)-c2cc(ncc2OC)C1C(F)(F)F] | 13-ethyl-8-methoxy-12-(trifluoromethyl)-12,13,15,16,17,18,19,20-octahydro-14H-6,22-(azeno)-11,7-(metheno)[1,2,4]triazolo[5,1-c][1,4,10,13,15]oxatetra-azacycloicosin-14-one | Calc'd 480.2, found 480.5 | 5-amino-pentan-1-ol | C65 |
| 36A | 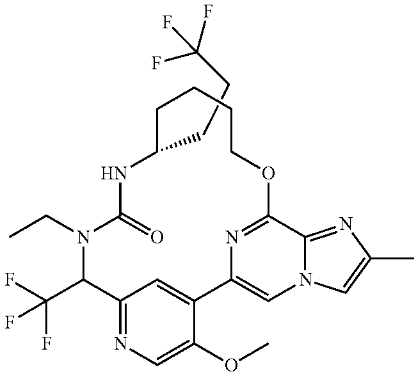 [SMILES: CCN1C(=O)N[C@@H](CCC(F)(F)F)CCCCOc2nc(cn3cc(C)nc23)-c2cc(ncc2OC)C1C(F)(F)F] | (16R)-13-ethyl-8-methoxy-2-methyl-12-(trifluoromethyl)-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacyclo-icosin-14-one | Calc'd 589.2, found 589.5 | A5 | C67 |

TABLE 6-continued

| Ex. # | Structure | Name | Exact Mass [M + H]+ | Interm A | Interm C |
|---|---|---|---|---|---|
| 36B | 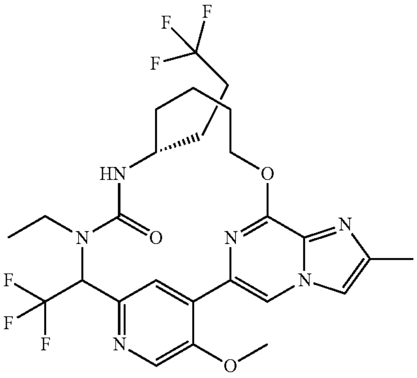 [SMILES: CCN1C(=O)N[C@@H](CCC(F)(F)F)CCCCOc2nc(cn3cc(C)nc23)-c2cc(ncc2OC)C1C(F)(F)F] | (16R)-13-ethyl-8-methoxy-2-methyl-12-(trifluoromethyl)-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacyclo-icosin-14-one | Calc'd 589.2, found 589.5 | A5 | C67 |
| 37 | 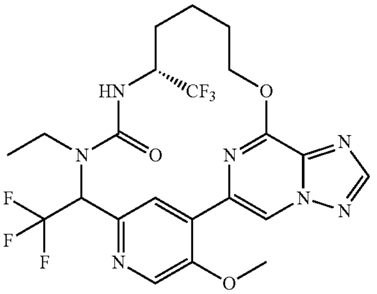 [SMILES: CCN1C(=O)N[C@@H](C(F)(F)F)CCCCOc2nc(cn3ncnc23)-c2cc(ncc2OC)C1C(F)(F)F] | (16R)-13-ethyl-8-methoxy-12,16-bis(trifluoromethyl)-12,13,15,16,17,18,19,20-octahydro-14H-6,22-(azeno)-11,7-(metheno)[1,2,4]triazolo[5,1-c][1,4,10,13,15]oxatetra-azacycloicosin-14-one | Calc'd 548.2, found 548.4 | A16 | C65 |
| 38 | 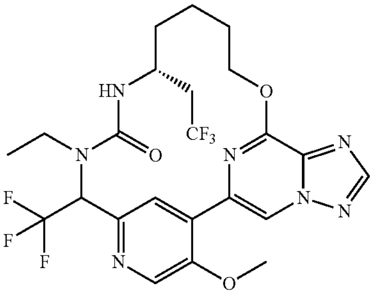 [SMILES: CCN1C(=O)N[C@@H](CC(F)(F)F)CCCCOc2nc(cn3ncnc23)-c2cc(ncc2OC)C1C(F)(F)F] | (16R)-13-ethyl-8-methoxy-16-(2,2,2-trifluoroethyl)-12-(trifluoromethyl)-12,13,15,16,17,18,19,20-octahydro-14H-6,22-(azeno)-11,7-(metheno)[1,2,4]triazolo[5,1-c][1,4,10,13,15]oxatetra-azacycloicosin-14-one | Calc'd 562.2, found 562.5 | A14 | C65 |
| 39A | 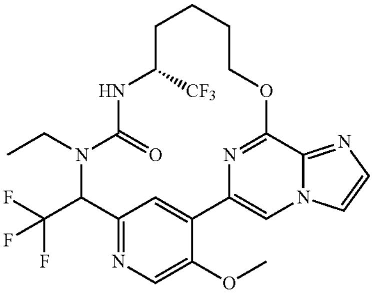 [SMILES: CCN1C(=O)N[C@@H](C(F)(F)F)CCCCOc2nc(cn3ccnc23)-c2cc(ncc2OC)C1C(F)(F)F] | (16R)-13-ethyl-8-methoxy-12,16-bis(trifluoromethyl)-12,13,15,16,17,18,19,20-octahydro-14H-6,22-(azeno)-11,7-(metheno)imidazo[2,1-c][1,4,10,13,15]oxatetra-azacycloicosin-14-one | Calc'd 547.2, found 547.4 | A16 | C68 |
| 39B | 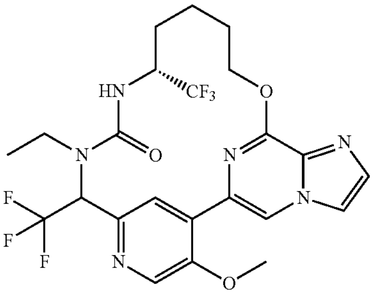 [SMILES: CCN1C(=O)N[C@@H](C(F)(F)F)CCCCOc2nc(cn3ccnc23)-c2cc(ncc2OC)C1C(F)(F)F] | (16R)-13-ethyl-8-methoxy-12,16-bis(trifluoromethyl)-12,13,15,16,17,18,19,20-octahydro-14H-6,22-(azeno)-11,7-(metheno)imidazo[2,1-c][1,4,10,13,15]oxatetra-azacycloicosin-14-one | Calc'd 547.2, found 547.4 | A16 | C68 |

TABLE 6-continued

| Ex. # | Structure | Name | Exact Mass [M + H]+ | Interm A | Interm C |
|---|---|---|---|---|---|
| 40 | 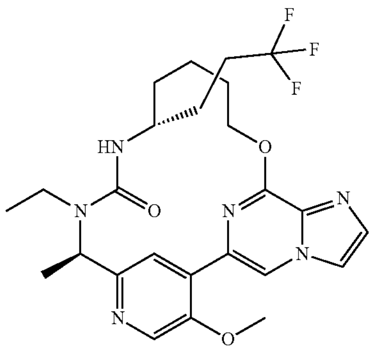 [SMILES: CCN1C(=O)N[C@@H](CCC(F)(F)F)CCCCOc2nc(cn3ccnc23)-c2cc(ncc2OC)[C@H]1C] | (12S,16R)-13-ethyl-8-methoxy-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetra-azacycloicosin-14-one | Calc'd 521.2, found 521.5 | A5 | C69 |
| 41A | 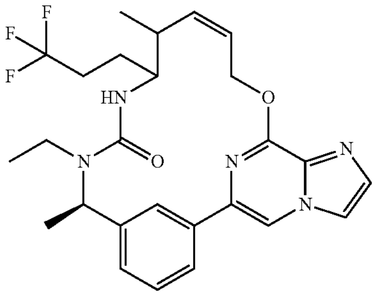 [SMILES: CCN1C(=O)NC(CCC(F)(F)F)C(C)/C=C\COc2nc(cn3ccnc23)-c2cccc(c2)[C@H]1C] | (12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriaza-cycloicosin-14-one | Calc'd 502.2, found 502.2 | A24 | C52 |
| 41B | 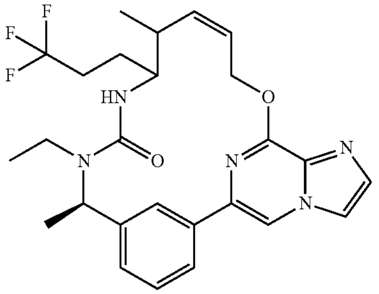 [SMILES: CCN1C(=O)NC(CCC(F)(F)F)C(C)/C=C\COc2nc(cn3ccnc23)-c2cccc(c2)[C@H]1C] | (12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriaza-cycloicosin-14-one | Calc'd 502.2, found 502.2 | A24 | C52 |
| 41C | 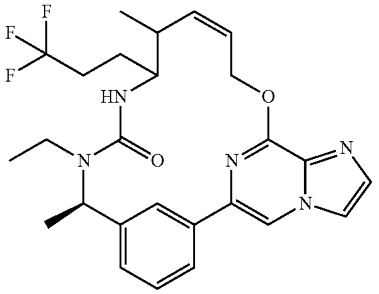 [SMILES: CCN1C(=O)NC(CCC(F)(F)F)C(C)/C=C\COc2nc(cn3ccnc23)-c2cccc(c2)[C@H]1C] | (12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriaza-cycloicosin-14-one | Calc'd 502.2, found 502.2 | A24 | C52 |
| 42A | 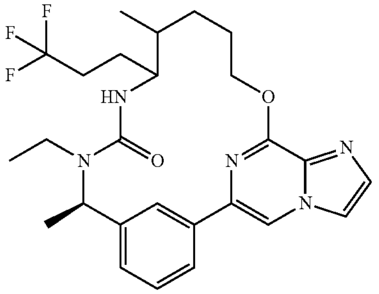 [SMILES: CCN1C(=O)NC(CCC(F)(F)F)C(C)CCCOc2nc(cn3ccnc23)-c2cccc(c2)[C@H]1C] | (12R)-13-ethyl-12,17-dimethyl-16-(3,3,3-trifluoropropyl)-12,13,15,16,17,18,19,20-octahydro-14H-6,22-(azeno)-11,7-(metheno) imidazo[2,1-c][1,4,13,15]oxatriaza-cycloicosin-14-one | Calc'd 504.3, found 504.3 | A24 | C52 |

TABLE 6-continued

| Ex. # | Structure | Name | Exact Mass [M + H]+ | Interm A | Interm C |
|---|---|---|---|---|---|
| 42B | 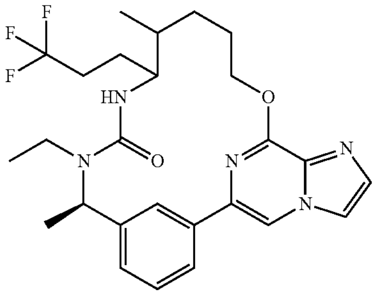 [SMILES: CCN1C(=O)NC(CCC(F)(F)F)C(C)CCCOc2nc(cn3ccnc23)-c2cccc(c2)[C@H]1C] | (12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriaza-cycloicosin-14-one | Calc'd 504.3, found 504.3 | A24 | C52 |
| 42C | 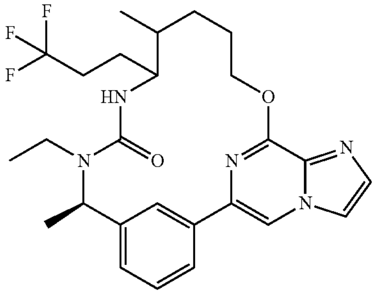 [SMILES: CCN1C(=O)NC(CCC(F)(F)F)C(C)CCCOc2nc(cn3ccnc23)-c2cccc(c2)[C@H]1C] | (12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriaza-cycloicosin-14-one | Calc'd 504.3, found 504.3 | A24 | C52 |
| 42D | 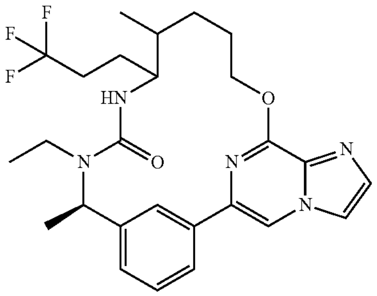 [SMILES: CCN1C(=O)NC(CCC(F)(F)F)C(C)CCCOc2nc(cn3ccnc23)-c2cccc(c2)[C@H]1C] | (12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13,15]oxatriaza-cycloicosin-14-one | Calc'd 504.3, found 504.3 | A24 | C52 |
| 43 | 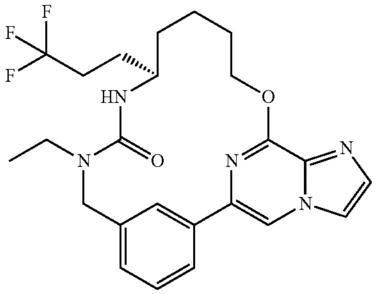 [SMILES: CCN1Cc2cccc(c2)-c2cn3ccnc3c(n2)OCCCC[C@H](CCC(F)(F)F)NC1=O] | (16R)-13-ethyl-16-(3,3,3-trifluoropropyl)-12,13,15,16,17,18,19,20-octahydro-14H-6,22-(azeno)-11,7-(metheno)imidazo[2,1-c][1,4,13,15]oxatriaza-cycloicosin-14-one | Calc'd 476.2, found 476.0 | A5 | C53 |
| 44 | 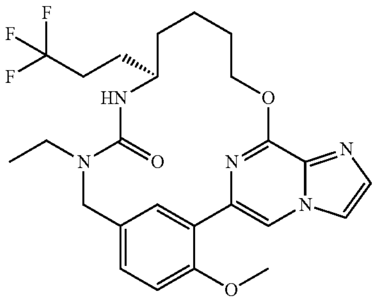 [SMILES: CCN1Cc2ccc(OC)c(c2)-c2cn3ccnc3c(n2)OCCCC[C@H](CCC(F)(F)F)NC1=O] | (16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,13,15]oxatriaza-cycloicosin-14-one | Calc'd 506.2, found 506.2 | A5 | C54 |

TABLE 6-continued
| Ex. # | Structure | Name | Exact Mass [M + H]+ | Interm A | Interm C |
|---|---|---|---|---|---|
| 45 | 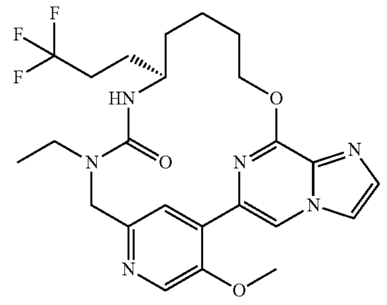 [SMILES: CCN1Cc2cc(c(OC)cn2)-c2cn3ccnc3c(n2)OCCCC[C@H](CCC(F)(F)F)NC1=O] | (16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,10,13,15]oxatetra-azacycloicosin-14-one | Calc'd 507.2, found 507.2 | A5 | C55 |
Ex. 41A and 41B were separated from a mixture by SFC separation ((S,S)-Whelk-01 ID column, 5-40% EtOH in $CO_2$ with 0.0500 diethylamine as additive).
Example 46 and 47
SCHEME 8
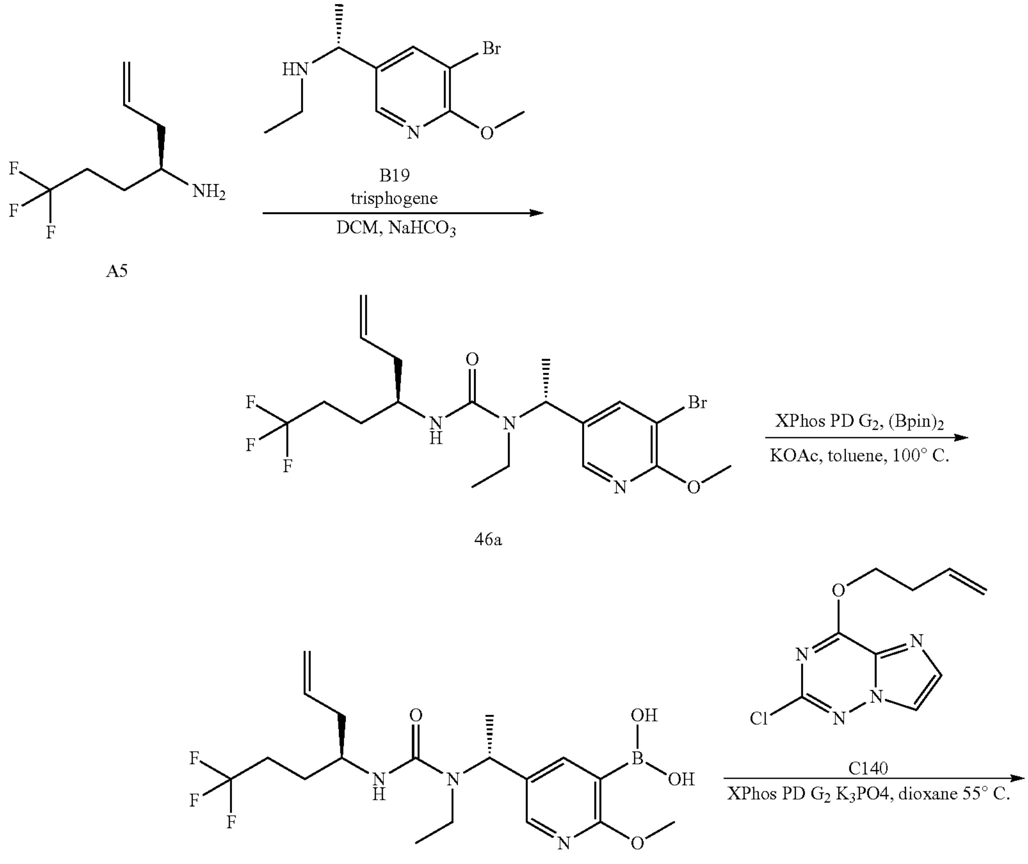
A5
46a
46b -continued

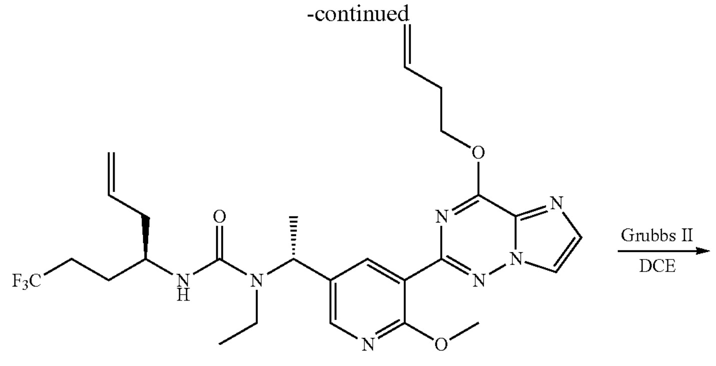

46c

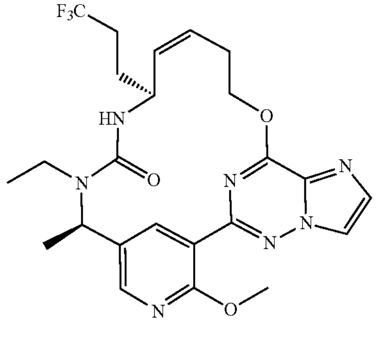

46d

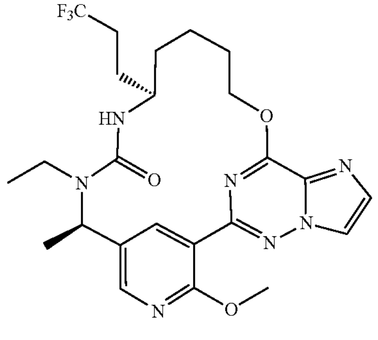

Example 46

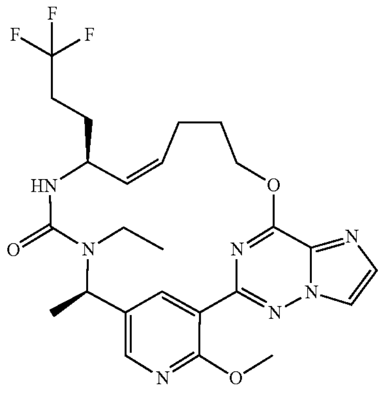

46e $H_2$, Pd/C
EtOAc

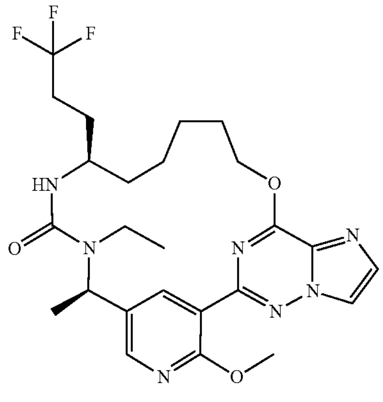

Example 47

Step 1: 1-((R)-1-(5-bromo-6-methoxypyridin-3-yl)ethyl)-1-ethyl-3-((S)-7,7,7-trifluorohept-1-en-4-yl)urea (46a)

Triphosgene (274 mg, 0.924 mmol) was added to a solution of (S)-7,7,7-trifluorohept-1-en-4-amine hydrochloride (A5, 620 mg, 3.04 mmol) in DCM (7 mL) and sat. aq. $NaHCO_3$(7 mL) at ambient temperature and the solution was stirred for 1 h. The organic layer was separated, and the aqueous layer washed with DCM (2×3 mL). The combined organics were dried ($Na_2SO_4$), filtered, and then added to (R)-1-(5-bromo-6-methoxypyridin-3-yl)-N-ethylethan-1-amine hydrochloride (B19, 300 mg, 1.015 mmol). Triethylamine (0.283 mL, 2.030 mmol) was added and the solution was stirred for 1 h. The mixture was concentrated to 2 mL and then purified by flash silica chromatography (0-50% EtOAc/EtOH 3:1 mix in hexanes gradient) to yield 1-((R)-1-(5-bromo-6-methoxypyridin-3-yl)ethyl)-1-ethyl-3-((S)-7,7,7-trifluorohept-1-en-4-yl)urea (46a). LC-MS: 452.2, 454.2 (M+1).

Step 2: (5-((R)-1-(1-ethyl-3-((S)-7,7,7-trifluorohept-1-en-4-yl)ureido)ethyl)-2-methoxypyridin-3-yl)boronic acid (46b)

1-((R)-1-(5-bromo-6-methoxypyridin-3-yl)ethyl)-1-ethyl-3-((S)-7,7,7-trifluorohept-1-en-4-yl)urea (46a, 150 mg, 0.332 mmol), bis(pinacolato)diboron (168 mg, 0.663 mmol), potassium acetate (98 mg, 0.995 mmol), and chloro (2-dicyclohexylphosphino-2',4',6'-tri-1-propyl-1,1'-biphenyl)(2'-amino-1,1'-biphenyl-2-yl) palladium(II) (26.1 mg, 0.033 mmol) were combined in degassed toluene (3 mL) and the reaction was heated at 100° C. for 1.5 h. The reaction mixture was filtered through a pad of Celite, concentrated and dried under high vacuum to yield (5-((R)-1-(1-ethyl-3-((S)-7,7,7-trifluorohept-1-en-4-yl)ureido)ethyl)-2-methoxypyridin-3-yl)boronic acid (46b). LC-MS: 418.3 (M+1).

Step 3: 1-((R)-1-(5-(4-(but-3-en-1-yloxy)imidazo[2,1-f][1,2,4]triazin-2-yl)-6-methoxypyridin-3-yl)ethyl)-1-ethyl-3-((S)-7,7,7-trifluorohept-1-en-4-yl)urea (46c)

A solution of (5-((R)-1-(1-ethyl-3-((S)-7,7,7-trifluorohept-1-en-4-yl)ureido)ethyl)-2-methoxypyridin-3-yl)boronic acid (46b, 107 mg, 0.256 mmol), 4-(but-3-en-1-yloxy)-2-chloroimidazo[2,1-f][1,2,4]triazine (C140, 23 mg, 0.102 mmol), and 1M aqueous tripotassium phosphate (0.205 mL, 0.205 mmol) in dioxane (1.1 mL) was degassed with nitrogen. XPhos Pd G2 (8.06 mg, 10.24 μmol) was added and the reaction was heated to 55° C. for 1 h. The reaction was concentrated and the crude material was purified by flash silica chromatography (0-50% EtOAc/EtOH 3:1 mix in hexanes gradient) to yield 1-((R)-1-(5-(4-(but-3-en-1-yloxy)imidazo[2,1-f][1,2,4]triazin-2-yl)-6-methoxypyridin-3-yl)ethyl)-1-ethyl-3-((S)-7,7,7-trifluorohept-1-en-4-yl)urea (46c). LC-MS: 562.3 (M+1).

Step 4: (13E,3R,7S,8Z)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-8-en-5-one (46d) and (13E,3R,7S,9E)-4-ethyl-22-methoxy-3-methyl-7-(3,3,3-trifluoropropyl)-13-oxa-4,6-diaza-1(2,4)-imidazo[2,1-][1,2,4]triazina-2(3,5)-pyridinacyclotridecaphan-9-en-5-one (46e)

A solution of 1-((R)-1-(5-(4-(but-3-en-1-yloxy)imidazo[2,1-f][1,2,4]triazin-2-yl)-6-methoxypyridin-3-yl)ethyl)-1-ethyl-3-((S)-7,7,7-trifluorohept-1-en-4-yl)urea (46c, 12.2 mg, 0.022 mmol) and acetic acid (1.368 μL, 0.024 mmol) in DCE (1086 μL) was degassed with nitrogen. Grubbs catalyst II (3.69 mg, 4.34 μmol) was added and the vial was sealed and stirred at ambient temperature for 3 h The reaction was quenched with water (3 drops) and concentrated. The crude material was purified by flash silica chromatography (0-100% EtOAc/EtOH 3:1 mix in hexanes gradient) to yield a mixture (13E,3R,7S,8Z)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclo-dodecaphan-8-en-5-one (46d) and (13E,3R,7S,9E)-4-ethyl-22-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-9-en-5-one (46e). 46d LC-MS: 520.3 (M+1). 46e LC/MS: 534.3 (M+1).

Step 5: (3R,7R,E)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-5-one (Example 46) and (3R,7R,E)-4-ethyl-22-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-5-one (Example 47)

To a degassed solution of (13E,3R,7S,8Z)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-8-en-5-one (46d) and (13E,3R,7S,9E)-4-ethyl-22-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-9-en-5-one (46e) (9.0 mg, 0.017 mmol) in EtOAc (2 mL) was added Pd (3.59 mg, 3.37 μmol) (10% on C) and the reaction was placed under a balloon of hydrogen for 2 h. The reaction mixture was filtered through a pad of Celite and concentrated. The crude mixture was dissolved in DMF (1 mL) and purified on reverse phase HPLC (10-100% ACN in water, with 0.1% TFA as modifier) to yield (3R,7R,E)-4-ethyl-22-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-5-one (Example 46) and (3R,7R,E)-4-ethyl-22-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-5-one (Example 47). Ex. 46: LC-MS: 522.3 (M+1). $^1$H NMR (500 MHz, Methanol-$d_4$) δ 8.23-8.19 (m, 3H), 7.82 (d, J=1.3 Hz, 1H), 5.85 (q, J=7.1 Hz, 1H), 4.86-4.78 (m, 1H), 4.76-4.68 (m, 1H), 4.04 (s, 3H), 4.02-3.96 (m, 1H), 3.20 (dd, J=15.9, 7.1 Hz, 1H), 3.00 (dq, J=15.1, 7.2 Hz, 1H), 2.30-2.15 (m, 2H), 2.15-2.06 (m, 1H), 1.84-1.63 (m, 8H), 1.63-1.54 (m, 2H), 1.11 (t, J=7.1 Hz, 3H).

Ex. 47: LC-MS: 536.3 (M+1). $^1$H NMR (500 MHz, Methanol-$d_4$) δ 8.42 (d, J=2.4 Hz, 1H), 8.29 (d, J=2.3, Hz, 1H), 8.27 (d, J=1.3, Hz, 1H), 7.87 (d, J=1.3 Hz, 1H), 5.95 (q, J=7.1 Hz, 1H), 4.90 (dt, J=10.9, 5.4 Hz, 1H), 4.82 (td, J=10.7, 6.0 Hz, 1H), 4.07 (s, 3H), 3.18-3.01 (m, 2H), 2.30-2.16 (m, 2H), 2.09-1.86 (m, 2H), 1.82-1.77 (m, 2H), 1.73-1.38 (m, TOH), 1.01 (t, J=7.1 Hz, 3H).

Example 48

Step 3: (3R,E)-4-ethyl-3,9-dimethyl-7-(3,3,3-trifluoropropyl)-12-oxa-4,6-diaza-1(6,8)-imidazo[1,2-a]pyrazina-2(1,3)-benzenacyclododecaphan-5-one (Example 48)

SCHEME 9

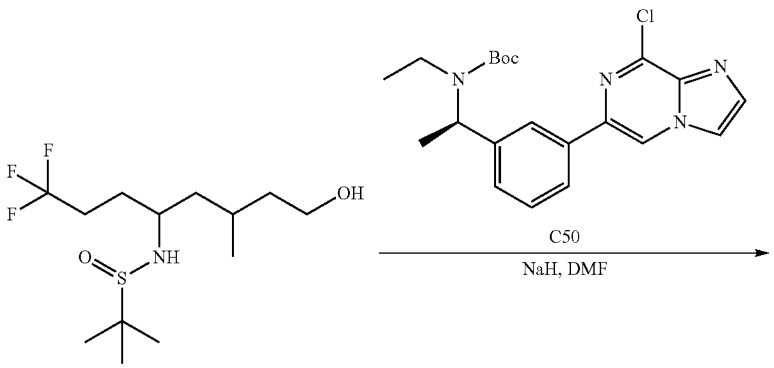

A31

-continued

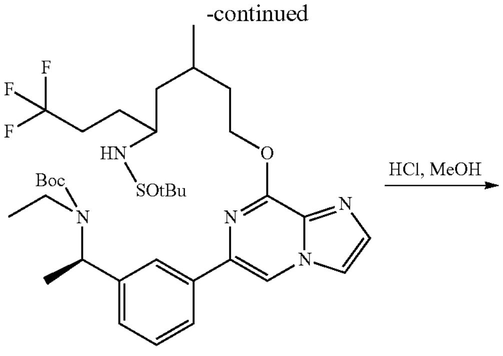

48a

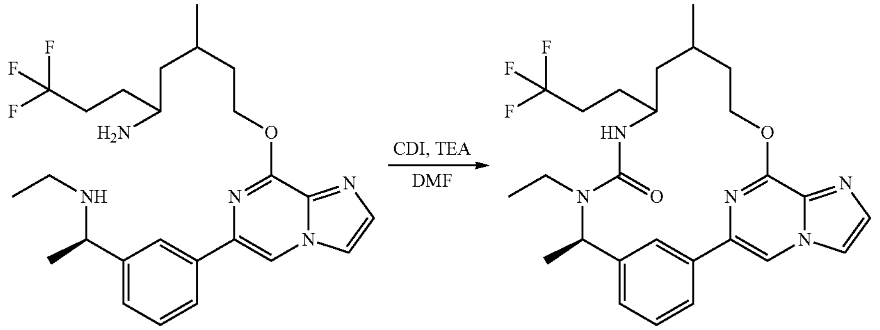

48b

Example 48

Step 1: tert-butyl ((1R)-1-(3-(8-((5-((tert-butylsulfinyl)amino)-8,8,8-trifluoro-3-methyloctyl)oxy)imidazo[1,2-a]pyrazin-6-yl)phenyl)ethyl)(ethyl)carbamate (48a)

To a solution of 2-methyl-N-(1,1,1-trifluoro-8-hydroxy-6-methyloctan-4-yl)propane-2-sulfinamide (A31, 297 mg, 0.935 mmol) in DMF (10 mL) was added sodium hydride (44.9 mg, 1.871 mmol) (60% in mineral oil) at 0° C. and the reaction stirred at 0° C. for 30 min. (R)-tert-butyl (1-(3-(8-chloroimidazo[1,2-a]pyrazin-6-yl)phenyl)ethyl) (ethyl)carbamate (C49, 250 mg, 0.624 mmol) was added and the reaction was stirred at 0° C. for 1 h. LCMS showed complete conversion. The reaction was poured into water (50 mL), extracted with EtOAc (3x20 mL). The combined organic layers were washed with brine (30 mL), dried ($Na_2SO_4$), filtered and concentrated. The crude material was purified by flash silica chromatography (100% EtOAc) to give tert-butyl ((1R)-1-(3-(8-((5-((tert-butylsulfinyl)amino)-8,8,8-trifluoro-3-methyloctyl)oxy)imidazo[1,2-a]pyrazin-6-yl)phenyl)ethyl)(ethyl)carbamate (48a). LC-MS: 682.6 (M+1).

Step 2: 8-((6-(3-((R)-1-(ethylamino)ethyl)phenyl)imidazo[1,2-a]pyrazin-8-yl)oxy)-1,1,1-trifluoro-6-methyloctan-4-amine (48b)

To a solution of tert-butyl ((1R)-1-(3-(8-((5-((tert-butylsulfinyl)amino)-8,8,8-trifluoro-3-methyloctyl)oxy)imidazo[1,2-a]pyrazin-6-yl)phenyl)ethyl)(ethyl)carbamate (48a, 190 mg, 0.279 mmol) in MeOH (3 mL) was added HCl (3 mL) (4 M in MeOH) and the reaction was stirred at 15° C. for 1 h. LCMS showed complete conversion. The reaction was concentrated to afford 8-((6-(3-((R)-1-(ethylamino)ethyl)phenyl)imidazo[1,2-a]pyrazin-8-yl)oxy)-1,1,1-trifluoro-6-methyloctan-4-amine (48b) as an HCl salt, which was carried forward without purification. LC-MS: 478.3 (M+1).

Step 3: (3R,E)-4-ethyl-3,9-dimethyl-7-(3,3,3-trifluoropropyl)-12-oxa-4,6-diaza-1(6,8)-imidazo[1,2-a]pyrazina-2(1,3)-benzenacyclododecaphan-5-one (Example 48)

To a solution of 8-((6-(3-((R)-1-(ethylamino)ethyl)phenyl)imidazo[1,2-a]pyrazin-8-yl)oxy)-1,1,1-trifluoro-6-methyloctan-4-amine (48b, 130 mg, 0.272 mmol) in DMF (4 mL) was added TEA (0.190 mL, 1.361 mmol) and CDI (88 mg, 0.544 mmol) at 15° C. and the reaction was stirred at 15° C. for 3 h. LCMS showed formation of the desired product mass. The reaction mixture was filtered. The crude material was purified by reverse phase HPLC (30-50% ACN in water, with 0.10% TFA as modifier) to give 2 sets of partially separable mixtures of diastereomers of (3R,E)-4-ethyl-3,9-dimethyl-7-(3,3,3-trifluoropropyl)-12-oxa-4,6-diaza-1(6,8)-imidazo[1,2-a]pyrazina-2(1,3)-benzenacyclododecaphan-5-one (Example 48A and Example 48B). Ex. 48A (mixture of 2 diastereomers): LC-MS: 504.3 (M+1). $^1$H NMR (400 MHz, $CD_3OD$) δ 8.83 (s, 1H), 8.16 (br d, J=3.9 Hz, 1H), 8.09-7.99 (m, 1H), 7.93 (br d, J=5.9 Hz, 1H), 7.82 (br d, J=7.4 Hz, 1H), 7.55-7.36 (m, 2H), 5.86 (br s, 1H), 4.70 (br s, 2H), 4.07 (br s, 2H), 3.26-3.15 (m, 1H), 3.08 (br d, J=7.0 Hz, 1H), 2.25 (br s, 2H), 2.17-1.82 (m, 4H), 1.74 (br s, 2H), 1.64 (br d, J=7.0 Hz, 3H), 1.18-0.88 (m, 6H)

Ex. 48B (mixture of 2 diastereomers): LC-MS: 504.3 (M+1). $^1$H NMR (400 MHz, $CD_3OD$) δ 8.80-8.68 (m, 1H), 8.20 (s, 1H), 8.11 (s, 1H), 8.16 (dd, J=1.8, 3.3 Hz, 1H), 7.96-7.90 (m, 1H), 7.75 (br dd, J=7.6, 15.1 Hz, 1H), 7.49-7.35 (m, 2H), 5.86 (br d, J=7.4 Hz, 1H), 5.02 (br d, J=8.6 Hz, 1H), 4.79 (br d, J=5.5 Hz, 1H), 4.12-3.87 (m, 1H), 3.25-2.92

(m, 2H), 2.38-1.85 (m, 6H), 1.75 (br d, J=6.7 Hz, 4H), 1.69-1.59 (m, 3H), 1.13-0.93 (m, 6H)

Examples 49 and 121

The following compound in Table 7 were prepared according to the general procedures herein and in an analogous manner of that described in Scheme 9 and used to synthesize Example 48 using the appropriate intermediates referenced in Table 7. For Example 121, step 3 was run in ACN with di-isopropylethylamine instead of triethylamine. The starting materials were either prepared as described in the intermediates section, commercially available, or prepared from commercially available reagents using conventional reactions well known in the art.

TABLE 7

| Ex. # | Structure | Name | Exact Mass [M + H]+ | Interm A | Interm C |
|---|---|---|---|---|---|
| 49 | 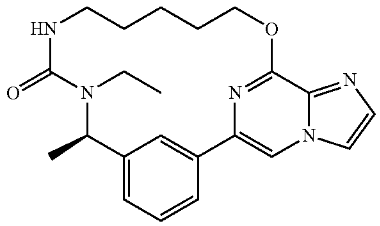 [SMILES: CCN1C(=O)NCCCCCOc2nc(cn3ccnc23)-c2cccc(c2)[C@H]1C] | (12R)-13-ethyl-12-methyl-12,13,15,16,17,18,19,20-octahydro-14H-6,22-(azeno)-11,7-(metheno)imidazo[2,1-c][1,4,13,15]oxatriaza-cycloicosin-14-one | Calc'd 394.2, found 394.3 | 5-(Boc-amino)-1-pentanol | C49 |
| 121A | 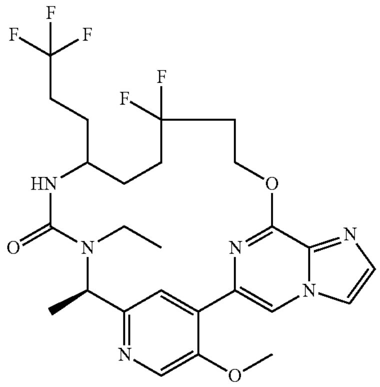 [SMILES: CCN1C(=O)NC(CCC(F)(F)F)CCC(F)(F)CCOc2nc(cn3ccnc23)-c2cc(ncc2OC)[C@H]1C] | (7R)-8-ethyl-14,14-difluoro-3-methoxy-7-methyl-11-(3,3,3-trifluoropropyl)-17-oxa-5,8,10,20,23,25-hexazatetracyclo[16.6.1.12,6.019,23]hexacosa-1(24),2(26),3,5,18(25),19,21-heptaen-9-one | Calc'd 571.2, found 571.2 | A79 | C47 |
| 121B | 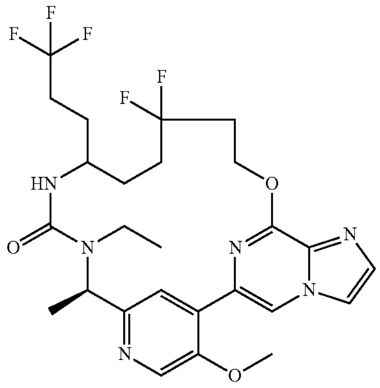 [SMILES: CCN1C(=O)NC(CCC(F)(F)F)CCC(F)(F)CCOc2nc(cn3ccnc23)-c2cc(ncc2OC)[C@H]1C] | (7R)-8-ethyl-14,14-difluoro-3-methoxy-7-methyl-11-(3,3,3-trifluoropropyl)-17-oxa-5,8,10,20,23,25-hexazatetracyclo[16.6.1.12,6.019,23]hexacosa-1(24),2(26),3,5,18(25),19,21-heptaen-9-one | Calc'd 571.2, found 571.2 | A79 | C47 |

Example 50

Step 3: (3R,7R,E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-5-one (Example 50)

SCHEME 10

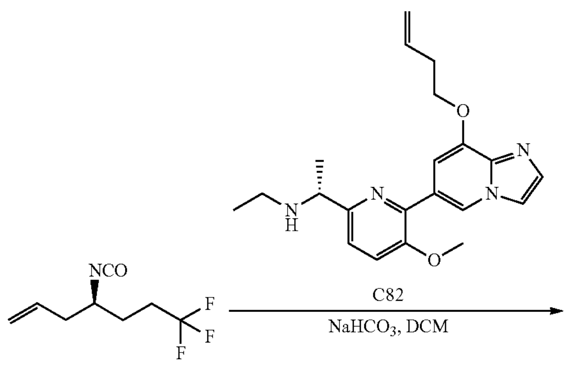

A126

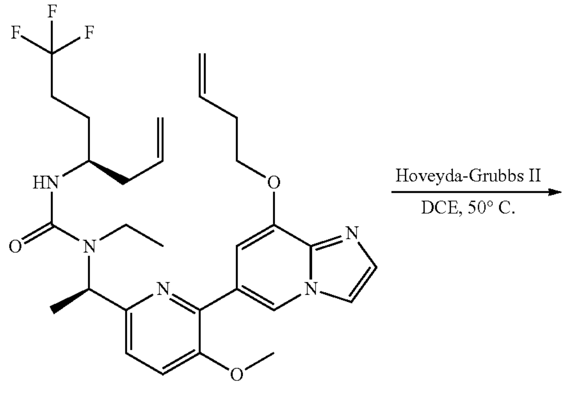

50A

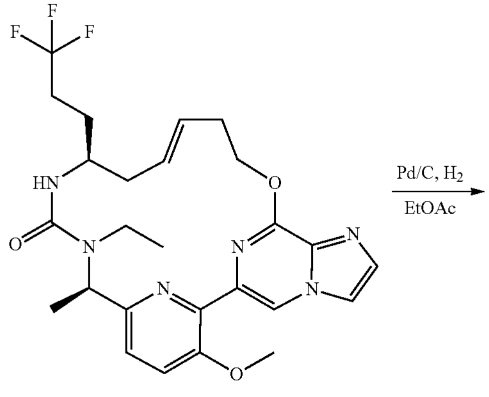

50B

-continued

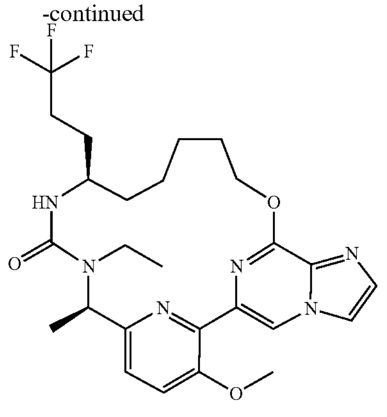

Example 50

Step 1: 1-((R)-1-(6-(8-(but-3-en-1-yloxy)imidazo[1,2-a]pyridin-6-yl)-5-methoxypyridin-2-yl)ethyl)-1-ethyl-3-((S)-7,7,7-trifluorohept-1-en-4-yl)urea (50a)

To a solution of (R)-1-(6-(8-(but-3-en-1-yloxy)imidazo[1,2-a]pyridin-6-yl)-5-methoxypyridin-2-yl)-N-ethylethan-1-amine (C82, 156 mg, 0.426 mmol) in DCM (2 mL) and sat. aq. $NaHCO_3$(2.0 mL) was added (S)-7,7,7-trifluoro-4-isocyanatohept-1-ene (A126, 82 mg, 0.426 mmol). The reaction was stirred at 20° C. for 2 h. LCMS showed complete conversion. The reaction was poured into water (20 mL), extracted with DCM (3×10 mL). The combined organic layers were washed with brine (10 mL), dried ($Na_2SO_4$), filtered and concentrated. The crude material was purified by flash silica chromatography (0-37% EtOAc in petroleum ether gradient) to afford 1-((R)-1-(6-(8-(but-3-en-1-yloxy)imidazo[1,2-a]pyridin-6-yl)-5-methoxypyridin-2-yl)ethyl)-1-ethyl-3-((S)-7,7,7-trifluorohept-1-en-4-yl)urea (50a). LC-MS: 560.3 (M+1).

Step 2: ($1^7$E,3R,7S,9E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-9-en-5-one (50b)

To a solution of 1-((R)-1-(6-(8-(but-3-en-1-yloxy)imidazo[1,2-a]pyridin-6-yl)-5-methoxypyridin-2-yl)ethyl)-1-ethyl-3-((S)-7,7,7-trifluorohept-1-en-4-yl)urea (50a, 100 mg, 0.179 mmol) in DCE (100 mL) was added Hoveyda Grubbs II catalyst (22.39 mg, 0.036 mmol) and the reaction was stirred at 50° C. for 12 h. LCMS showed complete conversion. The reaction mixture was concentrated and purified by flash silica chromatography (0-4% EtOAc in petroleum ether gradient) to give ($1^7$E,3R,7S,9E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-9-en-5-one (50b).

LC-MS: 532.3 (M+1).

Step 3: (3R,7R,E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-5-one (Example 50)

To a solution of ($1^7$E,3R,7S,9E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotri-decaphan-9- en-5-one (50b, 50 mg, 0.094 mmol) in EtOAc (1 mL) was added Pd (50.0 mg, 0.047 mmol) (10% on C) and the reaction was stirred at ambient temperature under H2 (15 psi) for 20 min. LCMS showed complete conversion. The reaction mixture was filtered, concentrated and purified by preparative TLC (20:1 EtOAc:MeOH) to afford (3R,7R,E)-4-ethyl-23-methoxy-3-methyl-7-(3,3,3-trifluoropropyl)-13-oxa-4,6-diaza-1(6,8)-imidazo[1,2-a]pyridina-2(2,6)-pyridinacyclotridecaphan-5-one (Example 50). LC-MS: 534.3 (M+1). $^1$H NMR (400 MHz, $CD_3OD$) δ 9.11 (d, J=1.2 Hz, 1H), 7.87 (d, J=1.2 Hz, 1H), 7.77 (s, 1H), 7.59-7.35 (m, 3H), 5.94-5.80 (m, 2H), 4.54-4.27 (m, 2H), 4.03 (s, 4H), 3.16-3.01 (m, 2H), 2.33-2.11 (m, 2H), 1.98-1.82 (m, 2H), 1.80-1.67 (m, 2H), 1.63-1.44 (m, 9H), 0.84 (t, J=7.0 Hz, 3H).

Example 51

The following compound in Table 8 were prepared according to the general procedures herein and in an analogous manner of that described in Scheme 10 and used to synthesize Example 50 using the appropriate intermediates referenced in Table 8. The starting materials were either prepared as described in the intermediates section, commercially available, or prepared from commercially available reagents using conventional reactions well known in the art.

TABLE 8

| Ex. # | Structure | Name | Exact Mass [M + H]+ | Interm A | Interm C |
|---|---|---|---|---|---|
| 51 | 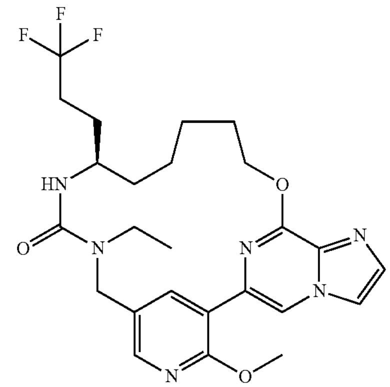 [SMILES: CCN1Cc2cnc(OC)c(c2)-c2cn3ccnc3c(n2)OCCCCC[C@H](CCC(F)(F)F)NC1=O] | (16R)-13-ethyl-8-methoxy-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one | Calc'd 521.2, found 521.3 | A126 | C112 |

Examples 52-73

The following compound in Table 9 were prepared according to the general procedures herein and in an analogous manner of that described in the last 2 steps of Scheme 10 and used to synthesize Example 50 using the appropriate intermediates referenced in Table 9. 1 eq of acetic acod was added to the ring closing metathesis step. The starting materials were either prepared as described in the intermediates section, commercially available, or prepared from commercially available reagents using conventional reactions well known in the art. The diastereomers were optionally separated by reverse phase HPLC or flash silica chromatography with the more active diastereomer assumed by analogy to be the same relative configuration as Example 111.

TABLE 9

| Ex. # | Structure | Name | Exact Mass [M + H]+ | Interm A |
|---|---|---|---|---|
| 52A | 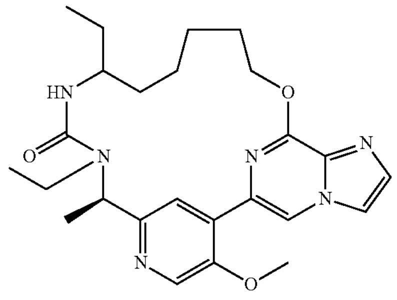 [SMILES: CCC1CCCCCOc2nc(cn3ccnc23)-c2cc(ncc2OC)[C@@H](C)N(CC)C(=O)N1] | (12R)-13,16-diethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 467.3, found 467.3 | A101 |
| 52B | 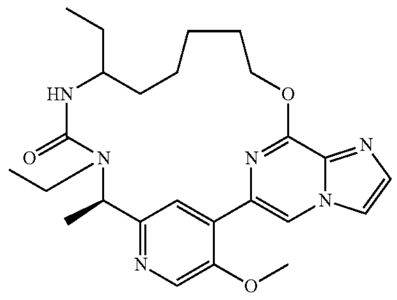 [SMILES: CCC1CCCCCOc2nc(cn3ccnc23)-c2cc(ncc2OC)[C@@H](C)N(CC)C(=O)N1] | (12R)-13,16-diethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 467.3, found 467.3 | A101 |
| 53A | 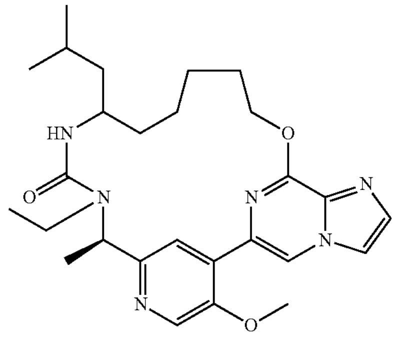 [SMILES: CCN1C(=O)NC(CC(C)C)CCCCCOc2nc(cn3ccnc23)-c2cc(ncc2OC)[C@H]1C] | (12R)-13-ethyl-8-methoxy-12-methyl-16-(2-methylpropyl)-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 495.3, found 495.3 | A100 |
| 53B | 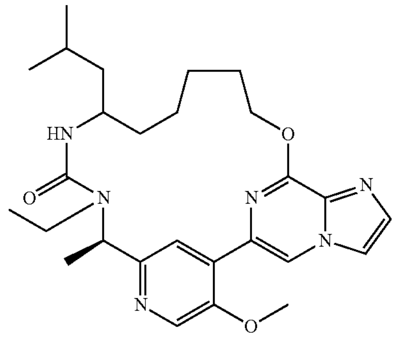 [SMILES: CCN1C(=O)NC(CC(C)C)CCCCCOc2nc(cn3ccnc23)-c2cc(ncc2OC)[C@H]1C] | (12R)-13-ethyl-8-methoxy-12-methyl-16-(2-methylpropyl)-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 495.3, found 495.3 | A100 |

TABLE 9-continued

| Ex. # | Structure | Name | Exact Mass [M + H]+ | Interm A |
|---|---|---|---|---|
| 54A | 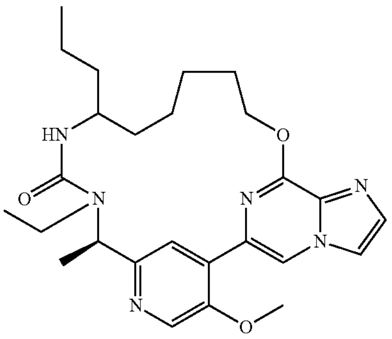 [SMILES: CCCC1CCCCCOc2nc(cn3ccnc23)-c2cc(ncc2OC)[C@@H](C)N(CC)C(=O)N1] | (12R)-13-ethyl-8-methoxy-12-methyl-16-propyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 481.3, found 481.3 | A102 |
| 54B | 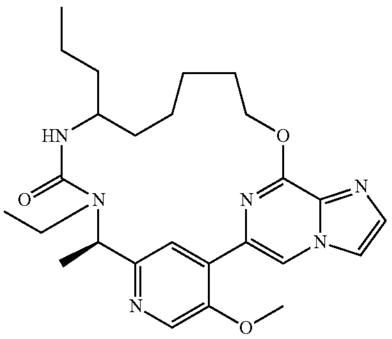 [SMILES: CCCC1CCCCCOc2nc(cn3ccnc23)-c2cc(ncc2OC)[C@@H](C)N(CC)C(=O)N1] | (12R)-13-ethyl-8-methoxy-12-methyl-16-propyl-12,13,16,17,18,19,20,21-octahydro-6,23-(azeno)-11,7-(metheno)imidazo[2,1-c][1,4,10,13,15]oxatetraazacy clohenicosin-14(15H)-one | Calc'd 481.3, found 481.3 | A102 |
| 55A | 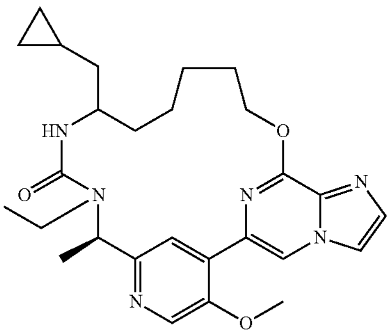 [SMILES: CCN1C(=O)NC(CC2CC2)CCCCCOc2nc(cn3ccnc23)-c2cc(ncc2OC)[C@H]1C] | (12R)-16-(cyclopropylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 493.3, found 493.3 | A107 |
| 55B | 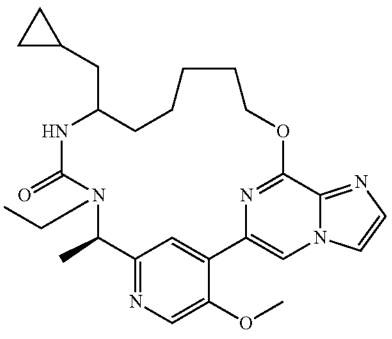 [SMILES: CCN1C(=O)NC(CC2CC2)CCCCCOc2nc(cn3ccnc23)-c2cc(ncc2OC)[C@H]1C] | (12R)-16-(cyclopropylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 493.3, found 493.3 | A107 |

TABLE 9-continued

| Ex. # | Structure | Name | Exact Mass [M + H]+ | Interm A |
|---|---|---|---|---|
| 56A | 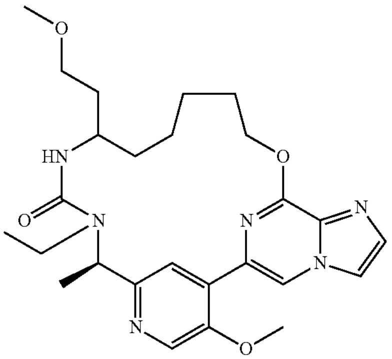 [SMILES: CCN1C(=O)NC(CCOC)CCCCCOc2nc(cn3ccnc23)-c2cc(ncc2OC)[C@H]1C] | (12R)-13-ethyl-8-methoxy-16-(2-methoxyethyl)-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 497.3, found 497.3 | A108 |
| 56B | 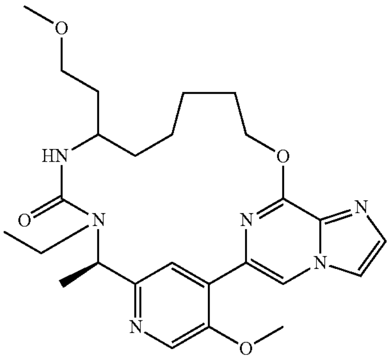 [SMILES: CCN1C(=O)NC(CCOC)CCCCCOc2nc(cn3ccnc23)-c2cc(ncc2OC)[C@H]1C] | (12R)-13-ethyl-8-methoxy-16-(2-methoxyethyl)-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 497.3, found 497.3 | A108 |
| 57A | 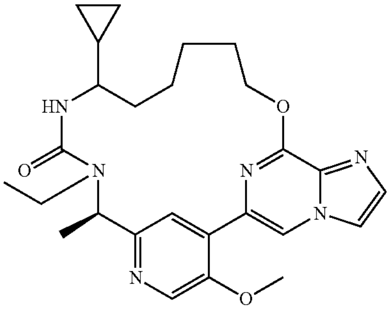 [SMILES: CCN1C(=O)NC(C2CC2)CCCCCOc2nc(cn3ccnc23)-c2cc(ncc2OC)[C@H]1C] | (12R)-16-cyclopropyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 479.3, found 479.4 | A106 |
| 57B | 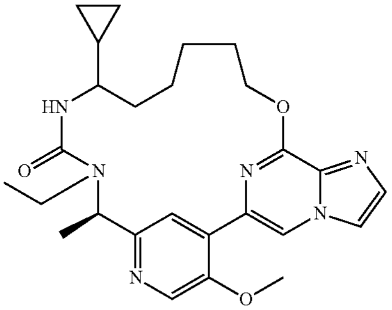 [SMILES: CCN1C(=O)NC(C2CC2)CCCCCOc2nc(cn3ccnc23)-c2cc(ncc2OC)[C@H]1C] | (12R)-16-cyclopropyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 479.3, found 479.4 | A106 |

TABLE 9-continued

| Ex. # | Structure | Name | Exact Mass [M + H]+ | Interm A |
|---|---|---|---|---|
| 58A | 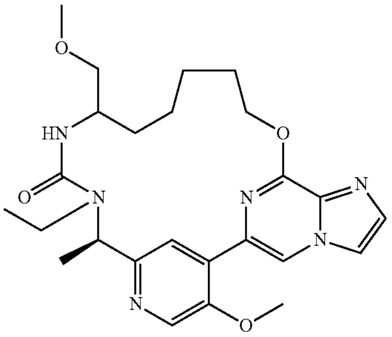 [SMILES: CCN1C(=O)NC(COC)CCCCCOc2nc(cn3ccnc23)-c2cc(ncc2OC)[C@H]1C] | (12R)-13-ethyl-8-methoxy-16-(methoxymethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 483.3, found 483.4 | A113 |
| 58B | 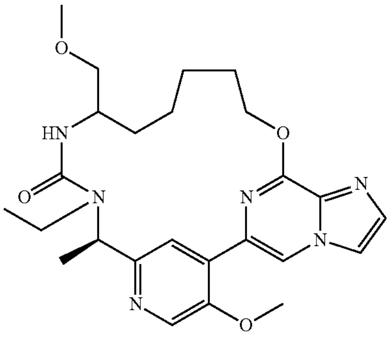 [SMILES: CCN1C(=O)NC(COC)CCCCCOc2nc(cn3ccnc23)-c2cc(ncc2OC)[C@H]1C] | (12R)-13-ethyl-8-methoxy-16-(methoxymethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 483.3, found 483.4 | A113 |
| 59A | 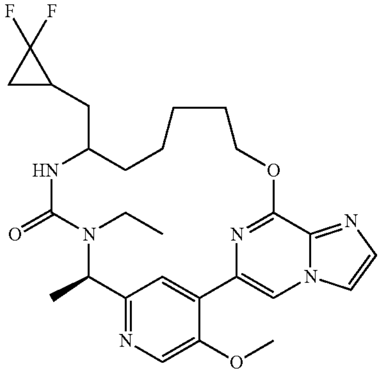 [SMILES: CCN1C(=O)NC(CC2CC2(F)F)CCCCCOc2nc(cn3ccnc23)-c2cc(ncc2OC)[C@H]1C] | (12R)-16-[(2,2-difluorocyclopropyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 529.3, found 529.4 | A114 |
| 59B | 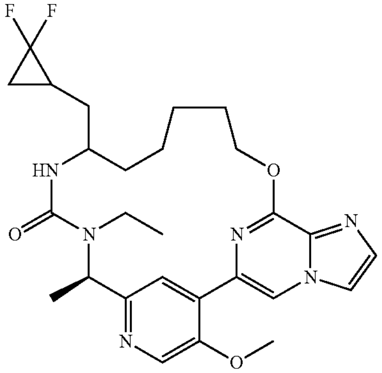 [SMILES: CCN1C(=O)NC(CC2CC2(F)F)CCCCCOc2nc(cn3ccnc23)-c2cc(ncc2OC)[C@H]1C] | (12R)-16-[(2,2-difluorocyclopropyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 529.3, found 529.4 | A114 |

TABLE 9-continued

| Ex. # | Structure | Name | Exact Mass [M + H]+ | Interm A |
| --- | --- | --- | --- | --- |
| 59C | 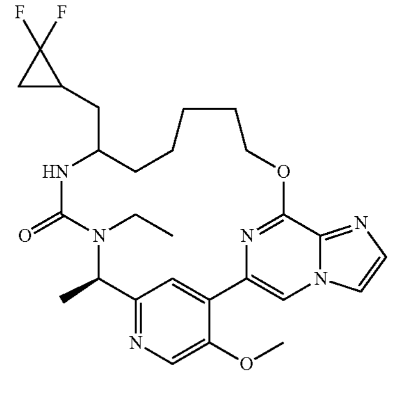 [SMILES: CCN1C(=O)NC(CC2CC2(F)F)CCCCCOc2nc(cn3ccnc23)-c2cc(ncc2OC)[C@H]1C] | (12R)-16-[(2,2-difluorocyclopropyl)methyl]-13-ethyl-8-methoxy-12-methyl-12,13,16,17,18, 19,20,21-octahydro-6,23-(azeno)-11,7-(metheno)imidazo[2,1-c][1,4,10,13,15]oxatetraazacyclohenicosin-14(15H)-one | Calc'd 529.3, found 529.4 | A114 |
| 59D | 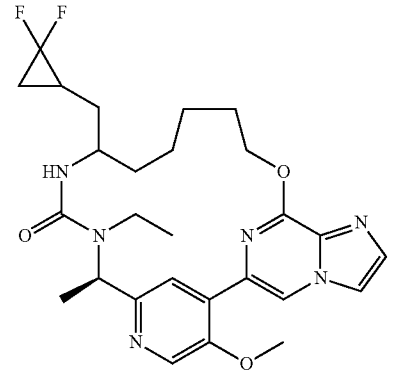 [SMILES: CCN1C(=O)NC(CC2CC2(F)F)CCCCCOc2nc(cn3ccnc23)-c2cc(ncc2OC)[C@H]1C] | (12R)-16-[(2,2-difluorocyclopropyl)methyl]-13-ethyl-8-methoxy-12-methyl-12,13, 16,17, 18,19,20,21-octahydro-6,23-(azeno)-11,7-(metheno) imidazo[2,1-c][1,4,10,13,15] oxatetraazacyclohenicosin-14(15H)-one | Calc'd 529.3, found 529.4 | A114 |
| 60A | 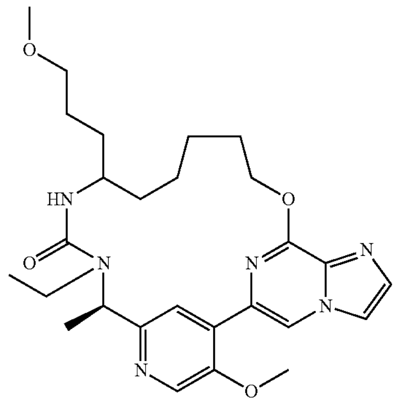 [SMILES: CCN1C(=O)NC(CCCOC)CCCCCOc2nc(cn3ccnc23)-c2cc(ncc2OC)[C@H]1C] | (12R)-13-ethyl-8-methoxy-16-(3-methoxypropyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 511.3, found 511.4 | A115 |
| 60B | 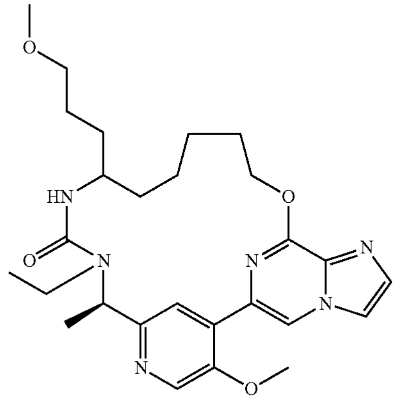 [SMILES: CCN1C(=O)NC(CCCOC)CCCCCOc2nc(cn3ccnc23)-c2cc(ncc2OC)[C@H]1C] | (12R)-13-ethyl-8-methoxy-16-(3-methoxypropyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 511.3, found 511.4 | A115 |

TABLE 9-continued

| Ex. # | Structure | Name | Exact Mass [M + H]+ | Interm A |
|---|---|---|---|---|
| 61A | 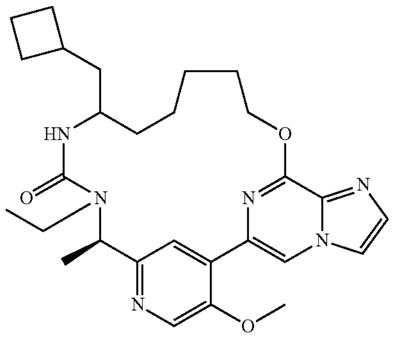 [SMILES: CCN1C(=O)NC(CC2CCC2)CCCCCOc2nc(cn3ccnc23)-c2cc(ncc2OC)[C@H]1C] | (12R)-16-(cyclobutylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 507.3, found 507.4 | A116 |
| 61B | 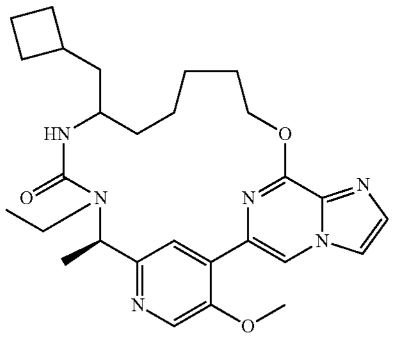 [SMILES: CCN1C(=O)NC(CC2CCC2)CCCCCOc2nc(cn3ccnc23)-c2cc(ncc2OC)[C@H]1C] | (12R)-16-(cyclobutylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 507.3, found 507.4 | A116 |
| 62A | 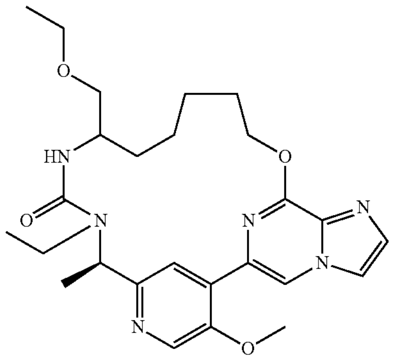 [SMILES: CCOCC1CCCCCOc2nc(cn3ccnc23)-c2cc(ncc2OC)[C@@H](C)N(CC)C(=O)N1] | (12R)-16-(ethoxymethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 497.3, found 497.4 | A117 |
| 62B | 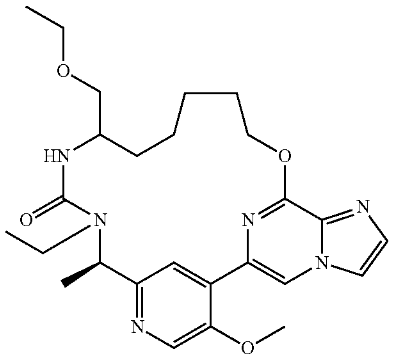 [SMILES: CCOCC1CCCCCOc2nc(cn3ccnc23)-c2cc(ncc2OC)[C@@H](C)N(CC)C(=O)N1] | (12R)-16-(ethoxymethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 497.3, found 497.4 | A117 |

TABLE 9-continued

| Ex. # | Structure | Name | Exact Mass [M + H]+ | Interm A |
|---|---|---|---|---|
| 63A | 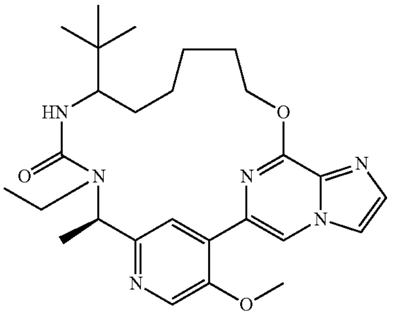 [SMILES: CCN1C(=O)NC(C(C)(C)C)CCCCCOc2nc(cn3ccnc23)-c2cc(ncc2OC)[C@H]1C] | (12R)-16-tert-butyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 495.3, found 495.4 | A103 |
| 63B | 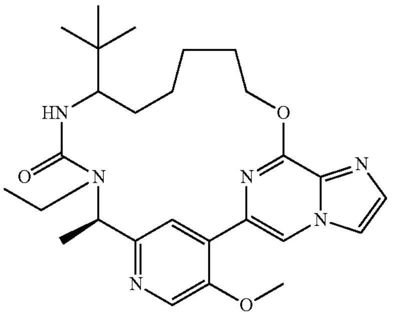 [SMILES: CCN1C(=O)NC(C(C)(C)C)CCCCCOc2nc(cn3ccnc23)-c2cc(ncc2OC)[C@H]1C] | (12R)-16-tert-butyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 495.3, found 495.4 | A103 |
| 64A | 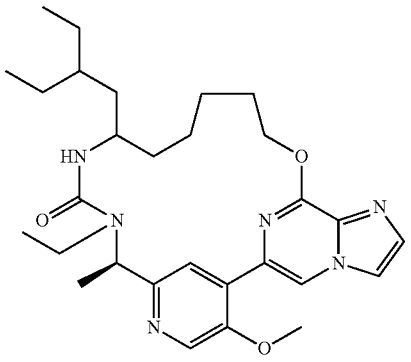 [SMILES: CCC(CC)CC1CCCCCOc2nc(cn3ccnc23)-c2cc(ncc2OC)[C@@H](C)N(CC)C(=O)N1] | (12R)-13-ethyl-16-(2-ethylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A120 |
| 64B | 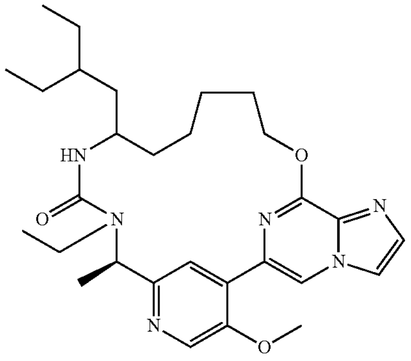 [SMILES: CCC(CC)CC1CCCCCOc2nc(cn3ccnc23)-c2cc(ncc2OC)[C@@H](C)N(CC)C(=O)N1] | (12R)-13-ethyl-16-(2-ethylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A120 |

TABLE 9-continued

| Ex. # | Structure | Name | Exact Mass [M + H]+ | Interm A |
|---|---|---|---|---|
| 65A | 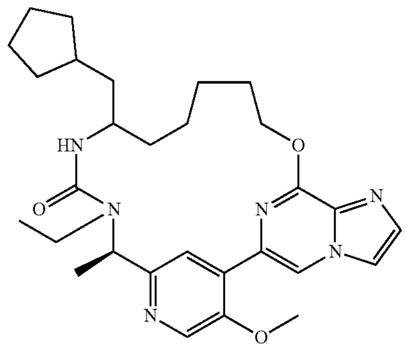 [SMILES: CCN1C(=O)NC(CC2CCCC2)CCCCCOc2nc(cn3ccnc23)-c2cc(ncc2OC)[C@H]1C] | (12R)-16-(cyclopentylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 521.3, found 521.4 | A118 |
| 65B | 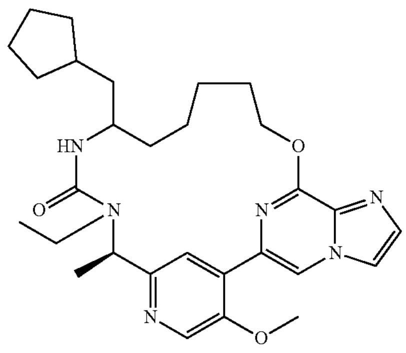 [SMILES: CCN1C(=O)NC(CC2CCCC2)CCCCCOc2nc(cn3ccnc23)-c2cc(ncc2OC)[C@H]1C] | (12R)-16-(cyclopentylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 521.3, found 521.4 | A118 |
| 66A | 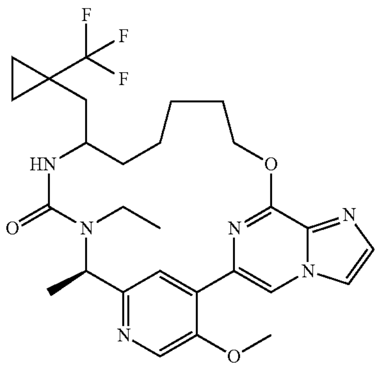 [SMILES: CCN1C(=O)NC(CC2(C(F)(F)F)CC2)CCCCCOc2nc(cn3ccnc23)-c2cc(ncc2OC)[C@H]1C] | (12R)-13-ethyl-8-methoxy-12-methyl-16-{[1-(trifluoromethyl)cyclopropyl] methyl}-12,13,16,17,18,19,20,21-octahydro-6,23-(azeno)-11,7-(metheno) imidazo[2,1c] [1,4,10,13,15]oxatetraazacyclo-henicosin-14(15H)-one | Calc'd 561.3, found 561.3 | A111 |
| 66B | 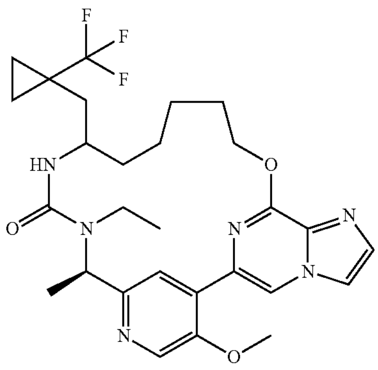 [SMILES: CCN1C(=O)NC(CC2(C(F)(F)F)CC2)CCCCCOc2nc(cn3ccnc23)-c2cc(ncc2OC)[C@H]1C] | (12R)-13-ethyl-8-methoxy-12-methyl-16-{[1-(trifluoromethyl)cyclopropyl] methyl}-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 561.3, found 561.3 | A111 |

TABLE 9-continued

| Ex. # | Structure | Name | Exact Mass [M + H]+ | Interm A |
|---|---|---|---|---|
| 67A | 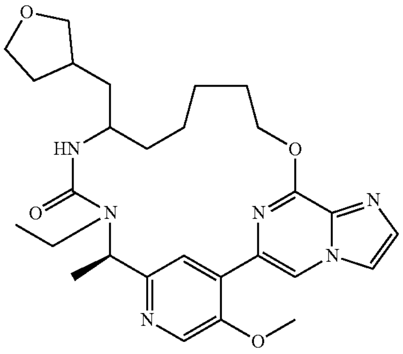 [SMILES: CCN1C(=O)NC(CC2CCOC2)CCCCCOc2nc(cn3ccnc23)-c2cc(ncc2OC)[C@H]1C] | (12R)-13-ethyl-8-methoxy-12-methyl-16-[(oxolan-3-yl)methyl]-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A121 |
| 67B | 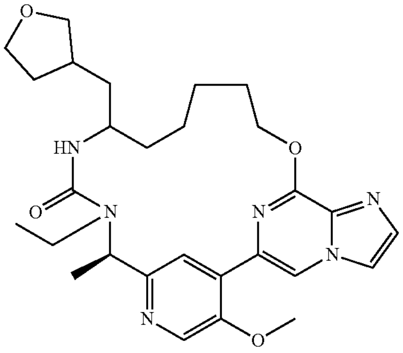 [SMILES: CCN1C(=O)NC(CC2CCOC2)CCCCCOc2nc(cn3ccnc23)-c2cc(ncc2OC)[C@H]1C] | (12R)-13-ethyl-8-methoxy-12-methyl-16-[(oxolan-3-yl)methyl]-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A121 |
| 68A | 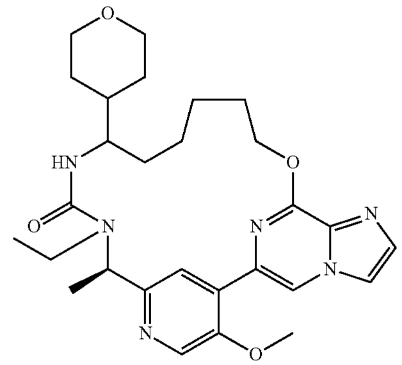 [SMILES: CCN1C(=O)NC(C2CCOCC2)CCCCCOc2nc(cn3ccnc23)-c2cc(ncc2OC)[C@H]1C] | (12R)-13-ethyl-8-methoxy-12-methyl-16-(oxan-4-yl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A119 |
| 68B | 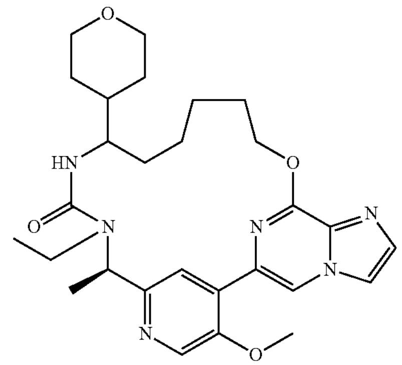 [SMILES: CCN1C(=O)NC(C2CCOCC2)CCCCCOc2nc(cn3ccnc23)-c2cc(ncc2OC)[C@H]1C] | (12R)-13-ethyl-8-methoxy-12-methyl-16-(oxan-4-yl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 523.3, found 523.4 | A119 |

TABLE 9-continued

| Ex. # | Structure | Name | Exact Mass [M + H]+ | Interm A |
|---|---|---|---|---|
| 69A | 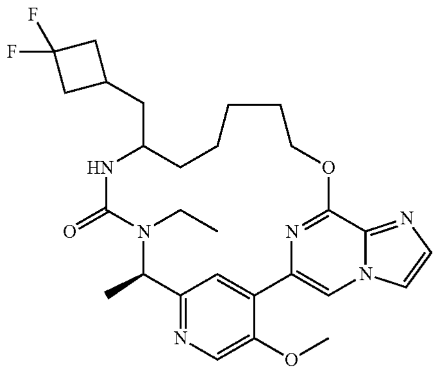 [SMILES: CCN1C(=O)NC(CC2CC(F)(F)C2)CCCCCOc2nc(cn3ccnc23)-c2cc(ncc2OC)[C@H]1C] | (12R)-16-[(3,3-difluorocyclobutyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 543.3, found 543.4 | A122 |
| 69B | 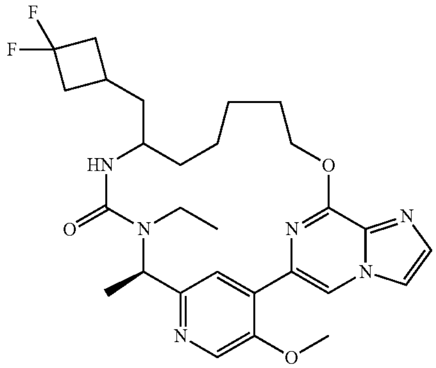 [SMILES: CCN1C(=O)NC(CC2CC(F)(F)C2)CCCCCOc2nc(cn3ccnc23)-c2cc(ncc2OC)[C@H]1C] | (12R)-16-[(3,3-difluorocyclobutyl)methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 543.3, found 543.4 | A122 |
| 70A | 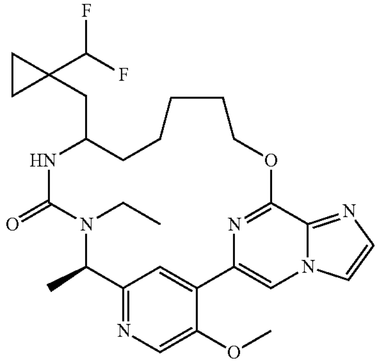 [SMILES: CCN1C(=O)NC(CC2(C(F)F)CC2)CCCCCOc2nc(cn3ccnc23)-c2cc(ncc2OC)[C@H]1C] | (12R)-16-{[1-(difluoromethyl)cyclopropyl]methyl}-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 543.3, found 543.4 | A112 |
| 70B | 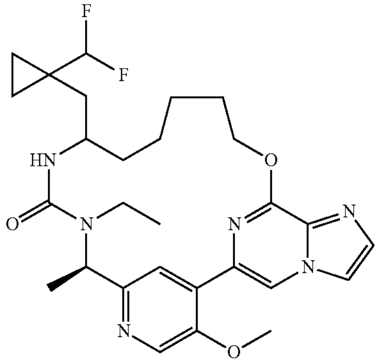 [SMILES: CCN1C(=O)NC(CC2(C(F)F)CC2)CCCCCOc2nc(cn3ccnc23)-c2cc(ncc2OC)[C@H]1C] | (12R)-16-{[1-(difluoromethyl)cyclopropyl]methyl}-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 543.3, found 543.4 | A112 |

TABLE 9-continued

| Ex. # | Structure | Name | Exact Mass [M + H]+ | Interm A |
|---|---|---|---|---|
| 71A | 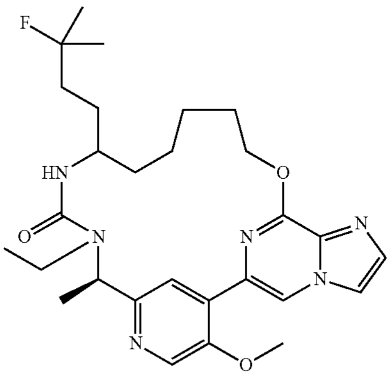 [SMILES: CCN1C(=O)NC(CCC(C)(C)F)CCCCCOc2nc(cn3ccnc23)-c2cc(ncc2OC)[C@H]1C] | (12R)-13-ethyl-16-(3-fluoro-3-methylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 527.3, found 527.4 | A123 |
| 71B | 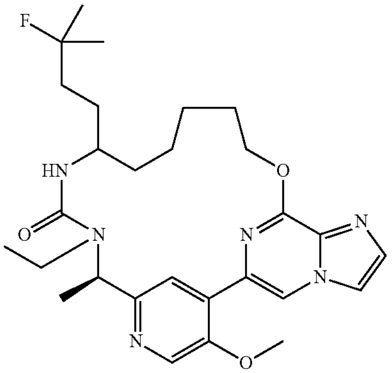 [SMILES: CCN1C(=O)NC(CCC(C)(C)F)CCCCCOc2nc(cn3ccnc23)-c2cc(ncc2OC)[C@H]1C] | (12R)-13-ethyl-16-(3-fluoro-3-methylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 527.3, found 527.4 | A123 |
| 72A | 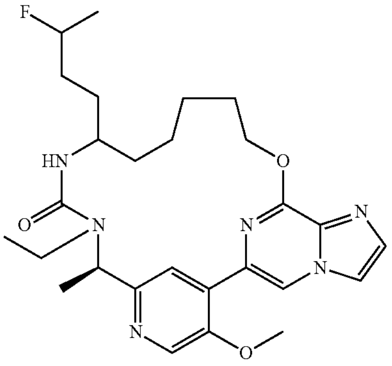 [SMILES: CCN1C(=O)NC(CCC(C)F)CCCCCOc2nc(cn3ccnc23)-c2cc(ncc2OC)[C@H]1C] | (12R)-13-ethyl-16-(3-fluorobutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 513.3, found 513.4 | A124 |
| 72B | 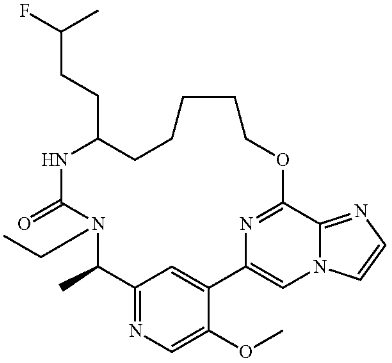 [SMILES: CCN1C(=O)NC(CCC(C)F)CCCCCOc2nc(cn3ccnc23)-c2cc(ncc2OC)[C@H]1C] | (12R)-13-ethyl-16-(3-fluorobutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 513.3, found 513.4 | A124 |

TABLE 9-continued

| Ex. # | Structure | Name | Exact Mass [M + H]+ | Interm A |
|---|---|---|---|---|
| 73A | 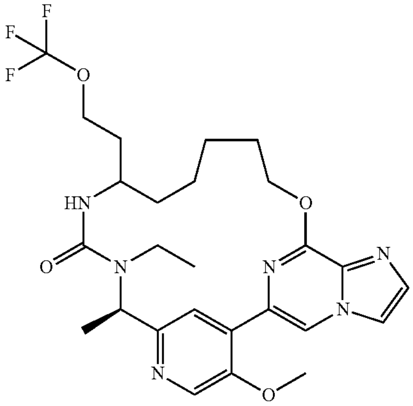 [SMILES: CCN1C(=O)NC(CCOC(F)(F)F)CCCCCOc2nc(cn3ccnc23)-c2cc(ncc2OC)[C@H]1C] | (12R)-13-ethyl-8-methoxy-12-methyl-16-[2-(trifluoromethoxy)ethyl]-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 551.3, found 551.4 | A125 |
| 73B | 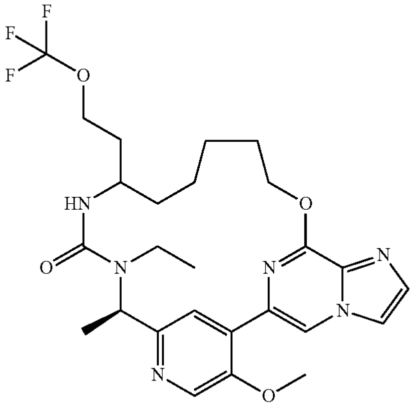 [SMILES: CCN1C(=O)NC(CCOC(F)(F)F)CCCCCOc2nc(cn3ccnc23)-c2cc(ncc2OC)[C@H]1C] | (12R)-13-ethyl-8-methoxy-12-methyl-16-[2-(trifluoromethoxy)ethyl]-12,13,16,17,18,19,20,21-octahydro-6,23-(azeno)-11,7-(metheno)imidazo[2,1-c][1,4,10,13,15]oxatetraazacy-clohenicosin-14(15H)-one | Calc'd 551.3, found 551.4 | A125 |
| 182 | 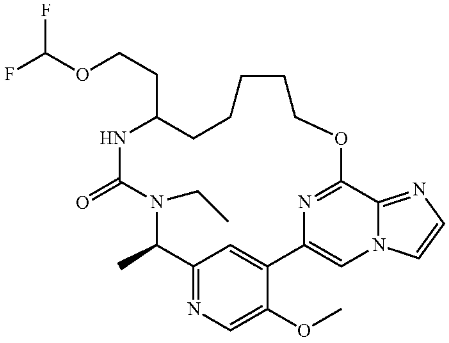 [SMILES: CCN1C(=O)NC(CCOC(F)F)CCCCCOc2nc(cn3ccnc23)-c2cc(ncc2OC)[C@H]1C] | (3R,E)-7-(2-(difluoromethoxy)ethyl)-4-ethyl-25-methoxy-3-methyl-13-oxa-4,6-diaza-1(6,8)-imidazo[1,2-a]pyrazina-2(4,2)-pyridinacyclotridecaphan-5-one | Calc'd 532.6, found 533.4 | A163 |
| 183 | 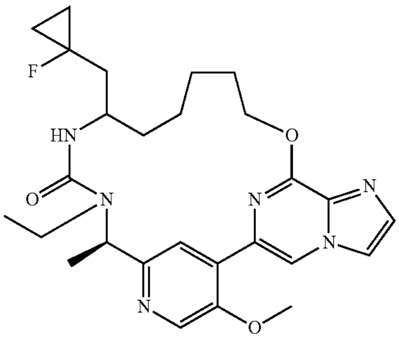 [SMILES: CCN1C(=O)NC(CC2(F)CC2)CCCCCOc2nc(cn3ccnc23)-c2cc(ncc2OC)[C@H]1C] | (3R,E)-4-ethyl-7-((1-fluorocyclopropyl)methyl)-25-methoxy-3-methyl-13-oxa-4,6-diaza-1(6,8)-imidazo[1,2-a]pyrazina-2(4,2)-pyridinacyclotridecaphan-5-one | Calc'd 510.6, found 511.4 | A164 |

TABLE 9-continued

| Ex. # | Structure | Name | Exact Mass [M + H]+ | Interm A |
|---|---|---|---|---|
| 184 | 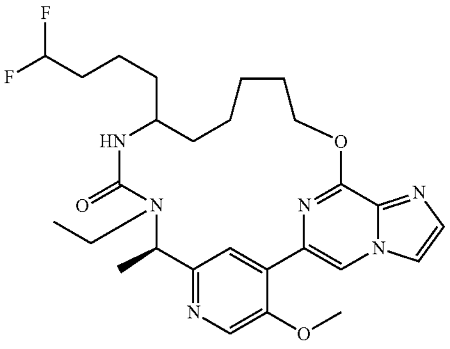 [SMILES: CCN1C(=O)NC(CCCC(F)F)CCCCCOc2nc(cn3ccnc23)-c2cc(ncc2OC)[C@H]1C] | (3R,E)-7-(4,4-difluorobutyl)-4-ethyl-25-methoxy-3-methyl-13-oxa-4,6-diaza-1(6,8)-imidazo[1,2-a]pyrazina-2(4,2)-pyridinacyclotridecaphan-5-one | Calc'd 530.6, found 531.4 | A165 |
| 185 | 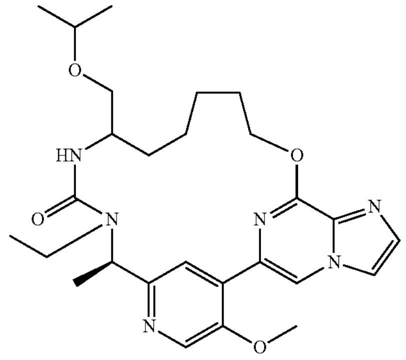 [SMILES: CCN1C(=O)NC(COC(C)C)CCCCCOc2nc(cn3ccnc23)-c2cc(ncc2OC)[C@H]1C] | (3R,E)-4-ethyl-7-(isopropoxymethyl)-25-methoxy-3-methyl-13-oxa-4,6-diaza-1(6,8)-imidazo[1,2-a]pyrazina-2(4,2)-pyridinacyclotridecaphan-5-one | Calc'd 510.6, found 511.4 | A166 |
| 186 | 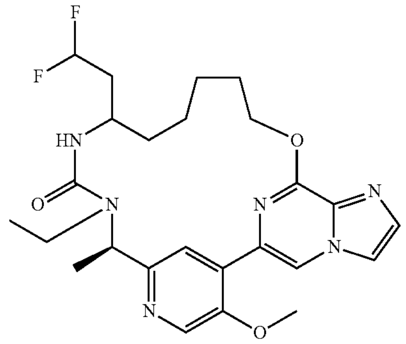 [SMILES: CCN1C(=O)NC(CC(F)F)CCCCCOc2nc(cn3ccnc23)-c2cc(ncc2OC)[C@H]1C] | (3R,E)-7-(2,2-difluoroethyl)-4-ethyl-25-methoxy-3-methyl-13-oxa-4,6-diaza-1(6,8)-imidazo[1,2-a]pyrazina-2(4,2)-pyridinacyclotridecaphan-5-one | Calc'd 502.5, found 503.4 | A157 |
| 187 | 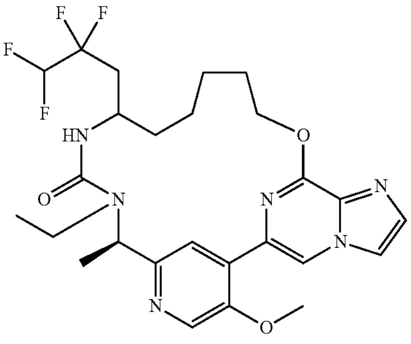 [SMILES: CCN1C(=O)NC(CC(F)(F)C(F)F)CCCCCOc2nc(cn3ccnc23)-c2cc(ncc2OC)[C@H]1C] | (3R,E)-4-ethyl-25-methoxy-3-methyl-7-(2,2,3,3-tetrafluoropropyl)-13-oxa-4,6-diaza-1(6,8)-imidazo[1,2-a] pyrazina-2(4,2)-pyridina-cyclotridecaphan-5-one | Calc'd 566.6, found 567.4 | A157 |

TABLE 9-continued

| Ex. # | Structure | Name | Exact Mass [M + H]+ | Interm A |
|---|---|---|---|---|
| 188 | 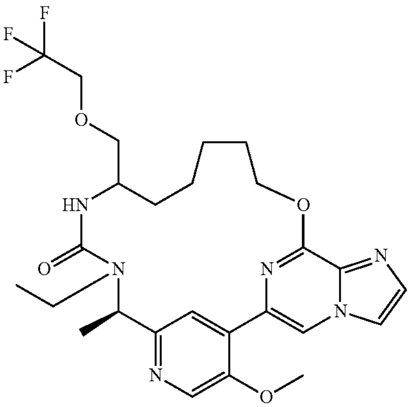 [SMILES: CCN1C(=O)NC(COCC(F)(F)F)CCCCCOc2nc(cn3ccnc23)-c2cc(ncc2OC)[C@H]1C] | (3R,E)-4-ethyl-25-methoxy-3-methyl-7-((2,2,2-trifluoroethoxy)methyl)-13-oxa-4,6-diaza-1(6,8)-imidazo[1,2-a]pyrazina-2(4,2)-pyridinacyclotridecaphan-5-one | Calc'd 550.5, found 551.4 | A168 |
| 189 | 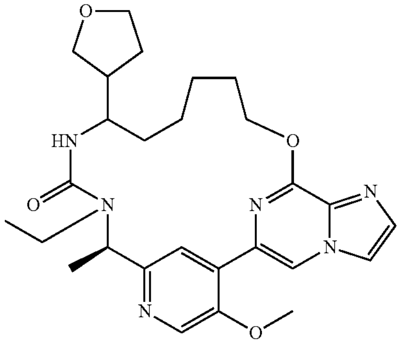 [SMILES: CCN1C(=O)NC(C2CCOC2)CCCCCOc2nc(cn3ccnc23)-c2cc(ncc2OC)[C@H]1C] | (3R,E)-4-ethyl-25-methoxy-3-methyl-7-(tetrahydrofuran-3-yl)-13-oxa-4,6-diaza-1(6,8)-imidazo[1,2-a]pyrazina-2(4,2)-pyridinacyclotridecaphan-5-one | Calc'd 508.6, found 509.4 | A169 |
| 190 | 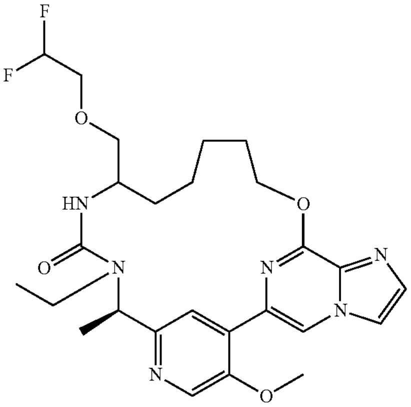 [SMILES: CCN1C(=O)NC(COCC(F)F)CCCCCOc2nc(cn3ccnc23)-c2cc(ncc2OC)[C@H]1C] | (3R,E)-7-((2,2-difluoroethoxy)methyl)-4-ethyl-25-methoxy-3-methyl-13-oxa-4,6-diaza-1(6,8)-imidazo[1,2-a]pyrazina-2(4,2)-pyridinacyclotridecaphan-5-one | Calc'd 532.6, found 533.4 | A170 |
| 191 | 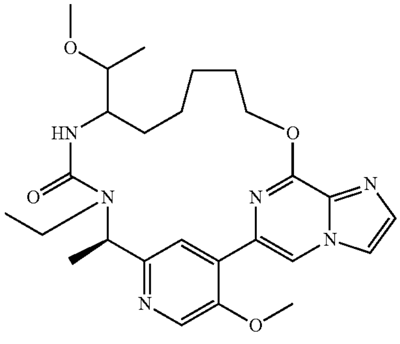 [SMILES: CCN1C(=O)NC(C(C)OC)CCCCCOc2nc(cn3ccnc23)-c2cc(ncc2OC)[C@H]1C] | (3R,E)-4-ethyl-25-methoxy-7-(1-methoxyethyl)-3-methyl-13-oxa-4,6-diaza-1(6,8)-imidazo[1,2-a]pyrazina-2(4,2)-pyridinacyclotridecaphan-5-one | Calc'd 496.6, found 497.4 | A171 |

TABLE 9-continued

| Ex. # | Structure | Name | Exact Mass [M + H]+ | Interm A |
|---|---|---|---|---|
| 194 | 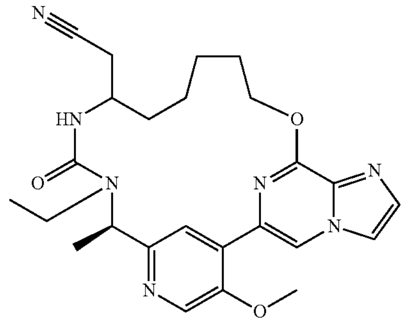 [SMILES: CCN1C(=O)NC(CC#N)CCCCCOc2nc(cn3ccnc23)-c2cc(ncc2OC)[C@H]1C] | 2-((3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-yl)acetonitrile | Calc'd 477.5, found 478.4 | A172 |
| 196 | 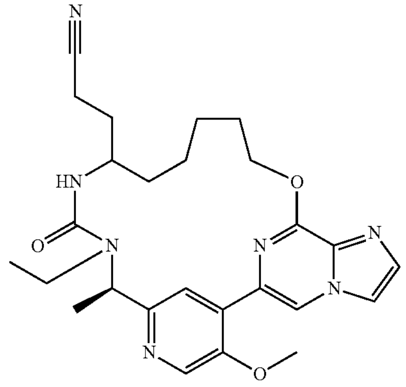 [SMILES: CCN1C(=O)NC(CCC#N)CCCCCOc2nc(cn3ccnc23)-c2cc(ncc2OC)[C@H]1C] | 3-((3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-yl)propanenitrile | Calc'd 491.6, found 492.4 | A173 |
| 197 | 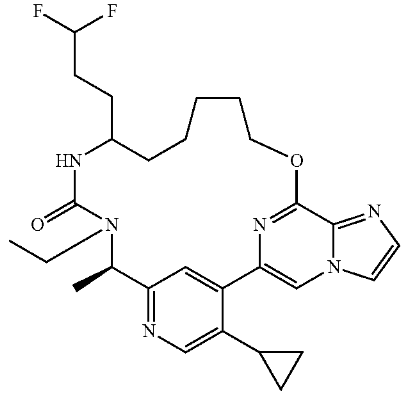 [SMILES: CCN1C(=O)NC(CCC(F)F)CCCCCOc2nc(cn3ccnc23)-c2cc(ncc2C2CC2)[C@H]1C] | (3R,E)-25-cyclopropyl-7-(3,3-difluoropropyl)-4-ethyl-3-methyl-13-oxa-4,6-diaza-1(6,8)-imidazo[1,2-a]pyrazina-2(4,2)-pyridina-cyclotridecaphan-5-one | Calc'd 526.6, found 527.3 | A158 |
| 199 | 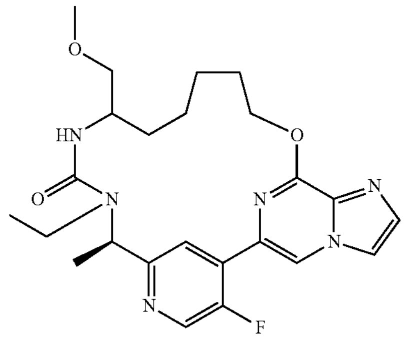 [SMILES: CCN1C(=O)NC(COC)CCCCCOc2nc(cn3ccnc23)-c2cc(ncc2F)[C@H]1C] | (3R,E)-4-ethyl-25-fluoro-7-(methoxymethyl)-3-methyl-13-oxa-4,6-diaza-1(6,8)-imidazo[1,2-a]pyrazina-2(4,2)-pyridinacyclotridecaphan-5-one | Calc'd 470.5, found 471.3 | A174 |

TABLE 9-continued

| Ex. # | Structure | Name | Exact Mass [M + H]+ | Interm A |
|---|---|---|---|---|
| 200 | 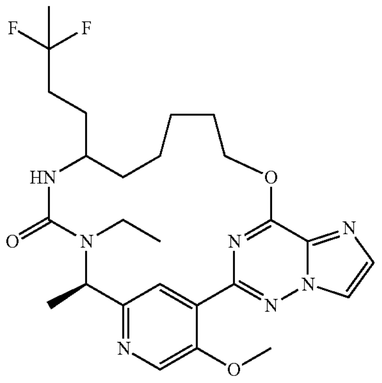 [SMILES: CCN1C(=O)NC(CCC(C)(F)F)CCCCCOc2nc(nn3ccnc23)-c2cc(ncc2OC)[C@H]1C] | (3R,E)-7-(3,3-difluorobutyl)-4-ethyl-25-methoxy-3-methyl-13-oxa-4,6-diaza-1(2,4)-imidazo[2,1-f][1,2,4]triazina-2(4,2)-pyridinacyclo-tridecaphan-5-one | Calc'd 531.6, found 532.2 | A153 |
| 201 | 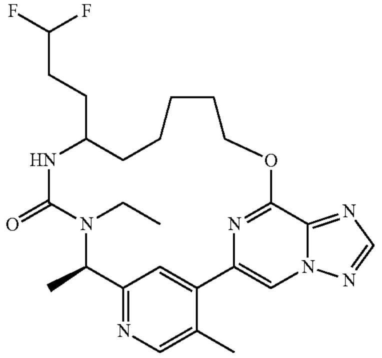 [SMILES: CCN1C(=O)NC(CCC(F)F)CCCCCOc2nc(cn3ncnc23)-c2cc(ncc2C)[C@H]1C] | (3R,E)-7-(3,3-difluoropropyl)-4-ethyl-25,3-dimethyl-13-oxa-4,6-diaza-1(6,8)-[1,2,4]triazolo[1,5-a]pyrazina-2(4,2)-pyridina-cyclotridecaphan-5-one | Calc'd 501.6, found 502.4 | A156 |
| 202 | 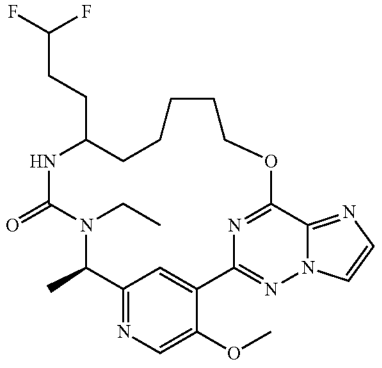 [SMILES: CCN1C(=O)NC(CCC(F)F)CCCCCOc2nc(nn3ccnc23)-c2cc(ncc2OC)[C@H]1C] | (3R,E)-7-(3,3-difluoropropyl)-4-ethyl-25-methoxy-3-methyl-13-oxa-4,6-diaza-1(2,4)-imidazo[2,1-f][1,2,4]triazina-2(4,2)-pyridina-cyclotridecaphan-5-one | Calc'd 517.6, found 518.3 | A152 |
| 203 | 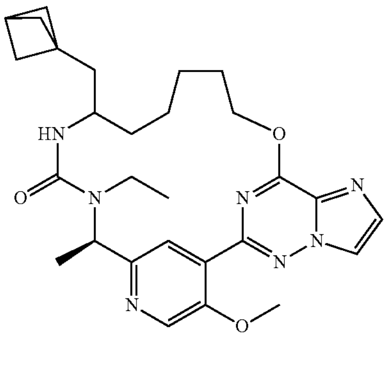 [SMILES: CCN1C(=O)NC(CC23CC(C2)C3)CCCCCOc2nc(nn3ccnc23)-c2cc(ncc2OC)[C@H]1C] | (3R,E)-7-(bicyclo[1.1.1]pentan-1-ylmethyl)-4-ethyl-25-methoxy-3-methyl-13-oxa-4,6-diaza-1(2,4)-imidazo[2,1-f][1,2,4]triazina-2(4,2)-pyridinacyclotridecaphan-5-one | Calc'd 519.6, found 520.2 | A162 |

TABLE 9-continued

| Ex. # | Structure | Name | Exact Mass [M + H]+ | Interm A |
|---|---|---|---|---|
| 204 | 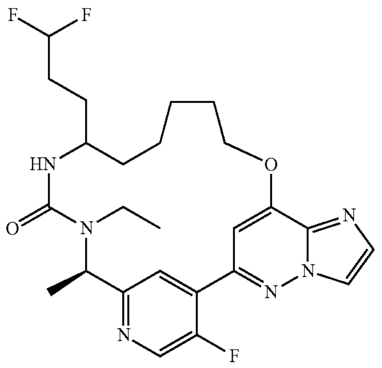 [SMILES: CCN1C(=O)NC(CCC(F)F)CCCCCOc2cc(nn3ccnc23)-c2cc(ncc2F)[C@H]1C] | (3R,E)-7-(3,3-difluoropropyl)-4-ethyl-25-fluoro-3-methyl-13-oxa-4,6-diaza-1(6,8)-imidazo[1,2-b]pyridazina-2(4,2)-pyridina-cyclotridecaphan-5-one | Calc'd 504.6, found 505.2 | A159 |
| 205 | 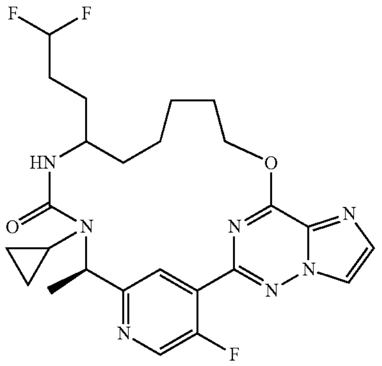 [SMILES: C[C@@H]1c2cc(c(F)cn2)-c2nc(c3nccn3n2)OCCCCCC(CCC(F)F)NC(=O)N1C1CC1] | (3R,E)-4-cyclopropyl-7-(3,3-difluoropropyl)-25-fluoro-3-methyl-13-oxa-4,6-diaza-1(2,4)-imidazo[2,1-f] [1,2,4] triazina-2(4,2)-pyridinacyclo-tridecaphan-5-one | Calc'd 517.6, found 518.2 | A160 |
| 206 | 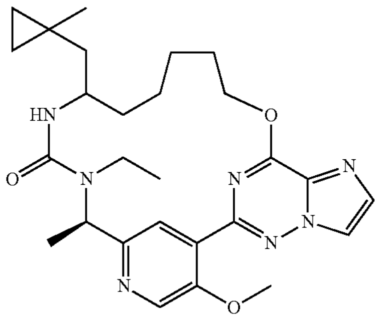 [SMILES: CCN1C(=O)NC(CC2(C)CC2)CCCCCOc2nc(nn3ccnc23)-c2cc(ncc2OC)[C@H]1C] | (3R,E)-4-ethyl-25-methoxy-3-methyl-7-((1-methylcyclo-propyl)methyl)-13-oxa-4,6-diaza-1(2,4)-imidazo[2,1-f] [1,2,4]triazina-2(4,2)-pyridina-cyclotridecaphan-5-one | Calc'd 507.6, found 508.3 | A154 |
| 207 | 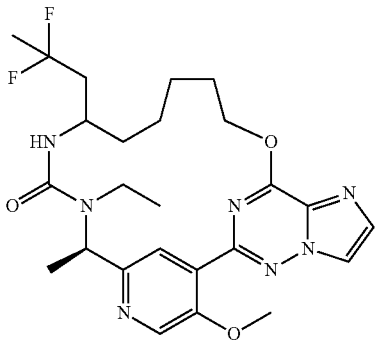 [SMILES: CCN1C(=O)NC(CC(C)(F)F)CCCCCOc2nc(nn3ccnc23)-c2cc(ncc2OC)[C@H]1C] | (3R,E)-7-(2,2-difluoropropyl)-4-ethyl-25-methoxy-3-methyl-13-oxa-4,6-diaza-1(2,4)-imidazo[2,1-f][1,2,4]triazina-2(4,2)-pyridinacyclo-tridecaphan-5-one | Calc'd 517.6, found 518.3 | A155 |

TABLE 9-continued

| Ex. # | Structure | Name | Exact Mass [M + H]+ | Interm A |
|---|---|---|---|---|
| 208 | 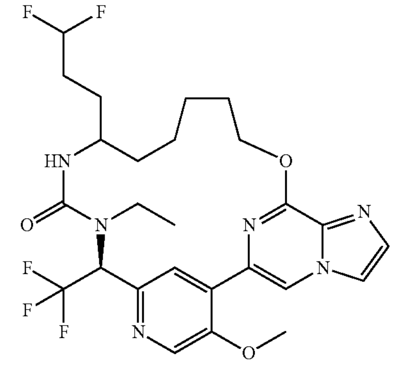 [SMILES: CCN1C(=O)NC(CCC(F)F)CCCCCOc2nc(cn3ccnc23)-c2cc(ncc2OC)[C@H]1C(F)(F)F] | (3S,E)-7-(3,3-difluoropropyl)-4-ethyl-25-methoxy-3-(trifluoromethyl)-13-oxa-4,6-diaza-1(6,8)-imidazo[1,2-a]pyrazina-2(4,2)-pyridinacyclotridecaphan-5-one | Calc'd 570.6, found 571.4 | A161 |

Ex. 59C and 59D were separated from a mixture by SFC separation (Chiral Art Cellulose SJ column, 20% EtOH 80% $CO_2$ with 0.1% diethylamine as additive).

Example 74

SCHEME 11

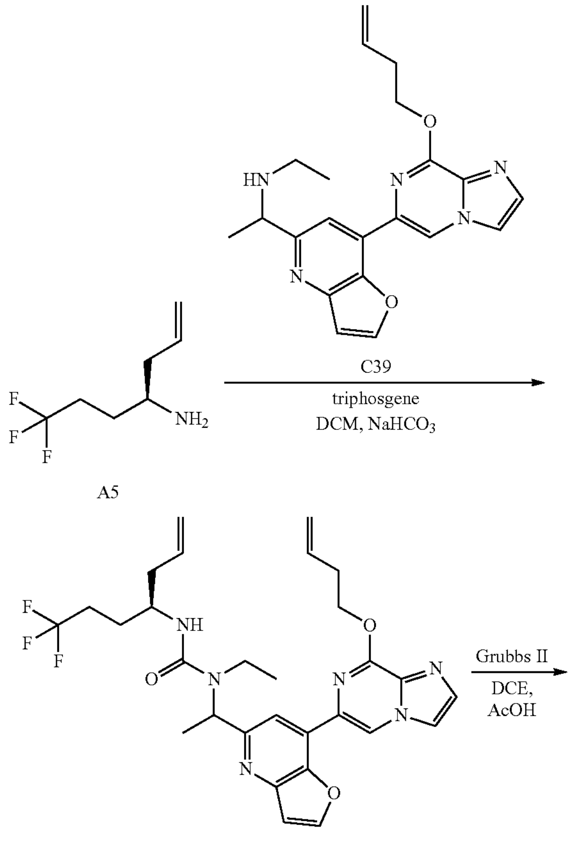

-continued

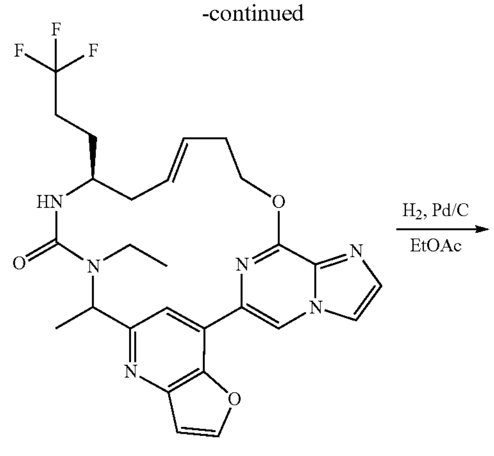

74b

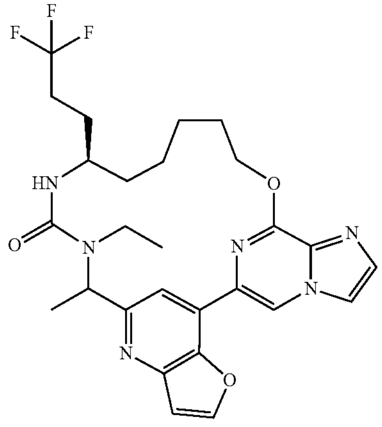

Example 74

Step 1: 1-(1-(7-(8-(But-3-en-1-yloxy)imidazo[1,2-a]pyrazin-6-yl)furo[3,2-b]pyridin-5-yl)ethyl)-1-ethyl-3-((S)-7,7,7-trifluorohept-1-en-4-yl)urea (74a)

(S)-7,7,7-trifluorohept-1-en-4-amine HCl salt (A5, 39 mg, 0.192 mmol) was taken up in DCM (0.2 mL). To this was added sat. aq. $NaHCO_3$(0.4 mL) then triphosgene (17 mg, 0.058 mmol) with rapid stirring at ambient temperature. After 1 h sat. aq. $NaHCO_3$(0.2 mL) was added followed by a solution of crude 1-(7-(8-(but-3-en-1-yloxy)imidazo[1,2-a]pyrazin-6-yl)furo[3,2-b]pyridin-5-yl)-N-ethylethan-1-amine TFA salt (C39, 30 mg, 0.064 mmol) in DCM (0.4 mL) with rapid stirring at ambient temperature. After 90 min the reaction was diluted with DCM then filtered through a pad of Celite washing with DCM and concentrated. The crude material was purified by flash silica chromatography (0-100% EtOAc in heptane gradient) to give 1-(1-(7-(8-(But-3-en-1-yloxy)imidazo[1,2-a]pyrazin-6-yl)furo[3,2-b]pyridin-5-yl)ethyl)-1-ethyl-3-((S)-7,7,7-trifluorohept-1-en-4-yl)urea (74a). LC-MS: 571.3 (M+1). $^1$H-NMR (500 MHz, $CDCl_3$) δ 9.01 (d, J=3.1 Hz, 1H), 8.19 (s, 1H), 7.99 (d, J=2.2 Hz, 1H), 7.76 (s, 1H), 7.73 (s, 1H), 7.06 (d, J=2.2 Hz, 1H), 6.01 (td, J=17.0, 6.7 Hz, 1H), 5.69 (dtd, J=52.5, 16.8, 7.2 Hz, 1H), 5.40 (d, J=16.5 Hz, 1H), 5.26 (dd, J=18.2, 7.7 Hz, 2H), 5.15 (d, J=10.3 Hz, 1H), 5.06-4.99 (m, 1H), 4.97-4.90 (m, 1H), 4.76 (td, J=6.9, 2.7 Hz, 2H), 3.94 (s, 1H), 3.57-3.39 (m, 2H), 2.77 (q, J=6.8 Hz, 2H), 2.32-2.01 (m, 3H), 1.91 (dd, J=51.2, 11.1 Hz, 1H), 1.80-1.73 (m, 3H), 1.69 (td, J=12.9, 6.7 Hz, 1H), 1.44 (m, 1H), 1.22 (tt, J=19.0, 7.1 Hz, 3H).

Step 2: (27E,6E,9S)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-6-en-11-one (74b)

To a solution of 1-(1-(7-(8-(but-3-en-1-yloxy)imidazo[1,2-a]pyrazin-6-yl)furo[3,2-b]pyridin-5-yl)ethyl)-1-ethyl-3-((S)-7,7,7-trifluorohept-1-en-4-yl)urea (74a, 20 mg, 0.035 mmol) in DCE (1 mL) was added AcOH (2.5 μL, 0.044 mmol). The mixture was degassed with nitrogen (3×pump/N2). Grubbs II catalyst (6 mg, 7.07 μmol) was added and the reaction was stirred at ambient temperature. After 4 h, 5 drops of TEA were added then the mixture was concentrated. The crude material was subjected to flash silica chromatography (0-100% EtOAc:EtOH 3:1 mix in heptane gradient) to give (27E,6E,9S)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-6-en-11-one (74b) as an approximate 1:1 mixture of diastereomers. LC-MS: 543.2 (M+1).

Step 3: (9R,E)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-11-one (TFA salt) (Example 74)

To a solution of (27E,6E,9S)-12-ethyl-3-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-6-en-11-one (74b, 15 mg, 0.028 mmol) in EtOAc (1 mL) was added Pd (6 mg, 5.64 μmol) (10% on C). The reaction was degassed with nitrogen (3×pump/N2) then placed under an atmosphere of H2 (1×pump/balloon H2) and stirred rapidly at ambient temperature overnight. The resulting mixture was degassed with nitrogen (3×pump/N2) to remove excess H2 then filtered directly through a syringe filter washing with EtOAc. The filtrate was concentrated. The crude material was purified by reverse phase HPLC (5-65% ACN in water, with 0.1% TFA as modifier) to afford the 2 diastereomers of (9R,E)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-11-one (TFA salt) (Example 74). Ex. 74a LC-MS: 545.2 (M+1). Ex. 74b LC-MS: 545.2 (M+1). $^1$H-NMR (500 MHz, DMSO-hd6) δ 9.32 (s, 1H), 8.46 (d, J=2.3 Hz, 1H), 8.39 (d, J=1.2 Hz, 1H), 8.03 (s, 1H), 7.80 (d, J=1.2 Hz, 1H), 7.31 (d, J=2.3 Hz, 1H), 6.08 (q, J=7.0 Hz, 2H), 5.96 (d, J=9.1 Hz, 1H), 4.85 (td, J=10.8, 4.7 Hz, 1H), 4.58 (td, J=10.8, 6.0 Hz, 1H), 4.04 (s, 1H), 3.14 (dd, J=15.5, 7.1 Hz, 1H), 3.02 (dd, J=15.6, 7.2 Hz, 1H), 2.30-2.21 (m, 2H), 1.91 (dd, J=11.5, 7.1 Hz, 1H), 1.82-1.77 (m, 1H), 1.68-1.60 (m, 2H), 1.56 (d, J=7.1 Hz, 3H), 1.49 (d, J=12.3 Hz, 2H), 1.46-1.39 (m, 2H), 1.30-1.23 (m, 1H), 0.87 (t, J=7.0 Hz, 3H).

The following compounds in Table 10 were prepared according to the general procedures herein and in an analogous manner of that described in Scheme 11 and used to synthesize Example 74 using the appropriate intermediates referenced in Table 10. The starting materials were either prepared as described in the intermediates section, commercially available, or prepared from commercially available reagents using conventional reactions well known in the art. For Example 93 and 109, Step 2 was run under the conditions of Step 3 from Scheme 13. For Examples 78-92 and 96-105 and 108, Step 2 was run under the conditions of Step 2 in Scheme 10. For Examples 104, 105 and 108, Step 3 was run in EtOH. The diastereomers were optionally separated by reverse phase HPLC or flash silica chromatography with the more active diastereomer assumed by analogy to be the same relative configuration as Example 111.

TABLE 10

| Ex. # | Structure | Name | Exact Mass [M + H]+ | Interm A | Interm C |
|---|---|---|---|---|---|
| 75A | 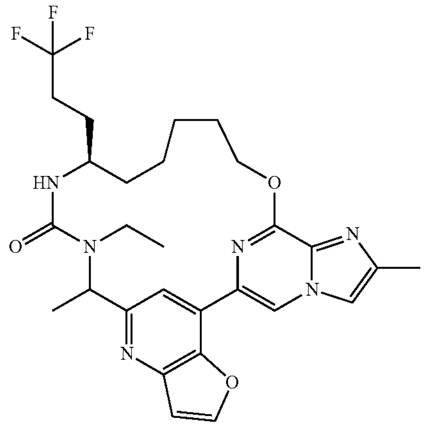 [SMILES: CCN1C(=O)N[C@@H](CCC(F)(F)F)CCCCCOc2nc(cn3cc(C)nc23)-c2cc(nc3ccoc23)C1C] | (10R)-7-ethyl-6,19-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one | Calc'd 559.3, found 559.2 | A5 | C45 |

TABLE 10-continued

| Ex. # | Structure | Name | Exact Mass [M + H]+ | Interm A | Interm C |
|---|---|---|---|---|---|
| 75B | 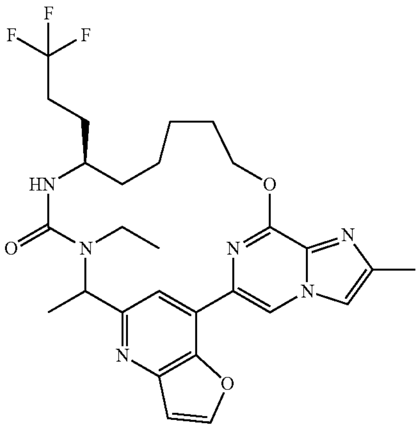 [SMILES: CCN1C(=O)N[C@@H](CCC(F)(F)F)CCCCCOc2nc(cn3cc(C)nc23)-c2cc(nc3ccoc23)C1C] | (10R)-7-ethyl-6,19-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one | Calc'd 559.3, found 559.2 | A5 | C45 |
| 76A | 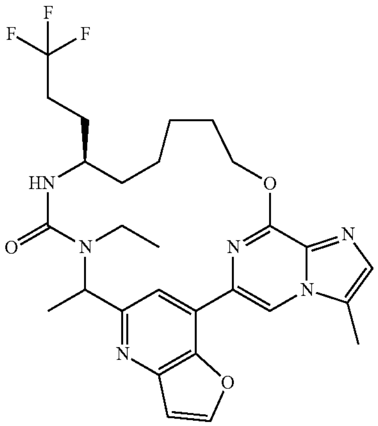 [SMILES: CCN1C(=O)N[C@@H](CCC(F)(F)F)CCCCCOc2nc(cn3c(C)cnc23)-c2cc(nc3ccoc23)C1C] | (10R)-7-ethyl-6,20-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one | Calc'd 559.3, found 559.2 | A5 | C46 |
| 76B | 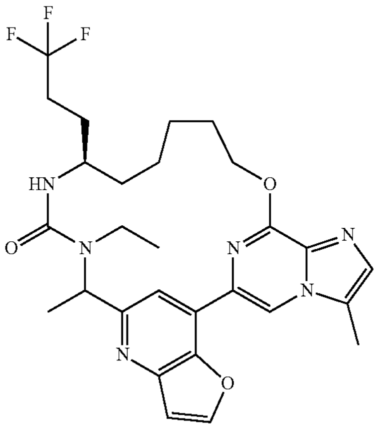 [SMILES: CCN1C(=O)N[C@@H](CCC(F)(F)F)CCCCCOc2nc(cn3c(C)cnc23)-c2cc(nc3ccoc23)C1C] | (10R)-7-ethyl-6,20-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one | Calc'd 559.3, found 559.2 | A5 | C46 |

TABLE 10-continued

| Ex. # | Structure | Name | Exact Mass [M + H]+ | Interm A | Interm C |
|---|---|---|---|---|---|
| 77 | 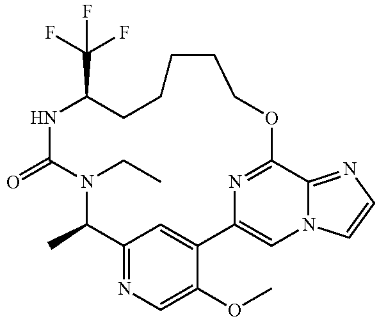 [SMILES: CCN1C(=O)N[C@@H](C(F)(F)F)CCCCCOc2nc(cn3ccnc23)-c2cc(ncc2OC)[C@H]1C] | (12R,16R)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 507.2, found 507.2 | A16 | C74 |
| 78 | 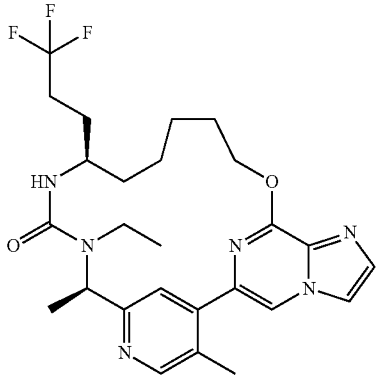 [SMILES: CCN1C(=O)N[C@@H](CCC(F)(F)F)CCCCCOc2nc(cn3ccnc23)-c2cc(ncc2C)[C@H]1C] | (12R,16R)-13-ethyl-8,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one | Calc'd 519.3, found 519.3 | A5 | C76 |
| 79 | 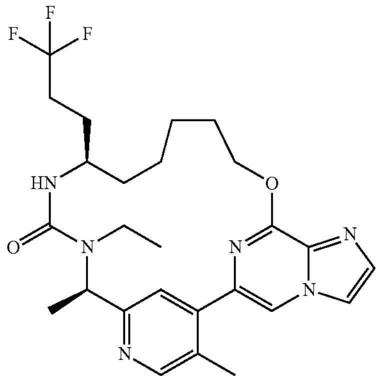 [SMILES: CCN1C(=O)N[C@@H](CCC(F)(F)F)CCCCCOc2nc(cn3ccnc23)-c2cc(ncc2C)[C@H]1C] | (12R,16R)-13-ethyl-8,12-dimethyl-16-(3,3,3-trifluoropropyl)-12,13,16,17,18,19,20,21-octahydro-6,23-(azeno)-11,7-(metheno) imidazo[2,1-c][1,4,10,13,15]oxatetraazacyclohenicosin-14(15H)-one | Calc'd 519.3, found 519.3 | A5 | C77 |
| 80A | 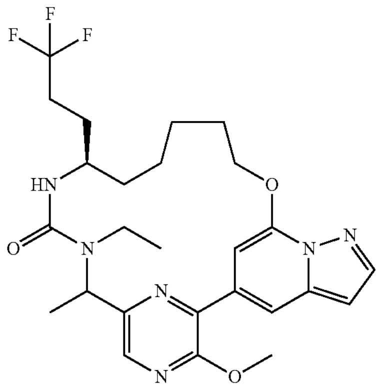 [SMILES: CCN1C(=O)N[C@@H](CCC(F)(F)F)CCCCCOc2cc(cc3ccnn23)-c2nc(cnc2OC)C1C] | (15R)-12-ethyl-7-methoxy-11-methyl-15-(3,3,3-trifluoropropyl)-11,12,15,16,17,18,19,20-octahydro-10,6-(azeno)-5,22-(metheno) pyrazolo[1,5-c][1,3,9,13,15]oxatetraazacyclohenicosin-13(14H)-one | Calc'd 535.3, found 535.3 | A5 | C88 |

TABLE 10-continued

| Ex. # | Structure | Name | Exact Mass [M + H]+ | Interm A | Interm C |
|---|---|---|---|---|---|
| 80B | 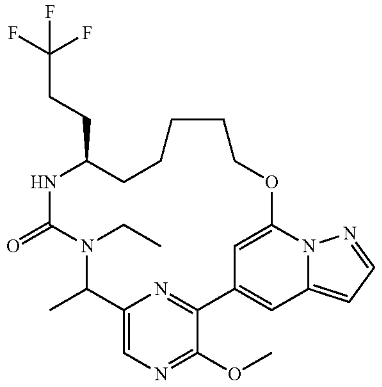 [SMILES: CCN1C(=O)N[C@@H](CCC(F)(F)F)CCCCCOc2cc(cc3ccnn23)-c2nc(cnc2OC)C1C] | (15R)-12-ethyl-7-methoxy-11-methyl-15-(3,3,3-trifluoro-propyl)-11,12,15,16,17,18,19,20-octa-hydro-10,6-(azeno)-5,22-(metheno) pyrazolo[1,5-c][1,3,9,13,15]oxatet-raazacyclohenicosin-13(14H)-one | Calc'd 535.3, found 535.3 | A5 | C88 |
| 81 | 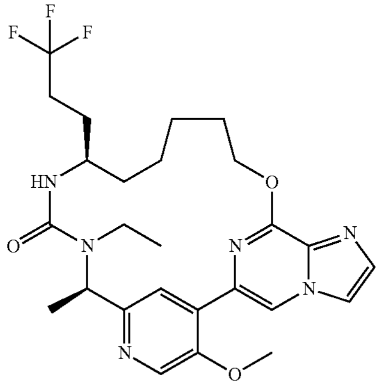 [SMILES: CCN1C(=O)N[C@@H](CCC(F)(F)F)CCCCCOc2nc(cn3ccnc23)-c2cc(ncc2OC)[C@H]1C] | (12R,16R)-13-ethyl-8-methoxy-12-methyl-16-(3,3,3-trifluoropropyl)-12,13,15,16,17,18,19,20,21,22-decahydro-14H-6,23-(azeno)-11,7-(metheno) imidazo[1,2-l][1,3,6,12]tetraazacy-clohenicosin-14-one | Calc'd 533.3, found 533.3 | A5 | C134 |
| 82 | 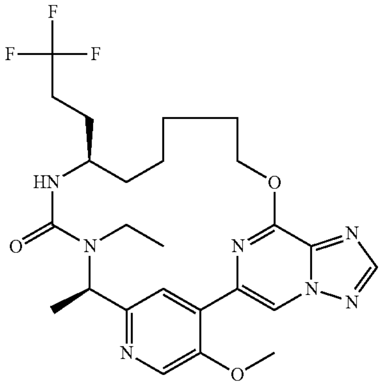 [SMILES: CCN1C(=O)N[C@@H](CCC(F)(F)F)CCCCCOc2nc(cn3ncnc23)-c2cc(ncc2OC)[C@H]1C] | (12R,16R)-13-ethyl-8-methoxy-12-methyl-16-(3,3,3-tri-fluoropropyl)-12,13,16,17,18,19,20,21-octahydro-6,23-(azeno)-11,7-(metheno)[1,2,4]tria-zolo[5,1-c][1,4,10,13,15]oxatetraazacyclo-henicosin-14(15H)-one | Calc'd 536.3, found 536.4 | A5 | C81 |
| 83 | 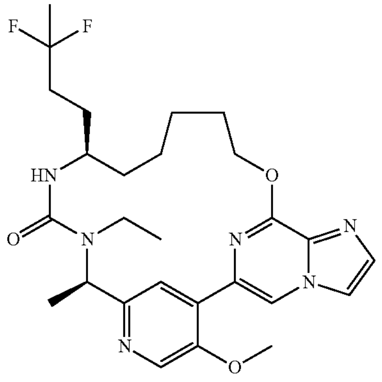 [SMILES: CCN1C(=O)N[C@@H](CCC(C)(F)F)CCCCCOc2nc(cn3ccnc23)-c2cc(ncc2OC)[C@H]1C] | (12R,16R)-16-(3,3-difluorobutyl)-13-ethyl-8-methoxy-12-methyl-12,13,16,17,18,19,20,21-octa-hydro-6,23-(azeno)-11,7-(metheno) imidazo[2,1-c][1,4,9,13,15]oxatetraazacy-clohenicosin-14(15H)-one | Calc'd 531.3, found 531.4 | A21 | C78 |

TABLE 10-continued

| Ex. # | Structure | Name | Exact Mass [M + H]+ | Interm A | Interm C |
|---|---|---|---|---|---|
| 84 | 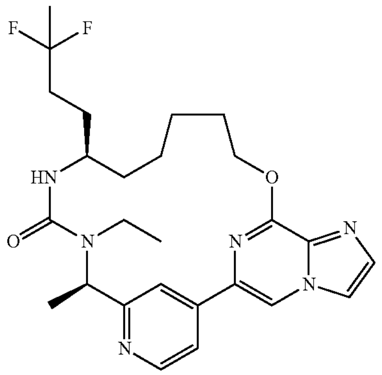 [SMILES: CCN1C(=O)N[C@@H](CCC(C)(F)F)CCCCCOc2nc(cn3ccnc23)-c2ccnc(c2)[C@H]1C] | (12R,16R)-16-(3,3-difluorobutyl)-13-ethyl-12-methyl-12,13,16,17,18,19,20,21-octahydro-6,23-(azeno)-11,7-(metheno)imidazo[2,1-c][1,4,10,13,15]oxatetraazacycloheni-cosin-14(15H)-one | Calc'd 501.3, found 501.3 | A21 | C75 |
| 85 | 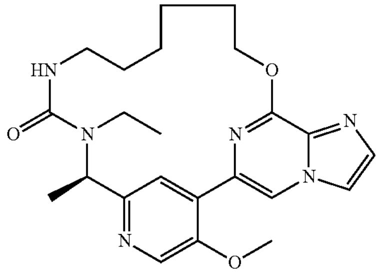 [SMILES: CCN1C(=O)NCCCCCCOc2nc(cn3ccnc23)-c2cc(ncc2OC)[C@H]1C] | (12R)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacycloheni-cosin-14(15H)-one | Calc'd 439.2, found 439.4 | but-3-en-1-amine | C74 |
| 86 | 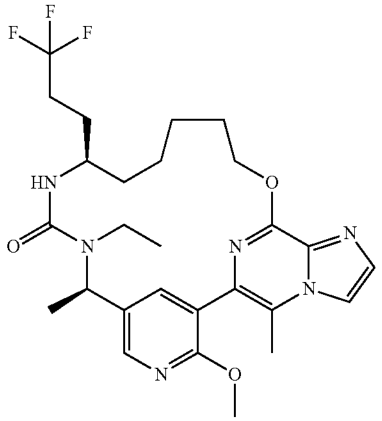 [SMILES: CCN1C(=O)N[C@@H](CCC(F)(F)F)CCCCCOc2nc(c(C)n3ccnc23)-c2cc(cnc2OC)[C@H]1C] | (12R,16R)-13-ethyl-8-methoxy-5,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacycloheni-cosin-14(15H)-one | Calc'd 549.3, found 549.2 | A5 | C6 |
| 87 | 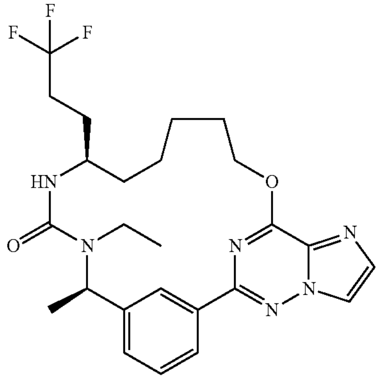 [SMILES: CCN1C(=O)N[C@@H](CCC(F)(F)F)CCCCCOc2nc(nn3ccnc23)-c2cccc(c2)[C@H]1C] | (12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,13,15]oxatetraazacycloheni-cosin-14(15H)-one | Calc'd 505.3, found 505.5 | A5 | C20 |

TABLE 10-continued

| Ex. # | Structure | Name | Exact Mass [M + H]+ | Interm A | Interm C |
| --- | --- | --- | --- | --- | --- |
| 88A | 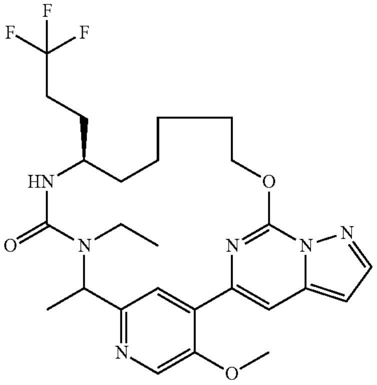 [SMILES: CCN1C(=O)N[C@@H](CCC(F)(F)F)CCCCCOc2nc(cc3ccnn23)-c2cc(ncc2OC)C1C] | (15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,10,13,15]oxatetraazacycloheni-cosin-13(14H)-one | Calc'd 535.3, found 535.5 | A5 | C110 |
| 88B | 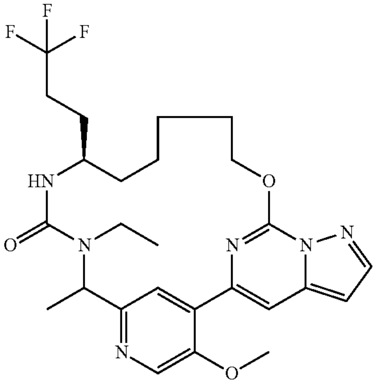 [SMILES: CCN1C(=O)N[C@@H](CCC(F)(F)F)CCCCCOc2nc(cc3ccnn23)-c2cc(ncc2OC)C1C] | (15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,10,13,15]oxatetraazacycloheni-cosin-13(14H)-one | Calc'd 535.3, found 535.5 | A5 | C110 |
| 89 | 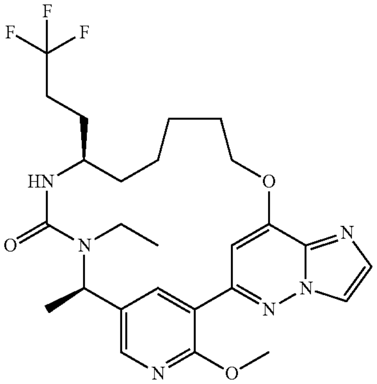 [SMILES: CCN1C(=O)N[C@@H](CCC(F)(F)F)CCCCCOc2cc(nn3ccnc23)-c2cc(cnc2OC)[C@H]1C] | (12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,5,9,13,15]oxapentaaza-cyclohenicosin-14(15H)-one | Calc'd 535.3, found 535.2 | A5 | C16 |
| 90 | 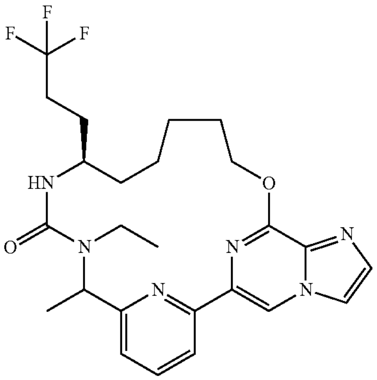 [SMILES: CCN1C(=O)N[C@@H](CCC(F)(F)F)CCCCCOc2nc(cn3ccnc23)-c2cccc(n2)C1C] | (16R)-13-ethyl-12-methyl-16-(3,3,3-trifluoropropyl)-12,13,16,17,18,19,20,21-octahydro-6,23:11,7-di(azeno)imidazo[2,1-c][1,4,13,15]oxatriazacyclo-henicosin-14(15H)-one | Calc'd 505.3, found 505.3 | A5 | C80 |

TABLE 10-continued

| Ex. # | Structure | Name | Exact Mass [M + H]+ | Interm A | Interm C |
|---|---|---|---|---|---|
| 91 | 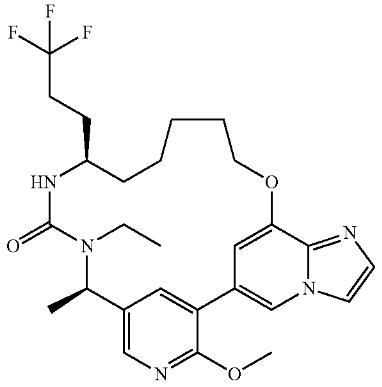 [SMILES: CCN1C(=O)N[C@@H](CCC(F)(F)F)CCCCCOc2cc(cn3ccnc23)-c2cc(cnc2OC)[C@H]1C] | (12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,9,13,15]oxatetraazacyclo-henicosin-14(15H)-one | Calc'd 534.3, found 534.5 | A5 | C15 |
| 92A | 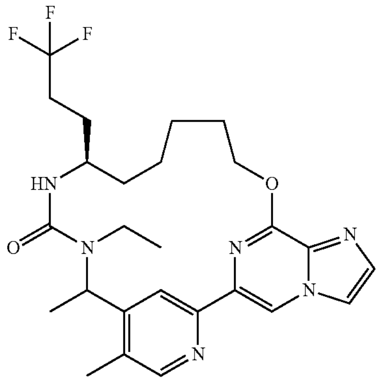 [SMILES: CCN1C(=O)N[C@@H](CCC(F)(F)F)CCCCCOc2nc(cn3ccnc23)-c2cc(c(C)cn2)C1C] | (16R)-13-ethyl-10,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacycloheni-cosin-14(15H)-one | Calc'd 519.3, found 519.1 | A5 | C90 |
| 92B | 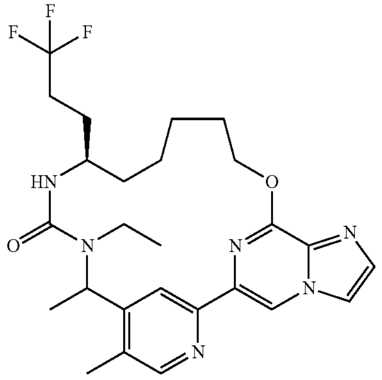 [SMILES: CCN1C(=O)N[C@@H](CCC(F)(F)F)CCCCCOc2nc(cn3ccnc23)-c2cc(c(C)cn2)C1C] | (16R)-13-ethyl-10,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacycloheni-cosin-14(15H)-one | Calc'd 519.3, found 519.1 | A5 | C90 |
| 93A | 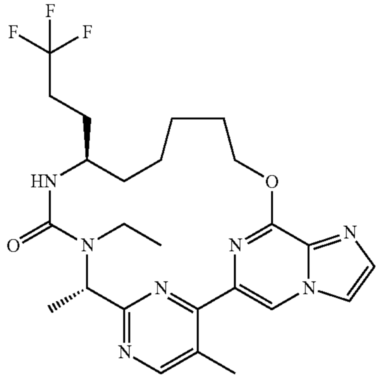 [SMILES: CCN1C(=O)N[C@@H](CCC(F)(F)F)CCCCCOc2nc(cn3ccnc23)-c2nc(ncc2C)[C@@H]1C] | (12S,16R)-13-ethyl-8,12-dimethyl-16-(3,3,3-trifluoro-propyl)-12,13,16,17,18,19,20,21-octa-hydro-6,23:11,7-di(azeno)imidazo[2,1-c][1,4,10,13,15]oxatet-raazacyclohenicosin-14(15H)-one | Calc'd 520.3, found 520.4 | A5 | C92 |

TABLE 10-continued

| Ex. # | Structure | Name | Exact Mass [M + H]+ | Interm A | Interm C |
|---|---|---|---|---|---|
| 93B | 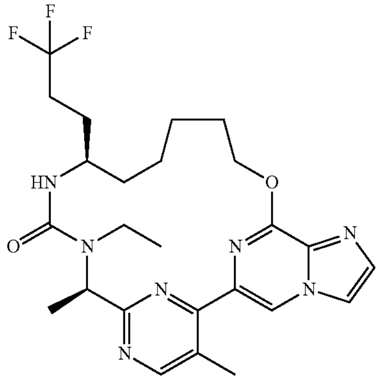 [SMILES: CCN1C(=O)N[C@@H](CCC(F)(F)F)CCCCCOc2nc(cn3ccnc23)-c2nc(ncc2C)[C@H]1C] | (12R,16R)-13-ethyl-8,12-dimethyl-16-(3,3,3-trifluoro-propyl)-12,13,16,17,18,19,20,21-octa-hydro-6,23:11,7-di(azeno)imidazo[2,1-c][1,4,10,13,15]oxatet-raazacyclohenicosin-14(15H)-one | Calc'd 520.3, found 520.4 | A5 | C92 |
| 94A | 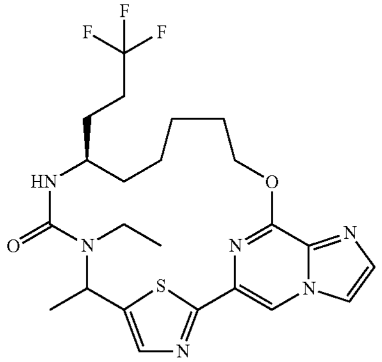 [SMILES: CCN1C(=O)N[C@@H](CCC(F)(F)F)CCCCCOc2nc(cn3ccnc23)C2=NC=C(S2)C1C] | (15R)-12-ethyl-11-methyl-15-(3,3,3-trifluoropropyl)-11,12,15,16,17,18,19,20-octahydro-6,22-(azeno)-7,10-epithioimidazo[2,1-c][1,4,8,12,14]oxatet-raazacycloicosin-13(14H)-one | Calc'd 511.2, found 511.2 | A5 | C129 |
| 94B | 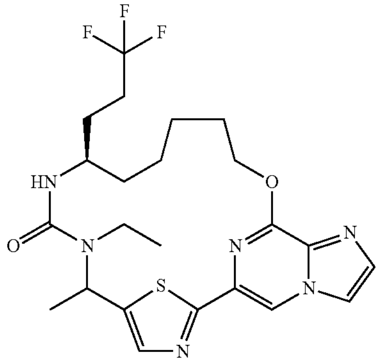 [SMILES: CCN1C(=O)N[C@@H](CCC(F)(F)F)CCCCCOc2nc(cn3ccnc23)C2=NC=C(S2)C1C] | (15R)-12-ethyl-11-methyl-15-(3,3,3-trifluoropropyl)-11,12,15,16,17,18,19,20-octahydro-6,22-(azeno)-7,10-epithioimidazo[2,1-c][1,4,8,12,14]oxatet-raazacycloicosin-13(14H)-one | Calc'd 511.2, found 511.2 | A5 | C129 |
| 95 | 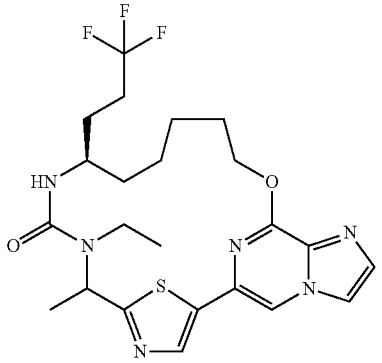 [SMILES: CCN1C(=O)N[C@@H](CCC(F)(F)F)CCCCCOc2nc(cn3ccnc23)C2=CN=C(S2)C1C] | (15R)-12-ethyl-11-methyl-15-(3,3,3-trifluoropropyl)-11,12,15,16,17,18,19,20-octahydro-6,22-(azeno)-7,10-epithioimidazo[2,1-c][1,4,9,12,14]oxatet-raazacycloicosin-13(14H)-one | Calc'd 511.2, found 511.2 | A5 | C128 |

TABLE 10-continued

| Ex. # | Structure | Name | Exact Mass [M + H]+ | Interm A | Interm C |
|---|---|---|---|---|---|
| 96A | 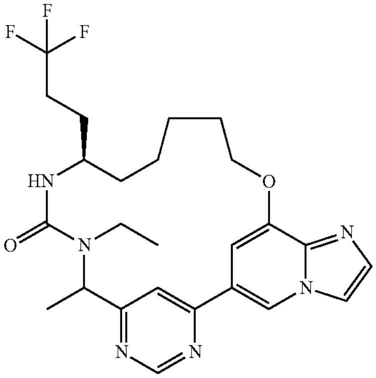 [SMILES: CCN1C(=O)N[C@@H](CCC(F)(F)F)CCCCCOc2cc(cn3ccnc23)-c2cc(ncn2)C1C] | (16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacycloheni-cosin-14(15H)-one | Calc'd 505.3, found 505.1 | A5 | C95 |
| 96B | 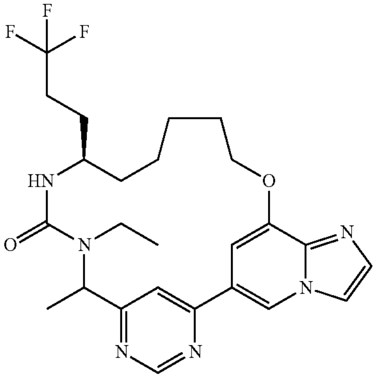 [SMILES: CCN1C(=O)N[C@@H](CCC(F)(F)F)CCCCCOc2cc(cn3ccnc23)-c2cc(ncn2)C1C] | (16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacycloheni-cosin-14(15H)-one | Calc'd 505.3, found 505.2 | A5 | C95 |
| 97 | 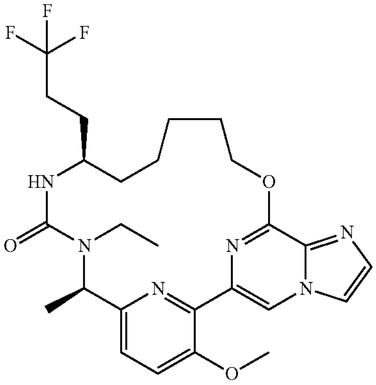 [SMILES: CCN1C(=O)N[C@@H](CCC(F)(F)F)CCCCCOc2nc(cn3ccnc23)-c2nc(ccc2OC)[C@H]1C] | (12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,13,15]oxatriaza-cyclohenicosin-14(15H)-one | Calc'd 535.3, found 535.5 | A5 | C79 |
| 98 | 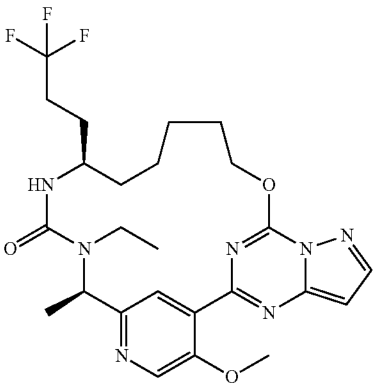 [SMILES: CCN1C(=O)N[C@@H](CCC(F)(F)F)CCCCCOc2nc(nc3ccnn23)-c2cc(ncc2OC)[C@H]1C] | (11R,15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,5,10,13,15]oxapentaazacycloheni-cosin-13(14H)-one | Calc'd 536.3, found 536.5 | A5 | C59 |

TABLE 10-continued

| Ex. # | Structure | Name | Exact Mass [M + H]+ | Interm A | Interm C |
|---|---|---|---|---|---|
| 99 | 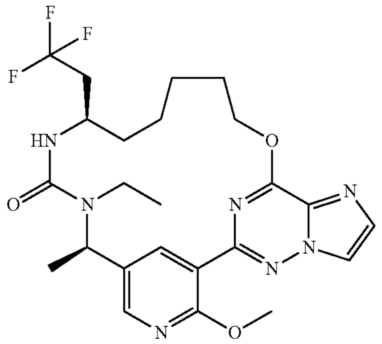 [SMILES: CCN1C(=O)N[C@@H](CC(F)(F)F)CCCCCOc2nc(nn3ccnc23)-c2cc(cnc2OC)[C@H]1C] | (12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,5,9,13,15]oxapentaazacycloheni-cosin-14(15H)-one | Calc'd 522.2, found 522.4 | A14 | C18 |
| 100 | 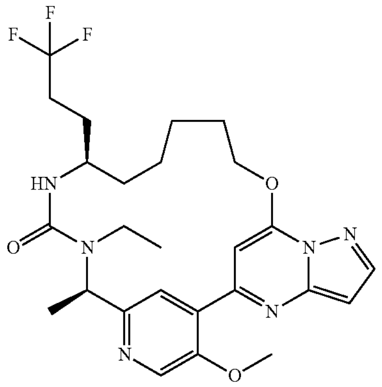 [SMILES: CCN1C(=O)N[C@@H](CCC(F)(F)F)CCCCCOc2cc(nc3ccnn23)-c2cc(ncc2OC)[C@H]1C] | (11R,15R)-12-ethyl-7-methoxy-11-methyl-15-(3,3,3-trifluoropropyl)-11,12,15,16,17,18,19,20-octahydro-5,22: 10,6-di(metheno)pyrazolo[1,5-c][1,3,5,10,13,15]oxapentaazacycloheni-cosin-13(14H)-one | Calc'd 535.3, found 535.3 | A5 | C17 |
| 101 | 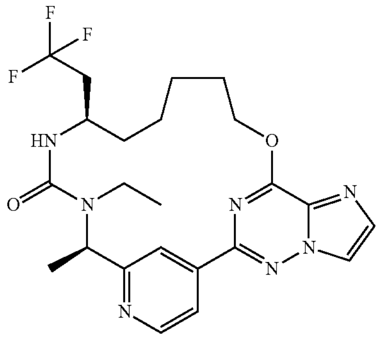 [SMILES: CCN1C(=O)N[C@@H](CC(F)(F)F)CCCCCOc2nc(nn3ccnc23)-c2ccnc(c2)[C@H]1C] | (12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,5,10,13,15]oxapentaazacycloheni-cosin-14(15H)-one | Calc'd 492.2, found 492.5 | A14 | C21 |
| 102 | 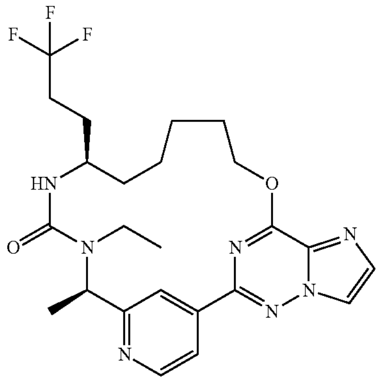 [SMILES: CCN1C(=O)N[C@@H](CCC(F)(F)F)CCCCCOc2nc(nn3ccnc23)-c2ccnc(c2)[C@H]1C] | (12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,10,13,15]oxapentaazacycloheni-cosin-14(15H)-one | Calc'd 506.2, found 506.3 | A5 | C21 |

TABLE 10-continued

| Ex. # | Structure | Name | Exact Mass [M + H]+ | Interm A | Interm C |
|---|---|---|---|---|---|
| 103 | 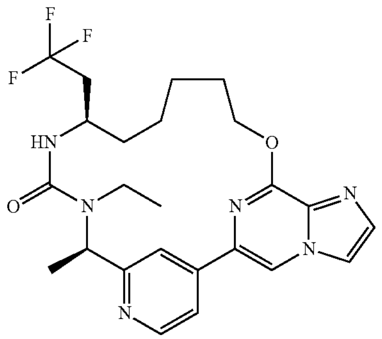 [SMILES: CCN1C(=O)N[C@@H](CC(F)(F)F)CCCCCOc2nc(cn3ccnc23)-c2ccnc(c2)[C@H]1C] | (12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacycloheni-cosin-14(15H)-one | Calc'd 491.2, found 491.5 | A14 | C75 |
| 104A | 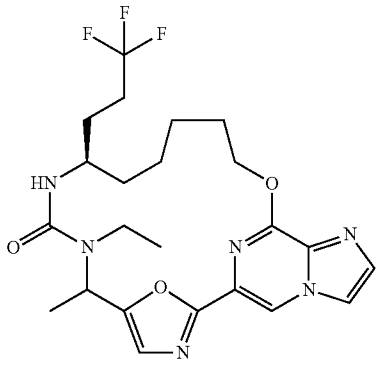 [SMILES: CCN1C(=O)N[C@@H](CCC(F)(F)F)CCCCCOc2nc(cn3ccnc23)C2=NC=C(O2)C1C] | (15R)-12-ethyl-11-methyl-15-(3,3,3-trifluoropropyl)-11,12,15,16,17,18,19,20-octahydro-6,22-(azeno)-7,10-epoxyimidazo[2,1-c][1,4,8,12,14]oxatet-raazacycloicosin-13(14H)-one | Calc'd 495.2, found 495 | A5 | C125 |
| 104B | 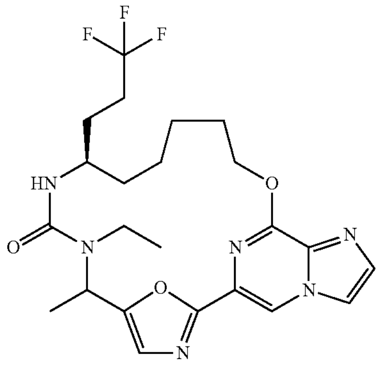 [SMILES: CCN1C(=O)N[C@@H](CCC(F)(F)F)CCCCCOc2nc(cn3ccnc23)C2=NC=C(O2)C1C] | (15R)-12-ethyl-11-methyl-15-(3,3,3-trifluoropropyl)-11,12,15,16,17,18,19,20-octahydro-6,22-(azeno)-7,10-epoxyimidazo[2,1-c][1,4,8,12,14]oxatet-raazacycloicosin-13(14H)-one | Calc'd 495.2, found 495.2 | A5 | C125 |
| 105A | 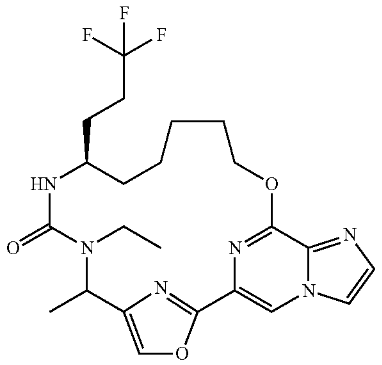 [SMILES: CCN1C(=O)N[C@@H](CCC(F)(F)F)CCCCCOc2nc(cn3ccnc23)-c2nc(co2)C1C] | (15R)-12-ethyl-11-methyl-15-(3,3,3-trifluoropropyl)-11,12,15,16,17,18,19,20-octahydro-6,22:10,7-di(azeno)imidazo[2,1-c][1,8,4,12,14]dioxatri-azacycloicosin-13(14H)-one | Calc'd 495.2, found 495.3 | A5 | C127 |

TABLE 10-continued

| Ex. # | Structure | Name | Exact Mass [M + H]+ | Interm A | Interm C |
|---|---|---|---|---|---|
| 105B | 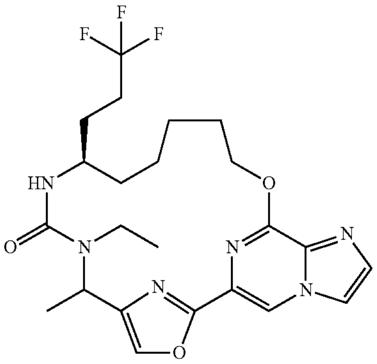 [SMILES: CCN1C(=O)N[C@@H](CCC(F)(F)F)CCCCCOc2nc(cn3ccnc23)-c2nc(co2)C1C] | (15R)-12-ethyl-11-methyl-15-(3,3,3-trifluoropropyl)-11,12,15,16,17,18,19,20-octahydro-6,22:10,7-di(azeno) imidazo[2,1-c][1,8,4,12,14]dioxatri-azacycloicosin-13(14H)-one | Calc'd 495.2, found 495.3 | A5 | C127 |
| 106 | 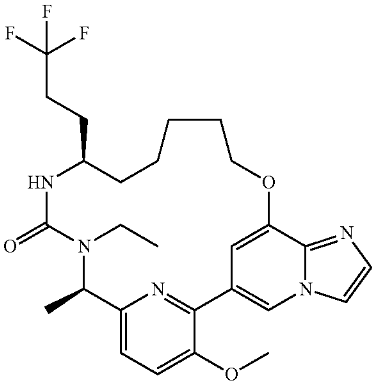 [SMILES: CCN1C(=O)N[C@@H](CCC(F)(F)F)CCCCCOc2cc(cn3ccnc23)-c2nc(ccc2OC)[C@H]1C] | (12R,16R)-13-ethyl-8-methoxy-12-methyl-16-(3,3,3-trifluoropropyl)-12,13,15,16,17,18,19,20,21,22-decahydro-14H-11,7-(azeno)-6,23-(metheno) imidazo[1,2-1][1,3,12] triazacyclohenicosin-14-one | Calc'd 532.3, found 532.3 | A5 | C139 |
| 107A | 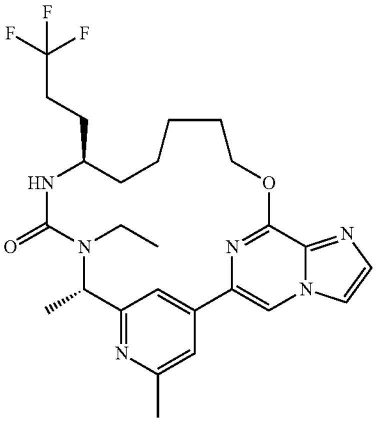 [SMILES: CCN1C(=O)N[C@@H](CCC(F)(F)F)CCCCCOc2nc(cn3ccnc23)-c2cc(C)nc(c2)[C@@H]1C] | (12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15] oxatetraazacycloheni-cosin-14(15H)-one | Calc'd 519.3, found 519.4 | A5 | C98 |

TABLE 10-continued

| Ex. # | Structure | Name | Exact Mass [M + H]+ | Interm A | Interm C |
|---|---|---|---|---|---|
| 107B | 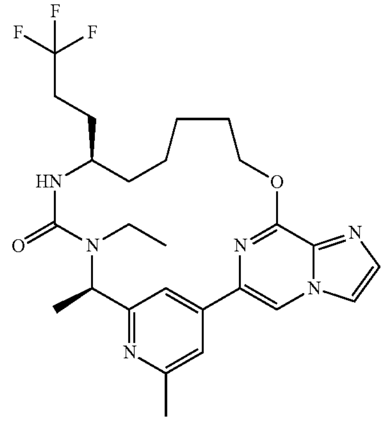 [SMILES: CCN1C(=O)N[C@@H](CCC(F)(F)F)CCCCCOc2nc(cn3ccnc23)-c2cc(C)nc(c2)[C@H]1C] | (12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacycloheni-cosin-14(15H)-one | Calc'd 519.3, found 519.4 | A5 | C98 |
| 108 | 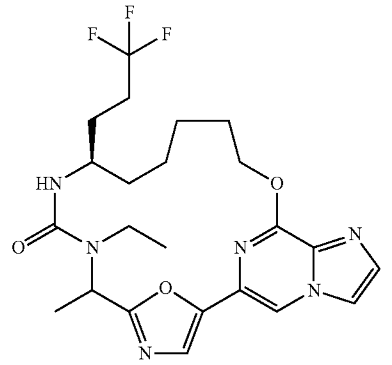 [SMILES: CCN1C(=O)N[C@@H](CCC(F)(F)F)CCCCCOc2nc(cn3ccnc23)C2=CN=C(O2)C1C] | (15R)-12-ethyl-11-methyl-15-(3,3,3-trifluoropropyl)-11,12,15,16,17,18,19,20-octahydro-6,22-(azeno)-7,10-epoxyimidazo[2,1-c][1,4,9,12,14]oxatet-raazacycloicosin-13(14H)-one | Calc'd 495.2, found 495.3 | A5 | C121 |
| 109 | 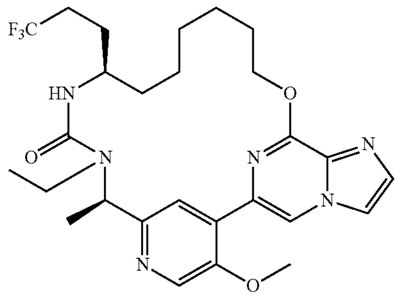 [SMILES: CCN1C(=O)N[C@@H](CCC(F)(F)F)CCCCCCOc2nc(cn3ccnc23)-c2cc(ncc2OC)[C@H]1C] | (3R,7R,E)-4-ethyl-25-methoxy-3-methyl-7-(3,3,3-trifluoropropyl)-14-oxa-4,6-diaza-1(6,8)-imidazo[1,2-a]pyrazina-2(4,2)-pyridinacyclotetra-decaphan-5-one | Calc'd 549.6, found 549.5 | A15 | C74 |
| 177 | 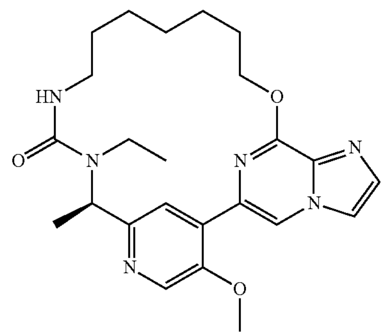 [SMILES: CCN1C(=O)NCCCCCCCOc2nc(cn3ccnc23)-c2cc(ncc2OC)[C@H]1C] | (R,E)-4-ethyl-25-methoxy-3-methyl-14-oxa-4,6-diaza-1(6,8)-imidazo[1,2-a]pyrazina-2(4,2)-pyridinacyclo-tetradecaphan-5-one | Calc'd 453.3, found 453.4 | 3-buten-1-amine | C74 |

TABLE 10-continued

| Ex. # | Structure | Name | Exact Mass [M + H]+ | Interm A | Interm C |
|---|---|---|---|---|---|
| 178 | 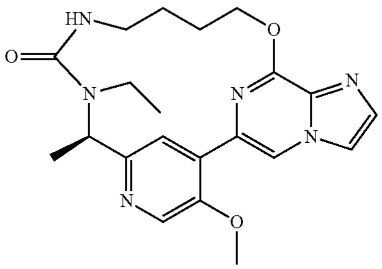 [SMILES: CCN1C(=O)NCCCCOc2nc(cn3ccnc23)-c2cc(ncc2OC)[C@H]1C] | (R,E)-4-ethyl-25-methoxy-3-methyl-11-oxa-4,6-diaza-1(6,8)-imidazo[1,2-a]pyrazina-2(4,2)-pyridinacycloun-decaphan-5-one | Calc'd 411.2, found 411.4 | 3-buten-1-amine | C74 |
| 192 | 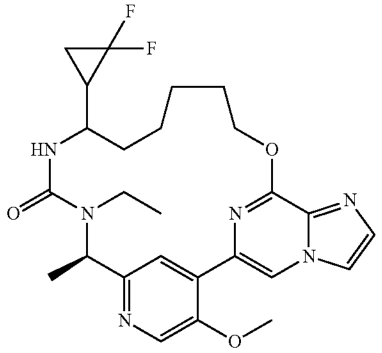 [SMILES: CCN1C(=O)NC(C2CC2(F)F)CCCCCOc2nc(cn3ccnc23)-c2cc(ncc2OC)[C@H]1C] | (3R,E)-7-(2,2-difluorocyclopropyl)-4-ethyl-25-methoxy-3-methyl-13-oxa-4,6-diaza-1(6,8)-imidazo[1,2-a]pyrazina-2(4,2)-pyridinacyclotri-decaphan-5-one | Calc'd 514.6, found 515.4 | A148 | C74 |
| 193 | 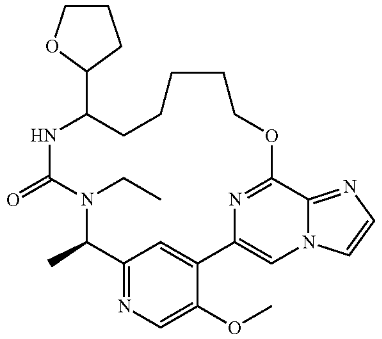 [SMILES: CCN1C(=O)NC(C2CCCO2)CCCCCOc2nc(cn3ccnc23)-c2cc(ncc2OC)[C@H]1C] | (3R,E)-4-ethyl-25-methoxy-3-methyl-7-(tetrahydrofuran-2-yl)-13-oxa-4,6-diaza-1(6,8)-imidazo[1,2-a]pyrazina-2(4,2)-pyridinacyclotri-decaphan-5-one | Calc'd 508.6, found 509.4 | A150 | C74 |
| 195 | 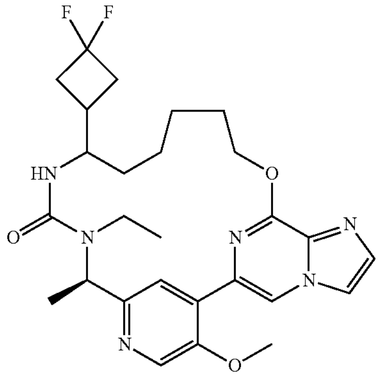 [SMILES: CCN1C(=O)NC(C2CC(F)(F)C2)CCCCCOc2nc(cn3ccnc23)-c2cc(ncc2OC)[C@H]1C] | (3R,E)-7-(3,3-difluorocyclobutyl)-4-ethyl-25-methoxy-3-methyl-13-oxa-4,6-diaza-1(6,8)-imidazo[1,2-a]pyrazina-2(4,2)-pyridinacyclotri-decaphan-5-one | Calc'd 528.6, found 529.4 | A152 | C74 |

TABLE 10-continued

| Ex. # | Structure | Name | Exact Mass [M + H]+ | Interm A | Interm C |
|---|---|---|---|---|---|
| 198 * | 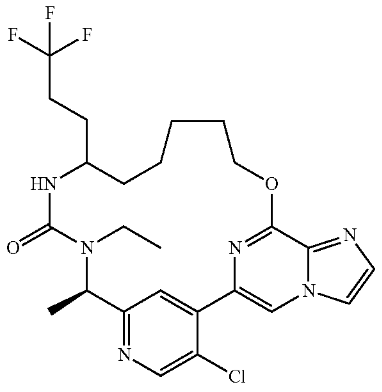 [SMILES: CCN1C(=O)NC(CCC(F)(F)F)CCCCCOc2nc(cn3ccnc23)-c2cc(ncc2Cl)[C@H]1C] | (3R,E)-25-chloro-4-ethyl-3-methyl-7-(3,3,3-trifluoropropyl)-13-oxa-4,6-diaza-1(6,8)-imidazo[1,2-a]pyrazina-2(4,2)-pyridinacyclotri-decaphan-5-one | Calc'd 539.0, found 540.2 | A5 | C153 |

Ex. 80A and 80B were separated from a mixture by SFC separation (Whelk-O1 column, 55% EtOH in $CO_2$, with 0.10% $NH_3H_2O$ as additive). Ex. 99 and 103 were separated from trace other diastereomers by SFC separation (Chiral CEL OD-3 column, 5-40% EtOH in $CO_2$ with 0.05% diethylamine as additive). Ex. 96A and 96B were separated from a mixture by SFC separation (Daicel Chiralpak AD-H column, 35% EtOH 65% $CO_2$ with 0.1% ammonia as additive). Ex. 198, in the last step Pd/C was replaced with $PtO_2$.

Example 110

(3R,7R,E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one (Example 110)

SCHEME 12

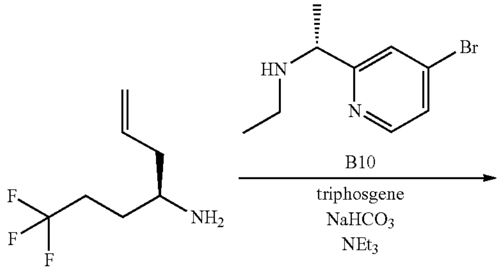

A5

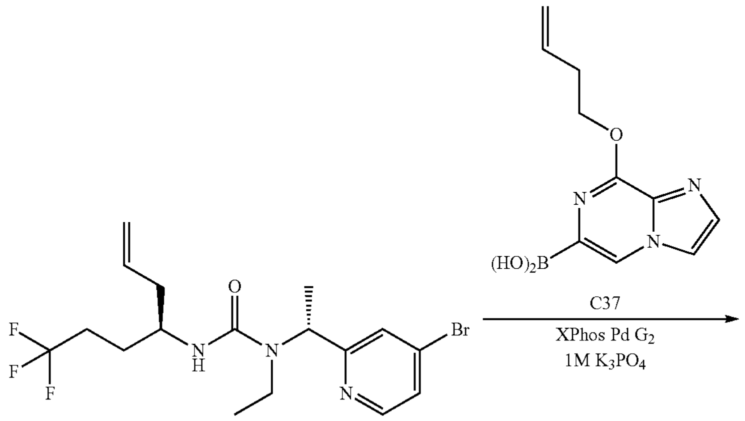

110a

-continued

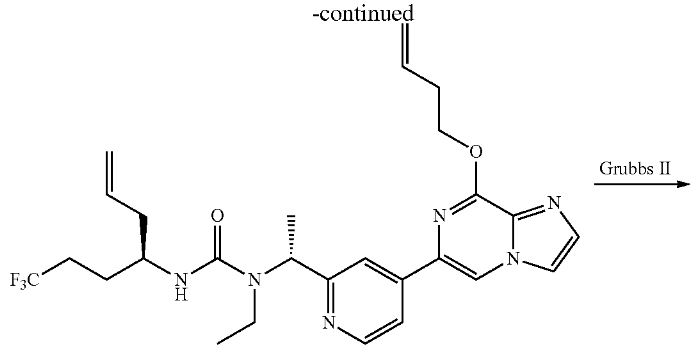

110b

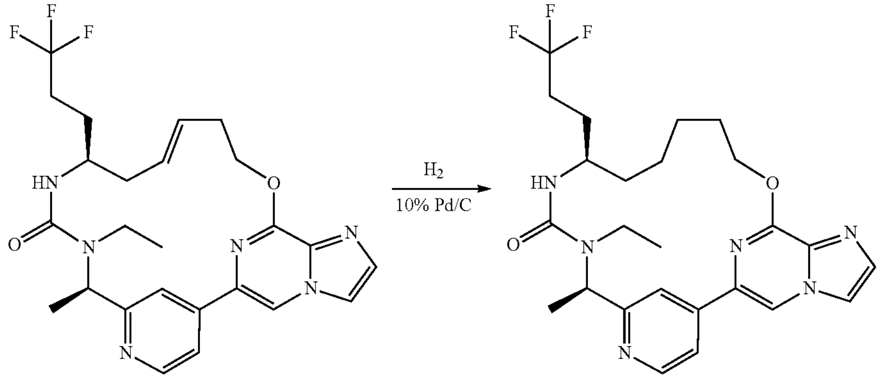

110c

Example 110

Step 1: 1-((R)-1-(4-bromopyridin-2-yl)ethyl)-1-ethyl-3-((S)-7,7,7-trifluorohept-1-en-4-yl)urea (110a)

Triphosgene (3.54 g, 11.92 mmol) was added to a solution of (S)-7,7,7-trifluorohept-1-en-4-amine hydrochloride (A5, 8.00 g, 39.3 mmol) in DCM (100 mL) and sat. aq. $NaHCO_3$ (100 mL) at ambient temperature and the reaction was stirred for 1 h. The mixture was poured onto water (100 mL) and the organic layer was separated. The aqueous layer was washed with DCM (2×50 mL). The combined organic layers were dried ($Na_2SO_4$), filtered through a pad of Celite and added directly to (R)-1-(4-bromopyridin-2-yl)-N-ethyl-ethan-1-amine hydrochloride (B10, 3.48 g, 13.10 mmol). Triethylamine (3.65 mL, 26.2 mmol) was added and the mixture was stirred at ambient temperature for 3 h. The reaction was concentrated and purified by flash silica gel chromatography (0-50% 3:1 mix EtOAc/EtOH in hexanes gradient) to yield 1-((R)-1-(4-bromopyridin-2-yl)ethyl)-1-ethyl-3-((S)-7,7,7-trifluorohept-1-en-4-yl)urea (110a). LC-MS: 422.1, 424.1 (M+1).

Step 2: 1-((R)-1-(4-(8-(but-3-en-1-yloxy)imidazo[1,2-a]pyrazin-6-yl)pyridin-2-yl)ethyl)-1-ethyl-3-((S)-7,7,7-trifluorohept-1-en-4-yl)urea (110b)

A solution of 1-((R)-1-(4-bromopyridin-2-yl)ethyl)-1-ethyl-3-((S)-7,7,7-trifluorohept-1-en-4-yl)urea (110a, 4.24 g, 10.04 mmol), (8-(but-3-en-1-yloxy)imidazo[1,2-a]pyrazin-6-yl)boronic acid (C37, 10.53 g, 45.2 mmol), and 1M aqueous tripotassium phosphate (20.08 mL, 20.08 mmol) in dioxane (100 mL) was degassed with nitrogen. XPhos Pd G2 (0.790 g, 1.004 mmol) was added and the mixture was heated to 55° C. for 1 h. The mixture was poured onto water (50 mL) and extracted with EtOAc (3×50 mL). The combined organic layers were dried over $Na_2SO_4$, filtered, and concentrated. The crude material was purified by flash silica chromatography (0-100% EtOAc/EtOH 3:1 mix in hexanes gradient) to yield 1-((R)-1-(4-(8-(but-3-en-1-yloxy)imidazo[1,2-a]pyrazin-6-yl)pyridin-2-yl)ethyl)-1-ethyl-3-((S)-7,7,7-trifluorohept-1-en-4-yl)urea (110b). LC-MS: 531.4 (M+1).

Step 3: ($1^7$E,3R,7S,9E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-9-en-5-one (110c)

A solution of 1-((R)-1-(4-(8-(but-3-en-1-yloxy)imidazo[1,2-a]pyrazin-6-yl)pyridin-2-yl)ethyl)-1-ethyl-3-((S)-7,7,7-trifluorohept-1-en-4-yl)urea (110b, 1.67 g, 3.15 mmol) and acetic acid (0.198 mL, 3.46 mmol) in DCE (157 mL) was degassed with nitrogen. Grubbs II catalyst (0.534 g, 0.629 mmol) was added and the vial was sealed and stirred at ambient temperature for 1.5 h The reaction was quenched with DMSO (0.1 mL) and concentrated. The reaction was then directly purified by column chromatography on silica gel (0 100% EtOAc/EtOH 3:1 mix in hexanes gradient) to yield ($1^7$E,3R,7S,9E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-9-en-5-one (110c). LC-MS: 503.2 (M+1).

Step 4: (3R,7R,E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one (Example 110)

A solution of ($1^7$E,3R,7S,9E)-4-ethyl-3-methyl-7-(3,3,3-trifluoropropyl)-13-oxa-4,6-diaza-1(6,8)-imidazo[1,2-a]

pyrazina-2(4,2)-pyridinacyclotridecaphan-9-en-5-one (110c, 1.37 g, 2.73 mmol) in EtOAc (20 mL) was degassed with nitrogen. Pd (0.580 g, 0.545 mmol) (10% on C) was added and the reaction was placed under a balloon of hydrogen and stirred at ambient temperature for 6 h. The reaction mixture was filtered through a pad of Celite and concentrated. The reaction mixture was then directly purified by column chromatography on silica gel (0-100% EtOAc/EtOH 3:1 mix in hexanes gradient) to yield a solid. To the solid dissolved in DCM (30 mL) was added Quadrapure TU resin (400 mg pretreated with DCM) and the mixture was stirred for 18 h. The solution was filtered through a Celite pad and concentrated and dried under high vacuum to yield (3R,7R,E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one (Example 110). LC-MS: 505.3 (M+1). $^{1}$H NMR (500 MHz, Methanol-$d_4$) δ 8.87 (s, 1H), 8.53 (d, J=5.4 Hz, 1H), 8.14 (s, 1H), 8.00 (d, J=1.2 Hz, 1H), 7.76 (dd, J=5.4, 1.6 Hz, 1H), 7.66 (d, J=1.2 Hz, 1H), 6.00 (dt, J=22.1, 8.0 Hz, 2H), 4.92 (dt, J=10.8, 5.5 Hz, 1H), 4.68 (td, J=10.9, 6.0 Hz, 1H), 4.12-4.06 (m, 1H), 3.29-3.19 (m, 2H), 3.12 (dd, J=15.8, 7.2 Hz, 1H), 2.29-2.17 (m, 2H), 2.05-1.96 (m, 1H), 1.90-1.67 (m, 3H), 1.67-1.48 (m, 7H), 1.02 (t, J=7.1 Hz, 3H).

Example 111

(3R,7R,E)-4-ethyl-25-methoxy-3-methyl-7-(3,3,3-trifluoropropyl)-13-oxa-4,6-diaza-1(6,8)-imidazo[1,2-a]pyrazina-2(4,2)-pyridinacyclotridecaphan-5-one (Example 111)

SCHEME 13

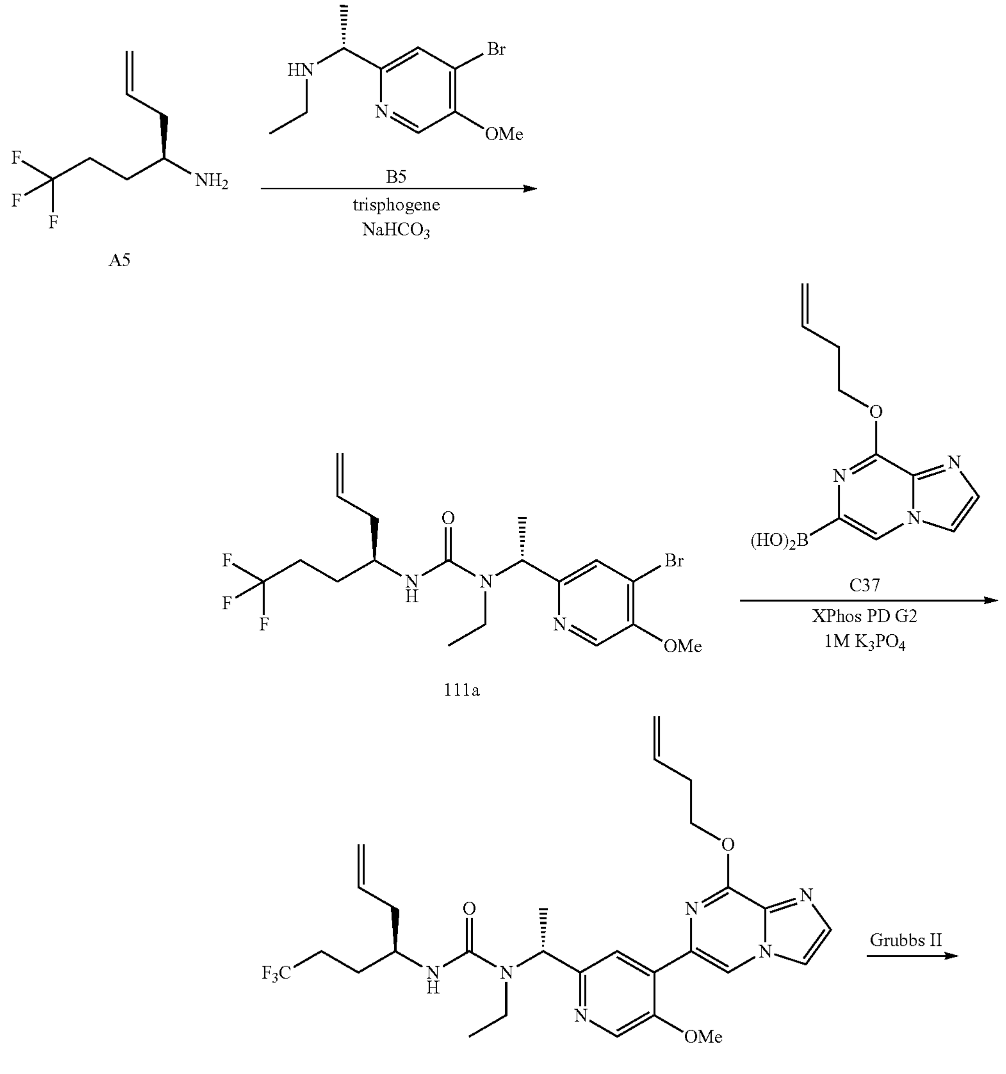

A5

111a

111b

-continued

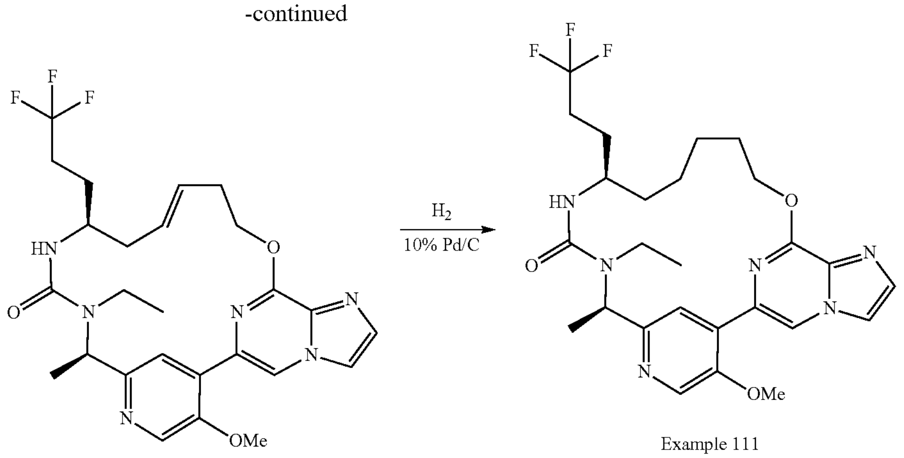

111c

Example 111

Step 1: 1-((R)-1-(4-bromo-5-methoxypyridin-2-yl) ethyl)-1-ethyl-3-((S)-7,7,7-trifluorohept-1-en-4-yl) urea (111a)

(S)-7,7,7-trifluorohept-1-en-4-amine hydrochloride (A5, 689 mg, 3.38 mmol) was dissolved in DCM (16.9 mL) and sat. aq. $NaHCO_3$(16.9 mL) and triphosgene (452 mg, 1.522 mmol) were added. The reaction was allowed to stir at ambient temperature for 1 h. The reaction mixture was then filtered through a hydrophobic frit into a vial containing (R)-1-(4-bromo-5-methoxypyridin-2-yl)-N-ethylethan-1-amine hydrochloride (B5, 500 mg, 1.691 mmol) and rinsed with DCM (0.5 mL). Triethylamine (472 μL, 3.38 mmol) was added and the reaction was heated to 50° C. for 5 min. LCMS analysis showed complete conversion. The reaction was quenched with sat. aq. $NaHCO_3$(10 mL) and extracted with DCM (3x20 mL). The combined organic layers were passed through a hydrophobic frit and concentrated. The crude material was purified by silica gel chromatography (0-100% EtOAc/EtOH 3:1 mix in hexanes gradient) to afford 1-((R)-1-(4-bromo-5-methoxypyridin-2-yl)ethyl)-1-ethyl-3-((S)-7,7,7-trifluorohept-1-en-4-yl)urea (111a). LC-MS: 452.3, 454.3 (M+1).

Step 2: 1-((R)-1-(4-(8-(but-3-en-1-yloxy)imidazo[1,2-a]pyrazin-6-yl)-5-methoxypyridin-2-yl)ethyl)-1-ethyl-3-((S)-7,7,7-trifluorohept-1-en-4-yl)urea (111b)

1-((R)-1-(4-bromo-5-methoxypyridin-2-yl)ethyl)-1-ethyl-3-((S)-7,7,7-trifluoro-hept-1-en-4-yl)urea (111a, 765 mg, 1.691 mmol) was combined with (8-(but-3-en-1-yloxy) imidazo[1,2-a]pyrazin-6-yl)boronic acid (C37, 788 mg, 3.38 mmol) and XPhos Pd G2 (133 mg, 0.169 mmol). The vial was taken into the glovebox and 1M aqueous tripotassium phosphate (6.765 mL, 6.77 mmol) and dioxane (16.9 mL) were added. The vial was sealed, removed from the glovebox and heated to 55° C. for 1.5 h. LCMS analysis showed complete conversion. The reaction was filtered through Celite and concentrated. The crude material was purified by silica gel chromatography (0-100% EtOAc/EtOH 3:1 mix in hexanes gradient) to afford 1-((R)-1-(4-(8-(but-3-en-1-yloxy)imidazo[1,2-a]pyrazin-6-yl)-5-methoxypyridin-2-yl) ethyl)-1-ethyl-3-((S)-7,7,7-trifluorohept-1-en-4-yl)urea (111b). LC-MS: 561.4 (M+1).

Step 3: ($1^7$E,3R,7S,9E)-4-ethyl-25-methoxy-3-methyl-7-(3,3,3-trifluoropropyl)-13-oxa-4,6-diaza-1(6,8)-imidazo[1,2-a]pyrazina-2(4,2)-pyridinacyclotridecaphan-9-en-5-one (111c)

1-((R)-1-(4-(8-(but-3-en-1-yloxy)imidazo[1,2-a]pyrazin-6-yl)-5-methoxypyridin-2-yl)ethyl)-1-ethyl-3-((S)-7,7,7-trifluorohept-1-en-4-yl)urea (111b, 228 mg, 0.407 mmol) was combined with Grubbs II catalyst (69.1 mg, 0.081 mmol) and the vial was taken into the glovebox. DCE (20 mL) was added, the vial was sealed and removed from the glovebox. The reaction was allowed to stir at ambient temperature for 45 min. LCMS analysis showed formation of the desired product mass. The reaction was quenched with DMSO (1 mL) and concentrated. The reaction mixture was then directly purified by reverse phase HPLC (10-95% ACN in water, with 0.1% TFA as modifier). The product containing fraction was neutralized with saturated aqueous $NaHCO_3$ and extracted with DCM to afford ($1^7$E,3R,7S,9E)-4-ethyl-25-methoxy-3-methyl-7-(3,3,3-trifluoropropyl)-13-oxa-4,6-diaza-1(6,8)-imidazo [1,2-a]pyrazina-2(4,2)-pyridinacyclotridecaphan-9-en-5-one (111c). LC-MS: 533.3 (M+1).

Step 4: (3R,7R,E)-4-ethyl-25-methoxy-3-methyl-7-(3,3,3-trifluoropropyl)-13-oxa-4,6-diaza-1(6,8)-imidazo[1,2-a]pyrazin-2(4,2)-pyridinacyclotridecaphan-5-one (Example 111)

($1^7$E,3R,7S,9Z)-4-ethyl-25-methoxy-3-methyl-7-(3,3,3-trifluoropropyl)-13-oxa-4,6-diaza-1(6,8)-imidazo[1,2-a] pyrazina-2(4,2)-pyridinacyclotridecaphan-9-en-5-one (111c, 222 mg, 0.417 mmol) was dissolved in EtOAc (20 mL) and MeOH (2.0 mL). Pd (89 mg, 0.083 mmol) (10% on C) was added and the reaction was degassed with a H2 balloon for 2 min. The exhaust needle was then removed, and the reaction was allowed to continue stirring at ambient temperature under a balloon of H2 for 1 h. LCMS analysis showed complete conversion. The reaction was filtered through Celite and concentrated. The crude material was purified by reverse phase HPLC (10-95% ACN in water, with 0.1% TFA as modifier). The product containing fraction was neutralized with saturated aqueous $NaHCO_3$ and extracted with DCM. The material was repurified by silica gel chromatography (0-100% EtOAc/EtOH 3:1 mix in hexanes gradient) to afford (3R,7R,E)-4-ethyl-25-methoxy- 3-methyl-7-(3,3,3-trifluoropropyl)-13-oxa-4,6-diaza-1(6,8)-imidazo[1,2-a]pyrazina-2(4,2)-pyridinacyclotridecaphan-5-one (Example 111).

LC-MS: 535.4 (M+1). $^1$H NMR (500 MHz, Chloroform-d) δ 8.81 (s, 1H), 8.33 (s, 1H), 8.22 (s, 1H), 7.66 (s, 2H), 6.07 (q, J=7.0 Hz, 1H), 4.91 (td, J=11.0, 5.1 Hz, 1H), 4.53 (td, J=11.0, 5.5 Hz, 1H), 4.19 (d, J=10.7 Hz, 1H), 4.10 (s, 3H), 3.95 (d, J=9.5 Hz, 1H), 3.07 (q, J=7.0 Hz, 2H), 2.34-2.16 (m, 2H), 2.10-1.97 (m, 1H), 1.91 (dq, J=11.9, 6.1 Hz, 1H), 1.79 (ddt, J=13.3, 8.6, 4.5 Hz, 1H), 1.73-1.63 (m, 1H), 1.60 (d, J=7.0 Hz, 3H), 1.58-1.48 (m, 3H), 1.44-1.30 (m, 2H), 1.03 (t, J=7.2 Hz, 3H).

Examples 112-120

The following compounds in Table 11 were prepared according to the general procedures herein and in an analogous manner of that described in Scheme 12 and used to synthesize Example 111 from the appropriate intermediates referenced in Table 11. The starting materials were either prepared as described in the intermediates section, commercially available, or prepared from commercially available reagents using conventional reactions well known in the art. For Examples 112 and 113 XPhos G3 Pd was used in Step 2. For Examples 116 and 120, Step 3 run under the conditions from Step 2 in Scheme 10. For Examples 114, 115 and 117, Step 3 was run under the conditions from Step 3 in Scheme 12. The diastereomers were optionally separated by reverse phase HPLC or flash silica chromatography with the more active diastereomer assumed by analogy to be the same relative configuration as Example 111.

TABLE 11

| Ex. # | Structure | Name | Exact Mass [M + H]+ | Interm A | Interm B | Interm C |
|---|---|---|---|---|---|---|
| 112A | 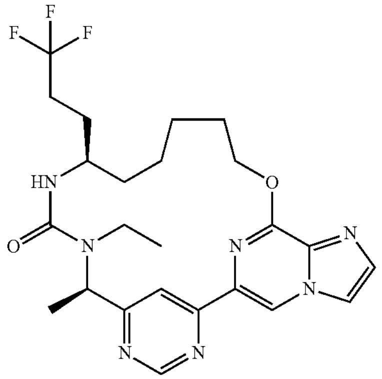 [SMILES: CCN1C(=O)N[C@@H](CCC(F)(F)F)CCCCCOc2nc(cn3ccnc23)-c2cc(ncn2)[C@H]1C] | (12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one | Calc'd 506.2, found 506.3 | A5 | B33 | C37 |
| 112B | 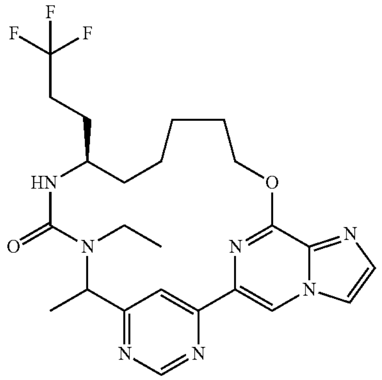 [SMILES: CCN1C(=O)N[C@@H](CCC(F)(F)F)CCCCCOc2nc(cn3ccnc23)-c2cc(ncn2)C1C] | (16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one | Calc'd 506.2, found 506.3 | A5 | B33 | C37 |
| 113A | 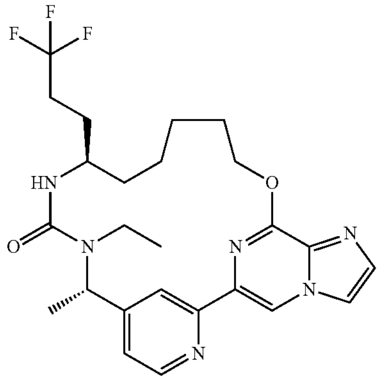 [SMILES: CCN1C(=O)N[C@@H](CCC(F)(F)F)CCCCCOc2nc(cn3ccnc23)-c2cc(ccn2)[C@@H]1C] | (12S,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one | Calc'd 505.3, found 505.3 | A5 | B35 | C37 |

TABLE 11-continued

| Ex. # | Structure | Name | Exact Mass [M + H]+ | Interm A | Interm B | Interm C |
|---|---|---|---|---|---|---|
| 113B | 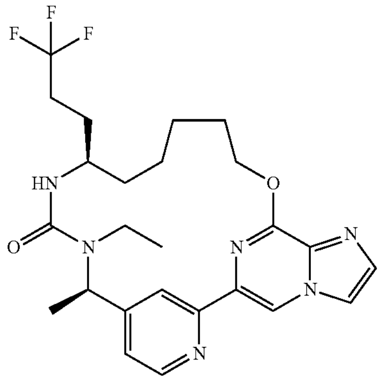 [SMILES: CCN1C(=O)N[C@@H](CCC(F)(F)F)CCCCCOc2nc(cn3ccnc23)-c2cc(ccn2)[C@H]1C] | (12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one | Calc'd 505.3, found 505.3 | A5 | B35 | C37 |
| 114 | 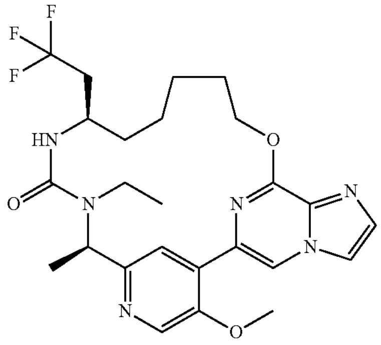 [SMILES: CCN1C(=O)N[C@@H](CC(F)(F)F)CCCCCOc2nc(cn3ccnc23)-c2cc(ncc2OC)[C@H]1C] | (12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 521.2, found 521.3 | A14 | B5 | C37 |
| 115 | 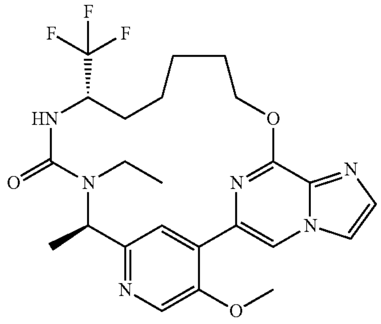 [SMILES: CCN1C(=O)N[C@H](C(F)(F)F)CCCCCOc2nc(cn3ccnc23)-c2cc(ncc2OC)[C@H]1C] | (12R,16S)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 507.2, found 507.3 | A17 | B5 | C37 |
| 116 | 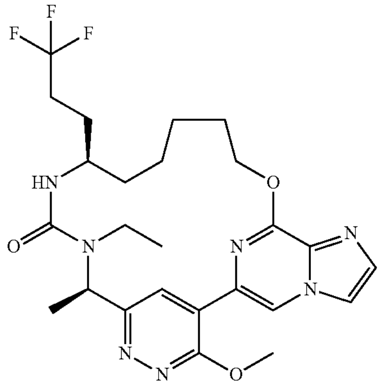 [SMILES: CCN1C(=O)N[C@@H](CCC(F)(F)F)CCCCCOc2nc(cn3ccnc23)-c2cc(nnc2OC)[C@H]1C] | (12R,16R)-13-ethyl-8-methoxy-12-methyl-16-(3,3,3-trifluoropropyl)-12,13,16,17,18,19,20,21-octahydro-6,23-(azeno)-11,7-(metheno)imidazo[2,1-c][1,4,9,10,13,15]oxapentaazacyclohenicosin-14(15H)-one | Calc'd 536.3, found 536.3 | A5 | B43 | C37 |

TABLE 11-continued

| Ex. # | Structure | Name | Exact Mass [M + H]+ | Interm A | Interm B | Interm C |
|---|---|---|---|---|---|---|
| 117A | 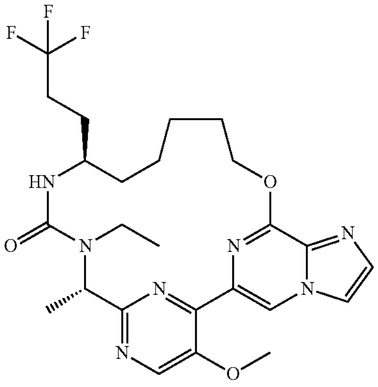 [SMILES: CCN1C(=O)N[C@@H](CCC(F)(F)F)CCCCCOc2nc(cn3ccnc23)-c2nc(ncc2OC)[C@@H]1C] | (12S,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one | Calc'd 536.3, found 536.3 | A5 | B48 | C37 |
| 117B | 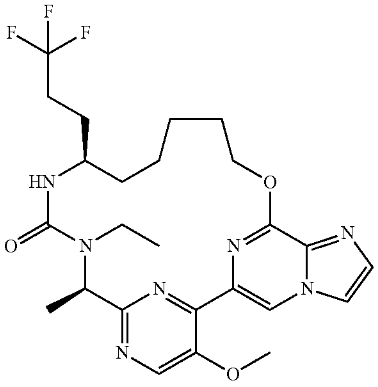 | (12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one | Calc'd 536.3, found 536.3 | A5 | B48 | C37 |
| 118A | 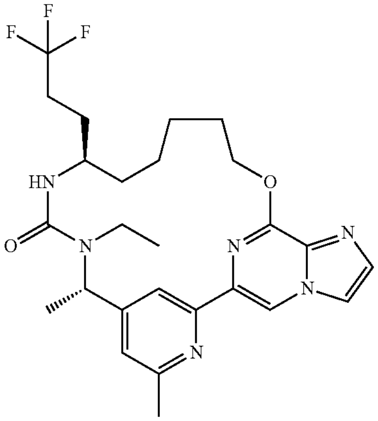 [SMILES: CCN1C(=O)N[C@@H](CCC(F)(F)F)CCCCCOc2nc(cn3ccnc23)-c2cc(cc(C)n2)[C@@H]1C] | (12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one | Calc'd 519.3, found 519.4 | A5 | B53 | C37 |

TABLE 11-continued

| Ex. # | Structure | Name | Exact Mass [M + H]+ | Interm A | Interm B | Interm C |
|---|---|---|---|---|---|---|
| 118B | 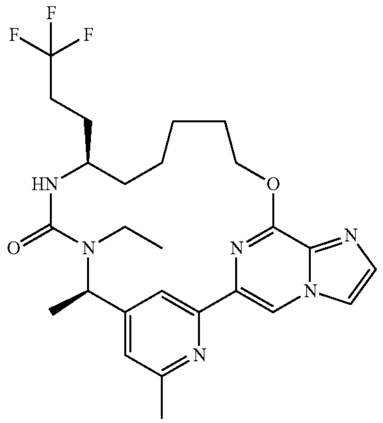 [SMILES: CCN1C(=O)N[C@@H](CCC(F)(F)F)CCCCCOc2nc(cn3ccnc23)-c2cc(cc(C)n2)[C@H]1C] | (12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one | Calc'd 519.3, found 519.4 | A5 | B53 | C37 |
| 119A | 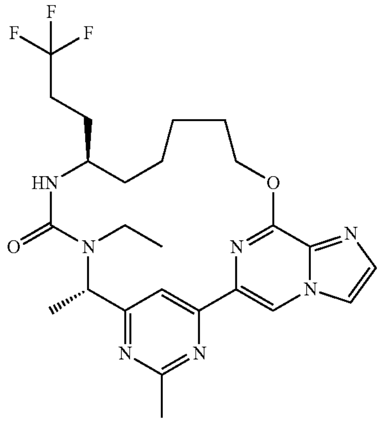 | (12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one | Calc'd 520.3, found 520.4 | A5 | B51 | C37 |
| 119B | 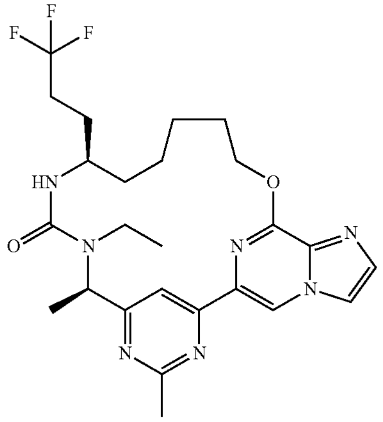 [SMILES: CCN1C(=O)N[C@@H](CCC(F)(F)F)CCCCCOc2nc(cn3ccnc23)-c2cc(nc(C)n2)[C@H]1C] | (12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one | Calc'd 520.3, found v | A5 | B51 | C37 |

TABLE 11-continued
| Ex. # | Structure | Name | Exact Mass [M + H]+ | Interm A | Interm B | Interm C |
|---|---|---|---|---|---|---|
| 120 | 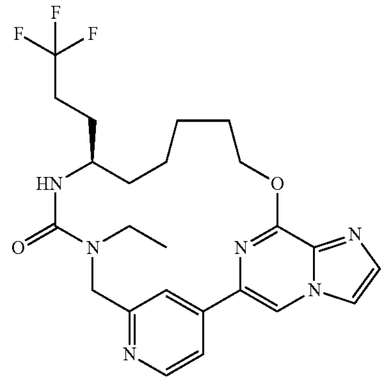 [SMILES: CCN1Cc2cc(ccn2)-c2cn3ccnc3c(n2)OCCCCC[C@H](CCC(F)(F)F)NC1=O] | (16R)-13-ethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one | Calc'd 491.2, found 491.2 | A5 | N-((4-chloropyridin-2-yl)methyl) ethanamine | C37 |
Example 122
(3R,E)-7-(2,2-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one (Example 122)
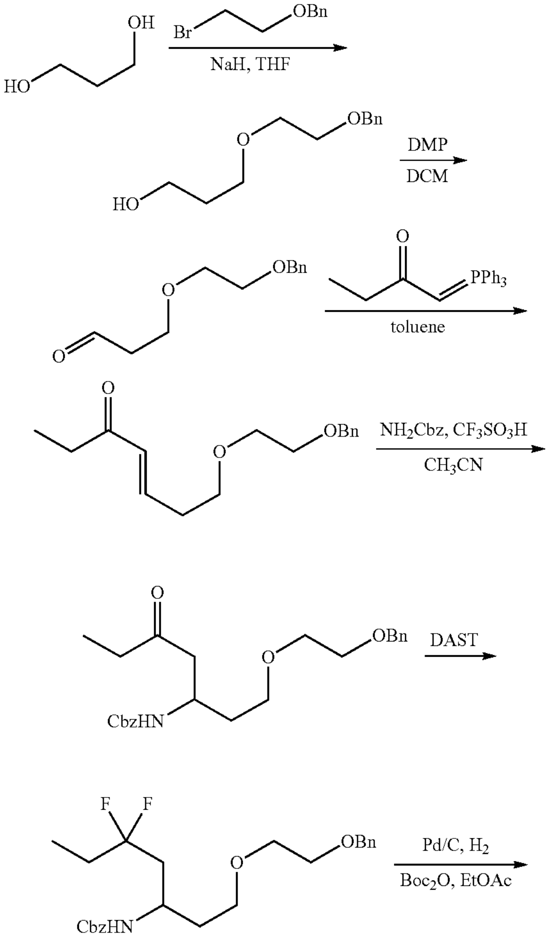
-continued
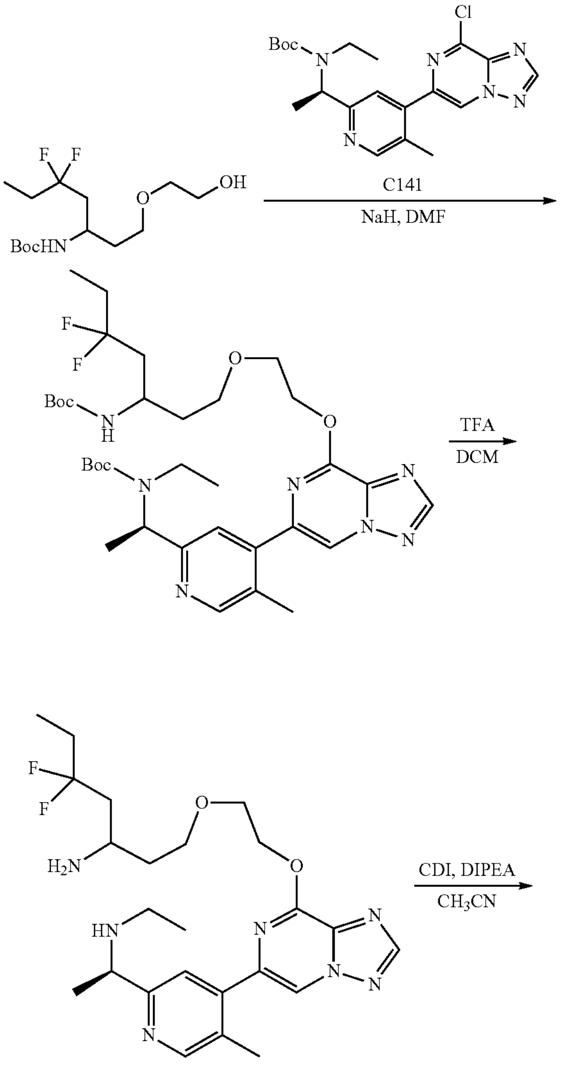

-continued

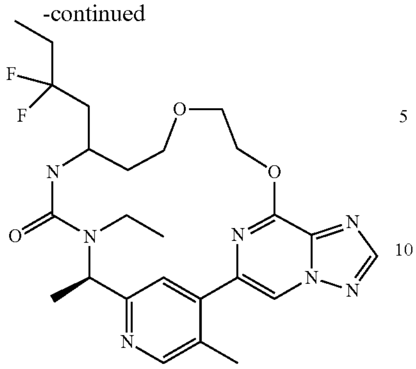

example 122

To a solution of NaH (6.97 g, 174 mmol) in THF (500 mL) were added propane-1,3-diol (26.5 g, 349 mmol) at 0° C. for 30 min. Benzyl 2-bromoethyl ether (25 g, 116 mmol) was added the reaction. The mixture was stirred at 20° C. for 8 hours. The reaction mixture was poured into water (100 mL), extracted with EtOAc (80 mL×3). The organic layer was washed with brine (50 mL), dried over $Na_2SO_4$ and filtered. The filtrate was concentrated and purified by flash silica gel chromatography (ISCO®; 120 g SepaFlash® Silica Flash Column, eluent of [20-30]% ethyl acetate/pet. ether gradient) to give 3-(2-(benzyloxy)ethoxy)propan-1-ol LCMS m/z (M+H): 211.1 required, 211.2 found.

To a solution of 3-(2-(benzyloxy)ethoxy)propan-1-ol (1 g, 4.76 mmol) in DCM (30 mL) was added DMP (3.03 g, 7.13 mmol). The mixture was stirred at 20° C. for 3 hours. The reaction mixture was poured into water (10 mL), extracted with DCM (10 mL×3). The organic layer was washed with brine (20 mL), dried over $Na_2SO_4$ and filtered. The filtrate was concentrated and purified by flash silica gel chromatography (ISCO®; 12 g SepaFlash® Silica Flash Column, eluent of [20~40]% ethyl acetate/pet. ether gradient) to 3-(2-(benzyloxy)ethoxy)propanal. $^1H$ NMR (500 MHz, $CDCl_3$) δ 9.72 (t, J=1.8 Hz, 1H), 7.29-7.25 (m, 4H), 7.23-7.18 (m, 1H), 4.49 (s, 2H), 3.76 (t, J=6.1 Hz, 2H), 3.58-3.52 (m, 4H), 2.62 (dt, J=1.8, 6.1 Hz, 2H).

A solution of 1-bromobutan-2-one (2 g, 13.24 mmol) and triphenylphosphine (3.47 g, 13.24 mmol) in THF (50 mL) was heated at reflux for 4 h until a precipitate formed. The suspension was cooled to room temperature before filtration; the precipitate was washed with THF (3×50 mL), and the precipitate was then redissolved in $CH_2Cl_2$ (60 mL) and $H_2O$(40 mL). Then 2 M NaOH (20 mL) was added, and the biphasic mixture was stirred overnight. The reaction mixture was extracted with $CH_2Cl_2$ (3×100 mL), and the combined organic layers were washed with brine, dried ($Na_2SO_4$), and concentrated under reduced pressure to give 1-(triphenyl-15-phosphanylidene)butan-2-one. $^1H$ NMR (500 MHz, $CDCl_3$) δ 7.51-7.42 (m, 6H), 7.39-7.32 (m, 3H), 7.31-7.20 (m, 6H), 3.53 (s, 1H), 3.48 (s, 1H), 2.14 (q, J=7.6 Hz, 2H), 0.99 (t, J=7.6 Hz, 3H).

To a solution of 3-(2-(benzyloxy)ethoxy)propanal (0.95 g, 4.56 mmol) in Toluene (30 mL) was added 1-(triphenyl-15-phosphaneylidene)butan-2-one (1.516 g, 4.56 mmol). The mixture was stirred at 90° C. for 12 hours. The reaction mixture was poured into water (10 mL), extracted with EtOAc (10 mL×3). The organic layer was washed with brine (10 mL), dried over $Na_2SO_4$ and filtered. The filtrate was concentrated and purified by flash silica gel chromatography (ISCO®; 20 g SepaFlash® Silica Flash Column, eluent of [1-20]% ethyl acetate/pet. ether gradient) to give (E)-7-(2-(benzyloxy)ethoxy)hept-4-en-3-one. $^1H$ NMR (500 MHz, $CDCl_3$) δ 7.29-7.17 (m, 5H), 6.77 (td, J=6.9, 16.0 Hz, 1H), 6.09 (td, J=1.4, 15.9 Hz, 1H), 4.49 (s, 2H), 3.57-3.52 (m, 6H), 2.51-2.38 (m, 4H), 1.01 (t, J=7.3 Hz, 3H).

To a solution of (E)-7-(2-(benzyloxy)ethoxy)hept-4-en-3-one (1.4 g, 5.34 mmol) and benzyl carbamate (1.210 g, 8.00 mmol) in $CH_3CN$ (20 mL) was added trifluoromethanesulfonic acid (0.080 g, 0.534 mmol). The mixture was stirred at 20° C. for 10 mins. The reaction mixture was poured into water (10 mL), extracted with EtOAc (10 mL×3). The organic layer was washed with brine (10 mL), dried over $Na_2SO_4$ and filtered. The filtrate was concentrated and purified by flash silica gel chromatography (ISCO®; 20 g SepaFlash® Silica Flash Column, eluent of [20~50]% ethyl acetate/pet. ether gradient) to give benzyl (1-(2-(benzyloxy)ethoxy)-5-oxoheptan-3-yl)carbamate.

A mixture of benzyl (1-(2-(benzyloxy)ethoxy)-5-oxoheptan-3-yl)carbamate (1.8 g, 4.35 mmol) and DAST (10 mL, 76 mmol) was stirred at 20° C. for 72 hours. The reaction mixture was poured into $NaHCO_3$(50 mL), extracted with DCM (20 mL×3). The organic layer was washed with brine (20 mL), dried over $Na_2SO_4$ and filtered. The filtrate was concentrated and purified by flash silica gel chromatography (ISCO®; 12 g SepaFlash® Silica Flash Column, eluent of 20% ethyl acetate/pet. ether gradient) to give benzyl (1-(2-(benzyloxy)ethoxy)-5,5-difluoroheptan-3-yl)carbamate. LCMS m/z (M+H): 436.1 required, 436.2 found.

To a solution of benzyl (1-(2-(benzyloxy)ethoxy)-5,5-difluoroheptan-3-yl)carbamate (1 g, 2.296 mmol) in EtOAc (20 mL) were added Pd/C (1 g, 0.470 mmol) (5%) and $Boc_2O$ (0.800 mL, 3.44 mmol). The mixture was stirred at 30° C. under H2 (excess) (50 psi) for 16 hours. The mixture was filtered and the filtrate was concentrated and purified by flash silica gel chromatography (ISCO®; 12 g SepaFlash® Silica Flash Column, eluent of [1-50]% ethyl acetate/pet. ether gradient) to give tert-butyl (5,5-difluoro-1-(2-hydroxyethoxy)heptan-3-yl)carbamate. LCMS m/z (M+H-Boc): 212.1 required, 212.1 found.

To a solution of tert-butyl (5,5-difluoro-1-(2-hydroxyethoxy)heptan-3-yl)carbamate (100 mg, 0.321 mmol) in DMF (5 mL) was added NaH (38.5 mg, 0.963 mmol) (60%) at 0° C. and stirred for 15 mins. Then C141 (120 mg, 0.288 mmol) was added to the mixture. $H_2O$(5 mL) was added to the mixture, extracted with EtOAc (5 mL×3). The organic layer was washed with brine (5 mL×2), dried over $Na_2SO_4$ and filtered. The filtrate was concentrated and purified by flash silica gel chromatography (ISCO®; 4 g SepaFlash® Silica Flash Column, eluent of 100% ethyl acetate) to give tert-butyl ((1R)-1-(4-(8-(2-((3-((tert-butoxycarbonyl)amino)-5,5-difluoroheptyl)oxy)ethoxy)-[1,2,4]triazolo[1,5-a]pyrazin-6-yl)-5-methylpyridin-2-yl)ethyl)(ethyl)carbamate. LCMS m/z (M+H): 692.3 required, 692.4 found.

To a solution of tert-butyl ((1R)-1-(4-(8-(2-((3-((tert-butoxycarbonyl)amino)-5,5-difluoroheptyl)oxy)ethoxy)-[1,2,4]triazolo[1,5-a]pyrazin-6-yl)-5-methylpyridin-2-yl)ethyl)(ethyl)carbamate (100 mg, 0.145 mmol) in DCM (2 mL) was added TFA (1 mL, 12.98 mmol) and at 25° C. stirred for 1 h. The mixture was concentrated to give 1-(2-((6-(2-((R)-1-(ethylamino)ethyl)-5-methylpyridin-4-yl)-[1,2,4]triazolo[1,5-a]pyrazin-8-yl)oxy)ethoxy)-5,5-difluoroheptan-3-amine, which was used in the next steps directly. LCMS m/z (M+H): 492.3 required, 492.3 found.

To a solution of 1-(2-((6-(2-((R)-1-(ethylamino)ethyl)-5-methylpyridin-4-yl)-[1,2,4]triazolo[1,5-a]pyrazin-8-yl)oxy)ethoxy)-5,5-difluoroheptan-3-amine (70 mg, 0.142 mmol) and DIPEA (0.124 mL, 0.712 mmol) in $CH_3CN$ (50 mL)

was added CDI (46.2 mg, 0.285 mmol) and stirred for 16 h under 25° C. $H_2O$(5 mL) was added to the mixture, extracted with EtOAc (20 mL×3). The organic layer was washed with brine (10 mL), dried over $Na_2SO_4$ and filtered. The filtrate was concentrated and purified by reverse phase HPLC (ODS, water (0.1% TFA)-ACN) to give (3R,E)-7-(2,2-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one, (example 122) as the second eluting diastereomer. LCMS m/z (M+H): 518.2 required, 518.3 found. $^1$H NMR (400 MHz, $CD_3OD$) δ 8.97 (s, 1H), 8.61 (s, 2H), 8.13 (s, 1H), 5.07-4.93 (m, 3H), 4.13 (br s, 1H), 3.95-3.79 (m, 2H), 3.63-3.35 (m, 4H), 2.69 (s, 3H), 2.29-2.16 (m, 1H), 2.06-1.89 (m, 3H), 1.88-1.82 (m, 4H), 1.78-1.68 (m, 1H), 1.26 (br t, J=7.0 Hz, 3H), 1.00 (t, J=7.5 Hz, 3H)

Examples 123 and 124

(3R,7R,E)-4-ethyl-25-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one (Example 123) and (3R,7R,E)-4-ethyl-25-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one (Example 124)

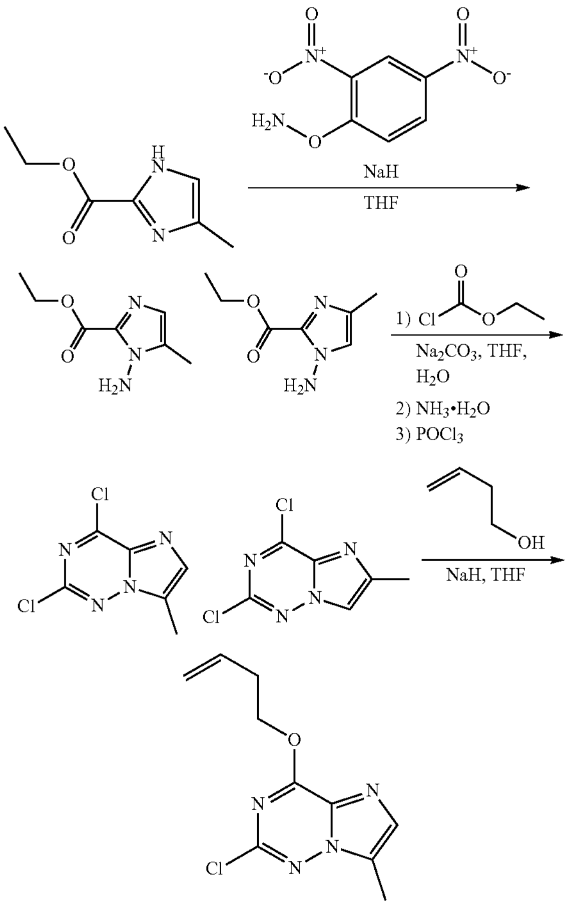

-continued

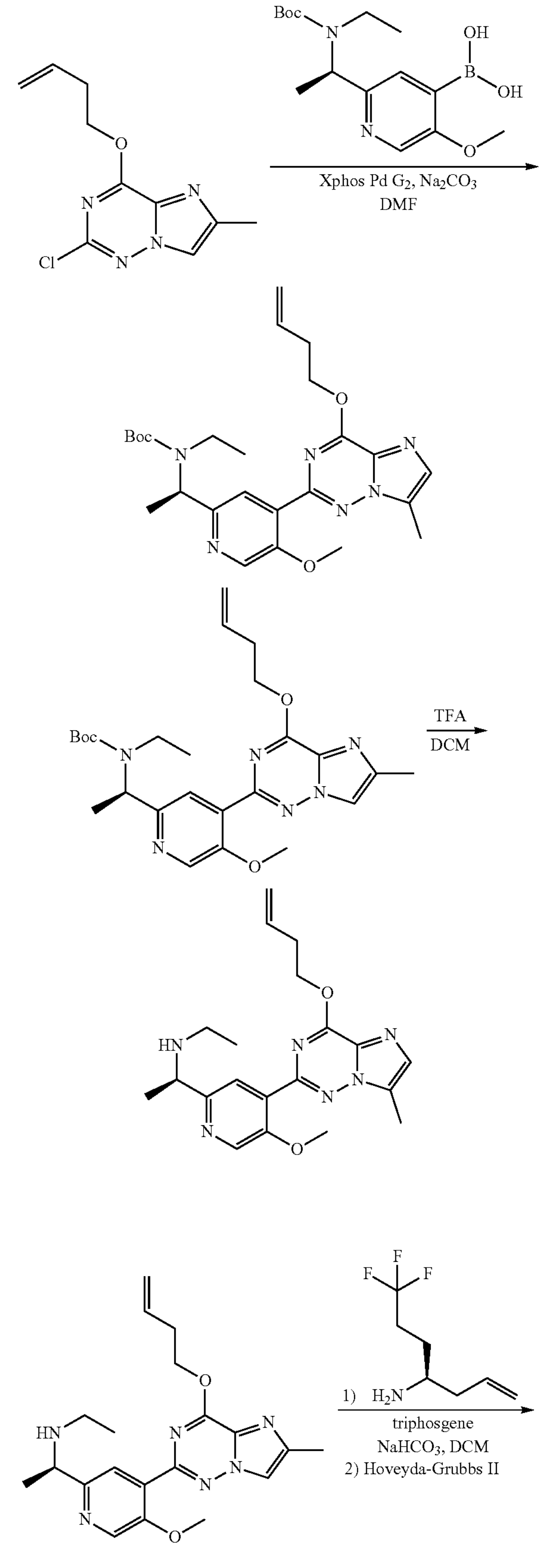

-continued

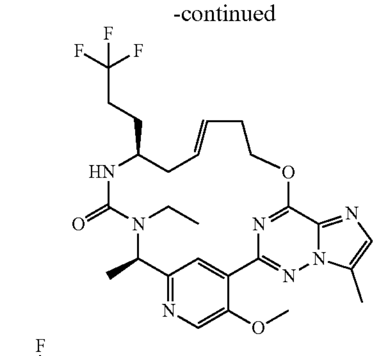

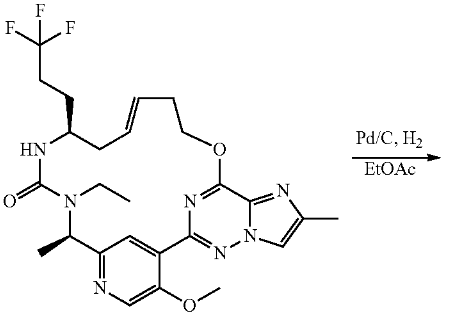

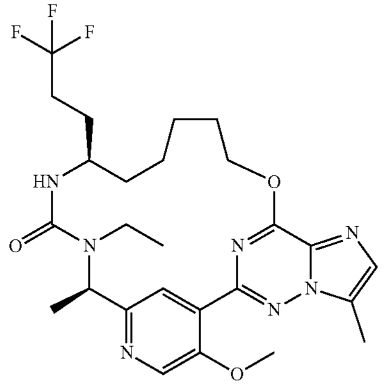

example 124

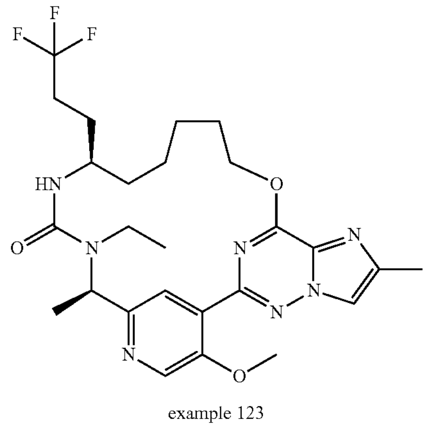

example 123

To a solution of ethyl 4-methyl-1H-imidazole-2-carboxylate (10 g, 64.9 mmol) in THF (200 mL) was added sodium hydride (3.11 g, 78 mmol) at 0° C. and stirred for 1 hour. 0-(2,4-dinitrophenyl)hydroxylamine (18.08 g, 91 mmol) was added and stirred at 25° C. for 12 hours. The reaction mixture was poured into water (50 mL), extracted with EtOAc (50 mL×3). The organic layer was washed with brine (50 mL), dried over $Na_2SO_4$ and filtered. The filtrate was concentrated and purified by flash silica gel chromatography (ISCO®; 80 g SepaFlash®Silica Flash Column, eluent of [50-100]% ethyl acetate/pet. ether gradient) to give a mixture of ethyl 1-amino-5-methyl-1H-imidazole-2-carboxylate and ethyl 1-amino-4-methyl-1H-imidazole-2-carboxylate. LCMS m/z (M+H): 170.1 required, 170.2 found.

To a solution of ethyl 1-amino-5-methyl-1H-imidazole-2-carboxylate and ethyl 1-amino-4-methyl-1H-imidazole-2-carboxylate (4.5 g, 26.6 mmol) in THF (60 mL) and Water (60 mL) were added $Na_2CO_3$ (19.73 g, 186 mmol) and ethyl carbonochloridate (7.78 g, 71.7 mmol). The mixture was stirred at 25° C. for 2 hours. The reaction mixture was poured into water (20 mL), extracted with EtOAc (50 mL×3). The combined organic phases were washed with brine (50 mL), and dried over $Na_2SO_4$. After filtration and concentration, the residue was purified by flash silica gel chromatography (ISCO®; 80 g SepaFlash® Silica Flash Column, Eluent of 0-40% EtOAc/Pet.ether gradient) to give a mixture of ethyl 1-[bis(ethoxycarbonyl)amino]-5-methyl-1H-imidazole-2-carboxylate and ethyl 1-[bis(ethoxycarbonyl)amino]-4-methyl-1H-imidazole-2-carboxylate. LCMS m/z (M+H): 314.0 found, 314.1 required. 242.1 found, 242.1 required.

To a solution of ethyl 1-[bis(ethoxycarbonyl)amino]-5-methyl-1H-imidazole-2-carboxylate and ethyl 1-[bis(ethoxycarbonyl)amino]-4-methyl-1H-imidazole-2-carboxylate (2.4 g, 3.83 mmol) in 2-Propanol (10 mL) was added ammonia hydrate (30 mL, 300 mmol) and the mixture was stirred in a sealed tube at 120° C. for 12 h. The mixture was concentrated to the crude product and the crude product was washed with MeOH: Pet.ether=1:10 (30 mL) and filtered to afford a mixture of 7-methylimidazo[2,1-f][1,2,4]triazine-2,4(1H,3H)-dione and 6-methylimidazo[2,1-f][1,2,4]triazine-2,4(1H,3H)-dione which was used to next step without further purification. To the crude mixture in $POCl_3$ (20 mL) was added triethylamine hydrochloride (1.988 g, 14.45 mmol) and stirred at 110° C. for 12 hours. The mixture was concentrated and the crude product was poured into $NaHCO_3$(20 mL) slowly, extracted with EtOAc (20 mL×3). The organic layer was washed with brine (15 mL), dried over $Na_2SO_4$ and filtered. The filtrate was concentrated to give a mixture of 2,4-dichloro-7-methylimidazo[2,1-f][1,2,4]triazine and 2,4-dichloro-6-methylimidazo[2,1-f][1,2,4]triazine which was used to the next step without further purification. LCMS m/z (M+H): 202.9 required, 203.0 found.

To a solution of 3-buten-1-ol (0.469 g, 6.50 mmol) in THF (25 mL) was added sodium hydride (0.355 g, 8.87 mmol) (60% wt) at 0° C. and stirred at 0° C. for 30 mins. 2,4-dichloro-7-methylimidazo[2,1-f][1,2,4]triazine and 2,4-dichloro-6-methylimidazo[2,1-f][1,2,4]triazine (1.2 g, 2.96 mmol) was added to the above mixture and stirred at 0° C. for 2 h. The mixture was quenched with $H_2O$(10 mL) and extracted with EtOAC (10 mL×3), washed with brine (10 mL), dried over $Na_2SO_4$, filtered and concentrated under reduced pressure. The crude was purified by Flash silica gel chromatography (ISCO®; 4 g SepaFlash® Silica Flash Column, Eluent of 20% EtOAc/Pet.ether gradient) to give a mixture of 4-(but-3-en-1-yloxy)-2-chloro-7-methylimidazo[2,1-f][1,2,4]triazine and 4-(but-3-en-1-yloxy)-2-chloro-6-methylimidazo[2,1-f][1,2,4]triazine. LCMS m/z (M+H): 239.1 required, 239.1 found.

To a solution of (R)-(2-(1-((tert-butoxycarbonyl)(ethyl)amino)ethyl)-5-methoxypyridin-4-yl)boronic acid B3-1 (200 mg, 0.617 mmol) in DMF (5 mL) was added the mixture of 4-(but-3-en-1-yloxy)-2-chloro-7-methylimidazo[2,1-f][1,2,4]triazine and 4-(but-3-en-1-yloxy)-2-chloro-6-methylimidazo[2,1-f][1,2,4]triazine (120 mg, 0.251 mmol), $Na_2CO_3$ (196 mg, 1.851 mmol) and chloro(2-dicyclohexylphosphino-2',4',6'-triisopropyl-1,1'-biphenyl)[2-(2'-amino-1,1'-biphenyl)]palladium(ii) (48.5 mg, 0.062 mmol). The mixture was stirred at 80° C. for 3 hours. The reaction mixture was poured into water (10 mL), extracted with EtOAc (10 mL×3). The organic phase layer was dried over $Na_2SO_4$ and filtered. The filtrate was concentrated and purified by flash silica gel chromatography (ISCO®; 4 g SepaFlash® Silica Flash Column, eluent of [0-100]% ethyl acetate/pet. ether gradient) to give a mixture of tert-butyl (R)-(1-(4-(4-(but-3-en-1-yloxy)-7-methylimidazo[2,1-f][1,2,4]triazin-2-yl)-5-methoxypyridin-2-yl)ethyl)(ethyl)carbamate and tert-butyl (R)-(1-(4-(4-(but-3-en-1-yloxy)-6-methylimidazo[2,1-f][1,2,4]triazin-2-yl)-5-methoxypyridin-2-yl)ethyl)(ethyl)carbamate. LCMS m/z (M+H): 482.2 required, 482.3 found.

To a solution of tert-butyl (R)-(1-(4-(4-(but-3-en-1-yloxy)-7-methylimidazo[2,1-f][1,2,4]triazin-2-yl)-5-methoxypyridin-2-yl)ethyl)(ethyl)carbamate and tert-butyl (R)-(1-(4-(4-(but-3-en-1-yloxy)-6-methylimidazo[2,1-f][1,2,4]triazin-2-yl)-5-methoxypyridin-2-yl)ethyl)(ethyl)carbamate (200 mg, 0.207 mmol) in DCM (5 mL) were added TFA (1 mL). The mixture was stirred at 20° C. for 2 hours. Then the mixture was concentrated and to give (R)-1-(4-(4-(but-3-en-1-yloxy)-7-methylimidazo[2,1-f][1,2,4]triazin-2-yl)-5-methoxypyridin-2-yl)-N-ethylethan-1-amine and (R)-1-(4-(4-(but-3-en-1-yloxy)-6-methylimidazo[2,1-f][1,2,4]triazin-2-yl)-5-methoxypyridin-2-yl)-N-ethylethan-1-amine. The crude product was used for next step without purification. LCMS m/z (M+H): 383.2 required, 383.2 found.

To a solution of (S)-7,7,7-trifluorohept-1-en-4-amine hydrochloride A5 (59.9 mg, 0.294 mmol) in DCM (10 mL) and TEA (0.137 mL, 0.980 mmol) was added bis(trichloromethyl) carbonate (29.1 mg, 0.098 mmol) and stirred at 0° C. for 30 min. The mixture of R)-1-(4-(4-(but-3-en-1-yloxy)-7-methylimidazo[2,1-f][1,2,4]triazin-2-yl)-5-methoxypyridin-2-yl)-N-ethylethan-1-amine and (R)-1-(4-(4-(but-3-en-1-yloxy)-6-methylimidazo[2,1-f][1,2,4]triazin-2-yl)-5-methoxypyridin-2-yl)-N-ethylethan-1-amine (150 mg, 0.196 mmol) was added and stirred at 25° C. for 1 hour. Then the mixture was quenched with water (5 mL), extracted with DCM (5 mL×3). The combined organic layers were washed with brine (5 mL), dried over $Na_2SO_4$, filtered and concentrated. The residue was purified by prep-TLC (EtOAc) to give the mixture of 1-((R)-1-(4-(4-(but-3-en-1-yloxy)-7-methylimidazo[2,1-f][1,2,4]triazin-2-yl)-5-methoxypyridin-2-yl)ethyl)-1-ethyl-3-((S)-7,7,7-trifluorohept-1-en-4-yl)urea and 1-((R)-1-(4-(4-(but-3-en-1-yloxy)-6-methylimidazo[2,1-f][1,2,4]triazin-2-yl)-5-methoxypyridin-2-yl)ethyl)-1-ethyl-3-((S)-7,7,7-trifluorohept-1-en-4-yl)urea. LCMS m/z (M+H): 576.3 found, 576.2 required.

To a solution of the mixture of 1-((R)-1-(4-(4-(but-3-en-1-yloxy)-7-methylimidazo[2,1-f][1,2,4]triazin-2-yl)-5-methoxypyridin-2-yl)ethyl)-1-ethyl-3-((S)-7,7,7-trifluorohept-1-en-4-yl)urea and 1-((R)-1-(4-(4-(but-3-en-1-yloxy)-6-methylimidazo[2,1-f][1,2,4]triazin-2-yl)-5-methoxypyridin-2-yl)ethyl)-1-ethyl-3-((S)-7,7,7-trifluorohept-1-en-4-yl)urea (130 mg, 0.113 mmol) in DCE (150 mL) were added (1,3-dimesitylimidazolidin-2-ylidene)(2-isopropoxybenzylidene)ruthenium(vi) chloride (14.15 mg, 0.023 mmol). The mixture was stirred at 50° C. for 12 h. The mixture was concentrated and was purified by prep-TLC (Pet. ether/EtOAc=1:1) to give (13E,3R,7S,9E)-4-ethyl-25-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-9-en-5-one and (13E,3R,7S,9E)-4-ethyl-25-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-9-en-5-one as separable diastereomers. LCMS m/z (M+H): 548.2 required, 548.2 found.

To a solution of (13E,3R,7S,9E)-4-ethyl-25-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-9-en-5-one (30 mg, 0.055 mmol) in EtOAc (5 mL) was added Pd-C (64.9 mg, 0.055 mmol) (10%). The mixture was stirred at 25° C. for 20 min under H2 balloon. The mixture was filtrated and the filtrate was concentrated and was purified by prep-TLC (Pet. ether/EtOAc=1:2) to give (3R,7R,E)-4-ethyl-25-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one, (Example 124). LCMS m/z (M+H): 550.2 required, 550.2 found. $^1H$ NMR (400 MHz, $CDCl_3$) δ 8.43 (s, 1H), 7.98 (s, 1H), 7.55 (s, 1H), 6.05 (br d, J=7.1 Hz, 1H), 4.95-4.81 (m, 1H), 4.77-4.63 (m, 1H), 4.15 (br d, J=10.5 Hz, 1H), 4.06 (s, 3H), 3.97 (br d, J=9.5 Hz, 1H), 3.09 (q, J=7.3 Hz, 2H), 2.60 (s, 3H), 2.30-2.15 (m, 3H), 2.10 (m, 2H), 2.05-1.88 (m, 2H), 1.84-1.76 (m, 2H), 1.53-1.48 (m, 3H), 1.41-1.29 (m, 4H), 1.05 (t, J=7.1 Hz, 4H)

To a solution of (13E,3R,7S,9E)-4-ethyl-25-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-9-en-5-one (60 mg, 0.110 mmol) in EtOAc (5 mL) were added Pd-C (130 mg, 0.110 mmol) (10%). The mixture was stirred at 25° C. for 20 min under H2 balloon. The mixture was filtrated and the filtrate was concentrated and was purified by prep-TLC (Pet. ether/EtOAc=1:2) to give (3R,7R,E)-4-ethyl-25-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one, (Example 123). LCMS m/z (M+H): 550.2 required, 550.2 found. $^1H$ NMR (400 MHz, $CDCl_3$) δ 8.41 (s, 1H), 7.94 (s, 1H), 7.77 (s, 1H), 6.05 (br d, J=7.1 Hz, 1H), 4.85 (dt, J=5.7, 10.3 Hz, 1H), 4.71 (dt, J=6.0, 10.5 Hz, 1H), 4.14 (br d, J=10.0 Hz, 1H), 4.05 (s, 3H), 3.97 (br d, J=9.5 Hz, 1H), 3.14-3.04 (m, 2H), 2.52 (s, 3H), 2.30-2.16 (m, 2H), 2.06-1.87 (m, 2H), 1.85-1.71 (m, 2H), 1.56-1.47 (m, 4H), 1.42-1.19 (m, 3H), 1.05 (t, J=7.1 Hz, 3H)

Example 125

(R,E)-7-(3,3-difluorobutyl)-4-ethyl-22-methoxy-13-oxa-4,6-diaza-1(2,4)-imidazo[2,1-f][1,2,4]triazina-2(3,5)-pyridinacyclotridecaphan-5-one (example 125)

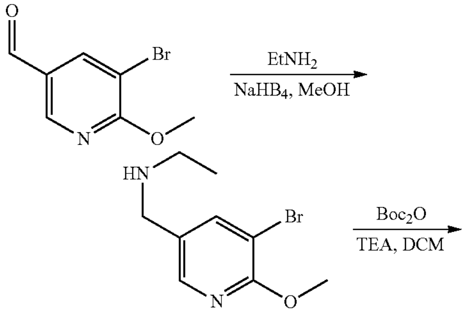

-continued

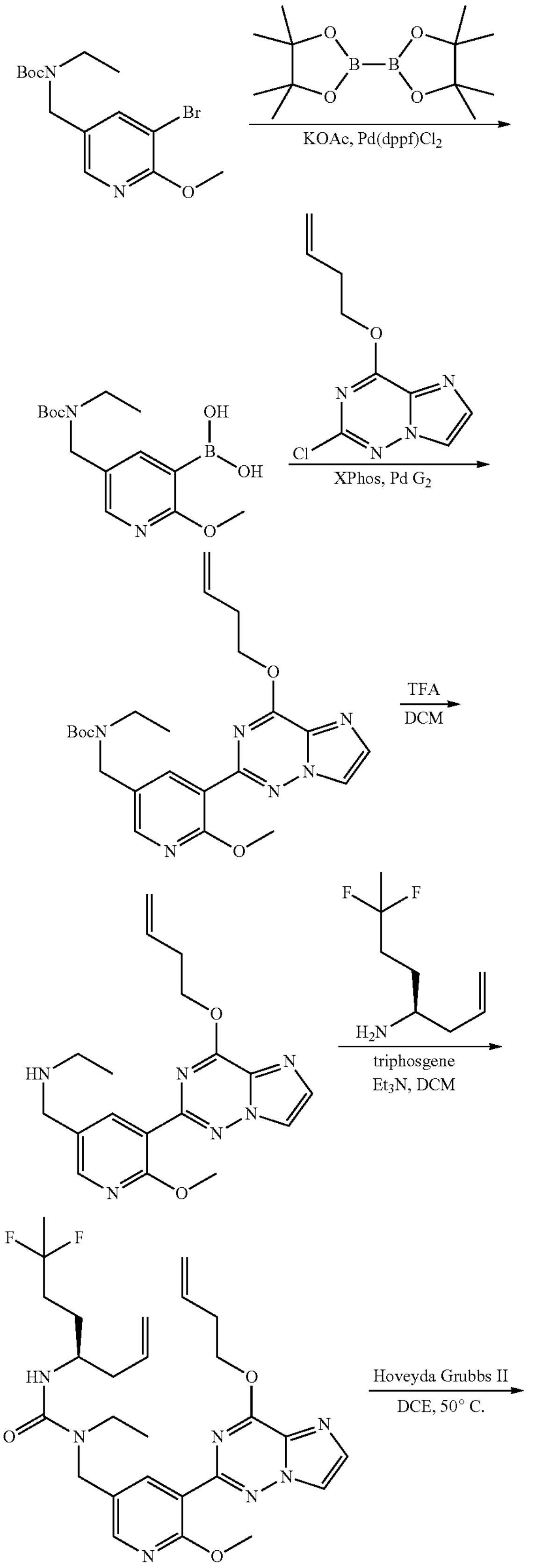

-continued

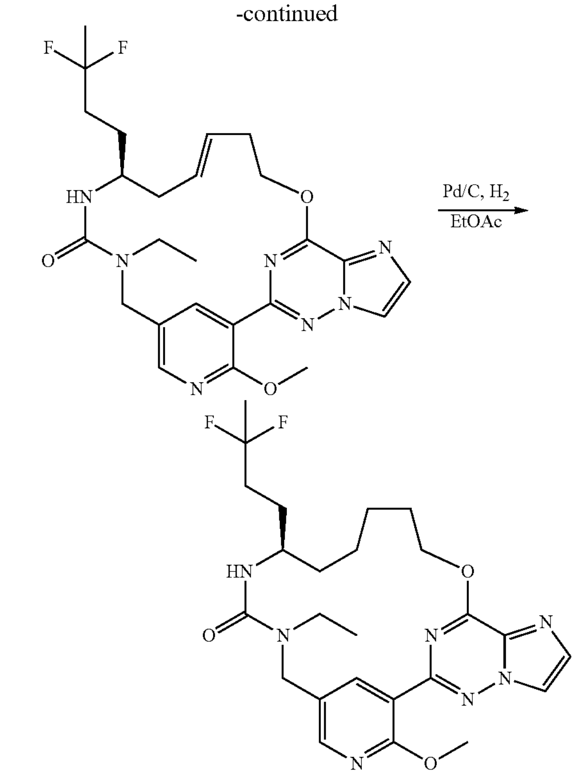

Example 125

To 5-bromo-6-methoxynicotinaldehyde (3 g, 13.89 mmol) was added ethanamine (15 mL, 13.89 mmol), the resulting mixture was stirred at 20° C. under $N_2$ protection for 2 hours. The mixture was concentrated and re-dissolved in MeOH (30 mL). Then $NaBH_4$ (1.576 g, 41.7 mmol) was added at 0° C., and stirred at 20° C. for 1 h. The reaction mixture was quenched with HCl to adjust pH to 7. The reaction was concentrated to the crude of N-((5-bromo-6-methoxypyridin-3-yl)methyl)ethanamine which was used to next step directly.

To the crude N-((5-bromo-6-methoxypyridin-3-yl) methyl)ethanamine in DCM (10 mL) was added TEA (3.87 mL, 27.7 mmol) and di-tert-butyl dicarbonate (3.63 g, 16.64 mmol) at 20° C. The resulting mixture was stirred at under N2 protection for 2 hours. The reaction mixture was poured into water (10 mL), extracted with DCM (5 mL×3). The organic layer was washed with brine (10 mL), dried over $Na_2SO_4$ and filtered. The filtrate was concentrated and purified by flash silica gel chromatography (ISCO®; 12 g SepaFlash® Silica Flash Column, eluent of [0-10]% ethyl acetate/pet. ether gradient) ($SiO_2$, Pet. ether:EtOAc=10:1) to give tert-butyl ((5-bromo-6-methoxypyridin-3-yl)methyl) (ethyl)carbamate. LCMS m/z (M+H): 347.2 required, 347.1 found.

To a solution of tert-butyl ((5-bromo-6-methoxypyridin-3-yl)methyl)(ethyl)carbamate (1 g, 2.90 mmol) in Dioxane (8 mL) were added 4,4,4',4',5,5,5',5'-octamethyl-2,2'-bi(1,3,2-dioxaborolane) (1.471 g, 5.79 mmol), potassium acetate (0.569 g, 5.79 mmol) and Pd(dppf)$Cl_2$ (0.212 g, 0.290 mmol). The resulting mixture was stirred at 80° C. under N2 protection for 4 hours. The reaction mixture was filtered and concentrated and purified by reverse phase HPLC to give (5-(((tert-butoxycarbonyl)(ethyl)amino)methyl)-2-methoxypyridin-3-yl)boronic acid. LCMS m/z (M+H): 311.2 required, 310.7 found To a solution of 4-(but-3-en-1-yloxy)-2-chloroimidazo[2,1-f][1,2,4]triazine, C140 (40 mg, 0.178 mmol) in DMF (2.5 mL) were added (5-(((tert-butoxycarbonyl)(ethyl)amino)methyl)-2-methoxypyridin-3-yl)boronic acid (66.3 mg, 0.214 mmol), Chloro(2-dicyclohexylphosphino-2',4',6'-triisopropyl-1,1'-biphenyl)[2-(2'-amino-1,1'-biphenyl)]palladium(II) (14.01 mg, 0.018 mmol) and $Na_2CO_3$ (56.6 mg, 0.534 mmol). The resulting mixture was stirred at 80° C. under N2 protection for 3 hours. The reaction mixture was poured into water (1 mL), extracted with EtOAc (5 mL×3). The organic layer was washed with brine (10 mL), dried over $Na_2SO_4$ and filtered. The filtrate was concentrated and purified by Prep-TLC (Pet. ether:EtOAc=5:1) to give tert-butyl ((5-(4-(but-3-en-1-yloxy)imidazo[2,1-f][1,2,4]triazin-2-yl)-6-methoxypyridin-3-yl)methyl)(ethyl)carbamate. LCMS m/z (M+H): 455.1 required, 455.6 found.

To a solution of tert-butyl ((5-(4-(but-3-en-1-yloxy)imidazo[2,1-f][1,2,4]triazin-2-yl)-6-methoxypyridin-3-yl)methyl)(ethyl)carbamate (80 mg, 0.176 mmol) in DCM (1 mL) was added TFA (0.25 mL, 3.24 mmol). The resulting mixture was stirred at 25° C. under N2 protection for 3 h. The reaction mixture was concentrated to give N-((5-(4-(but-3-en-1-yloxy)imidazo[2,1-f][1,2,4]triazin-2-yl)-6-methoxypyridin-3-yl)methyl)ethanamine. LCMS m/z (M+H): 355.1 required, 355.1 found.

To a solution of (S)-7,7-difluorooct-1-en-4-amine A21 (38.0 mg, 0.233 mmol) in DCM (5 mL) was added TEA (0.433 mL, 3.10 mmol) and bis(trichloromethyl) carbonate (34.5 mg, 0.116 mmol) at 0° C. under N2. The resulting mixture was stirred at 0° C. for 30 mins. Then N-((5-(4-(but-3-en-1-yloxy)imidazo[2,1-f][1,2,4]triazin-2-yl)-6-methoxypyridin-3-yl)methyl)ethanamine (55 mg, 0.155 mmol) was added to the mixture. The mixture was stirred at 0° C. for 30 mins. To the reaction mixture was added water (4 mL), extracted with DCM (5 mL×3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of [50-100]% ethyl acetate/pet. ether gradient) ($SiO_2$, EtOAc:EtOAc=1:1) to give (S)-1-((5-(4-(but-3-en-1-yloxy)imidazo[2,1-f][1,2,4]triazin-2-yl)-6-methoxypyridin-3-yl)methyl)-3-(7,7-difluorooct-1-en-4-yl)-1-ethylurea. LCMS m/z (M+H): 544.3 required, 544.2 found.

To a solution of (S)-1-((5-(4-(but-3-en-1-yloxy)imidazo[2,1-f][1,2,4]triazin-2-yl)-6-methoxypyridin-3-yl)methyl)-3-(7,7-difluorooct-1-en-4-yl)-1-ethylurea (90 mg, 0.166 mmol) in DCE (50 mL) was added (1,3-Bis-(2,4,6-trimethylphenyl)-2-imidazolidinylidene)dichloro(o-isopropoxyphenylmethylene)ruthenium (10.37 mg, 0.017 mmol). The resulting mixture was stirred at 50° C. under N2 protection for 16 hours. The reaction mixture was concentrated and purified by Prep-TLC (EtOAc) to give (S,13E,9E)-7-(3,3-difluorobutyl)-4-ethyl-22-methoxy-13-oxa-4,6-diaza-1(2,4)-imidazo[2,1-f][1,2,4]triazina-2(3,5)-pyridinacyclotridecaphan-9-en-5-one. LCMS m/z (M+H): 516.2 required, 516.2 found.

To a solution of (S,13E,9E)-7-(3,3-difluorobutyl)-4-ethyl-22-methoxy-13-oxa-4,6-diaza-1(2,4)-imidazo[2,1-f][1,2,4]triazina-2(3,5)-pyridinacyclotridecaphan-9-en-5-one (50 mg, 0.097 mmol) in EtOAc (6 mL) was added Pd-C(10.32 mg, 9.70 μmol) (10% wt.). The resulting mixture was stirred at 30° C. under H2 (15 psi) protection for 20 mins. The reaction mixture was filtrated and concentrated and purified by Prep-HPLC to give (R,E)-7-(3,3-difluorobutyl)-4-ethyl-22-methoxy-13-oxa-4,6-diaza-1(2,4)-imidazo[2,1-f][1,2,4]triazina-2(3,5)-pyridinacyclotridecaphan-5-one, (example 125). LCMS m/z (M+H): 518.3 required, 518.2 found. $^1H$ NMR (400 MHz, $CD_3OD$) δ 8.47 (s, 1H), 8.19 (s, 1H), 8.16 (s, 1H), 7.73 (s, 1H), 6.09 (br d, J=9.3 Hz, 1H), 5.20 (br d, J=13.4 Hz, 1H), 5.00-4.89 (m, 1H), 4.59 (br s, 1H), 4.05 (s, 3H), 4.02-3.88 (m, 2H), 3.40-3.12 (m, 2H), 2.05-1.83 (m, 4H), 1.70-1.42 (m, 11H), 1.11 (t, J 7.1 Hz, 3H).

Example 126

(3R,7R,E)-4-ethyl-7-(fluoromethyl)-25-methoxy-3-methyl-13-oxa-4,6-diaza-1(6,8)-imidazo[1,2-a]pyrazina-2(4,2)-pyridinacyclotridecaphan-5-one (example 126)

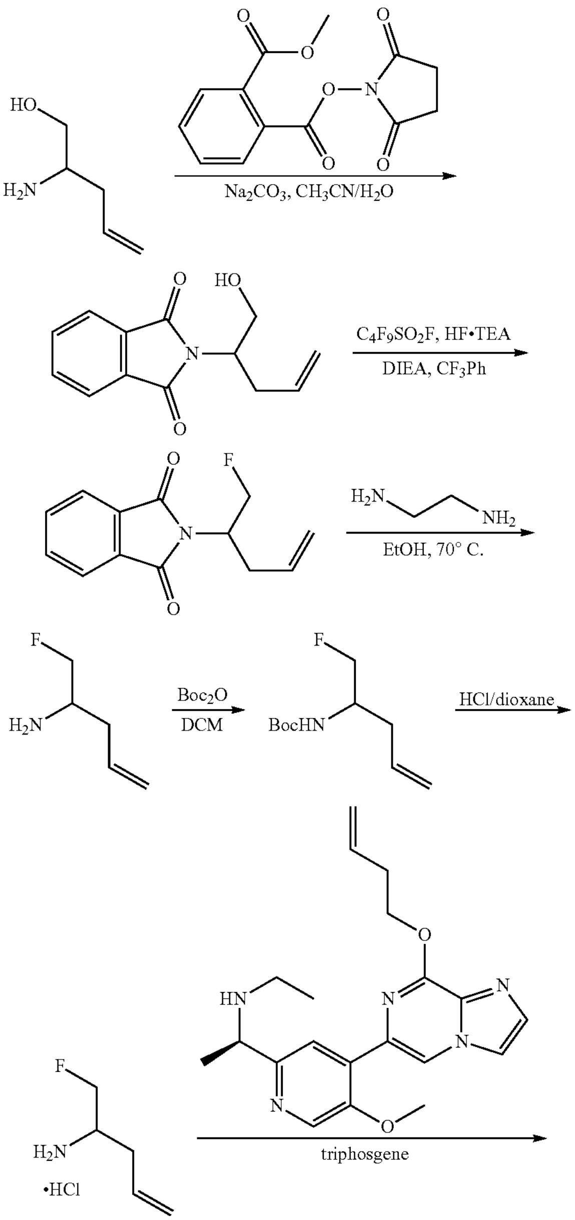

-continued

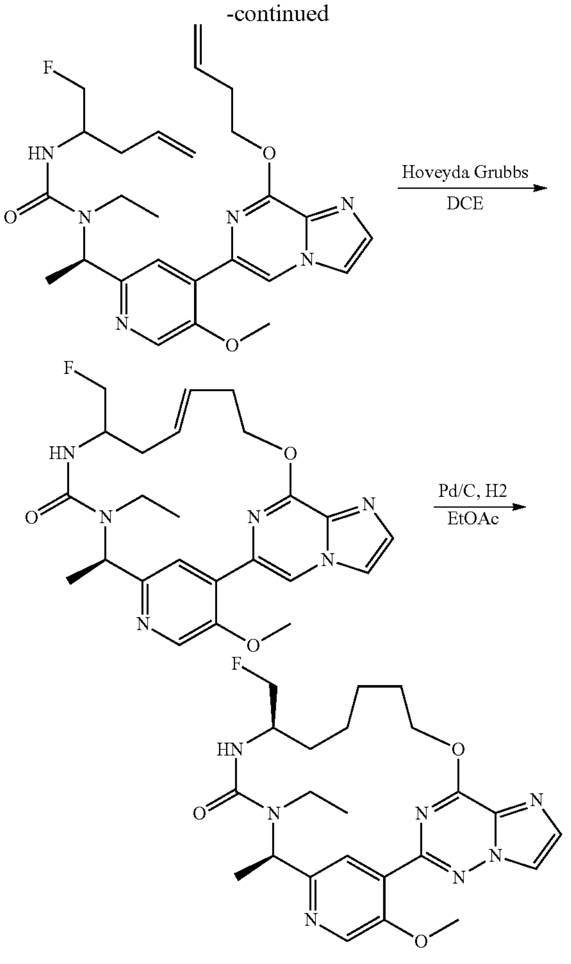

example 126

To a solution of 2-aminopent-4-en-1-ol (1.525 g, 15.08 mmol) and $Na_2CO_3$ (7.26 g, 68.5 mmol) in Water (50 mL) was added 2,5-dioxopyrrolidin-1-yl methyl phthalate (3.8 g, 13.71 mmol) in Acetonitrile (85 mL). The mixture was stirred at 25° C. for 2 h. The majority of the $CH_3CN$ was removed on a rotary evaporator and the remaining material was extracted with EtOAc (3×50 mL). The combined EtOAc extracts were washed with 0.5M HCl (2×100 mL) and brine (100 mL). The EtOAc phase was dried over $Na_2SO_4$. The filtrate was concentrated and purified by flash silica gel chromatography (ISCO®; 12 g SepaFlash® Silica Flash Column, eluent of [0-30]% ethyl acetate/pet. ether gradient) to give 2-(1-hydroxypent-4-en-2-yl)isoindoline-1,3-dione. LCMS m/z (M+H): 232.1 required, 232.1 found To a solution of 2-(1-hydroxypent-4-en-2-yl)isoindoline-1,3-dione (500 mg, 2.162 mmol) in $CF_3Ph$ (7.5 mL) was added DIEA (5.66 mL, 32.4 mmol), HF TEA (2.091 mL, 12.97 mmol) and nonafluorobutanesulfonyl chloride (653 mg, 2.162 mmol) stirred at 25° C. The mixture was stirred at 25° C. for 2 h. Then additional nonafluorobutanesulfonyl chloride (653 mg, 2.162 mmol) was added to the reaction mixture. Then the mixture was stirred at 25° C. for 12 h. The mixture was poured into water (30 mL), extracted with EtOAc (20 mL×3). The combined organic phases were dried over $Na_2SO_4$, filtered. The filtrate was concentrated to give 2-(1-fluoropent-4-en-2-yl)isoindoline-1,3-dione, which was used directly without further purification. LCMS m/z (M+H): 234.1 required, 234.1 found.

To a solution of 2-(1-fluoropent-4-en-2-yl)isoindoline-1,3-dione (500 mg, 2.144 mmol) in EtOH (10 mL) was added ethane-1,2-diamine (129 mg, 2.144 mmol). The mixture was stirred at 70° C. for 12 h. The mixture was filtered. The filtrate was poured into water (20 mL), extracted with DCM (15 mL×3). The combined DCM phase was dried over $Na_2SO_4$. The mixture was filtered to give a solution of 1-fluoropent-4-en-2-amine in DCM (45 mL), which was used directly to next step. LCMS m/z (M+H): 104.1 required, 104.1 found.

To a solution of 1-fluoropent-4-en-2-amine (45 mL, 2.115 mmol) (0.047M) in DCM was added Boc-Anhydride (0.982 mL, 4.23 mmol). The mixture was stirred at 25° C. for 24 h. The mixture was concentrated and purified by flash silica gel chromatography (ISCO®; 10 g SepaFlash® Silica Flash Column, eluent of [0-30]% ethyl acetate/pet. ether gradient) to give tert-butyl (1-fluoropent-4-en-2-yl)carbamate. LCMS m/z (M+H-tBu): 148.1 required, 148.1 found. $^1H$ NMR (400 MHz, $CDCl_3$) δ 5.85-5.69 (m, 1H), 5.21-5.04 (m, 2H), 4.65 (br s, 1H), 4.54-4.26 (m, 2H), 3.93-3.67 (m, 1H), 2.31 (qd, J=7.1, 14.3 Hz, 2H), 1.50 (s, 9H).

tert-butyl (1-fluoropent-4-en-2-yl)carbamate (200 mg, 0.984 mmol) was dissolved in 4N HCl Dioxane (10 mL). The mixture was stirred at 25° C. for 24 h. LCMS showed desired mass. The organic phase was concentrated to give 1-fluoropent-4-en-2-amine hydrochloride which was used in next step without further purification. LCMS m/z (M+H): 104.1 required, 104.2 found.

To a solution of 1-fluoropent-4-en-2-amine hydrochloride (39.3 mg, 0.381 mmol) in DCM (1 mL) and sat.$NaHCO_3$ (1.000 mL) was added triphosgene (40 mg, 0.135 mmol), and stirred at 0° C. for 1 h. (R)-1-(4-(8-(but-3-en-1-yloxy) imidazo[1,2-a]pyrazin-6-yl)-5-methoxypyridin-2-yl)-N-ethylethan-1-amine C74 (140 mg, 0.381 mmol) was added and stirred at 25° C. for 1 hour. The reaction mixture was poured into water (2 mL), extracted with EtOAc (1 mL×3). The organic phase layer was dried over $Na_2SO_4$ and filtered. The filtrate was concentrated and purified by TLC ($SiO_2$, EtOAc) to give 1-((R)-1-(4-(8-(but-3-en-1-yloxy)imidazo[1,2-a]pyrazin-6-yl)-5-methoxypyridin-2-yl)ethyl)-1-ethyl-3-(1-fluoropent-4-en-2-yl)urea. LCMS m/z (M+H): 497.3 required, 497.2 found.

To a solution of 1-((R)-1-(4-(8-(but-3-en-1-yloxy)imidazo[1,2-a]pyrazin-6-yl)-5-methoxypyridin-2-yl)ethyl)-1-ethyl-3-(1-fluoropent-4-en-2-yl)urea (90 mg, 0.181 mmol) in DCE (1 mL) was added (1,3-Bis-(2,4,6-trimethylphenyl)-2-imidazolidinylidene)dichloro(o-isopropoxyphenylmethylene)ruthenium (22.71 mg, 0.036 mmol). The mixture was stirred at 50° C. for 2 h. The mixture was filtered, and the fulfiller was concentrated to give ($1^7$E,3R,9E)-4-ethyl-7-(fluoromethyl)-25-methoxy-3-methyl-13-oxa-4,6-diaza-1(6,8)-imidazo[1,2-a]pyrazina-2(4,2)-pyridinacyclotridecaphan-9-en-5-one and it was used in next step without further purification. LCMS m/z (M+H): 469.5 required, 469.7 found.

To a solution of ($1^7$E,3R,9E)-4-ethyl-7-(fluoromethyl)-25-methoxy-3-methyl-13-oxa-4,6-diaza-1(6,8)-imidazo[1,2-a]pyrazina-2(4,2)-pyridinacyclotridecaphan-9-en-5-one (80 mg, 0.171 mmol) in EtOAc (5 mL) was added Pd-C(36.3 mg, 0.034 mmol). The mixture was stirred at 25° C. with a balloon of H2 for 1 h. The mixture was filtered and then the filtrate was concentrated and purified by HPLC (C18, water/TFA/ACN) to give (3R,7R,E)-4-ethyl-7-(fluoromethyl)-25-methoxy-3-methyl-13-oxa-4,6-diaza-1(6,8)-imidazo[1,2-a]pyrazina-2(4,2)-pyridinacyclotridecaphan-5-one as the second eluting diastereomer (example 126). LCMS m/z (M+H): 471.2 required, 471.2 found. $^1H$ NMR (500 MHz, $CD_3OD$) δ 9.32 (s, 1H), 8.44 (s, 1H), 8.36 (s, 1H), 8.25 (s, 1H), 7.90 (s, 1H), 6.03-5.99 (m, 1H), 4.75-4.70 (m, 1H), 4.45-4.34 (m, 3H), 4.22 (s, 3H), 3.33-3.17 (m, 3H), 2.03-1.95 (m, 2H), 1.66-1.41 (m, 9H), 1.04 (t, J=6.5 Hz, 3H).

Example 127

(3R,7S,E)-7-(3,3-difluoropropyl)-4-ethyl-25-fluoro-3-methyl-10,13-dioxa-4,6-diaza-1(2,4)-imidazo[2,1-f][1,2,4]triazina-2(4,2)-pyridinacyclotridecaphan-5-one (example 127)

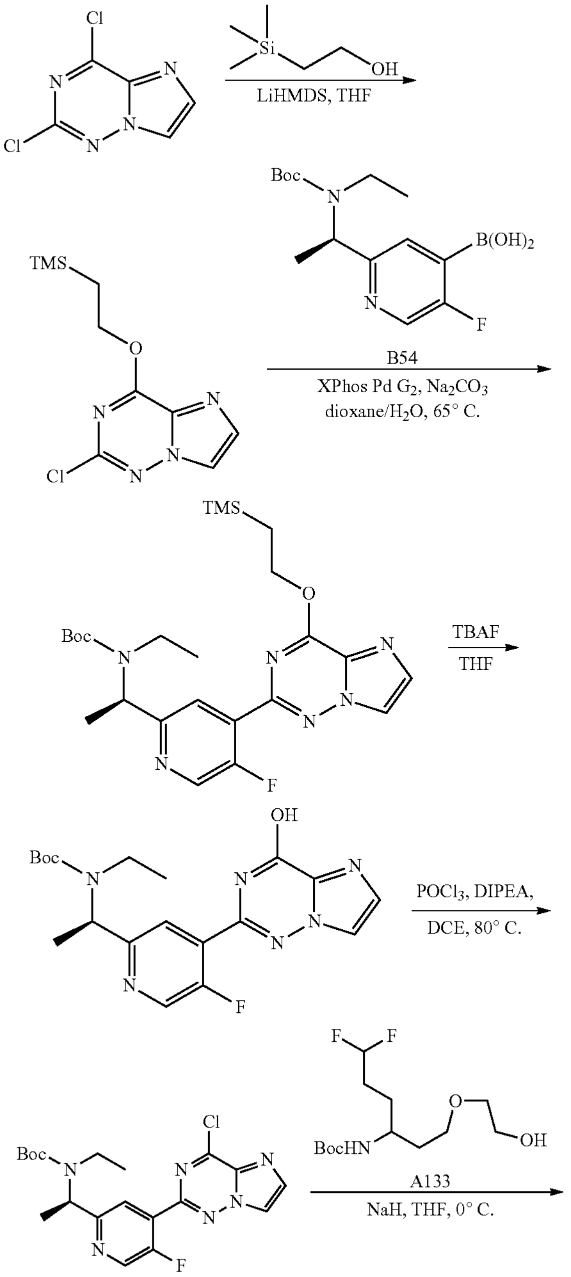

-continued

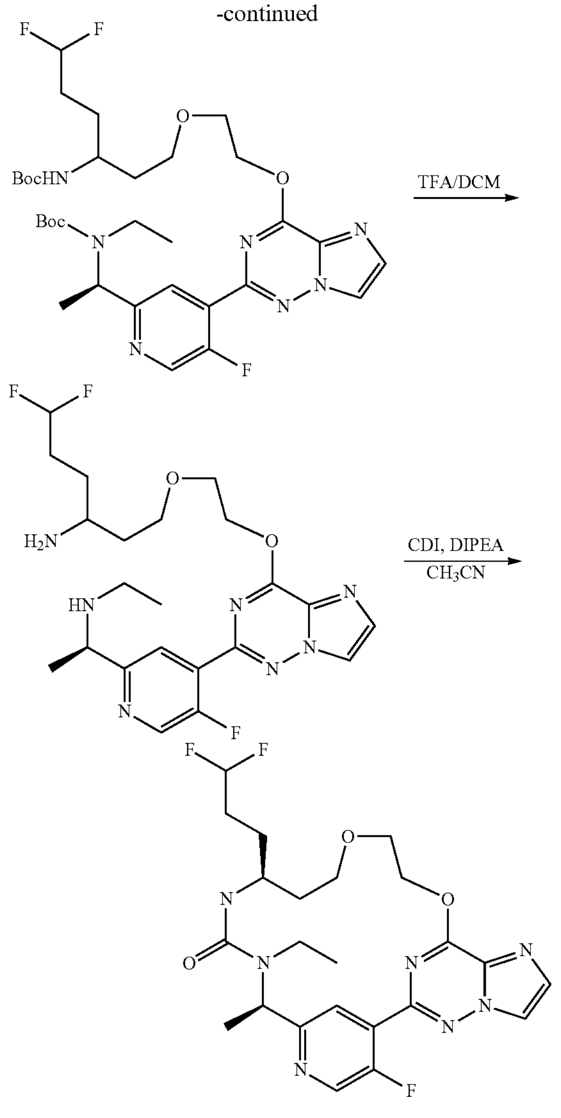

example 127

To a solution of 2-(trimethylsilyl)ethan-1-ol (313 mg, 2.65 mmol) in THF (10 mL) was added LiHMDS (2.65 mL, 2.65 mmol) (1 M in THF) at 0° C. and stirred for 30 mins. 2,4-dichloroimidazo[2,1-f][1,2,4]triazine (500 mg, 2.65 mmol) was added and stirred at 25° C. for 3 hours. The reaction mixture was poured into water (20 mL), extracted with EtOAc (10 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-20]% ethyl acetate/pet. ether gradient) to give 2-chloro-4-(2-(trimethylsilyl)ethoxy)imidazo[2,1-f][1,2,4]triazine. LCMS m/z (M+H): 271.1 required, 271.1 found.

To a solution of (R)-(2-(1-((tert-butoxycarbonyl)(ethyl)amino)ethyl)-5-fluoropyridin-4-yl)boronic acid B54 (10 mL, 1.720 mmol) in 10 mL dioxane was added Water (3 mL), $Na_2CO_3$ (547 mg, 5.16 mmol), 2-chloro-4-(2-(trimethylsilyl)ethoxy)imidazo[2,1-f][1,2,4]triazine (466 mg, 1.720 mmol) and chloro(2-dicyclohexylphosphino-2',4',6'-triisopropyl-1,1'-biphenyl)[2-(2'-amino-1,1'-biphenyl)]palladium (ii) (135 mg, 0.172 mmol). The mixture was stirred at 80° C. for 2 h. The reaction mixture was poured into water (50 mL), extracted with EtOAc (30 mL×3). The organic layer was washed with brine (50 mL), dried over $Na_2SO_4$, filtered and concentrated. The crude product was purified by Flash silica gel chromatography (ISCO®; 20 g SepaFlash® Silica Flash Column, Eluent of 20% EtOAc/Pet.ether gradient) to give tert-butyl (R)-ethyl(1-(5-fluoro-4-(4-(2-(trimethylsilyl)ethoxy)imidazo[2,1-f][1,2,4]triazin-2-yl)pyridin-2-yl)ethyl) carbamate. LCMS m/z (M+H): 503.3 required, 503.2 found.

To a solution of tert-butyl (R)-ethyl(1-(5-fluoro-4-(4-(2-(trimethylsilyl)ethoxy)imidazo[2,1-f][1,2,4]triazin-2-yl) pyridin-2-yl)ethyl)carbamate (700 mg, 1.393 mmol) in THF (10 mL) was added TBAF (2.089 mL, 2.089 mmol) (1 M in THF). The mixture was stirred at 20° C. for 2 h. The reaction mixture was poured into water (30 mL), extracted with EtOAc (20 mL×3). The organic layer was washed with brine (10 mL), dried over $Na_2SO_4$, filtered and concentrated to give tert-butyl (R)-ethyl(1-(5-fluoro-4-(4-hydroxyimidazo [2,1-f][1,2,4]triazin-2-yl)pyridin-2-yl)ethyl)carbamate, which was used to the next step without further purification. LCMS m/z (M+H): 403.2 required, 403.2 found.

To a solution of tert-butyl (R)-ethyl(1-(5-fluoro-4-(4-hydroxyimidazo[2,1-f][1,2,4]triazin-2-yl)pyridin-2-yl) ethyl)carbamate (560 mg, 1.392 mmol) in DCE (10 mL) were added DIPEA (1.458 mL, 8.35 mmol) and phosphoryl trichloride (0.648 mL, 6.96 mmol). The mixture was stirred at 80° C. for 2 h. The mixture was quenched with aq. $NaHCO_3$ and adjusted to pH=7-8, and then extracted with EtOAc (30 mL×3), washed with brine (30 mL), dried over $Na_2SO_4$, filtered and concentrated under reduced pressure. The crude was purified by Flash silica gel chromatography (ISCO®; 12 g SepaFlash® Silica Flash Column, Eluent of 40% EtOAc/Pet.ether gradient) to give tert-butyl (R)-(1-(4-(4-chloroimidazo[2,1-f][1,2,4]triazin-2-yl)-5-fluoropyridin-2-yl)ethyl)(ethyl)carbamate. LCMS m/z (M+H): 421.1 required, 421.1 found.

To a solution of NaH (77 mg, 1.917 mmol) in THF (2 mL) was added tert-butyl (6,6-difluoro-1-(2-hydroxyethoxy) hexan-3-yl)carbamate A133 (190 mg, 0.639 mmol) at 0° C. and stirred at 0° C. for 30 mins. tert-butyl (R)-(1-(4-(4-chloroimidazo[2,1-f][1,2,4]triazin-2-yl)-5-fluoropyridin-2-yl)ethyl)(ethyl)carbamate (323 mg, 0.767 mmol) was added and stirred for 10 mins. The reaction mixture was poured into water (10 mL), extracted with EtOAc (5 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-60]% ethyl acetate/pet. ether gradient) to give tert-butyl ((1R)-1-(4-(4-(2-((3-((tert-butoxycarbonyl)amino)-6,6-difluorohexyl)oxy) ethoxy)imidazo[2,1-f][1,2,4]triazin-2-yl)-5-fluoropyridin-2-yl)ethyl)(ethyl)carbamate. LCMS m/z (M+H): 682.3 required, 682.3 found.

To a solution of tert-butyl ((1R)-1-(4-(4-(2-((3-((tert-butoxycarbonyl)amino)-6,6-difluorohexyl)oxy)ethoxy)imidazo[2,1-f][1,2,4]triazin-2-yl)-5-fluoropyridin-2-yl)ethyl) (ethyl)carbamate (300 mg, 0.440 mmol) in DCM (10 mL) was added TFA (2 mL) and stirred at 25° C. for 30 mins. The reaction mixture was concentrated to give 1-(2-((2-(2-((R)-1-(ethylamino)ethyl)-5-fluoropyridin-4-yl)imidazo[2,1-f][1,2,4]triazin-4-yl)oxy)ethoxy)-6,6-difluorohexan-3-amine (212 mg, 0.440 mmol, 100% yield, which was used in next step without purification. LCMS m/z (M+H): 482.2 required, 482.2 found.

To a solution of 1-(2-((2-(2-((R)-1-(ethylamino)ethyl)-5-fluoropyridin-4-yl)imidazo[2,1-f][1,2,4]triazin-4-yl)oxy) ethoxy)-6,6-difluorohexan-3-amine (200 mg, 0.415 mmol) in MeCN (5 mL) were added DIPEA (0.218 mL, 1.246 mmol) and CDI (101 mg, 0.623 mmol). The mixture was stirred at 25° C. for 12 hours. The reaction mixture was poured into water (10 mL), extracted with EtOAc (5 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-100]% ethyl acetate/pet. ether gradient) to give (3R,E)-7-(3,3-difluoropropyl)-4-ethyl-25-fluoro-3-methyl-10,13-dioxa-4,6-diaza-1(2,4)-imidazo[2,1-f][1,2,4]triazina-2(4,2)-pyridinacyclotridecaphan-5-one as a mixture of diastereomers. LCMS m/z (M+H): 508.2 required, 508.2 found.

(3R,E)-7-(3,3-difluoropropyl)-4-ethyl-25-fluoro-3-methyl-10,13-dioxa-4,6-diaza-1(2,4)-imidazo[2,1-f][1,2,4] triazina-2(4,2)-pyridinacyclotridecaphan-5-one as a mixture of diastereomers (90 mg, 0.177 mmol) was separated by SFC (CHIRALPAK AD, 0.1% $NH_3H_2O$ EtOH) to give (3R,7S,E)-7-(3,3-difluoropropyl)-4-ethyl-25-fluoro-3-methyl-10,13-dioxa-4,6-diaza-1(2,4)-imidazo[2,1-f][1,2,4] triazina-2(4,2)-pyridinacyclotridecaphan-5-one (example 127) as the second eluting diastereomer (example 127). $^1H$ NMR (400 MHz, $CD_3OD$) δ 8.58 (d, J=3.0 Hz, 1H), 8.29-8.21 (m, 2H), 7.83 (s, 1H), 6.13-5.79 (m, 3H), 5.37-5.21 (m, 1H), 4.82-4.70 (m, 1H), 4.20 (br s, 1H), 3.98-3.82 (m, 2H), 3.73-3.59 (m, 2H), 3.31-3.17 (m, 1H), 3.16-2.97 (m, 1H), 2.03-1.85 (m, 3H), 1.78-1.64 (m, 6H), 1.08 (t, J=7.0 Hz, 3H)

Example 128

(3R,7R,E)-25-chloro-7-(3,3-difluoropropyl)-4-ethyl-3-methyl-13-oxa-4,6-diaza-1(6,8)-[1,2,4]triazolo[1,5-a] pyrazina-2(4,2)-pyridinacyclotridecaphan-5-one (Example 128)

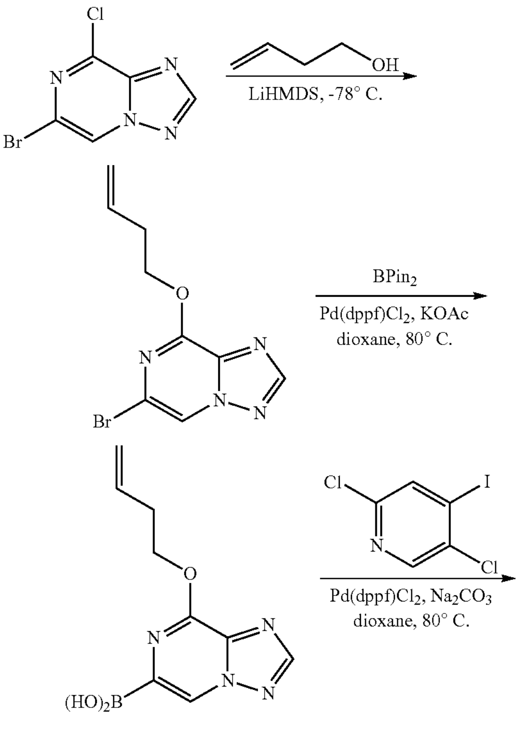

-continued

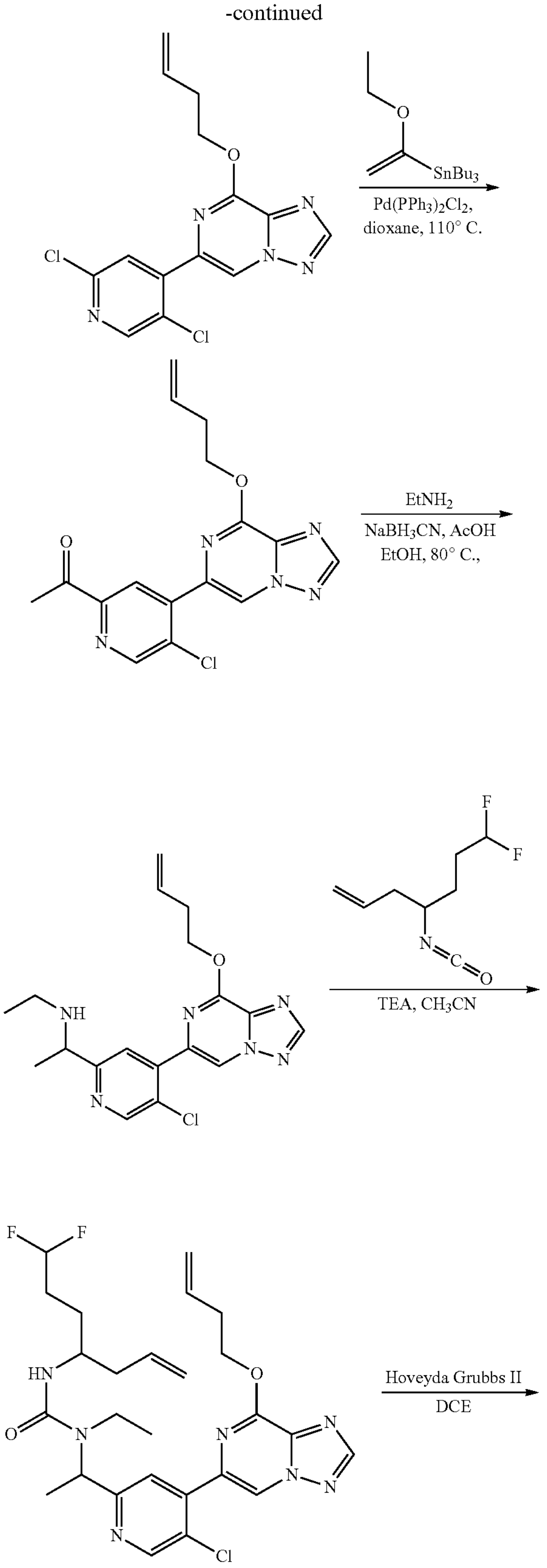

-continued

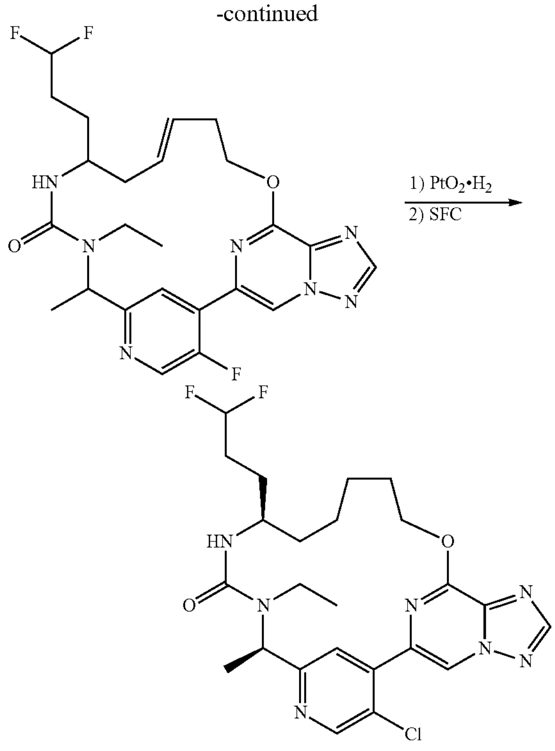

EXAMPLE 128

To a solution of but-3-en-1-ol (1.853 g, 25.7 mmol) in THF (50 mL) was added LiHMDS (25.7 mL, 25.7 mmol) (1 M in THF) at −78° C. and stirred at −78° C. for 30 mins. 6-bromo-8-chloro-[1,2,4]triazolo[1,5-a]pyrazine (4 g, 17.13 mmol) in THF (5 mL) was added to the above mixture and stirred at 25° C. for 12 hours. The mixture was quenched with water (100 mL), extracted with EtOAc (50 mL×3). The organic layer was dried over $Na_2SO_4$, filtered and concentrated. The crude product was purified by flash silica gel chromatography (ISCO®; 40 g Biotage® Silica Flash Column, Eluent of 0-20% EtOAc/Pet. ether gradient) to give 6-bromo-8-(but-3-en-1-yloxy)-[1,2,4]triazolo[1,5-a]pyrazine. LCMS m/z (M+H): 269.0 required, 269.0 found.

To a solution of 6-bromo-8-(but-3-en-1-yloxy)-[1,2,4]triazolo[1,5-a]pyrazine (1.5 g, 5.57 mmol) in Dioxane (15 mL) were added 4,4,4',4',5,5,5',5'-octamethyl-2,2'-bi(1,3,2-dioxaborolane) (1.699 g, 6.69 mmol), potassium acetate (1.641 g, 16.72 mmol) and Pd(dppf)$Cl_2$ (0.408 g, 0.557 mmol). The mixture was stirred at 80° C. for 2 hours. The reaction mixture of (8-(but-3-en-1-yloxy)-[1,2,4]triazolo[1,5-a]pyrazin-6-yl)boronic acid which was used in next step without purification. LCMS m/z (M+H): 235.1 required, 235.0 found.

To a solution of (8-(but-3-en-1-yloxy)-[1,2,4]triazolo[1,5-a]pyrazin-6-yl)boronic acid (14.72 mL, 5.48 mmol) (0.372 M in dioxane) in Water (3 mL) were added 2,5-dichloro-4-iodopyridine (1.5 g, 5.48 mmol), $Na_2CO_3$ (1.741 g, 16.43 mmol) and Pd(dppf)$Cl_2$ (0.401 g, 0.548 mmol). The mixture was stirred at 80° C. for 12 hours. The reaction mixture was poured into water (30 mL), extracted with EtOAc (20 mL×3). The organic layer was washed with brine (30 mL), dried over $Na_2SO_4$ and filtered. The filtrate was concentrated and purified by flash silica gel chromatography (ISCO®; 20 g SepaFlash® Silica Flash Column, eluent of [0-20]% ethyl acetate/pet. ether gradient) to give 8-(but-3- en-1-yloxy)-6-(2,5-dichloropyridin-4-yl)-[1,2,4]triazolo[1,5-a]pyrazine. LCMS m/z (M+H): 336.0 required, 336.0 found.

To a solution of 8-(but-3-en-1-yloxy)-6-(2,5-dichloropyridin-4-yl)-[1,2,4]triazolo[1,5-a]pyrazine (1.5 g, 4.46 mmol) in Dioxane (20 mL) were added tributyl(1-ethoxyvinyl)stannane (1.74 g, 4.82 mmol) and Dichlorobis(triphenylphosphine)palladium(II) (0.313 g, 0.446 mmol). The mixture was stirred at 110° C. for 8 hours. The reaction mixture was cooled to 25° C. and 1N HCl (10 mL) was added. The mixture was stirred at 25° C. for 2 hours. The reaction mixture was poured into water (10 mL) and 6N KF (30 mL), extracted with EtOAc (20 mL×3). The organic layer was washed with brine (50 mL), dried over $Na_2SO_4$ and filtered. The filtrate was concentrated and purified by flash silica gel chromatography (ISCO®; 12 g SepaFlash® Silica Flash Column, eluent of [0-20]% ethyl acetate/pet. ether gradient) to give 1-(4-(8-(but-3-en-1-yloxy)-[1,2,4]triazolo[1,5-a]pyrazin-6-yl)-5-chloropyridin-2-yl)ethan-1-one. LCMS m/z (M+H): 344.1 required, 344.0 found.

To a solution of 1-(4-(8-(but-3-en-1-yloxy)-[1,2,4]triazolo[1,5-a]pyrazin-6-yl)-5-chloropyridin-2-yl)ethan-1-one (500 mg, 1.454 mmol) in EtOH (10 mL) were added ethanamine (131 mg, 2.91 mmol), AcOH (8.33 μL, 0.145 mmol), $MgSO_4$ (875 mg, 7.27 mmol) and $NaBH_3CN$ (183 mg, 2.91 mmol). The mixture was stirred at 80° C. for 12 hours. The reaction mixture was poured into water (30 mL), extracted with EtOAc (20 mL×3). The organic layer was washed with brine (30 mL), dried over $Na_2SO_4$ and filtered. The filtrate was concentrated and purified by flash silica gel chromatography (ISCO®; 4 g SepaFlash® Silica Flash Column, eluent of [0-30]% ethyl acetate/pet. ether gradient) to give 1-(4-(8-(but-3-en-1-yloxy)-[1,2,4]triazolo[1,5-a]pyrazin-6-yl)-5-chloropyridin-2-yl)-N-ethylethan-1-amine. LCMS m/z (M+H): 373.1 required, 373.1 found.

To a solution of 1-(4-(8-(but-3-en-1-yloxy)-[1,2,4]triazolo[1,5-a]pyrazin-6-yl)-5-chloropyridin-2-yl)-N-ethylethan-1-amine (200 mg, 0.536 mmol) in MeCN (5 mL) were added $Et_3N$ (0.150 mL, 1.073 mmol) and 7,7-difluoro-4-isocyanatohept-1-ene A134 (3.33 mL, 0.966 mmol)(0.290 M in MeCN). The resulting mixture was stirred at 25° C. under N2 protection for 2 hours. The reaction mixture was poured into water (10 mL), extracted with EtOAc (5 mL×3). The organic layer was washed with brine (10 mL), dried over $Na_2SO_4$ and filtered. The filtrate was concentrated and purified by Prep-TLC ($SiO_2$, Pet. ether:EtOAc=1:1) to give 1-(1-(4-(8-(but-3-en-1-yloxy)-[1,2,4]triazolo[1,5-a]pyrazin-6-yl)-5-chloropyridin-2-yl)ethyl)-3-(7,7-difluorohept-1-en-4-yl)-1-ethylurea (180 mg, 0.328 mmol, 61.2% yield). LCMS m/z (M+H): 548.2 required, 548.2 found.

To a solution of 1-(1-(4-(8-(but-3-en-1-yloxy)-[1,2,4]triazolo[1,5-a]pyrazin-6-yl)-5-chloropyridin-2-yl)ethyl)-3-(7,7-difluorohept-1-en-4-yl)-1-ethylurea (180 mg, 0.328 mmol) in DCE (20 mL) was added (1,3-Bis-(2,4,6-trimethylphenyl)-2-imidazolidinylidene)dichloro(o-isopropoxyphenylmethylene)ruthenium (41.2 mg, 0.066 mmol) and stirred at 50° C. for 3 hours. The reaction mixture was concentrated and purified by Prep-TLC ($SiO_2$, Pet. ether:EtOAc=1:1) to give ($1^7$E,9E)-25-chloro-7-(3,3-difluoropropyl)-4-ethyl-3-methyl-13-oxa-4,6-diaza-1(6,8)-[1,2,4]triazolo[1,5-a]pyrazina-2(4,2)-pyridinacyclotridecaphan-9-en-5-one. LCMS m/z (M+H): 520.2 required, 520.1 found.

To a solution of ($1^7$E,9E)-25-chloro-7-(3,3-difluoropropyl)-4-ethyl-3-methyl-13-oxa-4,6-diaza-1(6,8)-[1,2,4]triazolo[1,5-a]pyrazina-2(4,2)-pyridinacyclotridecaphan-9-en-5-one (150 mg, 0.288 mmol) in EtOAc (5 mL) was added platinum(IV) oxide (65.5 mg, 0.288 mmol) and stirred at 25° C. under H2(15 psi) for 20 mins. The reaction mixture was filtered and concentrated and purified by Prep-TLC ($SiO_2$, Pet. ether:EtOAc=2:1) and separated by SFC (CHIRALPAK AD, 30% 0.1% $NH_3H_2O$/EtOH) to give (3R,7R,E)-25-chloro-7-(3,3-difluoropropyl)-4-ethyl-3-methyl-13-oxa-4,6-diaza-1(6,8)-[1,2,4]triazolo[1,5-a]pyrazina-2(4,2)-pyridinacyclotridecaphan-5-one Example 128 as the third eluting diastereomer (example 128). LCMS m/z (M+H): 522.2 required, 522.2 found.

Example 129

(3R,7S,E)-7-(3,3-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one (Example 129)

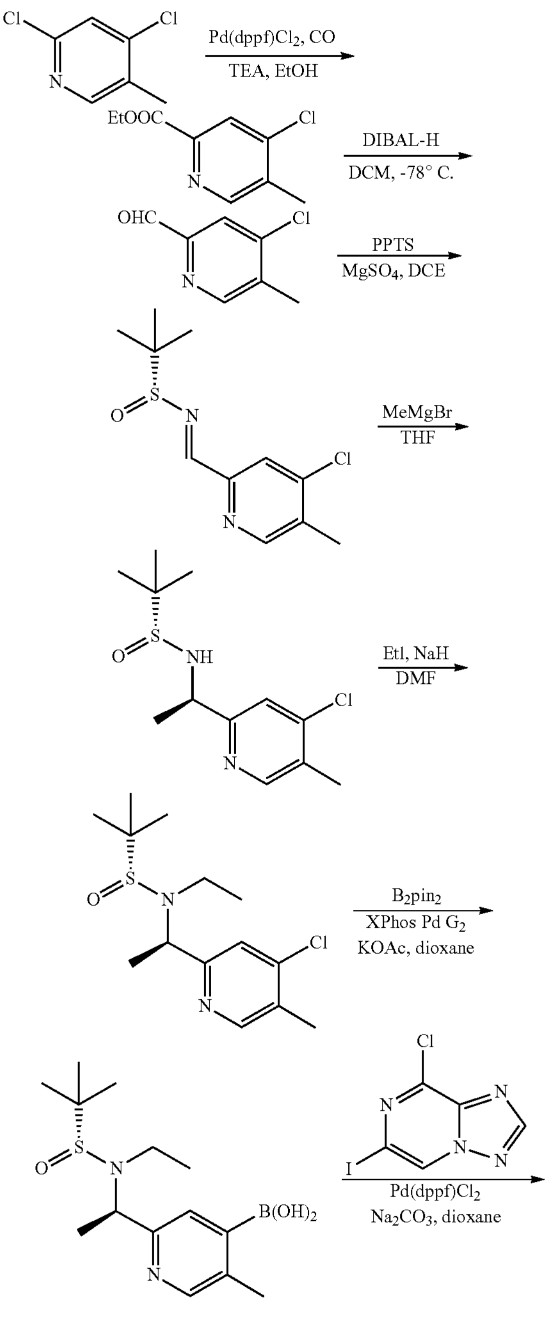

-continued

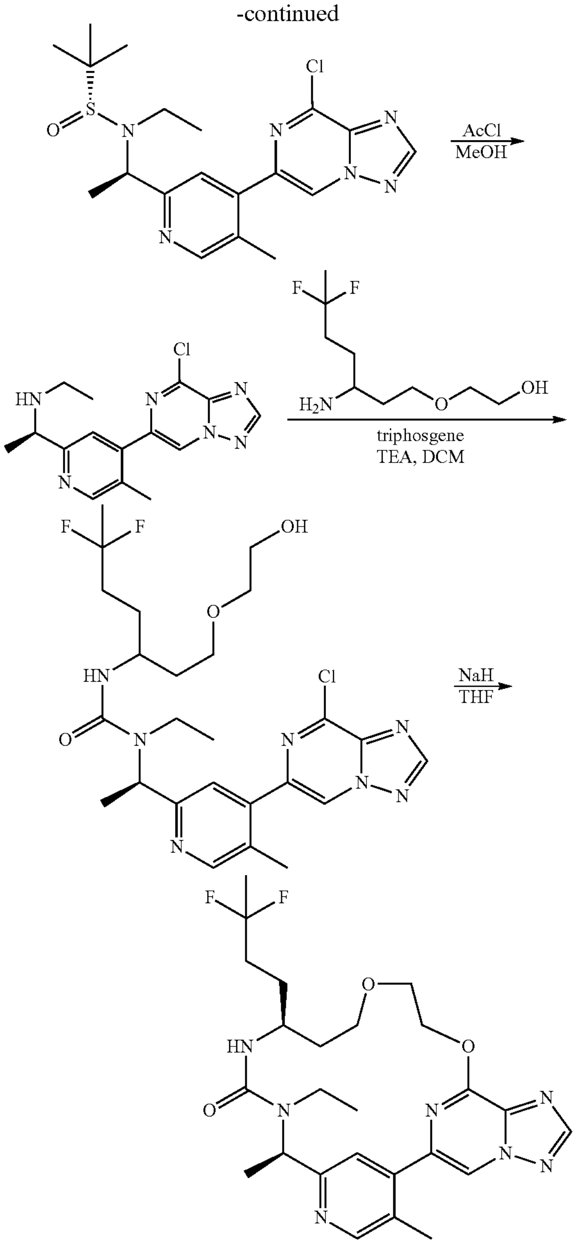

EXAMPLE 129

To a solution of 2,4-dichloro-5-methylpyridine (15 g, 93 mmol) in Ethanol (200 mL) and DMF (40 mL) were added TEA (38.7 mL, 278 mmol) and Pd(dppf)$Cl_2$ (3.39 g, 4.63 mmol). The mixture was stirred at 60° C. under CO (50 psi) for 12 h. The reaction mixture was concentrated and poured into water (500 mL), extracted with EtOAc (200 mL×3). The organic layer was washed with brine (200 mL), dried over $Na_2SO_4$ and filtered. The filtrate was concentrated and purified by flash silica gel chromatography (ISCO®; 120 g SepaFlash® Silica Flash Column, eluent of 50% ethyl acetate/pet. ether gradient) to give ethyl 4-chloro-5-methylpicolinate. LCMS m/z (M+H): 200.0 required, 200.1 found To a solution of ethyl 4-chloro-5-methylpicolinate (12 g, 60.1 mmol) in DCM (200 mL) was added DIBAL-H (72.1 mL, 72.1 mmol) (1 M in hexane). The mixture was stirred at −78° C. for 1 h. LCMS showed the reaction was completed. The reaction mixture was poured into water (150 mL), extracted with DCM (150 mL×3). The organic phases was dried over $Na_2SO_4$ and filtered. The crude was purified by Flash silica gel chromatography (ISCO®; 120 g SepaFlash® Silica Flash Column, Eluent of 10% EtOAc/Pet. ether gradient) to 4-chloro-5-methylpicolinaldehyde. LCMS m/z (M+H): 156.0 required, 156.0 found. $^1$H NMR 5049098-0053-1 (400 MHz, $CDCl_3$) δ 10.00 (s, 1H), 8.59 (s, 1H), 7.92 (s, 1H), 2.45 (s, 3H)

To a solution of 4-chloro-5-methylpicolinaldehyde (6 g, 38.6 mmol) in DCE (150 mL) were added $MgSO_4$ (27.9 g, 231 mmol), (R)-2-methylpropane-2-sulfinamide (5.61 g, 46.3 mmol) and PPTS (0.969 g, 3.86 mmol). The resulting mixture was stirred at 80° C. under N2 protection for 12 h. The mixture was concentrated under reduced pressure to give the crude. The crude was purified by Flash silica gel chromatography (ISCO®; 120 g SepaFlash® Silica Flash Column, Eluent of 80% EtOAc/Pet. ether gradient) to give (R,E)-N-((4-chloro-5-methylpyridin-2-yl)methylene)-2-methylpropane-2-sulfinamide. LCMS m/z (M+H): 259.1 required, 259.0 found To a solution of (R,E)-N-((4-chloro-5-methylpyridin-2-yl)methylene)-2-methylpropane-2-sulfinamide (8 g, 30.9 mmol) in THF (200 mL) was added methylmagnesium bromide (41.2 mL, 124 mmol) (3 M in $Et_2O$). The mixture was stirred at 0° C. under N2 protection for 1 h. The mixture was quenched with $H_2O$ (600 mL) and extracted with EtOAc (200 mL×3), washed with brine (200 mL), dried over $Na_2SO_4$, filtered and concentrated under reduced pressure. The crude was purified by Flash silica gel chromatography (ISCO®; 80 g SepaFlash® Silica Flash Column, Eluent of 80% EtOAc/Pet. ether gradient) to give (R)—N—((R)-1-(4-chloro-5-methylpyridin-2-yl)ethyl)-2-methylpropane-2-sulfinamide. LCMS m/z (M+H): 275.1 required, 275.1 found To a solution of (R)—N—((R)-1-(4-chloro-5-methylpyridin-2-yl)ethyl)-2-methylpropane-2-sulfinamide (6 g, 21.83 mmol) in DMF (150 mL) was added NaH (1.747 g, 43.7 mmol) (60% wt) at 0° C. under N2. The mixture was stirred at 0° C. for 30 mins. Iodoethane (2.62 mL, 32.8 mmol) was added and stirred at 0° C. for 2 h. The reaction mixture was poured into water (300 mL), extracted with EtOAc (100 mL×3). The combined organic layers were washed with brine (100 mL), dried over $Na_2SO_4$ and filtered. The filtrate was concentrated and purified by Flash silica gel chromatography (ISCO®; 80 g SepaFlash® Silica Flash Column, Eluent of 90% EtOAc/Pet.ether gradient) to give (R)—N—((R)-1-(4-chloro-5-methylpyridin-2-yl)ethyl)-N-ethyl-2-methylpropane-2-sulfinamide. LCMS m/z (M+H): 303.1 required, 303.2 found. $^1$H NMR 5049098-0079-1 (400 MHz, $CDCl_3$) δ 8.44-8.35 (m, 1H), 7.37 (s, 1H), 4.66 (q, J 6.8 Hz, 1H), 3.28 (qd, J=7.3, 14.7 Hz, 1H), 3.08-2.84 (m, 1H), 2.44-2.33 (m, 3H), 1.69-1.61 (m, 3H), 1.22-1.15 (m, 3H), 1.13 (s, 9H)

To a solution of (R)—N—((R)-1-(4-chloro-5-methylpyridin-2-yl)ethyl)-N-ethyl-2-methylpropane-2-sulfinamide (2 g, 6.60 mmol) in Dioxane (3 mL) were added 4,4,4',4',5,5,5',5'-octamethyl-2,2'-bi(1,3,2-dioxaborolane) (2.52 g, 9.91 mmol), potassium acetate (1.944 g, 19.81 mmol), chloro(2-dicyclohexylphosphino-2',4',6'-triisopropyl-1,1'-biphenyl)[2-(2'-amino-1,1'-biphenyl)]palladium(ii) (0.260 g, 0.330 mmol). And the resulting mixture was stirred at 80° C. under N2 protection for 12 h. The mixture was filtered and concentrated under reduced pressure to give (2-((R)-1-(((R)-tert-butylsulfinyl)(ethyl)amino)ethyl)-5-methylpyridin-4- yl)boronic acid which was used to the next step without further purification. LCMS m/z (M+H): 313.2 required, 313.1 found To a solution of (2-((R)-1-(((R)-tert-butylsulfinyl)(ethyl)amino)ethyl)-5-methylpyridin-4-yl)boronic acid (2 g, 6.41 mmol) in Dioxane (30 mL) were added Water (10 mL), $Na_2CO_3$ (2.037 g, 19.22 mmol), 8-chloro-6-iodo-[1,2,4]triazolo[1,5-a]pyrazine (2.156 g, 7.69 mmol) and Pd(dppf)$Cl_2$ (0.234 g, 0.320 mmol). The mixture was stirred at 80° C. for 12 h. The reaction mixture was poured into $H_2O$(60 mL) and extracted with EtOAc (50 mL×3). The combined organic layers were washed with brine (50 mL), dried over $Na_2SO_4$ and filtered, concentrated. The residue was purified by flash silica gel chromatography (ISCO®; 40 g SepaFlash® Silica Flash Column, eluent of 85% ethyl acetate/pet. ether gradient) to give (R)—N—((R)-1-(4-(8-chloro-[1,2,4]triazolo[1,5-a]pyrazin-6-yl)-5-methylpyridin-2-yl)ethyl)-N-ethyl-2-methylpropane-2-sulfinamide. LCMS m/z (M+H): 421.1 required, 421.1 found To a solution of (R)—N—((R)-1-(4-(8-chloro-[1,2,4]triazolo[1,5-a]pyrazin-6-yl)-5-methylpyridin-2-yl)ethyl)-N-ethyl-2-methylpropane-2-sulfinamide (1.4 g, 3.33 mmol) in MeOH (20 mL) was added AcCl (0.473 mL, 6.65 mmol). The mixture was stirred at 25° C. for 1 h. The reaction mixture was concentrated to give (R)-1-(4-(8-chloro-[1,2,4]triazolo[1,5-a]pyrazin-6-yl)-5-methylpyridin-2-yl)-N-ethylethan-1-amine, which was used in next step without purification. LCMS m/z (M+H): 317.1 required, 317.1 found To a solution of 2-((3-amino-6,6-difluoroheptyl)oxy)ethan-1-ol A135 (400 mg, 1.894 mmol) in DCM (10 mL) were added TEA (1.100 mL, 7.89 mmol) and bis(trichloromethyl) carbonate (234 mg, 0.789 mmol). The mixture was stirred at 0° C. for 30 min. Compound (R)-1-(4-(8-chloro-[1,2,4]triazolo[1,5-a]pyrazin-6-yl)-5-methylpyridin-2-yl)-N-ethylethan-1-amine (500 mg, 1.578 mmol) was added and stirred at 0° C. to 20° C. for 1 h. The reaction mixture was poured into $H_2O$(30 mL) and extracted with DCM (30 mL×3). The combined organic layers were dried over $Na_2SO_4$ and filtered, concentrated in vacuo. The crude was purified by Flash silica gel chromatography (ISCO®; 20 g SepaFlash® Silica Flash Column, Eluent of 80% EtOAc/Pet. ether gradient) to give 1-((R)-1-(4-(8-chloro-[1,2,4]triazolo[1,5-a]pyrazin-6-yl)-5-methylpyridin-2-yl)ethyl)-3-(6,6-difluoro-1-(2-hydroxyethoxy)heptan-3-yl)-1-ethylurea. LCMS m/z (M+H): 554.2 required, 554.2 found.

To a solution of 1-((R)-1-(4-(8-chloro-[1,2,4]triazolo[1,5-a]pyrazin-6-yl)-5-methylpyridin-2-yl)ethyl)-3-(6,6-difluoro-1-(2-hydroxyethoxy)heptan-3-yl)-1-ethylurea (450 mg, 0.812 mmol) in THF (8 mL) was added sodium hydride (65.0 mg, 1.624 mmol) (60% wt) at 0° C. and stirred at 0° C. for 2 h. The mixture was quenched with $H_2O$(20 mL) and extracted with EtOAc (20 mL×3), washed with brine (20 mL), dried over $Na_2SO_4$, filtered and concentrated under reduced pressure. The crude was purified by Flash silica gel chromatography (ISCO®; 12 g SepaFlash® Silica Flash Column, Eluent of 90% EtOAc/Pet.ether gradient) and separated by SFC (Chiralcel OD, 5-40% ethanol (0.05% DEA) in $CO_2$) to give (3R,7S,E)-7-(3,3-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one as the second eluting diastereomer (example 129). LCMS m/z (M+H): 518.3 required, 518.1 found. $^1H$ NMR (400 MHz, $CDCl_3$) δ 8.54-8.44 (m, 3H), 7.84 (s, 1H), 6.00 (q, J=7.0 Hz, 1H), 5.01-4.87 (m, 2H), 4.35 (br d, J=8.8 Hz, 1H), 4.24-4.11 (m, 1H), 3.93 (t, J=7.0 Hz, 2H), 3.67 (t, J=6.0 Hz, 2H), 3.21-3.01 (m, 2H), 2.57 (s, 3H), 2.11-1.84 (m, 3H), 1.78-1.61 (m, 7H), 1.59-1.43 (m, 2H), 1.14 (t, J=7.1 Hz, 3H)

Examples 130 and 131

(3R,7R,E)-4-ethyl-25-methoxy-3-methyl-7-((R)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one and (3R,7R,E)-4-ethyl-25-methoxy-3-methyl-7-((S)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one (examples 130 and 131)

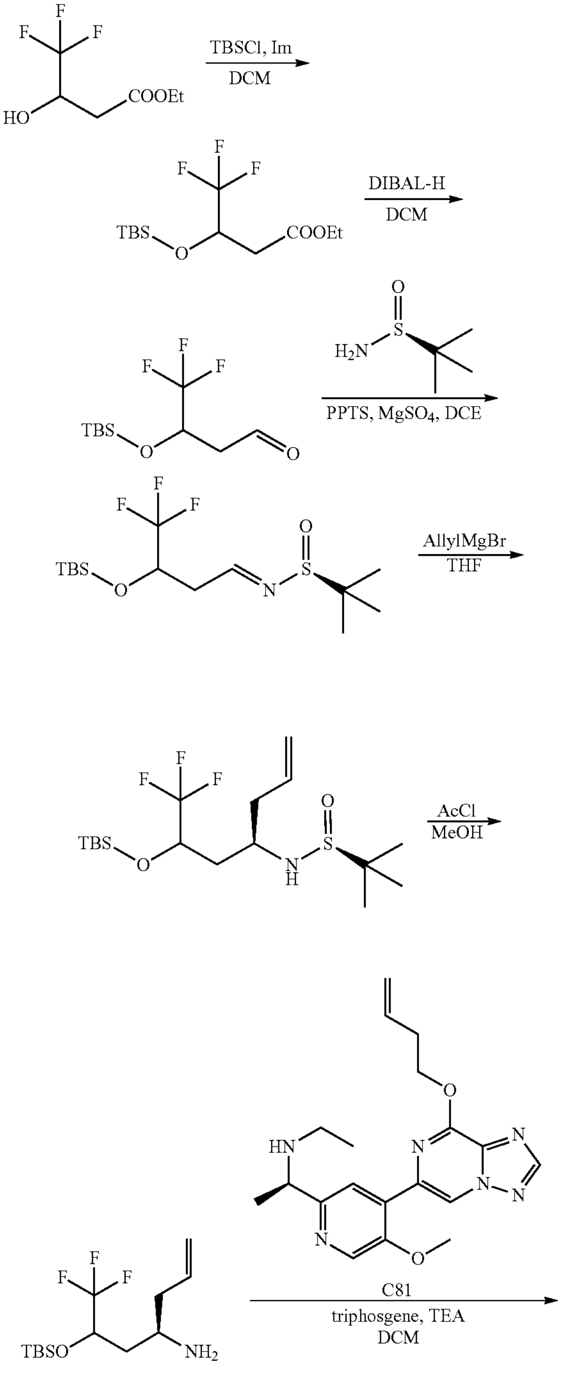

-continued

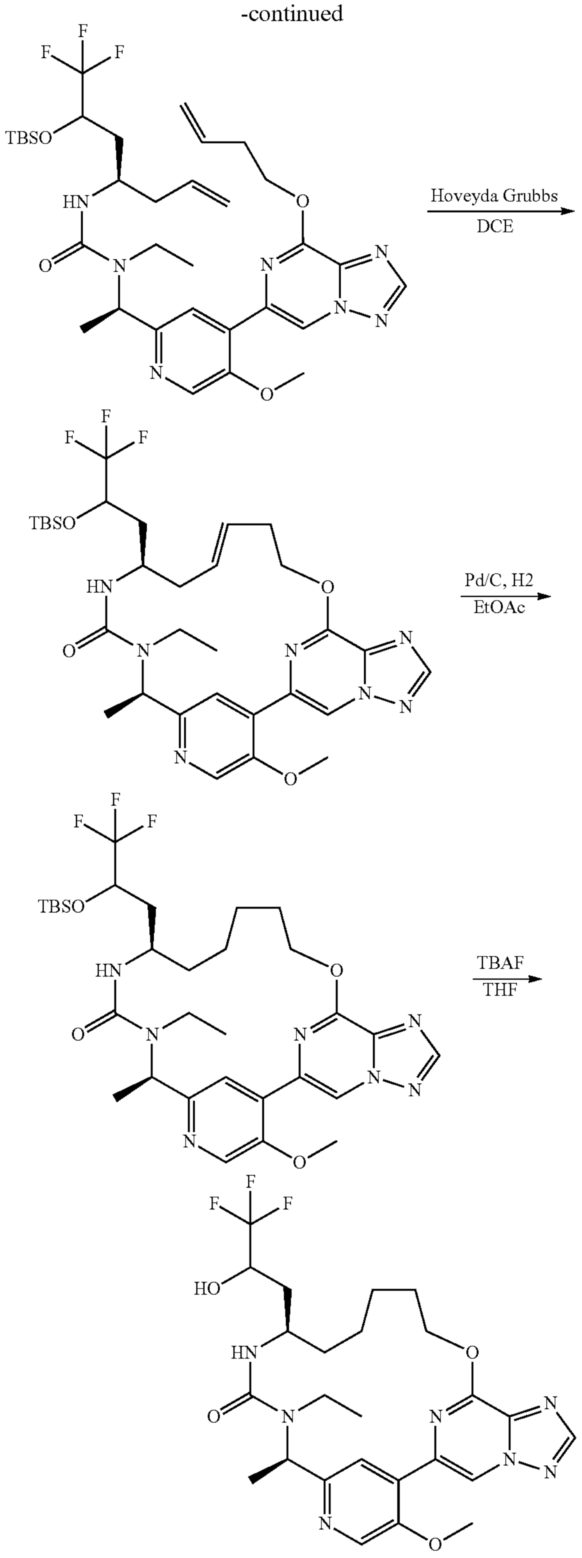

EXAMPLE 130 AND 131

To a solution of ethyl 4,4,4-trifluoro-3-hydroxybutanoate (5 g, 26.9 mmol) and 1H-imidazole (3.66 g, 53.7 mmol) in DCM (100 mL) was added tert-butylchlorodimethylsilane (4.45 g, 29.5 mmol) atn 0° C. The mixture was stirred at 15° C. for 16 hours. The reaction mixture was poured into water (20 mL), extracted with DCM (50 mL×3). The organic layer was washed with brine (50 mL), dried over $Na_2SO_4$ and filtered. The filtrate was concentrated and purified by flash silica gel chromatography (ISCO®; 80 g SepaFlash® Silica Flash Column, eluent of [0-50]% ethyl acetate/pet. ether gradient) to give ethyl 3-((tert-butyldimethylsilyl)oxy)-4,4,4-trifluorobutanoate.

To a solution of ethyl 3-((tert-butyldimethylsilyl)oxy)-4,4,4-trifluorobutanoate (0.5 g, 1.664 mmol) in DCM (10 mL) was added DIBAL-H (4.99 mL, 4.99 mmol) (1 M in tol) at −78° C. The mixture was stirred at −78° C. for 1 h. The reaction mixture was poured into aqueous saturated $NH_4Cl$ (6 mL), extracted with DCM (5 mL×3). The organic layer was washed with brine (5 mL), dried over $Na_2SO_4$ and filtered to give 3-((tert-butyldimethylsilyl)oxy)-4,4,4-trifluorobutanal which was used in the next steps directly.

To a solution of 3-((tert-butyldimethylsilyl)oxy)-4,4,4-trifluorobutanal (420 mg, 1.638 mmol) in DCE (10 mL) were added $MgSO_4$ (1183 mg, 9.83 mmol), (S)-2-methylpropane-2-sulfinamide (238 mg, 1.966 mmol) and PPTS (41.2 mg, 0.164 mmol). The resulting mixture was stirred at 80° C. under N2 protection for 2 h. The reaction mixture was poured into water (10 mL), extracted with DCM (10 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0~30]% ethyl acetate/pet. ether gradient) to give (S)—N-((E)-3-((tert-butyldimethylsilyl)oxy)-4,4,4-trifluorobutylidene)-2-methylpropane-2-sulfinamide. LCMS m/z (M+H): 360.0 required, 360.0 found.

To a mixture of (S)—N-((E)-3-((tert-butyldimethylsilyl)oxy)-4,4,4-trifluorobutylidene)-2-methylpropane-2-sulfinamide (310 mg, 0.862 mmol) in THF (4 mL) was added Allylmagnesium bromide solution (0.862 mL, 0.862 mmol) (1 M in tol) at 0° C. and stirred at 0° C. for 1 h. $NH_4Cl$ (5 mL, aqueous saturated) was added to the mixture, extracted with EtOAc (6 mL×3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of [20-50]% ethyl acetate/pet. ether gradient) to give (S)—N-((4R)-6-((tert-butyldimethylsilyl)oxy)-7,7,7-trifluorohept-1-en-4-yl)-2-methylpropane-2-sulfinamide. To a solution of (S)—N-((4R)-6-((tert-butyldimethylsilyl)oxy)-7,7,7-trifluorohept-1-en-4-yl)-2-methylpropane-2-sulfinamide (0.26 g, 0.647 mmol) in MeOH (3 mL) was added AcCl (0.092 mL, 1.295 mmol) at 0° C. The resulting mixture was stirred at 0° C. for 30 mins. The mixture was concentrated to give (4R)-6-((tert-butyldimethylsilyl)oxy)-7,7,7-trifluorohept-1-en-4-amine. which was used in the next steps directly. LCMS m/z (M+H): 298.2 required, 298.2 found.

To a solution of (4R)-6-((tert-butyldimethylsilyl)oxy)-7,7,7-trifluorohept-1-en-4-amine (170 mg, 0.572 mmol) in DCM (5 mL) were added TEA (0.797 mL, 5.72 mmol), bis(trichloromethyl) carbonate (85 mg, 0.286 mmol) and stirred at 0° C. for 30 mins. (R)-1-(4-(8-(but-3-en-1-yloxy)-[1,2,4]triazolo[1,5-a]pyrazin-6-yl)-5-methoxypyridin-2-yl)-N-ethylethan-1-amine C81 (147 mg, 0.400 mmol) was added and stirred at 0° C. for 30 mins. The reaction mixture was poured into 10 mL $H_2O$, and extracted with DCM (10 mL×3). The combined organic layers were washed with brine (10 mL), dried over $Na_2SO_4$, filtered, and the filtrate was concentrated in vacuo. The crude was purified by Flash silica gel chromatography (ISCO®; 4 g SepaFlash® Silica Flash Column, Eluent of 30-80% EtOAc/Pet. ether gradient) to give 1-((R)-1-(4-(8-(but-3-en-1-yloxy)-[1,2,4]triazolo[1, 5-a]pyrazin-6-yl)-5-methoxypyridin-2-yl)ethyl)-3-((4R)-6-((tert-butyldimethylsilyl)oxy)-7,7,7-trifluorohept-1-en-4-yl)-1-ethylurea. LCMS m/z (M+H): 692.2 required, 692.3 found.

To a solution of 1-((R)-1-(4-(8-(but-3-en-1-yloxy)-[1,2,4]triazolo[1,5-a]pyrazin-6-yl)-5-methoxypyridin-2-yl)ethyl)-3-((4R)-6-((tert-butyldimethylsilyl)oxy)-7,7,7-trifluoro-hept-1-en-4-yl)-1-ethylurea (295 mg, 0.426 mmol) in $ClCH_2CH_2Cl$ (100 mL) was added (1,3-dimesitylimidazo-lidin-2-ylidene)(2-isopropoxybenzylidene)ruthenium(VI) chloride (53.4 mg, 0.085 mmol) and stirred at 50° C. for 16 hours. The mixture was concentrated and purified by Flash silica gel chromatography (ISCO®; 4 g SepaFlash® Silica Flash Column, Eluent of 100% EtOAc) to give ($1^7$E,3R,7R,9E)-7-(2-((tert-butyldimethylsilyl)oxy)-3,3,3-trifluoropropyl)-4-ethyl-25-methoxy-3-methyl-13-oxa-4,6-diaza-1(6,8)-[1,2,4]triazolo[1,5-a]pyrazina-2(4,2)-pyridinacyclotridecaphan-9-en-5-one. LCMS m/z (M+H): 664.2 required, 664.3 found.

To a solution of ($1^7$E,3R,7R,9E)-7-(2-((tert-butyldimethylsilyl)oxy)-3,3,3-trifluoropropyl)-4-ethyl-25-methoxy-3-methyl-13-oxa-4,6-diaza-1(6,8)-[1,2,4]triazolo[1,5-a]pyrazina-2(4,2)-pyridinacyclotridecaphan-9-en-5-one (220 mg, 0.331 mmol) in EtOAc (20 mL) was added Pd-C(50 mg, 0.047 mmol) (10%), the resulting mixture was stirred at under H2 (excess) (15 psi) for 30 mins. The mixture was filtered and the filtrate was concentrated to give (3R,7R,E)-7-(2-((tert-butyldimethylsilyl)oxy)-3,3,3-trifluoropropyl)-4-ethyl-25-methoxy-3-methyl-13-oxa-4,6-diaza-1(6,8)-[1,2,4]triazolo[1,5-a]pyrazina-2(4,2)-pyridinacyclotridecaphan-5-one which was used in the next steps directly. LCMS m/z (M+H): 666.2 required, 666.3 found.

To a solution of (3R,7R,E)-7-(2-((tert-butyldimethylsilyl)oxy)-3,3,3-trifluoropropyl)-4-ethyl-25-methoxy-3-methyl-13-oxa-4,6-diaza-1(6,8)-[1,2,4]triazolo[1,5-a]pyrazina-2(4,2)-pyridinacyclotridecaphan-5-one (200 mg, 0.301 mmol) in THF (5 mL) was added TBAF (0.603 mL, 0.603 mmol) (1 M in THF) and stirred at 25° C. for 2 hours. The reaction mixture was poured into $H_2O$(3 mL), extracted with EtOAc (10 mL×3). The organic layer was washed with brine (10 mL), dried over $Na_2SO_4$ and filtered. The filtrate was concentrated and purified by purified by flash silica gel chromatography (ISCO®; 4 g SepaFlash® Silica Flash Column, eluent of [0-50]% ethyl acetate/pet. ether gradient) to give the (3R,7R,E)-4-ethyl-25-methoxy-3-methyl-7-(3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one as a mixture of diastereomers. The diastereomers was separated by prep-HPLC (water with 0.1% TFA, 40-60% ACN) to give (3R,7R,E)-4-ethyl-25-methoxy-3-methyl-7-((R)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one and (3R,7R,E)-4-ethyl-25-methoxy-3-methyl-7-((S)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one, (examples 130 and 131)—absolute configuration of the diastereomers was not determined. LCMS m/z (M+H): 552.2 required, 552.2 found. 1st eluting diastereomer (Example 130) 1H NMR (400 MHz, $CD_3OD$) δ 9.39 (s, 1H), 8.56 (s, 1H), 8.44 (s, 1H), 8.36 (s, 1H), 5.97 (q, J=7.1 Hz, 1H), 4.85-4.70 (m, 2H), 4.28 (br d, J=6.8 Hz, 1H), 4.21 (s, 3H), 4.08-3.97 (m, 1H), 3.27-3.13 (m, 2H), 2.04-1.89 (m, 2H), 1.87-1.77 (m, 2H), 1.71-1.59 (m, 5H), 1.55-1.35 (m, 4H), 1.04 (t, J=7.1 Hz, 3H). $2^{nd}$ eluting diastereomer (Example 131) $^1$H NMR (400 MHz, $CD_3OD$) δ 9.37 (s, 1H), 8.55 (s, 1H), 8.44 (s, 1H), 8.32 (s, 1H), 5.98 (q, J=7.1 Hz, 1H), 4.74 (dt, J=6.1, 10.8 Hz, 1H), 4.30 (br s, 1H), 4.20 (s, 3H), 4.05-3.90 (m, 1H), 3.28-3.08 (m, 2H), 2.10-1.88 (m, 2H), 1.86-1.76 (m, 1H), 1.72-1.67 (m, 1H), 1.62 (br d, J=7.1 Hz, 5H), 1.59-1.32 (m, 5H), 1.03 (t, J=7.0 Hz, 3H).

Examples 132 and 133

(3R,7R,E)-4-ethyl-25-methoxy-3-methyl-7-((R)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one and (3R,7R,E)-4-ethyl-25-methoxy-3-methyl-7-((S)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one (Examples 132 and 133)

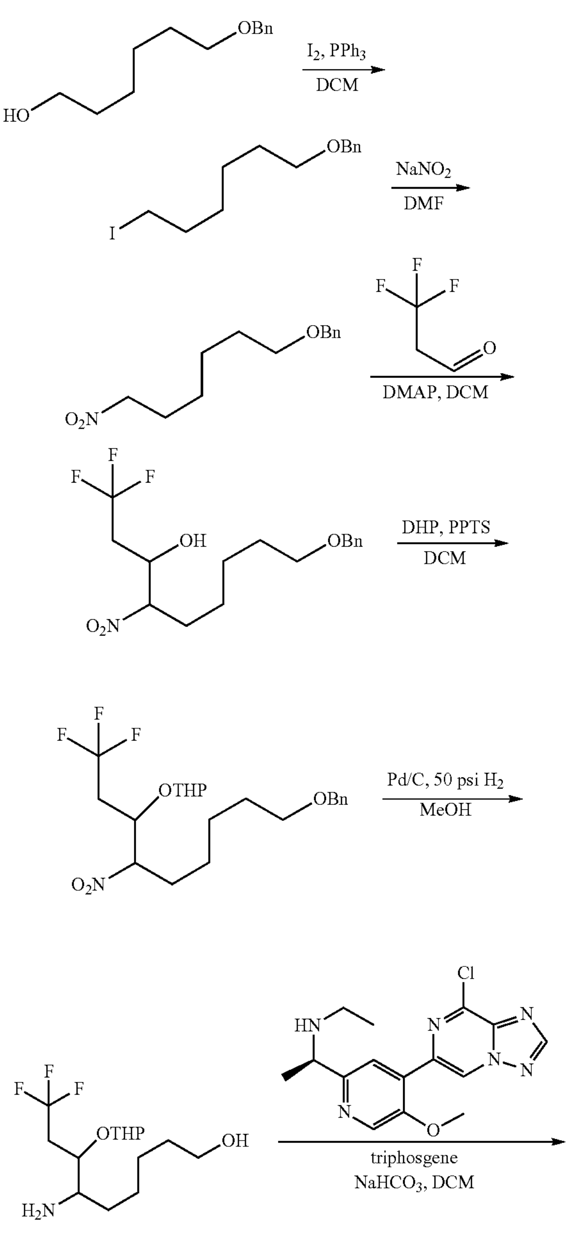

-continued

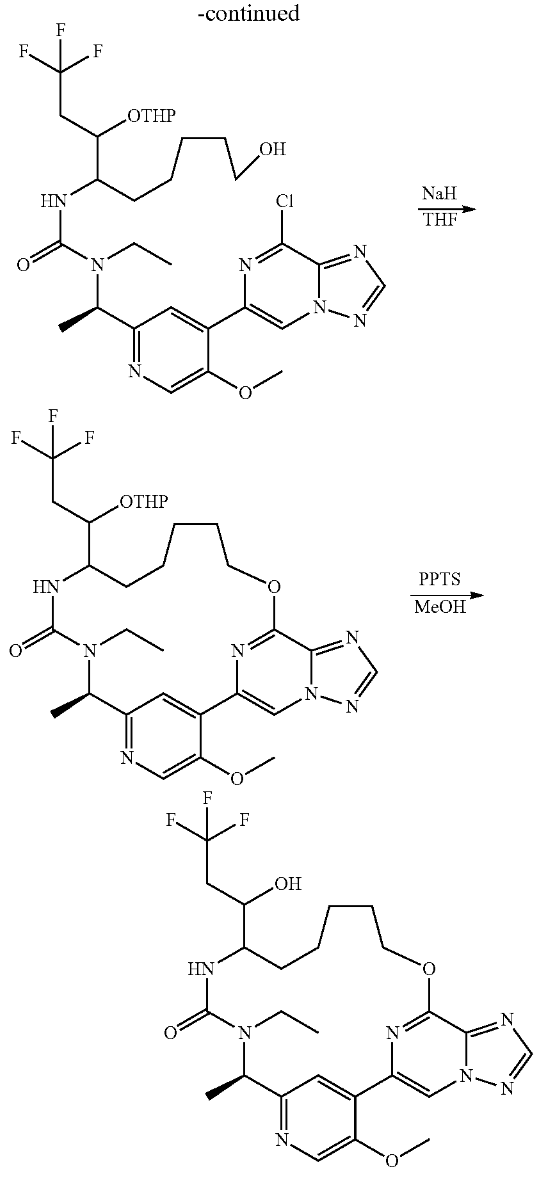

EXAMPLE
132, 133

To a solution of triphenylphosphane (8.84 g, 33.7 mmol) in DCM (300 mL) was added imidazole (2.87 g, 42.1 mmol) and 12 (9.62 g, 37.9 mmol). The mixture was stirred at 25° C. for 2 min, then added 6-(benzyloxy)hexan-1-ol (5.85 g, 28.1 mmol), and continue to stir for 2 h. The reaction mixture was concentrated and purified by flash silica gel chromatography (ISCO®; 80 g SepaFlash® Silica Flash Column, eluent of [0-20]% ethyl acetate/pet. ether gradient) to give (((6-iodohexyl)oxy)methyl)benzene. $^1$H NMR (500 MHz, $CDCl_3$) δ 7.31-7.16 (m, 5H), 4.44 (s, 2H), 3.39 (t, J=6.5 Hz, 2H), 3.10 (t, J=7.0 Hz, 2H), 1.78-1.65 (m, 2H), 1.62-1.51 (m, 2H), 1.42-1.26 (m, 4H).

To a solution of (((6-iodohexyl)oxy)methyl)benzene (7.5 g, 23.57 mmol) in DMF (40 mL) at 25° C. was added sodium nitrite (2.439 g, 35.4 mmol), and the reaction was stirred at 25° C. for 2 h. The reaction was poured into water (100 mL) and extracted with EtOAc (30 mL×3). The combined organic layers were washed with brine, dried over $Na_2SO_4$ and filtered. The filtrate was concentrated and purified by flash silica gel chromatography (ISCO®; 80 g SepaFlash® Silica Flash Column, eluent of [0-10]% ethyl acetate/pet. ether gradient) to give (((6-nitrohexyl)oxy)methyl)benzene.

(((6-nitrohexyl)oxy)methyl)benzene (1.8 g, 7.59 mmol) was added to a solution of 3,3,3-trifluoropropanal (11.49 mL, 7.59 mmol) in DCM (0.66 M), followed by DMAP (0.927 g, 7.59 mmol) at 25° C. The mixture was stirred 25° C. for 12 h. The reaction mixture was poured into water (20 mL), extracted with EtOAc (20 mL×3). The organic layer was washed with brine (20 mL), dried over $Na_2SO_4$ and filtered. The filtrate was concentrated and purified by flash silica gel chromatography (ISCO®; 24 g SepaFlash® Silica Flash Column, eluent of [0-30]% ethyl acetate/pet. ether gradient) to 9-(benzyloxy)-1,1,1-trifluoro-4-nitrononan-3-ol. To a solution of 9-(benzyloxy)-1,1,1-trifluoro-4-nitrononan-3-ol (300 mg, 0.859 mmol) in DCM (5 mL) was added 3,4-dihydro-2H-pyran (144 mg, 1.717 mmol) and PPTS (21.58 mg, 0.086 mmol) and the resulting mixture was stirred at 25° C. for 16 h. The mixture was diluted with $CH_2Cl_2$ (60 mL) and successively washed with saturated aqueous $NaHCO_3$, water and brine. The organic layer was dried over anhydrous $MgSO_4$ and evaporated under reduced pressure. The crude was purified by flash silica gel chromatography (ISCO®; 12 g SepaFlash® Silica Flash Column, eluent of [0-30]% ethyl acetate/pet. ether gradient) to give 2-((9-(benzyloxy)-1,1,1-trifluoro-4-nitrononan-3-yl)oxy)tetrahydro-2H-pyran.

To a solution of 2-((9-(benzyloxy)-1,1,1-trifluoro-4-nitrononan-3-yl)oxy)tetrahydro-2H-pyran (600 mg, 1.384 mmol) in MeOH (20 mL) was added Pd-C(737 mg, 0.692 mmol). The mixture was stirred under 50 psi H2 at 25° C. for 5 h. The mixture was filtered. The filtrate was concentrated to 6-amino-9,9,9-trifluoro-7-((tetrahydro-2H-pyran-2-yl)oxy)nonan-1-ol which was used without purification. LCMS m/z (M+H): 314.2 required, 314.2 found To a solution of 6-amino-9,9,9-trifluoro-7-((tetrahydro-2H-pyran-2-yl)oxy)nonan-1-ol (200 mg, 0.638 mmol) in DCM (5 mL) and sat. $NaHCO_3$(5 mL) was added triphosgene (90 mg, 0.303 mmol) at 0° C., and stirred at 0° C. for 1 h. (R)-1-(4-(8-chloro-[1,2,4]triazolo[1,5-a]pyrazin-6-yl)-5-methoxypyridin-2-yl)-N-ethylethan-1-amine C143 (191 mg, 0.574 mmol) was added and stirred at 0° C.-25° C. for 1 hour. The reaction mixture was poured into water (5 mL), extracted with EtOAc (5 mL×3). The organic phase layer was dried over $Na_2SO_4$ and filtered. The filtrate was concentrated and purified by flash silica gel chromatography (ISCO®; 20 g SepaFlash® Silica Flash Column, eluent of [0-80]% ethyl acetate/pet. ether gradient) to give 1-((R)-1-(4-(8-chloro-[1,2,4]triazolo[1,5-a]pyrazin-6-yl)-5-methoxypyridin-2-yl)ethyl)-1-ethyl-3-(1,1,1-trifluoro-9-hydroxy-3-((tetrahydro-2H-pyran-2-yl)oxy)nonan-4-yl)urea. LCMS (M+Na): 694.3 required, 694.2 found.

To a solution of NaH (24.99 mg, 0.625 mmol) in THF (2.8 mL) was added 1-((R)-1-(4-(8-chloro-[1,2,4]triazolo[1,5-a]pyrazin-6-yl)-5-methoxypyridin-2-yl)ethyl)-1-ethyl-3-(1,1,1-trifluoro-9-hydroxy-3-((tetrahydro-2H-pyran-2-yl)oxy)nonan-4-yl)urea (140 mg, 0.208 mmol). The mixture was stirred at 0° C. for 2 h. The mixture was poured into water (3 mL), extracted with EtOAc (3 mL×3). The organic layer was washed with brine (3 mL), dried over $Na_2SO_4$ and filtered. The filtrate was concentrated to give (3R,E)-4-ethyl-25-methoxy-3-methyl-7-(3,3,3-trifluoro-1-((tetrahydro-2H-pyran-2-yl)oxy)propyl)-13-oxa-4,6-diaza-1(6,8)-[1,2,4]triazolo[1,5-a]pyrazina-2(4,2)-pyridinacyclotridecaphan-5-one which was used without further purification. LCMS (M+H): 636.3 desired, 636.3 found.

To a solution of (3R,E)-4-ethyl-25-methoxy-3-methyl-7-(3,3,3-trifluoro-1-((tetrahydro-2H-pyran-2-yl)oxy)propyl)-13-oxa-4,6-diaza-1(6,8)-[1,2,4]triazolo[1,5-a]pyrazina-2(4,2)-pyridinacyclotridecaphan-5-one (100 mg, 0.157 mmol) in MeOH (5 mL) was added PPTS (119 mg, 0.472 mmol). The mixture was stirred at 45° C. for 24 h. The reaction mixture was poured into saturated $NaHCO_3$(10 mL), extracted with EtOAc (5 mL×3). The combined organic phases were dried over $Na_2SO_4$, filtered. The filtrate was concentrated and purified by TLC ($SiO_2$, EtOAc, 100%) to give (3R,E)-4-ethyl-25-methoxy-3-methyl-7-(3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one as a mixture of diastereomers. The diastereomers were separated by SFC (CHIRALPAK AD, 25% IPA with 0.1% $NH_3$ in $H_2O/CO_2$) and HPLC (ODS, 27-47% ACN with 0.1% TFA/water) to give (3R,7R,E)-4-ethyl-25-methoxy-3-methyl-7-((R)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one and (3R,7R,E)-4-ethyl-25-methoxy-3-methyl-7-((S)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one as the 2nd and 4th eluting diastereomers, (examples 132 and 133) absolute configuration of the diastereomers was not determined. LCMS (M+H): 552.3 desired, 552.2 found. 2nd eluting diastereomer (Example 133) $^1$H NMR (500 MHz, $CD_3OD$) δ 9.38 (s, 1H), 8.56 (s, 1H), 8.46 (s, 1H), 8.33 (s, 1H), 5.99 (q, J=7.1 Hz, 1H), 4.87-4.84 (m, 1H), 4.73 (dt, J=6.0, 10.9 Hz, 1H), 4.24-4.19 (m, 3H), 4.07 (br d, J=11.9 Hz, 1H), 3.99 (td, J=2.4, 9.0 Hz, 1H), 3.32-3.18 (m, 2H), 2.48-2.38 (m, 1H), 2.36-2.24 (m, 1H), 2.07-1.99 (m, 1H), 1.96-1.87 (m, 1H), 1.83-1.70 (m, 1H), 1.68-1.29 (m, 8H), 1.06 (t, J=7.1 Hz, 3H). It eluting diastereomer (Example 132) $^1$H NMR (500 MHz, $CD_3OD$) δ 9.39 (s, 1H), 8.57 (s, 1H), 8.45 (s, 1H), 8.32 (s, 1H), 6.00 (br d, J=6.6 Hz, 1H), 4.97-4.89 (m, 1H), 4.72 (m, 1H), 4.21 (s, 3H), 3.99 (br s, 1H), 3.91-3.83 (m, 1H), 3.29-3.08 (m, 2H), 2.55-2.45 (m, 1H), 2.35-2.35 (m, 1H), 2.06 (s, 1H), 1.90 (br dd, J=6.0, 11.9 Hz, 2H), 1.64-1.40 (m, 8H), 1.03 (t, J=7.0 Hz, 3H)

Example 134

(3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one (example 134)

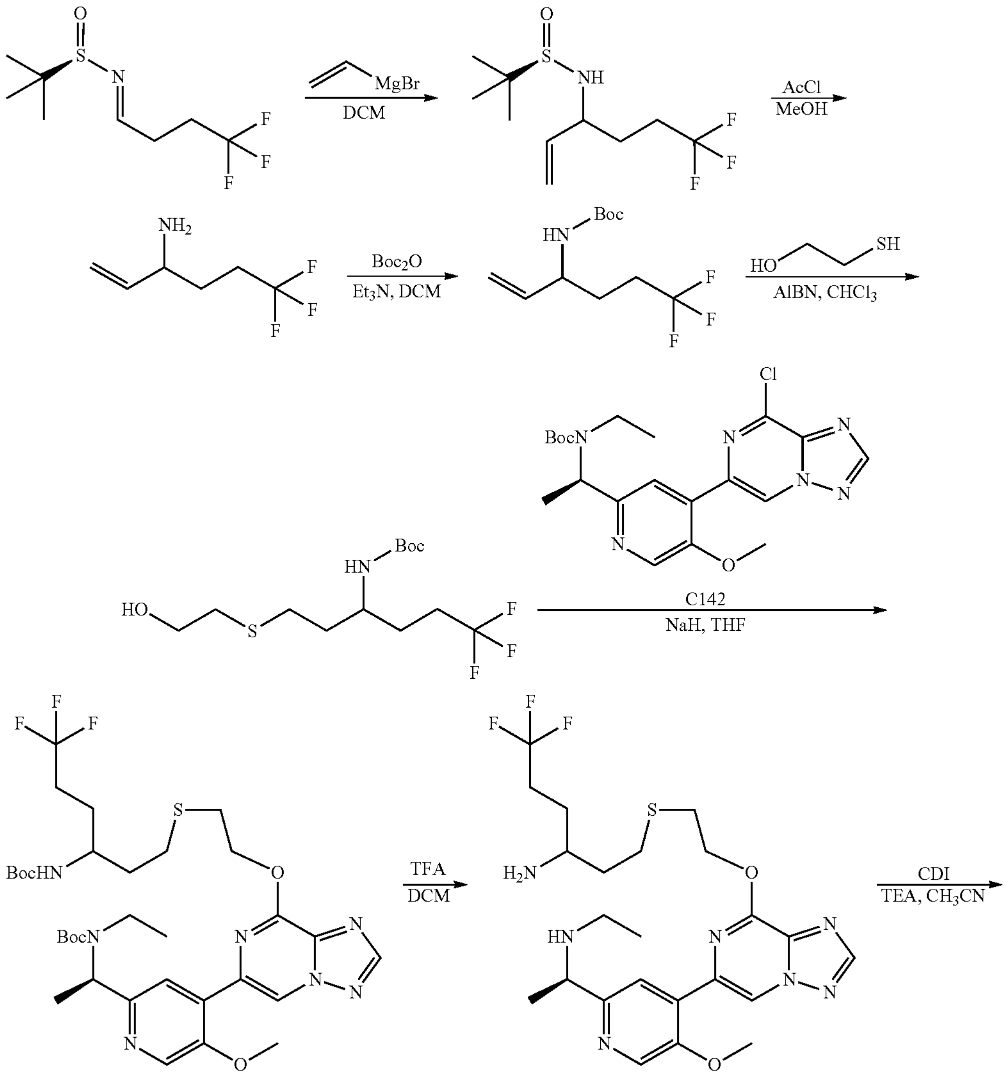

-continued

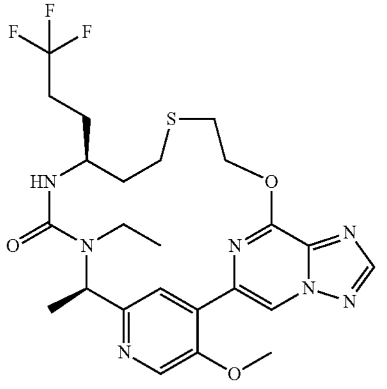

EXAMPLE 134

To a solution of (R,E)-2-methyl-N-(4,4,4-trifluorobutylidene)propane-2-sulfinamide (10 g, 43.6 mmol) in $CH_2Cl_2$ (100 mL) was added vinylmagnesium bromide (131 mL, 131 mmol) at 0° C. The mixture was stirred at 0° C. for 1 h. The reaction mixture was poured into water (120 mL), extracted with EtOAc (50 mL×3). The organic phase was dried over $Na_2SO_4$ and filtered. The filtrate was concentrated and purified by flash silica gel chromatography (ISCO®; 80 g SepaFlash® Silica Flash Column, eluent of [0-30]% ethyl acetate/pet. ether gradient) to give (R)-2-methyl-N-(6,6,6-trifluorohex-1-en-3-yl)propane-2-sulfinamide. LCMS m/z (M+H): 258.2 required, 258.2 found.

To a solution of (R)-2-methyl-N-(6,6,6-trifluorohex-1-en-3-yl)propane-2-sulfinamide (1.5 g, 5.83 mmol) in MeOH (15 mL) was added AcCl (1.243 mL, 17.49 mmol). The mixture was stirred at 25° C. for 1 h. The reaction mixture was concentrated to give 6,6,6-trifluorohex-1-en-3-amine which was used without purification.

To a solution of 6,6,6-trifluorohex-1-en-3-amine (890 mg, 5.81 mmol) in $CH_2Cl_2$ (10 mL) were added Di-tert-butyl pyrocarbonate (1902 mg, 8.72 mmol) and TEA (2.430 mL, 17.43 mmol). The mixture was stirred at 25° C. for 12 h. The reaction mixture was poured into water (15 mL), extracted with EtOAc (10 mL×3). The organic phase was dried over $Na_2SO_4$ and filtered. The filtrate was concentrated and purified by flash silica gel chromatography (ISCO®; 24 g SepaFlash® Silica Flash Column, eluent of [0-10]% ethyl acetate/pet. ether gradient) to give tert-butyl (6,6,6-trifluorohex-1-en-3-yl)carbamate. $^1H$ NMR (500 MHz, $CDCl_3$) δ 5.83-5.63 (m, 1H), 5.27-5.11 (m, 2H), 2.23-2.07 (m, 2H), 1.86-1.77 (m, 1H), 1.76-1.65 (m, 1H), 1.57 (s, 1H), 1.47-1.42 (m, 9H)

To a solution of tert-butyl (6,6,6-trifluorohex-1-en-3-yl)carbamate (700 mg, 2.76 mmol) in $CHCl_3$ (8 mL) was added 2-mercaptoethan-1-ol (410 mg, 5.25 mmol) and AIBN (45.4 mg, 0.276 mmol). The mixture was stirred at 60° C. for 12 hours. The reaction mixture was poured into water (10 mL), extracted with EtOAc (5 mL×3). The organic phase was dried over $Na_2SO_4$ and filtered. The filtrate was concentrated and purified by flash silica gel chromatography (ISCO®; 12 g SepaFlash® Silica Flash Column, eluent of [0-30]% ethyl acetate/pet. ether gradient) to give tert-butyl (6,6,6-trifluoro-1-((2-hydroxyethyl)thio)hexan-3-yl)carbamate. LCMS m/z (M+Na): 354.2 required, 354.1 found.

To a solution of tert-butyl (6,6,6-trifluoro-1-((2-hydroxyethyl)thio)hexan-3-yl)carbamate (200 mg, 0.604 mmol) in THF (5 mL) was added tert-butyl (R)-(1-(4-(8-chloro-[1,2,4]triazolo[1,5-a]pyrazin-6-yl)-5-methoxypyridin-2-yl)ethyl)(ethyl)carbamate C142 (261 mg, 0.604 mmol) and NaH (72.4 mg, 1.811 mmol) at 0° C. The mixture was stirred at 25° C. for 1 hour. The reaction mixture was poured into water (10 mL), extracted with EtOAc (5 mL×3). The organic phase was dried over $Na_2SO_4$ and filtered. The filtrate was concentrated and purified by flash silica gel chromatography (ISCO®; 12 g SepaFlash® Silica Flash Column, eluent of [0-100]% ethyl acetate/pet. ether gradient) to give tert-butyl ((1R)-1-(4-(8-(2-((3-((tert-butoxycarbonyl)amino)-6,6,6-trifluorohexyl)thio)ethoxy)-[1,2,4]triazolo[1,5-a]pyrazin-6-yl)-5-methoxypyridin-2-yl)ethyl)(ethyl)carbamate. LCMS m/z (M+H): 728.2 required, 728.3 found.

To a solution of tert-butyl ((1R)-1-(4-(8-(2-((3-((tert-butoxycarbonyl)amino)-6,6,6-trifluorohexyl)thio)ethoxy)-[1,2,4]triazolo[1,5-a]pyrazin-6-yl)-5-methoxypyridin-2-yl)ethyl)(ethyl)carbamate (20 mg, 0.027 mmol) in DCM (2 mL) was added TFA (0.2 mL, 2.60 mmol). The mixture was stirred at 25° C. for 2 h. The reaction mixture was poured into aq. $NaHCO_3$(5 mL), extracted with EtOAc (3 mL×3). The organic phase was dried over $Na_2SO_4$ and filtered. The filtrate was concentrated to give 1-((2-((6-(2-((R)-1-(ethylamino)ethyl)-5-methoxypyridin-4-yl)-[1,2,4]triazolo[1,5-a]pyrazin-8-yl)oxy)ethyl)thio)-6,6,6-trifluorohexan-3-amine. LCMS m/z (M+H): 528.2 required, 528.3 found.

To a solution of 1-((2-((6-(2-((R)-1-(ethylamino)ethyl)-5-methoxypyridin-4-yl)-[1,2,4]triazolo[1,5-a]pyrazin-8-yl)oxy)ethyl)thio)-6,6,6-trifluorohexan-3-amine (15 mg, 0.028 mmol) in MeCN (2 mL) was added TEA (0.012 mL, 0.085 mmol) and CDI (9.22 mg, 0.057 mmol) at 0° C. The mixture was stirred at 25° C. for 12 h. The reaction mixture was poured into water (5 mL), extracted with EtOAc (3 mL×3). The organic phase was dried over $Na_2SO_4$ and filtered. The filtrate was concentrated and purified by prep-HPLC (ODS, 35-55% ACN/water with 0.1% TFA) to give (3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one as the second eluting diastereomer (example 134). LCMS m/z (M+H): 554.2 required, 554.2 found. $^1H$ NMR (500 MHz, $CD_3OD$) δ 9.36 (s, 1H), 8.58 (s, 1H), 8.46 (s, 1H), 8.22 (s, 1H), 5.91 (q, J=7.0 Hz, 1H), 5.34-5.31 (m, 2H), 4.19 (s, 3H), 4.17-4.09 (m, 1H), 3.23-3.14 (m, 2H), 3.11-2.93 (m, 2H), 2.78-2.56 (m, 2H), 2.35-2.15 (m, 2H), 1.89-1.76 (m, 4H), 1.65 (d, J=7.2 Hz, 3H), 1.11 (t, J=7.0 Hz, 3H)

Example 135

(3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one 10,10-dioxide

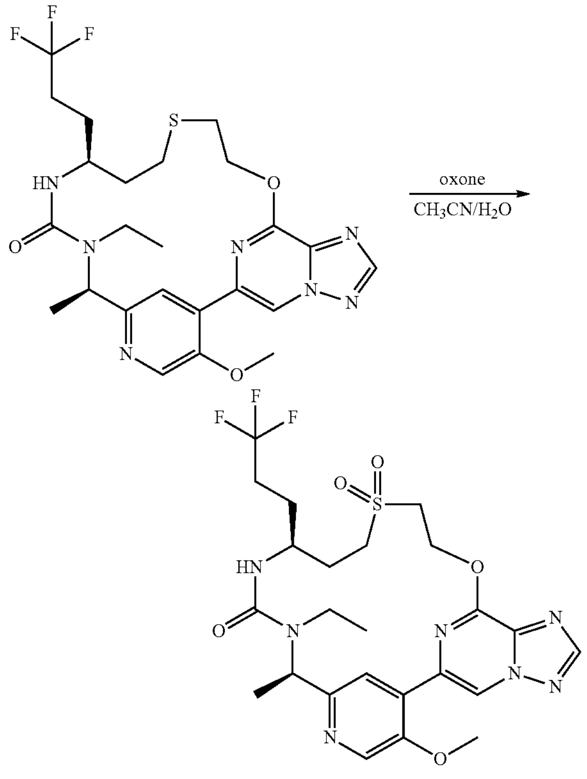

EXAMPLE 135

To a solution of (3R,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one mixture of diastereomers (30 mg, 0.054 mmol) in MeCN (1 mL) was added Potassium peroxymonosulfate (77 mg, 0.125 mmol) in Water (1 mL). The mixture was stirred at 25° C. for 12 hours. The reaction mixture was poured into water (2 mL), extracted with EtOAc (2 mL×3). The organic layer was dried over $Na_2SO_4$ and filtered. The filtrate was concentrated and purified by prep-HPLC (ODS, 28-48% ACN/water with 0.1% TFA) to give (3R,7S,E)-4-ethyl-25-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one 10,10-dioxide as the second eluting diastereomer (example 135). $^1H$ NMR (500 MHz, $CD_3OD$) δ 9.36 (s, 1H), 8.60 (s, 1H), 8.47 (s, 1H), 8.18 (s, 1H), 6.02-5.86 (m, 1H), 5.21 (br s, 2H), 4.19 (s, 3H), 4.12 (br d, J=11.9 Hz, 1H), 3.86-3.74 (m, 2H), 3.30-3.15 (m, 4H), 2.33-2.22 (m, 2H), 2.21-2.11 (m, 1H), 1.97-1.84 (m, 3H), 1.64 (d, J=7.2 Hz, 3H), 1.10 (t, J=7.0 Hz, 3H)

Example 136

(3R,7S,E)-4-ethyl-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one

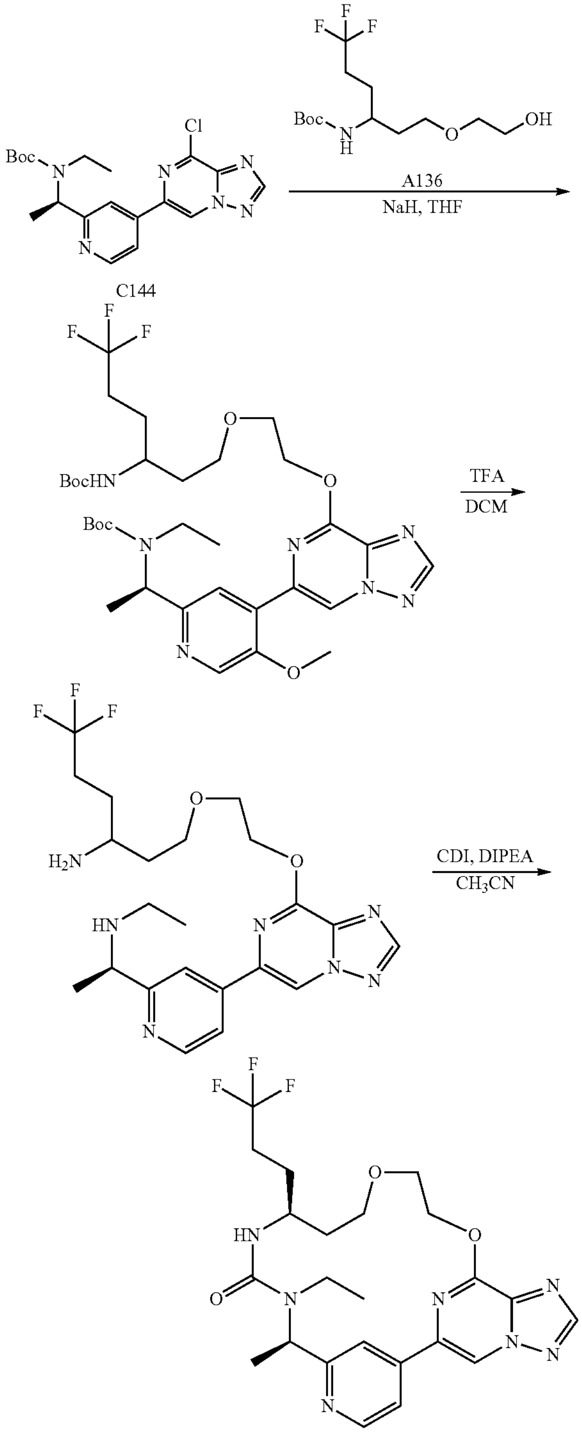

EXAMPLE 136

To a solution of tert-butyl (6,6,6-trifluoro-1-(2-hydroxyethoxy)hexan-3-yl)carbamate A136 (800 mg, 2.54 mmol) in THF (8 mL) was added NaH (203 mg, 5.07 mmol)(60% wt)

at 0° C. under N2 for 30 mins, then compound tert-butyl (R)-(1-(4-(8-chloro-[1,2,4]triazolo[1,5-a]pyrazin-6-yl)pyridin-2-yl)ethyl)(ethyl)carbamate C144 (1124 mg, 2.79 mmol) in THF (4 mL) was added to the above solution, and stirred at 0° C. under $N_2$ protection for 30 mins. The reaction mixture was poured into water (30 mL), extracted with EtOAc (20 mL×3). The organic layer was washed with brine (20 mL), dried over $Na_2SO_4$, filtered and concentrated. The crude product was purified by Flash silica gel chromatography (ISCO®; 12 g SepaFlash® Silica Flash Column, Eluent of 85% EtOAc/Pet.ether gradient) to give tert-butyl ((1R)-1-(4-(8-(2-((3-((tert-butoxycarbonyl)amino)-6,6,6-trifluorohexyl)oxy)ethoxy)-[1,2,4]triazolo[1,5-a]pyrazin-6-yl)pyridin-2-yl)ethyl)(ethyl)carbamate. LCMS m/z (M+H): 698.3 required, 698.2 found.

To a solution of tert-butyl ((1R)-1-(4-(8-(2-((3-((tert-butoxycarbonyl)amino)-6,6,6-trifluorohexyl)oxy)ethoxy)-[1,2,4]triazolo[1,5-a]pyrazin-6-yl)pyridin-2-yl)ethyl)(ethyl)carbamate (800 mg, 1.173 mmol) was added TFA (1.250 mL). The mixture was stirred at 20° C. for 1 h. LCMS showed the desired mass. The mixture was concentrated under reduced pressure and freeze-dried to give 1-(2-((6-(2-((R)-1-(ethylamino)ethyl)pyridin-4-yl)-[1,2,4]triazolo[1,5-a]pyrazin-8-yl)oxy)ethoxy)-6,6,6-trifluorohexan-3-amine, which was used to the next step without further purification. LCMS m/z (M+H): 482.2 required, 482.2 found.

To a solution of 1-(2-((6-(2-((R)-1-(ethylamino)ethyl)pyridin-4-yl)-[1,2,4]triazolo[1,5-a]pyrazin-8-yl)oxy)ethoxy)-6,6,6-trifluorohexan-3-amine (550 mg, 1.142 mmol) in MeCN (120 mL) were added DIPEA (1.995 mL, 11.42 mmol) and CDI (278 mg, 1.713 mmol). The reaction was stirred at 20° C. for 12 h. The mixture was concentrated and quenched with $H_2O$(30 mL) and extracted with EtOAc (50 mL×3), washed with brine (30 mL), dried over $Na_2SO_4$, filtered and concentrated under reduced pressure. The crude was purified by Flash silica gel chromatography (ISCO®; 12 g SepaFlash® Silica Flash Column, Eluent of 100% EtOAc/Pet. ether gradient) and separated by SFC (Chiralpak IG-3, 5-40% EtOH with 0.05% diethylamine/$CO_2$) to give (3R,7S,E)-4-ethyl-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one as the second eluting diastereomer (example 136). LCMS m/z (M+H): 508.2 required, 508.2 found. 1H NMR (400 MHz, $CDCl_3$) δ 8.76 (s, 1H), 8.68 (br d, J=5.1 Hz, 1H), 8.49-8.43 (m, 1H), 8.19 (s, 1H), 7.54 (d, J=5.8 Hz, 1H), 6.13-6.04 (m, 1H), 5.08 (dt, J=6.2, 9.8 Hz, 1H), 4.85 (dt, J=5.0, 10.1 Hz, 1H), 4.41 (br d, J=8.3 Hz, 1H), 4.28 (br d, J=3.7 Hz, 1H), 3.95-3.80 (m, 2H), 3.77-3.63 (m, 2H), 3.33-3.18 (m, 1H), 3.15-3.03 (m, 1H), 2.35-2.10 (m, 2H), 2.09-1.93 (m, 1H), 1.92-1.79 (m, 1H), 1.76-1.65 (m, 5H), 1.19 (br t, J=7.1 Hz, 3H)

Example 137

(3R,7R,E)-4-ethyl-10-hydroxy-22,3-dimethyl-7-(3,3,3-trifluoropropyl)-13-oxa-4,6-diaza-1(6,8)-imidazo[1,2-a]pyrazina-2(3,5)-pyridinacyclotridecaphan-5-one (Example 137)

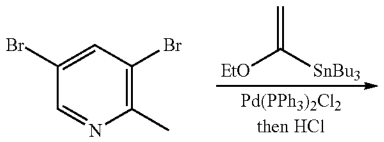

-continued

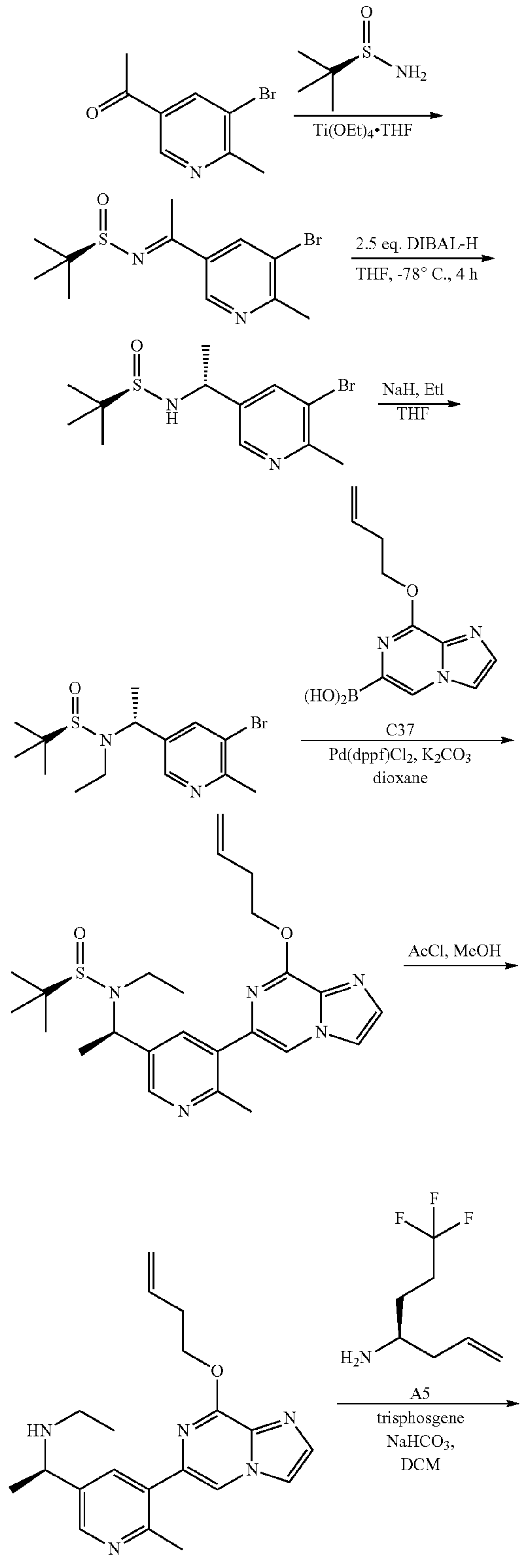

-continued

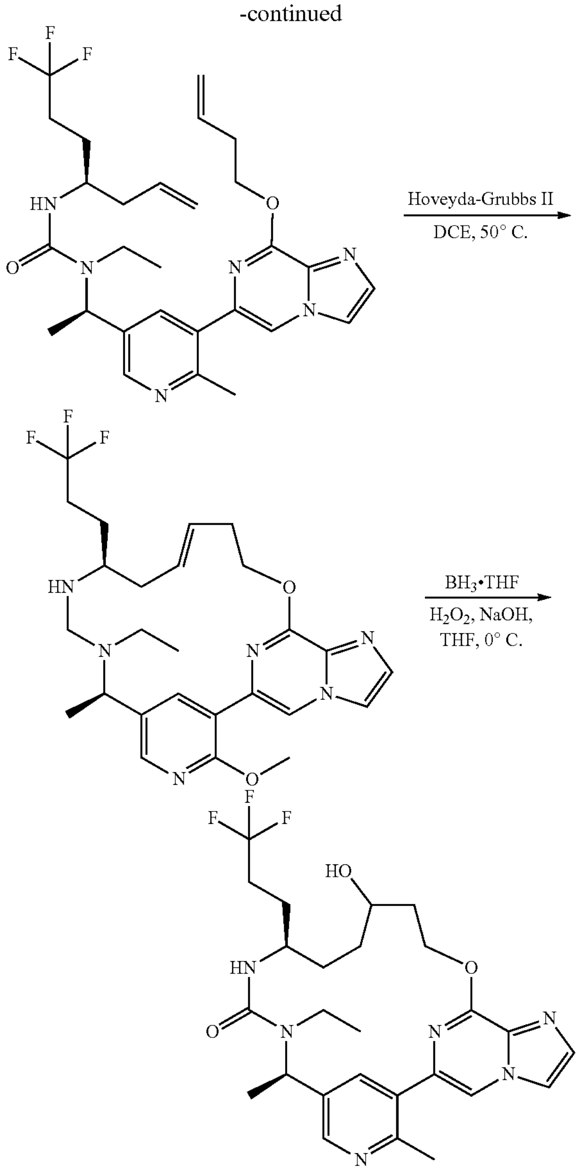

EXAMPLE 137

To a solution of 3,5-dibromo-2-methylpyridine (20 g, 80 mmol) in Dioxane (200 mL) were added tributyl(1-ethoxyvinyl)stannane (25.9 g, 71.7 mmol) and bis(triphenylphosphine)-palladium (ii) dichloride (2.80 g, 3.99 mmol), then the solution was stirred at 100° C. for 10 hours. LCMS showed the reaction was completed. The reaction mixture was cooled to 20° C. and 4M HCl (100 mL) was added to the above mixture and stirred for 1 hour. The reaction mixture was poured into 10% KF aqueous solution (300 mL), extracted with EtOAc (200 mLx3). The organic layer was washed with brine (200 mL), dried over $Na_2SO_4$ and filtered. After filtration, the mixture was concentrated to give crude product, which was purified by flash silica gel chromatography (ISCO®; 120 g SepaFlash® Silica Flash Column, eluent of 54% ethyl acetate/pet. ether gradient @ 30 mL/min) to give 1-(5-bromo-6-methylpyridin-3-yl)ethan-1-one. LCMS m/z (M+H): 216.1 required, 216.1 found. $^1$H NMR (400 MHz, $CDCl_3$) δ 8.92 (d, J=1.7 Hz, 1H), 8.31 (d, J=2.0 Hz, 1H), 2.87-2.64 (m, 3H), 2.60-2.53 (m, 3H)

To a solution of 1-(5-bromo-6-methylpyridin-3-yl)ethan-1-one (6.5 g, 30.4 mmol) in THF (100 mL) were added (R)-(+)-2-methyl-2-propanesulfinamide (4.42 g, 36.4 mmol) and titanium (iv) ethoxide (34.6 g, 152 mmol). The mixture was stirred at 80° C. for 12 h under N2. The mixture was poured into brine (300 mL). The filtrate was extracted with EtOAc (200 mLx3). The combined organic layers were dried over $Na_2SO_4$, filtered and concentrated. The residue was purified by flash silica gel chromatography (ISCO®; 80 g Biotage® Silica Flash Column, Eluent of 80% EtOAc/Pet. ether gradient) to give (R,E)-N-(1-(5-bromo-6-methylpyridin-3-yl)ethylidene)-2-methylpropane-2-sulfinamide. LCMS m/z (M+H): 319.0 found, 319.0 required. $^1$H NMR (400 MHz, $CDCl_3$) δ 8.85 (d, J=1.7 Hz, 1H), 8.23 (d, J=1.7 Hz, 1H), 2.72 (d, J=17.1 Hz, 6H), 1.43-1.22 (m, 9H).

To a solution of (R,E)-N-(1-(5-bromo-6-methylpyridin-3-yl)ethylidene)-2-methylpropane-2-sulfinamide (3 g, 9.46 mmol) in THF (100 mL) was added DIBAL-H (23.64 mL, 23.64 mmol) slowly (1 M in toluene) at −78° C. The resulting mixture was stirred at −78° C. for 4 hours. The reaction mixture was poured into saturated $NH_4Cl$ (300 mL) and filtered, extracted with EtOAc (100 mLx3). The combined organic phases were washed with brine (100 mL), and dried over $Na_2SO_4$. After filtration and concentration, the residue was purified by flash silica gel chromatography (ISCO®; 80 g SepaFlash® Silica Flash Column, eluent of 100% ethyl acetate/pet. ether gradient @ 30 mL/min) to give (R)—N—((R)-1-(5-bromo-6-methylpyridin-3-yl)ethyl)-2-methylpropane-2-sulfinamide. LCMS m/z (M+H): 321.0 required, 321.0 found. 1H NMR (400 MHz, $CDCl_3$) δ 8.38 (d, J=2.0 Hz, 1H), 7.78 (d, J=2.0 Hz, 1H), 4.52 (dq, J=3.5, 6.5 Hz, 1H), 3.47-3.30 (m, 1H), 2.63 (s, 3H), 1.51 (d, J=6.6 Hz, 3H), 1.30-1.17 (m, 9H)

To a solution of (R)—N—((R)-1-(5-bromo-6-methylpyridin-3-yl)ethyl)-2-methylpropane-2-sulfinamide (1.5 g, 4.70 mmol) in DMF (15 mL) was added NaH (0.282 g, 7.05 mmol) (60% wt) at 0° C. and stirred at 0° C. for 0.5 h under N2 protection, and then iodoethane (0.806 g, 5.17 mmol) was added dropwise at 0° C. and stirred at 20° C. for 13 h. The resulting mixture was poured into water (100 mL) and extracted with EtOAc (50 mLx3). The organic layers were combined and washed with brine (100 mL), dried over $Na_2SO_4$ and filtered. The filtrate was concentrated in vacuo. The residue was purified by flash silica gel chromatography (ISCO®; 40 g SepaFlash® Silica Flash Column, Eluent of 50% EtOAc/Pet. ether gradient) to give (R)—N—((R)-1-(5-bromo-6-methylpyridin-3-yl)ethyl)-N-ethyl-2-methylpropane-2-sulfinamide. LCMS m/z: 349.1 required. 349.1 found. $^1$H NMR (400 MHz, $CDCl_3$) δ 8.41 (d, J=1.7 Hz, 1H), 7.77 (d, J=1.7 Hz, 1H), 4.53 (br d, J=6.4 Hz, 1H), 3.23 (qd, J=7.3, 14.7 Hz, 1H), 2.93-2.74 (m, 1H), 2.63 (s, 3H), 1.68-1.56 (m, 3H), 1.33-1.13 (m, 3H), 1.09-1.01 (m, 9H)

To a solution of (8-(but-3-en-1-yloxy)imidazo[1,2-a]pyrazin-6-yl)boronic acid C37 (174 mg, 0.747 mmol) (in 5 mL dioxane) in Dioxane (2 mL) and water (2 mL) were added $Na_2CO_3$ (237 mg, 2.240 mmol), (R)—N—((R)-1-(5-bromo-6-methylpyridin-3-yl)ethyl)-N-ethyl-2-methylpropane-2-sulfinamide (259 mg, 0.747 mmol) and Pd (dppf)$Cl_2$ (54.6 mg, 0.075 mmol). The mixture was stirred at 80° C. for 3 hours. The mixture was poured into water (50 mL), extracted with EtOAc (30 mLx3). The combined organic phases were washed with brine (10 mL), and dried over $Na_2SO_4$. After filtration and concentration, the residue was purified by flash silica gel chromatography (ISCO®; 12 g SepaFlash® Silica Flash Column, eluent of 50% EtOAc/MeOH gradient @ 30 mL/min) to give (R)—N—((R)-1-(5-(8-(but-3-en-1-yloxy)imidazo[1,2-a]pyrazin-6-yl)-6-methylpyridin-3-yl)ethyl)-N-ethyl-2-methylpropane-2-sulfinamide. LCMS m/z (M+H): 456.3 required, 456.3 found.

To a solution of (R)—N—((R)-1-(5-(8-(but-3-en-1-yloxy)imidazo[1,2-a]pyrazin-6-yl)-6-methylpyridin-3-yl)ethyl)-N-ethyl-2-methylpropane-2-sulfinamide (200 mg, 0.439 mmol) in MeOH (5 mL) was added acetyl chloride (0.125 mL, 1.756 mmol) and stirred at 20° C. for 1 h. LCMS showed the desired product was found. The reaction mixture was concentrated to give (R)-1-(5-(8-(but-3-en-1-yloxy)imidazo[1,2-a]pyrazin-6-yl)-6-methylpyridin-3-yl)-N-ethylethan-1-amine, which was used in next step without purification. LCMS m/z (M+H): 352.2 required, 352.2 found.

To a solution of (S)-7,7,7-trifluorohept-1-en-4-amine hydrochloride A5 (89 mg, 0.438 mmol) in DCM (3 mL) and saturated $NaHCO_3$(3 mL) was added triphosgene (42.9 mg, 0.145 mmol) at 0° C. The resulting mixture was stirred at 0° C. for 0.5 hour. Then (R)-1-(5-(8-(but-3-en-1-yloxy)imidazo[1,2-a]pyrazin-6-yl)-6-methylpyridin-3-yl)-N-ethylethan-1-amine (170 mg, 0.438 mmol) was added and the mixture was stirred at 20° C. for 1 hour. LCMS showed the desired product was formed. The reaction mixture was poured into water (10 mL), extracted with DCM (10 mL×3). The combined organic phases were washed with brine (10 mL), and dried over $Na_2SO_4$. After filtration and concentration, the residue was purified by flash silica gel chromatography (ISCO®; 4 g SepaFlash® Silica Flash Column, Eluent of 50% EtOAc/MeOH gradient) to give 1-((R)-1-(5-(8-(but-3-en-1-yloxy)imidazo[1,2-a]pyrazin-6-yl)-6-methylpyridin-3-yl)ethyl)-1-ethyl-3-((S)-7,7,7-trifluorohept-1-en-4-yl)urea. LCMS m/z (M+H): 545.3 required, 545.3 found.

To a solution of 1-((R)-1-(5-(8-(but-3-en-1-yloxy)imidazo[1,2-a]pyrazin-6-yl)-6-methylpyridin-3-yl)ethyl)-1-ethyl-3-((S)-7,7,7-trifluorohept-1-en-4-yl)urea (150 mg, 0.275 mmol) in DCE (10 mL) was added (1,3-dimesitylimidazolidin-2-ylidene) (2-isopropoxybenzylidene)ruthenium (vi) chloride (34.5 mg, 0.055 mmol). The mixture was stirred at 50° C. for 18 h. The reaction mixture was concentrated to give the crude. The crude was purified by flash silica gel chromatography (ISCO®; 12 g SepaFlash® Silica Flash Column, Eluent of 50% EtOAc/MeOH gradient) to give ($1^{7}$E,3R,7S,9E)-4-ethyl-22,3-dimethyl-7-(3,3,3-trifluoropropyl)-13-oxa-4,6-diaza-1(6,8)-imidazo[1,2-a]pyrazina-2(3,5)-pyridinacyclotridecaphan-9-en-5-one. LCMS m/z (M+H): 517.2 required, 517.2 found.

To a solution of ($1^{7}$E,3R,7S,9E)-4-ethyl-22,3-dimethyl-7-(3,3,3-trifluoropropyl)-13-oxa-4,6-diaza-1(6,8)-imidazo[1,2-a]pyrazina-2(3,5)-pyridinacyclotridecaphan-9-en-5-one (40 mg, 0.077 mmol) in THF (1 mL) was added $BH_3$THF (0.116 mL, 0.116 mmol) at 0° C. dropwise. The mixture was stirred at 20° C. for 1 h. Then, sodium hydroxide (0.024 mL, 0.048 mmol) in Water (1 mL) and $H_2O_2$ (0.012 mL, 0.116 mmol) were added to the above solution at 0° C. The mixture was stirred at 20° C. for 2 h. LCMS showed the desired product. The mixture was filtered and concentrated under reduced pressure. The filtrate was purified by prep-HPLC (24-44% ACN/water (0.1% TFA) and SFC (ChiralPak IC-3, 40% MeOH with 0.05% DEA/$CO_2$) to give (3R,7R,E)-4-ethyl-10-hydroxy-22,3-dimethyl-7-(3,3,3-trifluoropropyl)-13-oxa-4,6-diaza-1(6,8)-imidazo[1,2-a]pyrazina-2(3,5)-pyridinacyclotridecaphan-5-one as the third eluting isomer with undefined stereochemistry at the 10-hydroxy position (example 137). LCMS m/z (M+H): 535.3 found, 535.3 required. $^{1}$H NMR 1013439-094-003 (400 MHz, $CD_3OD$) δ 8.50-8.45 (m, 2H), 8.22 (d, J=2.0 Hz, 1H), 8.02 (s, 1H), 7.67-7.63 (m, 2H), 5.99 (br d, J=9.0 Hz, 2H), 4.95-4.93 (m, 1H), 4.68-4.61 (m, 1H), 4.06 (br s, 1H), 3.92 (br s, 1H), 3.24-3.05 (m, 2H), 2.80 (s, 3H), 2.31-2.11 (m, 4H), 1.85-1.69 (m, 3H), 1.69-1.53 (m, 7H), 1.34-1.28 (m, 2H), 1.07-0.98 (m, 3H)

Example 138

(3R,7R,Z)-4-ethyl-23-methoxy-3-methyl-7-(3,3,3-trifluoropropyl)-4,6-diaza-1(6,8)-imidazo[1,2-a]pyridina-2(2,6)-pyridinacyclododecaphan-5-one (Example 138)

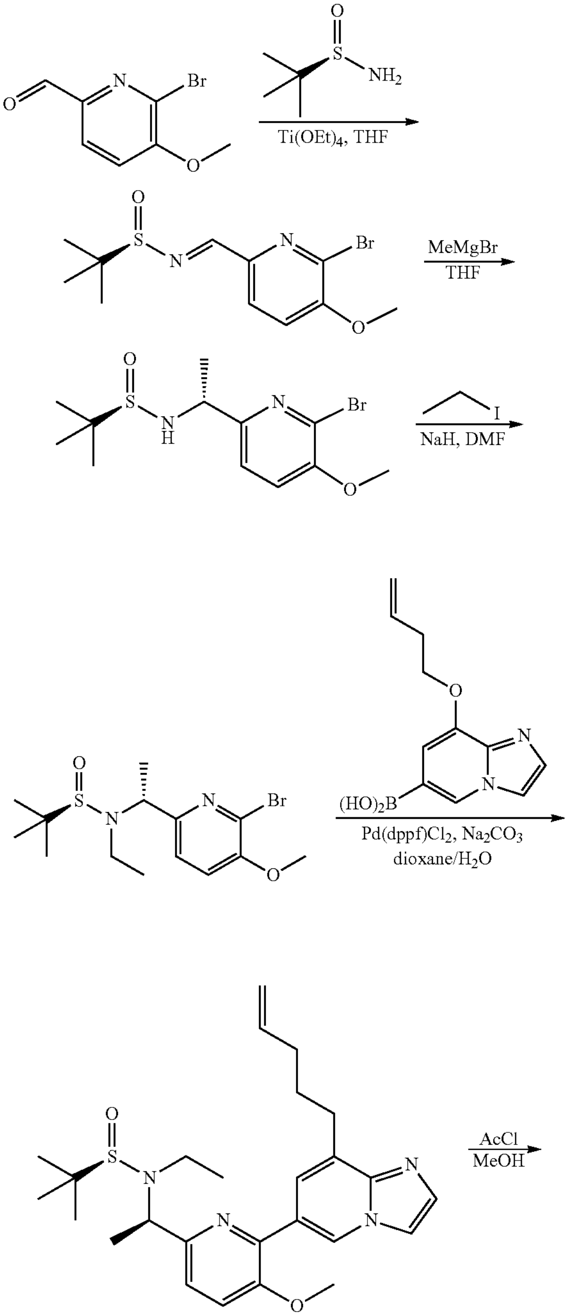

-continued

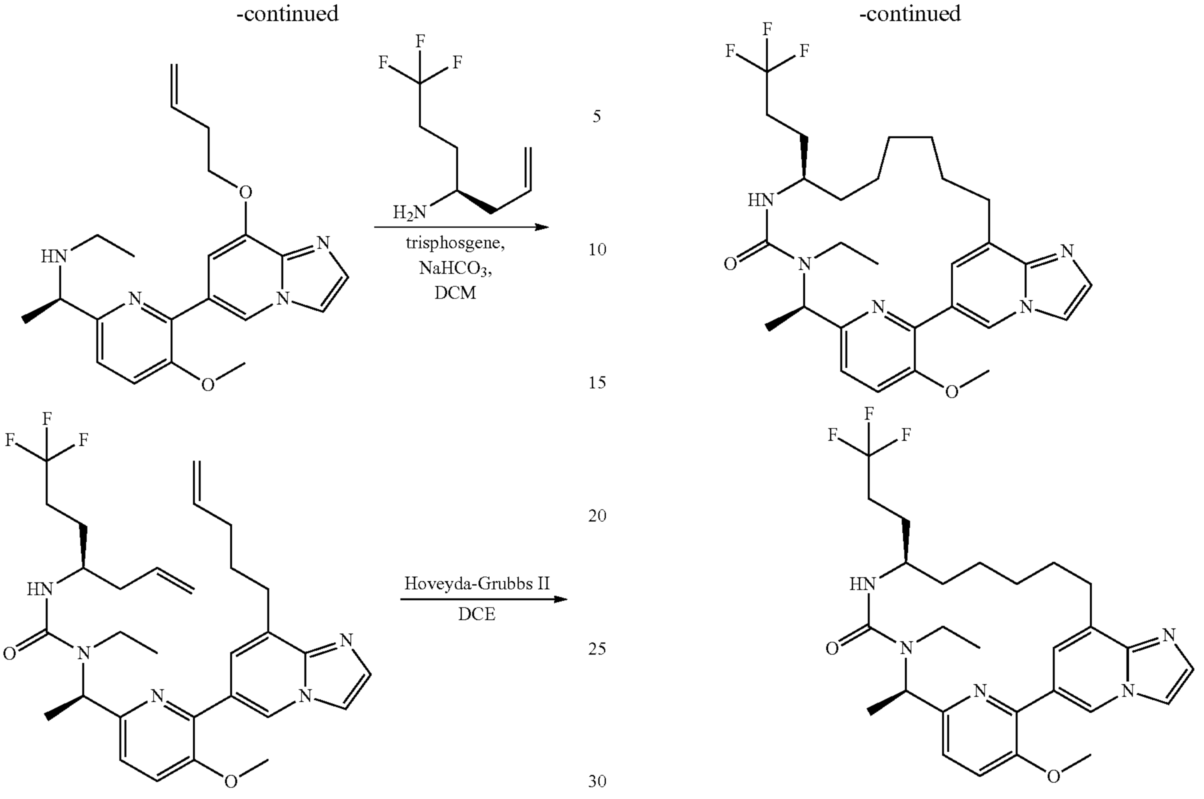

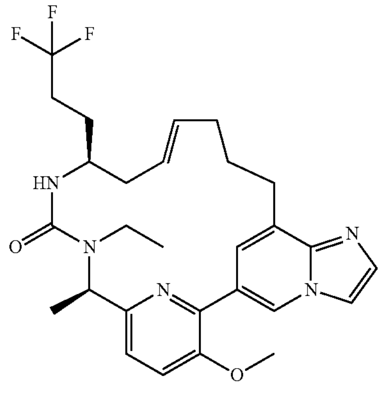

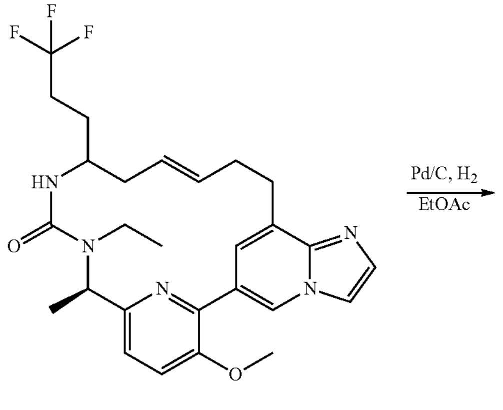

EXAMPLE 138

To a mixture of 6-bromo-5-methoxypicolinaldehyde (4 g, 18.52 mmol) and (R)-2-methylpropane-2-sulfinamide (2.69 g, 22.22 mmol) in THF (50 mL) was added tetraethoxytitanium (21.12 g, 93 mmol), the reaction mixture was stirred at 80° C. for 2 hours. The mixture was poured into brine (50 mL) and filtered. The filtrate was extracted with EtOAc (30 mL×3). The combined organic layers were dried over $Na_2SO_4$, filtered and the filtrate was concentrated. The crude product was purified by Flash silica gel chromatography (ISCO®; 80 g SepaFlash® Silica Flash Column, Eluent of 20% EtOAc/Pet.ether gradient) to give (R,E)-N-((6-bromo-5-methoxypyridin-2-yl)methylene)-2-methylpropane-2-sulfinamide. $^1H$ NMR (400 MHz, $CDCl_3$) δ 8.61 (s, 1H), 8.00 (d, J=8.31 Hz, 1H), 7.23 (d, J=8.56 Hz, 1H), 4.00 (s, 3H), 1.26 (s, 9H)

To a solution of (R,E)-N-((6-bromo-5-methoxypyridin-2-yl)methylene)-2-methylpropane-2-sulfinamide (4.5 g, 14.10 mmol) in THF (50 mL) was added methylmagnesium bromide (28.2 mL, 85 mmol) (3 M in $Et_2O$), the mixture was stirred at 0° C. under N2 protection for 1 hour. The reaction mixture was poured into $NH_4Cl$ (60 mL), extracted with EtOAc (30 mL×3), dried over $Na_2SO_4$ and filtered. The filtrate was concentrated and purified by Flash silica gel chromatography (ISCO®; 80 g SepaFlash® Silica Flash Column, Eluent of 60% EtOAc/Pet.ether gradient) to give (R)—N—((R)-1-(6-bromo-5-methoxypyridin-2-yl)ethyl)-2-methylpropane-2-sulfinamide. $^1H$ NMR (400 MHz, $CDCl_3$) δ 7.26-7.18 (m, 1H), 7.08 (d, J=8.07 Hz, 1H), 4.59-4.45 (m, 1H), 3.90-3.86 (m, 3H), 1.58-1.46 (m, 3H), 1.22-1.16 (m, 9H)

To a solution of (R)—N—((R)-1-(6-bromo-5-methoxypyridin-2-yl)ethyl)-2-methylpropane-2-sulfinamide (4 g, 11.93 mmol) in DMF (45 mL) was added sodium hydride (0.954 g, 23.86 mmol) (60%) at 0° C. under N2. The mixture was stirred at 0° C. for 30 min. iodoethane (1.909 mL, 23.86 mmol) was added and stirred at 25° C. for 1 hours. The reaction mixture was poured into water (40 mL), extracted with EtOAc (20 mL×3). The combined organic layers were washed with brine (40 mL), dried over $Na_2SO_4$ and filtered. The filtrate was concentrated and purified by Flash silica gel chromatography (ISCO®; 20 g SepaFlash® Silica Flash Column, Eluent of 30-70% EtOAc/Pet.ether gradient) to give (R)—N—((R)-1-(6-bromo-5-methoxypyridin-2-yl) ethyl)-N-ethyl-2-methylpropane-2-sulfinamide. $^1$H NMR (400 MHz, $CDCl_3$) δ 7.32 (d, J=8.31 Hz, 1H), 7.12 (d, J=8.44 Hz, 1H), 4.67 (q, J=7.01 Hz, 1H), 3.92 (s, 3H), 3.26 (qd, J=7.39, 14.52 Hz, 1H), 3.04-2.90 (m, 1H), 1.65 (d, J=7.09 Hz, 3H), 1.18-1.14 (m, 12H)

To a solution of C145 (63.3 mg, 0.275 mmol) in Dioxane (2 mL) and Water (1 mL) were added (R)—N—((R)-1-(6-bromo-5-methoxypyridin-2-yl)ethyl)-N-ethyl-2-methylpropane-2-sulfinamide (100 mg, 0.275 mmol), $Na_2CO_3$ (88 mg, 0.826 mmol) and Pd(dppf)$Cl_2$ (20.14 mg, 0.028 mmol). The mixture was stirred at 90° C. for 3 hours. The mixture was extracted with EtOAc (10 mL×3), washed with brine (10 mL), dried over $Na_2SO_4$ and filtered. The crude product was purified by prep-TLC (Pet.ether:EtOAc=1:1) to give (R)—N-ethyl-N—((R)-1-(5-methoxy-6-(8-(pent-4-en-1-yl)imidazo[1,2-a]pyridin-6-yl)pyridin-2-yl)ethyl)-2-methylpropane-2-sulfinamide. LCMS m/z (M+H): 469.3 required, 469.3 found.

To a solution of (R)—N-ethyl-N—((R)-1-(5-methoxy-6-(8-(pent-4-en-1-yl)imidazo[1,2-a]pyridin-6-yl)pyridin-2-yl) ethyl)-2-methylpropane-2-sulfinamide (75 mg, 0.160 mmol) in MeOH (2 mL) was added acetyl chloride (62.8 mg, 0.800 mmol), the mixture was stirred at 0° C. for 30 mins. The mixture was concentrated to give (R)—N-ethyl-1-(5-methoxy-6-(8-(pent-4-en-1-yl)imidazo[1,2-a]pyridin-6-yl) pyridin-2-yl)ethan-1-amine, which was used without purification. LCMS m/z (M+H): 365.2 required, 365.2 found.

To a solution of (R)—N-ethyl-1-(5-methoxy-6-(8-(pent-4-en-1-yl)imidazo[1,2-a]pyridin-6-yl)pyridin-2-yl)ethan-1-amine (60 mg, 0.165 mmol) in DCM (1 mL) and sat.$NaHCO_3$(1 mL) was added (S)-7, 7, 7-trifluoro-4-isocyanatohept-1-ene A126 (31.8 mg, 0.165 mmol). The mixture was stirred at 20° C. for 1 hours. The reaction mixture was poured into water (10 mL), extracted with DCM (10 mL×3). The organic layer was washed with brine (10 mL), dried over $Na_2SO_4$ and filtered. The filtrate was concentrated and purified by prep-TLC (Pet.ether:EtOAc=1:1) to give 1-ethyl-1-((R)-1-(5-methoxy-6-(8-(pent-4-en-1-yl)imidazo[1,2-a]pyridin-6-yl)pyridin-2-yl)ethyl)-3-((S)-7,7,7-trifluorohept-1-en-4-yl)urea. LCMS m/z (M+H): 558.4 required, 558.3 found.

To a solution of 1-ethyl-1-((R)-1-(5-methoxy-6-(8-(pent-4-en-1-yl)imidazo[1,2-a]pyridin-6-yl)pyridin-2-yl)ethyl)-3-((S)-7,7,7-trifluorohept-1-en-4-yl)urea (95 mg, 0.170 mmol) in DCE (50 mL) was added (1, 3-dimesitylimidazolidin-2-ylidene) (2-isopropoxybenzylidene) ruthenium (VI) chloride (21.35 mg, 0.034 mmol). The mixture was stirred at 50° C. for 16 hours. The mixture was stirred at 20° C. for 30 mins. The mixture was filtered, and the filtrate was concentrated. The crude was purified by prep-TLC (EtOAc) to give (17Z,3R,7S,9E)-4-ethyl-23-methoxy-3-methyl-7-(3,3,3-trifluoropropyl)-4,6-diaza-1(6,8)-imidazo [1,2-a]pyridina-2(2,6)-pyridinacyclotridecaphan-9-en-5-one, LCMS m/z (M+H): 530.3 required, 530.3 found, and (17Z,3R,7S,9E)-4-ethyl-23-methoxy-3-methyl-7-(3,3,3-trifluoropropyl)-4,6-diaza-1(6,8)-imidazo[1,2-a]pyridina-2(2,6)-pyridinacyclododecaphan-9-en-5-one. LCMS m/z (M+H): 516.3 required, 516.3 found.

To a solution of (17Z,3R,7S,9E)-4-ethyl-23-methoxy-3-methyl-7-(3,3,3-trifluoropropyl)-4,6-diaza-1(6,8)-imidazo [1,2-a]pyridina-2(2,6)-pyridinacyclododecaphan-9-en-5-one (15 mg, 0.029 mmol) in EtOAc (2 mL) was added Pd-C(15.48 mg, 0.015 mmol) (10%) and stirred at 20° C. under H2 (0.059 mg, 0.029 mmol) (15 psi) for 1 h. The reaction was filtered and the filtrate was concentrated. The crude product was purity by prep-HPLC (ODS, water (0.1% TFA) and 35-100% acetonitrile) to give (3R,7R,Z)-4-ethyl-23-methoxy-3-methyl-7-(3,3,3-trifluoropropyl)-4,6-diaza-1 (6,8)-imidazo[1,2-a]pyridina-2(2,6)-pyridinacyclododecaphan-5-one (example 138). LCMS m/z (M+H): 518.3 found, 518.3 required. $^1$H NMR 1014161-063-001a (400 MHz, $CD_3OD$) δ 9.48-9.57 (m, 1H), 8.62 (s, 1H), 8.30 (d, J=1.96 Hz, 1H), 8.02 (d, J=1.96 Hz, 1H), 7.60 (d, J=8.80 Hz, 1H), 7.46 (d, J=8.56 Hz, 1H), 5.80 (br d, J=7.09 Hz, 1H), 4.03 (s, 3H), 3.95-3.84 (m, 1H), 3.28-3.21 (m, 2H), 3.18-3.09 (m, 2H), 2.94-2.83 (m, 1H), 2.28-2.14 (m, 2H), 1.97-1.87 (m, 2H), 1.79-1.71 (m, 2H), 1.65 (d, J=7.09 Hz, 3H), 1.58 (br d, J=7.34 Hz, 2H), 1.51-1.44 (m, 1H), 1.34-1.24 (m, 2H), 1.10 (t, J=7.09 Hz, 3H)

Example 139

(3R,7R,E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclotridecaphan-5-one

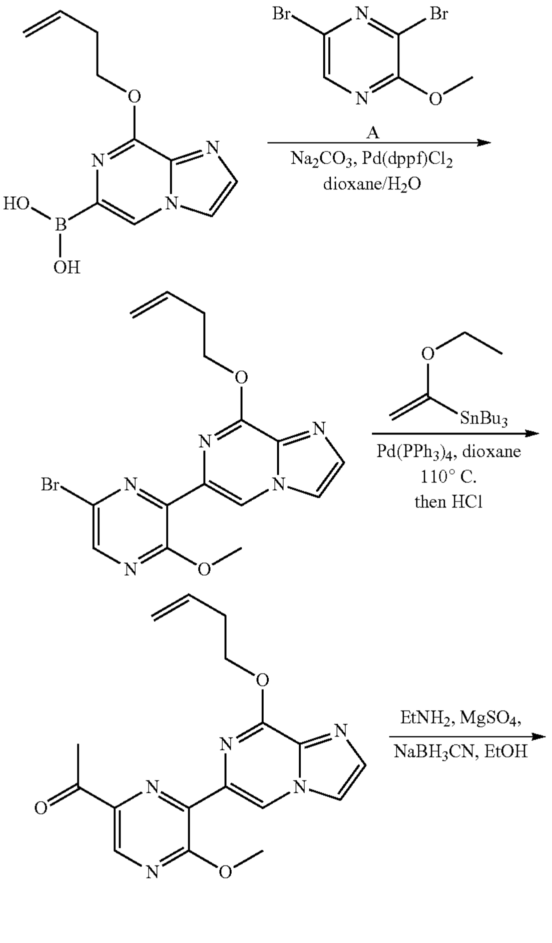

-continued

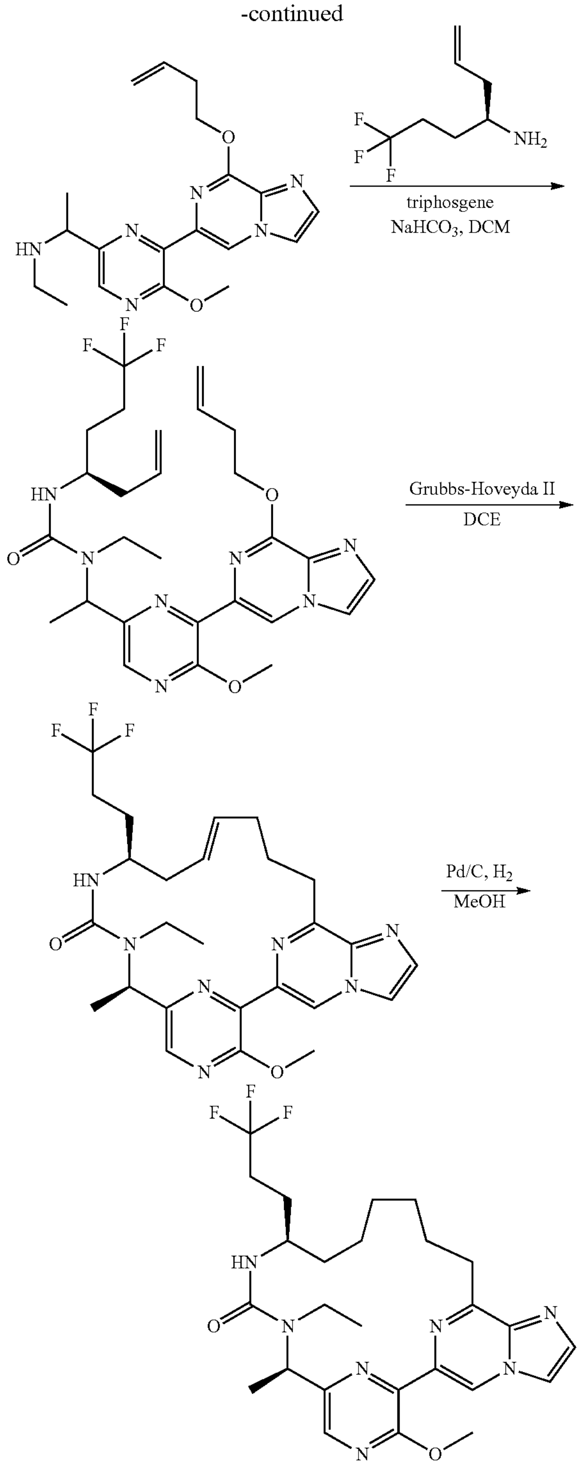

EXAMPLE 139

To a solution of (8-(but-3-en-1-yloxy)imidazo[1,2-a]pyrazin-6-yl)boronic acid C37 (0.869 g, 3.73 mmol) in dioxane (20 mL) were added Water (4 mL), 3,5-dibromo-2-methoxypyrazine (0.999 g, 3.73 mmol), $Na_2CO_3$ (1.186 g, 11.19 mmol) and Pd(dppf)$Cl_2$ (0.273 g, 0.373 mmol), the mixture was stirred at 90° C. for 16 h. The mixture was poured into water (20 mL), extracted with EtOAc (20 mL×3). The combined organic phases were washed with brine (20 mL), and dried over $Na_2SO_4$. After filtration and concentration. The residue was purified by flash silica gel chromatography (ISCO®; 12 g SepaFlash® Silica Flash Column, eluent of [60]% ethyl acetate/pet. ether gradient) to give 6-(6-bromo-3-methoxypyrazin-2-yl)-8-(but-3-en-1-yloxy)imidazo[1,2-a]pyrazine. LCMS m/z (M+H): 378.1 required, 378.1 found.

To a solution of 6-(6-bromo-3-methoxypyrazin-2-yl)-8-(but-3-en-1-yloxy)imidazo[1,2-a]pyrazine (650 mg, 1.728 mmol) in dioxane (10 mL) were added tributyl(1-ethoxyvinyl)stannane (686 mg, 1.901 mmol) and Pd($Ph_3P$)$_4$ (200 mg, 0.173 mmol), and then the mixture was stirred at 100° C. for 15 hours. The mixture was cooled to 25° C. and 4M HCl (2 mL) was added to the above solution and stirred at 25° C. for 3 hours. The reaction mixture was poured into water (10 mL), extracted with EtOAc (20 mL×3). The organic layer was washed with brine (10 mL), dried over $Na_2SO_4$ and filtered. After filtrate was concentrated to give crude product, the crude product was purified by flash silica gel chromatography (ISCO®; 12 g SepaFlash® Silica Flash Column, eluent of [30]% ethyl acetate/pet. ether gradient) to give 1-(6-(8-(but-3-en-1-yloxy)imidazo[1,2-a]pyrazin-6-yl)-5-methoxypyrazin-2-yl)ethan-1-one. LCMS m/z (M+H): 340.1 required, 340.0 found.

To a solution of 1-(6-(8-(but-3-en-1-yloxy)imidazo[1,2-a]pyrazin-6-yl)-5-methoxypyrazin-2-yl)ethan-1-one (200 mg, 0.589 mmol) in EtOH (5 mL) was added ethanamine (80 mg, 1.768 mmol) and acetic acid (3.37 μl, 0.059 mmol) was added to adjusted pH=6. $MgSO_4$ (142 mg, 1.179 mmol) and $NaBH_3CN$ (111 mg, 1.768 mmol) were added to the above solution and stirred at 90° C. for 3 hours. The reaction mixture was filtered and concentrated to give crude. The crude was purified by TLC ($SiO_2$, EtOAc) to give 1-(6-(8-(but-3-en-1-yloxy)imidazo[1,2-a]pyrazin-6-yl)-5-methoxypyrazin-2-yl)-N-ethylethan-1-amine. LCMS m/z (M+H): 369.2 required, 369.3 found. $^1H$ NMR (500 MHz, MeOD) δ 8.87-8.69 (m, 1H), 8.14 (s, 1H), 8.02-7.87 (m, 1H), 7.59 (d, J=1.1 Hz, 1H), 6.00-5.78 (m, 1H), 5.19-4.93 (m, 2H), 4.66-4.57 (m, 2H), 4.22-4.14 (m, 1H), 4.09-3.95 (m, 3H), 2.77-2.56 (m, 4H), 1.47 (d, J=6.7 Hz, 3H), 1.11 (t, J=7.2 Hz, 3H).

To a solution of (S)-7,7,7-trifluorohept-1-en-4-amine hydrochloride A5 (85 mg, 0.417 mmol) in DCM (2 mL) and sat.$NaHCO_3$(2 mL) was added bis(trichloromethyl) carbonate (40.9 mg, 0.138 mmol) and stirred at 0° C. for 30 min. 1-(6-(8-(but-3-en-1-yloxy)imidazo[1,2-a]pyrazin-6-yl)-5-methoxypyrazin-2-yl)-N-ethylethan-1-amine (150 mg, 0.407 mmol) was added and stirred at 25° C. for 2 hours. The reaction mixture was poured into water (5 mL), extracted with DCM (5 mL×3). The organic layer was washed with brine (5 mL), dried over $Na_2SO_4$ and filtered. After filtrate was concentrated to give crude product, the crude product was purified by TLC ($SiO_2$, ethyl acetate/pet. ether=1:1) to give 1-(1-(6-(8-(but-3-en-1-yloxy)imidazo[1,2-a]pyrazin-6-yl)-5-methoxypyrazin-2-yl)ethyl)-1-ethyl-3-((S)-7,7,7-trifluorohept-1-en-4-yl)urea. LCMS m/z (M+H): 562.3 required, 562.4 found.

To a solution of 1-(1-(6-(8-(but-3-en-1-yloxy)imidazo[1,2-a]pyrazin-6-yl)-5-methoxypyrazin-2-yl)ethyl)-1-ethyl-3-((S)-7,7,7-trifluorohept-1-en-4-yl)urea (200 mg, 0.356 mmol) in DCE (100 mL) was added (1,3-dimesitylimidazolidin-2-ylidene)(2-isopropoxybenzylidene)ruthenium(vi) chloride (44.6 mg, 0.071 mmol), and the mixture was stirred at 50° C. for 16 h. The mixture was concentrated and purified by TLC (ethyl acetate) to give ($1^7$E,3R,7S,9E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclotridecaphan-9-en-5-one as the second eluting diastereomer. LCMS m/z (M+H): 534.2 required, 534.2 found.

To a solution of ($1^7$E,3R,7S,9E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclo tridecaphan-9-en-5-one (40 mg, 0.075 mmol) in MeOH (3 mL) was added Pd-C(39.9 mg, 0.037 mmol) (10% wt) and stirred at 25° C. under H2 (15 psi) for 15 minutes. The mixture was filtered and concentrated. The crude was purified by HPLC (TFA, Instrument EJ, Method Column Boston Green ODS 150x30 mmx5 um, water (0.1% TFA)-ACN 27-47%) to give (3R,7R,E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclotridecaphan-5-one, (example 139). LCMS m/z (M+H): 536.3 required, 536.3 found. $^1$H NMR (500 MHz, $CD_3OD$) δ 9.12 (s, 1H), 8.27 (s, 1H), 8.19 (d, J=1.4 Hz, 1H), 7.85 (d, J=1.4 Hz, 1H), 5.90 (q, J=7.2 Hz, 1H), 4.75 (dt, J=5.6, 10.3 Hz, 1H), 4.19-4.11 (m, 3H), 3.98 (br s, 1H), 3.22-3.08 (m, 2H), 2.31-2.15 (m, 2H), 2.10-1.85 (m, 2H), 1.76-1.68 (m, 2H), 1.65-1.56 (m, 6H), 1.53-1.33 (m, 4H), 0.97 (t, J=7.1 Hz, 3H).

Example 140

(3R,7R,E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-5-one (Example 140)

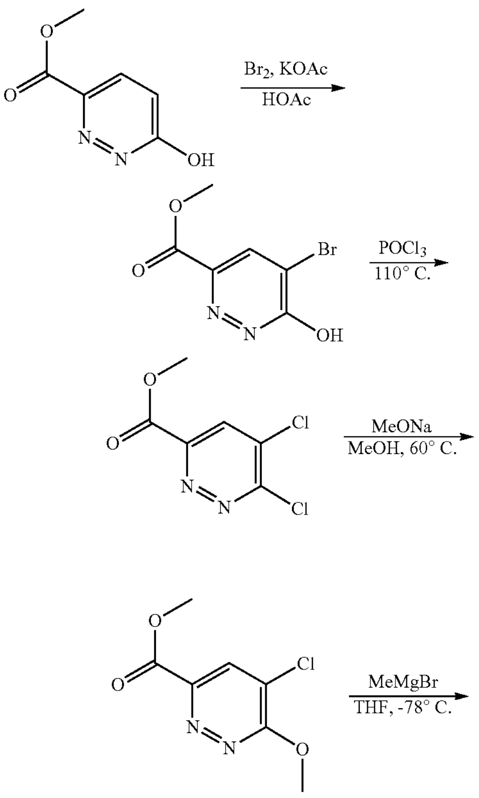

-continued

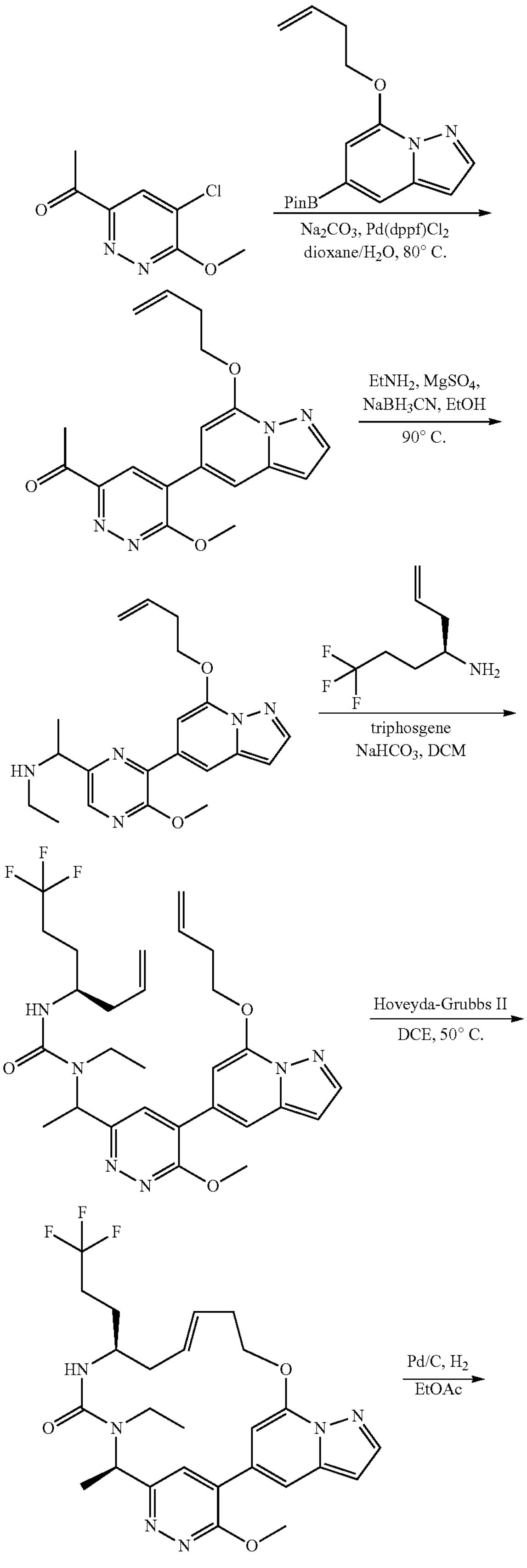

-continued

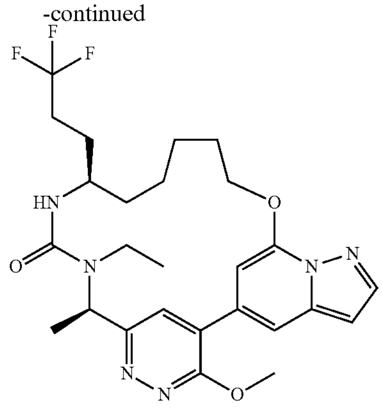

EXAMPLE 140

To a solution of methyl 6-hydroxypyridazine-3-carboxylate (25 g, 162 mmol) in AcOH (250 mL) were added potassium acetate (80 g, 811 mmol) and dibromine (104 g, 649 mmol) slowly and stirred at 80° C. for 3 hours. The reaction mixture was poured into water (500 mL) and filtered to give methyl 5-bromo-6-hydroxypyridazine-3-carboxylate, which was used in next step without purification-.LCMS m/z (M+H): 232.9 required, 232.8 found. $^1$H NMR (400 MHz, $CD_3OD$) δ 8.32 (s, 1H), 3.92 (s, 3H)

A solution of methyl 5-bromo-6-hydroxypyridazine-3-carboxylate (21 g, 90 mmol) in $POCl_3$ (150 mL) was stirred at 110° C. for 2 hours. The mixture was concentrated under reduced pressure and the residue was poured into ice-water and extracted with ethyl acetate (100 mL×3). The combined organic extracts were dried over sodium sulfate, filtered, concentrated to give methyl 5,6-dichloropyridazine-3-carboxylate, which was used in next step without purification. LCMS m/z (M+H): 207.0 required, 206.9 found.

To a solution of methyl 5,6-dichloropyridazine-3-carboxylate (10 g, 48.3 mmol) in MeOH (100 mL) was added sodium methanolate (2.61 g, 48.3 mmol) and stirred at 60° C. for 3 hours. The reaction mixture was poured into water (200 mL), extracted with EtOAc (100 mL×3). The organic layer was washed with brine (100 mL), dried over $Na_2SO_4$ and filtered. The filtrate was concentrated and purified by flash silica gel chromatography (ISCO®; 80 g SepaFlash® Silica Flash Column, eluent of [0-27]% ethyl acetate/pet. ether gradient) to give methyl 5-chloro-6-methoxypyridazine-3-carboxylate. LCMS m/z (M+H): 203.0 required, 203.0 found. $^1$H NMR (400 MHz, $CDCl_3$) δ 8.12 (s, 1H), 4.27 (s, 3H), 4.01 (s, 3H)

To a solution of methyl 5-chloro-6-methoxypyridazine-3-carboxylate (5.4 g, 26.7 mmol) in THF (100 mL) was added methylmagnesium bromide (17.77 mL, 53.3 mmol) (3 M in $Et_2O$) at −78° C. and stirred at −78° C. for 3 hours. The reaction mixture was poured into water (200 mL), extracted with EtOAc (100 mL×3). The organic layer was washed with brine (50 mL), dried over $Na_2SO_4$ and filtered. The filtrate was concentrated and purified by flash silica gel chromatography (ISCO®; 25 g SepaFlash® Silica Flash Column, eluent of [0-25]% ethyl acetate/pet. ether gradient) to give 1-(5-chloro-6-methoxypyridazin-3-yl)ethan-1-one. LCMS m/z (M+H): 187.1 required, 187.0 found.

To a solution of 1-(5-chloro-6-methoxypyridazin-3-yl)ethan-1-one (139 mg, 0.748 mmol) in Water (1 mL) was added 7-(but-3-en-1-yloxy)-5-(4,4,5,5-tetramethyl-1,3,2-dioxaborolan-2-yl)pyrazolo[1,5-a]pyridine C85 (2.5 mL, 0.748 mmol), $Na_2CO_3$ (158 mg, 1.495 mmol) and Pd(dppf)$Cl_2$ (54.7 mg, 0.075 mmol). The mixture was stirred at 80° C. for 15 hours. The reaction mixture was poured into water (30 mL), extracted with EtOAc (20 mL×3). The organic layer was washed with brine (30 mL), dried over $Na_2SO_4$ and filtered. The filtrate was concentrated and purified by flash silica gel chromatography (ISCO®; 4 g SepaFlash® Silica Flash Column, eluent of [0-30]% ethyl acetate/pet. ether gradient) to give 1-(5-(7-(but-3-en-1-yloxy)pyrazolo[1,5-a]pyridin-5-yl)-6-methoxypyridazin-3-yl)ethan-1-one. LCMS m/z (M+H): 339.3 required, 339.4 found.

To a solution of 1-(5-(7-(but-3-en-1-yloxy)pyrazolo[1,5-a]pyridin-5-yl)-6-methoxypyridazin-3-yl)ethan-1-one (280 mg, 0.828 mmol) in EtOH (5 mL) were added ethanamine (37.3 mg, 0.828 mmol), AcOH (4.74 μL, 0.083 mmol), $MgSO_4$ (498 mg, 4.14 mmol) and $NaBH_3CN$ (104 mg, 1.655 mmol). The mixture was stirred at 90° C. for 12 hours. The reaction mixture was filtered, concentrated and purified by flash silica gel chromatography (ISCO®; 4 g SepaFlash® Silica Flash Column, eluent of [0-30]% MeOH/ethyl acetate gradient) to give 1-(5-(7-(but-3-en-1-yloxy)pyrazolo[1,5-a]pyridin-5-yl)-6-methoxypyridazin-3-yl)-N-ethylethan-1-amine. LCMS m/z (M+H): 368.2 required, 368.2 found.

To a solution of (S)-7,7,7-trifluorohept-1-en-4-amine hydrochloride A5 (78 mg, 0.381 mmol) (78 mg, 0.381 mmol) in DCM (2 mL) and sat. $NaHCO_3$(2 mL) was added bis(trichloromethyl) carbonate (37.3 mg, 0.126 mmol) at 0° C. for 30 mins. 1-(5-(7-(but-3-en-1-yloxy)pyrazolo[1,5-a]pyridin-5-yl)-6-methoxypyridazin-3-yl)-N-ethylethan-1-amine (140 mg, 0.381 mmol) was added to the mixture and stirred for 1 hour. The reaction mixture was poured into water (20 mL), extracted with DCM (10 mL×3). The organic layer was washed with brine (10 mL), dried over $Na_2SO_4$ and filtered. The filtrate was concentrated and purified by prep-TLC ($SiO_2$, Pet. ether:EtOAc=1:1) to give 1-(1-(5-(7-(but-3-en-1-yloxy)pyrazolo[1,5-a]pyridin-5-yl)-6-methoxypyridazin-3-yl)ethyl)-1-ethyl-3-((S)-7,7,7-trifluorohept-1-en-4-yl)urea. LCMS m/z (M+H): 561.2 required, 561.7 found. $^1$H NMR (400 MHz, $CDCl_3$) δ 8.05 (t, J=2.0 Hz, 1H), 7.51 (d, J=1.6 Hz, 1H), 7.47 (dd, J=1.4, 13.1 Hz, 1H), 6.62 (t, J=2.2 Hz, 1H), 6.34-6.27 (m, 1H), 6.07-5.89 (m, 1H), 5.83-5.60 (m, 2H), 5.34-4.92 (m, 4H), 4.49-4.33 (m, 3H), 4.21 (d, J=0.8 Hz, 3H), 3.99 (br s, 1H), 3.42-3.09 (m, 2H), 2.80 (q, J=6.7 Hz, 2H), 2.41-1.95 (m, 5H), 1.87-1.77 (m, 1H), 1.73 (d, J=7.0 Hz, 3H), 1.17-1.03 (m, 3H)

To a solution of (3R,7R,E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-5-one (130 mg, 0.232 mmol) in DCE (130 mL) was added (1,3-dimesitylimidazolidin-2-ylidene)(2-isopropoxybenzylidene)ruthenium(VI) chloride (29.1 mg, 0.046 mmol) and stirred at 50° C. for 15 hours. The reaction mixture was concentrated to give (16E,7S,9E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-9-en-5-one as a mixture of diastereomers, which was used in next step without purification. LCMS m/z (M+H): 535.2 required, 535.3 found.

To a solution of (16E,7S,9E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-9-en-5-one (120 mg, 0.225 mmol) in EtOAc (2 mL) was added Pd-C (120 mg, 0.113 mmol) (10% wt) and stirred at 25° C. under H2 (15 psi) for 30 mins. The reaction was filtered, concentrated and purified by prep-HPLC (TFA) to give (3R,7R,E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-5-one as the second eluting diastereomer (example 140). LCMS m/z (M+H): 535.2 required, 535.3 found. $^1$H NMR (400 MHz, $CD_3OD$) δ 8.14-8.00 (m, 2H), 7.72 (s, 1H), 6.78 (d, J=2.3 Hz, 1H), 6.35 (s, 1H), 6.00 (q, J=7.4 Hz, 1H), 4.77-4.52 (m, 2H), 4.24 (s, 3H), 4.04 (br s, 1H), 3.29-3.06 (m, 2H), 2.31-2.13 (m, 2H), 1.96 (br s, 2H), 1.86-1.67 (m, 5H), 1.64-1.33 (m, 6H), 1.06 (t, J=7.0 Hz, 3H)

Example 141

(3R,7S,E)-4-ethyl-8,8-difluoro-25-methoxy-3,7-dimethyl-13-oxa-4,6-diaza-1(6,8)-imidazo[1,2-a]pyrazina-2(4,2)-pyridinacyclotridecaphan-5-one (Example 141)

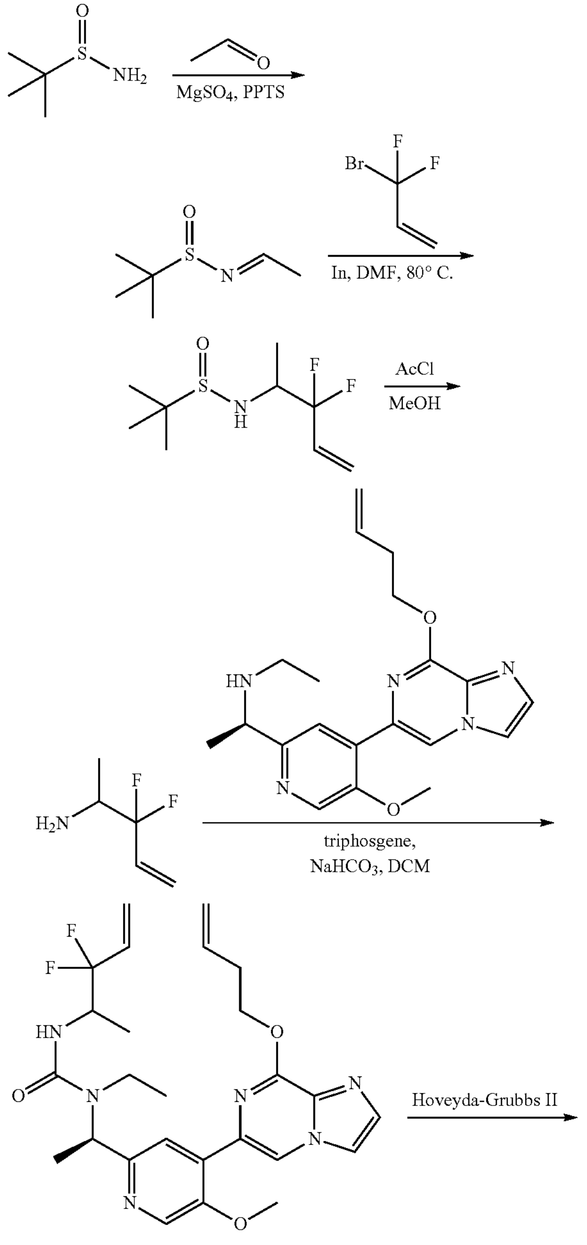

-continued

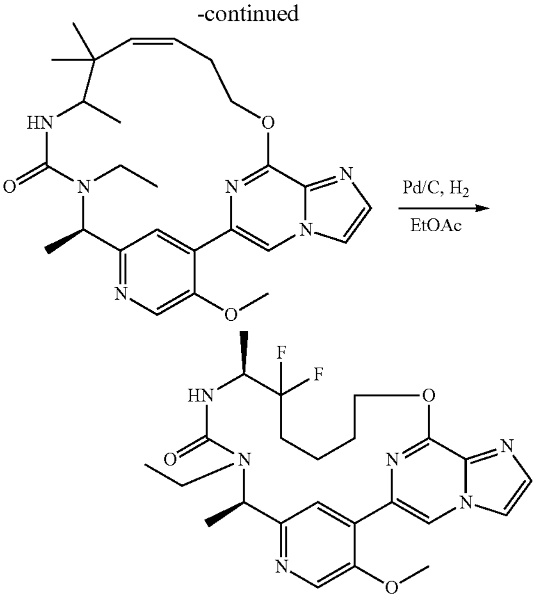

EXAMPLE 141

To a solution of 2-methylpropane-2-sulfinamide (4 g, 33.0 mmol) in DCM (14 mL) were added acetaldehyde (13.09 g, 297 mmol), magnesium sulfate (11.92 g, 99 mmol) and pyridine 4-methylbenzenesulfonate (0.415 g, 1.650 mmol). The reaction was stirred at 25° C. for 12 hours. The reaction mixture was filtered. The filtrate was concentrated and purified by flash silica gel chromatography (ISCO®; 40 g SepaFlash® Silica Flash Column, eluent of [0-6]% ethyl acetate/pet. ether gradient) to give (E)-N-ethylidene-2-methylpropane-2-sulfinamide. LCMS m/z (M+H): 148.2 required, 148.1 found. $^1$H NMR (400 MHz, $CDCl_3$) δ 8.06 (q, J=5.1 Hz, 1H), 2.21 (d, J=5.1 Hz, 3H), 1.17 (s, 9H)

To a solution of (E)-N-ethylidene-2-methylpropane-2-sulfinamide (600 mg, 4.08 mmol) and 3-bromo-3,3-difluoroprop-1-ene (959 mg, 6.11 mmol) in DMF (3 mL) was added indium (702 mg, 6.11 mmol) at 0° C. The mixture was stirred at 80° C. for 16 hours. The reaction mixture was poured into water (30 mL), extracted with EtOAc (20 mL×3). The combined organic layers were washed with brine (20 mL), dried over $Na_2SO_4$ and filtered. The filtrate was concentrated and purified by prep-TLC ($SiO_2$, Pet. ether:EtOAc=1:1) to give N-(3,3-difluoropent-4-en-2-yl)-2-methylpropane-2-sulfinamide. LCMS m/z (M+H): 226.2 required, 226.0 found. $^1$H NMR (400 MHz, $CDCl_3$) δ 6.05-5.85 (m, 1H), 5.80-5.67 (m, 1H), 5.57 (d, J=11.0 Hz, 1H), 3.76-3.64 (m, 1H), 3.54 (br s, 1H), 1.30 (d, J=6.7 Hz, 3H), 1.22 (s, 9H)

To a solution of N-(3,3-difluoropent-4-en-2-yl)-2-methylpropane-2-sulfinamide (220 mg, 0.976 mmol) in MeOH (5 mL) was added acetyl chloride (383 mg, 4.88 mmol) and stirred at 25° C. for 2 hours. The reaction mixture was concentrated to give 3,3-difluoropent-4-en-2-amine, which was used in next step without purification. To a solution of 3,3-difluoropent-4-en-2-amine (95 mg, 0.784 mmol) in DCM (3 mL) and sat. $NaHCO_3$(3 mL) was added bis (trichloromethyl) carbonate (77 mg, 0.259 mmol) at 0° C. and stirred at 0° C. for 30 mins. C74 (288 mg, 0.784 mmol) was added to the mixture and stirred for 1 hour. The reaction mixture was poured into water (20 mL), extracted with DCM (10 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-60]% ethyl acetate/pet. ether gradient) to give 1-((R)-1-(4-(8-(but-3-en-1-yloxy)imidazo[1,2-a]pyrazin-6-yl)-5-methoxypyridin-2-yl)ethyl)-3-(3,3-difluoropent-4-en-2-yl)-1-ethylurea. LCMS m/z (M+H): 515.2 required, 515.5 found.

To a solution of 1-((R)-1-(4-(8-(but-3-en-1-yloxy)imidazo[1,2-a]pyrazin-6-yl)-5-methoxypyridin-2-yl)ethyl)-3-(3,3-difluoropent-4-en-2-yl)-1-ethylurea (150 mg, 0.292 mmol) in DCE (150 mL) was added (1,3-dimesitylimidazolidin-2-ylidene)(2-isopropoxybenzylidene)ruthenium(VI) chloride (36.5 mg, 0.058 mmol) and stirred at 50° C. for 12 hours. The reaction mixture was concentrated to give ($1^7$E,3R,9Z)-4-ethyl-8,8-difluoro-25-methoxy-3,7-dimethyl-13-oxa-4,6-diaza-1(6,8)-imidazo[1,2-a]pyrazina-2(4,2)-pyridinacyclotridecaphan-9-en-5-one, which was used in next step without purification. LCMS m/z (M+H): 487.2 required, 487.1 found.

To a solution of ($1^7$E,3R,9Z)-4-ethyl-8,8-difluoro-25-methoxy-3,7-dimethyl-13-oxa-4,6-diaza-1(6,8)-imidazo[1,2-a]pyrazina-2(4,2)-pyridinacyclotridecaphan-9-en-5-one (140 mg, 0.288 mmol) in EtOAc (2 mL) was added Pd-C (306 mg, 0.288 mmol) (10% wt) and stirred at 25° C. under H2 (15 psi) for 30 mins. The reaction was filtered, concentrated and purified by prep-HPLC (water (0.1% TFA)/30-50% ACN) to give (3R,7S,E)-4-ethyl-8,8-difluoro-25-methoxy-3,7-dimethyl-13-oxa-4,6-diaza-1(6,8)-imidazo[1,2-a]pyrazina-2(4,2)-pyridinacyclotridecaphan-5-one as the second eluting diastereomer (example 141). LCMS m/z (M+H): 489.2 required, 489.2 found. $^1$H NMR (400 MHz, $CD_3OD$) δ 9.24 (s, 1H), 8.38 (s, 1H), 8.31 (s, 1H), 8.18 (s, 1H), 7.81 (s, 1H), 6.20 (d, J=9.0 Hz, 1H), 6.12-5.95 (m, 1H), 5.03 (br d, J=4.7 Hz, 1H), 4.60-4.42 (m, 2H), 4.17 (s, 3H), 3.29-3.03 (m, 2H), 2.12-1.61 (m, 6H), 1.57 (d, J=7.4 Hz, 3H), 1.30 (d, J=7.0 Hz, 3H), 0.80 (t, J=7.0 Hz, 3H)

Example 142

(3R,7R,E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-5-one (Example 142)

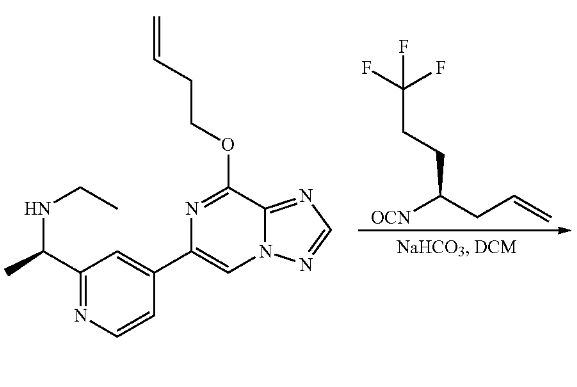

-continued

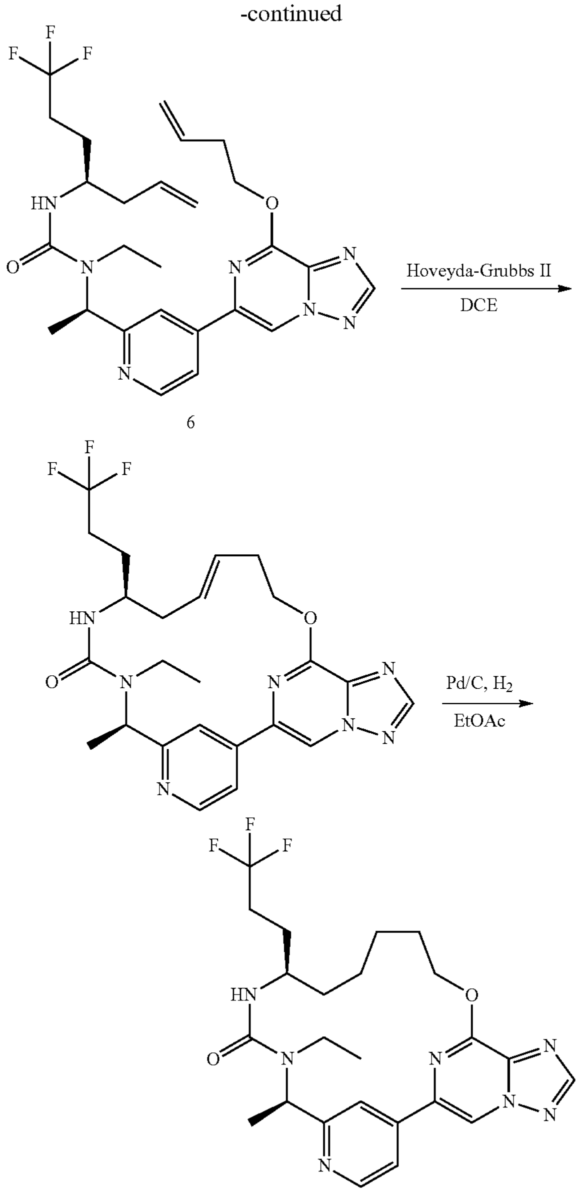

6

EXAMPLE 142

To a solution of (S)-7,7,7-trifluorohept-1-en-4-amine hydrochloride A5 (100 mg, 0.491 mmol) and TEA (0.684 mL, 4.91 mmol) in DCM (3 mL) was added bis(trichloromethyl) carbonate (48.1 mg, 0.162 mmol) and stirred at 0° C. for 30 mins. (R)-1-(4-(8-(but-3-en-1-yloxy)-[1,2,4]triazolo[1,5-a]pyrazin-6-yl)pyridin-2-yl)-N-ethylethan-1-amine C146 (150 mg, 0.443 mmol) was added and stirred at 0° C. for 30 mins. $H_2O$(2 mL) was added to the mixture. The reaction mixture was extracted with DCM (5 mLx3). The combined organic layers were washed with brine (5 mL), dried over $Na_2SO_4$ and filtered. The filtrate was concentrated and purified by Flash silica gel chromatography (ISCO®; 4 g SepaFlash® Silica Flash Column, Eluent of 50% EtOAc/Pet.ether gradient) to give 1-((R)-1-(4-(8-(but-3-en-1-yloxy)-[1,2,4]triazolo[1,5-a]pyrazin-6-yl)pyridin-2-yl)ethyl)-1-ethyl-3-((S)-7,7,7-trifluorohept-1-en-4-yl)urea.

To a solution of 1-((R)-1-(4-(8-(but-3-en-1-yloxy)-[1,2,4]triazolo[1,5-a]pyrazin-6-yl)pyridin-2-yl)ethyl)-1-ethyl-3-((S)-7,7,7-trifluorohept-1-en-4-yl)urea (100 mg, 0.188 mmol) in DCE (100 mL) was added (1,3-dimesitylimidazolidin-2-ylidene)(2-isopropoxybenzylidene)ruthenium(vi) chloride (23.58 mg, 0.038 mmol). The mixture was stirred at 50° C. for 16 hours. The mixture was filtered and the filtrate was concentrated. The crude was purified by Flash silica gel chromatography (ISCO®; 4 g SepaFlash® Silica Flash Column, Eluent of 80% EtOAc/Pet.ether gradient) to give ($1^7$E,3R,7S,9E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-9-en-5-one. LCMS m/z (M+H): 504.3 required, 504.3 found.

To a mixture of ($1^7$E,3R,7S,9E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-9-en-5-one (45 mg, 0.089 mmol) in EtOAc (20 mL) was added Pd/C (10 mg, 9.40 μmol) (10%), and the resulting mixture was stirred at 25° C. for 1 h under $H_2$ (excess) (15 psi). LCMS showed desired mass. The mixture was filtered and the filtrate was concentrated. The crude product was purified by Flash silica gel chromatography (ISCO®; 4 g SepaFlash® Silica Flash Column, Eluent of 70% EtOAc/Pet.ether gradient) to give (3R,7R,E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-5-one (example 142). LCMS m/z (M+H): 506.3 required, 506.3 found. $^1$H NMR (400 MHz, $CD_3OD$) δ 9.23-9.17 (m, 1H), 8.57 (d, J=5.5 Hz, 1H), 8.53 (s, 1H), 8.14 (s, 1H), 7.86 (dd, J=1.6, 5.5 Hz, 1H), 6.08-5.86 (m, 2H), 5.01-4.93 (m, 1H), 4.74-4.53 (m, 2H), 4.10 (br d, J=7.4 Hz, 1H), 3.29-3.19 (m, 1H), 3.16-3.04 (m, 1H), 2.33-2.14 (m, 2H), 2.06-1.95 (m, 1H), 1.86 (dt, J=6.3, 11.7 Hz, 1H), 1.78-1.69 (m, 2H), 1.62 (d, J=7.0 Hz, 3H), 1.59-1.47 (m, 3H), 1.40-1.29 (m, 1H), 1.00 (t, J=7.0 Hz, 3H).

Example 143

(R,E)-4-ethyl-3,3-dimethyl-7-(3,3,3-trifluoropropyl)-13-oxa-4,6-diaza-1(6,8)-imidazo[1,2-a]pyrazina-2(4,2)-pyridinacyclotridecaphan-5-one (example 143)

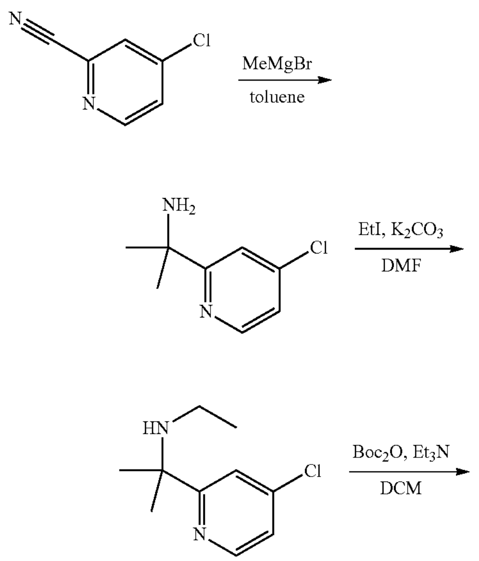

-continued

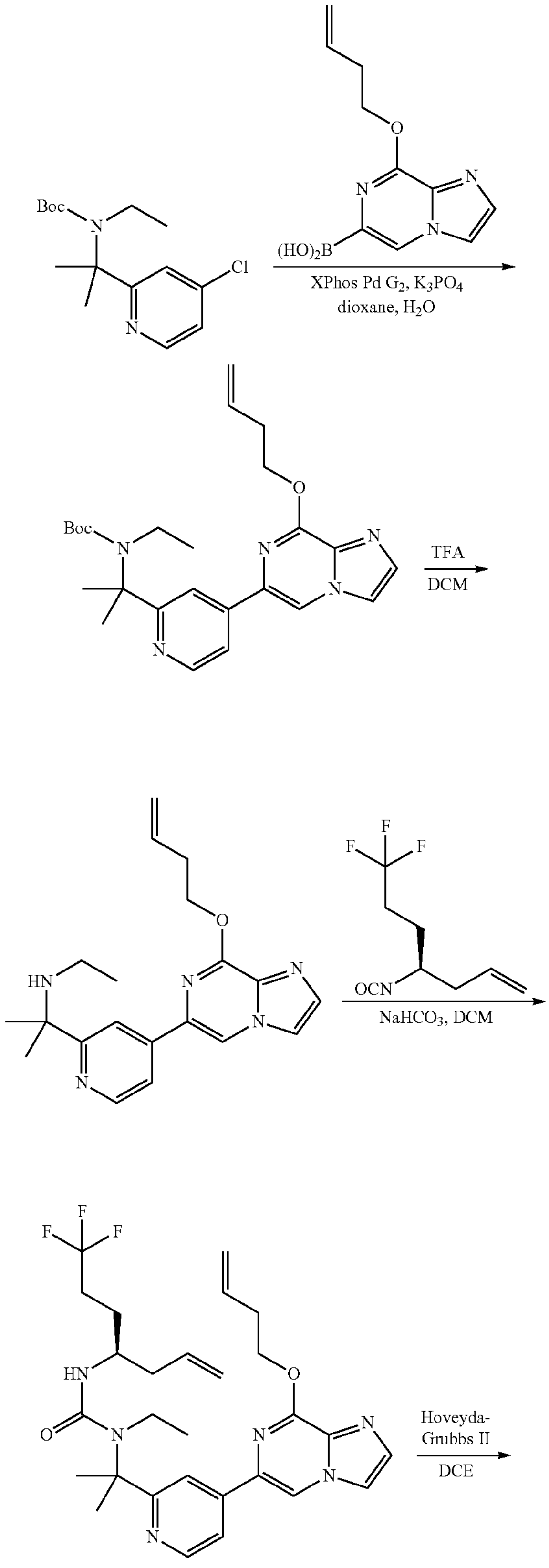

-continued

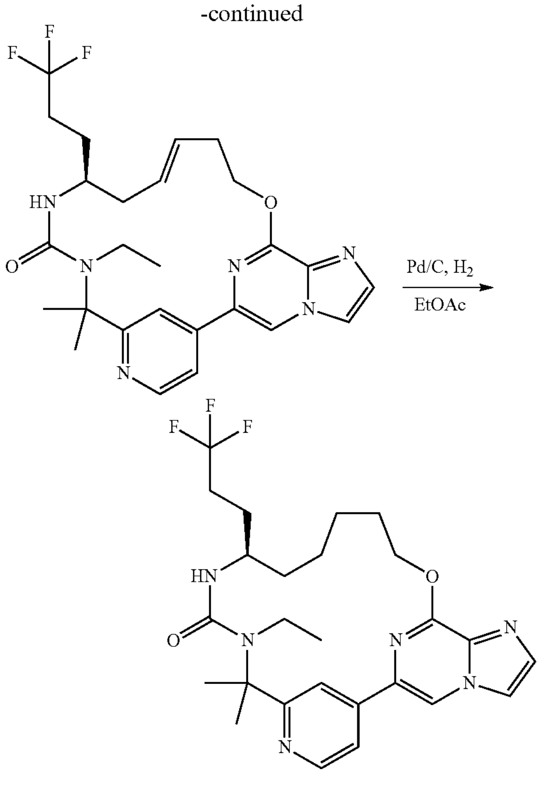

EXAMPLE 143

To a solution of 4-chloropicolinonitrile (1 g, 7.22 mmol) in Toluene (30 mL) was added methylmagnesium bromide (9.62 mL, 28.9 mmol) (3 M in THF) at ice bath, then ice bath was remove and the mixture was stirred at 110° C. for 12 h. The mixture was dropped into water (20 mL), extracted with EtOAc (15 mL×3). The organic layer was washed with brine (15 mL), dried over $Na_2SO_4$ and filtered. The filtrate was concentrated. The crude product was purified by flash silica gel chromatography (Biotage; 4 g Agela Silica Flash Column, Eluent of 0-30% EtOAc/Pet.ether gradient @ 35 mL/min) to give 2-(4-chloropyridin-2-yl)propan-2-amine. LCMS m/z (M+H+2): 171.2 required, 171.2 found. $^1H$ NMR 1014690-029-1 (400 MHz, $CDCl_3$) δ 8.43 (d, J=5.38 Hz, 1H), 7.48 (d, J=1.71 Hz, 1H), 7.12 (dd, J=1.83, 5.26 Hz, 1H), 1.47 (s, 6H)

To a solution of 2-(4-chloropyridin-2-yl)propan-2-amine (350 mg, 2.051 mmol) in DMF (8 mL) were added K2C03 (850 mg, 6.15 mmol) and iodoethane (0.164 mL, 2.051 mmol). The mixture was stirred at 25° C. for 12 h. The reaction was poured into water (10 mL), and extracted with EtOAc (10 mL×3). The organic layer was washed with brine (10 mL), dried over $Na_2SO_4$, filtered and concentrated. The crude product was purified by flash silica gel chromatography (Biotage; 4 g Agela Silica Flash Column, Eluent of 0~50% EtOAc/Pet.ether gradient @ 35 mL/min) to give 2-(4-chloropyridin-2-yl)-N-ethylpropan-2-amine. LCMS m/z (M+H): 199.2 required, 199.2 found.

To a solution of 2-(4-chloropyridin-2-yl)-N-ethylpropan-2-amine (230 mg, 1.158 mmol) in DCM (6 mL) were added $Et_3N$ (0.484 mL, 3.47 mmol) and BOC-Anhydride (0.323 mL, 1.389 mmol). The mixture was stirred at 25° C. for 24 hours. The reaction mixture was poured into water (10 mL), extracted with DCM (10 mL×3). The organic layer was washed with brine (10 mL), dried over $Na_2SO_4$ and filtered. The filtrate was concentrated and purified by Flash silica gel chromatography (ISCO®; 4 g SepaFlash® Silica Flash Column, Eluent of 0-30% EtOAc/Pet.ether gradient) to give tert-butyl (2-(4-chloropyridin-2-yl)propan-2-yl)(ethyl)carbamate. LCMS m/z (M+H): 299.2 required, 299.2 found.)

To a solution of tert-butyl (2-(4-chloropyridin-2-yl)propan-2-yl)(ethyl)carbamate (70 mg, 0.234 mmol) in Dioxane (1 mL) and Water (0.5 mL) were added $K_3PO_4$ (149 mg, 0.703 mmol), (8-(but-3-en-1-yloxy)imidazo[1,2-a]pyrazin-6-yl)boronic acid C37 (65.5 mg, 0.281 mmol) and XPhos Pd G2 (18.43 mg, 0.023 mmol). The mixture was stirred at 90° C. for 3 hours. The reaction mixture was poured into water (10 mL), extracted with EtOAc (10 mL×3). The organic layer was washed with brine (10 mL), dried over $Na_2SO_4$ and filtered. The filtrate was concentrated and purified by TLC (Pet:tOAc=1:1) to give tert-butyl (2-(4-(8-(but-3-en-1-yloxy)imidazo[1,2-a]pyrazin-6-yl)pyridin-2-yl)propan-2-yl)(ethyl)carbamate. LCMS m/z (M+H): 452.2 required, 452.2 found To a solution of tert-butyl (2-(4-(8-(but-3-en-1-yloxy)imidazo[1,2-a]pyrazin-6-yl)pyridin-2-yl)propan-2-yl)(ethyl)carbamate (80 mg, 0.177 mmol) in DCM (1 mL) was added TFA (0.5 mL, 6.49 mmol) at 25° C. and the mixture was stirred for 1 h. The reaction was filtered and the filtrate was concentrated to give 2-(4-(8-(but-3-en-1-yloxy)imidazo[1,2-a]pyrazin-6-yl)pyridin-2-yl)-N-ethylpropan-2-amine, which was used without additional purification. LCMS m/z (M+H): 352.2 required, 352.2 found.

To a solution of (S)-7,7,7-trifluorohept-1-en-4-amine hydrochloride A5 (29.0 mg, 0.142 mmol) in $CH_2Cl_2$ (1 mL) and sat.$NaHCO_3$(2 mL) was added bis(trichloromethyl) carbonate (13.93 mg, 0.047 mmol) and stirred at 0° C. for 30 min. 2-(4-(8-(but-3-en-1-yloxy)imidazo[1,2-a]pyrazin-6-yl) pyridin-2-yl)-N-ethylpropan-2-amine (50 mg, 0.142 mmol) was added and stirred at 25° C. for 2 hours. The mixture was extracted with EtOAc (10 mL×3), washed with brine (10 mL), dried over $Na_2SO_4$ and filtered. The filtrate was concentrated and purified by Flash silica gel chromatography (ISCO®; 4 g SepaFlash® Silica Flash Column, Eluent of 80% EtOAc/Pet.ether gradient) to give (S)-1-(2-(4-(8-(but-3-en-1-yloxy)imidazo[1,2-a]pyrazin-6-yl)pyridin-2-yl)propan-2-yl)-1-ethyl-3-(7,7,7-trifluorohept-1-en-4-yl)urea. LCMS m/z (M+H): 545.2 required, 545.2 found.

To a solution of (S)-1-(2-(4-(8-(but-3-en-1-yloxy)imidazo[1,2-a]pyrazin-6-yl)pyridin-2-yl)propan-2-yl)-1-ethyl-3-(7,7,7-trifluorohept-1-en-4-yl)urea (60 mg, 0.110 mmol) in DCE (50 mL) was added (1,3-dimesitylimidazolidin-2-ylidene)(2-isopropoxybenzylidene) ruthenium(vi) chloride (13.81 mg, 0.022 mmol). The mixture was stirred at 50° C. for 16 hours. The mixture was extracted with EtOAc (10 mL×3), washed with brine (10 mL), dried over $Na_2SO_4$ and filtered. The filtrate was concentrated and purified by Flash silica gel chromatography (ISCO®; 4 g SepaFlash® Silica Flash Column, Eluent of 80% EtOAc/Pet.ether gradient) to give (S,$1^7$E,9E)-4-ethyl-3,3-dimethyl-7-(3,3,3-trifluoropropyl)-13-oxa-4,6-diaza-1(6,8)-imidazo[1,2-a]pyrazina-2(4,2)-pyridinacyclotridecaphan-9-en-5-one. LCMS m/z (M+H): 517.2 required, 517.2 found.

To a solution of (S,$1^7$E,9E)-4-ethyl-3,3-dimethyl-7-(3,3,3-trifluoropropyl)-13-oxa-4,6-diaza-1(6,8)-imidazo[1,2-a]pyrazina-2(4,2)-pyridinacyclotridecaphan-9-en-5-one in EtOAc (2 mL) was added Pd-C(82 mg, 0.077 mmol) (10%) and stirred at 20° C. under H2 (0.156 mg, 0.077 mmol) (15 psi) for 1 h. The reaction was filtered and the filtrate was concentrated. The crude product was purified by Flash silica gel chromatography (ISCO®; 4 g SepaFlash® Silica Flash Column, Eluent of 100% EtOAc) to give (R,E)-4-ethyl-3, 3-dimethyl-7-(3,3,3-trifluoropropyl)-13-oxa-4,6-diaza-1(6,8)-imidazo[1,2-a]pyrazina-2(4,2)-pyridinacyclotridecaphan-5-one, (Example 143). LCMS m/z (M+H): 519.2 required, 519.2 found. $^{1}H$ NMR (400 MHz, $CD_3OD$) δ 8.75 (s, 1H), 8.41 (d, J=5.38 Hz, 1H), 8.10 (s, 1H), 7.97 (d, J=0.98 Hz, 1H), 7.67-7.55 (m, 2H), 5.96 (br d, J=9.29 Hz, 1H), 5.67-5.55 (m, 1H), 4.27-4.15 (m, 1H), 3.76-3.56 (m, 3H), 2.18-1.99 (m, 2H), 1.90-1.63 (m, 9H), 1.49-1.37 (m, 9H), 1.26-1.10 (m, 2H).

Example 144

(3R,7R,E)-4-ethyl-25-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-5-one (example 144)

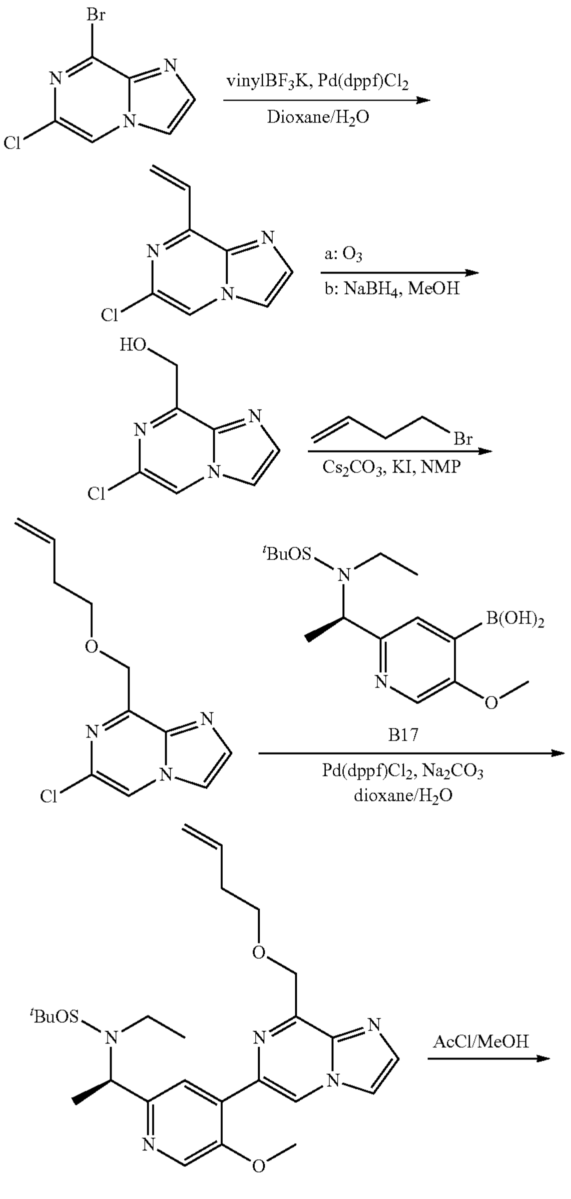

-continued

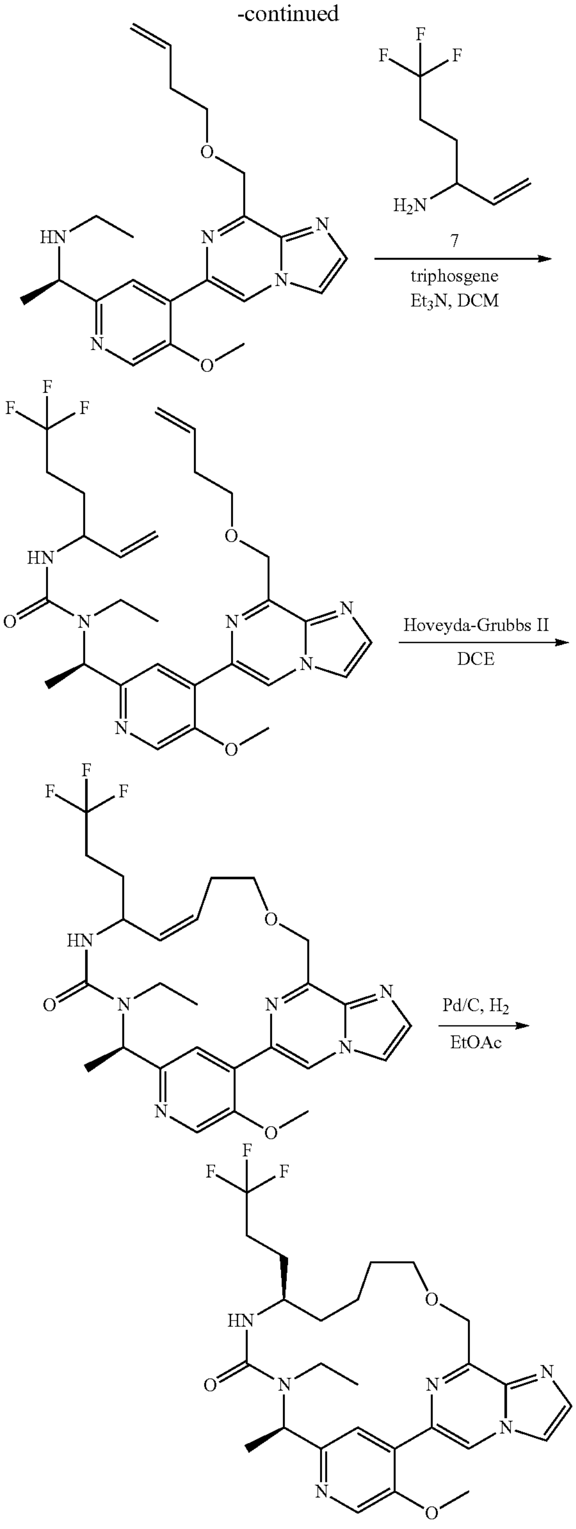

EXAMPLE 144

To a solution of 8-bromo-6-chloroimidazo[1,2-a]pyrazine (6 g, 25.8 mmol) in Dioxane (70 mL) and Water (20 mL) were added sodium carbonate (8.21 g, 77 mmol), potassium trifluoro(vinyl)borate (4.15 g, 31.0 mmol) and Pd(dppf)$Cl_2$ (0.944 g, 1.291 mmol), then the solution was stirred at 80° C. for 12 hours. The mixture was extracted with EtOAc (20 mL×3), washed with brine (15 mL), dried over $Na_2SO_4$ and filtered. The filtrate was concentrated and purified by Flash silica gel chromatography (ISCO®; 25 g SepaFlash® Silica Flash Column, Eluent of 80% EtOAc/Pet.ether gradient) to give 6-chloro-8-vinylimidazo[1,2-a]pyrazine. LCMS m/z (M+H): 180.2 required, 180.2 found.

To a solution of 6-chloro-8-vinylimidazo[1,2-a]pyrazine (3 g, 16.70 mmol) in DCM (50 mL) and MeOH (20 mL) was bubbling with ozone (excess) at −78° C. for 30 min. The mixture was stirred at 25° C. for 0.5 h. The reaction mixture of 6-chloroimidazo[1,2-a]pyrazine-8-carbaldehyde in 50 mL DCM and 20 mL MeOH was used in next step without purification. LCMS m/z (M+H): 182.1 required, 182.1 found.

To the mixture of 6-chloroimidazo[1,2-a]pyrazine-8-carbaldehyde (3 g, 16.52 mmol) in MeOH (70 mL) was added $NaBH_4$ (3.13 g, 83 mmol) at 0° C., then the mixture was stirred at 25° C. for 1 h. The reaction mixture was poured into water (10 mL), extracted with EtOAC (10 mL×3). The organic layer was washed with brine (10 mL), dried over $Na_2SO_4$ and filtered. The filtrate was concentrated and purified by Flash silica gel chromatography (ISCO®; 12 g SepaFlash® Silica Flash Column, Eluent of 80% EtOAc/Pet.ether gradient) to give (6-chloroimidazo[1,2-a]pyrazin-8-yl)methanol. LCMS m/z (M+H): 184.1 required, 184.1 found.

To a solution of (6-chloroimidazo[1,2-a]pyrazin-8-yl)methanol (500 mg, 2.72 mmol) in NMP (20 mL) were added $Cs_2CO_3$ (3549 mg, 10.89 mmol), potassium iodide (452 mg, 2.72 mmol) and 4-bromobut-1-ene (1103 mg, 8.17 mmol). The mixture was heat to 80° C. for 5 h. The reaction mixture was poured into water (50 mL) and extracted with EtOAc (3×30 mL), washed with brine (50 mL). The organic layer was dried over anhydrous sodium sulfate and evaporated under reduced pressure. The mixture was purified by Flash silica gel chromatography (ISCO®; 4 g SepaFlash® Silica Flash Column, Eluent of 100% EtOAc) to give 8-((but-3-en-1-yloxy)methyl)-6-chloroimidazo[1,2-a]pyrazine.
LCMS m/z (M+H): 238.1 required, 238.1 found.

To a mixture of B17 (250 mg, 0.762 mmol) in 1,4-Dioxane (4 mL) and Water (1 mL) were added 8-((but-3-en-1-yloxy)methyl)-6-chloroimidazo[1,2-a]pyrazine (120 mg, 0.505 mmol), $Na_2CO_3$ (161 mg, 1.515 mmol) and Xphos Pd G2 (31.8 mg, 0.040 mmol). The resulting mixture was stirred at 80° C. for 2 h. The reaction was extracted with EtOAc (5 mL×3), washed with brine (5 mL). The combined organic layers were dried over $Na_2SO_4$, filtered and the filtrate was concentrated. The residue was purified by Flash silica gel chromatography (ISCO®; 4 g SepaFlash® Silica Flash Column, Eluent of 100% EtOAc/Pet.ether to gradient) to give N—((R)-1-(4-(8-((but-3-en-1-yloxy)methyl)imidazo[1,2-a]pyrazin-6-yl)-5-methoxypyridin-2-yl)ethyl)-N-ethyl-2-methylpropane-2-sulfinamide.

To a mixture of N—((R)-1-(4-(8-((but-3-en-1-yloxy)methyl)imidazo[1,2-a]pyrazin-6-yl)-5-methoxypyridin-2-yl)ethyl)-N-ethyl-2-methylpropane-2-sulfinamide (160 mg, 0.329 mmol) in MeOH (3 mL) was added AcCl (0.047 mL, 0.659 mmol) at 0° C. The mixture was stirred at 0° C. for 30 mins. The mixture was concentrated to give (R)-1-(4-(8-((but-3-en-1-yloxy)methyl)imidazo[1,2-a]pyrazin-6-yl)-5-methoxypyridin-2-yl)-N-ethylethan-1-amine, which was used without purification. LCMS m/z (M+H): 382.2 required, 382.2 found.

To a solution of A8 (60 mg, 0.316 mmol) and TEA (0.221 mL, 1.582 mmol) in DCM (2 mL) was added bis(trichloromethyl) carbonate (31.0 mg, 0.104 mmol) at 0° C. and stirred for 30 mins. (R)-1-(4-(8-((but-3-en-1-yloxy)methyl)imidazo[1,2-a]pyrazin-6-yl)-5-methoxypyridin-2-yl)-N-ethylethan-1-amine (60 mg, 0.157 mmol) in DCM (1 mL) was added to the mixture. The mixture was stirred at 0° C. for 30 mins. The reaction mixture was poured into water (1 mL), extracted with DCM (2 mL×3). The organic layer was washed with brine (1 mL), dried over $Na_2SO_4$ and filtered. The filtrate was concentrated and purified by Flash silica gel chromatography (ISCO®; 4 g SepaFlash® Silica Flash Column, Eluent of 100% EtOAc) to give 1-((R)-1-(4-(8-((but-3-en-1-yloxy)methyl)imidazo[1,2-a]pyrazin-6-yl)-5-methoxypyridin-2-yl)ethyl)-1-ethyl-3-(6,6,6-trifluorohex-1-en-3-yl)urea. LCMS m/z (M+H): 561.3 required, 561.3 found.

To a solution of 1-((R)-1-(4-(8-((but-3-en-1-yloxy)methyl)imidazo[1,2-a]pyrazin-6-yl)-5-methoxypyridin-2-yl)ethyl)-1-ethyl-3-(6,6,6-trifluorohex-1-en-3-yl)urea (40 mg, 0.071 mmol) in DCE (20 mL) was added (1,3-dimesitylimidazolidin-2-ylidene)(2-isopropoxybenzylidene)ruthenium(VI) chloride (10 mg, 0.016 mmol) and stirred at 50° C. for 16 hours. The reaction was concentrated and purified by prep-TLC ($SiO_2$, EtOAc:MeOH=20:1) to give ($1^7$E,3R,8Z)-4-ethyl-25-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-8-en-5-one. LCMS m/z (M+H): 533.2 required, 533.3 found.

To a mixture of ($1^7$E,3R,8Z)-4-ethyl-25-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-8-en-5-one (15 mg, 0.028 mmol) in EtOAc (10 mL) was added Pd-C (10 mg, 9.40 μmol) (10%), and the resulting mixture was stirred at 20° C. for 30 mins under H2 (excess) (15 psi). The mixture was filtered and the filtrate was purified by prep-HPLC (29-59% ACN/water (0.1%)TFA) to give (3R,7R,E)-4-ethyl-25-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-5-one as the second eluting diastereomer (example 144). LCMS m/z (M+H): 535.2 required, 535.3 found. $^1$H NMR (400 MHz, $CD_3OD$) δ 9.59 (s, 1H), 8.53 (s, 1H), 8.45 (s, 1H), 8.25 (d, J=1.2 Hz, 1H), 7.91 (d, J=1.2 Hz, 1H), 5.89 (q, J=7.2 Hz, 1H), 5.20-5.04 (m, 2H), 4.22 (s, 3H), 4.04-3.91 (m, 1H), 3.83-3.72 (m, 1H), 3.68-3.56 (m, 1H), 3.45-3.33 (m, 1H), 3.24-3.09 (m, 1H), 2.33-2.16 (m, 2H), 1.84-1.70 (m, 4H), 1.67 (d, J=7.1 Hz, 3H), 1.63-1.54 (m, 2H), 1.46-1.37 (m, 1H), 1.14 (t, J=7.0 Hz, 3H).

Example 145

(3R,E)-4-ethyl-25-methoxy-3-methyl-12-oxa-4,6-diaza-1(6,8)-imidazo[1,2-a]pyrazina-2(4,2)-pyridina-7(1,2)-cyclopropanacyclododecaphan-5-one (example 145)

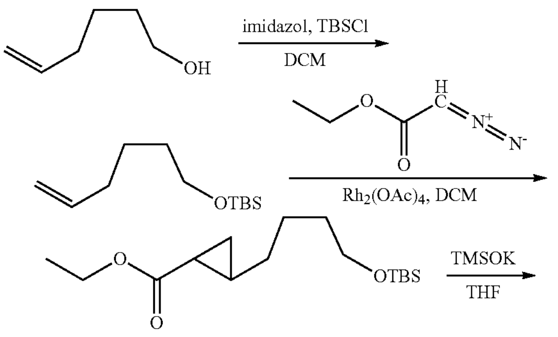

-continued

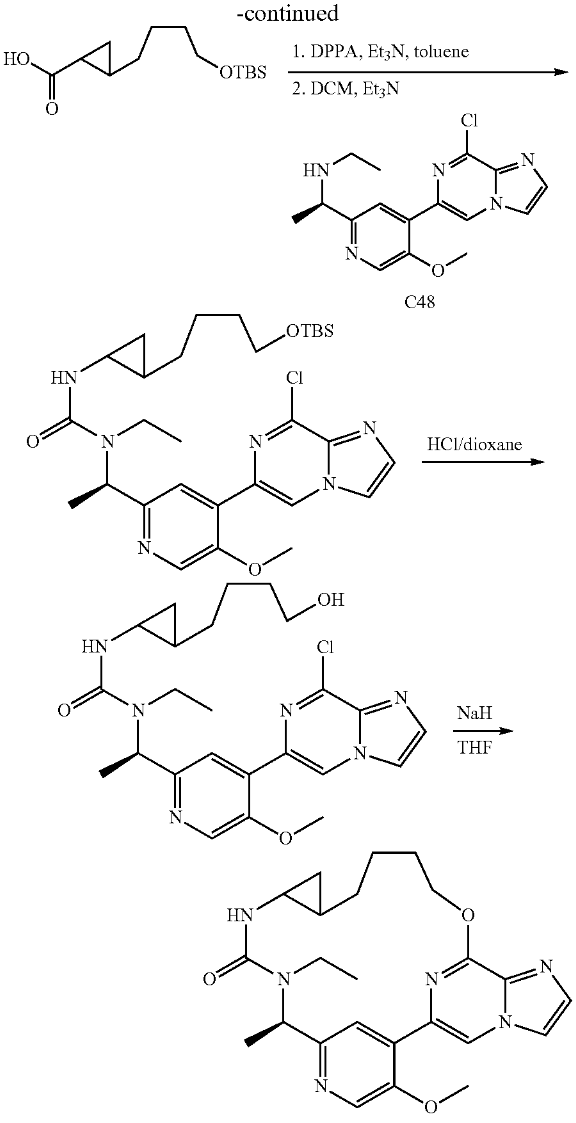

C48

EXAMPLE 145

To a mixture of hex-5-en-1-ol (10 g, 100 mmol) and imidazole (7.00 g, 103 mmol) in $CH_2Cl_2$ (150 mL) was added TBS-Cl(15.35 g, 102 mmol) at 0° C. The resulting mixture was stirred at 20° C. for 16 h. The reaction mixture was poured into water (50 mL) and extracted with DCM (3×50 mL), washed with brine (30 mL). The organic layer was dried over anhydrous sodium sulfate and evaporated under reduced pressure. The mixture was purified by Flash silica gel chromatography (ISCO®; 80 g SepaFlash® Silica Flash Column, Eluent of 100% Pet.ether gradient) to give tert-butyl(hex-5-en-1-yloxy)dimethylsilane. $^1$H NMR (400 MHz, $CDCl_3$) δ 5.82 (tdd, J=6.6, 10.3, 17.1 Hz, 1H), 5.07-4.88 (m, 2H), 3.62 (t, J=6.5 Hz, 2H), 2.07 (q, J=7.1 Hz, 2H), 1.60-1.50 (m, 2H), 1.47-1.38 (m, 2H), 0.90 (s, 9H), 0.06 (s, 6H).

To a mixture of tert-butyl(hex-5-en-1-yloxy)dimethylsilane (4 g, 18.65 mmol) and Rhodium(ii) acetate dimer (0.412 g, 0.933 mmol) in DCM (30 mL) was added ethyl 2-diazoacetate (4.26 g, 37.3 mmol) in DCM (10 mL) within 5 h. The resulting mixture was stirred at 20° C. for 16 h. The reaction mixture was filtered and the filtrate was concentrated. The mixture was purified by Flash silica gel chromatography (ISCO®; 40 g SepaFlash® Silica Flash Column, Eluent of 20% EtOAc/Pet.ether gradient) to give ethyl 2-(4-((tert-butyldimethylsilyl)oxy)butyl)cyclopropane-1-carboxylate. $^1$H NMR (400 MHz, $CDCl_3$) δ 4.31-4.21 (m, 1H), 4.17-4.02 (m, 2H), 3.60 (dt, J=3.8, 6.3 Hz, 2H), 1.70-1.40 (m, 4H), 1.36-1.22 (m, 7H), 1.19-1.09 (m, 0.5H), 0.95-0.85 (m, 9H), 0.73-0.61 (m, 0.5H), 0.12-0.04 (m, 6H).

To a mixture of ethyl 2-(4-((tert-butyldimethylsilyl)oxy)butyl)cyclopropane-1-carboxylate (1 g, 3.33 mmol) in THF (20 mL) was added potassium trimethylsilanolate (4.27 g, 33.3 mmol). The resulting mixture was stirred at 20° C. for 16 h. The mixture was adjusted to pH=3. The layers were separated and the aqueous phase was extracted with EtOAc (10 mL×2). The combined organics were dried over $Na_2SO_4$, filtered and the filtrate was concentrated give 2-(4-((tert-butyldimethylsilyl)oxy)butyl)cyclopropane-1-carboxylic acid. $^1$H NMR (400 MHz, $CDCl_3$) δ 3.61 (t, J=6.2 Hz, 2H), 1.74-1.51 (m, 3H), 1.45 (br dd, J=7.1, 13.7 Hz, 2H), 1.40-1.30 (m, 3H), 1.29-1.21 (m, 1H), 1.11-0.95 (m, 0.5H), 0.90 (s, 9H), 0.83-0.77 (m, 0.5H), 0.05 (s, 6H).

To a solution of 2-(4-((tert-butyldimethylsilyl)oxy)butyl)cyclopropane-1-carboxylic acid (300 mg, 1.101 mmol) in Toluene (5 mL) was added triethylamine (557 mg, 5.51 mmol) and diphenylphosphinyl azide (321 mg, 1.321 mmol). The mixture was stirred at 90° C. for 1 h. The mixture was concentrated, and DCM (6 mL) was added and then TEA (0.750 mL, 5.38 mmol) was added, and then C48 (250 mg, 0.753 mmol). The mixture was stirred at 0° C. for 30 mins. The reaction was diluted with $H_2O$(3 mL) and extracted with DCM (5 mL×3). The combined organic layers were dried over sodium sulfate. Filtrated and the filtrate was concentrated in vacuo. The crude product was purified by silica gel chromatography (ISCO®; 4 g SepaFlash® Silica Flash Column, eluent of 50-100% ethyl acetate/pet. ether gradient @ 20 mL/min) to give 3-(2-(4-((tert-butyldimethylsilyl)oxy)butyl)cyclopropyl)-1-((R)-1-(4-(8-chloroimidazo[1,2-a]pyrazin-6-yl)-5-methoxypyridin-2-yl)ethyl)-1-ethylurea. LCMS m/z (M+H): 601.3 found, 601.2 required.

To a mixture of 3-(2-(4-((tert-butyldimethylsilyl)oxy)butyl)cyclopropyl)-1-((R)-1-(4-(8-chloroimidazo[1,2-a]pyrazin-6-yl)-5-methoxypyridin-2-yl)ethyl)-1-ethylurea (200 mg, 0.333 mmol) in Dioxane (4 mL) was added HCl-dioxane (0.166 mL, 0.665 mmol) (4 M in dioxane), and the resulting mixture was stirred at 0° C. for 30 mins. Aqueous $NaHCO_3$(4 mL) was added to the mixture. The reaction mixture was extracted with EtOAc (4 mL×3). The combined organic layers were washed with brine (2 mL), dried over $Na_2SO_4$ and filtered. The filtrate was concentrated to give 1-((R)-1-(4-(8-chloroimidazo[1,2-a]pyrazin-6-yl)-5-methoxypyridin-2-yl)ethyl)-1-ethyl-3-(2-(4-hydroxybutyl)cyclopropyl)urea which was used without further purification. LCMS m/z (M+H): 487.1 required, 486.8 found.

To a mixture of 1-((R)-1-(4-(8-chloroimidazo[1,2-a]pyrazin-6-yl)-5-methoxypyridin-2-yl)ethyl)-1-ethyl-3-(2-(4-hydroxybutyl)cyclopropyl)urea (160 mg, 0.329 mmol) in THF (5 mL) was added NaH (65.7 mg, 1.643 mmol) (60%), and the resulting mixture was stirred at 0° C. for 2 h. $H_2O$(3 mL) was added to the mixture. The reaction mixture was extracted with EtOAc (5 mL×3).The combined organic layers were washed with brine (5 mL), dried over $Na_2SO_4$ and filtered. The filtrate was concentrated and purified by silica gel chromatography (ISCO®; 4 g SepaFlash® Silica Flash Column, eluent of 100% ethyl acetate/pet. ether gradient @ 20 mL/min) to give 2 separable isomers which were further separated by SFC ((R,R)WHELK-01, 50% 0.1%

$NH_4OH/MeOH—CO_2$) to give (3R,E)-4-ethyl-25-methoxy-3-methyl-12-oxa-4,6-diaza-1(6,8)-imidazo[1,2-a]pyrazina-2(4,2)-pyridina-7(1,2)-cyclopropanacyclododecaphan-5-one as 4 separable but stereochemically unassigned diastereomers with the most active being the last eluting of the second eluting isomer after initial silica chromatography (example 145). LCMS m/z (M+H): 451.2 required, 451.4 found. 1H NMR (400 MHz, $CD_3OD$) δ 9.22 (s, 1H), 8.35 (d, J=4.7 Hz, 2H), 8.04 (d, J=0.8 Hz, 1H), 7.63 (d, J=1.2 Hz, 1H), 6.12-6.01 (m, 2H), 5.16-4.97 (m, 1H), 4.33 (dt, J=4.5, 11.1 Hz, 1H), 4.17 (s, 3H), 3.13-2.90 (m, 2H), 2.79 (br d, J=3.1 Hz, 1H), 2.07-1.95 (m, 1H), 1.77-1.59 (m, 3H), 1.54 (d, J=7.0 Hz, 3H), 1.44 (br d, J=10.6 Hz, 1H), 1.17-1.05 (m, 1H), 0.93-0.87 (m, 2H), 0.72 (t, J=7.0 Hz, 3H), 0.39-0.29 (m, 1H).

Example 146

(3R,7R,E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-5-one (example 146)

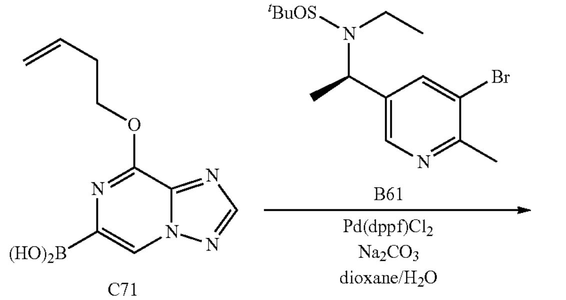

C71

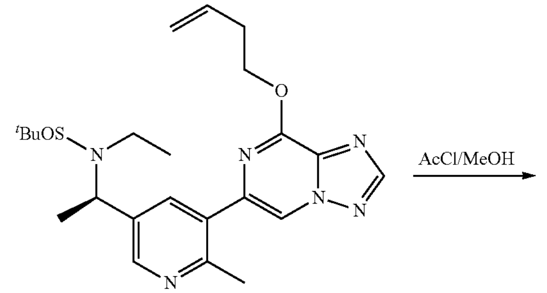

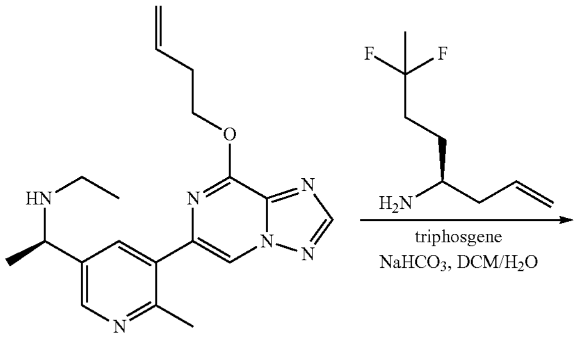

-continued

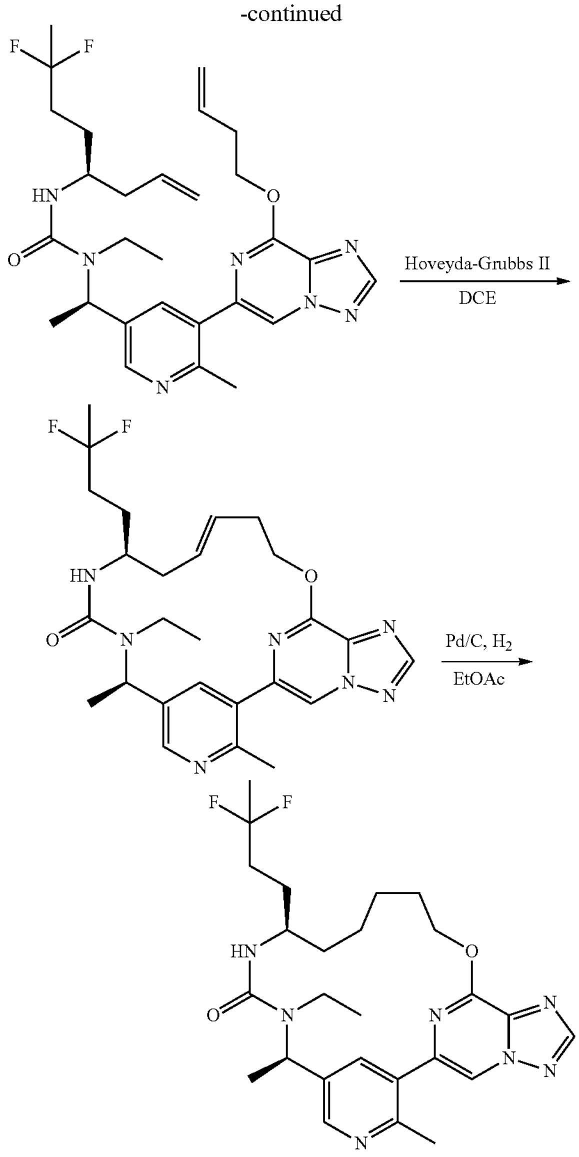

EXAMPLE 146

To a solution of C71 (290 mg, 1.239 mmol) (0.186 M in dioxane) in Water (1.5 mL) was added N—((R)-1-(5-bromo-6-methylpyridin-3-yl) ethyl)-N-ethyl-2-methylpropane-2-sulfinamide B61 (344 mg, 0.991 mmol), $Na_2CO_3$ (394 mg, 3.72 mmol) and Pd(dppf)$Cl_2$ (91 mg, 0.124 mmol). The mixture was stirred at 90° C. for 3 hours. The reaction mixture was poured into water (5 mL), extracted with EtOAc (5 mL×3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of [80-90]% ethyl acetate/pet. ether gradient) to give N—((R)-1-(5-(8-(but-3-en-1-yloxy)-[1,2,4]triazolo[1,5-a]pyrazin-6-yl)-6-methylpyridin-3-yl)ethyl)-N-ethyl-2-methylpropane-2-sulfinamide. LCMS m/z (M+H): 457.2 required, 457.3 found.

To a solution of N—((R)-1-(5-(8-(but-3-en-1-yloxy)-[1,2,4]triazolo[1,5-a]pyrazin-6-yl)-6-methylpyridin-3-yl) ethyl)-N-ethyl-2-methylpropane-2-sulfinamide (230 mg, 0.504 mmol) in MeOH (4 mL) were added AcCl (0.072 mL, 1.007 mmol). The mixture was stirred at 20° C. for 2 hours. The crude product (R)-1-(5-(8-(but-3-en-1-yloxy)-[1,2,4]triazolo[1,5-a]pyrazin-6-yl)-6-methylpyridin-3-yl)-N-ethylethan-1-amine was used for next step without purification. LCMS m/z (M+H): 353.2 required, 352.8 found.

To a solution of (S)-7,7-difluorooct-1-en-4-amine A21 (104 mg, 0.638 mmol) in DCM (3 mL) and sat.$NaHCO_3$(3 mL) was added triphosgene (63.1 mg, 0.213 mmol) and stirred at 0° C. for 30 min. (R)-1-(5-(8-(but-3-en-1-yloxy)-[1,2,4]triazolo[1,5-a]pyrazin-6-yl)-6-methylpyridin-3-yl)-N-ethylethan-1-amine (150 mg, 0.426 mmol) was added and stirred at 15° C. for 1 hour. Then the mixture was quenched with water (3 mL), extracted with DCM (3 mL×3). The combined organic layers were washed with brine (5 mL), dried over $Na_2SO_4$. The crude product was purified by prep-TLC ($SiO_2$, EtOAc) to give 1-((R)-1-(5-(8-(but-3-en-1-yloxy)-[1,2,4]triazolo[1,5-a]pyrazin-6-yl)-6-methylpyridin-3-yl)ethyl)-3-((S)-7,7-difluorooct-1-en-4-yl)-1-ethylurea. LCMS m/z (M+H): 542.6 found, 542.3 required.

To a solution of 1-((R)-1-(5-(8-(but-3-en-1-yloxy)-[1,2,4]triazolo[1,5-a]pyrazin-6-yl)-6-methylpyridin-3-yl)ethyl)-3-((S)-7,7-difluorooct-1-en-4-yl)-1-ethylurea (200 mg, 0.369 mmol) in DCE (200 mL) were added (1,3-dimesitylimidazolidin-2-ylidene)(2-isopropoxybenzylidene)ruthenium(vi) chloride (23.14 mg, 0.037 mmol). The mixture was stirred at 50° C. for 12 hours. The reaction mixture was concentrated and part of the product was purified by flash silica gel chromatography (ISCO®; 4 g SepaFlash® Silica Flash Column, eluent of [20~30]% ethyl acetate/pet. ether gradient) to give ($1^7$E,3R,7S,9E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-9-en-5-one. LCMS m/z (M+H): 514.2 required, 514.2 found.

To a solution of ($1^7$E,3R,7S,9E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-9-en-5-one (80 mg, 0.156 mmol) in EtOAc (5 mL) were added Pd-C(16.58 mg, 0.016 mmol). The mixture was stirred at 20° C. for 2 hours under H2 (15 psi). The mixture was filtered and concentrated and purified by prep-HPLC (ODS, 18-48% ACN/water with 0.1% TFA) to give (3R,7R,E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-5-one (example 146). LCMS m/z (M+H): 516.2 required, 516.3 found. $^1$H NMR (400 MHz, MeOD) δ 8.90 (s, 1H), 8.69 (br d, J=20.0 Hz, 2H), 8.58 (s, 1H), 6.07-5.90 (m, 1H), 5.05-4.94 (m, 1H), 4.65-4.55 (m, 1H), 4.00-3.87 (m, 1H), 3.28-3.09 (m, 2H), 2.99 (s, 3H), 2.06-1.83 (m, 5H), 1.68 (br d, J=7.0 Hz, 4H), 1.64-1.52 (m, 8H), 1.40 (br d, J=5.1 Hz, 2H), 1.10 (br t, J=7.0 Hz, 3H)

Example 147

(3R,7R,E)-4-ethyl-25-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-5-one (example 147)

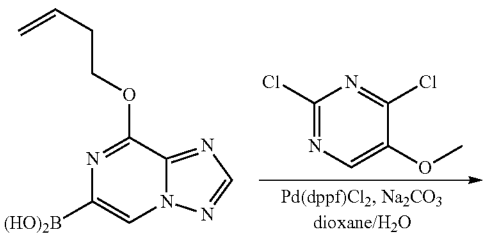

C71

-continued

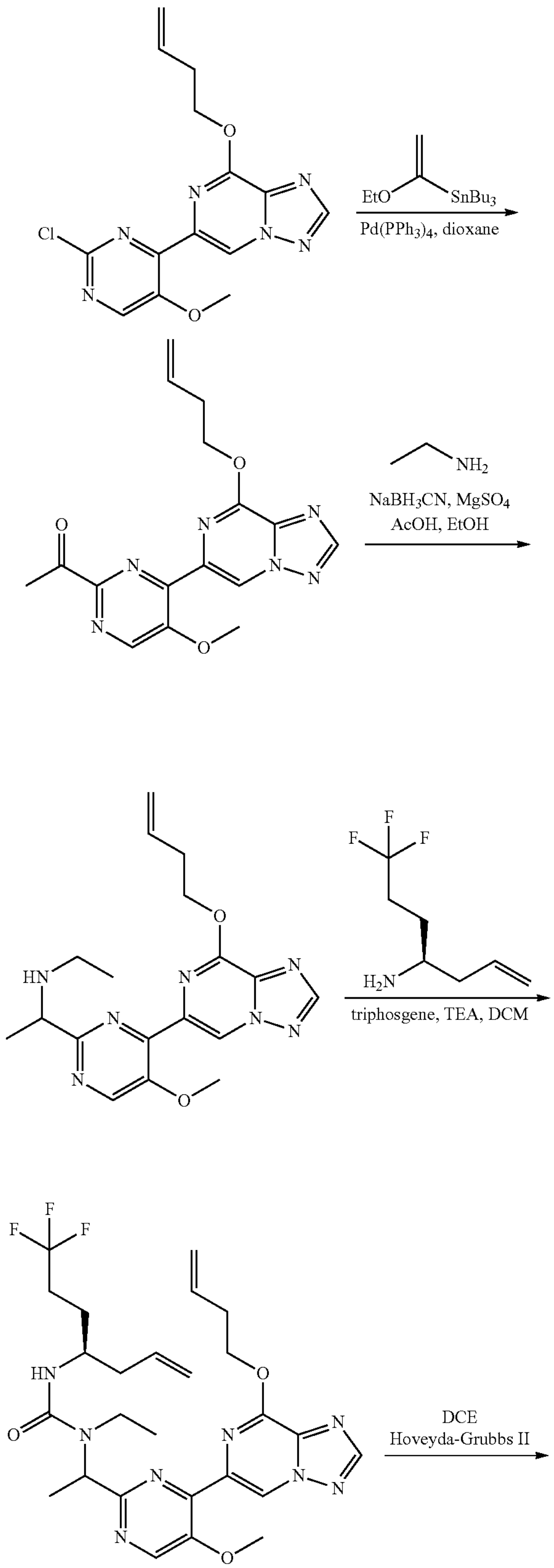

-continued

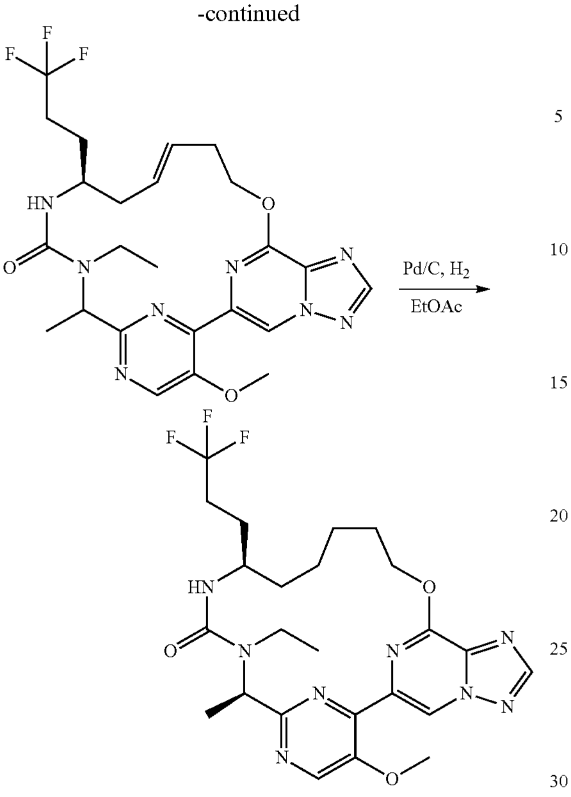

EXAMPLE 147

To a mixture of (8-(but-3-en-1-yloxy)-[1,2,4]triazolo[1,5-a]pyrazin-6-yl)boronic acid C71 (500 mg, 2.137 mmol) in 1,4-Dioxane (12 mL) and water (3 mL) was added 2,4-dichloro-5-methoxypyrimidine (382 mg, 2.137 mmol), $Na_2CO_3$ (679 mg, 6.41 mmol) and Pd(dppf)$Cl_2$ (78 mg, 0.107 mmol). The resulting mixture was stirred at 90° C. for 2 h. The reaction mixture was poured into water (10 mL), extracted with EtOAc (10 mL×3), washed with brine (10 mL). The organic layer was dried over $Na_2SO_4$, filtered and concentrated. The reaction mixture was filtered and concentrated. The residue was purified by flash silica gel chromatography (ISCO®; 12 g Biotage® Silica Flash Column, Eluent of 30%-50% EtOAc/Pet.ether gradient) to give 8-(but-3-en-1-yloxy)-6-(2-chloro-5-methoxypyrimidin-4-yl)-[1,2,4]triazolo[1,5-a]pyrazine. LCMS m/z (M+H): 333.2 required, 333.2 found.

To a mixture of 8-(but-3-en-1-yloxy)-6-(2-chloro-5-methoxypyrimidin-4-yl)-[1,2,4]triazolo[1,5-a]pyrazine (612 mg, 1.695 mmol) in 1,4-Dioxane (6 mL) was added Pd($Ph_3P$)$_4$ (163 mg, 0.141 mmol). The resulting mixture was stirred at 90° C. for 16 h. Aq KF (10 mL) was added to the mixture and stirred 15 mins, extracted with EtOAc (10 mL×3), washed with brine (5 mL). The organic layer was dried over $Na_2SO_4$, filtered and the filtrate was concentrated to give the crude vinyl ether which was dissolved in THF (4 mL). HCl (4 mL, 16.00 mmol) (4 M in $H_2O$) was added and the mixture was stirred at 20° C. for 1 h. aq. $NaHCO_3$(20 mL) was added to the mixture, and extracted with EtOAc (3×10 mL), washed with brine (5 mL). The organic layer was dried over anhydrous sodium sulfate, filtered and the filtrate was concentrated. The residue was purified by Flash silica gel chromatography (ISCO®; 4 g SepaFlash® Silica Flash Column, Eluent of 100% EtOAc) to give 1-(4-(8-(but-3-en-1-yloxy)-[1,2,4]triazolo[1,5-a]pyrazin-6-yl)-5-methoxypyrimidin-2-yl)ethan-1-one. LCMS m/z (M+H): 341.2 required, 341.2 found.

To a mixture of 1-(4-(8-(but-3-en-1-yloxy)-[1,2,4]triazolo[1,5-a]pyrazin-6-yl)-5-methoxypyrimidin-2-yl)ethan-1-one (53.0 mg, 1.175 mmol) in EtOH (3 mL) was added $NaCNBH_3$ (73.9 mg, 1.175 mmol), $MgSO_4$ (354 mg, 2.94 mmol) and AcOH (0.034 mL, 0.588 mmol). The resulting mixture was stirred at 90° C. for 5 h. $H_2O$(5 mL) was added to the mixture, extracted with EtOAc (5 mL×3), washed with brine (5 mL). The organic layer was dried over $Na_2SO_4$, filtered and concentrated. The reaction mixture was filtered and concentrated. The residue was purified by Flash silica gel chromatography (ISCO®; 4 g SepaFlash® Silica Flash Column, Eluent of 100% EtOAc) to give 1-(4-(8-(but-3-en-1-yloxy)-[1,2,4]triazolo[1,5-a]pyrazin-6-yl)-5-methoxypyrimidin-2-yl)-N-ethylethan-1-amine. LCMS m/z (M+H): 370.2 required, 370.2 found.

To a solution of (S)-7,7,7-trifluorohept-1-en-4-amine A5 (0.1 g, 0.598 mmol) and TEA (0.834 mL, 5.98 mmol) in DCM (2 mL) was added triphosgene (0.089 g, 0.299 mmol) at 0° C. and stirred for 30 mins. 1-(4-(8-(but-3-en-1-yloxy)-[1,2,4]triazolo[1,5-a]pyrazin-6-yl)-5-methoxypyrimidin-2-yl)-N-ethylethan-1-amine (0.15 g, 0.406 mmol) in DCM (1 mL) was added to the mixture. The mixture was stirred at 0° C. for 30 mins. The reaction mixture was poured into water (2 mL), extracted with DCM (2 mL×3). The organic layer was washed with brine (2 mL), dried over $Na_2SO_4$ and filtered. The filtrate was concentrated and purified by Flash silica gel chromatography (ISCO®; 4 g SepaFlash® Silica Flash Column, Eluent of 100% EtOAc) to give 1-(1-(4-(8-(but-3-en-1-yloxy)-[1,2,4]triazolo[1,5-a]pyrazin-6-yl)-5-methoxypyrimidin-2-yl)ethyl)-1-ethyl-3-((S)-7,7,7-trifluorohept-1-en-4-yl)urea. LCMS m/z (M+H): 563.3 required, 563.3 found.

To a solution of 1-(1-(4-(8-(but-3-en-1-yloxy)-[1,2,4]triazolo[1,5-a]pyrazin-6-yl)-5-methoxypyrimidin-2-yl)ethyl)-1-ethyl-3-((S)-7,7,7-trifluorohept-1-en-4-yl)urea (175 mg, 0.311 mmol) in $ClCH_2CH_2Cl$ (60 mL) was added (1,3-dimesitylimidazolidin-2-ylidene)(2-isopropoxybenzylidene)ruthenium(VI) chloride (39.0 mg, 0.062 mmol) and stirred at 50° C. for 16 hours. The mixture was purified by Flash silica gel chromatography (ISCO®; 4 g SepaFlash® Silica Flash Column, Eluent of 100% EtOAc) to give ($1^7$E,7S,9E)-4-ethyl-25-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-9-en-5-one. LCMS m/z (M+H): 535.2 required, 535.3 found.

To a mixture of ($1^7$E,7S,9E)-4-ethyl-25-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-9-en-5-one (105 mg, 0.196 mmol) in EtOAc (15 mL) was added Pd-C (40 mg, 0.038 mmol) (10%), and the resulting mixture was stirred at 15° C. for 30 mins under H2 (excess) (15 psi). The mixture was filtered and the filtrate was concentrated. The residue was purified by Flash silica gel chromatography (ISCO®; 4 g SepaFlash® Silica Flash Column, Eluent of 100% EtOAc) and prep-HPLC (ODS, 46-66% ACN/water with 0.1% TFA) to give (3R,7R,E)-4-ethyl-25-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-5-one (example 147) as the second eluting diastereomer. LCMS m/z (M+H): 537.3 required, 537.3 found. $^1$H NMR (400 MHz, $CD_3OD$) δ 9.25 (s, 1H), 8.70 (s, 1H), 8.56 (s, 1H), 5.91 (q, J=6.9 Hz, 1H), 4.96-4.91 (m, 1H), 4.83-4.74 (m, 1H), 4.15 (s, 3H), 3.96 (br s, 1H), 3.27-3.13 (m, 2H), 2.29-2.15 (m, 2H), 2.07-1.91 (m, 2H), 1.79-1.68 (m, 2H), 1.62 (br d, J=7.1 Hz, 6H), 1.51-1.27 (m, 3H), 0.98 (t, J=7.1 Hz, 3H).

Example 148

(3R,7S,E)-7-(3,3-difluorobutyl)-4-ethyl-22-methoxy-3-methyl-10,13-dioxa-4,6-diaza-1(6,8)-[1,2,4]triazolo[1,5-a]pyrazina-2(3,5)-pyridinacyclotridecaphan-5-one (example 148)

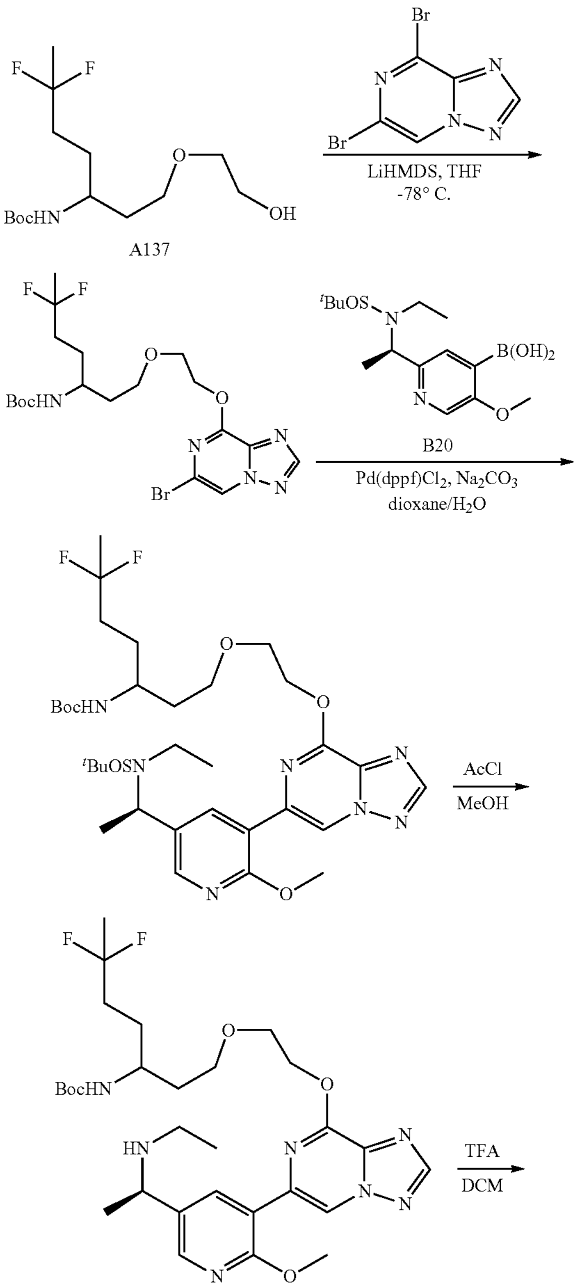

-continued

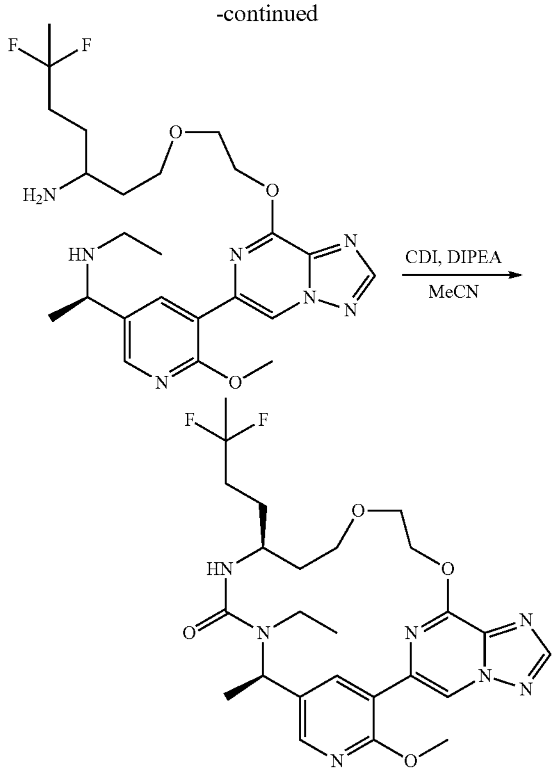

EXAMPLE 148

To a solution of A137 (200 mg, 0.642 mmol) in THF (5 mL) was added LiHMDS (0.963 mL, 0.963 mmol) (1M in THF) at −78° C. and stirred at −78° C. for 30 mins. Then 6,8-dibromo-[1,2,4]triazolo[1,5-a]pyrazine (182 mg, 0.655 mmol) was added to the above mixture and stirred at 20° C. for 1 hour. The mixture was quenched with $H_2O$(15 mL) and extracted with EtOAc (20 mL×3), washed with brine (20 mL), dried over $Na_2SO_4$, filtered and concentrated under reduced pressure. The crude was purified by Flash silica gel chromatography (ISCO®; 12 g SepaFlash® Silica Flash Column, Eluent of 80% EtOAc/Pet.ether gradient) to give tert-butyl (1-(2-((6-bromo-[1,2,4]triazolo[1,5-a]pyrazin-8-yl)oxy)ethoxy)-6,6-difluoroheptan-3-yl)carbamate. LCMS m/z (M+H): 510.1 required, 510.0 found.

To a solution of (5-((1R)-1-((tert-butylsulfinyl)(ethyl)amino)ethyl)-2-methoxypyridin-3-yl)boronic acid B20 (142 mg, 0.433 mmol) in Dioxane (5 mL) and Water (1 mL) were added compound tert-butyl (1-(2-((6-bromo-[1,2,4]triazolo[1,5-a]pyrazin-8-yl)oxy)ethoxy)-6,6-difluoroheptan-3-yl)carbamate (200 mg, 0.393 mmol), $Na_2CO_3$ (83 mg, 0.787 mmol) and $Pd(dppf)Cl_2$ (28.8 mg, 0.039 mmol). The mixture was stirred at 80° C. for 12 hours. The reaction mixture was poured into water (20 mL), extracted with EtOAc (20 mL×3). The organic layer was washed with brine (20 mL), dried over $Na_2SO_4$ and filtered. The filtrate was concentrated and purified by flash silica gel chromatography (ISCO®; 12 g SepaFlash® Silica Flash Column, eluent of 90% ethyl acetate/pet. ether gradient) to give tert-butyl (1-(2-((6-(5-((1R)-1-((tert-butylsulfinyl)(ethyl)amino)ethyl)-2-methoxypyridin-3-yl)-[1,2,4]triazolo[1,5-a]pyrazin-8-yl)oxy)ethoxy)-6,6-difluoroheptan-3-yl)carbamate. LCMS m/z (M+H): 712.4 required, 712.4 found.

To a solution of tert-butyl (1-(2-((6-(5-((1R)-1-((tert-butylsulfinyl)(ethyl)amino)ethyl)-2-methoxypyridin-3-yl)-[1,2,4]triazolo[1,5-a]pyrazin-8-yl)oxy)ethoxy)-6,6-difluoroheptan-3-yl)carbamate (160 mg, 0.225 mmol) in MeOH (2 mL) was added acetyl chloride (52.9 mg, 0.674 mmol). The mixture was stirred at 20° C. for 12 hours. The mixture was concentrated to give tert-butyl (1-(2-((6-(5-((R)-1-(ethylamino)ethyl)-2-methoxypyridin-3-yl)-[1,2,4]triazolo[1,5-a]pyrazin-8-yl)oxy)ethoxy)-6,6-difluoroheptan-3-yl)carbamate which was used to the next step without further purification. LCMS m/z (M+H): 608.3 required, 608.4 found.

To a solution of tert-butyl (1-(2-((6-(5-((R)-1-(ethylamino)ethyl)-2-methoxypyridin-3-yl)-[1,2,4]triazolo[1,5-a]pyrazin-8-yl)oxy)ethoxy)-6,6-difluoroheptan-3-yl)carbamate (137 mg, 0.225 mmol) in DCM (1 mL) was added TFA (0.5 mL). The mixture was stirred at 20° C. for 12 hours. The mixture was concentrated to give 1-(2-((6-(5-((R)-1-(ethylamino)ethyl)-2-methoxypyridin-3-yl)-[1,2,4]triazolo[1,5-a]pyrazin-8-yl)oxy)ethoxy)-6,6-difluoroheptan-3-amine which was used to the next step without further purification. LCMS m/z (M+H): 508.3 required, 508.3 found.

To the mixture of 1-(2-((6-(5-((R)-1-(ethylamino)ethyl)-2-methoxypyridin-3-yl)-[1,2,4]triazolo[1,5-a]pyrazin-8-yl)oxy)ethoxy)-6,6-difluoroheptan-3-amine (117 mg, 0.231 mmol) and DIPEA (0.403 mL, 2.305 mmol) in MeCN (5 mL) was added CDI (74.8 mg, 0.461 mmol). The mixture was stirred at 30° C. for 24 h. The mixture was quenched with $H_2O$(10 mL) and extracted with EtOAc (20 mL×3), washed with brine (20 mL), dried over $Na_2SO_4$, filtered and concentrated under reduced pressure. The crude product was purified by Flash silica gel chromatography (ISCO®; 4 g SepaFlash® Silica Flash Column, Eluent of 100% EtOAc/Pet.ether gradient) and separated by SFC (Chiralpak AS, 5-40% EtOH with 0.05% DEA/$CO_2$) to give (3R,7S,E)-7-(3,3-difluorobutyl)-4-ethyl-22-methoxy-3-methyl-10,13-dioxa-4,6-diaza-1(6,8)-[1,2,4]triazolo[1,5-a]pyrazina-2(3,5)-pyridinacyclotridecaphan-5-one (example 148) as the first eluting diastereomer. LCMS m/z (M+H): 534.3 required, 534.3 found. $^1$H NMR (400 MHz, $CDCl_3$) δ 9.28 (s, 1H), 8.57 (d, J=2.0 Hz, 1H), 8.40 (s, 1H), 8.12 (d, J=1.6 Hz, 1H), 6.01 (q, J=6.8 Hz, 1H), 5.04 (dt, J=5.9, 10.2 Hz, 1H), 4.77 (dt, J=5.1, 10.4 Hz, 1H), 4.37 (d, J 8.2 Hz, 1H), 4.28-4.18 (m, 1H), 4.14 (s, 3H), 3.93 (dt, J=5.1, 9.6 Hz, 1H), 3.85-3.75 (m, 1H), 3.70-3.61 (m, 2H), 3.16-2.94 (m, 2H), 2.06-1.90 (m, 3H), 1.79-1.49 (m, 10H), 1.16 (t, J=7.0 Hz, 3H)

Example 149

(3R,7R,E)-4-ethyl-25-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-5-one (example 149)

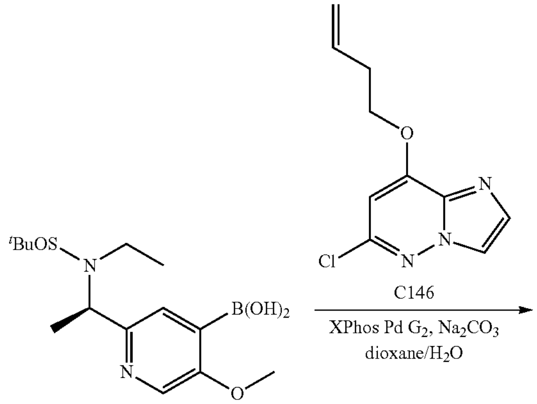

C146

B17

-continued

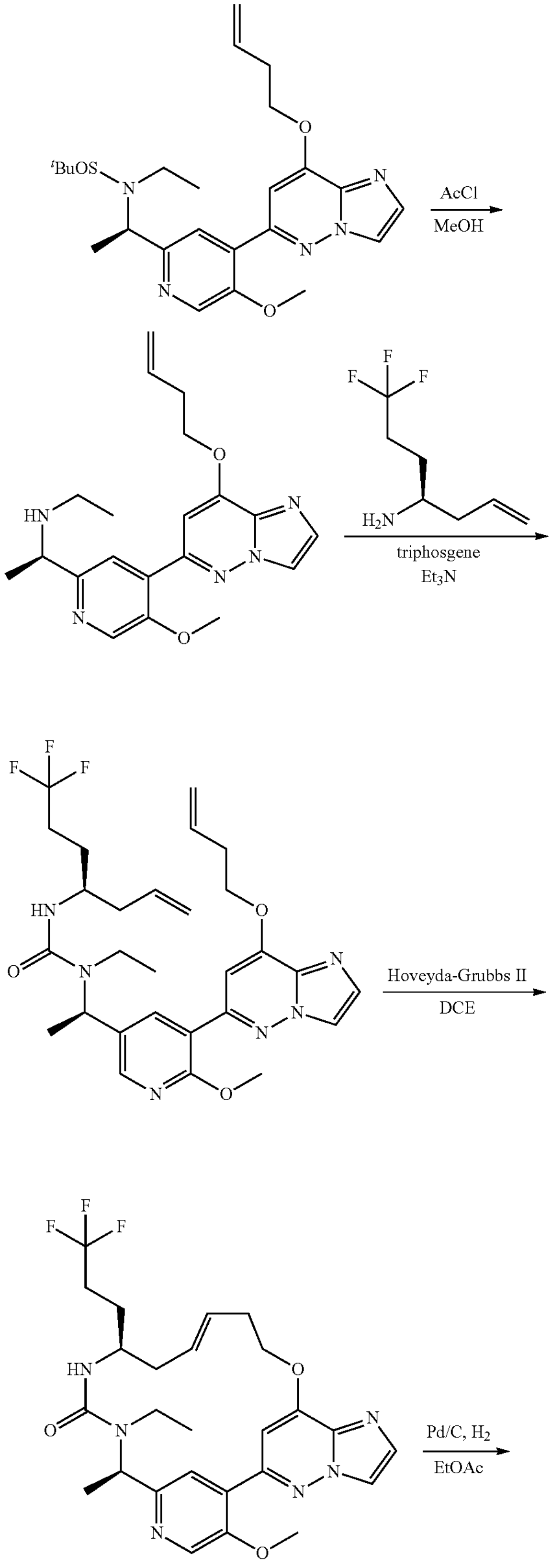

-continued

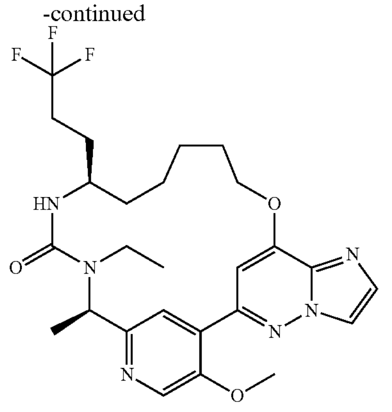

EXAMPLE 149

To a solution of B17 (200 mg, 0.609 mmol) in 14 mL dioxane were added water (4 mL), $Na_2CO_3$ (194 mg, 1.828 mmol), C146 (164 mg, 0.731 mmol) and chloro (2-dicyclohexylphosphino-2', 4', 6'-triisopropyl-1, 1'-biphenyl) [2-(2'-amino-1, 1'-biphenyl)]palladium (II) (47.9 mg, 0.061 mmol). The mixture was stirred at 80° C. for 2 h. The reaction mixture was poured into water (20 mL), extracted with EtOAc (20 mL×3). The organic layer was washed with brine (10 mL), dried over $Na_2SO_4$, filtered and concentrated. The crude was purified by Flash silica gel chromatography (ISCO®; 4 g SepaFlash® Silica Flash Column, Eluent of 100% EtOAc/Pet.ether gradient) to give N—((R)-1-(4-(8-(but-3-en-1-yloxy)imidazo[1,2-b]pyridazin-6-yl)-5-methoxypyridin-2-yl)ethyl)-N-ethyl-2-methylpropane-2-sulfinamide. LCMS m/z (M+H): 472.2 required, 472.3 found.

To a solution of N—((R)-1-(4-(8-(but-3-en-1-yloxy)imidazo[1,2-b]pyridazin-6-yl)-5-methoxypyridin-2-yl)ethyl)-N-ethyl-2-methylpropane-2-sulfinamide (195 mg, 0.413 mmol) in MeOH (3 mL) were added AcCl (0.059 mL, 0.827 mmol). The solution was stirred at 25° C. for 1 h. LCMS showed the desired product was found. The mixture was concentrated to give (R)-1-(4-(8-(but-3-en-1-yloxy)imidazo[1,2-b]pyridazin-6-yl)-5-methoxypyridin-2-yl)-N-ethylethan-1-amine which was used to the next step without further purification. LCMS m/z (M+H): 368.2 required, 368.1 found.

To a solution of (S)-7, 7, 7-trifluorohept-1-en-4-amine A5 (100 mg, 0.598 mmol) in DCM (3 mL) was added TEA (0.417 mL, 2.99 mmol), TRIPHOSGENE (89 mg, 0.299 mmol) and stirred at 0° C. for 30 min. (R)-1-(4-(8-(but-3-en-1-yloxy)imidazo[1,2-b]pyridazin-6-yl)-5-methoxypyridin-2-yl)-N-ethylethan-1-amine (154 mg, 0.419 mmol) was added and stirred at 15° C. for 2 hours. The mixture was quenched with $H_2O$(10 mL) and extracted with EtOAc (10 mL×3), washed with brine (10 mL), dried over $Na_2SO_4$, filtered and concentrated under reduced pressure to give the crude. The filtrate was concentrated and purified by flash silica gel chromatography (ISCO®; 4 g SepaFlash® Silica Flash Column, eluent of 100% ethyl acetate/pet. ether gradient) to give 1-((R)-1-(4-(8-(but-3-en-1-yloxy)imidazo[1,2-b]pyridazin-6-yl)-5-methoxypyridin-2-yl)ethyl)-1-ethyl-3-((S)-7,7,7-trifluorohept-1-en-4-yl)urea. LCMS m/z (M+H): 561.2 required, 561.2 found.

To a solution of 1-((R)-1-(4-(8-(but-3-en-1-yloxy)imidazo[1,2-b]pyridazin-6-yl)-5-methoxypyridin-2-yl)ethyl)-1-ethyl-3-((S)-7,7,7-trifluorohept-1-en-4-yl)urea (200 mg, 0.357 mmol) in DCE (200 mL) was added (1, 3-dimesitylimidazolidin-2-ylidene) (2-isopropoxybenzylidene) ruthenium (VI) chloride (22.35 mg, 0.036 mmol). The mixture was stirred at 50° C. for 12 hours. The reaction was concentrated and purified by flash silica gel chromatography (ISCO®; 4 g SepaFlash® Silica Flash Column, eluent of [50-80]% ethyl acetate/pet. ether gradient) to give ($1^7$E,3R,7S,9E)-4-ethyl-25-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-9-en-5-one. LCMS m/z (M+H): 533.2 required, 533.4 found.

To a solution of ($1^7$E,3R,7S,9E)-4-ethyl-25-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-9-en-5-one (100 mg, 0.188 mmol) in EtOAc (5 mL) were added Pd-C (200 mg, 0.188 mmol). The solution was stirred at 25° C. for 20 min under H2 (excess) (15 psi). The mixture was filtered and concentrated to give (3R,7R,E)-4-ethyl-25-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-5-one (example 149). LCMS m/z (M+H): 535.2 required, 535.2 found. $^1$H NMR (400 MHz, MeOD) δ 8.32 (s, 1H), 7.98 (d, J=1.1 Hz, 1H), 7.56 (d, J=1.1 Hz, 1H), 7.27 (s, 1H), 6.56 (s, 1H), 5.97-5.69 (m, 2H), 4.54-4.36 (m, 2H), 3.87 (s, 4H), 3.16-3.05 (m, 2H), 2.16-2.07 (m, 2H), 1.86-1.78 (m, 2H), 1.70-1.59 (m, 2H), 1.54 (d, J=7.2 Hz, 3H), 1.47-1.32 (m, 6H), 0.95 (t, J=7.0 Hz, 3H)

Example 150

(3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyridina-2(4,2)-pyridinacyclotridecaphan-5-one (example 150)

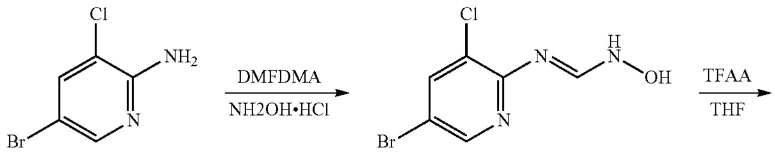

-continued

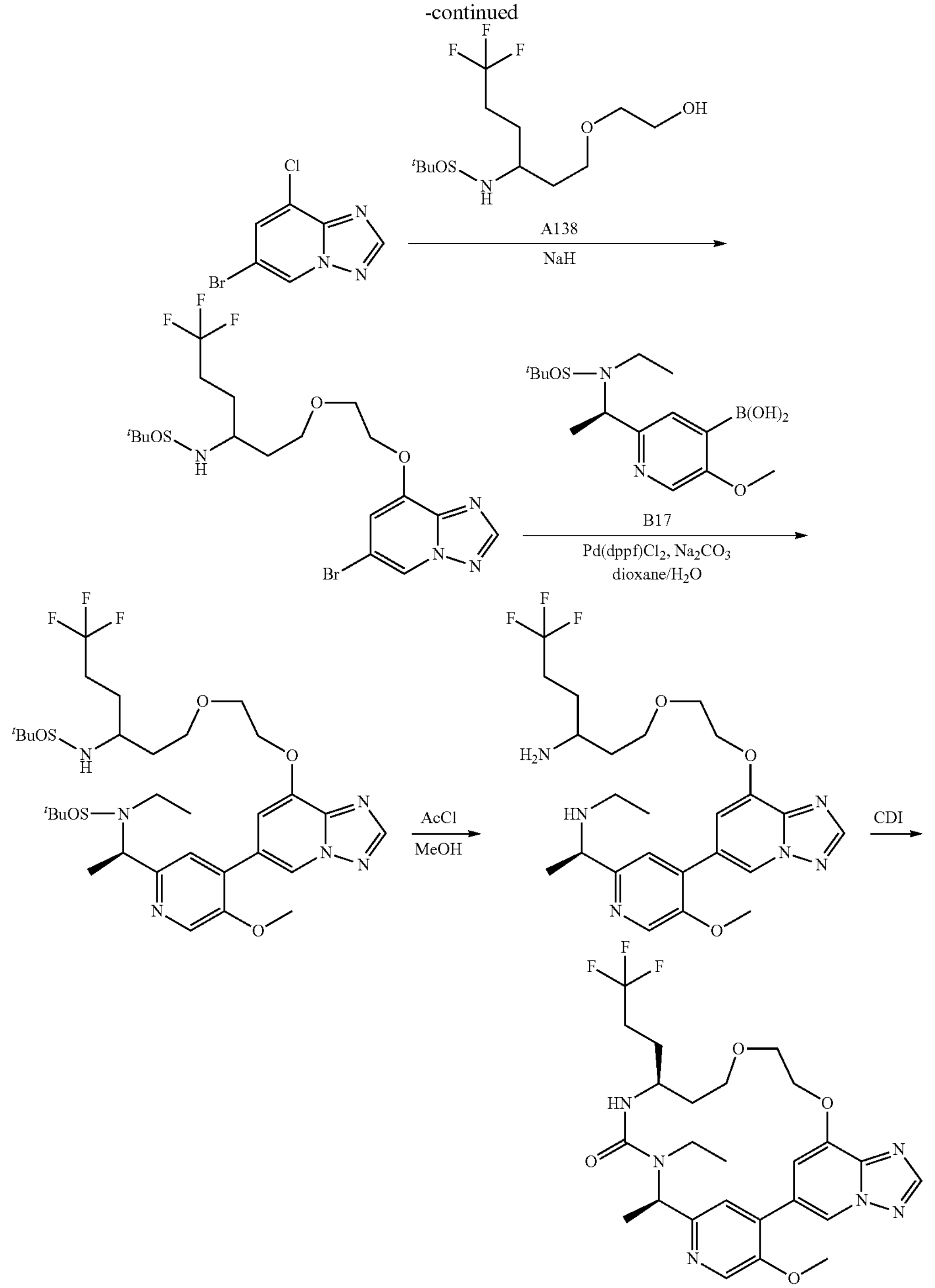

EXAMPLE 150

To a solution of 5-bromo-3-chloropyridin-2-amine (5 g, 24.10 mmol) in 2-Propanol (50 mL) was added n,n-dimethylformamide dimethyl acetal (3.73 g, 31.3 mmol) and stirred at 85° C. for 3 hours. The mixture was cooled to 50° C. and hydroxylamine hydrochloride (2.177 g, 31.3 mmol) was added. The mixture was stirred at 50° C. for 1 hour. The reaction mixture was concentrated and washed with EtOAc (100 mL) to give (E)-N'-(5-bromo-3-chloropyridin-2-yl)-N-hydroxyformimidamide, which was used in next step without purification. LCMS m/z (M+H): 249.9; 251.9 required, 252.0 found.

To a solution of (E)-N'-(5-bromo-3-chloropyridin-2-yl)-N-hydroxyformimidamide (6 g, 23.95 mmol) in THF (100 mL) was added TFAA (6.77 mL, 47.9 mmol). The mixture was stirred at 25° C. for 3 hours. The reaction mixture was poured into sat.$NaHCO_3$(200 mL), extracted with EtOAc (100 mL×3). The organic layer was washed with brine (100 mL), dried over $Na_2SO_4$ and filtered. The filtrate was concentrated and washed with EtOAc to give 6-bromo-8-chloro-[1,2,4]triazolo[1,5-a]pyridine, which was used in next step without purification. LCMS m/z (M+H): 231.9; 233.9 required, 234.0 found.

To a solution of 2-methyl-N-(6,6,6-trifluoro-1-(2-hydroxyethoxy)hexan-3-yl)propane-2-sulfinamide A138 (200 mg, 0.626 mmol) in THF (2 mL) was added NaH (50.1 mg, 1.252 mmol) at 0° C. and stirred for 30 mins. 6-bromo-8-chloro-[1,2,4]triazolo[1,5-a]pyridine (146 mg, 0.626 mmol) was added and stirred at 25° C. for 12 hours. The reaction mixture was poured into water (10 mL), extracted with EtOAc (20 mL×3). The organic layer was washed with brine (10 mL), dried over $Na_2SO_4$ and filtered. The filtrate was concentrated and purified by prep-TLC ($SiO_2$, EtOAc: MeOH=20:1) to give N-(1-(2-((6-bromo-[1,2,4]triazolo[1,5-a]pyridin-8-yl)oxy)ethoxy)-6,6,6-trifluorohexan-3-yl)-2-methylpropane-2-sulfinamide. LCMS m/z (M+H): 515.1; 513.1 required, 516.7 found.

To a solution of N-(1-(2-((6-bromo-[1,2,4]triazolo[1,5-a]pyridin-8-yl)oxy)ethoxy)-6,6,6-trifluorohexan-3-yl)-2-methylpropane-2-sulfinamide (200 mg, 0.388 mmol) in Dioxane (1 mL) and Water (0.4 mL) were added (2-((1R)-1-((tert-butylsulfinyl)(ethyl)amino)ethyl)-5-methoxypyridin-4-yl)boronic acid B17 (1.236 mL, 0.388 mmol)(0.314 M in dioxane), $Na_2CO_3$ (82 mg, 0.776 mmol) and Pd(dppf)$Cl_2$ (28.4 mg, 0.039 mmol). The mixture was stirred at 80° C. for 2 hours. The reaction mixture was poured into water (10 mL), extracted with EtOAc (5 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-50]% MeOH/ethyl acetate gradient) to give N-((1R)-1-(4-(8-(2-((3-((tert-butylsulfinyl)amino)-6,6,6-trifluorohexyl)oxy)ethoxy)-[1,2,4]triazolo[1,5-a]pyridin-6-yl)-5-methoxypyridin-2-yl)ethyl)-N-ethyl-2-methylpropane-2-sulfinamide. LCMS m/z (M+H): 719.3 required, 719.3 found.

To a solution of N-((1R)-1-(4-(8-(2-((3-((tert-butylsulfinyl)amino)-6,6,6-trifluorohexyl)oxy)ethoxy)-[1,2,4]triazolo[1,5-a]pyridin-6-yl)-5-methoxypyridin-2-yl)ethyl)-N-ethyl-2-methylpropane-2-sulfinamide (230 mg, 0.320 mmol) in MeOH (5 mL) was added acetyl chloride (75 mg, 0.960 mmol) and stirred at 25° C. for 2 hours. LCMS showed the reaction was completed. The reaction mixture was concentrated to give 1-(2-((6-(2-((R)-1-(ethylamino)ethyl)-5-methoxypyridin-4-yl)-[1,2,4]triazolo[1,5-a]pyridin-8-yl)oxy)ethoxy)-6,6,6-trifluorohexan-3-amine, which was used in next step without purification. LCMS m/z (M+H): 511.3 required, 511.2 found.

To a solution of 1-(2-((6-(2-((R)-1-(ethylamino)ethyl)-5-methoxypyridin-4-yl)-[1,2,4]triazolo[1,5-a]pyridin-8-yl)oxy)ethoxy)-6,6,6-trifluorohexan-3-amine (160 mg, 0.313 mmol) in THF (2 mL) were added CDI (152 mg, 0.940 mmol) and DMAP (57.4 mg, 0.470 mmol). The mixture was stirred at 25° C. for 2 hours. MeCN: $H_2O$(4:1, 4 mL) was added and stirred at 25° C. for 12 hours. The reaction mixture was poured into water (10 mL), extracted with EtOAc (5 mL×3). The organic layer was washed with brine (10 mL), dried over $Na_2SO_4$ and filtered. The filtrate was concentrated and purified by prep-HPLC (38-58 ACN in water with 0.1% TFA) to give (3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyridina-2(4,2)-pyridinacyclotridecaphan-5-one (example 150) as the second eluting diastereomer. LCMS m/z (M+H): 537.2 required, 537.2 found. $^1H$ NMR (500 MHz, $CD_3OD$) δ 8.99 (s, 1H), 8.48 (s, 1H), 8.43 (s, 1H), 7.65 (s, 1H), 7.51 (s, 1H), 4.83-4.71 (m, 2H), 4.57 (td, J=3.7, 13.1 Hz, 1H), 4.11 (s, 4H), 3.99 (td, J=3.5, 10.7 Hz, 1H), 3.84 (dt, J=3.5, 11.2 Hz, 1H), 3.78-3.71 (m, 1H), 3.55-3.39 (m, 3H), 2.33-2.20 (m, 2H), 2.14-2.04 (m, 1H), 1.93 (d, J=6.9 Hz, 3H), 1.86-1.72 (m, 2H), 1.66-1.55 (m, 1H), 1.25 (t, J=7.0 Hz, 3H)

Example 151

(3R,7R,E)-7-(2,2-difluoropropyl)-4-ethyl-25-methoxy-3-methyl-13-oxa-4,6-diaza-1(6,8)-imidazo[1,2-a]pyrazina-2(4,2)-pyridinacyclotridecaphan-5-one (example 151)

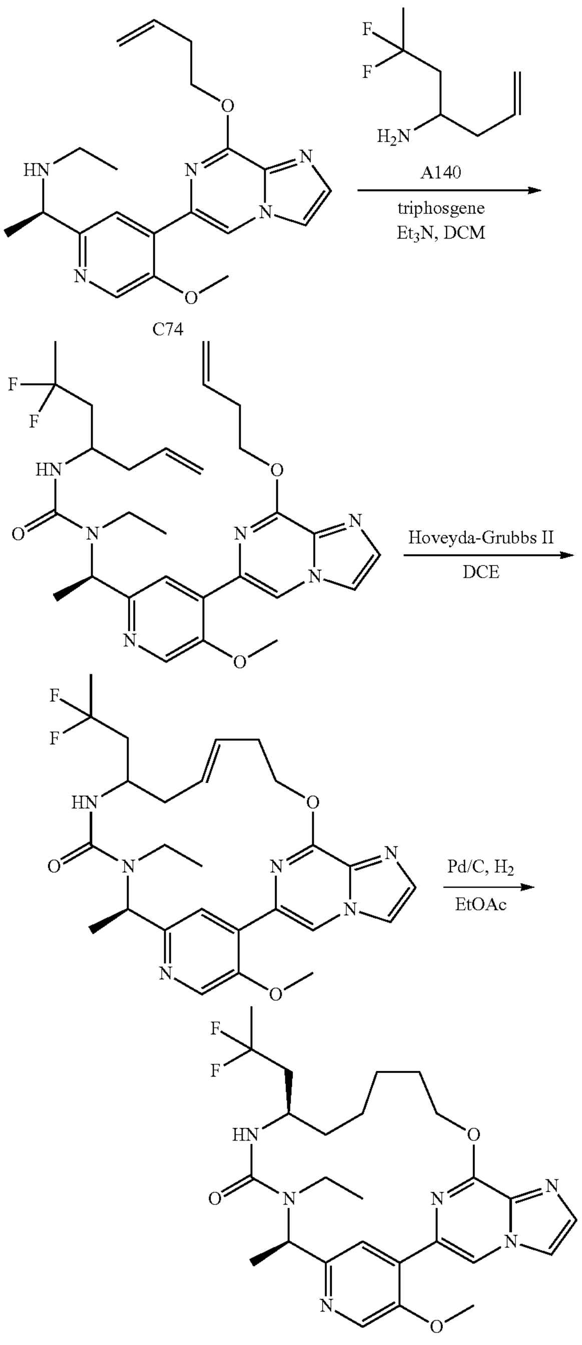

C74

EXAMPLE 151

To a solution of A140 (200 mg, 1.341 mmol) in DCM (8 mL) was added TEA (0.934 mL, 6.70 mmol), triphosgene (199 mg, 0.670 mmol) and stirred at 0° C. for 30 min. C74 (345 mg, 0.938 mmol) was added and stirred at 15° C. for 2 h. The mixture was quenched with H2O (10 mL) and extracted with EtOAc (10 mL×3), washed with brine (10 mL), dried over $Na_2SO_4$, filtered and concentrated under reduced pressure to give the crude. The crude product was purified by flash silica gel chromatography (ISCO®; 4 g SepaFlash® Silica Flash Column, eluent of 100% ethyl acetate/pet. ether gradient) to give 1-((R)-1-(4-(8-(but-3-en-1-yloxy)imidazo[1,2-a]pyrazin-6-yl)-5-methoxypyridin-2-yl)ethyl)-3-(6,6-difluorohept-1-en-4-yl)-1-ethylurea. LCMS m/z (M+H): 543.2 required, 543.4 found.

To a solution of 1-((R)-1-(4-(8-(but-3-en-1-yloxy)imidazo[1,2-a]pyrazin-6-yl)-5-methoxypyridin-2-yl)ethyl)-3-(6,6-difluorohept-1-en-4-yl)-1-ethylurea (250 mg, 0.461 mmol) in DCE (10 mL) were added (1, 3-dimesitylimidazolidin-2-ylidene) (2-isopropoxybenzylidene) ruthenium (VI) chloride (28.9 mg, 0.046 mmol). The mixture was stirred at 50° C. for 12 hours. The reaction was concentrated and purified by flash silica gel chromatography (ISCO®; 4 g SepaFlash® Silica Flash Column, eluent of 100% ethyl acetate/pet. ether gradient) to give ($1^7$E,3R,9E)-7-(2,2-difluoropropyl)-4-ethyl-25-methoxy-3-methyl-13-oxa-4,6-diaza-1(6,8)-imidazo[1,2-a]pyrazina-2(4,2)-pyridinacyclotridecaphan-9-en-5-one. LCMS m/z (M+H): 515.2 required, 515.2 found.

To a solution of ($1^7$E,3R,9E)-7-(2,2-difluoropropyl)-4-ethyl-25-methoxy-3-methyl-13-oxa-4,6-diaza-1(6,8)-imidazo[1,2-a]pyrazina-2(4,2)-pyridinacyclotridecaphan-9-en-5-one (100 mg, 0.194 mmol) in EtOAc (5 mL) were added Pd-C(20.68 mg, 0.019 mmol). The solution was stirred at 25° C. for 20 min under H2 (excess) (15 psi). The mixture was filtered and concentrated to give crude product which was separated on SFC (Chiralpak AD, 30-70% EtOH with 0.1% $NH_4OH/CO_2$) to give (3R,7R,E)-7-(2,2-difluoropropyl)-4-ethyl-25-methoxy-3-methyl-13-oxa-4,6-diaza-1(6,8)-imidazo[1,2-a]pyrazina-2(4,2)-pyridinacyclotridecaphan-5-one (example 151) as the second eluting diastereomer (example 151). LCMS m/z (M+H): 517.2 required, 517.2 found. $^1$H NMR (400 MHz, MeOD) δ 9.09 (s, 1H), 8.33 (s, 1H), 8.21 (s, 1H), 8.03 (s, 1H), 7.63 (s, 1H), 6.07-5.80 (m, 2H), 4.60-4.36 (m, 2H), 4.14 (s, 3H), 3.21-2.95 (m, 2H), 2.25-2.11 (m, 1H), 2.06-1.93 (m, 2H), 1.85 (dt, J=6.1, 11.9 Hz, 1H), 1.73-1.61 (m, 5H), 1.56 (d, J=7.0 Hz, 4H), 1.52-1.45 (m, 2H), 1.39-1.28 (m, 1H), 0.95 (t, J=7.1 Hz, 3H)

Example 152

(3R,7R,E)-4-ethyl-25-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-5-one (example 152)

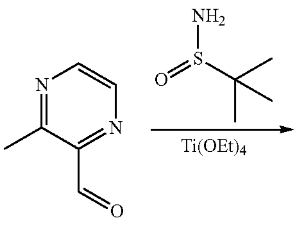

-continued

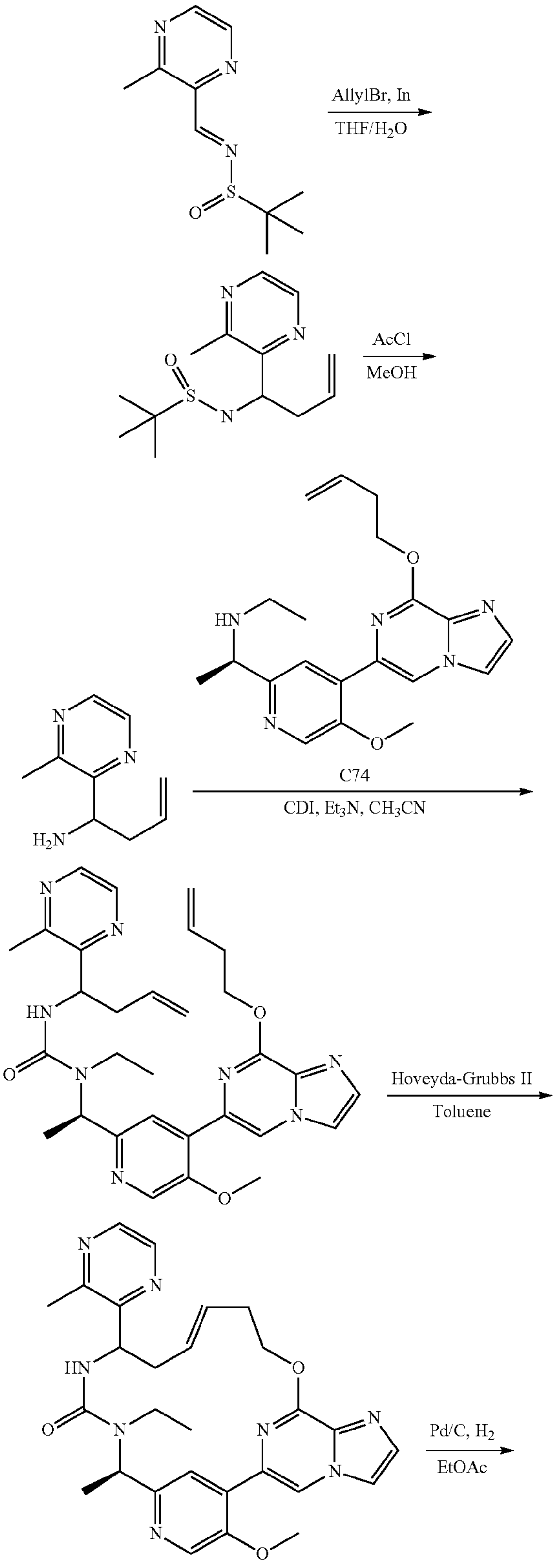

-continued

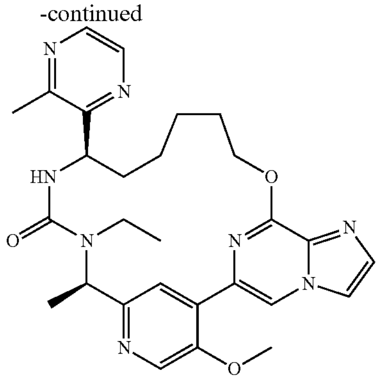

EXAMPLE 152

To a solution of 3-methylpyrazine-2-carbaldehyde (1.2 g, 9.83 mmol) in THF (20 mL) was added 2-methylpropane-2-sulfinamide (1.429 g, 11.79 mmol) and tetraethoxytitanium (11.21 g, 49.1 mmol). The mixture was stirred at 80° C. for 2 hours. The reaction mixture was poured into water (30 mL), extracted with EtOAc (20 mL×3). The organic layer was washed with brine (30 mL), dried over $Na_2SO_4$ and filtered. The filtrate was concentrated and purified by flash silica gel chromatography (ISCO®; 4 g SepaFlash® Silica Flash Column, eluent of [0-100]% ethyl acetate/pet. ether gradient) to give (E)-2-methyl-N-((3-methylpyrazin-2-yl)methylene)propane-2-sulfinamide. LCMS m/z (M+H): 228.1 required, 228.2 found. $^1$H NMR (400 MHz, $CDCl_3$) δ 8.84 (s, 1H), 8.59 (d, J=1.6 Hz, 1H), 8.53 (d, J=2.3 Hz, 1H), 2.89 (s, 3H), 1.30 (s, 9H)

To a solution of (E)-2-methyl-N-((3-methylpyrazin-2-yl)methylene)propane-2-sulfinamide (900 mg, 3.99 mmol) and 3-bromoprop-1-ene (966 mg, 7.99 mmol) in THF (10 mL) and Water (10 mL) was added indium (1376 mg, 11.98 mmol) at 0° C. The mixture was stirred at 0° C. for 2 hours. The reaction mixture was poured into water (30 mL), extracted with EtOAc (20 mL×3). The organic layer was washed with brine (10 mL), dried over $Na_2SO_4$ and filtered. The filtrate was concentrated and purified by flash silica gel chromatography (ISCO®; 12 g SepaFlash® Silica Flash Column, eluent of [0-100]% ethyl acetate/pet. ether gradient) to give 2-methyl-N-(1-(3-methylpyrazin-2-yl)but-3-en-1-yl)propane-2-sulfinamide. $^1$H NMR (400 MHz, $CDCl_3$) δ 8.36 (s, 2H), 5.73 (tdd, J=6.9, 10.3, 16.9 Hz, 1H), 5.09-4.99 (m, 2H), 4.87 (br d, J=8.2 Hz, 1H), 4.72-4.60 (m, 1H), 2.64 (s, 3H), 2.50 (t, J=6.8 Hz, 2H), 1.25 (s, 9H)

To a solution of 2-methyl-N-(1-(3-methylpyrazin-2-yl)but-3-en-1-yl)propane-2-sulfinamide (1 g, 3.74 mmol) in MeOH (10 mL) was added acetyl chloride (0.881 g, 11.22 mmol) and stirred at 25° C. for 1 hour. LCMS showed the reaction was completed. The reaction mixture was concentrated to give 1-(3-methylpyrazin-2-yl)but-3-en-1-amine, which was used in next step without purification. LCMS m/z (M+H): 164.1 required, 164.2 found.

To a solution of 1-(3-methylpyrazin-2-yl)but-3-en-1-amine (200 mg, 1.225 mmol) in MeCN (4 mL) were added $Et_3N$ (0.512 mL, 3.68 mmol) and CDI (596 mg, 3.68 mmol) at 0° C. and stirred for 1 h. The mixture was poured into water (10 mL), extracted with EtOAc (5 mL×3). The organic layer was washed with brine (10 mL), dried over $Na_2SO_4$ and filtered. The filtrate was concentrated and then dissolved in MeCN (4 mL). (R)-1-(4-(8-(but-3-en-1-yloxy)imidazo[1,2-a]pyrazin-6-yl)-5-methoxypyridin-2-yl)-N-ethylethan-1-amine C74 (270 mg, 0.735 mmol) was added and stirred at 25° C. for 1 hour. The reaction mixture was poured into water (10 mL), extracted with EtOAc (20 mL×3). The organic layer was washed with brine (10 mL), dried over $Na_2SO_4$ and filtered. The filtrate was concentrated and purified by prep-TLC ($SiO_2$, EtOAc:MeOH=20:1) to give 1-ethyl-1-((R)-1-(5-methoxy-4-(8-propoxyimidazo[1,2-a]pyrazin-6-yl)pyridin-2-yl)ethyl)-3-(1-(3-methylpyrazin-2-yl)but-3-en-1-yl)urea. LCMS m/z (M+H): 557.3 required, 557.4 found.

To a solution of 1-ethyl-1-((R)-1-(5-methoxy-4-(8-propoxyimidazo[1,2-a]pyrazin-6-yl)pyridin-2-yl)ethyl)-3-(1-(3-methylpyrazin-2-yl)but-3-en-1-yl)urea (100 mg, 0.180 mmol) in Toluene (20 mL) was added (1,3-dimesitylimidazolidin-2-ylidene)(2-isopropoxybenzylidene)ruthenium(VI) chloride (22.51 mg, 0.036 mmol). The mixture was stirred at 80° C. for 5 hours. The reaction mixture was poured into water (30 mL), extracted with EtOAc (20 mL×3). The organic layer was washed with brine (10 mL), dried over $Na_2SO_4$ and filtered. The filtrate was concentrated and purified by prep-TLC ($SiO_2$, EtOAc:MeOH=20:1) to give ($1^7$E,3R,9E)-4-ethyl-25-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-9-en-5-one. LCMS m/z (M+H): 529.3 required, 529.3 found.

To a solution of ($1^7$E,3R,9E)-4-ethyl-25-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-9-en-5-one (50 mg, 0.095 mmol) in EtOAc (2 mL) was added Pd-C(50.3 mg, 0.047 mmol) and stirred at 25° C. under H2 (15 psi) for 20 mins. The reaction mixture was filtered, concentrated and purified by prep-HPLC (27-47% ACN/water with 0.1% TFA) to give (3R,7R,E)-4-ethyl-25-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-5-one as the second eluting diastereomer (example 152). LCMS m/z (M+H): 531.3 required, 531.3 found. $^1$H NMR (400 MHz, $CD_3OD$) δ 9.24 (s, 1H), 8.47 (d, J=2.4 Hz, 1H), 8.42 (s, 1H), 8.40 (d, J=2.5 Hz, 1H), 8.35 (s, 1H), 8.17 (d, J=1.0 Hz, 1H), 7.79 (s, 1H), 5.97 (q, J=7.1 Hz, 1H), 5.56 (dd, J=4.2, 10.4 Hz, 1H), 5.02-4.93 (m, 1H), 4.71 (dt, J=6.6, 10.3 Hz, 1H), 4.20 (s, 3H), 3.31 (br s, 1H), 3.22-3.08 (m, 1H), 2.71 (s, 3H), 2.11-1.97 (m, 2H), 1.90-1.65 (m, 5H), 1.63-1.49 (m, 4H), 1.12 (t, J=7.1 Hz, 3H)

Example 153
(3R,7S,E)-7-(3,3-difluorobutyl)-4-ethyl-25,3-dimethyl-9,13-dioxa-4,6-diaza-1(6,8)-[1,2,4]triazolo[1,5-a]pyrazina-2(4,2)-pyridinacyclotridecaphan-5-one (example 153)
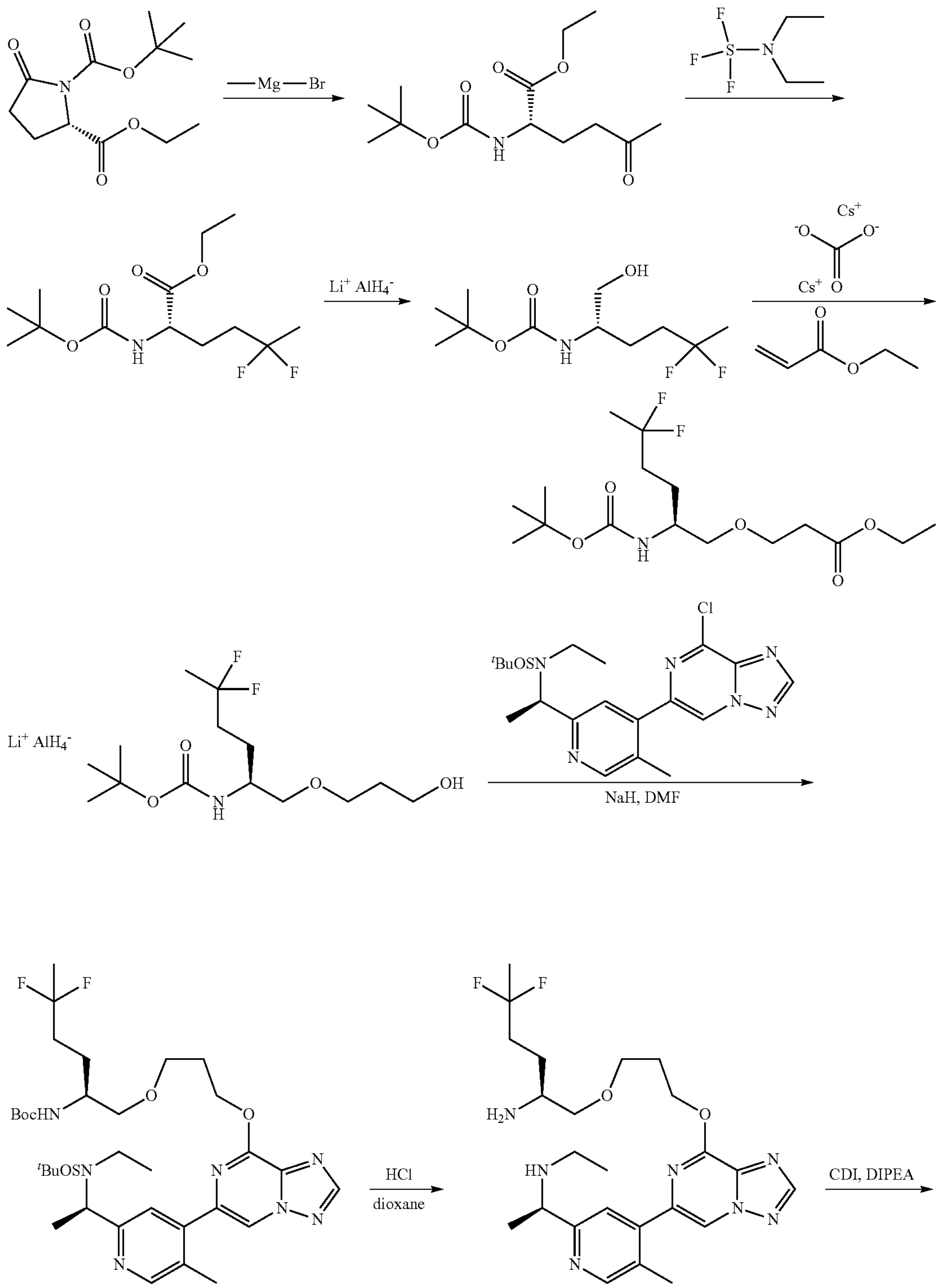

-continued

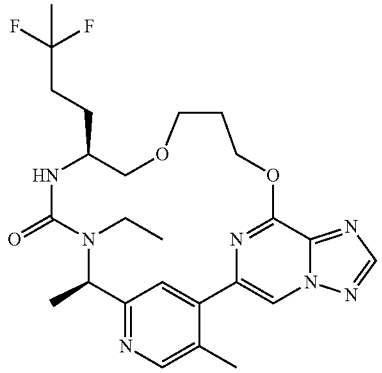

EXAMPLE 153

To a solution of 1-(tert-butyl) 2-ethyl (S)-5-oxopyrrolidine-1,2-dicarboxylate (18 g, 70.0 mmol) in THF (200 mL) was methylmagnesium bromide (24.49 mL, 73.5 mmol) (3 M in THF) at −40° C. The resulting mixture was stirred at −40° C. for 2 h and then at 10° C. for 16 h. The mixture was quenched with aq $NH_4Cl$ (100 mL) and then extracted with EtOAc (3×100 mL). The combined organic layers were washed with brine (100 mL), dried over $Na_2SO_4$, filtered and the filtrate was concentrated. The mixture was purified by flash silica gel chromatography (ISCO®; 120 g SepaFlash® Silica Flash Column, eluent of 20% ethyl acetate/pet. ether gradient) to give ethyl (S)-2-((tert-butoxycarbonyl)amino)-5-oxohexanoate. A mixture of ethyl (S)-2-((tert-butoxycarbonyl)amino)-5-oxohexanoate (13.5 g, 49.4 mmol) and DAST (60 ml, 454 mmol) was stirred at 15° C. for 16 h. The reaction mixture was poured into aq. $NaHCO_3$ (500 mL), extracted with DCM (3*100 mL), washed with brine (50 mL). The organic layer was dried over $Na_2SO_4$, filtered and the filtrate was concentrated. The residue was purified by flash silica gel chromatography (ISCO®; 120 g SepaFlash® Silica Flash Column, eluent of 30% ethyl acetate/pet. ether gradient) to give ethyl (S)-2-((tert-butoxycarbonyl)amino)-5,5-difluorohexanoate. LCMS m/z (M+H-Boc): 196.1 required, 196.1 found.

To a stirred solution of $LiAlH_4$ (1 g, 26.3 mmol) in THF (80 mL) was added ethyl (S)-2-((tert-butoxy carbonyl) amino)-5,5-difluorohexanoate (7 g, 23.70 mmol) in THF (20 mL) at 0° C. The reaction was allowed to stir for 1 h at 0° C. The reaction was detected by TLC. The starting material was consumed completely. The reaction was diluted with $H_2O$(1 mL), NaOH (15%, 1 mL), $H_2O$(3 mL) and dried over $MgSO_4$, filtered and the filtrate was concentrated to give tert-butyl (S)-(5,5-difluoro-1-hydroxyhexan-2-yl)carbamate which was used in the next step directly. LCMS m/z (M+H): 254.1 required, 254.1 found.

To a mixture of tert-butyl (S)-(5,5-difluoro-1-hydroxyhexan-2-yl)carbamate (5.5 g, 21.71 mmol) and $Cs_2CO_3$ (14.15 g, 43.4 mmol) in MeCN (60 mL) was added ethyl acrylate (11.84 mL, 109 mmol). The mixture was stirred at 15° C. for 5 h. $H_2O$(50 mL) was added to the mixture, extracted with EtOAc (50 mL×3). The organic layer was washed with brine (50 mL), dried over $Na_2SO_4$ and filtered. The filtrate was concentrated and purified by flash silica gel chromatography (ISCO®; 80 g SepaFlash® Silica Flash Column, eluent of [0-20]% ethyl acetate/pet. ether gradient) to give ethyl (S)-3-((2-((tert-butoxycarbonyl)amino)-5,5-difluorohexyl)oxy)propanoate. LCMS m/z (M+H-Boc): 254.1 required, 254.1 found.

To a stirred solution of $LiAlH_4$ (0.5 g, 13.17 mmol) in THF (30 Ml) was added ethyl (S)-3-((2-((tert-butoxycarbonyl)amino)-5,5-difluorohexyl)oxy)propanoate (3.5 g, 9.90 mmol) in THF (10 mL) at 0° C. The reaction was allowed to stir for 1 h at 0° C. The reaction was detected by TLC. The starting material was consumed completely. The reaction was diluted with $H_2O$(0.5 mL), NaOH (15%, 0.5 mL), $H_2O$(1.5 mL) and dried over $MgSO_4$, filtered and the filtrate was concentrated to give tert-butyl (S)-(5,5-difluoro-1-(3-hydroxypropoxy)hexan-2-yl)carbamate which was used in the next step directly. To a solution of tert-butyl (S)-(5,5-difluoro-1-(3-hydroxypropoxy)hexan-2-yl)carbamate (100 mg, 0.321 mmol) in DMF (2 mL) was added NaH (26 mg, 0.650 mmol) (60%) at 0° C., and then N—((R)-1-(4-(8-chloro-[1,2,4]triazolo[1,5-a]pyrazin-6-yl)-5-methylpyridin-2-yl)ethyl)-N-ethyl-2-methylpropane-2-sulfinamide (135 mg, 0.321 mmol) was added to the mixture and stirred for 30 mins. $H_2O$ (5 mL) was added to the mixture, extracted with EtOAc (5 mL×3). The organic layer was washed with brine (5 mL×2), dried over $Na_2SO_4$ and filtered. The filtrate was concentrated and purified by flash silica gel chromatography (ISCO®; 4 g SepaFlash® Silica Flash Column, eluent of 100% ethyl acetate) to give tert-butyl ((2S)-1-(3-((6-(2-((1R)-1-((tert-butylsulfinyl)(ethyl)amino)ethyl)-5-methylpyridin-4-yl)-[1,2,4]triazolo[1,5-a]pyrazin-8-yl)oxy)propoxy)-5,5-difluorohexan-2-yl)carbamate. LCMS m/z (M+H): 592.3 required, 592.4 found.

A mixture of tert-butyl ((2S)-1-(3-((6-(2-((1R)-1-((tert-butylsulfinyl)(ethyl)amino)ethyl)-5-methylpyridin-4-yl)-[1,2,4]triazolo[1,5-a]pyrazin-8-yl)oxy)propoxy)-5,5-difluorohexan-2-yl)carbamate (120 mg, 0.172 mmol) and HCl-dioxane (3 mL, 12.00 mmol) (4 M in dioxane) was stirred at 15° C. for 1 h. LCMS showed the desired product was formed. The mixture was concentrated to give (S)-1-(3-((6-(2-((R)-1-(ethylamino)ethyl)-5-methylpyridin-4-yl)-[1,2,4]triazolo[1,5-a]pyrazin-8-yl)oxy)propoxy)-5,5-difluorohexan-2-amine, which was used in the next steps directly. LCMS m/z (M+H): 492.2 required, 492.3 found.

To a solution of (S)-1-(3-((6-(2-((R)-1-(ethylamino)ethyl)-5-methylpyridin-4-yl)-[1,2,4]triazolo[1,5-a]pyrazin-8-yl)oxy)propoxy)-5,5-difluorohexan-2-amine (70 mg, 0.142 mmol) and DIPEA (0.124 mL, 0.712 mmol) in $CH_3CN$ (2 mL) was added CDI (46.2 mg, 0.285 mmol) and stirred for 16 h under 25° C. $H_2O$(1 mL) was added to the mixture, extracted with EtOAc (2 mL×3). The organic layer was washed with brine (2 mL), dried over $Na_2SO_4$ and filtered. The filtrate was concentrated and purified by prep-HPLC (ODS, 22-42% ACN/water with 0.1% TFA) and silica gel chromatography (ISCO®; 4 g SepaFlash® Silica Flash Column, Eluent of 50% EtOAc/Pet.ether gradient) to give (3R,7S,E)-7-(3,3-difluorobutyl)-4-ethyl-25,3-dimethyl-9,13-dioxa-4,6-diaza-1(6,8)-[1,2,4]triazolo[1,5-a]pyrazina-2(4,2)-pyridinacyclotridecaphan-5-one (example 153). LCMS m/z (M+H): 518.3 required, 518.3 found. $^1$H NMR (400 MHz, $CD_3OD$) δ 8.83 (s, 1H), 8.54 (s, 1H), 8.47 (s, 1H), 7.93 (s, 1H), 5.98-5.85 (m, 2H), 5.15-4.99 (m, 1H), 4.68-4.55 (m, 1H), 4.18 (br d, J=3.9 Hz, 1H), 3.70 (td, J=5.1, 9.6 Hz, 1H), 3.63-3.52 (m, 2H), 3.49-3.40 (m, 1H), 3.25-3.05 (m, 2H), 2.62 (s, 3H), 2.22 (quin, J=6.7 Hz, 2H), 1.98-1.87 (m, 2H), 1.72-1.65 (m, 1H), 1.63-1.54 (m, 6H), 1.03 (t, J=7.0 Hz, 3H).

Example 154

(3R,7R,E)-4-ethyl-25-methoxy-3-methyl-7-(2-(methylsulfonyl)ethyl)-13-oxa-4,6-diaza-1(6,8)-[1,2,4]triazolo[1,5-a]pyrazina-2(4,2)-pyridinacyclotridecaphan-5-one (example 154)

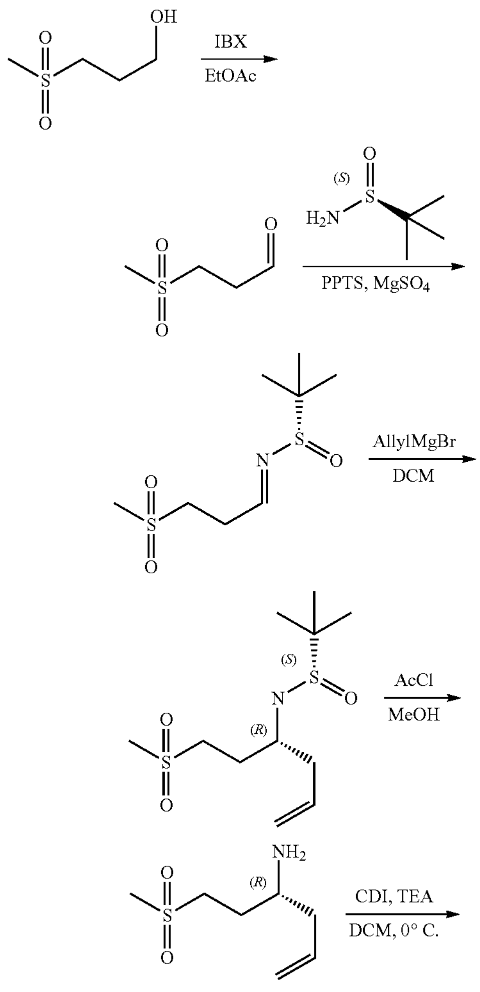

-continued

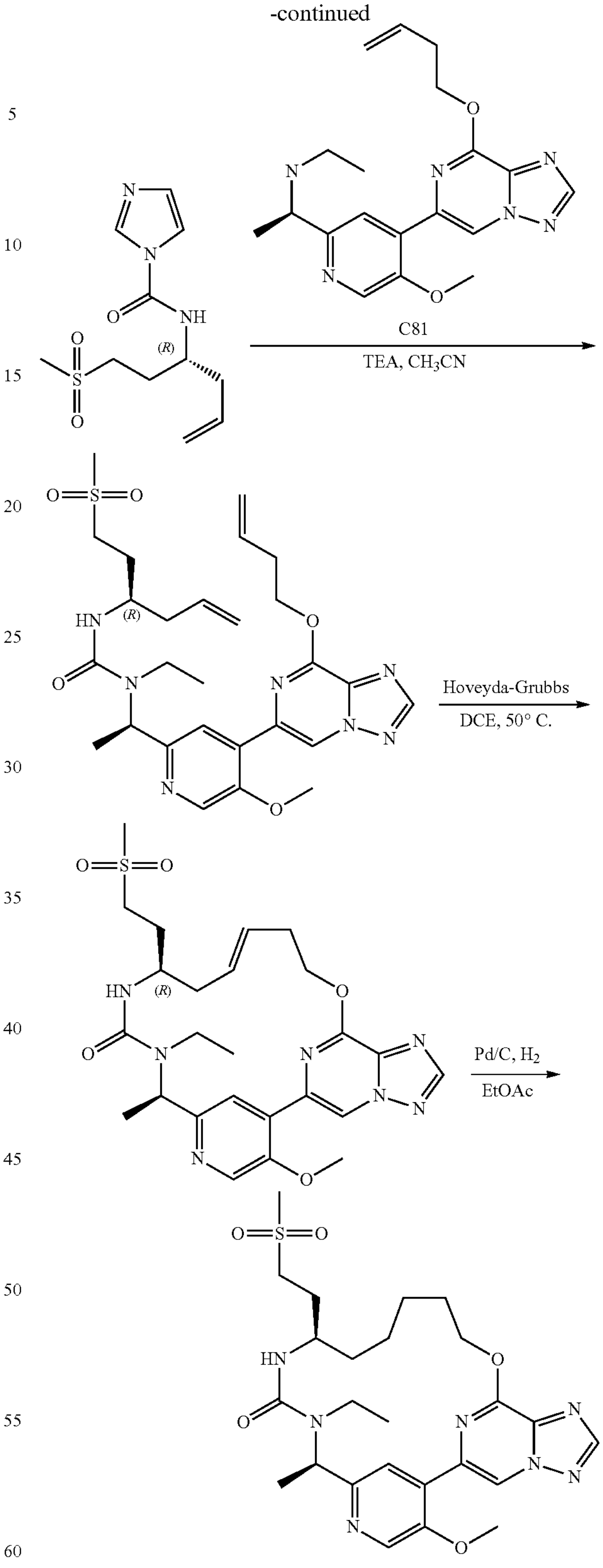

EXAMPLE 154

To a solution of 3-(methylsulfonyl)propan-1-ol (3.2 g, 23.16 mmol) in EtOAc (50 mL) was added IBX (8.43 g, 30.1 mmol). The mixture was stirred at 85° C. for 3 h. The reaction mixture was filtered, the cake was washed with EtOAc (10 mL×3). The filtrate was concentrated to give 3-(methylsulfonyl)propanal, which was used directly to next step without further purification. To a solution of 3-(methylsulfonyl)propanal (3.1 g, 22.77 mmol) in DCE (10 mL) was added (S)-2-methylpropane-2-sulfinamide (3.04 g, 25.04 mmol), $MgSO_4$ (5.48 g, 45.5 mmol) and PPTS (0.572 g, 2.277 mmol). The reaction mixture was stirred at 85° C. for 10 h. The reaction mixture was filtered and concentrated. The residue was purified by flash silica gel chromatography (ISCO®; 4 g Biotage® Silica Flash Column, Eluent of 0-100% EtOAc/Pet. ether gradient) to give (S,E)-2-methyl-N-(3-(methylsulfonyl)propylidene)propane-2-sulfinamide. LCMS m/z (M+H): 240.0 required, 239.7 found.

To a solution of (S,E)-2-methyl-N-(3-(methylsulfonyl)propylidene)propane-2-sulfinamide (2 g, 8.36 mmol) in DCM (40 mL) was added allylmagnesium bromide (12.53 mL, 25.07 mmol) (2 M in $Et_2O$) at 0° C. The mixture was stirred at 0° C. for 2 h. The mixture was poured into $NH_4Cl$ (40 mL), extracted with EtOAc (20 mL×3). The organic phase was dried over $Na_2SO_4$ and filtered. The filtrate was concentrated and purified by flash silica gel chromatography (ISCO®; 10 g SepaFlash® Silica Flash Column, eluent of [0-100]% ethyl acetate/pet. ether gradient) to give (S)-2-methyl-N—((R)-1-(methylsulfonyl)hex-5-en-3-yl)propane-2-sulfinamide. $^1$H NMR (400 MHz, $CDCl_3$) δ 5.86-5.67 (m, 1H), 5.26-5.09 (m, 2H), 3.55-3.37 (m, 1H), 3.23-3.04 (m, 2H), 2.97-2.81 (m, 3H), 2.49-2.38 (m, 1H), 2.23-2.04 (m, 2H), 2.01-1.88 (m, 1H), 1.29-1.15 (s, 9H)

To a solution of (S)-2-methyl-N—((R)-1-(methylsulfonyl)hex-5-en-3-yl)propane-2-sulfinamide (800 mg, 2.84 mmol) in MeOH (10 mL) was added AcCl (0.404 mL, 5.69 mmol). The mixture was stirred at 25° C. for 2 h. The reaction mixture was concentrated to give (R)-1-(methylsulfonyl)hex-5-en-3-amine. LCMS m/z (M+H): 178.0 required, 177.6 found.

To a solution of (R)-1-(methylsulfonyl)hex-5-en-3-amine (100 mg, 0.468 mmol) in DCM (2 mL) was added TEA (0.196 mL, 1.404 mmol) and CDI (114 mg, 0.702 mmol) at 0° C. The mixture was stirred at 0° C. for 1 h. The reaction mixture was poured into water (2 mL), extracted with EtOAc (2 mL×3). The combined organic phases were dried over $Na_2SO_4$, filtered. The filtrate was concentrated to give (R)—N-(1-(methylsulfonyl)hex-5-en-3-yl)-1H-imidazole-1-carboxamide. LCMS m/z (M+H): 272.1 required, 272.3 found.

To a solution of (R)-1-(4-(8-(but-3-en-1-yloxy)-[1,2,4]triazolo[1,5-a]pyrazin-6-yl)-5-methoxypyridin-2-yl)-N-ethylethan-1-amine C81 (120 mg, 0.326 mmol) in MeCN (3 mL) was added TEA (0.091 mL, 0.651 mmol) and (R)—N-(1-(methylsulfonyl)hex-5-en-3-yl)-1H-imidazole-1-carboxamide (88 mg, 0.326 mmol). The mixture was stirred at 25° C. for 12 h. The mixture was poured into water (5 mL), extracted with EtOAc (5 mL×3). The combined organic phases were dried over $Na_2SO_4$, filtered. The filtrate was concentrated and purified by prep-TLC ($SiO_2$, EtOAc: EtOH=20:1) to give 1-((R)-1-(4-(8-(but-3-en-1-yloxy)-[1,2,4]triazolo[1,5-a]pyrazin-6-yl)-5-methoxypyridin-2-yl)ethyl)-1-ethyl-3-((R)-1-(methylsulfonyl)hex-5-en-3-yl)urea. LCMS m/z (M+H): 572.2 required, 572.0 found.

To a solution of 1-((R)-1-(4-(8-(but-3-en-1-yloxy)-[1,2,4]triazolo[1,5-a]pyrazin-6-yl)-5-methoxypyridin-2-yl)ethyl)-1-ethyl-3-((R)-1-(methylsulfonyl)hex-5-en-3-yl)urea (100 mg, 0.175 mmol) in DCE (10 mL) was added (1,3-dimesitylimidazolidin-2-ylidene)(2-isopropoxybenzylidene)ruthenium(VI) chloride (10.96 mg, 0.017 mmol). The mixture was stirred at 50° C. for 2 h. The reaction mixture was concentrated to give ($1^7$E,3R,7R,9E)-4-ethyl-25-methoxy-3-methyl-7-(2-(methylsulfonyl)ethyl)-13-oxa-4,6-diaza-1(6,8)-[1,2,4]triazolo[1,5-a]pyrazina-2(4,2)-pyridinacyclotridecaphan-9-en-5-one, which was used without further purification. LCMS m/z (M+H): 544.2 required, 543.9 found.

To a solution of ($1^7$E,3R,7R,9E)-4-ethyl-25-methoxy-3-methyl-7-(2-(methylsulfonyl)ethyl)-13-oxa-4,6-diaza-1(6,8)-[1,2,4]triazolo[1,5-a]pyrazina-2(4,2)-pyridinacyclotridecaphan-9-en-5-one (80 mg, 0.147 mmol) in EtOAc (10 mL) and MeOH (3 mL) was added Pd-C(15.66 mg, 0.015 mmol) (10% weight). The mixture was stirred at 20° C. with a balloon of H2 for 1 h. The mixture was filtered. The filtrate was concentrated and purified by prep-TLC ($SiO_2$, EtOAc: EtOH=20:1) to and then by HPLC (20-40% ACN/water with 0.1% TFA) to give (3R,7R,E)-4-ethyl-25-methoxy-3-methyl-7-(2-(methylsulfonyl)ethyl)-13-oxa-4,6-diaza-1(6,8)-[1,2,4]triazolo[1,5-a]pyrazina-2(4,2)-pyridinacyclotridecaphan-5-one (example 154). LCMS m/z (M+H): 545.2 required, 545.9 found. $^1$H NMR (400 MHz, $CD_3OD$) δ 9.38 (s, 1H), 8.53 (s, 1H), 8.43 (s, 1H), 8.35 (s, 1H), 5.94 (q, J=7.3 Hz, 1H), 4.80-4.66 (m, 2H), 4.19 (s, 3H), 4.08 (dt, J=4.8, 9.6 Hz, 1H), 3.27-3.05 (m, 4H), 2.97 (s, 3H), 2.07-1.80 (m, 4H), 1.67-1.27 (m, 9H), 1.02 (t, J=7.1 Hz, 3H)

Example 155

(3R,7S,E)-7-(3,3-difluorobutyl)-4-ethyl-25-methoxy-3-methyl-10,13-dioxa-4,6-diaza-1(2,4)-imidazo[2,1-f][1,2,4]triazina-2(4,2)-pyridinacyclotridecaphan-5-one (example 155)

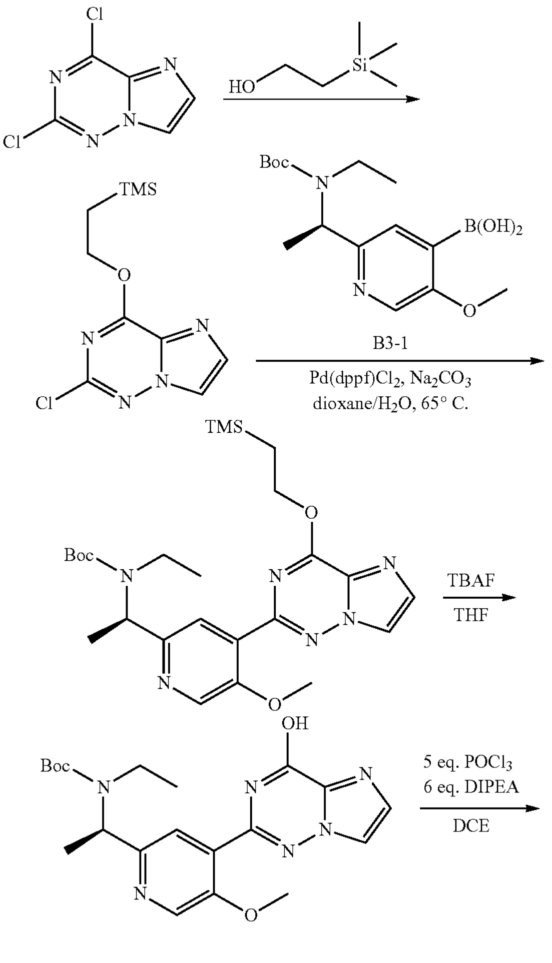

-continued

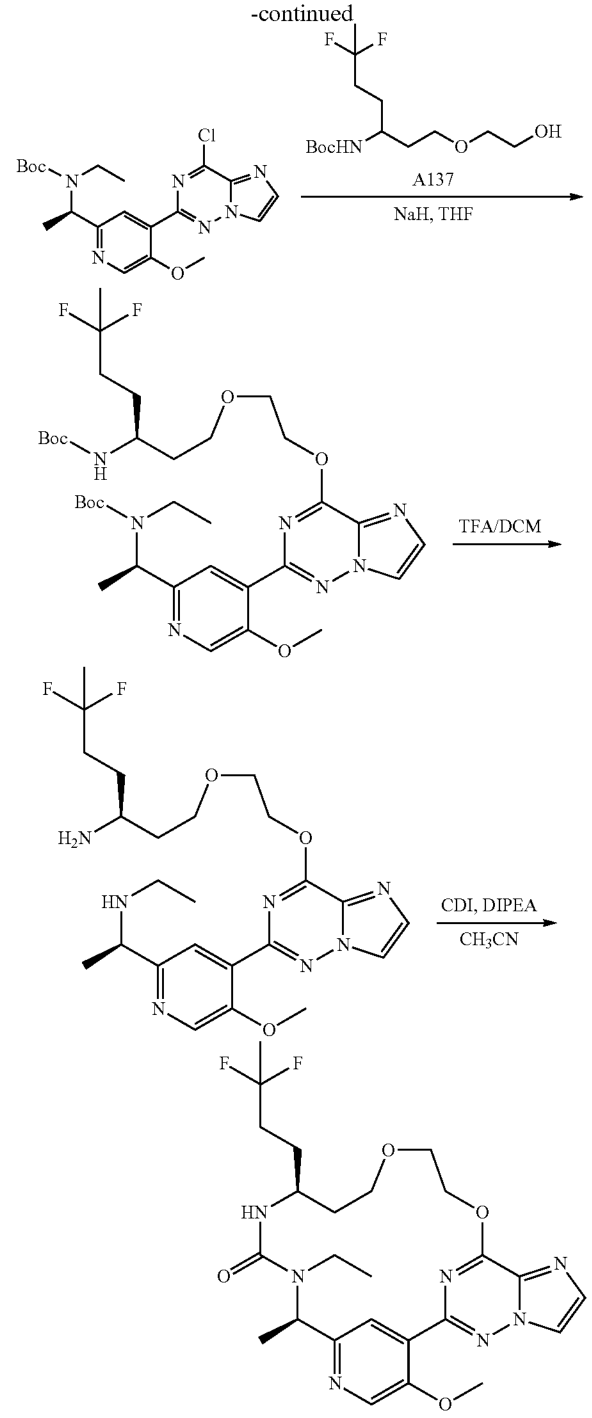

EXAMPLE 155

To a solution of 2-(trimnethylsilyl)ethan-1-ol (313 mg, 2.65 mmol) in THF (15 ml) was added LiHMDS (2.91 ml, 2.91 mmol) (1 M in THF) at 0° C. and stirred for 30 mins. 2,4-dichloroimidazo[2,1-f][1,2,4]triazine (500 mg, 2.65 mmol) was added and stirred at 25° C. for 3 hours. The reaction mixture was poured into water (60 mL), extracted with EtOAc (20 mLx3). The organic layer was washed with brine (20 mL), dried over $Na_2SO_4$ and filtered. The filtrate was concentrated and purified by flash silica gel chromatography (ISCO®; 12 g SepaFlash® Silica Flash Column, eluent of [0-20]% ethyl acetate/pet. ether gradient) to give 2-chloro-4-(2-(trimethylsilyl)ethoxy)imidazo[2,1-f][1,2,4]triazine. LCMS m/z (M+H): 271.1 required, 271.1 found.

To a solution of 2-chloro-4-(2-(trimethylsilyl)ethoxy)imidazo[2,1-f][1,2,4]triazine (400 mg, 1.477 mmol) in Dioxane (8 mL) and Water (2 mL) were added B3-1 (479 mg, 1.477 mmol), $Na_2CO_3$ (470 mg, 4.43 mmol) and X Phos Pd G2 (116 mg, 0.148 mmol), the resulting mixture was stirred at 90° C. under N2 protection for 3 hours. The reaction mixture was poured into water (4 mL), extracted with EtOAc (10 mLx3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-100]% ethyl acetate/pet. ether gradient) to give tert-butyl (R)-ethyl(1-(5-methoxy-4-(4-(2-(trimethylsilyl)ethoxy)imidazo[2,1-f][1,2,4]triazin-2-yl)pyridin-2-yl)ethyl)carbamate. LCMS m/z (M+H): 515.3 required, 515.2 found.

To a solution of tert-butyl (R)-ethyl(1-(5-methoxy-4-(4-(2-(trimethylsilyl)ethoxy)imidazo[2,1-f][1,2,4]triazin-2-yl)pyridin-2-yl)ethyl)carbamate (800 mg, 1.554 mmol) in THF (10 mL) was added TBAF (3.11 mL, 3.11 mmol). The mixture was stirred at 25° C. for 2 h. The mixture was concentrated under reduced pressure. The crude was purified by Flash silica gel chromatography (ISCO®; 4 g Sepa-Flash® Silica Flash Column, Eluent of 70% EtOAc/Pet. ether gradient) to give tert-butyl (R)-ethyl(1-(4-(4-hydroxy-imidazo[2,1-f][1,2,4]triazin-2-yl)-5-methoxypyridin-2-yl)ethyl)carbamate. LCMS m/z (M+H): 415.2 required, 415.2 found.

To a solution of tert-butyl (R)-ethyl(1-(4-(4-hydroxyimidazo[2,1-f][1,2,4]triazin-2-yl)-5-methoxypyridin-2-yl)ethyl)carbamate (700 mg, 1.689 mmol) in DCE (6 mL) were added DIPEA (1.770 mL, 10.13 mmol) and phosphoryl trichloride (0.787 mL, 8.44 mmol). The mixture was stirred at 80° C. for 12 h. The mixture was quenched with $NaHCO_3$ (50 mL) and extracted with EtOAc (10 mLx3), washed with brine (10 mL), dried over $Na_2SO_4$, filtered and concentrated under reduced pressure. The crude was purified by Flash silica gel chromatography (ISCO®; 12 g SepaFlash® Silica Flash Column, Eluent of 70% EtOAc/Pet. ether gradient) to give tert-butyl (R)-(1-(4-(4-chloroimidazo[2,1-f][1,2,4]triazin-2-yl)-5-methoxypyridin-2-yl)ethyl)(ethyl)carbamate. LCMS m/z (M+H): 433.2 required, 433.2 found.

To a solution of tert-butyl (6,6-difluoro-1-(2-hydroxy-ethoxy)heptan-3-yl)carbamate A137 (108 mg, 0.346 mmol) (dried) in THF (4 mL) was added NaH (27.7 mg, 0.693 mmol) at 0° C. under N2 for 30 mins, then to the mixture was added tert-butyl (R)-(1-(4-(4-chloroimidazo[2,1-f][1,2,4]triazin-2-yl)-5-methoxypyridin-2-yl)ethyl)(ethyl)carbamate (150 mg, 0.346 mmol) stirred at 0° C. under $N_2$ protection for 5 mins. The reaction mixture was poured into water (2 mL), extracted with EtOAc (5 mLx3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of 0-80% ethyl acetate/pet. ether gradient) ($SiO_2$, Pet. ether:EtOAc=1:1) to give tert-butyl ((1R)-1-(4-(4-(2-((3-((tert-butoxycarbonyl)amino)-6,6-difluoroheptyl)oxy)ethoxy)imidazo[2,1-f][1,2,4]triazin-2-yl)-5-methoxypyridin-2-yl)ethyl)(ethyl)carbamate. LCMS m/z (M+H): 708.4 required, 708.3 found.

To a solution of tert-butyl ((1R)-1-(4-(4-(2-((3-((tert-butoxycarbonyl)amino)-6,6-difluoroheptyl)oxy)ethoxy)imidazo[2,1-f][1,2,4]triazin-2-yl)-5-methoxypyridin-2-yl)ethyl)(ethyl)carbamate (150 mg, 0.212 mmol) in DCM (4 mL) was added TFA (1 mL, 12.98 mmol), the resulting mixture was stirred at 25° C. under N2 protection for 3 hours. The reaction mixture was concentrated to give the crude of 1-(2-((2-(2-((R)-1-(ethylamino)ethyl)-5-methoxy-pyridin-4-yl)imidazo[2,1-f][1,2,4]triazin-4-yl)oxy)ethoxy)-6,6-difluoroheptan-3-amine. LCMS m/z (M+H): 508.3 required, 508.3 found.

To a solution of 1-(2-((2-(2-((R)-1-(ethylamino)ethyl)-5-methoxypyridin-4-yl)imidazo[2,1-f][1,2,4]triazin-4-yl)oxy) ethoxy)-6,6-difluoroheptan-3-amine (110 mg, 0.217 mmol) in $CH_3CN$ (5 mL) was added DIPEA (0.757 mL, 4.33 mmol) and CDI (70.3 mg, 0.433 mmol) at 25° C. under N2, the resulting mixture was stirred at 25° C. under N2 protection for 2 h. The reaction was poured into water (2 mL), extracted with EtOAc (5 mL×3). The organic layer was washed with brine (5 mL), dried over $Na_2SO_4$ and filtered. The filtrate was concentrated and purified by flash silica gel chromatography (ISCO®; 4 g SepaFlash® Silica Flash Column, eluent of [0-80]% ethyl acetate/pet. ether gradient) ($SiO_2$, Pet. ether:EtOAc=1:1) to give (3R,7S,E)-7-(3,3-difluorobutyl)-4-ethyl-25-methoxy-3-methyl-10,13-dioxa-4,6-diaza-1(2,4)-imidazo[2,1-f][1,2,4]triazina-2(4,2)-pyridinacyclotridecaphan-5-one as the second eluting diastereomer (example 155). LCMS m/z (M+H): 534.3 required, 534.2 found. $^1H$ NMR (400 MHz, $CH_3COD$) δ 8.43 (s, 1H), 8.20 (s, 1H), 7.95 (s, 1H), 7.78 (s, 1H), 6.00-5.84 (m, 2H), 5.24-5.14 (m, 1H), 4.81-4.67 (m, 1H), 4.15-4.07 (m, 1H), 4.04 (s, 3H), 3.99-3.83 (m, 2H), 3.72-3.55 (m, 2H), 3.27-3.13 (m, 1H), 3.11-2.99 (m, 1H), 2.02-1.82 (m, 3H), 1.67-1.55 (m, 6H), 1.72-1.54 (m, 3H), 1.05 (t, J=7.1 Hz, 3H)

Example 156

(3R,7R,E)-4-ethyl-3-methyl-7-(3,3,3-trifluoropropyl)-13-oxa-4,6-diaza-1(5,7)-pyrazolo[1,5-a]pyridina-2(4,2)-pyridinacyclotridecaphan-5-one (example 156)

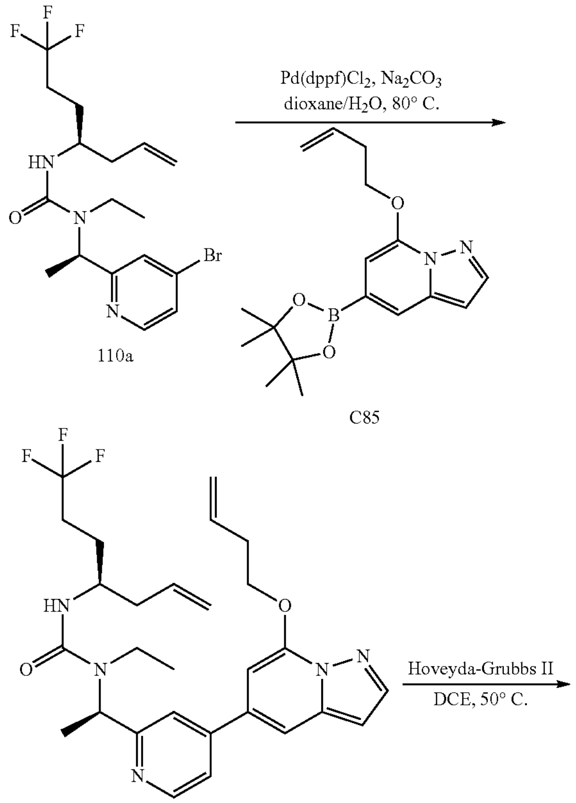

110a

C85

-continued

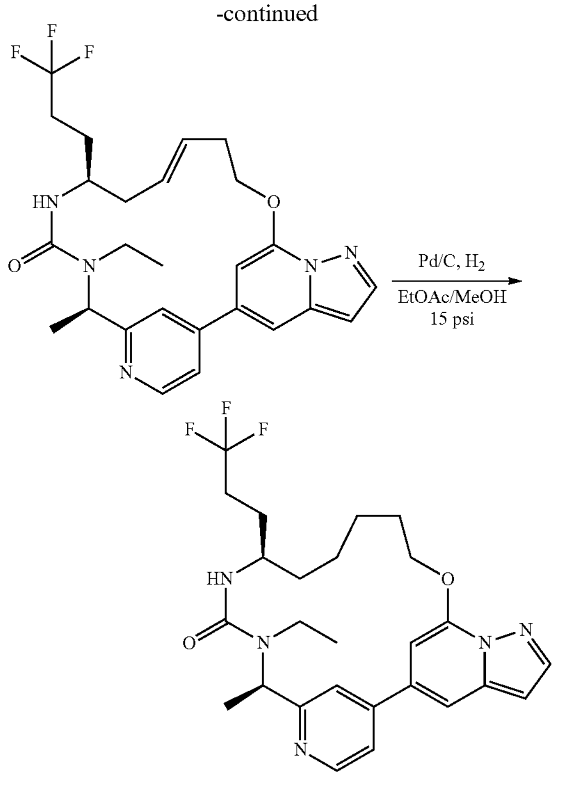

EXAMPLE 156

To a solution of C85 (4 mL, 0.744 mmol) (0.186M in Dioxane) in Water (0.8 mL) were added 110a (157 mg, 0.372 mmol), $Na_2CO_3$ (158 mg, 1.488 mmol) and Pd(dppf)$Cl_2$ (54.4 mg, 0.074 mmol). The mixture was stirred at 80° C. for 12 hours. The reaction mixture was poured into water (10 mL), extracted with EtOAc (20 mL×3). The organic layer was washed with brine (10 mL), dried over $Na_2SO_4$ and filtered. The filtrate was concentrated and purified by flash silica gel chromatography (ISCO®; 4 g SepaFlash® Silica Flash Column, eluent of [0-30]% ethyl acetate/pet. ether gradient) to give 1-((R)-1-(4-(7-(but-3-en-1-yloxy)pyrazolo [1,5-a]pyridin-5-yl)pyridin-2-yl)ethyl)-1-ethyl-3-((S)-7,7,7-trifluorohept-1-en-4-yl)urea. LCMS m/z (M+H): 530.2 required, 530.2 found.

To a solution of 1-((R)-1-(4-(7-(but-3-en-1-yloxy)pyrazolo[1,5-a]pyridin-5-yl)pyridin-2-yl)ethyl)-1-ethyl-3-((S)-7,7,7-trifluorohept-1-en-4-yl)urea (180 mg, 0.340 mmol) in DCE (180 mL) was added (1,3-dimesitylimidazolidin-2-ylidene)(2-isopropoxybenzylidene)ruthenium(vi) chloride (42.6 mg, 0.068 mmol) and stirred at 50° C. for 12 hours. The reaction mixture was concentrated and purified by prep-TLC ($SiO_2$, EtOAc) to give (16E,3R,7S,9E)-4-ethyl-3-methyl-7-(3,3,3-trifluoropropyl)-13-oxa-4,6-diaza-1(5,7)-pyrazolo[1,5-a]pyridina-2(4,2)-pyridinacyclotridecaphan-9-en-5-one. LCMS m/z (M+H): 532.2 required, 532.2 found.

To a solution of (16E,3R,7S,9E)-4-ethyl-3-methyl-7-(3,3,3-trifluoropropyl)-13-oxa-4,6-diaza-1(5,7)-pyrazolo[1,5-a] pyridina-2(4,2)-pyridinacyclotridecaphan-9-en-5-one (70 mg, 0.140 mmol) in EtOAc (5 mL) and MeOH (5.00 mL) was added Pd-C(149 mg, 0.140 mmol) (10% wt) and stirred at 25° C. under H2 (15 psi) for 10 mins. The reaction mixture was filtered and concentrated. The crude product was purified by prep-HPLC (30-60% ACN/water with 0.1% TFA) to give (3R,7R,E)-4-ethyl-3-methyl-7-(3,3,3-trifluoropropyl)-

13-oxa-4,6-diaza-1(5,7)-pyrazolo[1,5-a]pyridina-2(4,2)-pyridinacyclotridecaphan-5-one (example 156). LCMS m/z (M+H): 504.2 required, 504.2 found. $^1$H NMR (500 MHz, $CD_3OD$) δ 8.69 (d, J=5.8 Hz, 1H), 8.14-8.04 (m, 2H), 7.93 (s, 1H), 7.81 (s, 1H), 6.85 (d, J=2.1 Hz, 1H), 6.50 (s, 1H), 5.88 (q, J=7.2 Hz, 1H), 4.79-4.59 (m, 2H), 4.03 (br s, 1H), 3.57-3.42 (m, 1H), 3.32-3.21 (m, 1H), 2.32-2.16 (m, 2H), 2.07-1.90 (m, 2H), 1.87-1.70 (m, 5H), 1.61 (br d, J=8.1 Hz, 5H), 1.43 (br s, 1H), 1.19 (t, J=7.0 Hz, 3H)

Example 157

(3R,7R)-4-ethyl-25-methoxy-3-methyl-7-(3,3,3-trifluoropropyl)-13-oxa-4,6-diaza-1(6,8)-quinolina-2(4,2)-pyridinacyclotridecaphan-5-one (example 157)

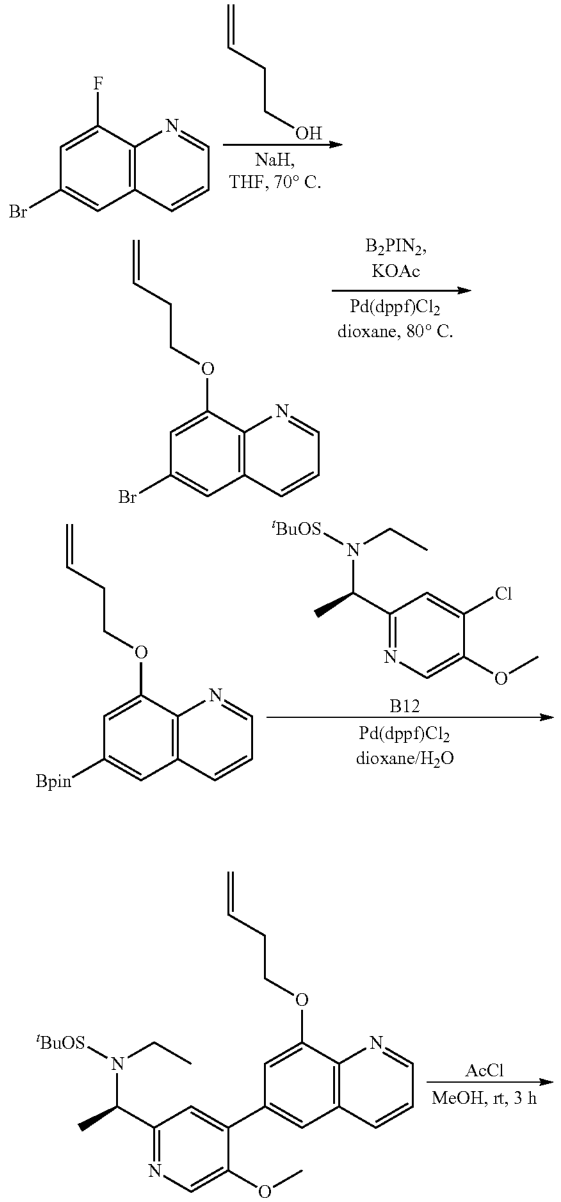

-continued

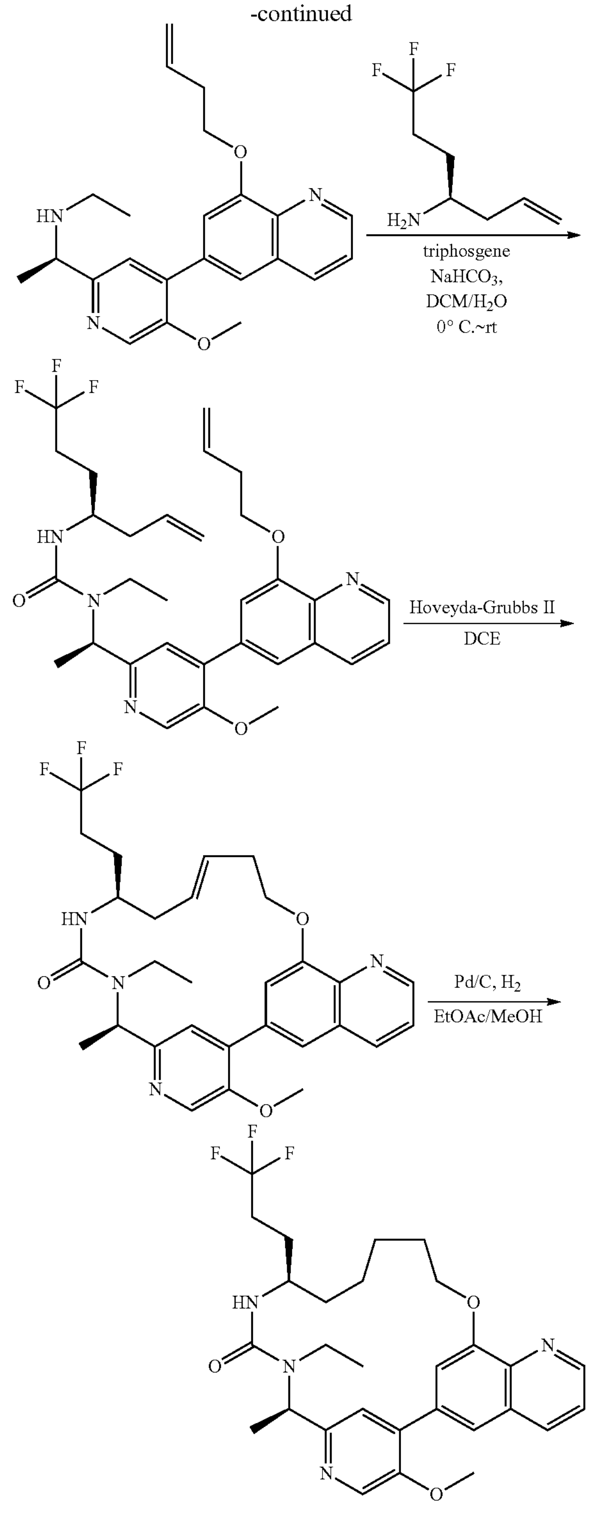

EXAMPLE 157

To a solution of but-3-en-1-ol (447 mg, 6.19 mmol) (447 mg, 6.19 mmol) in THF (10 mL) was added NaH (248 mg, 6.19 mmol) at 0° C. Then stirred at 0° C. for 0.5 h. Then 6-bromo-8-fluoroquinoline (400 mg, 1.438 mmol) was added and stirred at 70° C. for 2 h. The reaction mixture was poured into water (30 mL) and extracted with EtOAc (30 mL×3). The combined organic layers were washed with brine (30 mL), dried over $Na_2SO_4$, filtered and concentrated. The residue was purified by flash silica gel chromatography (ISCO®; 12 g SepaFlash® Silica Flash Column, eluent of [0-30]% ethyl acetate/pet. ether gradient) to give 6-bromo-8-(but-3-en-1-yloxy)quinoline. LCMS m/z (M+H): 279.9 required, 279.9 found.

To a solution of 6-bromo-8-(but-3-en-1-yloxy)quinoline (350 mg, 1.258 mmol) in Dioxane (6 mL) were added 4,4,4',4',5,5,5',5'-octamethyl-2,2'-bi(1,3,2-dioxaborolane) (351 mg, 1.384 mmol), potassium acetate (247 mg, 2.52 mmol) and $Pd(dppf)Cl_2$ (92 mg, 0.126 mmol). The mixture was stirred at 80° C. for 2 hours. LCMS showed the desired product was found. The reaction mixture 8-(but-3-en-1-yloxy)-6-(4,4,5,5-tetramethyl-1,3,2-dioxaborolan-2-yl)quinoline was used for the next step directly without purification. LCMS m/z (M+H): 244.0 required, 244.0 found.

To a solution of 8-(but-3-en-1-yloxy)-6-(4,4,5,5-tetramethyl-1,3,2-dioxaborolan-2-yl)quinoline (306 mg, 1.259 mmol) in 1,4-Dioxane (6 mL) were added (R)—N—((R)-1-(4-chloro-5-methoxypyridin-2-yl)ethyl)-N-ethyl-2-methylpropane-2-sulfinamide B12 (401 mg, 1.259 mmol), $Na_2CO_3$ (267 mg, 2.52 mmol), water (1 mL) and Pd(dppf) $Cl_2$ (92 mg, 0.126 mmol). The mixture was stirred at 80° C. for 12 hours. The reaction mixture was poured into water (10 mL), extracted with EtOAc (10 mL×3). The organic layer was washed with brine (10 mL), dried over $Na_2SO_4$ and filtered. The filtrate was concentrated and purified by flash silica gel chromatography (ISCO®; 12 g SepaFlash® Silica Flash Column, eluent of [0-80]% ethyl acetate/pet. ether gradient) to give N—((R)-1-(4-(8-(but-3-en-1-yloxy)quinolin-6-yl)-5-methoxypyridin-2-yl)ethyl)-N-ethyl-2-methylpropane-2-sulfinamide. LCMS m/z (M+H): 482.2 required, 482.2 found.

To a solution of N—((R)-1-(4-(8-(but-3-en-1-yloxy)quinolin-6-yl)-5-methoxypyridin-2-yl)ethyl)-N-ethyl-2-methylpropane-2-sulfinamide (340 mg, 0.706 mmol) in MeOH (5 mL) was added AcCl (0.100 mL, 1.412 mmol). The mixture was stirred at 30° C. for 3 hours. Then the mixture was concentrated to give (R)-1-(4-(8-(but-3-en-1-yloxy)quinolin-6-yl)-5-methoxypyridin-2-yl)-N-ethylethan-1-amine, which was used in next step without purification. LCMS m/z (M+H): 378.4 required, 378.2 found.

To a solution of (S)-7,7,7-trifluorohept-1-en-4-amine hydrochloride A5 (144 mg, 0.705 mmol) in DCM (5 mL) and sat.$NaHCO_3$(5 mL) was added bis(trichloromethyl) carbonate (69.1 mg, 0.233 mmol) and stirred at 0° C. for 30 min. (R)-1-(4-(8-(but-3-en-1-yloxy)quinolin-6-yl)-5-methoxypyridin-2-yl)-N-ethylethan-1-amine (292 mg, 0.705 mmol) was added and stirred at 30° C. for 12 hours. LCMS showed the desired mass was formed. The reaction mixture was extracted with DCM (10 mL×3). The combined organic layers were washed with brine (10 mL), dried over $Na_2SO_4$ and filtered. The mixture was purified by flash silica gel chromatography (ISCO®; 4 g SepaFlash® Silica Flash Column, Eluent of 40% EtOAc/Pet.ether gradient) to give 1-((R)-1-(4-(8-(but-3-en-1-yloxy)quinolin-6-yl)-5-methoxypyridin-2-yl)ethyl)-1-ethyl-3-((S)-7,7,7-trifluorohept-1-en-4-yl)urea. LCMS m/z (M+H): 571.4 required, 571.4 found To a solution of 1-((R)-1-(4-(8-(but-3-en-1-yloxy)quinolin-6-yl)-5-methoxypyridin-2-yl)ethyl)-1-ethyl-3-((S)-7,7,7-trifluorohept-1-en-4-yl)urea (260 mg, 0.456 mmol) in 1,2-dichloroethane (233 mL) was added Hoveyda-Grubbs II (57.1 mg, 0.091 mmol), and the mixture was stirred at 50° C. for 16 h. The reaction mixture was concentrated. The residue was purified by Prep-TLC ($SiO_2$, EtOAc=1) to give (3R,7S,E)-4-ethyl-25-methoxy-3-methyl-7-(3,3,3-trifluoropropyl)-13-oxa-4,6-diaza-1(6,8)-quinolina-2(4,2)-pyridinacyclotridecaphan-9-en-5-one. LCMS m/z (M+H): 679.4 required, 679.4 found.

To a solution of (3R,7S,E)-4-ethyl-25-methoxy-3-methyl-7-(3,3,3-trifluoropropyl)-13-oxa-4,6-diaza-1(6,8)-quinolina-2(4,2)-pyridinacyclotridecaphan-9-en-5-one (90 mg, 0.166 mmol) in EtOAc (10 mL) and MeOH (10 mL) was added Pd-C(177 mg, 0.166 mmol) (10% wt) and stirred at 30° C. under H2 (15 psi) for 1 h. The reaction mixture was concentrated in vacuo to give the crude product. Then the crude product was purified by prep-TLC ($SiO_2$, 100% EtOAc) and SFC (IG, 35-70% EtOH with 0.1% $NH_4OH$/ $CO_2$) to give (3R,7R)-4-ethyl-25-methoxy-3-methyl-7-(3,3,3-trifluoropropyl)-13-oxa-4,6-diaza-1(6,8)-quinolina-2(4,2)-pyridinacyclotridecaphan-5-one (example 157). LCMS m/z (M+H): 545.2 required, 545.2 found. $^1H$ NMR 1014866-087-p2 (400 MHz, $CD_3OD$) δ 8.70 (dd, J=1.47, 4.16 Hz, 1H), 8.21-8.29 (m, 2H), 7.90 (d, J=1.22 Hz, 1H), 7.47 (dd, J=4.16, 8.31 Hz, 1H), 7.35 (s, 1H), 7.07 (d, J=1.22 Hz, 1H), 5.78-5.94 (m, 2H), 4.26-4.60 (m, 3H), 3.94 (br dd, J=4.40, 8.80 Hz, 1H), 3.90 (s, 3H), 3.02-3.16 (m, 2H), 2.03-2.26 (m, 2H), 1.76-1.89 (m, 2H), 1.57-1.72 (m, 2H), 1.51 (d, J=7.09 Hz, 3H), 1.29-1.46 (m, 5H), 0.90 (t, J=6.97 Hz, 3H).

Intermediate B90

(R)—N—((R)-1-(4-chloropyridin-2-yl)ethyl)-N,2-dimethylpropane-2-sulfinamide (B90)

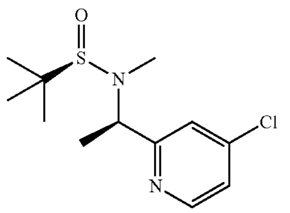 [SMILES: C[C@H](c1cc(Cl)ccn1)N(C)[S@](=O)C(C)(C)C]

(R)—N—((R)-1-(4-chloropyridin-2-yl)ethyl)-2-methylpropane-2-sulfinamide was prepared according to the method described for B9. To a solution of (R)—N—((R)-1-(4-chloropyridin-2-yl)ethyl)-2-methylpropane-2-sulfinamide in DMF (20 mL) was added sodium hydride (0.613 g, 15.34 mmol) (60%) at 0° C. under $N_2$. The mixture was stirred at 0° C. for 30 mins. MeI (0.959 mL, 15.34 mmol) was added and stirred at 25° C. for 1 h. The reaction mixture was poured into water (50 mL), extracted with EtOAc (50 mL×3). The combined organic layers were washed with brine (50 mL×2), dried over $Na_2SO_4$ and filtered. The filtrate was concentrated and purified by Flash silica gel chromatography (ISCO®; 25 g SepaFlash® Silica Flash Column, Eluent of 50% EtOAc/Pet.ether gradient) to give (R)—N—((R)-1-(4-chloropyridin-2-yl)ethyl)-N,2-dimethylpropane-2-sulfinamide B90. LCMS m/z (M+H): 275.1 required, 275.1 found.

Example 158

(3R,7R,E)-3,4-dimethyl-7-(3,3,3-trifluoropropyl)-13-oxa-4,6-diaza-1(6,8)-imidazo[1,2-a]pyrazina-2(4,2)-pyridinacyclotridecaphan-5-one (example 158)

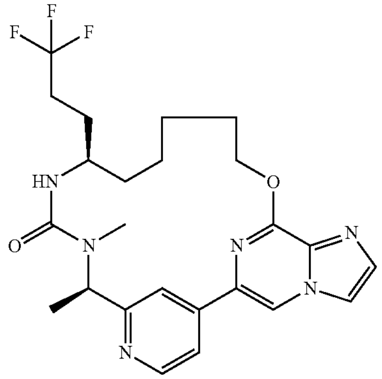 [SMILES: C[C@@H]1c2cc(ccn2)-c2cn3ccnc3c(n2)OCCCCC[C@H](CCC(F)(F)F)NC(=O)N1C]

(3R,7R,E)-3,4-dimethyl-7-(3,3,3-trifluoropropyl)-13-oxa-4,6-diaza-1(6,8)-imidazo[1,2-a]pyrazina-2(4,2)-pyridinacyclotridecaphan-5-one was prepared using the method described for example 137 using B90 in place of (R)—N—((R)-1-(5-bromo-6-methylpyridin-3-yl)ethyl)-N-ethyl-2-methylpropane-2-sulfinamide. LCMS m/z (M+H): 491.2 required, 491.3 found. $^1$H NMR (400 MHz, $CD_3OD$) δ 8.87 (s, 1H), 8.52 (d, J=5.4 Hz, 1H), 8.06 (s, 1H), 7.99 (s, 1H), 7.75 (br d, J=4.6 Hz, 1H), 7.65 (s, 1H), 6.15 (br d, J=9.3 Hz, 1H), 5.89 (q, J=7.0 Hz, 1H), 4.84-4.75 (m, 1H), 4.64 (dt, J=5.9, 10.9 Hz, 1H), 4.11-3.90 (m, 1H), 2.83-2.64 (m, 3H), 2.36-2.20 (m, 2H), 2.02-1.91 (m, 1H), 1.88-1.69 (m, 3H), 1.63-1.48 (m, 7H), 1.41-1.29 (m, 1H).

Example 159

(3R,7R,E)-4-ethyl-3-methyl-7-(3,3,3-trifluoropropyl)-13-oxa-4,6-diaza-1(6,8)-imidazo[1,2-a]pyrazina-2(5,3)-pyridazinacyclotridecaphan-5-one (example 159)

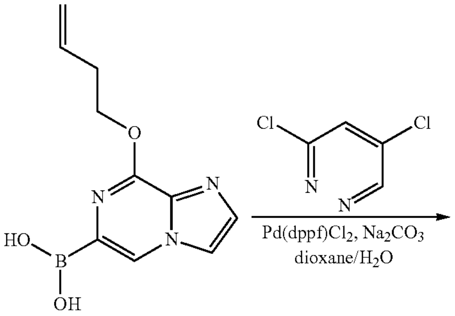

C37

-continued

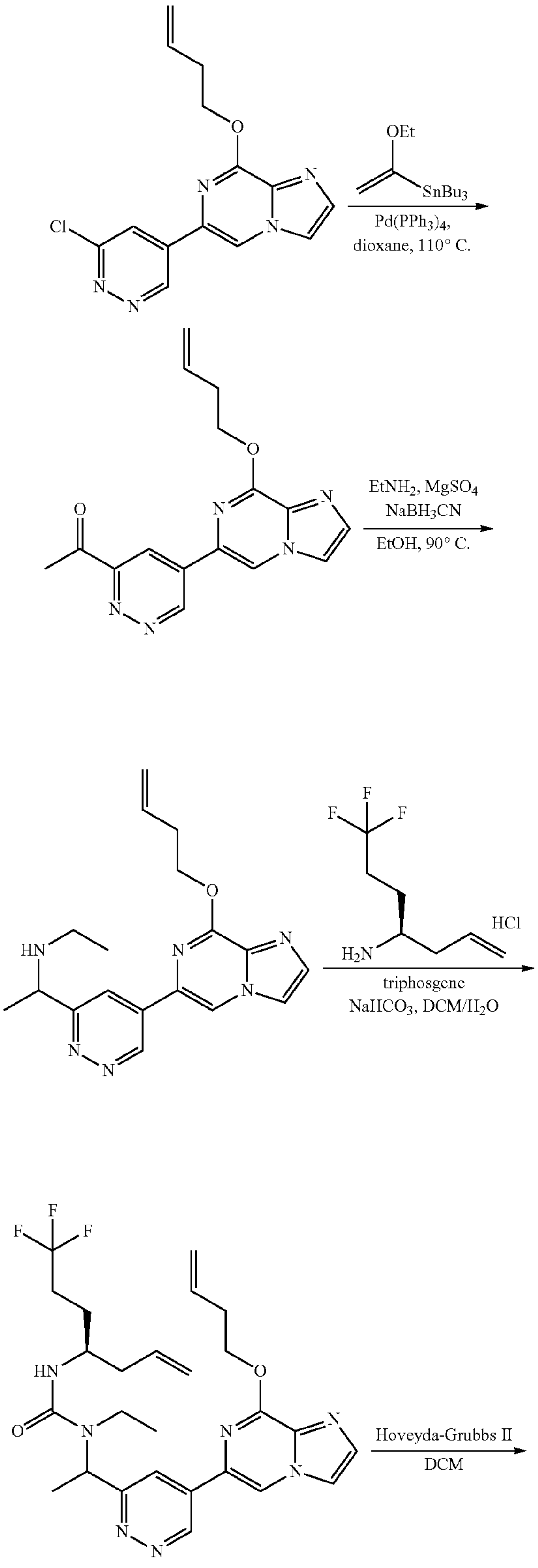

-continued

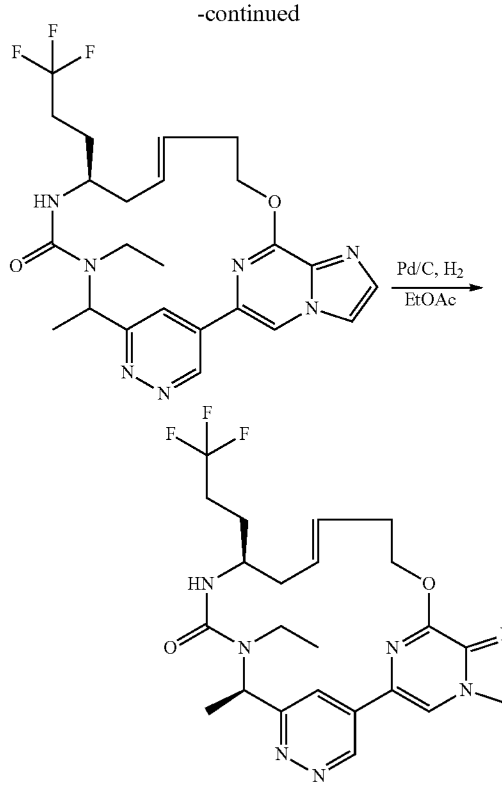

EXAMPLE 159

To a solution of B37 (1.738 g, 7.46 mmol) in 1,4-Dioxane (30 mL) and Water (6 mL) were added 3,5-dichloropyridazine (1.333 g, 8.95 mmol), $Na_2CO_3$ (1.581 g, 14.92 mmol) and Pd(dppf)$Cl_2$ (0.546 g, 0.746 mmol) at 25° C., the mixture was stirred at 85° C. under N2 for 12 h. The reaction mixture was poured into water (30 mL) to pH=9, extracted with EtOAc (30 mL×3). The organic layer was washed with brine (30 mL), dried over $Na_2SO_4$ and filtered. The filtrate was concentrated and purified by flash silica gel chromatography (ISCO®; 40 g SepaFlash® Silica Flash Column, eluent of [0-80]% ethyl acetate/pet. ether gradient) to give 8-(but-3-en-1-yloxy)-6-(6-chloropyridazin-4-yl)imidazo[1,2-a]pyrazine. LCMS m/z (M+H): 302.0 required, 302.0 found To a solution of 8-(but-3-en-1-yloxy)-6-(6-chloropyridazin-4-yl)imidazo[1,2-a]pyrazine (1.2 g, 3.98 mmol) in 1,4-Dioxane (30 mL) were added tributyl(1-ethoxyvinyl) stannane (4.31 g, 11.93 mmol) and Pd($Ph_3P$)$_4$ (0.460 g, 0.398 mmol). The mixture was stirred at 110° C. for 15 hours. The reaction mixture was cooled to room temperature. 1 M HCl (20 mL) was added to the mixture and stirred at 60° C. for 6 hours. The reaction mixture was poured into water (50 mL), extracted with EtOAc (30 mL×3). The organic layer was washed with brine (30 mL), dried over $Na_2SO_4$ and filtered. The filtrate was concentrated and purified by flash silica gel chromatography (ISCO®; 25 g SepaFlash® Silica Flash Column, eluent of [0-30]% ethyl acetate/pet. ether gradient) to give 1-(5-(8-(but-3-en-1-yloxy)imidazo[1,2-a]pyrazin-6-yl)pyridazin-3-yl)ethan-1-one. LCMS m/z (M+H): 310.1 required, 310.1 found.

To a solution of 1-(5-(8-(but-3-en-1-yloxy)imidazo[1,2-a]pyrazin-6-yl)pyridazin-3-yl)ethan-1-one (0.3 g, 0.970 mmol) in EtOH (5 mL) was added ethanamine (0.131 g, 2.91 mmol) and acetic acid (5.55 μl, 0.097 mmol) was added to adjusted pH=6. $MgSO_4$ (0.233 g, 1.940 mmol) and $NaBH_3CN$ (0.183 g, 2.91 mmol) were added to the above solution and stirred at 90° C. for 3 hours. The reaction mixture was filtered and concentrated to give crude. The crude was purified by flash silica gel chromatography (ISCO®; 4 g SepaFlash® Silica Flash Column, eluent of 3% ethyl acetate/MeOH gradient) to give 1-(5-(8-(but-3-en-1-yloxy)imidazo[1,2-a]pyrazin-6-yl)pyridazin-3-yl)-N-ethylethan-1-amine. LCMS (M+H): 339.1 required, 339.1 found.

To a solution of (S)-7,7,7-trifluorohept-1-en-4-amine hydrochloride A5 (60.2 mg, 0.295 mmol) in DCM (5 mL) and sat.$NaHCO_3$(5 mL) was added bis(trichloromethyl) carbonate (28.9 mg, 0.098 mmol) and stirred at 0° C. for 30 min. 1-(5-(8-(but-3-en-1-yloxy)imidazo[1,2-a]pyrazin-6-yl) pyridazin-3-yl)-N-ethylethan-1-amine (100 mg, 0.295 mmol) was added and stirred at 30° C. for 12 hours. The reaction mixture was extracted with DCM (10 mL).The combined organic layers were washed with brine (10 mL), dried over $Na_2SO_4$ and filtered. The mixture was purified by flash silica gel chromatography (ISCO®; 4 g SepaFlash® Silica Flash Column, Eluent of 100% EtOAc) to give 1-(1-(5-(8-(but-3-en-1-yloxy)imidazo[1,2-a]pyrazin-6-yl) pyridazin-3-yl)ethyl)-1-ethyl-3-((S)-7,7,7-trifluorohept-1-en-4-yl)urea. LCMS m/z (M+H): 532.2 required, 532.2 found To a solution of 1-(1-(5-(8-(but-3-en-1-yloxy)imidazo[1,2-a]pyrazin-6-yl)pyridazin-3-yl)ethyl)-1-ethyl-3-((S)-7,7,7-trifluorohept-1-en-4-yl)urea (60 mg, 0.113 mmol) in $CH_2Cl_2$ (60 mL) was added Hoveyda-Grubbs II (14.15 mg, 0.023 mmol) and the mixture was stirred at 50° C. for 16 h. The reaction mixture was concentrated. The residue was purified by Prep-TLC ($SiO_2$, 100% EtOAc) to give ($1^7$E,7S,9E)-4-ethyl-3-methyl-7-(3,3,3-trifluoropropyl)-13-oxa-4,6-diaza-1(6,8)-imidazo[1,2-a]pyrazina-2(5,3)-pyridazinacyclotridecaphan-9-en-5-one. LCMS m/z (M+H): 504.1 required, 504.1 found.

To a solution of ($1^7$E,7S,9E)-4-ethyl-3-methyl-7-(3,3,3-trifluoropropyl)-13-oxa-4,6-diaza-1(6,8)-imidazo[1,2-a] pyrazina-2(5,3)-pyridazinacyclotridecaphan-9-en-5-one (60 mg, 0.119 mmol) in EtOAc (10 mL) and was added Pd-C (12.68 mg, 0.119 mmol) (10% wt) and stirred at 25° C. under H2 (15 psi) for 1 h. The reaction mixture was concentrated in vacuo to give the crude product. Then the crude product was purified by prep_HPLC (36-56% ACN/water with 0.1% TFA) to give (3R,7R,E)-4-ethyl-3-methyl-7-(3,3,3-trifluoropropyl)-13-oxa-4,6-diaza-1(6,8)-imidazo[1,2-a]pyrazina-2(5,3)-pyridazinacyclotridecaphan-5-one as the second eluting diastereomer (example 159). LCMS m/z (M+H): 506.2 required, 506.2 found. $^1$H NMR 5037040-0005-p2 (500 MHz, $CD_3OD$) δ 9.32 (s, 1H), 9.25 (d, J=1.53 Hz, 1H), 8.27 (s, 1H), 8.16 (s, 1H), 7.76 (s, 1H), 6.15 (br d, J=9.31 Hz, 1H), 5.98 (br d, J=7.63 Hz, 1H), 4.83-4.78 (m, 2H), 4.07 (br s, 1H), 3.40-3.35 (m, 1H), 3.19-3.09 (m, 1H), 2.31-2.14 (m, 2H), 2.06-1.95 (m, 1H), 1.87 (br s, 1H), 1.82-1.69 (m, 6H), 1.61-1.56 (m, 2H), 1.50 (br s, 1H), 1.35 (br s, 2H), 1.15 (t, J=7.02 Hz, 3H)

Example 160

(3R,7R,E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-5-one (example 160)

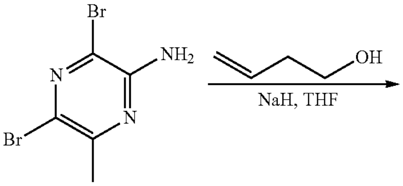

-continued

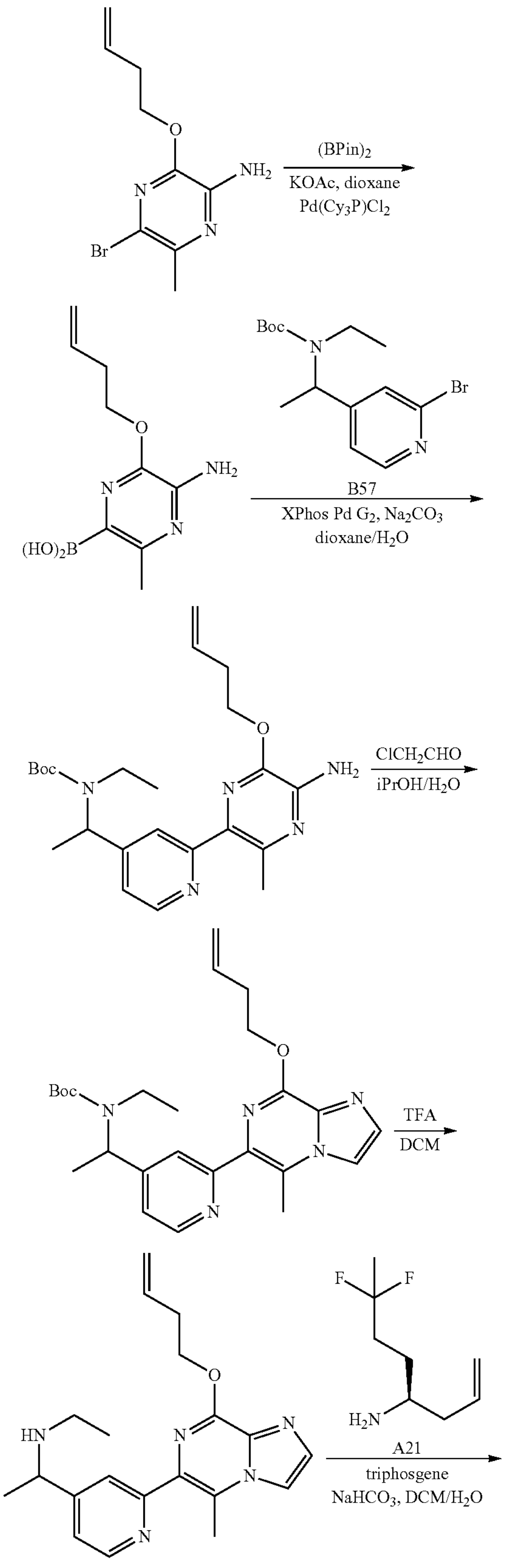

-continued

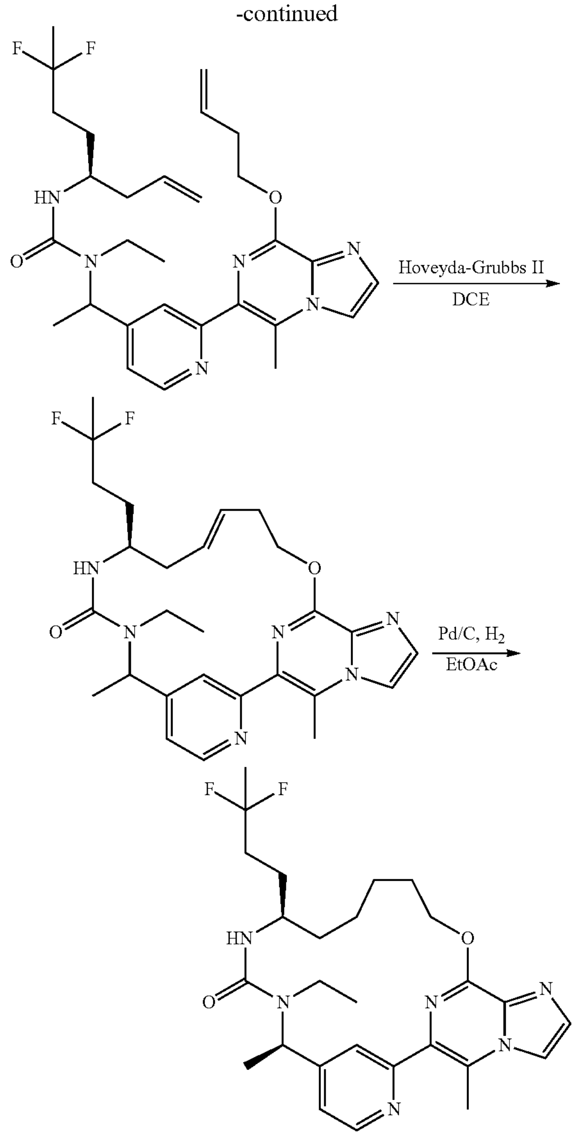

EXAMPLE 160

To a solution of but-3-en-1-ol (1.540 g, 21.35 mmol) in THF (10 mL) was added sodium hydride (1.025 g, 25.6 mmol)(60%), the mixture was stirred at 0° C. under N2 protection for 30 mins. The mixture was added to a solution of 3,5-dibromo-6-methylpyrazin-2-amine (1.9 g, 7.12 mmol) in THF (20 mL) at 0° C. The mixture was stirred at 70° C. for 30 hours. The reaction mixture was poured into water (20 mL), extracted with EtOAc (20 mL×3). The organic layer was washed with brine (10 mL), dried over $Na_2SO_4$ and filtered. The filtrate was concentrated and purified by flash silica gel chromatography (ISCO®; [weight]25 g SepaFlash® Silica Flash Column, eluent of [0-10]% ethyl acetate/pet. ether gradient) to give 5-bromo-3-(but-3-en-1-yloxy)-6-methylpyrazin-2-amine (350 mg, 1.085 mmol, 15.24% yield) as a yellow solid. LCMS m/z (M+H): 260.1 required, 260.1 found.

To a solution of 5-bromo-3-(but-3-en-1-yloxy)-6-methylpyrazin-2-amine (350 mg, 1.356 mmol) in Dioxane (15 mL) were added 4,4,4',4',5,5,5',5'-octamethyl-2,2'-bi(1,3,2-dioxaborolane) (689 mg, 2.71 mmol), potassium acetate (399 mg, 4.07 mmol) and Pd($PCy_3$)C12 (621 mg, 1.356 mmol). The mixture was stirred at 110° C. for 2 hours. The mixture was cooled to rt and filtered. The filtrate was concentrated to give crude (5-amino-6-(but-3-en-1-yloxy)-3-methylpyrazin-2-yl)boronic acid, which was used in the next step without further purification. LCMS m/z (M+H): 224.1 required, 223.6 found.

To a solution of (5-amino-6-(but-3-en-1-yloxy)-3-methylpyrazin-2-yl)boronic acid (0.302 g, 1.354 mmol) in Dioxane (15 mL) and water (5 mL) were added B91 (0.446 g, 1.354 mmol), sodium carbonate (0.431 g, 4.06 mmol) and Xphos Pd G2 (0.107 g, 0.135 mmol). The mixture was stirred at 90° C. for 5 hours. The mixture was concentrated, and the residue was partitioned between water (10 mL) and EtOAc (10 mL). The water layer was extracted by EtOAc (10 mL×3). The combined organic layers were washed with brine (10 mL), dried over $Na_2SO_4$, filtered and concentrated. The residue was purified by column chromatography on silica gel (20 g, Pet. ether:EtOAc=1:1) to give tert-butyl (1-(2-(5-amino-6-(but-3-en-1-yloxy)-3-methylpyrazin-2-yl) pyridin-4-yl)ethyl)(ethyl)carbamate. LCMS m/z (M+H): 428.3 required, 428.1 found.

To a solution of tert-butyl (1-(2-(5-amino-6-(but-3-en-1-yloxy)-3-methylpyrazin-2-yl)pyridin-4-yl)ethyl)(ethyl)carbamate (480 mg, 1.123 mmol) in Water (10 mL) and 2-Propanol (2 mL) was added 2-chloroacetaldehyde (441 mg, 2.245 mmol) and stirred at 110° C. for 4 hours. The reaction mixture was extracted to give crude tert-butyl (1-(2-(8-(but-3-en-1-yloxy)-5-methylimidazo[1,2-a] pyrazin-6-yl)pyridin-4-yl)ethyl)(ethyl)carbamate, which was used in the next step without further purification. LCMS m/z (M+H): 452.3 required, 451.9 found.

To a solution of tert-butyl (1-(2-(8-(but-3-en-1-yloxy)-5-methylimidazo[1,2-a]pyrazin-6-yl)pyridin-4-yl)ethyl) (ethyl)carbamate (380 mg, 0.842 mmol) in DCM (3 mL) was added TFA (2 mL, 26.0 mmol). The mixture was stirred at 15° C. for 2 h. The mixture was concentrated to give 1-(2-(8-(but-3-en-1-yloxy)-5-methylimidazo[1,2-a]pyrazin-6-yl)pyridin-4-yl)-N-ethylethan-1-amine, which was used in the next steps directly. LCMS m/z (M+H): 352.2 required, 352.2 found.

To a solution of (S)-7,7-difluorooct-1-en-4-amine hydrochloride A21 (200 mg, 1.002 mmol) and TEA (0.698 mL, 5.01 mmol) in DCM (3 mL) was added bis(trichloromethyl) carbonate (98 mg, 0.331 mmol) at 0° C. and stirred for 30 mins. 1-(2-(8-(but-3-en-1-yloxy)-5-methylimidazo[1,2-a] pyrazin-6-yl)pyridin-4-yl)-N-ethylethan-1-amine (180 mg, 0.512 mmol) in DCM (2 mL) was added to the mixture. The mixture was stirred at 0° C. for 30 mins. The reaction mixture was poured into water (2 mL), extracted with DCM (2 mL×3). The organic layer was washed with brine (2 mL), dried over $Na_2SO_4$ and filtered. The filtrate was concentrated and purified by Flash silica gel chromatography (ISCO®; 4 g SepaFlash® Silica Flash Column, Eluent of 100% EtOAc) to give 1-(1-(2-(8-(but-3-en-1-yloxy)-5-methylimidazo[1,2-a]pyrazin-6-yl)pyridin-4-yl)ethyl)-3-((S)-7,7-difluorooct-1-en-4-yl)-1-ethylurea. LCMS m/z (M+H): 541.3 required, 541.3 found.

To a solution of 1-(1-(2-(8-(but-3-en-1-yloxy)-5-methylimidazo[1,2-a]pyrazin-6-yl)pyridin-4-yl)ethyl)-3-((S)-7,7-difluorooct-1-en-4-yl)-1-ethylurea (120 mg, 0.222 mmol) in DCE (50 mL) was added (1,3-dimesitylimidazolidin-2-ylidene)(2-isopropoxybenzylidene)ruthenium(VI) chloride (28 mg, 0.045 mmol) and stirred at 50° C. for 16 hours. The mixture was purified by Flash silica gel chromatography (ISCO®; 4 g SepaFlash® Silica Flash Column, Eluent of 100% EtOAc) to give ($1^7$E,7S,9E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-9-en-5-one. LCMS m/z (M+H): 513.2 required, 513.3 found. $^1$H NMR (400 MHz, $CD_3OD$) δ 8.69-8.55 (m, 1H), 8.10 (br d, J=3.9 Hz, 1H), 8.03 (s, 1H), 7.72 (s, 1H), 7.42 (br dd, J=5.0, 12.6 Hz, 1H), 5.99-5.84 (m, 1H), 5.65-5.52 (m, 2H), 4.81-4.62 (m, 2H), 4.12-3.74 (m, 1H), 3.13 (q, J=6.8 Hz, 1H), 2.98-2.92 (m, 3H), 2.68-2.51 (m, 2H), 2.45-2.16 (m, 2H), 2.06-1.86 (m, 2H), 1.73 (br d, J=6.8 Hz, 2H), 1.69-1.62 (m, 2H), 1.61-1.53 (m, 3H), 1.19-0.99 (m, 3H).

To a mixture of ($1^7$E,7S,9E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-9-en-5-one (70 mg, 0.137 mmol) in EtOAc (20 mL) was added Pd-C(20 mg, 0.019 mmol) (10%), and the resulting mixture was stirred at 20° C. for 30 mins under H2 (excess) (15 psi). The mixture was filtered, the filtrate was concentrated, and purified by SFC (AD, 5-40% EtOH with 0.05% DEA/$CO_2$) to give (3R,7R,E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-5-one as the second eluting diastereomer (example 160). LCMS m/z (M+H): 515.3 required, 515.3 found. $^1$H NMR (400 MHz, $CD_3OD$) δ 8.63 (d, J=5.1 Hz, 1H), 8.01 (d, J=1.5 Hz, 2H), 7.71 (s, 1H), 7.44 (d, J=4.6 Hz, 1H), 5.99-5.77 (m, 2H), 4.84-4.73 (m, 1H), 4.62 (dt, J=5.4, 10.3 Hz, 1H), 3.98 (br s, 1H), 3.28-3.16 (m, 1H), 3.12-2.99 (m, 1H), 2.90 (s, 3H), 2.05-1.83 (m, 4H), 1.72-1.66 (m, 1H), 1.64-1.58 (m, 7H), 1.53-1.36 (m, 2H), 1.07 (t, J=7.0 Hz, 3H).

Example 161

(3R,7S,E)-4-ethyl-3-methyl-7-(3,3,3-trifluoropropyl)-10,13-dioxa-4,6-diaza-1(6,8)-imidazo[1,2-a]pyrazina-2(2,4)-pyridinacyclotridecaphan-5-one (example 161)

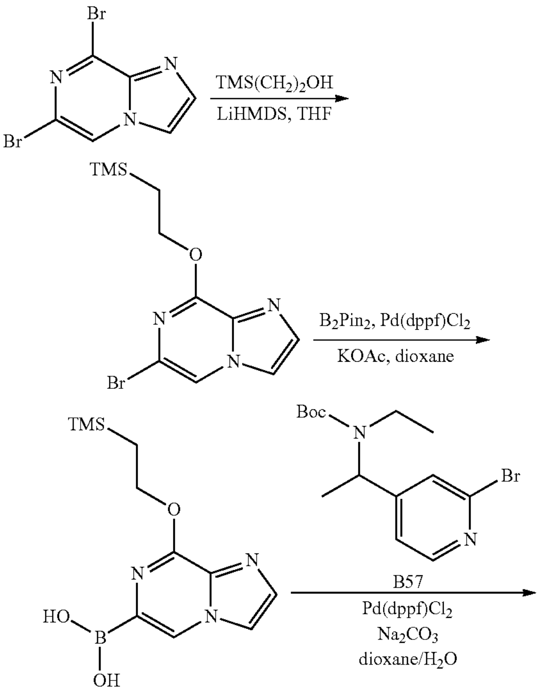

-continued

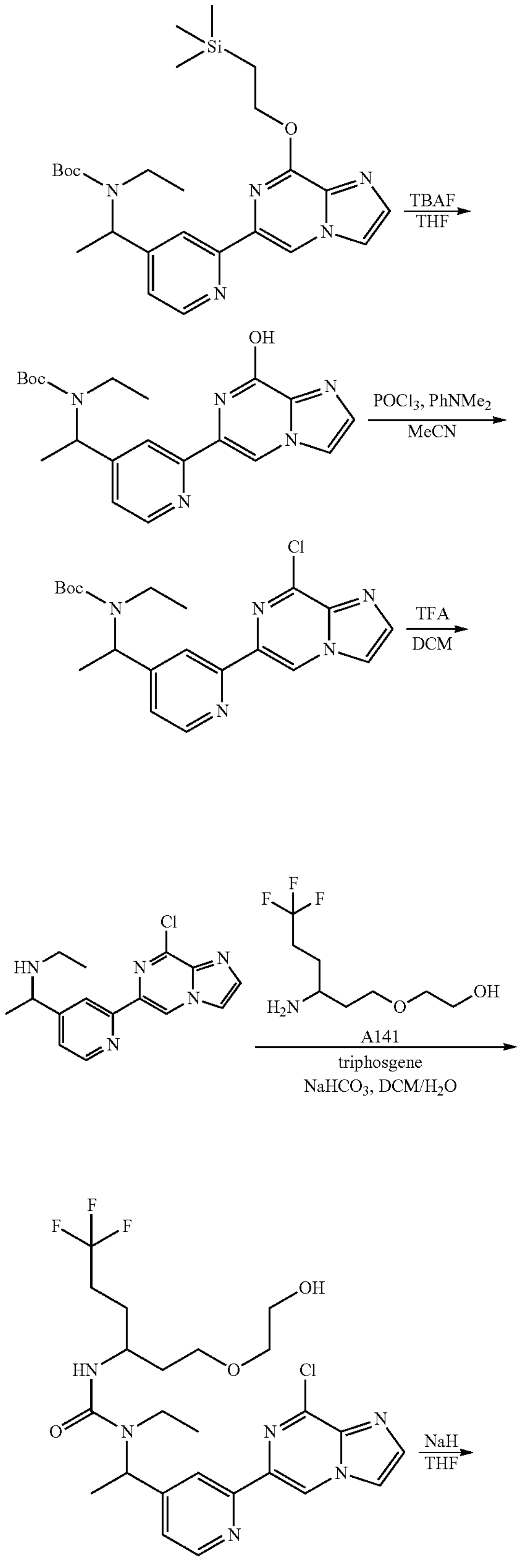

-continued

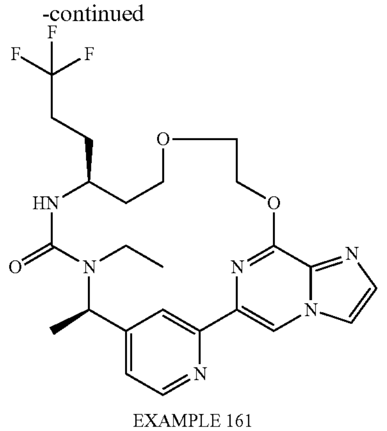

EXAMPLE 161

To a solution of 2-(trimethylsilyl)ethan-1-ol (256 mg, 2.167 mmol) in THF (10 mL) was added LiHMDS (1.986 mL, 1.986 mmol) (1 M in THF) at 0° C. and stirred for 30 mins. 6,8-dibromoimidazo[1,2-a]pyrazine (500 mg, 1.806 mmol) was added and stirred at 25° C. for 12 hours. The reaction mixture was poured into water (10 mL), extracted with EtOAc (20 mL×3). The organic layer was washed with brine (10 mL), dried over $Na_2SO_4$ and filtered. The filtrate was concentrated to give 6-bromo-8-(2-(trimethylsilyl)ethoxy)imidazo[1,2-a]pyrazine. LCMS m/z (M+H): 314.0 required, 314.6 found.

To a solution of 6-bromo-8-(2-(trimethylsilyl)ethoxy)imidazo[1,2-a]pyrazine (400 mg, 1.273 mmol) in dioxane (8 mL) were added 4,4,4',4',5,5,5',5'-octamethyl-2,2'-bi(1,3,2-dioxaborolane) (485 mg, 1.909 mmol), potassium acetate (375 mg, 3.82 mmol), Pd(dppf)$Cl_2$ (93 mg, 0.127 mmol) and the resulting mixture was stirred at 80° C. under N2 protection for 12 hours. The mixture was filtered and the filtrate was concentrated to give (8-(2-(trimethylsilyl)ethoxy)imidazo[1,2-a]pyrazin-6-yl)boronic acid. LCMS m/z (M+H): 280.1 required, 279.5 found.

To a solution of (8-(2-(trimethylsilyl)ethoxy)imidazo[1,2-a]pyrazin-6-yl)boronic acid (320 mg, 1.146 mmol) in dioxane (10 mL) and water (2 mL) were added tert-butyl (R)-(1-(2-bromopyridin-4-yl)ethyl)(ethyl)carbamate B91 (340 mg, 1.032 mmol), $Na_2CO_3$ (364 mg, 3.44 mmol), Pd(dppf)$Cl_2$ (84 mg, 0.115 mmol) and the resulting mixture was stirred at 80° C. under N2 protection for 12 hours. The mixture was filtered and the filtrate was concentrated and purified by prep-TLC (Pet.ether:EtOAc=1:1) to give tert-butyl ethyl(1-(2-(8-(2-(trimethylsilyl)ethoxy)imidazo[1,2-a]pyrazin-6-yl)pyridin-4-yl)ethyl)carbamate. LCMS m/z (M+H): 484.3 required, 484.3 found.

To a solution of tert-butyl ethyl(1-(2-(8-(2-(trimethylsilyl)ethoxy)imidazo[1,2-a]pyrazin-6-yl)pyridin-4-yl)ethyl)carbamate (500 mg, 1.034 mmol) in THF (8 mL) was added a solution of TBAF (1.034 mL, 2.067 mmol) in 2-Me-THF (2 M) dropwise, and the reaction mixture was stirred at 20° C. for 3 h. Then the mixture was concentrated to give tert-butyl ethyl(1-(2-(8-hydroxyimidazo[1,2-a]pyrazin-6-yl)pyridin-4-yl)ethyl)carbamate. LCMS m/z (M+H): 383.8 found, 384.2 required.

To a solution of tert-butyl ethyl(1-(2-(8-hydroxyimidazo[1,2-a]pyrazin-6-yl)pyridin-4-yl)ethyl)carbamate (300 mg, 0.782 mmol) in MeCN (5 mL) were added N,N-dimethylaniline (758 mg, 6.26 mmol) and phosphoryl trichloride (480 mg, 3.13 mmol). The mixture was stirred at 80° C. for 2 hours. The reaction mixture was poured into water (10 mL), extracted with EtOAc (20 mL×3). The organic layer was washed with brine (10 mL), dried over $Na_2SO_4$ and filtered. The filtrate was concentrated and purified by prep-TLC ($SiO_2$, EtOAc) to give tert-butyl (1-(2-(8-chloroimidazo[1,2-a]pyrazin-6-yl)pyridin-4-yl)ethyl)(ethyl)carbamate. LCMS m/z (M+H): 402.2 required, 401.9 found.

To a solution of tert-butyl (1-(2-(8-chloroimidazo[1,2-a]pyrazin-6-yl)pyridin-4-yl)ethyl)(ethyl)carbamate (90 mg, 0.224 mmol) in DCM (3 mL) were added TFA (0.5 mL) and the mixture was stirred at 20° C. for 2 hours. The reaction mixture was concentrated to give 1-(2-(8-chloroimidazo[1,2-a]pyrazin-6-yl)pyridin-4-yl)-N-ethylethan-1-amine. LCMS m/z (M+H): 302.1 required, 301.6 found.

To a solution of 2-((3-amino-6,6,6-trifluorohexyl)oxy)ethan-1-ol A141 (160 mg, 0.746 mmol) in DCM (2 mL) and sat.$NaHCO_3$(2 mL) was added bis(trichloromethyl) carbonate (73.7 mg, 0.249 mmol) and stirred at 0° C. for 30 min. 1-(2-(8-chloroimidazo[1,2-a]pyrazin-6-yl)pyridin-4-yl)-N-ethylethan-1-amine (60 mg, 0.179 mmol) was added and stirred at 25° C. for 1 hour. Then the mixture was quenched with water (5 mL), extracted with DCM (5 mL×3). The combined organic layers were washed with brine (5 mL), dried over $Na_2SO_4$, filtered and concentrated to give 1-(1-(2-(8-chloroimidazo[1,2-a]pyrazin-6-yl)pyridin-4-yl)ethyl)-1-ethyl-3-(6,6,6-trifluoro-1-(2-hydroxyethoxy)hexan-3-yl)urea. LCMS m/z (M+H): 542.8 found, 543.1 required.

To a solution of 1-(1-(2-(8-chloroimidazo[1,2-a]pyrazin-6-yl)pyridin-4-yl)ethyl)-1-ethyl-3-(6,6,6-trifluoro-1-(2-hydroxyethoxy)hexan-3-yl)urea (95 mg, 0.175 mmol) in DMF (5 mL) was added NaH (35.0 mg, 0.875 mmol) (60%) at 0° C. The mixture was stirred at 20° C. for 1 hour. Then the mixture was quenched with water (5 mL), extracted with EtOAc (5 mL×3). The combined organic layers were washed with brine (5 mL), dried over $Na_2SO_4$, filtered, concentrated and purified by prep-TLC (100% EtOAc) and SFC (AD, 25% EtOH with 0.1% $NH_4OH/CO_2$) to give two mixtures of isomers, the second eluting of which was further separated by SFC (OD, 30% EtOH with 0.1% $NH_4OH/CO_2$) to give (3R,7S,E)-4-ethyl-3-methyl-7-(3,3,3-trifluoropropyl)-10,13-dioxa-4,6-diaza-1(6,8)-imidazo[1,2-a]pyrazina-2(2,4)-pyridinacyclotridecaphan-5-one as the second eluting diastereomer (example 161). LCMS m/z (M+H): 507.1 found, 507.1 required. $^1H$ NMR (400 MHz, $CD_3OD$) δ 9.00 (s, 1H), 8.59 (d, J=5.0 Hz, 1H), 8.23 (s, 1H), 8.06 (s, 1H), 7.66 (s, 1H), 7.39 (d, J=5.0 Hz, 1H), 5.95 (q, J=7.1 Hz, 1H), 5.19 (dt, J=5.6, 10.2 Hz, 1H), 4.67-4.60 (m, 1H), 4.28-4.19 (m, 1H), 3.93-3.78 (m, 2H), 3.66 (dd, J=4.7, 7.6 Hz, 2H), 3.29-3.17 (m, 1H), 3.09-2.97 (m, 1H), 2.36-2.10 (m, 2H), 2.05-1.87 (m, 1H), 1.84-1.67 (m, 3H), 1.64 (d, J=7.2 Hz, 3H), 1.10 (t, J=7.1 Hz, 3H)

Example 163

(3R,7S,E)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-9-en-5-one (example 163)

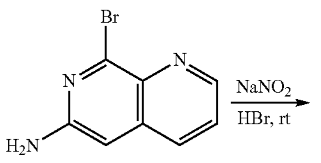

-continued

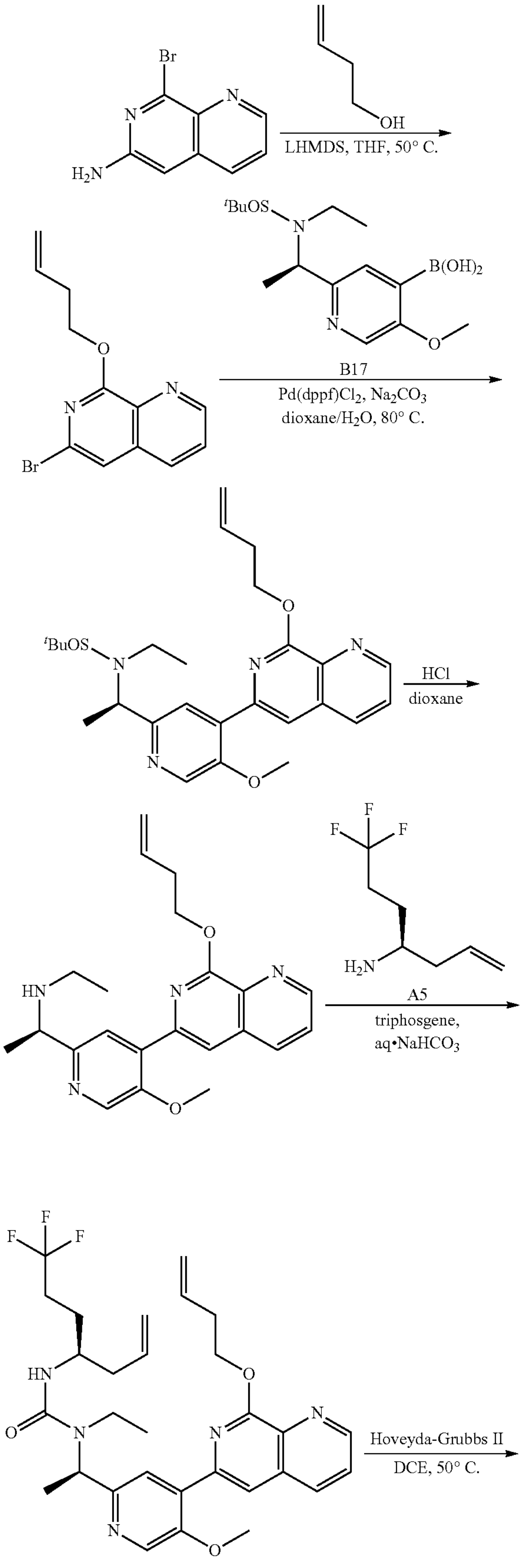

-continued

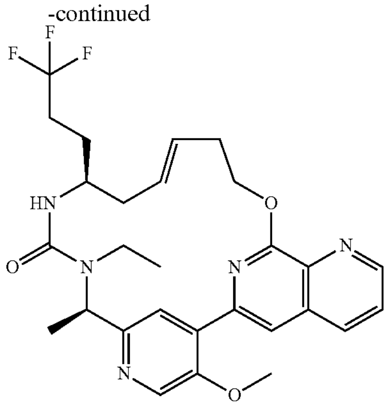

EXAMPLE 163

To a solution of 6,8-Dibromo-1,7-naphthyridine (300 mg, 1.042 mmol) and but-3-en-1-ol (75 mg, 1.042 mmol) in THF (10 mL) was added LHMDS (3.13 mL, 3.13 mmol) (1 M in hexane) at 0° C. Then it was stirred at 50° C. for 12 h. The reaction mixture was poured into water (5 mL), extracted with EtOAc (5 mL×3). The resulting organic layer was washed with water, dried (over $MgSO_4$), filtered and evaporated to the crude product. The crude product was purified by prep-TLC ($SiO_2$, Pet.ether:EtOAc=5:1) to give 6-bromo-8-(but-3-en-1-yloxy)-1,7-naphthyridine. LCMS m/z (M+H): 279.0 required, 280.5 found.

To a solution of B17 (154 mg, 0.469 mmol) in Water (0.5 mL) and 1,4-Dioxane (3 mL) were added $Pd(dppf)Cl_2$ (18.35 mg, 0.025 mmol), $Na_2CO_3$ (53.2 mg, 0.502 mmol) and 6-bromo-8-(but-3-en-1-yloxy)-1,7-naphthyridine (70 mg, 0.251 mmol). The mixture was stirred at 80° C. for 3 hours. The mixture was poured into water (10 mL), extracted with EtOAc (10 mL×3). The combined organic layers were washed with brine (10 mL), dried over $Na_2SO_4$ and filtered. The filtrate was concentrated and purified by Flash silica gel chromatography (ISCO®; 4 g SepaFlash® Silica Flash Column, Eluent of 100% EtOAc/Pet.ether gradient) to give N—((R)-1-(4-(8-(but-3-en-1-yloxy)-1,7-naphthyridin-6-yl)-5-methoxypyridin-2-yl)ethyl)-N-ethyl-2-methylpropane-2-sulfinamide. LCMS m/z (M+H): 483.2 required, 483.0 found.

To a solution of N—((R)-1-(4-(8-(but-3-en-1-yloxy)-1,7-naphthyridin-6-yl)-5-methoxypyridin-2-yl)ethyl)-N-ethyl-2-methylpropane-2-sulfinamide (69 mg, 0.143 mmol) in MeOH (7 mL) were added acetyl chloride (33.7 mg, 0.429 mmol). The mixture was stirred at 15° C. for 2 hours. The mixture was concentrated in vacuo to give (R)-1-(4-(8-(but-3-en-1-yloxy)-1,7-naphthyridin-6-yl)-5-methoxypyridin-2-yl)-N-ethylethan-1-amine. LCMS m/z (M+H): 379.2 required, 378.8 found.

To a solution of A5 (34.3 mg, 0.169 mmol) in DCM (2 mL) and aq.$NaHCO_3$(2 mL) was added bis(trichloromethyl) carbonate (15.01 mg, 0.051 mmol) at 0° C. The mixture was stirred for 30 mins. Then (R)-1-(4-(8-(but-3-en-1-yloxy)-1,7-naphthyridin-6-yl)-5-methoxypyridin-2-yl)-N-ethylethan-1-amine (63.6 mg, 0.153 mmol) was added and stirred at 15° C. for 12 hour. The mixture was poured into water (10 mL), extracted with DCM (10 mL×3). The combined organic layers were washed with brine (10 mL), dried over $Na_2SO_4$ and filtered. The filtrate was concentrated and purified by Flash silica gel chromatography (ISCO®; 4 g SepaFlash® Silica Flash Column, Eluent of 100% EtOAc/Pet.ether gradient) to give 1-((R)-1-(4-(8-(but-3-en-1-yloxy)-1,7-naphthyridin-6-yl)-5-methoxypyridin-2-yl)ethyl)-1-ethyl-3-((S)-7,7,7-trifluorohept-1-en-4-yl)urea. LCMS m/z (M+H): 572.3 required, 572.0 found.

To a solution of 1-((R)-1-(4-(8-(but-3-en-1-yloxy)-1,7-naphthyridin-6-yl)-5-methoxypyridin-2-yl)ethyl)-1-ethyl-3-((S)-7,7,7-trifluorohept-1-en-4-yl)urea (60 mg, 0.105 mmol) in DCE (60 mL) was added Hoveyda-Grubbs 11(65.8 mg, 0.105 mmol) and the mixture was stirred at 50° C. for 3 h. The reaction mixture was concentrated. The residue was purified by Prep-TLC ($SiO_2$, EtOAc=1) to give (3R,7S,E)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-9-en-5-one (example 163). LCMS m/z (M+H): 544.2 required, 543.9 found. $^1H$ NMR (400 MHz, $CD_3OD$) δ 8.86 (dd, J=1.6, 4.3 Hz, 1H), 8.37 (dd, J=1.6, 8.2 Hz, 1H), 8.34 (s, 1H), 8.30 (s, 1H), 8.24 (s, 1H), 7.75 (dd, J=4.3, 8.2 Hz, 1H), 6.04-5.82 (m, 2H), 5.70-5.50 (m, 2H), 4.81 (br d, J=5.1 Hz, 1H), 4.70-4.59 (m, 1H), 4.19-4.05 (m, 4H), 3.23-3.04 (m, 2H), 2.70-2.57 (m, 1H), 2.55-2.34 (m, 2H), 2.32-2.12 (m, 3H), 1.88-1.67 (m, 2H), 1.56 (d, J=7.0 Hz, 3H), 0.95 (t, J=7.0 Hz, 3H)

Example 162

(3R,7R)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-5-one (example 162)

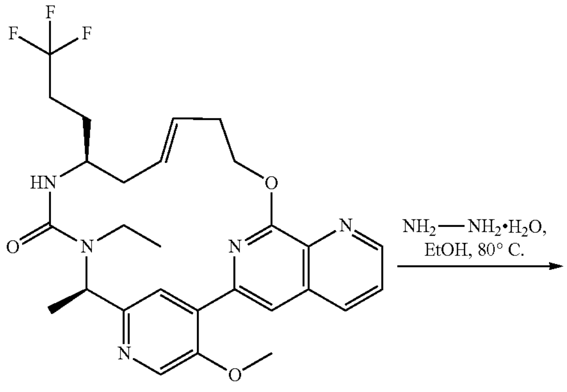

EXAMPLE 163

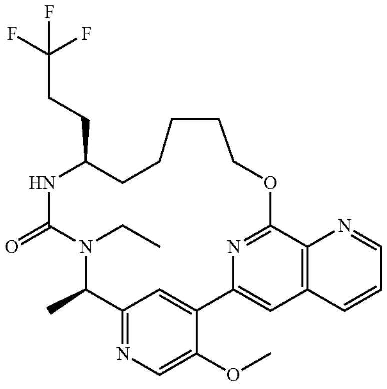

EXAMPLE 162

To a solution of give (3R,7S,E)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-9-en-5-one (20 mg, 0.037 mmol) in EtOH (3 mL) was added hydrazinium hydroxide (21.67 mg, 0.368 mmol). The mixture was stirred at 80° C. for 3 days. The mixture was poured into water (5 mL), extracted with ethyl acetate (3×5 mL). The combined organic layers were dried over $Na_2SO_4$. After concentration, the crude material was purified by prep-HPLC (39-59% ACN/water with 0.1% TFA) to give (3R,7R)-4-ethyl-25-methoxy-3-methyl-7-(3,3,3-trifluoropropyl)-13-oxa-4,6-diaza-1(6,8)-naphthyridina-2(4,2)-pyridinacyclotridecaphan-5-one (example 162). LCMS m/z (M+H): 546.3 required, 546.1 found. $^1$H NMR (400 MHz, $CD_3OD$) δ 8.95 (br d, J=2.7 Hz, 1H), 8.56-8.35 (m, 4H), 7.83 (br dd, J=4.4, 8.3 Hz, 1H), 5.95 (br d, J=7.1 Hz, 1H), 4.85-4.70 (m, 2H), 4.18 (s, 3H), 4.19 (s, 2H), 4.03 (br s, 1H), 3.28 (br s, 2H), 2.35-2.15 (m, 2H), 2.11-1.86 (m, 2H), 1.82-1.30 (m, 11H), 1.07 (br t, J=6.8 Hz, 3H)

Example 164

(3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one (Example 164)

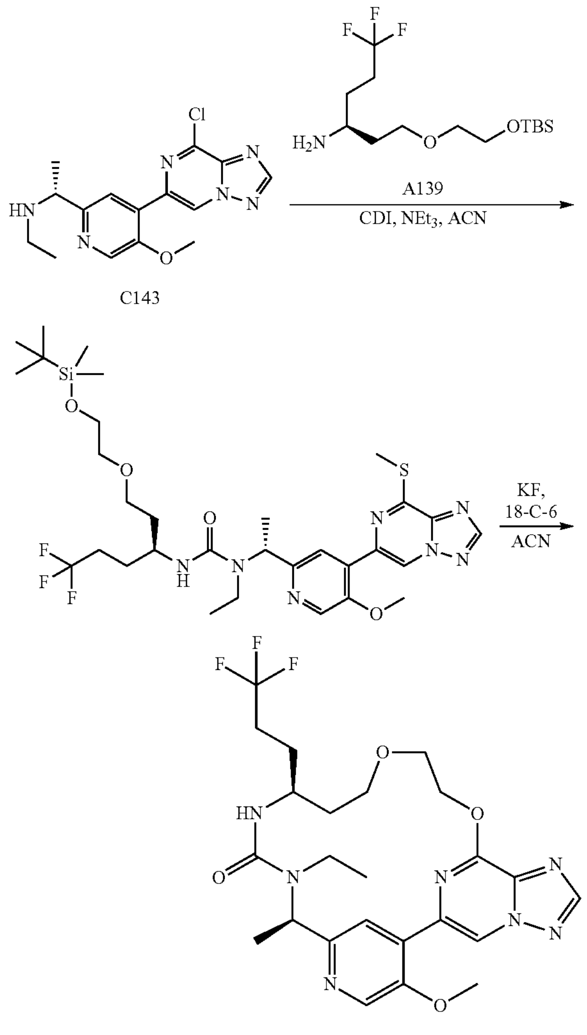

Example 164

Step 1: 3-((S)-1-(2-((tert-butyldimethylsilyl)oxy)ethoxy)-6,6,6-trifluorohexan-3-yl)-1-((R)-1-(4-(8-chloro-[1,2,4]triazolo[1,5-a]pyrazin-6-yl)-5-methoxypyridin-2-yl)ethyl)-1-ethylurea To a solution of (S)-1-(2-((tert-butyldimethylsilyl)oxy)ethoxy)-6,6,6-trifluorohexan-3-amine (A139, 299 mg, 0.907 mmol) in acetonitrile (18.9 mL) was added CDI (159 mg, 0.982 mmol) and the reaction was stirred at ambient temperature for 2 hours. (R)-1-(4-(8-chloro-[1,2,4]triazolo[1,5-a]pyrazin-6-yl)-5-methoxypyridin-2-yl)-N-ethylethan-1-amine hydrochloride (C143, 279 mg, 0.756 mmol) and triethylamine (0.527 mL, 3.78 mmol) were then added and the reaction was stirred at 50° C. for 3 hours. The reaction was concentrated and purified by flash silica chromatography (0-50% EtOAc/EtOH 3:1 mix in hexanes gradient) to give 3-((S)-1-(2-((tert-butyldimethylsilyl)oxy)ethoxy)-6,6,6-trifluorohexan-3-yl)-1-((R)-1-(4-(8-chloro-[1,2,4]triazolo[1,5-a]pyrazin-6-yl)-5-methoxypyridin-2-yl)ethyl)-1-ethylurea. LC-MS: 688.4 (M+1).

Step 2: (3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one (Example 164)

A mixture of 3-((S)-1-(2-((tert-butyldimethylsilyl)oxy)ethoxy)-6,6,6-trifluorohexan-3-yl)-1-((R)-1-(4-(8-chloro-[1,2,4]triazolo[1,5-a]pyrazin-6-yl)-5-methoxypyridin-2-yl)ethyl)-1-ethylurea (207 mg, 0.301 mmol), potassium fluoride (175 mg, 3.01 mmol), and 18-crown-6 (79.0 mg, 0.301 mmol) in acetonitrile (7.5 mL) was heated at 85° C. for 18 hours. The reaction was filtered and concentrated. The crude material was purified by reverse phase HPLC (5-70% ACN in water, with 0.1% TFA as modifier) to yield (3R,7S,E)-4-ethyl-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one (Example 164). LC-MS: 538.3 (M+1). $^1$H NMR (500 MHz, Chloroform-d) δ 9.31 (s, 1H), 8.43 (s, 1H), 8.39 (s, 1H), 8.22 (s, 1H), 6.02 (q, J=7.1 Hz, 1H), 5.01 (td, J=10.2, 5.8 Hz, 1H), 4.84 (td, J=10.3, 5.1 Hz, 1H), 4.43 (d, J=8.4 Hz, 1H), 4.32-4.24 (m, 1H), 4.12 (s, 3H), 3.92 (td, J=9.6, 5.1 Hz, 1H), 3.80 (td, J=9.7, 5.8 Hz, 1H), 3.73-3.59 (m, 2H), 3.20 (dq, J=14.1, 7.0 Hz, 1H), 3.08 (dq, J=14.6, 7.2 Hz, 1H), 2.25 (ddt, J=14.6, 7.7, 3.3 Hz, 2H), 1.98 (ddt, J=15.9, 8.1, 4.0 Hz, 1H), 1.83 (ddt, J=16.9, 11.0, 5.4 Hz, 1H), 1.74-1.62 (m, 4H), 1.56 (ddd, J=14.9, 10.3, 4.9 Hz, 1H), 1.16 (t, J=7.1 Hz, 3H).

The following compound in Table 11 was prepared according to the general procedures herein and in an analogous manner of that used to synthesize Example 165 using the appropriate intermediates referenced in Table 11. The starting materials were either prepared as described in the intermediates section, commercially available, or prepared from commercially available reagents using reactions well known in the art.

TABLE 11

| Ex. # | Structure | Name | Exact Mass [M + H]+ | Interm A | Interm C |
| --- | --- | --- | --- | --- | --- |
| 180 | 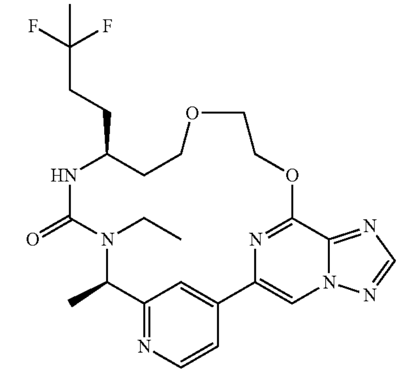 | (3R,7S,E)-7-(3,3-difluorobutyl)-4-ethyl-3-methyl-10,13-dioxa-4,6-diaza-1(6,8)-[1,2,4]triazolo[1,5-a]pyrazina-2(4,2)-pyridinacyclotridecaphan-5-one | Calc'd 504.2, found 504.2 | A143 | C144 |

Example 165

(3R,7S,E)-4-ethyl-25-methoxy-3-methyl-7-(3,3,3-trifluoropropyl)-10,13-dioxa-4,6-diaza-1(5,7)-pyrazolo[1,5-c]pyrimidina-2(4,2)-pyridinacyclotridecaphan-5-one

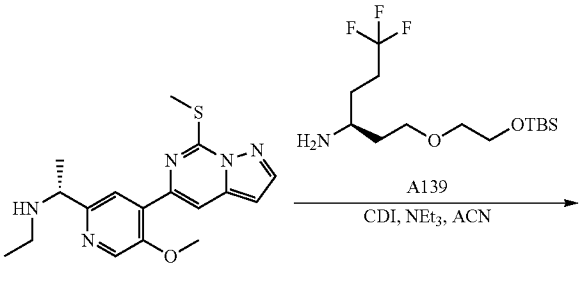

C147

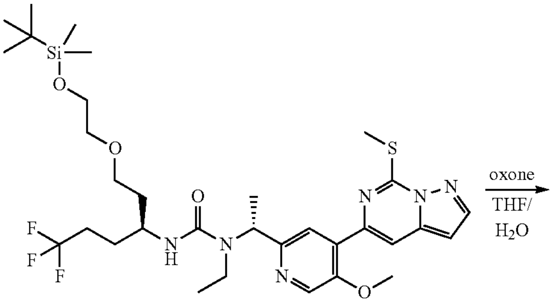

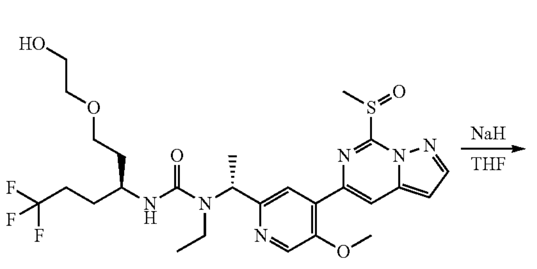

-continued

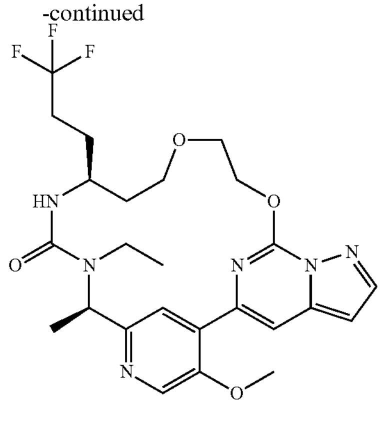

Example 165

Step 1: 3-((S)-1-(2-((tert-butyldimethylsilyl)oxy)ethoxy)-6,6,6-trifluorohexan-3-yl)-1-ethyl-1-((R)-1-(5-methoxy-4-(7-(methylthio)pyrazolo[1,5-c]pyrimidin-5-yl)pyridin-2-yl)ethyl)urea To a solution of (S)-1-(2-((tert-butyldimethylsilyl)oxy)ethoxy)-6,6,6-trifluorohexan-3-amine (A139, 104 mg, 0.316 mmol) in acetonitrile (6.58 mL) was added CDI (49.1 mg, 0.303 mmol) and the reaction was stirred at ambient temperature for 2 hours. (R)—N-ethyl-1-(5-methoxy-4-(7-(methylthio)pyrazolo[1,5-c]pyrimidin-5-yl)pyridin-2-yl)ethan-1-amine hydrochloride (C147, 100 mg, 0.756 mmol) and triethylamine (0.183 mL, 1.32 mmol) were then added and the reaction was stirred at 50° C. for 18 hours. The reaction was concentrated and purified by flash silica chromatography (0-50% EtOAc/EtOH 3:1 mix in hexanes gradient) to give 3-((S)-1-(2-((tert-butyldimethylsilyl)oxy)ethoxy)-6,6,6-trifluorohexan-3-yl)-1-ethyl-1-((R)-1-(5-methoxy-4-(7-(methylthio)pyrazolo[1,5-c]pyrimidin-5-yl)pyridin-2-yl)ethyl)urea. LC-MS: 699.4 (M+1).

Step 2: 1-ethyl-1-((1R)-1-(5-methoxy-4-(7-(methylsulfinyl)pyrazolo[1,5-c]pyrimidin-5-yl)pyridin-2-yl)ethyl)-3-((S)-6,6,6-trifluoro-1-(2-hydroxyethoxy)hexan-3-yl)urea Oxone® (129 mg, 0.210 mmol) was added to a solution of 3-((S)-1-(2-((tert-butyldimethylsilyl)oxy)ethoxy)-6,6,6- trifluorohexan-3-yl)-1-ethyl-1-((R)-1-(5-methoxy-4-(7-(methylthio)pyrazolo[1,5-c]pyrimidin-5-yl)pyridin-2-yl) ethyl)urea (98.0 g, 0.140 mmol) in tetrahydrofuran (2 mL) and water (0.4 mL). The reaction was stirred at ambient temperature for 4.5 hours, with additional oxone (129 mg, 0.210 mmol) added after 2 hours. The reaction was poured into saturated aqueous sodium bicarbonate (10 mL) and extracted with DCM (3×10 mL). The combined organic layers were dried ($Na_2SO_4$), filtered and concentrated to give 1-ethyl-1-((1R)-1-(5-methoxy-4-(7-(methylsulfinyl)pyrazolo[1,5-c]pyrimidin-5-yl)pyridin-2-yl)ethyl)-3-((S)-6,6,6-trifluoro-1-(2-hydroxyethoxy)hexan-3-yl)urea. LC-MS: 601.2 (M+1).

Step 3: (3R,7S,E)-4-ethyl-25-methoxy-3-methyl-7-(3,3,3-trifluoropropyl)-10,13-dioxa-4,6-diaza-1(5,7)-pyrazolo[1,5-c]pyrimidina-2(4,2)-pyridinacyclotridecaphan-5-one (Example 165)

To a mixture of 1-ethyl-1-((1R)-1-(5-methoxy-4-(7-(methylsulfinyl)pyrazolo[1,5-c]pyrimidin-5-yl)pyridin-2-yl)ethyl)-3-((S)-6,6,6-trifluoro-1-(2-hydroxyethoxy)hexan-3-yl)urea (84.0 mg, 0.140 mmol) in tetrahydrofuran (3.5 mL) at ambient temperature was added sodium hydride (60 wt %, 16.8 mg, 0.420 mmol). The reaction was stirred for 0.5 hours and concentrated. The crude material was purified by flash silica chromatography (0-100% EtOAc/EtOH 3:1 mix in hexanes gradient) to yield (3R,7S,E)-4-ethyl-25-methoxy-3-methyl-7-(3,3,3-trifluoropropyl)-10,13-dioxa-4,6-diaza-1(5,7)-pyrazolo[1,5-c]pyrimidina-2(4,2)-pyridinacyclotridecaphan-5-one (Example 165). LC-MS: 537.2 (M+1). $^1$H NMR (500 MHz, Methanol-$d_4$) δ 8.35 (s, 1H), 8.31 (s, 1H), 8.27 (s, 1H), 8.10 (d, J=2.1 Hz, 1H), 6.76 (d, J=2.1 Hz, 1H), 5.98 (q, J=8.5, 7.8 Hz, 2H), 5.24 (ddd, J=10.8, 9.0, 6.0 Hz, 1H), 4.74-4.65 (m, 1H), 4.12 (s, 3H), 3.90 (dtd, J=23.9, 9.4, 5.7 Hz, 2H), 3.63 (dtd, J=23.7, 9.6, 5.4 Hz, 2H), 3.23-3.16 (m, 1H), 3.08 (dd, J=15.8, 7.3 Hz, 1H), 2.30-2.19 (m, 2H), 1.89 (dt, J=8.4, 4.3 Hz, 1H), 1.84-1.64 (m, 3H), 1.61 (d, J=7.2 Hz, 3H), 1.01 (t, J=7.1 Hz, 3H).

The following compound in Table 12 were prepared according to the general procedures herein and in an analogous manner of that used to synthesize Example 165 using the appropriate intermediates referenced in Table 12. The starting materials were either prepared as described in the intermediates section, commercially available, or prepared from commercially available reagents using conventional reactions well known in the art.

TABLE 12

| Ex. # | Structure | Name | Exact Mass [M + H]+ | Interm A | Interm C |
|---|---|---|---|---|---|
| 167 | 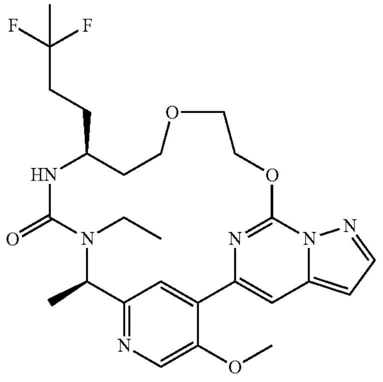 [SMILES: CCN1C(=O)N[C@@H](CCC(C)(F)F)CCOCCOc2nc(cc3ccnn23)-c2cc(ncc2OC)[C@H]1C] | (3R,7S,E)-7-(3,3-difluorobutyl)-4-ethyl-25-methoxy-3-methyl-10,13-dioxa-4,6-diaza-1(5,7)-pyrazolo[1,5-c]pyrimidina-2(4,2)-pyridinacyclotridecaphan-5-one | Calc'd 533.3, found 533.3 | A143 | C147 |
| 170 | 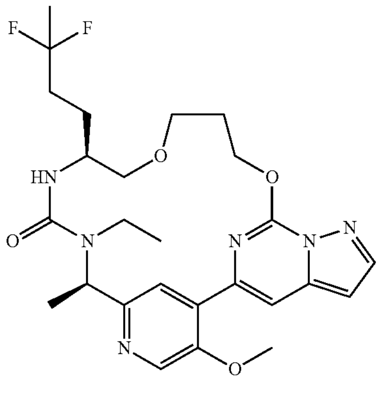 [SMILES: CCN1C(=O)N[C@@H](CCC(C)(F)F)COCCCOc2nc(cc3ccnn23)-c2cc(ncc2OC)[C@H]1C] | (3R,7S,E)-7-(3,3-difluorobutyl)-4-ethyl-25-methoxy-3-methyl-9,13-dioxa-4,6-diaza-1(5,7)-pyrazolo[1,5-c]pyrimidina-2(4,2)-pyridinacyclotridecaphan-5-one | Calc'd 533.3, found 533.3 | A144 | C147 |

TABLE 12-continued

| Ex. # | Structure | Name | Exact Mass [M + H]+ | Interm A | Interm C |
|---|---|---|---|---|---|
| 171 | 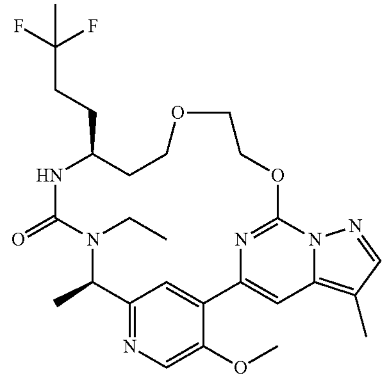 [SMILES: CCN1C(=O)N[C@@H](CCC(C)(F)F)CCOCCOc2nc(cc3c(C)cnn23)-c2cc(ncc2OC)[C@H]1C] | (3R,7S,E)-7-(3,3-difluorobutyl)-4-ethyl-25-methoxy-3-methyl-9,13-dioxa-4,6-diaza-1(5,7)-pyrazolo[1,5-c]pyrimidina-2(4,2)-pyridinacyclotridecaphan-5-one | Calc'd 547.3, found 547.3 | A143 | C149 |
| 181 | 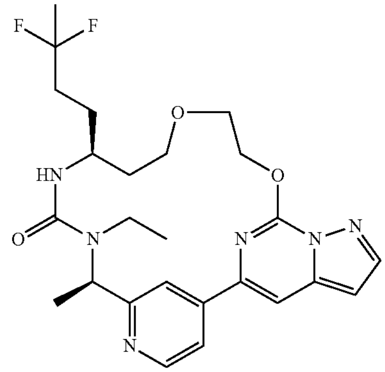 [SMILES: CCN1C(=O)N[C@@H](CCC(C)(F)F)CCOCCOc2nc(cc3ccnn23)-c2ccnc(c2)[C@H]1C] | (3R,7S,E)-7-(3,3-difluorobutyl)-4-ethyl-3-methyl-10,13-dioxa-4,6-diaza-1(5,7)-pyrazolo[1,5-c]pyrimidina-2(4,2)-pyridinacyclotridecaphan-5-one | Calc'd 503.2, found 503.3 | A143 | C151 |

Example 166

(3R,7R,E)-4-ethyl-25-methoxy-12,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one

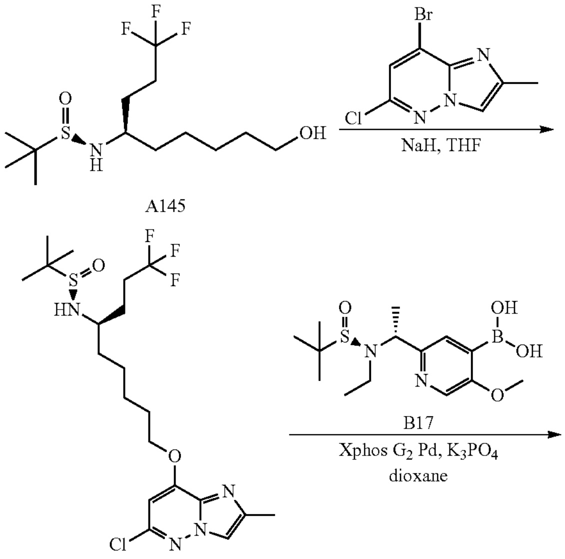

-continued

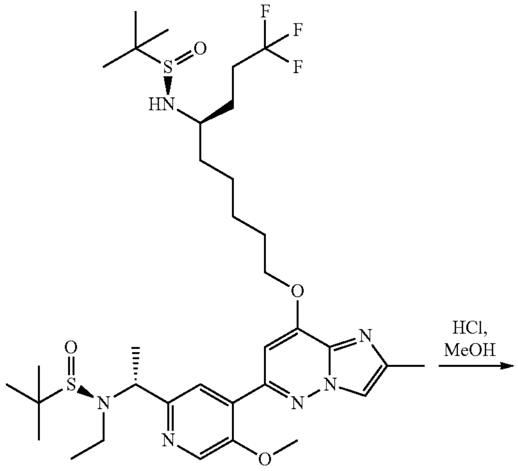

-continued

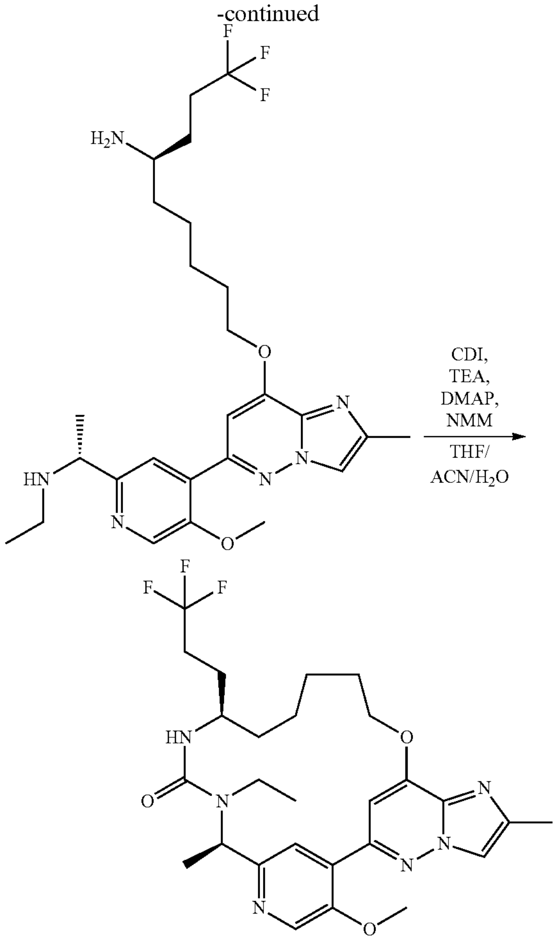

Example 166

Step 1: (S)—N—((R)-9-((6-chloro-2-methylimidazo[1,2-b]pyridazin-8-yl)oxy)-1,1,1-trifluorononan-4-yl)-2-methylpropane-2-sulfinamide To a solution of (S)-2-methyl-N—((R)-1,1,1-trifluoro-9-hydroxynonan-4-yl)propane-2-sulfinamide (A145, 105 mg, 0.331 mmol) in tetrahydrofuran (3.3 mL) was added sodium hydride (29.1 mg, 0.728 mmol) (60% in mineral oil) at ambient temperature and the reaction was stirred for 1 hour. 8-Bromo-6-chloro-2-methylimidazo[1,2-b]pyridazine (98.0 mg, 0.397 mmol) was added and the reaction was stirred for 2 hours. The reaction was concentrated and the crude material was purified by flash silica chromatography (0-1000% EtOAc/EtOH 3:1 mix in hexanes gradient) to give (S)—N—((R)-9-((6-chloro-2-methylimidazo[1,2-b]pyridazin-8-yl)oxy)-1,1,1-trifluorononan-4-yl)-2-methylpropane-2-sulfinamide. LC-MS: 483.3 (M+1).

Step 2: (S)—N—((R)-1-(4-(8-(((R)-6-(((S)-tert-butylsulfinyl)amino)-9,9,9-trifluorononyl)oxy)-2-methylimidazo[1,2-b]pyridazin-6-yl)-5-methoxypyridin-2-yl)ethyl)-N-ethyl-2-methylpropane-2-sulfinamide To a solution of (S)—N—((R)-9-((6-chloro-2-methylimidazo[1,2-b]pyridazin-8-yl)oxy)-1,1,1-trifluorononan-4-yl)-2-methylpropane-2-sulfinamide (147 mg, 0.304 mmol), (2-((R)-1-(((S)-tert-butylsulfinyl)(ethyl)amino)ethyl)-5-methoxypyridin-4-yl)boronic acid (B17, 175 mg, 0.533 mmol), 1M $K_3PO_4$ (0.609 mL, 0.609 mmol) in dioxane (3.0 mL) was added XPhos G2 Pd (24.0 mg, 0.030 mmol). The reaction was stirred at 60° C. for 3 hours. The reaction was concentrated and the crude material was purified by flash silica chromatography (0-100% EtOAc/EtOH 3:1 mix in hexanes gradient) to give (S)—N—((R)-1-(4-(8-(((R)-6-(((S)-tert-butylsulfinyl)amino)-9,9,9-trifluorononyl)oxy)-2-methylimidazo[1,2-b]pyridazin-6-yl)-5-methoxypyridin-2-yl)ethyl)-N-ethyl-2-methylpropane-2-sulfinamide. LC-MS: 731.4 (M+1).

Step 3: (R)-9-((6-(2-((R)-1-(ethylamino)ethyl)-5-methoxypyridin-4-yl)-2-methylimidazo[1,2-b]pyridazin-8-yl)oxy)-1,1,1-trifluorononan-4-amine 4M HCl (0.380 mL, 1.52 mmol) in dioxane was added to (S)—N—((R)-1-(4-(8-(((R)-6-(((S)-tert-butylsulfinyl)amino)-9,9,9-trifluorononyl)oxy)-2-methylimidazo[1,2-b]pyridazin-6-yl)-5-methoxypyridin-2-yl)ethyl)-N-ethyl-2-methylpropane-2-sulfinamide (222 mg, 0.304 mmol). The reaction was aged at ambient temperature for 2 hours. The reaction was concentrated to afford (R)-9-((6-(2-((R)-1-(ethylamino)ethyl)-5-methoxypyridin-4-yl)-2-methylimidazo[1,2-b]pyridazin-8-yl)oxy)-1,1,1-trifluorononan-4-amine as an HCl salt. LC-MS: 523.3 (M+1).

Step 4: (3R,7R,E)-4-ethyl-25-methoxy-12,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one (Example 166)

To a solution of (R)-9-((6-(2-((R)-1-(ethylamino)ethyl)-5-methoxypyridin-4-yl)-2-methylimidazo[1,2-b]pyridazin-8-yl)oxy)-1,1,1-trifluorononan-4-amine dihydrochloride (40.0 mg, 0.067 mmol), TEA (0.0187 mL, 0.134 mmol) and DMAP (4.10 mg, 0.034 mmol) in tetrahydrofuran (1 mL) at −78° C. was added CDI (13.1 mg, 0.081 mmol). The reaction was stirred at −78° C. for 5 hours. The reaction mixture was added dropwise via a cannula to a solution of N-methylmorpholine (0.00591 mL, 0.054 mmol) in acetonitrile (1 mL) and water (0.25 mL) at 60° C. The reaction mixture was stirred at 60° C. for 1 hour and then concentrated. The crude material was was purified by flash silica chromatography (0-100% EtOAc/EtOH 3:1 mix in hexanes gradient) to give (3R,7R,E)-4-ethyl-25-methoxy-12,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one (Example 166). LC-MS: 549.3 (M+1). $^1H$ NMR (500 MHz, Methanol-$d_4$) δ 8.41 (s, TH), 7.83 (s, TH), 7.35 (s, TH), 6.62 (s, TH), 5.99 (d, J=9.2 Hz, TH), 5.85 (q, J=7.2 Hz, TH), 4.59 (td, J=10.8, 10.0, 6.2 Hz, TH), 4.48 (td, J=11.6, 10.8, 6.7 Hz, TH), 4.02-3.97 (in, TH), 3.96 (s, 3H), 3.19 (ddt, J=30.2, 14.8, 7.9 Hz, 2H), 2.44 (s, 3H), 2.21 (dq, J=19.6, 11.0 Hz, 2H), 1.92 (d, J=9.2 Hz, 2H), 1.83-1.72 (in, TH), 1.72-1.66 (in, TH), 1.64 (d, J=7.2 Hz, 3H), 1.56-1.46 (m, 5H), 1.05 (t, J=7.0 Hz, 3H).

The following compound in Table 13 were prepared according to the general procedures herein and in an analogous manner of that used to synthesize Example 166 using the appropriate intermediates referenced in Table 13. The starting materials were either prepared as described in the intermediates section, commercially available, or prepared from commercially available reagents using conventional reactions well known in the art.

TABLE 13

| Ex. # | Structure | Name | Exact Mass [M + H]+ | Interm A | Interm B | Dihalide |
|---|---|---|---|---|---|---|
| 168 | 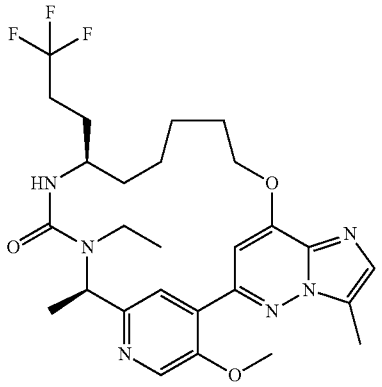 [SMILES: CCN1C(=O)N[C@@H](CCC(F)(F)F)CCCCCOc2cc(nn3c(C)cnc23)-c2cc(ncc2OC)[C@H]1C] | (3R,7R,E)-4-ethyl-25-methoxy-13,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one | Calc'd 549.3, found 549.4 | A145 | B17 | 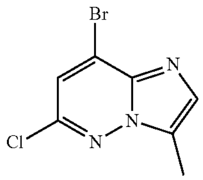 B. Mao et al., European J. of Medicinal Chemistry 129 (2017) 135-150. |
| 172 | 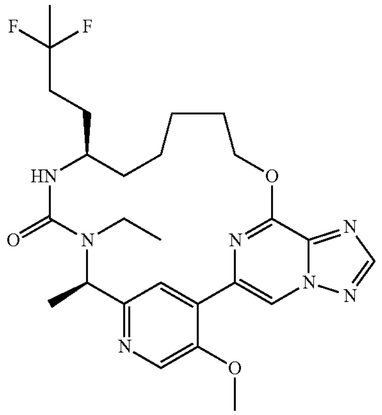 [SMILES: CCN1C(=O)N[C@@H](CCC(C)(F)F)CCCCCOc2nc(cn3ncnc23)-c2cc(ncc2OC)[C@H]1C] | (3R,7R,E)-7-(3,3-difluorobutyl)-4-ethyl-25-methoxy-15,3-dimethyl-13-oxa-4,6-diaza-1(6,8)-[1,2,4]triazolo[1,5-a]pyrazina-2(4,2)-pyridinacyclotridecaphan-5-one | Calc'd 544.3, found 546.3 | A146 | B17 | C150 |
| 173 | 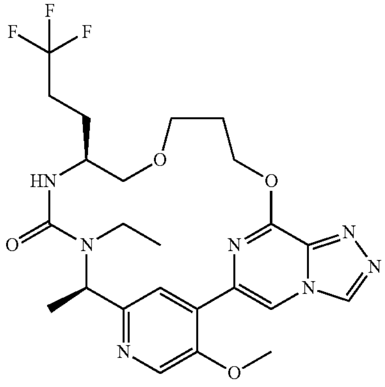 [SMILES: CCN1C(=O)N[C@@H](CCC(F)(F)F)COCCCOc2nc(cn3cnnc23)-c2cc(ncc2OC)[C@H]1C] | (3R,7S,E)-4-ethyl-25-methoxy-3-methyl-7-(3,3,3trifluoropropyl)-9,13-dioxa-4,6-diaza-1(6,8)-[1,2,4]triazolo[4,3-a]pyrazina-2(4,2)-pyridinacyclotridecaphan-5-one | Calc'd 537.2, found 538.2 | A142 | B17 | 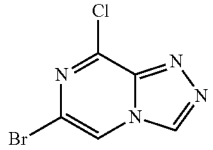 [SMILES: Clc1nc(Br)cn2cnnc12] |

TABLE 13-continued

| Ex. # | Structure | Name | Exact Mass [M + H]+ | Interm A | Interm B | Dihalide |
|---|---|---|---|---|---|---|
| 175* | 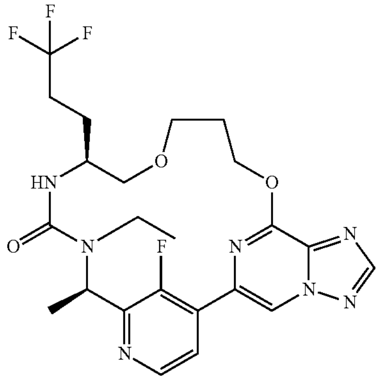 [SMILES: CCN1C(=O)N[C@@H](CCC(F)(F)F)COCCCOc2nc(cn3ncnc23)-c2ccnc(c2F)[C@H]1C] | (3R,7S,E)-4-ethyl-23-fluoro-3-methyl-7-(3,3,3trifluoropropyl)-9,13-dioxa-4,6-diaza-1(6,8)-[1,2,4]triazolo[1,5-a]Pyrazina-2(4,2)-pyridinacyclotridecaphan-5-one | Calc'd 526.2, found 526.2 | A142 | B94 | 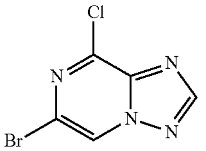 [SMILES: Clc1nc(Br)cn2ncnc12] |

The diastereomers of example 175 were resolved via SFC on an OD-H (2×25 cm) column using 35% methanol/$CO^2$ (100 bar) as eluent at a flow rate of 55 mL/min, with example 175 being the first eluting isomer.

Example 169

(3R,E)-7-(3,3-difluorobutyl)-4-ethyl-25-methoxy-3-methyl-10,13-dioxa-4,6-diaza-1(7,5)-[1,2,4]triazolo[1,5-c]pyrimidina-2(4,2)-pyridinacyclotridecaphan-5-one

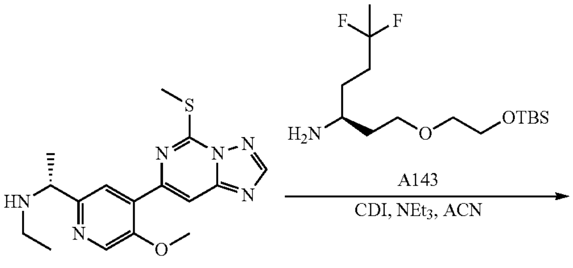

C148

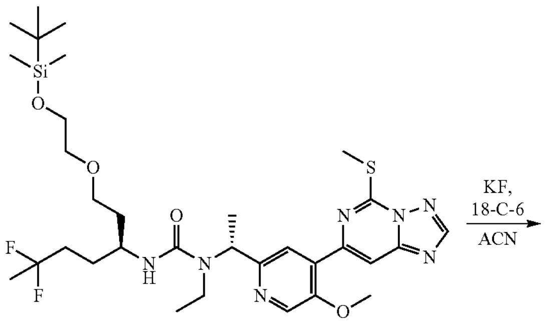

-continued

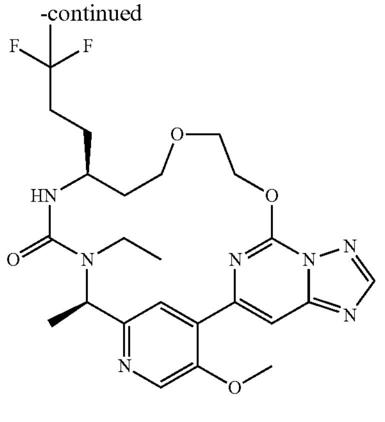

Example 169

Step 1: 3-((S)-1-(2-((tert-butyldimethylsilyl)oxy)ethoxy)-6,6-difluoroheptan-3-yl)-1-ethyl-1-((R)-1-(5-methoxy-4-(5-(methylthio)-[1,2,4]triazolo[1,5-c]pyrimidin-7-yl)pyridin-2-yl)ethyl)urea To a solution of (S)-1-(2-((tert-butyldimethylsilyl)oxy)ethoxy)-6,6-difluoroheptan-3-amine (A143, 89.0 mg, 0.274 mmol) in acetonitrile (5.3 mL) was added CDI (42.7 mg, 0.264 mmol) and the reaction was stirred at ambient temperature for 2 hours. (R)—N-ethyl-1-(5-methoxy-4-(5-(methylthio)-[1,2,4]triazolo[1,5-c]pyrimidin-7-yl)pyridin-2-yl)ethan-1-amine dihydrochloride (C148, 88.0 mg, 0.211 mmol) and triethylamine (0.147 mL, 1.05 mmol) were then added and the reaction was stirred at 50° C. for 1.5 hours. The reaction was concentrated and purified by flash silica chromatography (0-100% EtOAc/EtOH 3:1 mix in hexanes gradient) to give 3-((S)-1-(2-((tert-butyldimethylsilyl)oxy)ethoxy)-6,6,6-trifluorohexan-3-yl)-1-((R)-1-(4-(8-chloro-[1,2,4]triazolo[1,5-a]pyrazin-6-yl)-5-methoxypyridin-2-yl)ethyl)-1-ethylurea. LC-MS: 696.5 (M+1).

Step 2: (3R,E)-7-(3,3-difluorobutyl)-4-ethyl-25-methoxy-3-methyl-10,13-dioxa-4,6-diaza-1(7,5)-[1,2,4]triazolo[1,5-c]pyrimidina-2(4,2)-pyridinacyclotridecaphan-5-one (Example 169)

A mixture of 3-((S)-1-(2-((tert-butyldimethylsilyl)oxy)ethoxy)-6,6,6-trifluorohexan-3-yl)-1-((R)-1-(4-(8-chloro-

[1,2,4]triazolo[1,5-a]pyrazin-6-yl)-5-methoxypyridin-2-yl) ethyl)-1-ethylurea (57.0 mg, 0.082 mmol), potassium fluoride (47.6 mg, 0.819 mmol), and 18-crown-6 (21.6 mg, 0.082 mmol) in acetonitrile (2 mL) was heated at 85° C. for 5 hours. The reaction was filtered and concentrated. The crude material was purified by flash silica chromatography (0-100% EtOAc/EtOH 3:1 mix in hexanes gradient) to give yield (3R,E)-7-(3,3-difluorobutyl)-4-ethyl-25-methoxy-3-methyl-10,13-dioxa-4,6-diaza-1(7,5)-[1,2,4]triazolo[1,5-c] pyrimidina-2(4,2)-pyridinacyclotridecaphan-5-one (Example 169). LC-MS: 534.2 (M+1). $^1$H NMR (500 MHz, Methanol-$d_4$) δ 8.50 (s, 1H), 8.42 (s, 1H), 8.32 (s, 1H), 8.24 (s, 1H), 5.97 (q, J=7.1 Hz, 1H), 5.88 (d, J=9.0 Hz, 1H), 5.31-5.23 (m, 1H), 4.75 (ddd, J=10.9, 8.7, 5.6 Hz, 1H), 4.16 (d, J=2.9 Hz, 1H), 4.20-4.13 (m, 1H), 4.03-3.85 (m, 2H), 3.70-3.57 (m, 2H), 3.21 (dt, J=15.6, 7.0 Hz, 1H), 3.06 (dq, J=14.5, 7.1 Hz, 1H), 2.02-1.84 (m, 4H), 1.76-1.56 (m, 9H), 1.02 (t, J=7.0 Hz, 3H).

The following compound in Table 14 were prepared according to the general procedures herein and in an analogous manner used to synthesize Example 165 using the appropriate intermediates referenced in Table 14. The starting materials were either prepared as described in the intermediates section, commercially available, or prepared from commercially available reagents using conventional reactions well known in the art.

-continued

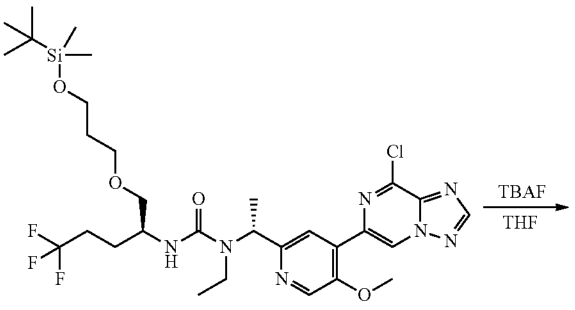

TABLE 14

| Ex. # | Structure | Name | Exact Mass [M + H]+ | Interm A | Interm C |
|---|---|---|---|---|---|
| 176 | 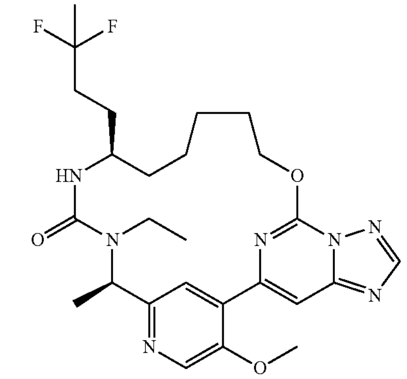 [SMILES: CCN1C(=O)N[C@@H](CCC(C)(F)F)CCCCCOc2nc(cc3ncnn23)-c2cc(ncc2OC)[C@H]1C] | (3R,7R,E)-7-(3,3-difluorobutyl)-4-ethyl-25-methoxy-3-methyl-13-oxa-4,6-diaza-1(7,5)-[1,2,4]triazolo[1,5-c]pyrimidina-2(4,2)-pyridinacyclotridecaphan-5-one | Calc'd 532.3, found 532.4 | A146 | C148 |

Example 174

(3R,7S,E)-4-ethyl-25-methoxy-3-methyl-7-(3,3,3-trifluoropropyl)-9,13-dioxa-4,6-diaza-1(6,8)-[1,2,4]triazolo[1,5-a] pyrazina-2(4,2)-pyridinacyclotridecaphan-5-one

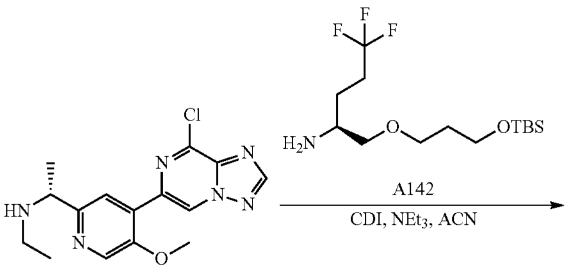

C143

-continued

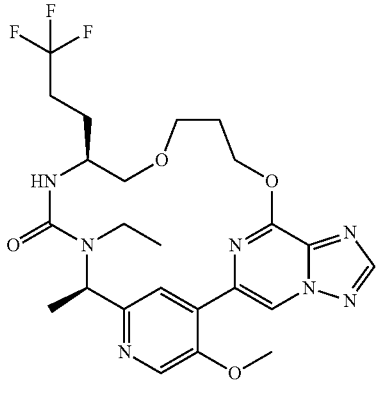

Example 174

Step 1: 3-((S)-1-(3-((tert-butyldimethylsilyl)oxy)propoxy)-5,5,5-trifluoropentan-2-yl)-1-((R)-1-(4-(8-chloro-[1,2,4]triazolo[1,5-a]pyrazin-6-yl)-5-methoxypyridin-2-yl)ethyl)-1-ethylurea To a solution of (S)-1-(3-((tert-butyldimethylsilyl)oxy)propoxy)-5,5,5-trifluoropentan-2-amine (A142, 363 mg, 1.10 mmol) in acetonitrile (12 mL) was added CDI (97.0 mg, 0.599 mmol) and the reaction was stirred at ambient temperature for 2 hours. (R)-1-(4-(8-chloro-[1,2,4]triazolo[1,5-a]pyrazin-6-yl)-5-methoxypyridin-2-yl)-N-ethylethan-1-amine hydrochloride (C143, 177 mg, 0.479 mmol) and triethylamine (0.334 mL, 2.40 mmol) were then added and the reaction was stirred at 50° C. for 2 hours. The reaction was concentrated and purified by flash silica chromatography (0-30% EtOAc/EtOH 3:1 mix in hexanes gradient) to give 3-((S)-1-(3-((tert-butyldimethylsilyl)oxy)propoxy)-5,5,5-trifluoropentan-2-yl)-1-((R)-1-(4-(8-chloro-[1,2,4]triazolo[1,5-a]pyrazin-6-yl)-5-methoxypyridin-2-yl)ethyl)-1-ethylurea. LC-MS: 688.4 (M+1).

Step 2: (3R,7S,E)-4-ethyl-25-methoxy-3-methyl-7-(3,3,3-trifluoropropyl)-9,13-dioxa-4,6-diaza-1(6,8)-[1,2,4]triazolo[1,5-a]pyrazina-2(4,2)-pyridinacyclotridecaphan-5-one (Example 174)

A 1M solution of TBAF (0.523 mL, 0.523 mmol) in tetrahydrofuran was added to a solution of 3-((S)-1-(3-((tert-butyldimethylsilyl)oxy)propoxy)-5,5,5-trifluoropentan-2-yl)-1-((R)-1-(4-(8-chloro-[1,2,4]triazolo[1,5-a]pyrazin-6-yl)-5-methoxypyridin-2-yl)ethyl)-1-ethylurea (180 mg, 0.262 mmol) in tetrahydrofuran (12 mL). The reaction was stirred at ambient temperature for 16 hours and at 60° C. for 3 hours. The reaction was filtered and concentrated. The crude material was purified by reverse phase HPLC (10-80% ACN in water, with 0.1% TFA as modifier) to yield (3R,7S,E)-4-ethyl-25-methoxy-3-methyl-7-(3,3,3-trifluoropropyl)-9,13-dioxa-4,6-diaza-1(6,8)-[1,2,4]triazolo[1,5-a]pyrazina-2(4,2)-pyridinacyclotridecaphan-5-one (Example 174). LC-MS: 538.2 (M+1). $^1$H NMR (500 MHz, Methanol-$d_4$) δ 9.32 (s, 1H), 8.53 (s, 1H), 8.40 (s, 1H), 8.29 (s, 1H), 6.05 (d, J=8.8 Hz, 1H), 5.91 (d, J=7.1 Hz, 1H), 4.96 (td, J=11.2, 5.3 Hz, 3H), 4.74 (td, J=11.0, 4.9 Hz, 1H), 4.16 (s, 3H), 3.65-3.55 (m, 3H), 3.52-3.45 (m, 2H), 3.11 (d, J=7.3 Hz, 1H), 2.30-2.23 (m, 3H), 1.62 (d, J=7.1 Hz, 3H), 1.29 (s, 1H), 1.09 (t, J=7.1 Hz, 3H).

Example 179

(7S,E)-4-ethyl-23-fluoro-25-methoxy-3-methyl-7-(3,3,3-trifluoropropyl)-10,13-dioxa-4,6-diaza-1(6,8)-[1,2, 4]triazolo[1, 5-a]pyrazina-2(4,2)-pyridinacyclotridecaphan-5-one

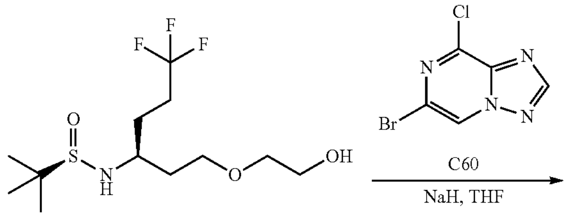

A139

-continued

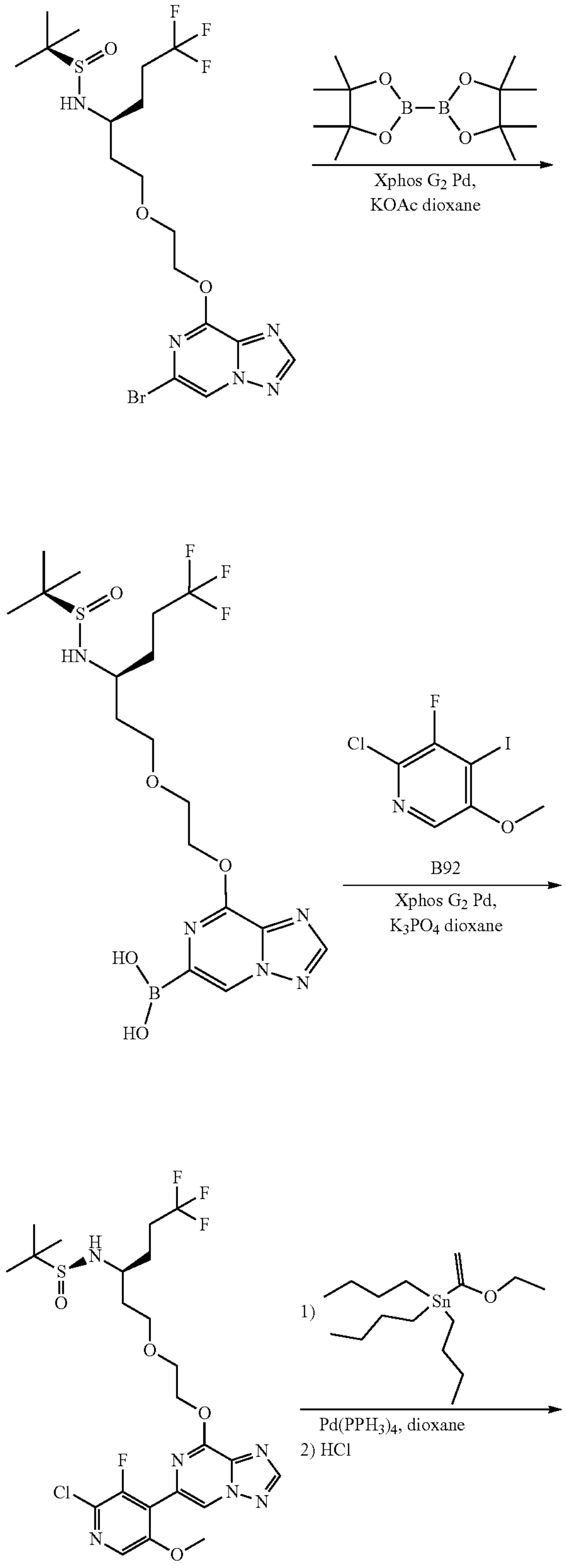

-continued

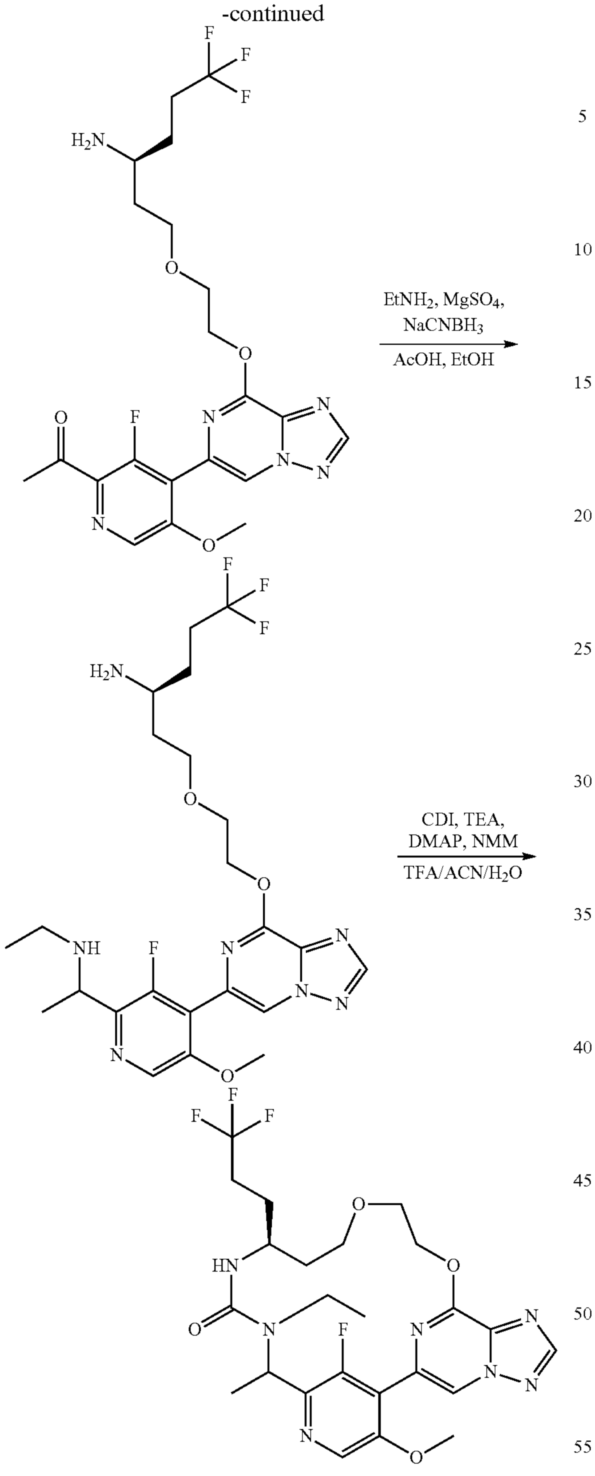

Example 179

Step 1: (R)—N—((S)-1-(2-((6-bromo-[1,2,4]triazolo[1,5-a]pyrazin-8-yl)oxy)ethoxy)-6,6,6-trifluorohexan-3-yl)-2-methylpropane-2-sulfinamide To a solution of (R)-2-methyl-N—((S)-6,6,6-trifluoro-1-(2-hydroxyethoxy)hexan-3-yl)propane-2-sulfinamide (A139, 606 mg, 1.90 mmol) in tetrahydrofuran (10 mL) was added sodium hydride (114 mg, 2.85 mmol) (60% in mineral oil) at ambient temperature and the reaction was stirred for 0.5 hours. 6-Bromo-8-chloro-[1,2,4]triazolo[1,5-a]pyrazine (C60, 443 mg, 1.90 mmol) was added and the reaction was stirred for 2.5 hours. The reaction was concentrated and the crude material was purified by flash silica chromatography (0-100% EtOAc/EtOH 3:1 mix in hexanes gradient) to give (R)—N—((S)-1-(2-((6-bromo-[1,2,4]triazolo[1,5-a]pyrazin-8-yl)oxy)ethoxy)-6,6,6-trifluorohexan-3-yl)-2-methylpropane-2-sulfinamide. LC-MS: 516.4, 518.4 (M+1).

Step 2: (8-(2-(((S)-3-(((S)-tert-butylsulfinyl)amino)-6,6,6-trifluorohexyl)oxy)ethoxy)-[1,2,4]triazolo[1,5-a]pyrazin-6-yl)boronic acid To a solution of (R)—N—((S)-1-(2-((6-bromo-[1,2,4]triazolo[1,5-a]pyrazin-8-yl)oxy)ethoxy)-6,6,6-trifluorohexan-3-yl)-2-methylpropane-2-sulfinamide (777 mg, 1.51 mmol), bis(pinacolato)diboron (497 mg, 1.96 mmol), and potassium acetate (443 mg, 4.51 mmol) in dioxane (15 mL) was added XPhos G2 Pd (59.2 mg, 0.075 mmol). The reaction was stirred at 90° C. for 1.5 hours. The reaction was filtered through a pad of Celite, rinsing with EtOAc (2×5 mL, and concentrated to give (8-(2-(((S)-3-(((S)-tert-butylsulfinyl)amino)-6,6,6-trifluorohexyl)oxy)ethoxy)-[1,2,4]triazolo[1,5-a]pyrazin-6-yl)boronic acid, which was used without further purification. LC-MS: 482.5 (M+1).

Step 3: (S)—N—((S)-1-(2-((6-(2-chloro-3-fluoro-5-methoxypyridin-4-yl)-[1,2,4]triazolo[1,5-a]pyrazin-8-yl)oxy)ethoxy)-6,6,6-trifluorohexan-3-yl)-2-methylpropane-2-sulfinamide To a solution of (8-(2-(((S)-3-(((S)-tert-butylsulfinyl)amino)-6,6,6-trifluorohexyl)oxy)ethoxy)-[1,2,4]triazolo[1,5-a]pyrazin-6-yl)boronic acid (1.34 g, 2.78 mmol), 2-chloro-3-fluoro-4-iodo-5-methoxypyridine (B92, 400 mg, 1.39 mmol), and 1M $K3PO_4$ (2.78 mL, 2.78 mmol) in dioxane (13.9 mL) was added XPhos G2 Pd (109 mg, 0.139 mmol). The reaction was stirred at 50° C. for 6 hours. The reaction was concentrated and the crude material was purified by flash silica chromatography (0-100% EtOAc/EtOH 3:1 mix in hexanes gradient) to give (S)—N—((S)-1-(2-((6-(2-chloro-3-fluoro-5-methoxypyridin-4-yl)-[1,2,4]triazolo[1,5-a]pyrazin-8-yl)oxy)ethoxy)-6,6,6-trifluorohexan-3-yl)-2-methylpropane-2-sulfinamide. LC-MS: 597.5 (M+1).

Step 4: (S)-1-(4-(8-(2-((3-amino-6,6,6-trifluorohexyl)oxy)ethoxy)-[1,2,4]triazolo[1,5-a]pyrazin-6-yl)-3-fluoro-5-methoxypyridin-2-yl)ethan-1-one To a solution of (S)—N—((S)-1-(2-((6-(2-chloro-3-fluoro-5-methoxypyridin-4-yl)-[1,2,4]triazolo[1,5-a]pyrazin-8-yl)oxy)ethoxy)-6,6,6-trifluorohexan-3-yl)-2-methylpropane-2-sulfinamide (115 mg, 0.193 mmol) and tributyl(1-ethoxyvinyl)stannane (0.098 mL, 0.289 mmol) in dioxane (13.9 mL) was added tetrakis(triphenylphosphine)palladium(0) (22.3 mg, 0.019 mmol). The reaction was stirred at 100° C. for 8 hours. Additional tetrakis(triphenylphosphine)palladium(0) (3.0 mg) was added after 6 hours. The reaction mixture was cooled to ambient temperature and 10% HCl (0.5 mL) was added and stirring continued for 1 hour. The reaction was concentrated and the crude material was purified by flash silica chromatography (0-30% MeOH/$NH_4OH$ 99:1 mix in dichloromethane gradient) to give (S)-1-(4-(8-(2-((3-amino-6,6,6-trifluorohexyl)oxy)

ethoxy)-[1,2,4]triazolo[1,5-a]pyrazin-6-yl)-3-fluoro-5-methoxypyridin-2-yl)ethan-1-one. LC-MS: 501.5 (M+1).

Step 5: (3S)-1-(2-((6-(2-(1-(ethylamino)ethyl)-3-fluoro-5-methoxypyridin-4-yl)-[1,2,4]triazolo[1,5-a]pyrazin-8-yl)oxy)ethoxy)-6,6,6-trifluorohexan-3-amine A solution of (S)-1-(4-(8-(2-((3-amino-6,6,6-trifluorohexyl)oxy)ethoxy)-[1,2,4]triazolo[1,5-a]pyrazin-6-yl)-3-fluoro-5-methoxypyridin-2-yl)ethan-1-one (70.0 mg, 0.140 mmol), 2M ethylamine in tetrahydrofuran (0.699 mL, 1.40 mmol), acetic acid (0.040 mL, 0.699 mmol), and magnesium sulfate (33.7 mg, 0.280 mmol) in ethanol (1.4 mL) was stirred at ambient temperature for 1 hour. Sodium cyanoborohydride (17.6 mg, 0.280 mmol) was added and the reaction was stirred at ambient temperature for 20 hours. The reaction mixture was filtered and concentrated and the crude material was purified by reverse phase HPLC (10-100% ACN in water, with 0.1% $NH_4OH$ as modifier) to give (3S)-1-(2-((6-(2-(1-(ethylamino)ethyl)-3-fluoro-5-methoxypyridin-4-yl)-[1,2,4]triazolo[1,5-a]pyrazin-8-yl)oxy)ethoxy)-6,6,6-trifluorohexan-3-amine. LC-MS: 530.6 (M+1).

Step 6: (7S,E)-4-ethyl-23-fluoro-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one (Ex 179)

To a solution of (3S)-1-(2-((6-(2-(1-(ethylamino)ethyl)-3-fluoro-5-methoxypyridin-4-yl)-[1,2,4]triazolo[1,5-a]pyrazin-8-yl)oxy)ethoxy)-6,6,6-trifluorohexan-3-amine (24.1 mg, 0.046 mmol) and DMAP (2.78 mg, 0.023 mmol) in tetrahydrofuran (2 mL) at −55° C. was added CDI (8.86 mg, 0.055 mmol). The reaction was stirred at −55° C. for 5 hours and then warmed to ambient temperature over 16 hours. The reaction mixture was added dropwise via a cannula to a solution of N-methylmorpholine (0.0040 mL, 0.036 mmol) in acetonitrile (2.0 mL) and water (0.506 mL) at 55° C. The reaction mixture was stirred at 55° C. for 0.5 h and then concentrated. The crude material was was purified by flash silica chromatography (0-100% EtOAc/EtOH 3:1 mix in hexanes gradient) to give (7S,E)-4-ethyl-23-fluoro-25-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one as a mixture of diastereomers (Example 179). LC-MS: 556.4 (M+1). $^1H$ NMR (500 MHz, Methanol-$d_4$) δ 8.80 (s, 1H), 8.78 (s, 1H), 8.55 (s, 2H), 8.33 (s, 2H), 6.33 (d, J=8.0 Hz, 1H), 6.12 (q, J=7.5, 6.5 Hz, 1H), 5.83 (d, J=9.3 Hz, 1H), 5.38 (s, 1H), 5.14 (td, J=9.7, 6.2 Hz, 1H), 4.43-4.32 (m, 2H), 4.14-3.99 (m, 8H), 3.82 (ddq, J=9.9, 7.5, 3.9 Hz, 4H), 3.74 (ddd, J=11.6, 6.7, 4.1 Hz, 1H), 3.70-3.57 (m, 2H), 3.56-3.47 (m, 1H), 3.23 (ddd, J=28.4, 14.3, 7.2 Hz, 2H), 3.09 (q, J=7.1 Hz, 1H), 2.20 (ddp, J=17.3, 11.3, 6.3, 5.6 Hz, 4H), 1.96-1.84 (m, 1H), 1.84-1.64 (m, 11H), 1.57 (d, J=7.1 Hz, 2H), 0.98-0.87 (m, 6H).

Example 209

(9R,13R,E)-14-Cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-11-one

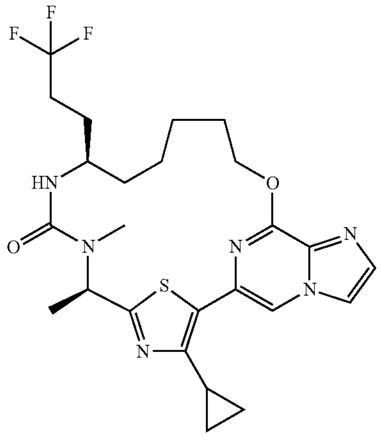 [SMILES: C[C@@H]1C2=NC(C3CC3)=C(S2)c2cn3ccnc3c(n2)OCCCCC[C@H](CCC(F)(F)F)NC(=O)N1C]

Benzyl (R)-(1-amino-1-thioxopropan-2-yl)carbamate (step 1)

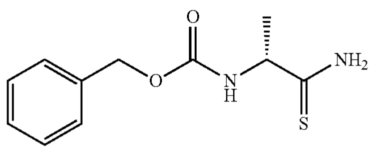 [SMILES: C[C@@H](NC(=O)OCc1ccccc1)C(N)=S]

To a solution of benzyl (R)-(1-amino-1-oxopropan-2-yl) carbamate (1.00 g, 4.50 mmol) in THF (25 mL) was added Lawesson's reagent (1.1 g, 2.72 mmol) all at once as a solid at ambient temperature. After stirring overnight the mixture was concentrated. The crude product was subjected to silica gel chromatography (ISCO© RediSep-Rf-40 g, 0-50% EtOAc/heptane, 15 minute gradient) to give the title compound. LC/MS: (M+H)+239.1. $^1H$-NMR (500 MHz, $CDCl_3$) δ 7.71 (bs, 1H), 7.48 (bs, 1H), 7.40-7.30 (m, 5H), 5.59 (d, J=7.1 Hz, 1H), 5.18-5.03 (m, 2H), 4.59 (p, J=7.0 Hz, 1H), 1.49 (d, J=6.9 Hz, 3H).

Benzyl (R)-(1-(4-cyclopropylthiazol-2-yl)ethyl)carbamate (step 2)

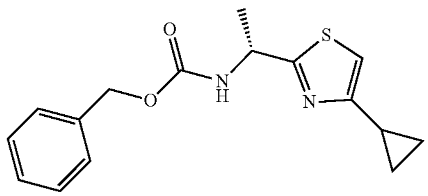 [SMILES: C[C@@H](NC(=O)OCc1ccccc1)c1nc(C2CC2)cs1]

To a solution of benzyl (R)-(1-amino-1-thioxopropan-2-yl)carbamate (1.15 g, 4.83 mmol) in EtOH (25 mL) was added $CaCO_3$ (1.45 g, 14.49 mmol) then 2-bromo-1-cyclopropylethan-1-one (0.62 mL, 6.35 mmol) then the mixture was heated to 80° C. overnight. The mixture was cooled to ambient temperature then diluted with EtOH then filtered through a pad of Celite© washing with EtOH then the filtrate was concentrated. The crude product was subjected to silica gel chromatography (ISCO© RediSep-Rf-80 g, 0-50% EtOAc/heptane, 15 minute gradient) to give the title compound. LC/MS: (M+H)+303.1. $^1H$-NMR (500 MHz, $CDCl_3$) δ 7.35 (m, 5H), 6.72 (s, 1H), 5.50 (bs, 1H), 5.13 (d, J=2.8 Hz, 2H), 5.12-5.06 (m, 1H), 2.01 (tt, J=8.3, 5.0 Hz, 1H), 1.58 (d, J=5.3 Hz, 3H), 0.91 (dq, J=8.2, 3.4, 2.6 Hz, 2H), 0.88-0.82 (m, 2H).

Benzyl (R)-(1-(4-cyclopropylthiazol-2-yl)ethyl)(ethyl) carbamate (step 3)

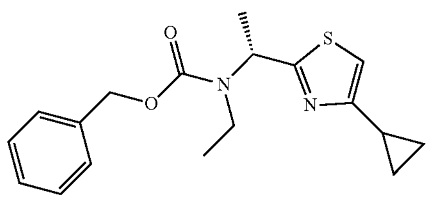 [SMILES: CCN(C(=O)OCc1ccccc1)[C@H](C)c1nc(C2CC2)cs1]

To a solution of benzyl (R)-(1-(4-cyclopropylthiazol-2-yl)ethyl)carbamate (1.28 g, 4.23 mmol) in THF (25 mL) was added NaH (60% dispersion in mineral oil, 0.254 g, 6.35 mmol) all at once as a solid at ambient temperature. After 30 minutes iodoethane (0.52 mL, 6.43 mmol) was added then the mixture was heated to 60° C. After stirring overnight the mixture was cooled to ambient temperature then diluted with saturated aqueous $NH_4Cl$ then extracted with EtOAc (3 x). The combined organic layers were dried ($MgSO_4$) then filtered then the filtrate was concentrated. The crude product was subjected to silica gel chromatography (ISCO© RediSep-Rf-40 g, 0-25% EtOAc/heptane, 15 minute gradient) to give the title compound. LC/MS: (M+H)+331.2. $^1$H-NMR (500 MHz, $CDCl_3$) δ 7.34 (m, 5H), 6.74 (s, 1H), 5.50 (bs, 1H), 5.19 (s, 2H), 3.36 (bs, 1H), 3.15 (bs, 1H), 2.01 (ddd, J=13.1, 8.3, 5.1 Hz, 1H), 1.65 (d, J=7.1 Hz, 3H), 1.06 (bs, 3H), 0.90 (dq, J=5.0, 3.5, 2.8 Hz, 2H), 0.84 (td, J=6.6, 5.8, 2.2 Hz, 2H).

Benzyl (R)-(1-(5-bromo-4-cyclopropylthiazol-2-yl)ethyl) (ethyl)carbamate (step 4)

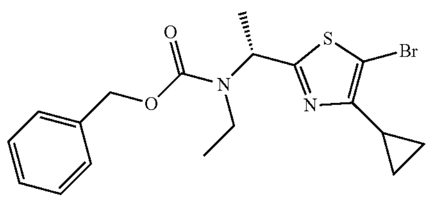 [SMILES: CCN(C(=O)OCc1ccccc1)[C@H](C)c1nc(C2CC2)c(Br)s1]

To a solution of benzyl (R)-(1-(4-cyclopropylthiazol-2-yl)ethyl)(ethyl)carbamate (100 mg, 0.303 mmol) in $CH_3CN$ (2 mL) was added NBS (70.0 mg, 0.393 mmol) at ambient temperature. After stirring overnight the mixture was concentrated. The crude product was subjected to silica gel chromatography (ISCO© RediSep-Rf-24 g, 0-25% EtOAc/heptane, 15 minute gradient) to give the title compound. LC/MS: (M+H)+409/411. $^1$H-NMR (500 MHz, $CDCl_3$) δ 7.40-7.29 (m, 5H), 5.45 (s, 1H), 5.18 (s, 2H), 3.35 (bs, 1H), 3.12 (bs, 1H), 2.03 (p, J=6.6 Hz, 1H), 1.58 (d, J=7.1 Hz, 3H), 1.08 (s, 3H), 0.94 (d, J=7.7 Hz, 4H).

(R)-1-(5-(8-(But-3-en-1-yloxy)imidazo[1,2-a]pyrazin-6-yl)-4-cyclopropylthiazol-2-yl)-N-ethylethan-1-amine (step 5)

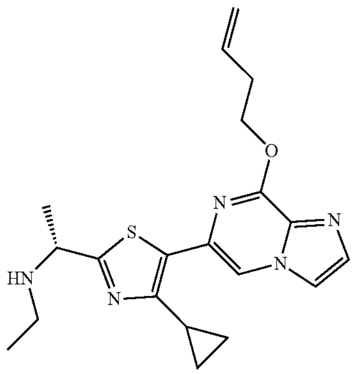 [SMILES: C=CCCOc1nc(-c2sc([C@@H](C)NCC)nc2C2CC2)cn2ccnc12]

To a solution of benzyl (R)-(1-(5-bromo-4-cyclopropylthiazol-2-yl)ethyl)(ethyl)carbamate (96 mg, 0.235 mmol) and (8-(but-3-en-1-yloxy)imidazo[1,2-a]pyrazin-6-yl)boronic acid, TFA (163 mg, 0.469 mmol) in DME (1 mL) was added 1M $K_3PO_4$ (1.2 mL, 1.200 mmol). The mixture was degassed (3×pump/N2). X-Phos Pd G2 (19 mg, 0.024 mmol) was added then the mixture was heated to 80° C. overnight. The mixture was cooled to ambient temperature then diluted with EtOAc then filtered through a pad of Celite® washing with EtOAc then the filtrate was concentrated. The crude product was subjected to silica gel chromatography (ISCO® RediSep-Rf-12 g, 0-100% EtOAc/heptane, 15 minute gradient) to give the title compound. LC/MS: (M+H)+384.2. $^1$H-NMR (500 MHz, $CDCl_3$) δ 8.12 (s, 1H), 7.67 (s, 1H), 7.64 (s, 1H), 6.01-5.90 (m, 1H), 5.21 (dd, J=17.2, 1.6 Hz, 1H), 5.15-5.08 (m, 1H), 4.63 (t, J=7.0 Hz, 2H), 4.07 (q, J=6.7 Hz, 1H), 2.71 (q, J=7.0 Hz, 4H), 2.37-2.28 (m, 1H), 2.25 (bs, 1H), 1.48 (d, J=6.7 Hz, 3H), 1.14 (t, J=7.1 Hz, 3H), 1.11-1.06 (m, 2H), 1.05-0.98 (m, 2H).

1-((R)-1-(5-(8-(But-3-en-1-yloxy)imidazo[1,2-a]pyrazin-6-yl)-4-cyclopropylthiazol-2-yl)ethyl)-1-ethyl-3-((S)-7,7,7-trifluorohept-1-en-4-yl)urea (step 6)

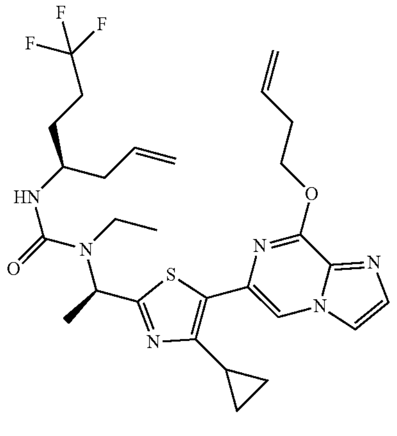 [SMILES: C=CCCOc1nc(-c2sc([C@@H](C)N(CC)C(=O)N[C@H](CC=C)CCC(F)(F)F)nc2C2CC2)cn2ccnc12]

To a solution of (S)-7,7,7-trifluorohept-1-en-4-amine, HCl (33 mg, 0.162 mmol) in $CH_3CN$ (2.5 mL) was added CDI (29 mg, 0.179 mmol) at ambient temperature. After 2 hr the mixture was transferred to a flask containing (R)-1-(5-(8-(but-3-en-1-yloxy)imidazo[1,2-a]pyrazin-6-yl)-4-cyclopropylthiazol-2-yl)-N-ethylethan-1-amine (52 mg, 0.136 mmol) and TEA (0.06 mL, 0.430 mmol). The resulting mixture was heated to 50° C. overnight. The mixture was cooled to ambient temperature then concentrated. The crude product was subjected to silica gel chromatography (ISCO® RediSep-Rf-12 g, 0-100% EtOAc/heptane, 15 minute gradient) to give the title compound. LC/MS: (M+H)+577.4. $^1$H-NMR (500 MHz, $CDCl_3$) δ 8.11 (s, 1H), 7.67 (s, 1H), 7.64 (s, 1H), 5.95 (ddt, J=17.1, 10.2, 6.8 Hz, 1H), 5.86-5.72 (m, 1H), 5.50 (d, J=6.9 Hz, 1H), 5.20 (dd, J=17.2, 1.5 Hz, 1H), 5.11 (q, J=9.0 Hz, 2H), 4.70 (d, J=8.8 Hz, 1H), 4.61 (t, J=7.0 Hz, 2H), 4.01 (d, J=5.4 Hz, 1H), 3.25 (dt, J=11.8, 5.9 Hz, 2H), 2.70 (q, J=6.9 Hz, 2H), 2.39-2.11 (m, 7H), 1.91-1.78 (m, 1H), 1.65 (d, J=7.1 Hz, 3H), 1.16 (t, J=7.2 Hz, 3H), 1.11-1.06 (m, 2H), 1.06-0.98 (m, 2H).

(27E,6E,9S,13R)-14-cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-6-en-11-one (step 7)

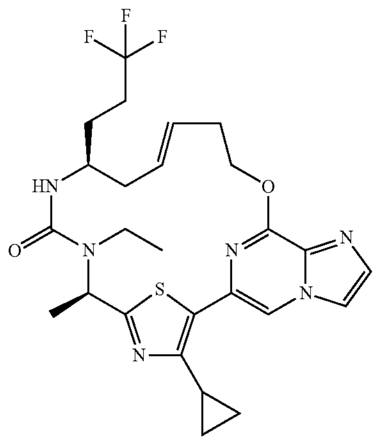 [SMILES: CCN1C(=O)N[C@@H](CCC(F)(F)F)C/C=C/CCOc2nc(cn3ccnc23)C2=C(C3CC3)N=C(S2)[C@H]1C]

A solution of 1-((R)-1-(5-(8-(but-3-en-1-yloxy)imidazo[1,2-a]pyrazin-6-yl)-4-cyclopropylthiazol-2-yl)ethyl)-1-ethyl-3-((S)-7,7,7-trifluorohept-1-en-4-yl)urea (56 mg, 0.097 mmol) in toluene (2 mL) was degassed (3×pump/N2). To this was added Hoveyda-Grubbs II catalyst (6 mg, 9.58 μmol) then the mixture was heated to 50° C. After 2 hr the mixture was cooled to ambient temperature then concentrated. The crude product was subjected to silica gel chromatography (ISCO© RediSep-Rf-12 g, 0-100% 3:1 EtOAc:EtOH/heptane, 15 minute gradient) to give the title compound. LC/MS: (M+H)+549.3

(9R,13R,E)-14-Cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-11-one (step 8) (example 209)

A solution of (27E,6E,9S,13R)-14-cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-6-en-II-one (25 mg, 0.046 mmol) in EtOH (3 mL) was transferred to a Parr flask containing 10% Pd/C (10 mg, 9.40 μmol). The flask was placed on a Parr shaker then degassed (3×pump/N2) then placed under H2 (2×pump/H2) at 50 psi at ambient temperature. After 3 hr the mixture was degassed (3×pump/N2) then removed from the Parr shaker then filtered through a pad of Celite® washing with EtOH then the filtrate was concentrated. The crude product was subjected to silica gel chromatography (ISCO® RediSep-Rf-12 g, 0-100% 3:1 EtOAc:EtOH/heptane, 15 minute gradient) to give the title compound. LC/MS: (M+H)+551.4. $^1$H-NMR (500 MHz, $CDCl_3$) δ 8.25 (s, 1H), 7.64 (s, 2H), 5.90 (q, J=7.1 Hz, 1H), 4.80 (td, J=12.4, 4.5 Hz, 1H), 4.46 (td, J=12.1, 5.5 Hz, 1H), 4.16 (td, J=16.8, 15.1, 8.6 Hz, 2H), 3.20 (dq, J=14.2, 7.0 Hz, 1H), 3.07 (dq, J=15.1, 7.5 Hz, 1H), 2.26 (ddt, J=14.3, 7.1, 3.1 Hz, 2H), 2.04 (q, J=6.6 Hz, 2H), 1.94-1.77 (m, 2H), 1.76-1.66 (m, 2H), 1.65 (d, J=7.2 Hz, 3H), 1.59-1.44 (m, 2H), 1.42-1.24 (m, 3H), 1.21 (t, J=7.2 Hz, 3H), 1.17-1.12 (m, 1H), 1.07 (p, J=5.8, 5.4 Hz, 3H).

Example 210

(16E,22E,7R)-25-cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-5-one

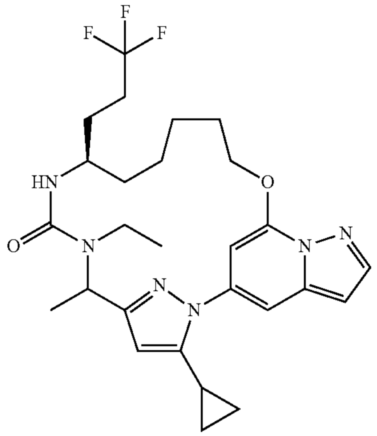 [SMILES: CCN1C(=O)N[C@@H](CCC(F)(F)F)CCCCCOc2cc(cc3ccnn23)-n2nc(cc2C2CC2)C1C]

Ethyl 1-(7-(but-3-en-1-yloxy)pyrazolo[1,5-a]pyridin-5-yl)-5-cyclopropyl-1H-pyrazole-3-carboxylate (step 1)

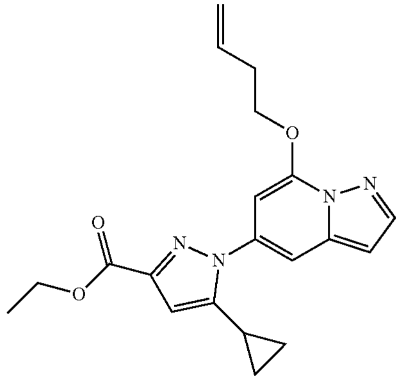 [SMILES: C=CCCOc1cc(-n2nc(C(=O)OCC)cc2C2CC2)cc2ccnn12]

7-(But-3-en-1-yloxy)-5-(4,4,5,5-tetramethyl-1,3,2-dioxaborolan-2-yl)pyrazolo[1,5-a]pyridine (1.46 g, 4.65 mmol), ethyl 5-cyclopropyl-1H-pyrazole-3-carboxylate (1.1 g, 6.10 mmol), $Cu(OAc)_2$ (1.3 g, 7.16 mmol), and boric acid (2.6 g, 42.1 mmol) were combined in $CH_3CN$ (25 mL) then the mixture was heated to 80° C. open to the air overnight. The mixture was cooled to ambient temperature then diluted with EtOAc then filtered through a pad of Celite® washing with EtOAc then the filtrate was concentrated. The crude product was subjected to silica gel chromatography (ISCO® RediSep-Rf-80 g, 0-50% EtOAc/heptane, 15 minute gradient) to give the title compound. LC/MS. (M+H)+367.2. $^{1}$H-NMR (500 MHz, $CDCl_3$) δ 8.07 (d, J=2.1 Hz, 1H), 7.49 (d, J=1.9 Hz, 1H), 6.62 (d, J=2.2 Hz, 1H), 6.54 (s, 1H), 6.51 (d, J=1.9 Hz, 1H), 5.95 (ddt, J=17.0, 10.2, 6.7 Hz, 1H), 5.25 (dd, J=17.2, 1.5 Hz, 1H), 5.21-5.15 (m, 1H), 4.42 (q, J=6.9 Hz, 4H), 2.80 (q, J=7.0 Hz, 2H), 1.91 (ddd, J=13.4, 8.3, 5.2 Hz, 1H), 1.41 (t, J=7.1 Hz, 2H), 1.27 (d, J=12.6 Hz, 1H), 1.15-0.99 (m, 2H), 0.93-0.81 (m, 2H).

1-(7-(But-3-en-1-yloxy)pyrazolo[1,5-a]pyridin-5-yl)-5-cyclopropyl-N-methoxy-N-methyl-1H-pyrazole-3-carboxamide (step 2)

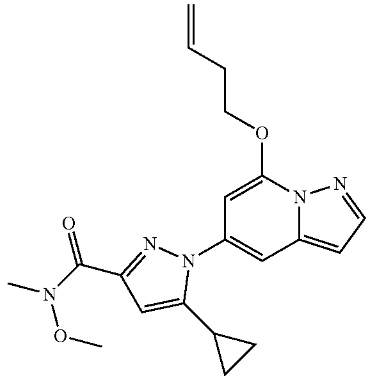 [SMILES: C=CCCOc1cc(-n2nc(C(=O)N(C)OC)cc2C2CC2)cc2ccnn12]

Ethyl 1-(7-(but-3-en-1-yloxy)pyrazolo[1,5-a]pyridin-5-yl)-5-cyclopropyl-1H-pyrazole-3-carboxylate (234 mg, 0.639 mmol) and N,O-dimethylhydroxylamine hydrochloride (93 mg, 0.958 mmol) were combined in THF (3 mL) then the mixture was cooled to −20° C. To this was added 2M iPrMgCl (0.96 mL, 1.920 mmol) in THF slowly. After 1 hr the mixture was warmed to 0° C. Saturated $NH_4Cl$ (10 drops) was added. After stirring for 1 minute the mixture was warmed to ambient temperature, diluted with EtOAc, then filtered through a pad of Celite® washing with EtOAc. The filtrate was concentrated. The crude product was subjected to silica gel chromatography (ISCO® RediSep-Rf-24 g, 0-95% EtOAc/heptane, 15 minute gradient) to give the title compound. LC/MS. (M+H)+382.3. $^{1}$H-NMR (500 MHz, $CDCl_3$) δ 8.07 (d, J=2.1 Hz, 1H), 7.51 (d, J=1.8 Hz, 1H), 6.62 (d, J=2.2 Hz, 1H), 6.56 (s, 1H), 6.50 (s, 1H), 5.96 (ddt, J=17.1, 10.3, 6.8 Hz, 1H), 5.26 (ddd, J=17.2, 8.0, 1.4 Hz, 1H), 5.22-5.15 (m, 1H), 4.40 (t, J=7.0 Hz, 2H), 3.81 (s, 3H), 3.47 (bs, 3H), 2.80 (q, J=7.1 Hz, 2H), 1.97-1.85 (m, 1H), 1.13-1.05 (m, 2H), 0.90-0.85 (m, 2H).

1-(1-(7-(But-3-en-1-yloxy)pyrazolo[1,5-a]pyridin-5-yl)-5-cyclopropyl-1H-pyrazol-3-yl)ethan-1-one (step 3)

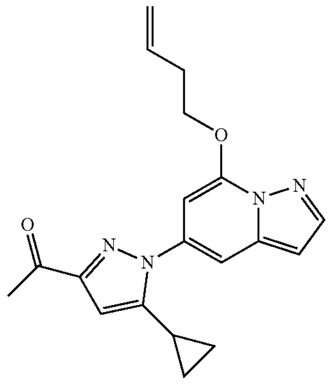 [SMILES: C=CCCOc1cc(-n2nc(C(C)=O)cc2C2CC2)cc2ccnn12]

A solution of 1-(7-(but-3-en-1-yloxy)pyrazolo[1,5-a]pyridin-5-yl)-5-cyclopropyl-N-methoxy-N-methyl-TH-pyrazole-3-carboxamide (47 mg, 0.123 mmol) in THF (1 mL) was cooled to 0° C. To this was added 3M MeMgBr (0.07 ml, 0.210 mmol) in $Et_2O$ slowly. After 1 hr the mixture was quenched with saturated $NH_4Cl$ then warmed to ambient temperature. The resulting mixture was diluted with $H_2O$ then extracted with EtOAc (3 x). The combined organic layers were dried ($MgSO_4$) then filtered then the filtrate was concentrated to give the crude title compound. LC/MS: (M+H)+337.2

1-(1-(7-(But-3-en-1-yloxy)pyrazolo[1,5-a]pyridin-5-yl)-5-cyclopropyl-1H-pyrazol-3-yl)-N-ethylethan-1-amine (step 4)

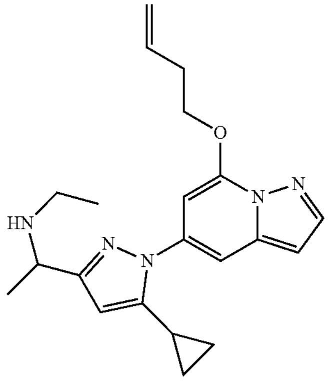 [SMILES: C=CCCOc1cc(-n2nc(C(C)NCC)cc2C2CC2)cc2ccnn12]

Crude 1-(1-(7-(but-3-en-1-yloxy)pyrazolo[1,5-a]pyridin-5-yl)-5-cyclopropyl-TH-pyrazol-3-yl)ethan-1-one (41.4 mg, 0.123 mmol) was taken up in EtOH (1 mL) then transferred to a screw cap vial. To this was added 2M ethanamine (0.31 mL, 0.620 mmol) in THF, AcOH (0.036 mL, 0.629 mmol), $MgSO_4$ (29.6 mg, 0.246 mmol), then $NaBH_3CN$ (15.46 mg, 0.246 mmol). The vial was capped then heated to 80° C. overnight. The mixture was cooled to ambient temperature then 10 drops of $H_2O$ were added with stirring until all solids dissolved. The resulting mixture was diluted with EtOAc, filtered through a pad of Celite washing with EtOAc then the filtrate was concentrated. The crude material was taken up in DMSO (1.0 mL), filtered using a 0.45 μm PTFE syringe filter, then purified by preparative reversed-phase HPLC (30×100 mm Phenomenex AXIA-Gemini-NX (0.1% TFA), 10-70% $CH_3CN$/water over 18 min at 50 mL/min). Fractions containing product were pooled then concentrated. The residue was taken up in 4:1 $H_2O$:$CH_3CN$. The mixture was transferred to a screw cap vial then frozen (dry ice/acetone) then lyophilized overnight to give the TFA salt of the title compound. LC/MS: (M+H)+366.3. $^{1}$H-NMR (500 MHz, $CDCl_3$) δ 9.37 (bs, 1H), 8.65 (bs, 1H), 8.18 (d, J=2.3 Hz, 1H), 7.50 (d, J=1.8 Hz, 1H), 6.66 (d, J=2.3 Hz, 1H), 6.59 (d, J=1.8 Hz, 1H), 6.20 (s, 1H), 6.04-5.87 (m, 1H), 5.32-5.23 (m, 1H), 5.18 (d, J=10.4 Hz, 1H), 4.42 (t, J=6.7 Hz, 2H), 3.05 (bs, 2H), 2.78 (q, J=6.7 Hz, 2H), 1.90 (ddd, J=13.4, 8.4, 5.3 Hz, 1H), 1.70 (d, J=6.9 Hz, 3H), 1.32 (t, J=7.3 Hz, 3H), 1.12 (d, J=7.0 Hz, 2H), 0.89 (t, J=5.2 Hz, 2H).

1-(1-(1-(7-(But-3-en-1-yloxy)pyrazolo[1,5-a]pyridin-5-yl)-5-cyclopropyl-1H-pyrazol-3-yl)ethyl)-1-ethyl-3-((S)-7,7,7-trifluorohept-1-en-4-yl)urea (step 5)

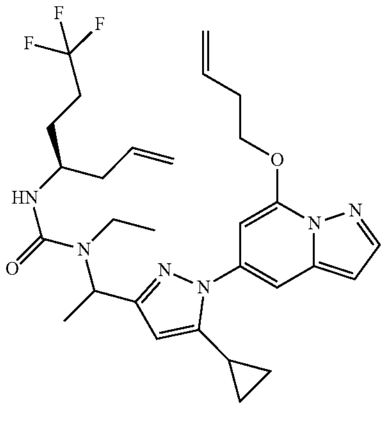 [SMILES: C=CCCOc1cc(-n2nc(C(C)N(CC)C(=O)N[C@H](CC=C)CCC(F)(F)F)cc2C2CC2)cc2ccnn12]

To a solution of (S)-7,7,7-trifluorohept-1-en-4-amine, HCl (23 mg, 0.113 mmol) in $CH_3CN$ (2 mL) was added CDI (20 mg, 0.123 mmol) at ambient temperature. After 2 hr the mixture was transferred to a vial containing 1-(1-(7-(but-3-en-1-yloxy)pyrazolo[1,5-a]pyridin-5-yl)-5-cyclopropyl-1H-pyrazol-3-yl)-N-ethylethan-1-amine, TFA (44 mg, 0.092 mmol). TEA (0.065 mL, 0.466 mmol) was added then the vial was capped then the mixture was heated to 50° C. overnight. The mixture was cooled to ambient temperature then concentrated. The crude product was subjected to silica gel chromatography (ISCO© RediSep-Rf-12 g, 0-75% EtOAc/heptane, 15 minute gradient) to give the title compound. LC/MS. (M+H)+559.4. 1H-NMR (500 MHz, $CDCl_3$) δ 8.05 (d, J=2.1 Hz, 1H), 7.43 (s, 1H), 6.60-6.57 (m, 1H), 6.50 (d, J=1.8 Hz, 1H), 5.96 (ddt, J=17.1, 10.3, 6.8 Hz, 1H), 5.89 (d, J=3.6 Hz, 1H), 5.80-5.65 (m, 1H), 5.28-5.14 (m, 2H), 5.04 (d, J=10.9 Hz, 2H), 4.61 (d, J=8.2 Hz, 1H), 4.39 (t, J=7.0 Hz, 2H), 3.99 (s, 1H), 3.37-3.18 (m, 2H), 2.80 (q, J=6.9 Hz, 2H), 2.32-2.02 (m, 4H), 1.88 (td, J=5.7, 2.6 Hz, 1H), 1.77 (ddd, J=14.6, 10.4, 5.8 Hz, 1H), 1.61 (d, J=7.1 Hz, 3H), 1.58-1.44 (m, 1H), 1.26 (t, J=7.1 Hz, 1H), 1.14 (q, J=7.3 Hz, 3H), 1.08-1.02 (m, 2H), 0.84-0.78 (m, 2H).

(16E,22E,7S,9E)-25-Cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-9-en-5-one (step 6)

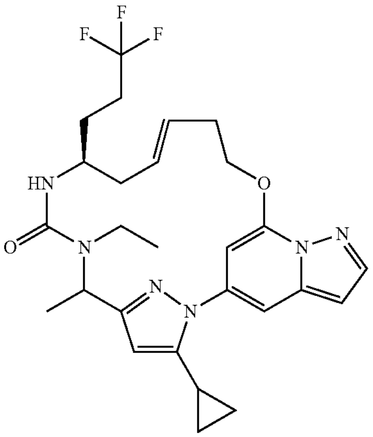 [SMILES: CCN1C(=O)N[C@@H](CCC(F)(F)F)C/C=C/CCOc2cc(cc3ccnn23)-n2nc(cc2C2CC2)C1C]

A solution of 1-(1-(1-(7-(but-3-en-1-yloxy)pyrazolo[1,5-a]pyridin-5-yl)-5-cyclopropyl-TH-pyrazol-3-yl)ethyl)-1-ethyl-3-((S)-7,7,7-trifluorohept-1-en-4-yl)urea (37 mg, 0.066 mmol) in DCE (1.5 mL) was degassed (3×pump/N2). Hoveyda-Grubbs II catalyst (5 mg, 7.98 μmol) was added then the mixture was heated to 50° C. Aftr 2 hr more Hoveyda-Grubbs II catalyst (5 mg, 7.98 μmol) was added and heating continued. After 2 hr the mixture was cooled to ambient temperature then concentrated. The crude product was subjected to silica gel chromatography (ISCO® RediSep-Rf-12 g, 0-100% EtOAc/heptane, 15 minute gradient) to give the title compound. LC/MS: (M+H)+531.4

Step 7: (16E,22E,7R)-25-cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-5-one (example 210) A solution of (16E,22E,7S,9E)-25-cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-9-en-5-one (16 mg, 0.030 mmol) in EtOH (2 mL) was transferred to a Parr flask containing 10% Pd/C (7 mg, 6.58 μmol). The flask was placed on a Parr shaker then degassed (3×pump/N2) then placed under H2 (2×pump/H2) at 50 psi at ambient temperature. After 2 hr the mixture was degassed (3×pump/N2) then removed from the Parr shaker. The mixture was filtered directly using a 0.45 μm PTFE syringe filter washing with EtOH then the filtrate was concentrated. The crude material was taken up in DMSO (1.0 mL) then purified by preparative reversed-phase HPLC (30×100 mm Phenomenex AXIA-Gemini-NX (0.1% TFA), 30-75% $CH_3CN$/water over 18 min at 50 mL/min). Fractions containing product were pooled then concentrated to give the title compound as a mixture of diastereomers. LC/MS: (M+H)+533.4. $^1$H-NMR (500 MHz, d6-DMSO) δ 8.01 (m, 1H), 7.74-7.62 (m, 1H), 6.75 (m, 1H), 6.67 (m, 1H), 6.30 (s, 1H), 6.19 (s, 1H), 5.82 (d, J=8.9 Hz, 1H), 5.64 (q, J=7.0 Hz, 1H), 4.50 (m, 2H), 3.91 (bs, 1H), 3.28 (td, J=15.4, 14.8, 7.2 Hz, 1H), 2.96 (dd, J=15.7, 7.5 Hz, 1H), 2.22 (m, 2H), 2.15-2.05 (m, 1H), 1.79 (m, 2H), 1.73-1.55 (m, 2H), 1.55-1.40 (m, 6H), 1.23 (m, 2H), 1.05 (m, 5H), 0.90-0.73 (m, 2H).

Example 211

(9R,13R,E)-14-Cyclopropyl-12-ethyl-13-methyl-9-(3,3,3-trifluoropropyl)-3-oxa-10,12-diaza-1(5,2)-oxazola-2(6,8)-imidazo[1,2-a]pyrazinacyclotridecaphan-11-one

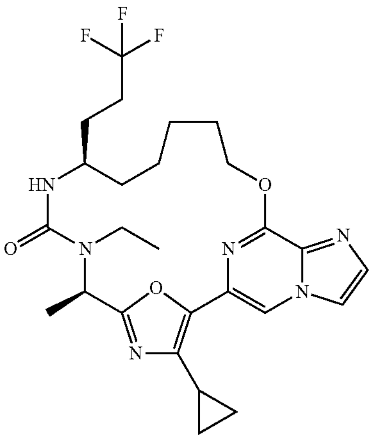 [SMILES: CCN1C(=O)N[C@@H](CCC(F)(F)F)CCCCCOc2nc(cn3ccnc23)C2=C(C3CC3)N=C(O2)[C@H]1C]

Step 1: Tert-butyl (R)-(1-(4-cyclopropyloxazol-2-yl) ethyl)carbamate

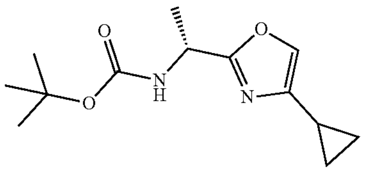 [SMILES: C[C@@H](NC(=O)OC(C)(C)C)c1nc(C2CC2)co1]

2-Bromo-1-cyclopropylethan-1-one (2.00 g, 12.27 mmol), tert-butyl (R)-(1-amino-1-oxopropan-2-yl)carbamate (2.89 g, 15.34 mmol), and AgOTf (3.94 g, 15.34 mmol) were combined in EtOAc (40 mL) then heated to 50° C. The mixture was cooled to ambient temperature then 40 mL saturated NaCl was added with rapid stirring. After 4 hr the mixture was filtered through a pad of Celite® washing with EtOAc. The filtrate layers were separated and the aqueous layer was extracted with EtOAc (3 x). The combined organic layers were dried ($MgSO_4$) then filtered then the filtrate was concentrated. The crude product was subjected to silica gel chromatography (ISCO® RediSep-Rf-40 g, 0-25% EtOAc/heptane, 15 minute gradient) to give the title compound. LC/MS: (M+H)+253.2. $^1$H-NMR (500 MHz, $CDCl_3$) δ 7.29 (s, 1H), 5.15 (bs, 1H), 4.88 (bs, 1H), 1.75 (ddd, J=13.3, 8.3, 5.0 Hz, 1H), 1.49 (d, J=6.9 Hz, 3H), 1.45 (s, 9H), 0.88-0.82 (m, 2H), 0.76-0.68 (m, 2H).

Step 2: Tert-butyl (R)-(1-(4-cyclopropyloxazol-2-yl) ethyl)(ethyl)carbamate

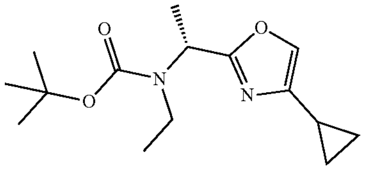 [SMILES: CCN(C(=O)OC(C)(C)C)[C@H](C)c1nc(C2CC2)co1]

To a solution of tert-butyl (R)-(1-(4-cyclopropyloxazol-2-yl)ethyl)carbamate (1.08 g, 4.28 mmol) in THF (20 mL) was added NaH (60% dispersion in mineral oil, 0.257 g, 6.42 mmol) all at once as a solid at ambient temperature. After 30 minutes iodoethane (0.52 mL, 6.43 mmol) was added and stirring was continued at ambient temperature for 1 hr. The mixture was heated to 60° C. overnight. The mixture was cooled to ambient temperature then quenched with saturated $NH_4Cl$. The resulting mixture was diluted with $H_2O$ then extracted with EtOAc (3 x). The combined organic layers were dried ($MgSO_4$) then filtered then the filtrate was concentrated. The crude product was subjected to silica gel chromatography (ISCO© RediSep-Rf-40 g, 0-25% EtOAc/heptane, 15 minute gradient) to give the title compound. LC/MS: (M+H)+281.2. 1H-NMR (500 MHz, $CDCl_3$) δ 7.28 (s, 1H), 5.47 (bs, 0.5H), 4.90 (bs, 0.5H), 3.15 (bs, 2H), 1.76 (ddd, J=13.4, 8.4, 5.1 Hz, 1H), 1.56 (bs, 3H), 1.45 (bs, 9H), 0.95 (bs, 3H), 0.87-0.82 (m, 2H), 0.72-0.67 (m, 2H).

Step 3: Tert-butyl (R)-(1-(4-cyclopropyl-5-(4,4,5,5-tetramethyl-1,3,2-dioxaborolan-2-yl)oxazol-2-yl)ethyl)(ethyl) carbamate

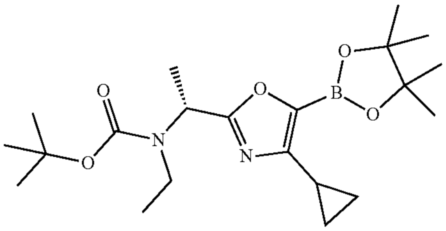 [SMILES: CCN(C(=O)OC(C)(C)C)[C@H](C)c1nc(C2CC2)c(B2OC(C)(C)C(C)(C)O2)o1]

In a screw cap vial a solution of tert-butyl (R)-(1-(4-cyclopropyloxazol-2-yl)ethyl)(ethyl)carbamate (200 mg, 0.713 mmol) in THF (7 mL) was purged with N2 by bubbling. To this was added bis(pinacolato)diboron (272 mg, 1.070 mmol), bis(1,5-cyclooctadiene)dimethoxydiiridium (24 mg, 0.036 mmol), and 4,4'-di-tert-butyl-2,2'-bipyridine (20 mg, 0.075 mmol). N2 was bubbled for 1 minute. The vial was capped then heated to 80° C. overnight. The mixture was cooled to ambient temperature then concentrated. The crude product was subjected to silica gel chromatography (ISCO© RediSep-Rf-40 g, 0-100% EtOAc/heptane, 15 minute gradient) to give the title compound. LC/MS (boronic acid): (M+H)+325.2. $^1$H-NMR (500 MHz, $CDCl_3$) δ 5.43 (bs, 0.5H), 4.94 (bs, 0.5H), 3.22 (bs, 2H), 2.24 (ddd, J=13.5, 8.2, 5.0 Hz, 1H), 1.56-1.37 (m, 12H), 1.34 (bs, 12H), 0.99 (bs, 3H), 0.96-0.85 (m, 4H).

Step 4: Tert-butyl (R)-(1-(5-(8-(but-3-en-1-yloxy)imidazo [1,2-a]pyrazin-6-yl)-4-cyclopropyloxazol-2-yl)ethyl)(ethyl) carbamate

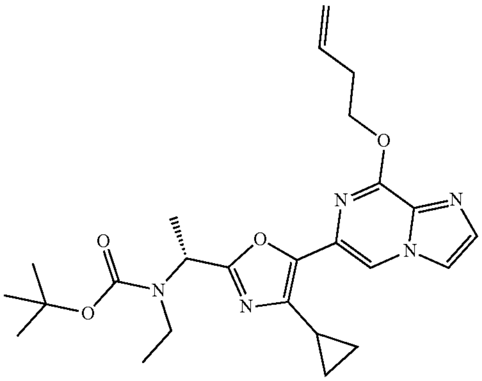 [SMILES: C=CCCOc1nc(-c2oc([C@@H](C)N(CC)C(=O)OC(C)(C)C)nc2C2CC2)cn2ccnc12]

6-Bromo-8-(but-3-en-1-yloxy)imidazo[1,2-a]pyrazine (100 mg, 0.373 mmol) and tert-butyl (R)-(1-(4-cyclopropyl-5-(4,4,5,5-tetramethyl-1,3,2-dioxaborolan-2-yl)oxazol-2-yl) ethyl)(ethyl)carbamate (195 mg, 0.480 mmol) were combined in DME (3 mL). To this was added 1M K3PO4 (1.2 mL, 1.200 mmol). The mixture was degassed (3×pump/N2) then X-Phos Pd G2 (30 mg, 0.038 mmol) was added then the mixture was heated to 80° C. overnight. The mixture was cooled to ambient temperature then diluted with EtOAc then filtered through a pad of Celite© washing with EtOAc then the filtrate was concentrated. The crude product was subjected to silica gel chromatography (ISCO© RediSep-Rf-12 g, 0-50% EtOAc/heptane, 15 minute gradient) to give the title compound. LC/MS: (M+H)+468.8. $^1$H-NMR (500 MHz, $CDCl_3$) δ 7.98 (bs, 1H), 7.65 (s, 1H), 7.62 (s, 1H), 5.92 (ddt, J=17.0, 10.2, 6.7 Hz, 1H), 5.50 (bs, 0.5H), 5.17 (d, J=17.2 Hz, 1H), 5.10 (d, J=10.3 Hz, 1H), 4.86 (bs, 0.5H), 4.62 (t, J=7.1 Hz, 2H), 3.28 (bs, 2H), 2.83 (tt, J=8.6, 5.0 Hz, 1H), 2.71 (q, J=6.9 Hz, 2H), 1.61 (s, 3H), 1.53 (m, 12H), 1.01 (m, 2H), 0.93 (dq, J=6.7, 4.3, 3.8 Hz, 2H).

Step 5: 1-((R)-1-(5-(8-(But-3-en-1-yloxy)imidazo[1,2-a]pyrazin-6-yl)-4-cyclopropyloxazol-2-yl)ethyl)-1-ethyl-3-((S)-7,7,7-trifluorohept-1-en-4-yl)urea

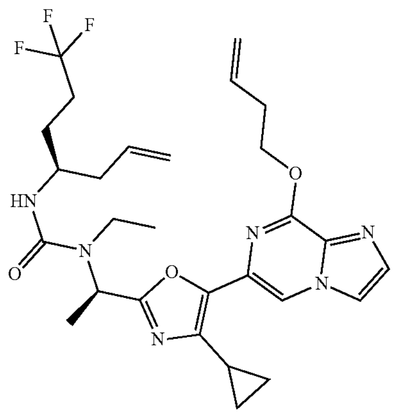 [SMILES: C=CCCOc1nc(-c2oc([C@@H](C)N(CC)C(=O)N[C@H](CC=C)CCC(F)(F)F)nc2C2CC2)cn2ccnc12]

To a solution of tert-butyl (R)-(1-(5-(8-(but-3-en-1-yloxy)imidazo[1,2-a]pyrazin-6-yl)-4-cyclopropyloxazol-2-yl)ethyl)(ethyl)carbamate (133 mg, 0.284 mmol) in DCM (1 mL) was added TFA (1 mL) at ambient temperature. After 90 minutes the mixture was concentrated. The crude material was used directly in the next step. LC/MS: (M+H)+368.3 To a solution of (S)-7,7,7-trifluorohept-1-en-4-amine, HCl (173 mg, 0.852 mmol) in DCM (1.5 mL) was added saturated $NaHCO_3$(1.5 mL) then triphosgene (76 mg, 0.256 mmol) with rapid stirring at ambient temperature. After 90 minutes a solution of crude (R)-1-(5-(8-(but-3-en-1-yloxy)imidazo[1,2-a]pyrazin-6-yl)-4-cyclopropyloxazol-2-yl)-N-ethyl-ethan-1-amine, TFA (104 mg, 0.284 mmol) in 1 mL DCM was added then 1 mL saturated $NaHCO_3$with rapid stirring at ambient temperature. After stirring overnight the mixture was diluted with $H_2O$ then extracted with DCM (3 x). The combined organic layers were dried ($MgSO_4$) then filtered then the filtrate was concentrated. The crude product was subjected to silica gel chromatography (ISCO© RediSep-Rf-24 g, 0-100% EtOAc/heptane, 20 minute gradient) to give the title compound. LC/MS: (M+H)+561.3. $^1$H-NMR (500 MHz, $CDCl_3$) δ 8.01 (s, 1H), 7.66 (d, J=0.9 Hz, 1H), 7.62 (d, J=0.9 Hz, 1H), 5.92 (ddt, J=17.0, 10.3, 6.7 Hz, 1H), 5.79 (ddt, J=14.5, 9.5, 7.2 Hz, 1H), 5.51 (q, J=7.0 Hz, 1H), 5.17 (dd, J=17.2, 1.6 Hz, 1H), 5.13-5.07 (m, 3H), 4.61 (t, J=7.1 Hz, 2H), 4.55 (d, J=8.3 Hz, 1H), 4.01 (m, 1H), 3.23 (hept, J=8.3 Hz, 2H), 2.84 (ddd, J=13.4, 8.3, 5.0 Hz, 1H), 2.70 (q, J=7.0 Hz, 2H), 2.38-2.12 (m, 5H), 1.89-1.78 (m, 1H), 1.58 (d, J=7.2 Hz, 3H), 1.06 (t, J=7.2 Hz, 3H), 1.03-0.98 (m, 2H), 0.95 (dt, J=8.5, 2.7 Hz, 2H).

Step 6: (27E,6E,9S,13R)-14-Cyclopropyl-12-ethyl-13-methyl-9-(3,3,3-trifluoropropyl)-3-oxa-10,12-diaza-1(5,2)-oxazola-2(6,8)-imidazo[1,2-a]pyrazina-cyclotridecaphan-6-en-11-one

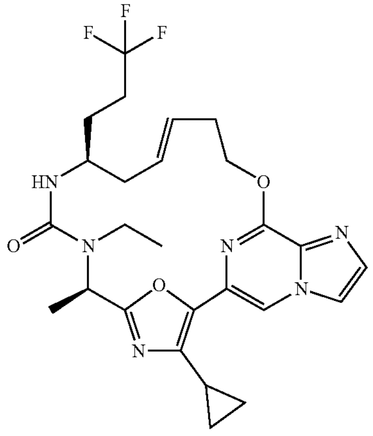 [SMILES: CCN1C(=O)N[C@@H](CCC(F)(F)F)C/C=C/CCOc2nc(cn3ccnc23)-c2oc(nc2C2CC2)[C@H]1C]

A solution of 1-(®-1-(5-(8-(but-3-en-1-yloxy)imidazo[1,2-a]pyrazin-6-yl)-4-cyclopropyloxazol-2-yl)ethyl)-1-ethyl-3-((S)-7,7,7-trifluorohept-1-en-4-yl)urea (160 mg, 0.285 mmol) in DCE (6 mL) was degassed (3×pump/N2). Hoveyda-Grubbs II catalyst (10 mg, 0.016 mmol) was added then the mixture was heated to 50° C. After 3 hr the mixture was cooled to ambient temperature then concentrated. The crude product was subjected to silica gel chromatography (ISCO© RediSep-Rf-24 g, 0-100% 3:1 EtOAc:EtOH/heptane, 15 minute gradient) to give the title compound (56 mg, 37%). LC/MS (M+H)+533.3. $^1$H-NMR (500 MHz, $CDCl_3$) δ 8.11 (s, 1H), 7.67 (s, 1H), 7.65 (s, 1H), 6.00 (q, J=7.1 Hz, 1H), 5.62-5.48 (m, 2H), 4.74 (dd, J=9.2, 7.6 Hz, 2H), 4.23-4.14 (m, 1H), 4.08 (d, J=8.9 Hz, 1H), 3.11 (ddt, J=49.9, 16.2, 7.3 Hz, 2H), 2.60 (dd, J=9.2, 5.1 Hz, 2H), 2.50 (d, J=14.0 Hz, 1H), 2.24 (dq, J=20.5, 10.7 Hz, 2H), 2.02 (ddd, J=15.0, 11.2, 5.9 Hz, 1H), 1.91 (p, J=7.2 Hz, 1H), 1.86-1.76 (m, 1H), 1.28 (d, J=19.0 Hz, 2H), 1.09-1.01 (m, 5H), 1.00-0.85 (m, 4H).

Step 7: (9R,13R,E)-14-Cyclopropyl-12-ethyl-13-methyl-9-(3,3,3-trifluoropropyl)-3-oxa-10,12-diaza-1(5,2)-oxazola-2(6,8)-imidazo[1,2-a]pyrazinacy-clotridecaphan-11-one (example 211)

To a solution of (27E,6E,9S,13R)-14-cyclopropyl-12-ethyl-13-methyl-9-(3,3,3-trifluoropropyl)-3-oxa-10,12-diaza-1(5,2)-oxazola-2(6,8)-imidazo[1,2-a]pyrazinacyclotri-decaphan-6-en-11-one (56 mg, 0.105 mmol) in EtOH (2 mL) in a Parr flask was added 10% Pd/C (20 mg, 0.019 mmol). The flask was placed on a Parr shaker then degassed (3×pump/N2) then placed under H2 (2×pump/H2) at 50 psi at ambient temperature. After 3 hr the mixture was degassed (3×pump/N2) then removed from the Parr shaker then filtered through a pad of Celite® washing with EtOH then the filtrate was concentrated. The crude product was subjected to silica gel chromatography (ISCO® RediSep-Rf-12 g, 0-100% 3:1 EtOAc:EtOH/heptane, 15 minute gradient) to give the title compound (example 211). LC/MS: (M+H)+535.3. $^1$H-NMR (500 MHz, $CDCl_3$) δ 8.10 (s, 1H), 7.66 (s, 1H), 7.64 (s, 1H), 5.99 (q, J=7.2 Hz, 1H), 4.77-4.70 (m, 2H), 4.14 (d, J=10.4 Hz, 1H), 4.03 (d, J=9.4 Hz, 1H), 3.24-3.15

(m, 1H), 3.11-3.00 (m, 1H), 2.23 (ddd, J=16.2, 10.6, 5.2 Hz, 2H), 2.02-1.70 (m, 4H), 1.59 (d, J=7.2 Hz, 3H), 1.57-1.46 (m, 2H), 1.29 (dt, J=20.6, 10.7 Hz, 4H), 1.06 (dt, J=13.0, 6.9 Hz, 5H), 0.99-0.85 (m, 3H).
Example 212
(3R,E)-4-ethyl-25-methoxy-3-methyl-7[4]-(trifluoromethyl)-11-oxa-4,6-diaza-1(6,8)-imidazo[1,2-a]pyrazina-2(4,2)-pyridina-7(3,1)-pyrrolidinacycloundecaphan-5-one
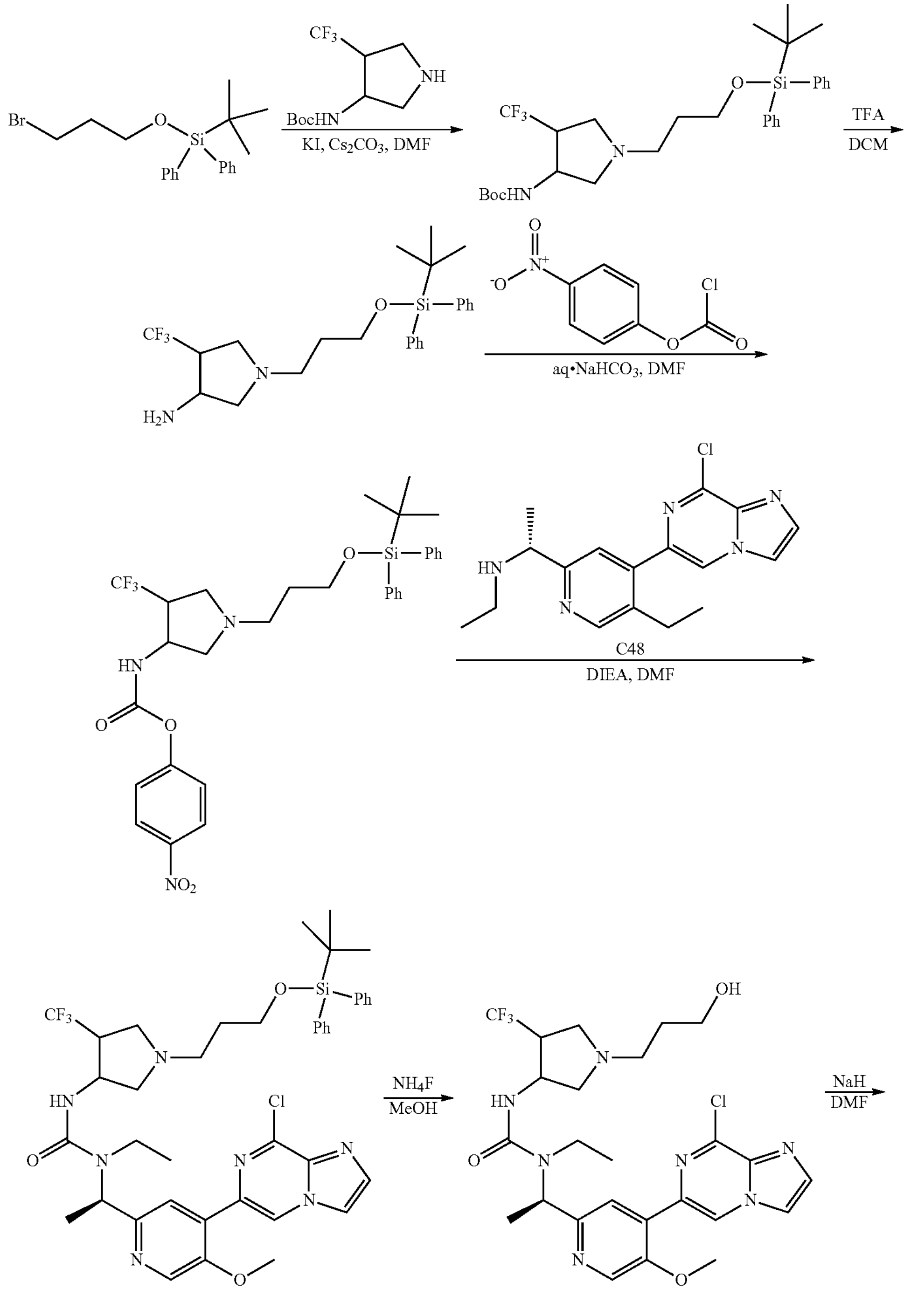

-continued

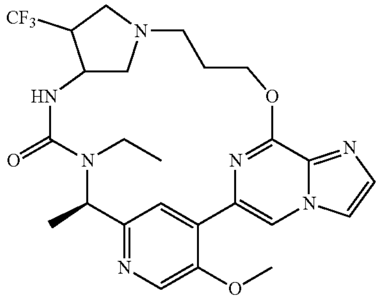

EXAMPLE 212

Step 1: tert-butyl (1-(3-((tert-butyldiphenylsilyl)oxy)propyl)-4-(trifluoromethyl)pyrrolidin-3-yl)carbamate A sealable vial was charged with tert-butyl (4-(trifluoromethyl)pyrrolidin-3-yl)carbamate (100 mg, 0.393 mmol) which was dissolved in DMF (1967 μl) and treated with (3-bromopropoxy)(tert-butyl)diphenylsilane (178 mg, 0.472 mmol), potassium iodide (131 mg, 0.787 mmol) and cesium carbonate (256 mg, 0.787 mmol). The vial was sealed and the contents were heated to 80° C. and stirred 18 h. Work-up involved diluting with EtOAc, washing with water, drying by filtering through a hydrophobic frit and evaporating to give an oil. This was purified via flash silica chromatography (0-50% 3:1 EtOAc:EtOH/hexanes, to afford tert-butyl (1-(3-((tert-butyldiphenylsilyl)oxy)propyl)-4-(trifluoromethyl)pyrrolidin-3-yl)carbamate. LC-MS: 551.6 (M+1).

Step 2: 1-(3-((tert-butyldiphenylsilyl)oxy)propyl)-4-(trifluoromethyl)pyrrolidin-3-amine The tert-butyl (1-(3-((tert-butyldiphenylsilyl)oxy)propyl)-4-(trifluoromethyl)pyrrolidin-3-yl)carbamate (144 mg, 0.261 mmol) was dissolved in DCM (1307 μl) and treated with TFA (583 μl, 7.58 mmol) and stirred, ambient temperature, 30 min. This was concentrated to afford 1-(3-((tert-butyldiphenylsilyl)oxy)propyl)-4-(trifluoromethyl)pyrrolidin-3-amine. LC-MS: 451.4 (M+1).

Step 3: 4-nitrophenyl (1-(3-((tert-butyldiphenylsilyl)oxy)propyl)-4-(trifluoromethyl)pyrrolidin-3-yl)carbamate The 1-(3-((tert-butyldiphenylsilyl)oxy)propyl)-4-(trifluoromethyl)pyrrolidin-3-amine (178 mg, 0.262 mmol) was dissolved in DCM (1311 μl) and treated with saturated $NaHCO_3$(1311 μl) and 4-nitrophenyl chloroformate (63.4 mg, 0.315 mmol) and stirred, ambient temperature, 18 h. This was diluted with DCM and the organic portion was filtered through a hydrophobic frit and concentrated to give 4-nitrophenyl (1-(3-((tert-butyldiphenylsilyl)oxy)propyl)-4-(trifluoromethyl)pyrrolidin-3-yl)carbamate. LC-MS: 616.6 (M+1).

Steps 4, 5, and 6: (3R,E)-4-ethyl-25-methoxy-3-methyl-$7^4$-(trifluoromethyl)-11-oxa-4,6-diaza-1(6,8)-imidazo[1,2-a]pyrazina-2(4,2)-pyridina-7(3,1)-pyrrolidinacycloundecaphan-5-one Example 212

The (R)-1-(4-(8-chloroimidazo[1,2-a]pyrazin-6-yl)-5-methoxypyridin-2-yl)-N-ethylethan-1-amine (C48, 25 mg, 0.075 mmol) was dissolved in DMF (377 μl) and treated with 4-nitrophenyl (1-(3-((tert-butyldiphenylsilyl)oxy)propyl)-4-(trifluoromethyl)pyrrolidin-3-yl)carbamate (55.7 mg, 0.090 mmol) and DIEA (39.5 μl, 0.226 mmol) and stirred, ambient temperature, 18 h. Work-up involved diluting with EtOAc, washing with saturated $NaHCO_3$, drying by filtering through a hydrophobic frit and evaporating to give a residue. This was purified via flash silica chromatography (0-50% 3:1 EtOAc:EtOH/hexanes to afford 3-(1-(3-((tert-butyldiphenylsilyl)oxy)propyl)-4-(trifluoromethyl)pyrrolidin-3-yl)-1-((R)-1-(4-(8-chloroimidazo[1,2-a]pyrazin-6-yl)-5-methoxypyridin-2-yl)ethyl)-1-ethylurea. A sealable vial was charged with 3-(1-(3-((tert-butyldiphenylsilyl)oxy)propyl)-4-(trifluoromethyl)pyrrolidin-3-yl)-1-((R)-1-(4-(8-chloroimidazo[1,2-a]pyrazin-6-yl)-5-methoxypyridin-2-yl)ethyl)-1-ethylurea (27.5 mg, 0.034 mmol) which was dissolved in MeOH (170 μl), heated to 50° C. and stirred 18 h. Work-up involved diluting with $CH_2Cl_2$, washing with saturated $NaHCO_3$, drying by filtering through a hydrophobic frit and evaporating to give 1-((R)-1-(4-(8-chloroimidazo[1,2-a]pyrazin-6-yl)-5-methoxypyridin-2-yl)ethyl)-1-ethyl-3-(1-(3-hydroxypropyl)-4-(trifluoromethyl)pyrrolidin-3-yl)urea. The 1-((R)-1-(4-(8-chloroimidazo[1,2-a]pyrazin-6-yl)-5-methoxypyridin-2-yl)ethyl)-1-ethyl-3-(1-(3-hydroxypropyl)-4-(trifluoromethyl)pyrrolidin-3-yl)urea (19.4 mg, 0.034 mmol) was dissolved in DMF (340 μl) and treated with sodium hydride (4.54 mg, 0.170 mmol) and stirred, ambient temperature, 30 min. This was diluted with DMSO and purified via reverse phase chromatography with direct injection (SunFire Prep C18 OBD column, 5 micron, 30×150 mm, 5-95% $CH_3CN$/Water/0.1% TFA, 25 min, 50 mL/min) to afford separate diastereomers. The fractions containing the first eluting product were treated with saturated $NaHCO_3$, extracted with DCM and the organic portion was filtered through a hydrophobic frit and concentrated to give (3R,E)-4-ethyl-25-methoxy-3-methyl-74-(trifluoromethyl)-11-oxa-4,6-diaza-1(6,8)-imidazo[1,2-a]pyrazina-2(4,2)-pyridina-7(3,1)-pyrrolidinacycloundecaphan-5-one (Example 212). LC-MS: 534.5 (M+1).

The following compounds in the table were prepared according to the general procedures herein and in an analogous manner of that described in Example 212 using the appropriate intermediates referenced in the table. For Example 214, step 1 was run without KI. The starting materials were either prepared as described in the intermediates section, commercially available, or prepared from commercially available reagents using conventional reactions well known in the art. Examples are single enantiomers of undefined stereochemistry unless denoted with * in which case it was obtained as a mixture of isomers.

| Ex. # | Structure | Name | Exact Mass [M + H]+ | Interm | Interm C |
|---|---|---|---|---|---|
| 213* | 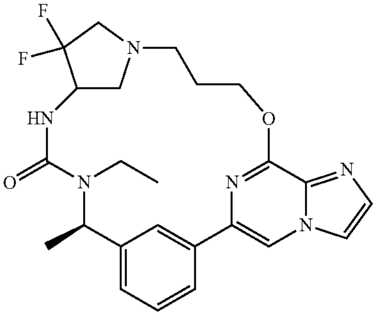 [SMILES: CCN1C(=O)NC2CN(CCCOc3nc(cn4ccnc34)-c3cccc(c3)[C@H]1C)CC2(F)F] | (3R,E)-4-ethyl-$7^4$,$7^4$-difluoro-3-methyl-11-oxa-4,6-diaza-1(6,8)-imidazo[1,2-a]pyrazina-7(3,1)-pyrrolidina-2(1,3)-benzenacycloundecaphan-5-one | Calc'd 470.5, found 471.4 | (3-bromopropoxy)(tert-butyl)diphenylsilane | C50 |
| 214 | 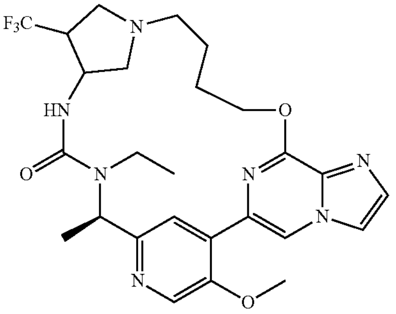 [SMILES: CCN1C(=O)NC2CN(CCCCOc3nc(cn4ccnc34)-c3cc(ncc3OC)[C@H]1C)CC2C(F)(F)F] | (3R,E)-4-ethyl-25-methoxy-3-methyl-$7^4$-(trifluoromethyl)-12-oxa-4,6-diaza-1(6,8)-imidazo[1,2-a]pyrazina-2(4,2)-pyridina-7(3,1)-pyrrolidinacyclododecaphan-5-one | Calc'd 547.6, found 548.5 | 1,4-butanediol | C48 |

Example 215

(3R,E)-4-ethyl-22-methoxy-3-methyl-7-(2-methylthiazol-4-yl)-13-oxa-4,6-diaza-1(6,8)-imidazo[1,2-a]pyrazina-2(3,5)-pyridinacyclotridecaphan-5-one

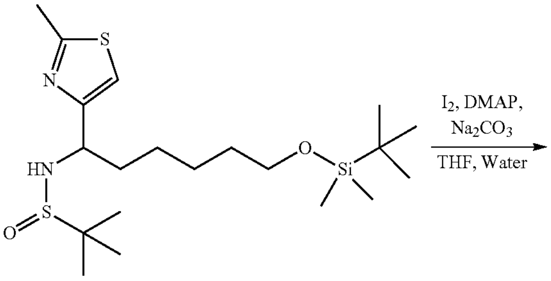

A175

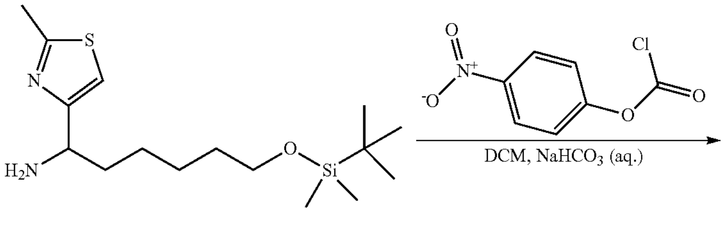

-continued

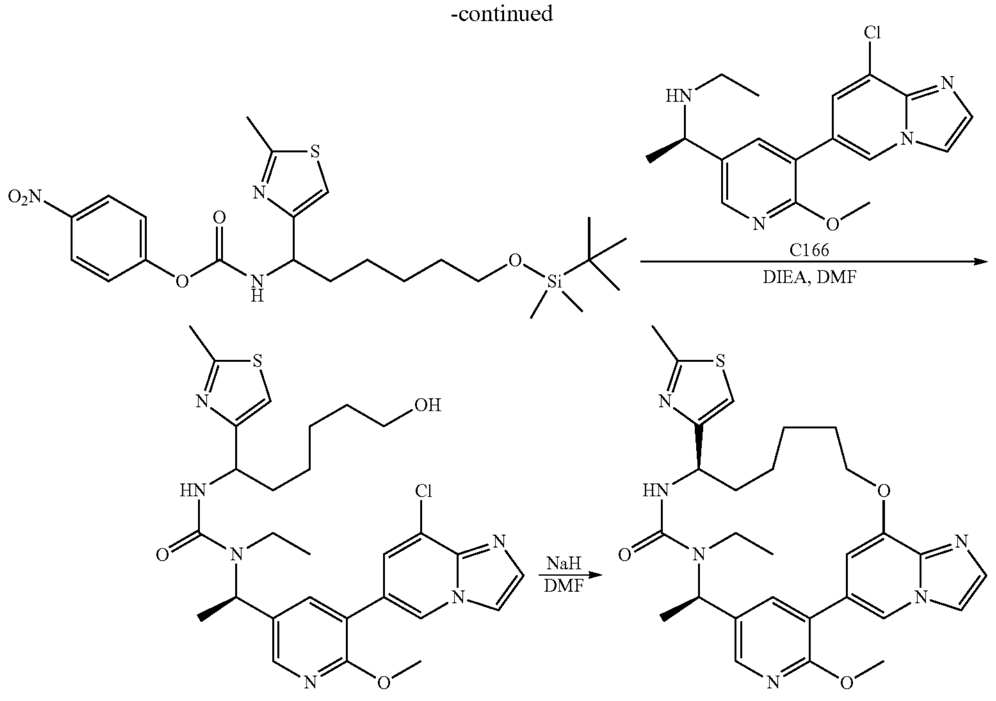

EXAMPLE 215

Steps 1 and 2: 4-nitrophenyl (6-((tert-butyldimethylsilyl)oxy)-1-(2-methylthiazol-4-yl)hexyl)carbamate The N-(6-((tert-butyldimethylsilyl)oxy)-1-(2-methylthiazol-4-yl)hexyl)-2-methylpropane-2-sulfinamide (A175, 259 mg, 0.598 mmol was was dissolved in THF (5985 μl) and treated with Water (5985 μl) followed by iodine (380 mg, 1.496 mmol), sodium carbonate (190 mg, 1.795 mmol) and DMAP (14.62 mg, 0.120 mmol). The reaction contents were heated to 50° C. for 3 h. Work-up involved diluting with $CH_2Cl_2$, washing with saturated $NaHCO_3$, drying ($Na_2SO_4$), filtering and evaporating to give 6-((tert-butyldimethylsilyl)oxy)-1-(2-methylthiazol-4-yl)hexan-1-amine which was used directly without purification. The 6-((tert-butyldimethylsilyl)oxy)-1-(2-methylthiazol-4-yl)hexan-1-amine (197 mg, 0.600 mmol) was dissolved in DCM (1499 μl) and treated with saturated $NaHCO_3$(1499 μl) and 4-nitrophenyl chloroformate (145 mg, 0.719 mmol) and stirred, ambient temperature, 18 h. Work-up involved diluting with EtOAc, washing with saturated NaCl, drying ($Na_2SO_4$), filtering and evaporating to give an oil. This was purified via flash silica gel chromatography (0-50% EtOAc/Hexanes) to give 4-nitrophenyl (6-((tert-butyldimethylsilyl)oxy)-1-(2-methylthiazol-4-yl)hexyl)carbamate.

Steps 3 and 4: (3R,E)-4-ethyl-22-methoxy-3-methyl-7-(2-methylthiazol-4-yl)-13-oxa-4,6-diaza-1(6,8)-imidazo[1,2-a]pyrazina-2(3,5)-pyridinacyclotridecaphan-5-one (Example 215)

The (R)-1-(5-(8-chloroimidazo[1,2-a]pyrazin-6-yl)-6-methoxypyridin-3-yl)-N-ethylethan-1-amine (C166, 20 mg, 0.060 mmol) was dissolved in DMF (301 μl) and treated with 4-nitrophenyl (6-((tert-butyldimethylsilyl)oxy)-1-(2-methylthiazol-4-yl)hexyl)carbamate (78 μl, 0.078 mmol) and DIEA (31.6 μl, 0.181 mmol) and stirred at ambient temperature for 18 h. Work-up involved diluting with EtOAc, washing with saturated $NaHCO_3$, drying by filtering through a hydrophobic frit and evaporating to give 1-((R)-1-(5-(8-chloroimidazo[1,2-a]pyrazin-6-yl)-6-methoxypyridin-3-yl)ethyl)-1-ethyl-3-(6-hydroxy-1-(2-methylthiazol-4-yl)hexyl)urea. The 1-((R)-1-(5-(8-chloroimidazo[1,2-a]pyrazin-6-yl)-6-methoxypyridin-3-yl)ethyl)-1-ethyl-3-(6-hydroxy-1-(2-methylthiazol-4-yl)hexyl)urea (34.5 mg, 0.060 mmol) was dissolved in DMF (603 μl) and treated with sodium hydride (8.04 mg, 0.302 mmol) and stirred at ambient temperature for 1 h. This was diluted with water and DMSO and purified via reverse phase chromatography via direct injection (SunFire Prep C18 OBD column, 5 micron, 30×150 mm, 13-38% $CH_3CN$/Water/0.1% TFA, 25 min, 50 mL/min). The fractions containing the second eluting product were treated with saturated $NaHCO_3$, extracted with DCM and the organic portion was filtered through a hydrophobic frit and concentrated to give (3R,E)-4-ethyl-22-methoxy-3-methyl-7-(2-methylthiazol-4-yl)-13-oxa-4,6-diaza-1(6,8)-imidazo[1,2-a]pyrazina-2(3,5)-pyridinacyclotridecaphan-5-one (Example 215). LC-MS: 536.4 (M+1).

Example 216

(3R,E)-4-ethyl-25-methoxy-3-methyl-7-(2-methylthiazol-5-yl)-13-oxa-4,6-diaza-1(6,8)-imidazo[1,2-a]pyrazina-2(4,2)-pyridinacyclotridecaphan-5-one

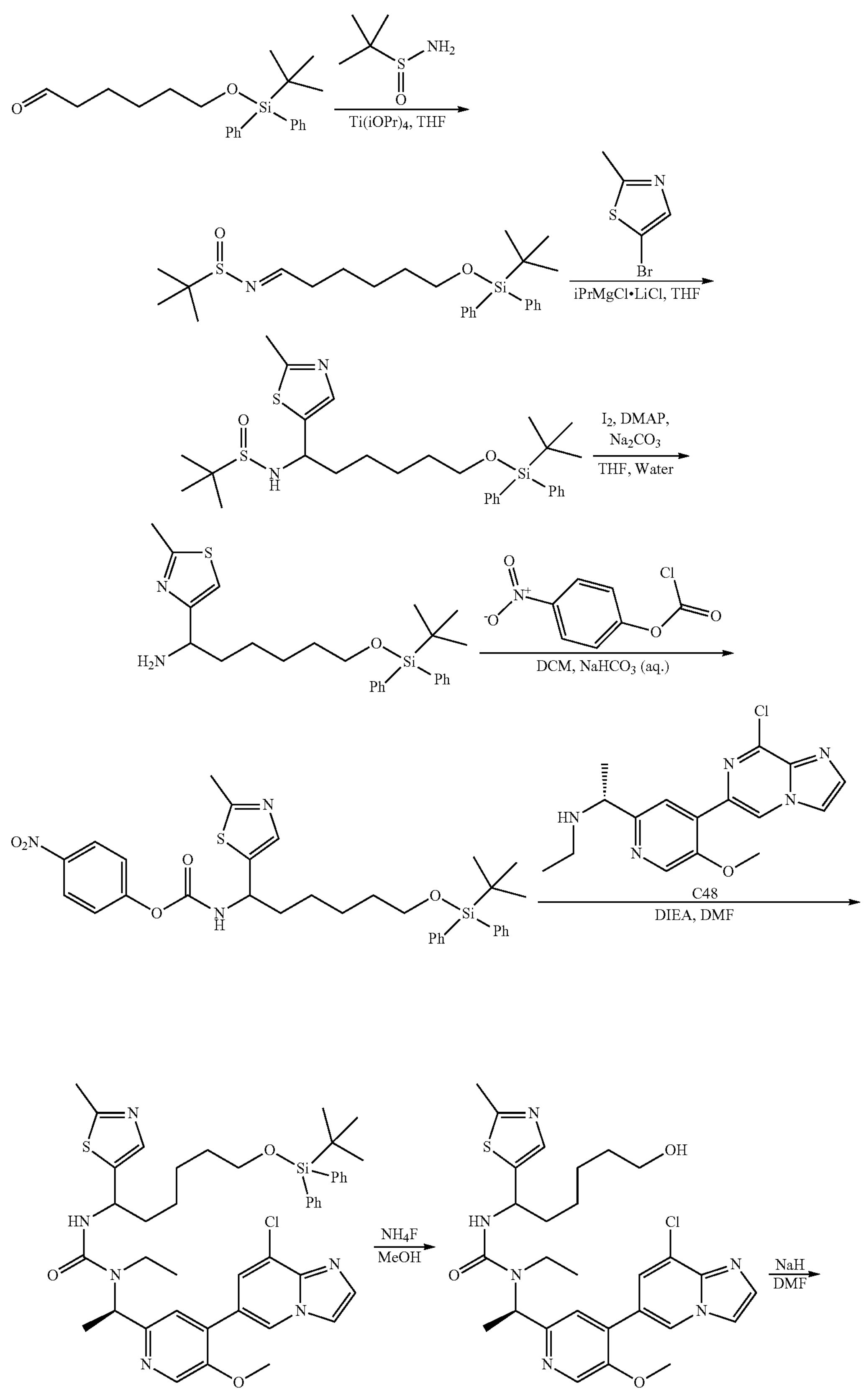
Ti(iOPr)4, THF
iPrMgCl•LiCl, THF
I2, DMAP, Na2CO3
THF, Water
DCM, NaHCO3 (aq.)
C48
DIEA, DMF
NH4F
MeOH
NaH
DMF -continued

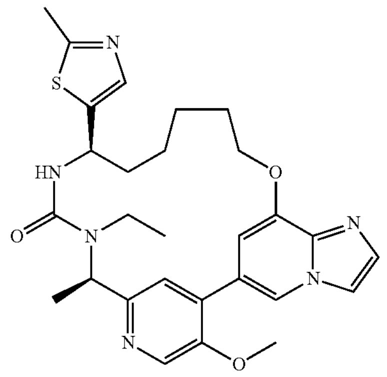

EXAMPLE 216

Step 1: (E)-N-(6-((tert-butyldiphenylsilyl)oxy)hexylidene)-2-methylpropane-2-sulfinamide A sealable vial was charged with 6-((tert-butyldiphenylsilyl)oxy)hexanal (1.88 g, 5.30 mmol) which was dissolved in THF (26.5 ml) and treated with 2-methylpropane-2-sulfinamide (0.771 g, 6.36 mmol) and titanium(IV) isopropoxide (4.71 ml, 15.91 mmol). The vial was capped and the reaction contents were heated to 60° C. and stirred 18 h. This was diluted with EtOAc and saturated $NaHCO_3$ and filtered over a bed of celite. The organic portion of the filtrate was dried ($Na_2SO_4$), filtered and concentrated to give an oil. This was purified via flash silica gel chromatography (0-30% EtOAc/Hexanes to give (E)-N-(6-((tert-butyldiphenylsilyl)oxy)hexylidene)-2-methylpropane-2-sulfinamide.

Step 2: N-(6-((tert-butyldiphenylsilyl)oxy)-1-(2-methylthiazol-5-yl)hexyl)-2-methylpropane-2-sulfinamide The 5-bromo-2-methylthiazole (207 mg, 1.162 mmol) was dissolved in THF (2906 μl) and treated with 1.3 M isopropylmagnesium chloride lithium chloride complex in THF (894 μl, 1.162 mmol) and stirred, ambient temperature, 30 min. The (E)-N-(6-((tert-butyldiphenylsilyl)oxy)hexylidene)-2-methylpropane-2-sulfinamide (266 mg, 0.581 mmol) was added and the reaction contents were stirred, ambient temperature, 1 h. This was quenched with saturated $NH_4Cl$ and extracted with EtOAc. The organic portion was dried ($Na_2SO_4$), filtered and concentrated to give an oil. This was purified via flash silica gel chromatography 0-40% 3:1 EtOAc:EtOH/hexanes) to give N-(6-((tert-butyldiphenylsilyl)oxy)-1-(2-methylthiazol-5-yl)hexyl)-2-methylpropane-2-sulfinamide. LC-MS: 557.5 (M+1).

Step 3: 6-((tert-butyldiphenylsilyl)oxy)-1-(2-methylthiazol-5-Yl)hexan-1-amine

A sealable vial was charged with N-(6-((tert-butyldiphenylsilyl)oxy)-1-(2-methylthiazol-5-yl)hexyl)-2-methylpropane-2-sulfinamide (197 mg, 0.354 mmol) and this was dissolved in THF (3537 μl) and Water (3537 μl) and treated with sodium carbonate (112 mg, 1.061 mmol), DMAP (8.64 mg, 0.071 mmol) and iodine (180 mg, 0.707 mmol). The vial was capped and the reaction contents were heated to 50° C. and stirred 2 h. Work-up involved diluting with $CH_2Cl_2$, washing with saturated $NaHCO_3$, drying by filtering through a hydrophobic frit and evaporating to give a residue. This was purified via reverse phase chromatography (SunFire Prep C18 OBD column, 5 micron, 30×150 mm, 5-95% $CH_3CN$/Water/0.1% TFA, 25 min, 50 mL/min). The fractions containing product were lyophilized to afford 6-((tert-butyldiphenylsilyl)oxy)-1-(2-methylthiazol-5-yl)hexan-1-amine. LC-MS: 453.4 (M+1).

Step 4: 4-nitrophenyl (6-((tert-butyldiphenylsilyl)oxy)-1-(2-methylthiazol-5-yl)hexyl)carbamate The 6-((tert-butyldiphenylsilyl)oxy)-1-(2-methylthiazol-5-yl)hexan-1-amine (91 mg, 0.161 mmol) was dissolved in DCM (803 μl) and sat'd $NaHCO_3$(803 μl) and treated with 4-nitrophenyl chloroformate (38.8 mg, 0.193 mmol) and stirred, ambient temperature, 15 min. Work-up involved diluting with $CH_2Cl_2$, washing with saturated $NaHCO_3$, drying by filtering through a hydrophobic frit and evaporating to give 4-nitrophenyl (6-((tert-butyldiphenylsilyl)oxy)-1-(2-methylthiazol-5-yl)hexyl)carbamate. LC-MS: 618.5 (M+1).

Steps 5, 6, and 7: (3R,E)-4-ethyl-25-methoxy-3-methyl-7-(2-methylthiazol-5-yl)-13-oxa-4,6-diaza-1(6,8)-imidazo[1,2-a]pyrazina-2(4,2)-pyridinacyclotridecaphan-5-one (Example 216)

The (R)-1-(4-(8-chloroimidazo[1,2-a]pyrazin-6-yl)-5-methoxypyridin-2-yl)-N-ethylethan-1-amine (25 mg, 0.075 mmol) was dissolved in DMF (377 μl) and treated with 4-nitrophenyl (6-((tert-butyldiphenylsilyl)oxy)-1-(2-methylthiazol-5-yl)hexyl)carbamate (C48, 51.2 mg, 0.083 mmol) and DIEA (39.5 μl, 0.226 mmol) and stirred, ambient temperature for 18 h. Work-up involved diluting with EtOAc, washing with saturated $NaHCO_3$, drying by filtering through a hydrophobic frit and evaporating to give an oil. This was purified via flash silica gel chromatography (0-70% 3:1 EtOAc:EtOH/hexanes) to afford 3-(6-((tert-butyldiphenylsilyl)oxy)-1-(2-methylthiazol-5-yl)hexyl)-1-((R)-1-(4-(8-chloroimidazo[1,2-a]pyrazin-6-yl)-5-methoxypyridin-2-yl)ethyl)-1-ethylurea. A sealable vial was charged with 3-(6-((tert-butyldiphenylsilyl)oxy)-1-(2-methylthiazol-5-yl)hexyl)-1-((R)-1-(4-(8-chloroimidazo[1,2-a]pyrazin-6-yl)-5-methoxypyridin-2-yl)ethyl)-1-ethylurea (32.1 mg, 0.040 mmol) was dissolved in MeOH (396 μl) and treated with ammonium fluoride (29.3 mg, 0.792 mmol). The vial was capped and the reaction contents were heated to 50° C. and stirred 18 h. Work-up involved diluting with EtOAc, washing with saturated $NaHCO_3$, drying by filtering through a hydrophobic frit and evaporating to give 1-((R)-1-(4-(8-chloroimidazo[1,2-a]pyrazin-6-yl)-5-methoxypyridin-2-yl)ethyl)-1-ethyl-3-(6-hydroxy-1-(2-methylthiazol-5-yl)hexyl)urea. The 1-((R)-1-(4-(8-chloroimidazo[1,2-a]pyrazin-6-yl)-5-methoxypyridin-2-yl)ethyl)-1-ethyl-3-(6-hydroxy-1-(2-methylthiazol-5-yl)hexyl)urea (22.6 mg, 0.040 mmol) was dissolved in DMF (395 μl) and treated with NaH (4.99 mg, 0.198 mmol) and stirred, ambient temperature, 18 h. This was diluted with water and DMSO and was purified via reverse phase chromatography (SunFire Prep C18 OBD column, 5 micron, 30×150 mm, 5-30% $CH_3CN$/Water/0.1% TFA, 25 min, 50 mL/min). The fractions containing the 2nd eluting isomer were treated with saturated $NaHCO_3$, extracted with DCM and the organic portion was filtered through a hydrophobic frit and concentrated to give (3R,E)-4-ethyl-25-methoxy-3-methyl-7-(2-methylthiazol-5-yl)-13-oxa-4,6-diaza-1(6,8)-imidazo[1,2-a]pyrazina-2(4,2)-pyridinacyclotridecaphan-5-one (Example 216). LC-MS: 536.2 (M+1).

Examples 217, 218 and 219

| Ex. # | Structure | Name | Exact Mass [M + H]+ | Heterocycle |
|---|---|---|---|---|
| 217 | 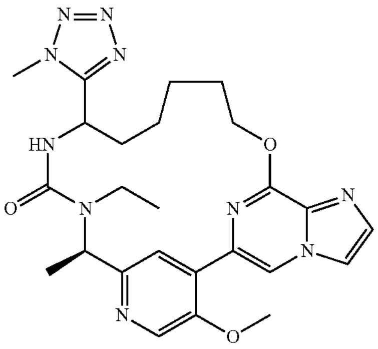 [SMILES: CCN1C(=O)NC(c2nnnn2C)CCCCCOc2nc(cn3ccnc23)-c2cc(ncc2OC)[C@H]1C] | (3R,E)-4-ethyl-$2^5$-methoxy-3-methyl-7-(1-methyl-1H-tetrazol-5-yl)-13-oxa-4,6-diaza-1(6,8)-imidazo[1,2-a]pyrazina-2(4,2)-pyridinacyclotridecaphan-5-one | Calc'd 520.6, found 521.2 | 5-bromo-1-methyl-1H-tetrazole |
| 218 | 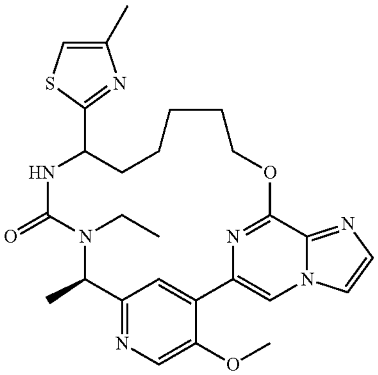 [SMILES: CCN1C(=O)NC(c2nc(C)cs2)CCCCCOc2nc(cn3ccnc23)-c2cc(ncc2OC)[C@H]1C] | (3R,E)-4-ethyl-$2^5$-methoxy-3-methyl-7-(4-methylthiazol-2-yl)-13-oxa-4,6-diaza-1(6,8)-imidazo[1,2-a]pyrazina-2(4,2)-pyridinacyclotridecaphan-5-one | Calc'd 535.7, found 536.2 | 2-bromo-4-methylthiazole |
| 219 | 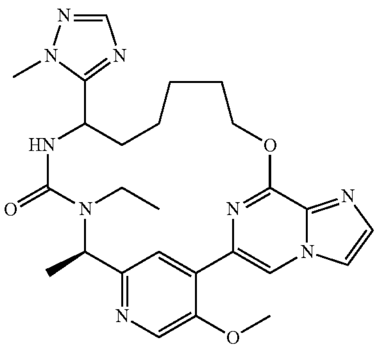 [SMILES: CCN1C(=O)NC(c2ncnn2C)CCCCCOc2nc(cn3ccnc23)-c2cc(ncc2OC)[C@H]1C] | (3R,E)-4-ethyl-$2^5$-methoxy-3-methyl-7-(1-methyl-1H-1,2,4-triazol-5-yl)-13-oxa-4,6-diaza-1(6,8)-imidazo[1,2-a]pyrazina-2(4,2)-pyridinacyclotridecaphan-5-one | Calc'd 519.6, found 520.2 | 5-bromo-1-methyl-1H-1,2,4-triazole |

Example 220

($1^7$E,3R,8E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one

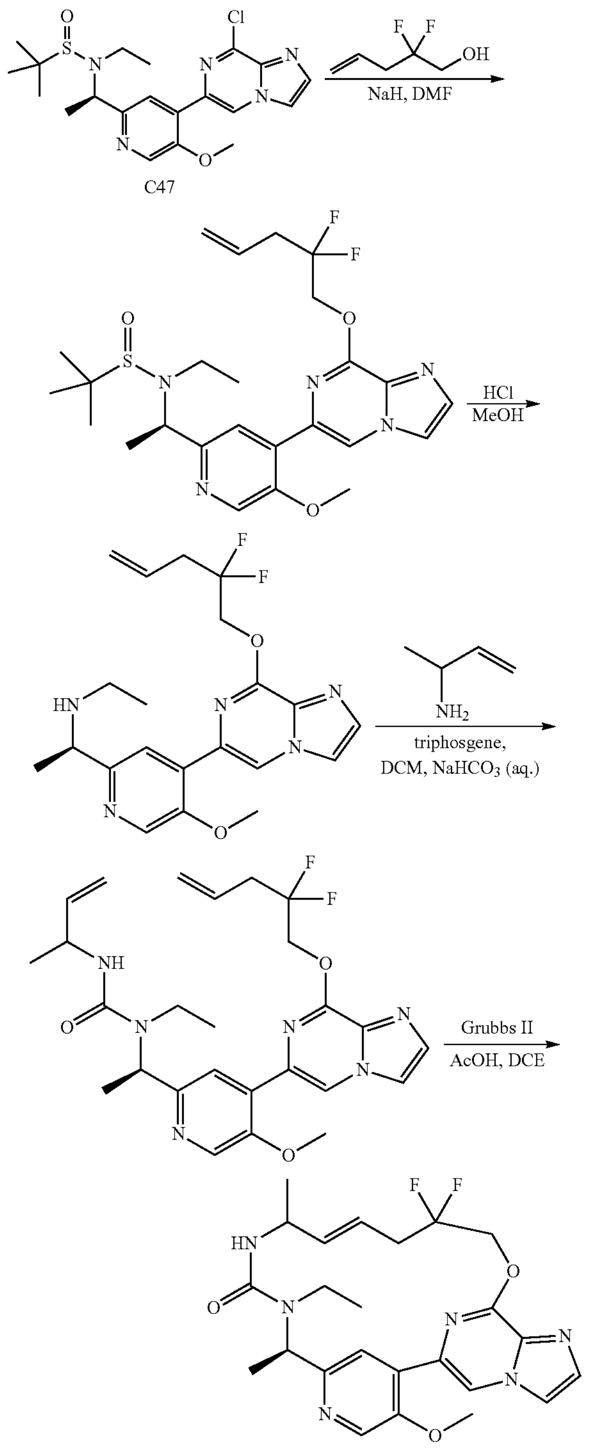

EXAMPLE 220

Step 1: N—((R)-1-(4-(8-((2,2-difluoropent-4-en-1-yl)oxy)imidazo[1,2-a]pyrazin-6-yl)-5-methoxypyridin-2-yl)ethyl)-N-ethyl-2-methylpropane-2-sulfinamide The 2,2-difluoropent-4-en-1-ol (220a, 63.0 mg, 0.516 mmol) was dissolved in DMF (860 μl) and treated with sodium hydride (13.04 mg, 0.516 mmol) and stirred for 15 min, then treated with N—((R)-1-(4-(8-chloroimidazo[1,2-a]pyrazin-6-yl)-5-methoxypyridin-2-yl)ethyl)-N-ethyl-2-methylpropane-2-sulfinamide (C47, 75 mg, 0.172 mmol) and stirred for 1 hour, ambient temperature. Work-up involved diluting with EtOAc, washing with sat'd $NaHCO_3$, drying ($Na_2SO_4$), filtering and evaporating to give an oil. This was purified via flash silica gel chromatography (0-80% 3:1 EtOAc:EtOH/hexanes) to give N—((R)-1-(4-(8-((2,2-difluoropent-4-en-1-yl)oxy)imidazo[1,2-a]pyrazin-6-yl)-5-methoxypyridin-2-yl)ethyl)-N-ethyl-2-methylpropane-2-sulfinamide. LC-MS: 522.4 (M+1).

Step 2: (R)-1-(4-(8-((2,2-difluoropent-4-en-1-yl)oxy)imidazo[1,2-a]pyrazin-6-yl)-5-methoxypyridin-2-yl)-N-ethylethan-1-amine The N—((R)-1-(4-(8-((2,2-difluoropent-4-en-1-yl)oxy)imidazo[1,2-a]pyrazin-6-yl)-5-methoxypyridin-2-yl)ethyl)-N-ethyl-2-methylpropane-2-sulfinamide (66 mg, 0.127 mmol) was dissolved in MeOH (1582 μl) and treated with 4 M HCl in dioxane (127 μl, 0.506 mmol) and stirred, ambient temperature, 1 hr. This was concentrated to afford (R)-1-(4-(8-((2,2-difluoropent-4-en-1-yl)oxy)imidazo[1,2-a]pyrazin-6-yl)-5-methoxypyridin-2-yl)-N-ethylethan-1-amine. LC-MS: 418.3 (M+1).

Step 3: 3-(but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea The but-3-en-2-amine (27.0 mg, 0.379 mmol) was dissolved in DCM (790 μl) and treated with saturated $NaHCO_3$ (790 μl) followed by triphosgene (37.5 mg, 0.126 mmol) and stirred for 1 hr at ambient temperature. To this, (R)-1-(4-(8-((2,2-difluoropent-4-en-1-yl)oxy)imidazo[1,2-a]pyrazin-6-yl)-5-methoxypyridin-2-yl)-N-ethylethan-1-amine (62 mg, 0.126 mmol) was added and the reaction contents were stirred at ambient temperature for 18 h. Work-up involved diluting with DCM, washing with saturated $NaHCO_3$, drying by filtering through a hydrophobic frit and evaporating to give a residue. This was purified via chromatography (0-100% 3:1 EtOAc:EtOH/hexanes) to give 3-(but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea. LC-MS: 515.4 (M+1).

Step 4: ($1^7$E,3R,8E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one (Example 220)

The 3-(but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea (31.7 mg, 0.062 mmol) was dissolved in DCE (3080 μl) and treated with acetic acid (7.05 μl, 0.123 mmol) and Grubbs catalyst 2nd generation (31.4 mg, 0.037 mmol) and stirred for 2 hours at ambient temperature. A drop of DMSO was added and the contents were stirred for 5 min. Work-up involved diluting with DCM, washing with saturated $NaHCO_3$, drying by filtering through a hydrophobic frit and evaporating to give a residue. This was purified via reverse phase chromatography (SunFire Prep C18 OBD column, 5 micron, 30×150 mm, 10-35% $CH_3CN$/Water/0.1% TFA, 25 min, 50 mL/min). The fractions containing the second eluting isomer were treated with saturated $NaHCO_3$, extracted with DCM and the organic portion was filtered through a hydrophobic frit and concentrated to give ($1^7$E,3R,8Z)-4-ethyl-11,11-difluoro-$2^5$-methoxy-3,7-dimethyl-13-oxa-4,6-diaza-1(6,8)-imidazo[1,2-a]pyrazina-2(4,2)-pyridinacyclotridecaphan-8-en-5-one (Example 220). LC-MS: 487.2 (M+1).

Example 221

(3R,7S,E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-5-one

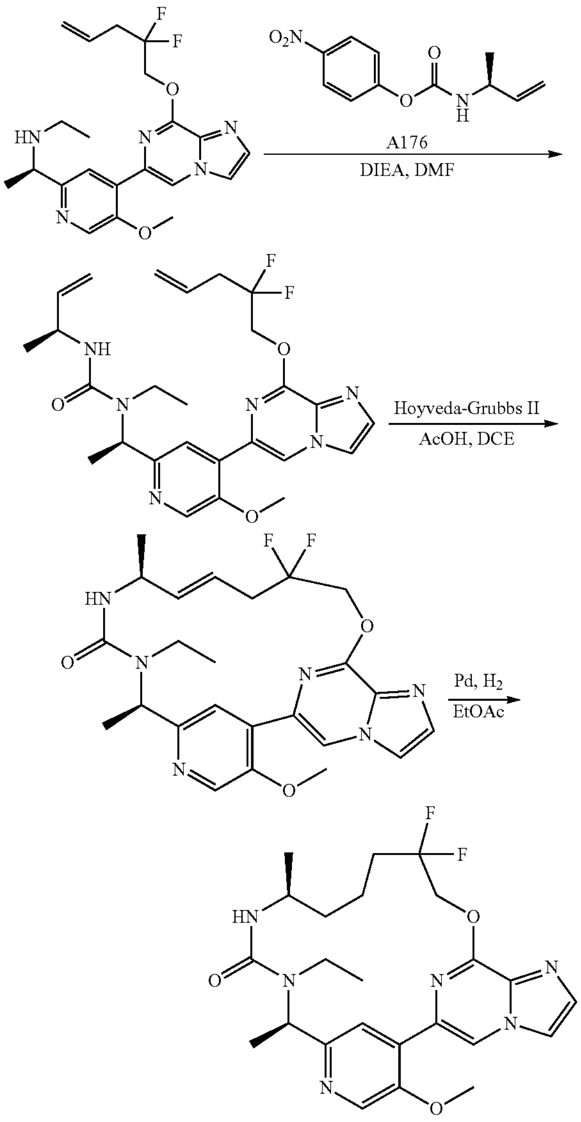

EXAMPLE 221

Step 1: 3-((S)-but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea The (R)-1-(4-(8-((2,2-difluoropent-4-en-1-yl)oxy)imidazo[1,2-a]pyrazin-6-yl)-5-methoxypyridin-2-yl)-N-ethylethan-1-amine (0.252 g, 0.604 mmol) was dissolved in DMF (3.02 ml) and treated with 4-nitrophenyl (S)-but-3-en-2-ylcarbamate (A176, 0.214 g, 0.905 mmol) and DIEA (0.316 ml, 1.811 mmol) and stirred at ambient temperature for 18 h. Work-up involved diluting with EtOAc, washing with saturated $NaHCO_3$, drying ($Na_2SO_4$), filtering and evaporating to give an oil. This was purified via reverse phase chromatography (SunFire Prep C18 OBD column, 5 micron, 30×150 mm, 5-95% $CH_3CN$/Water/0.1% TFA, 25 min, 50 mL/min). The fractions containing product were treated with saturated $NaHCO_3$, extracted with DCM and the organic portion was filtered through a hydrophobic frit and concentrated to give 3-((S)-but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea. LC-MS: 515.4 (M+1).

Step 2: ($1^7$E,3R,7S,8E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one A sealable vial was charged with 3-((S)-but-3-en-2-yl)-1-((R)-1-(4-(8-((2,2-difluoropent-4-en-1-yl)oxy)imidazo[1,2-a]pyrazin-6-yl)-5-methoxypyridin-2-yl)ethyl)-1-ethylurea (30 mg, 0.058 mmol) which was dissolved in DCE (2915 μl) which had been sparged with nitrogen for 10 min. To this, acetic acid (6.68 μl, 0.117 mmol) and (1,3-dimesitylimidazolidin-2-ylidene)(2-isopropoxybenzylidene)ruthenium(VI) chloride (21.92 mg, 0.035 mmol) were added and the reaction contents were stirred at ambient temperature for 18 h. Work-up involved diluting with DCM, washing with saturated $NaHCO_3$, drying by filtering through a hydrophobic frit and evaporating to give an oil. This was purified via flash silica gel chromatography (0-50% 3:1 EtOAc:EtOH/hexanes) to give ($1^7$E,3R,7S,8Z)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one. LC-MS: 487.4 (M+1).

Step 3: (3R,7S,E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-5-one (Example 221)

The ($1^7$E,3R,7S,8Z)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-8-en-5-one (5040072-0190) (12.6 mg, 0.026 mmol) was dissolved in ethyl acetate (1295 μl) and treated with 10% palladium on carbon (5.51 mg, 5.18 μmol). The reaction contents were inundated with hydrogen gas while stirring at ambient temperature for 5 hrs. This was filtered through a SPE cartridge containing celite and concentrated to afford (3R,7S,E)-4-ethyl-11,11-difluoro-25-methoxy-3,7-dimethyl-13-oxa-4,6-diaza-1(6,8)-imidazo[1,2-a]pyrazina-2(4,2)-pyridinacyclotridecaphan-5-one (Example 221). LC-MS: 489.3 (M+1).

Example 222

(3'R,7'S,7'E,8'E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphanen]-8'-en-5'-one

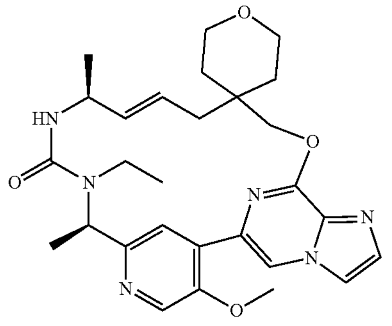 [SMILES: CCN1C(=O)N[C@@H](C)/C=C/CC2(CCOCC2)COc2nc(cn3ccnc23)-c2cc(ncc2OC)[C@H]1C]

The title compound was prepared from the starting material (4-allyltetrahydro-2H-pyran-4-yl)methanol according to the general procedures herein and in an analogous manner of that described in Example 220 and steps 1 and 2 used to synthesize Example 221. LC-MS: 521.4 (M+1).

Example 223

(3'R,7'S,E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphan]-5'-one

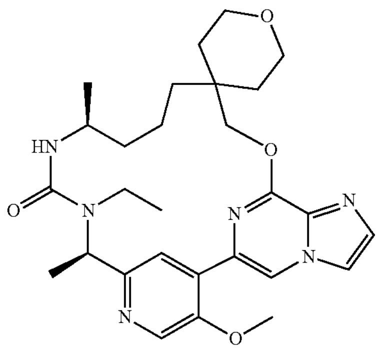 [SMILES: CCN1C(=O)N[C@@H](C)CCCC2(CCOCC2)COc2nc(cn3ccnc23)-c2cc(ncc2OC)[C@H]1C]

The title compound was prepared from the starting material (4-allyltetrahydro-2H-pyran-4-yl)methanol according to the general procedures herein and in an analogous manner of that described in steps 1 and 2 used to synthesize Example 220 and steps 1 through 3 used to synthesize Example 221. LC-MS: 523.4 (M+1).

Example 224

(3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-carbonitrile

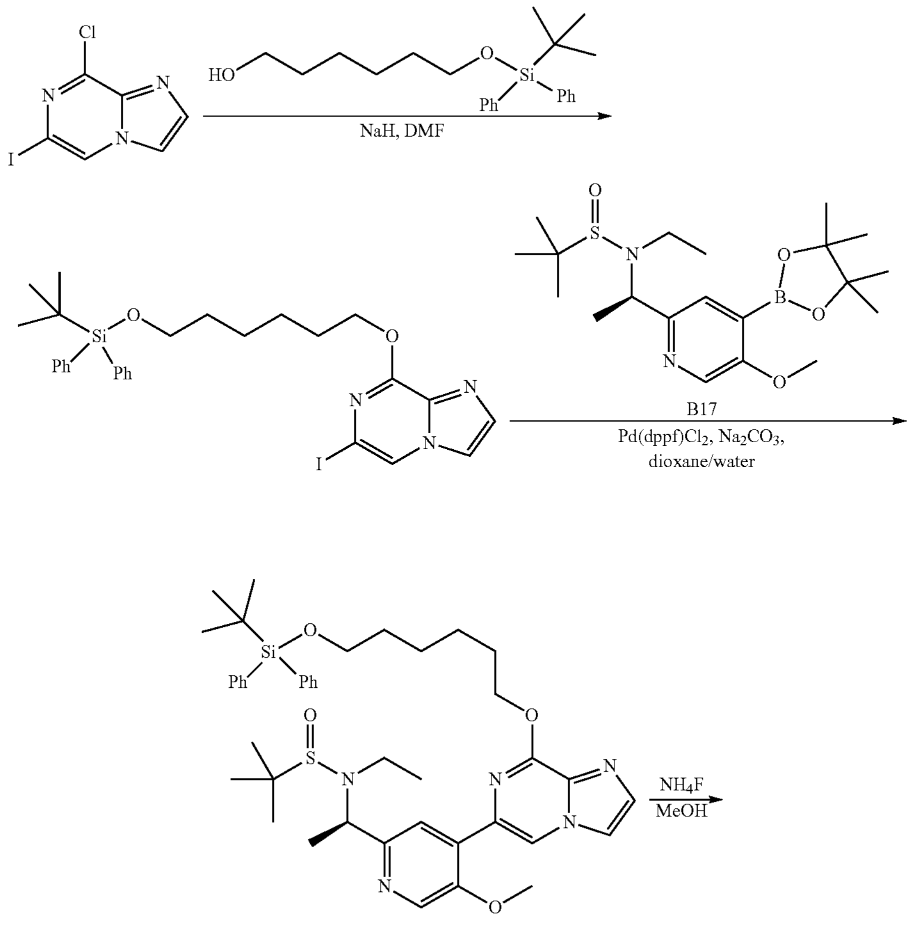

-continued
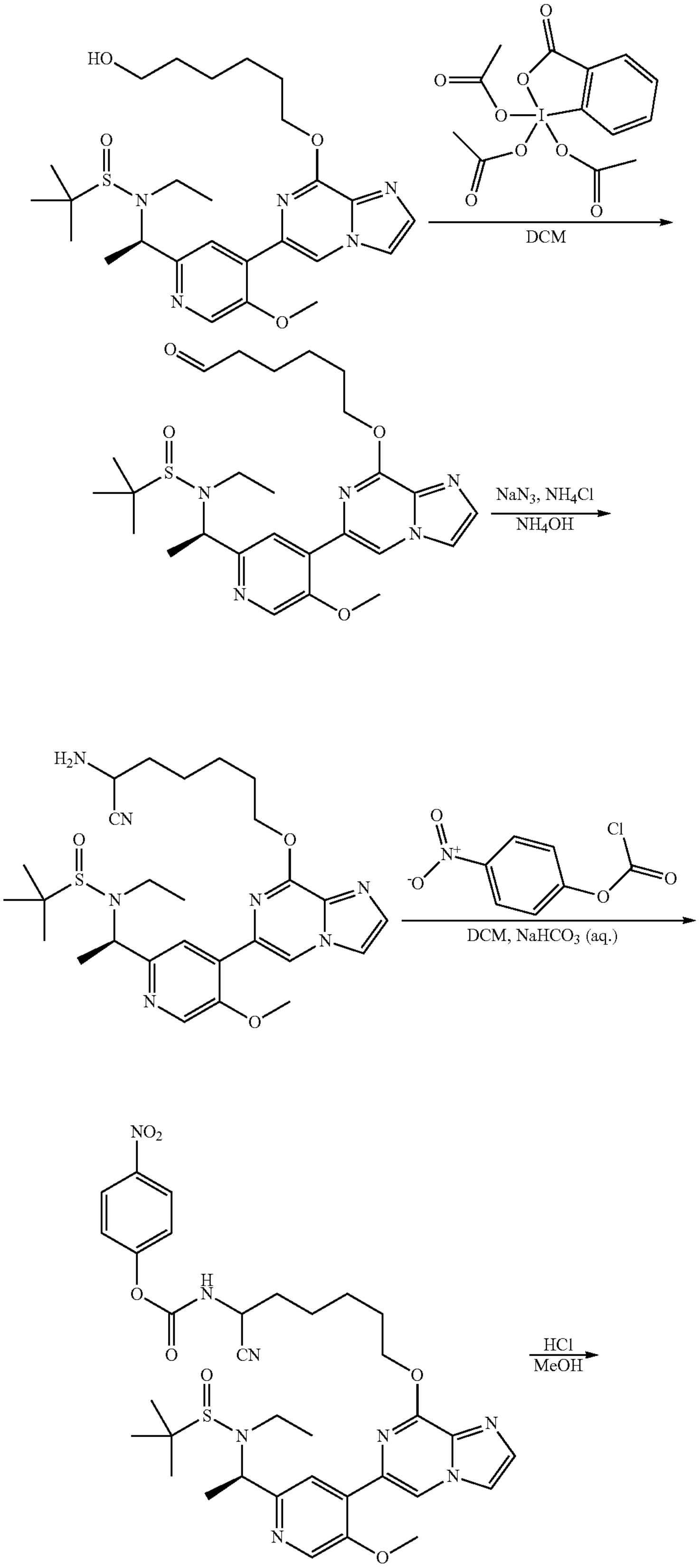

-continued

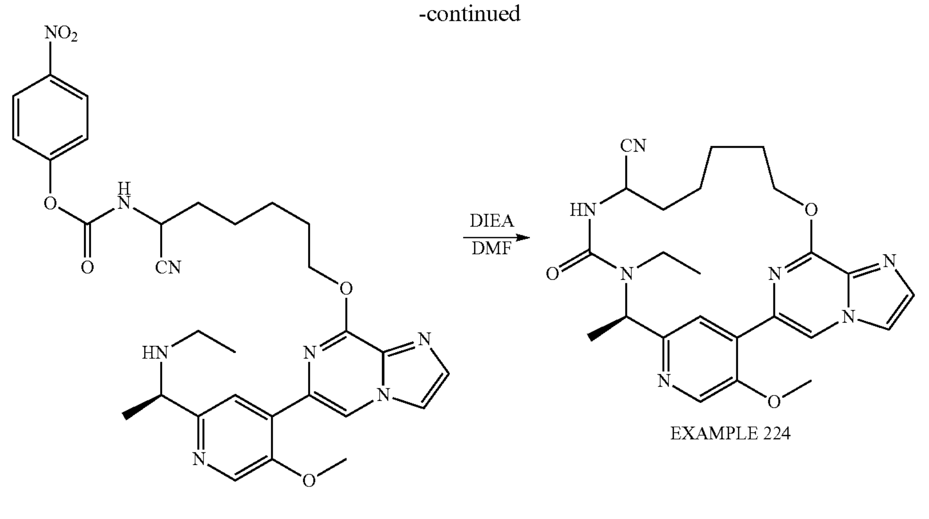

EXAMPLE 224

Step 1: 8-((6-((tert-butyldiphenylsilyl)oxy)hexyl)oxy)-6-iodoimidazo[1,2-a]pyrazine A flask was charged with 6-((tert-butyldiphenylsilyl)oxy)hexan-1-ol (0.846 g, 2.372 mmol) which was dissolved in DMF (9.12 ml) and cooled to 0° C. and treated with NaH (0.146 g, 5.47 mmol) and stirred for 5 min before being treated with 8-chloro-6-iodoimidazo[1,2-a]pyrazine (0.510 g, 1.825 mmol). This was stirred, 0° C. for 1 h. This was quenched with water and diluted with EtOAc, washed with saturated $NaHCO_3$, filtered and concentrated to afford an oil. This was purified via flash silica gel chromatography (0-30% EtOAc/Hexanes give 8-((6-((tert-butyldiphenylsilyl)oxy)hexyl)oxy)-6-iodoimidazo[1,2-a]pyrazine. LC-MS: 600.4 (M+1). Steps 2 and 3: N-ethyl-N—((R)-1-(4-(8-((6-hydroxyhexyl)oxy)imidazo[1,2-a]pyrazin-6-yl)-5-methoxypyridin-2-yl)ethyl)-2-methylpropane-2-sulfinamide.

A sealable vial was charged with 8-((6-((tert-butyldiphenylsilyl)oxy)hexyl)oxy)-6-iodoimidazo[1,2-a]pyrazine (0.767 g, 1.279 mmol) and N-ethyl-N—((R)-1-(5-methoxy-4-(4,4,5,5-tetramethyl-1,3,2-dioxaborolan-2-yl)pyridin-2-yl)ethyl)-2-methylpropane-2-sulfinamide (B17, 0.901 g, 2.196 mmol) which were dissolved in Dioxane (7.18 ml) which had been sparged with nitrogen for 10 min. To this was added Water (1.025 ml) which had also been sparged with nitrogen for 10 min. The [1,1'-bis(diphenylphosphino)ferrocene]dichloropalladium(II) (0.187 g, 0.256 mmol) was added and the vial was capped and heated to 60° C. and stirred 18 h. This was filtered over a bed of celite. The filtrate was diluted with EtOAc and the organic portion was washed with saturated $NaHCO_3$, dried ($Na_2SO_4$), filtered and concentrated to afford an oil. This was purified via chromatography (20-100% 3:1 EtOAc:EtOH/hexanes) to afford N—((R)-1-(4-(8-((6-((tert-butyldiphenylsilyl)oxy)hexyl)oxy)imidazo[1,2-a]pyrazin-6-yl)-5-methoxypyridin-2-yl)ethyl)-N-ethyl-2-methylpropane-2-sulfinamide. A sealable vial was charged with N—((R)-1-(4-(8-((6-((tert-butyldiphenylsilyl)oxy)hexyl)oxy)imidazo[1,2-a]pyrazin-6-yl)-5-methoxypyridin-2-yl)ethyl)-N-ethyl-2-methylpropane-2-sulfinamide (0.822 g, 1.087 mmol) which was dissolved in MeOH (10.87 ml) and treated with ammonium fluoride (0.805 g, 21.74 mmol). The vial was capped and the reaction contents were heated to 50° C. and stirred 18 h. The contents were concentrated to afford an oil. Work-up involved diluting with DCM, washing with saturated $NaHCO_3$, drying by filtering through a hydrophobic frit and evaporating to give an oil. This was purified via flash silica gel chromatography (20-100% 3:1 EtOAc:EtOH/hexanes) to give N-ethyl-N—((R)-1-(4-(8-((6-hydroxyhexyl)oxy)imidazo[1,2-a]pyrazin-6-yl)-5-methoxypyridin-2-yl)ethyl)-2-methylpropane-2-sulfinamide. LC-MS: 518.5 (M+1).

Step 4: N-ethyl-N—((R)-1-(5-methoxy-4-(8-((6-oxohexyl)oxy)imidazo[1,2-a]pyrazin-6-yl)pyridin-2-yl)ethyl)-2-methylpropane-2-sulfinamide The N-ethyl-N—((R)-1-(4-(8-((6-hydroxyhexyl)oxy)imidazo[1,2-a]pyrazin-6-yl)-5-methoxypyridin-2-yl)ethyl)-2-methylpropane-2-sulfinamide (300 mg, 0.579 mmol) was dissolved in DCM (2897 μl) and cooled to 0° C. and treated with Dess-Martin Periodinane (369 mg, 0.869 mmol) and stirred 2 h. This was diluted with a solution of 1:1 saturated $NaHCO_3$:5% $Na_2S203$ and DCM and stirred until the layers separated. The organic portion was dried ($Na_2SO_4$), filtered and concentrated to afford N-ethyl-N—((R)-1-(5-methoxy-4-(8-((6-oxohexyl)oxy)imidazo[1,2-a]pyrazin-6-yl)pyridin-2-yl)ethyl)-2-methylpropane-2-sulfinamide. LC-MS: 516.5 (M+1).

Step 5: N-((1R)-1-(4-(8-((6-amino-6-cyanohexyl)oxy)imidazo[1,2-a]pyrazin-6-yl)-5-methoxypyridin-2-yl)ethyl)-N-ethyl-2-methylpropane-2-sulfinamide The N-ethyl-N—((R)-1-(5-methoxy-4-(8-((6-oxohexyl)oxy)imidazo[1,2-a]pyrazin-6-yl)pyridin-2-yl)ethyl)-2-methylpropane-2-sulfinamide (299 mg, 0.580 mmol) was dissolved in ammonium hydroxide (5798 μl) and treated with sodium cyanide (114 mg, 2.319 mmol) and ammonia chloride (124 mg, 2.319 mmol) and stirred at ambient temperature for 18 h. Work-up involved diluting with DCM, washing with saturated $NaHCO_3$, drying by filtering through a hydrophobic frit and evaporating to give an oil. This was purified via flash silica gel chromatography (30-100% 3:1 EtOAc:EtOH/hexanes) to give N-((1R)-1-(4-(8-((6-amino-6-cyanohexyl)oxy)imidazo[1,2-a]pyrazin-6-yl)-5-methoxypyridin-2-yl)ethyl)-N-ethyl-2-methylpropane-2-sulfinamide. LC-MS: 542.5 (M+1).

Step 6: 4-nitrophenyl (6-((6-(2-((1R)-1-((tert-butylsulfinyl)(ethyl)amino)ethyl)-5-methoxypyridin-4-yl)imidazo[1,2-a]pyrazin-8-yl)oxy)-1-cyanohexyl)carbamate The N-((1R)-1-(4-(8-((6-amino-6-cyanohexyl)oxy)imidazo[1,2-a]pyrazin-6-yl)-5-methoxypyridin-2-yl)ethyl)-N- ethyl-2-methylpropane-2-sulfinamide (58 mg, 0.107 mmol) was dissolved in DCM (535 μl) and treated with saturated $NaHCO_3$(535 μl) and treated with 4-nitrophenyl chloroformate (25.9 mg, 0.128 mmol) and stirred for 10 min. This was diluted with DCM and saturated $NaHCO_3$ and the organic portion was dried by filtering through a hydrophobic frit and concentrated to afford 4-nitrophenyl (6-((6-(2-((1R)-1-((tert-butylsulfinyl)(ethyl)amino)ethyl)-5-methoxypyridin-4-yl) imidazo[1,2-a]pyrazin-8-yl)oxy)-1-cyanohexyl)carbamate. LC-MS: 707.5 (M+1).

Step 7: 4-nitrophenyl (1-cyano-6-((6-(2-((R)-1-(ethylamino)ethyl)-5-methoxypyridin-4-yl)imidazo[1,2-a]pyrazin-8-yl)oxy)hexyl)carbamate The 4-nitrophenyl (6-((6-(2-((1R)-1-((tert-butylsulfinyl)(ethyl)amino)ethyl)-5-methoxypyridin-4-yl)imidazo[1,2-a]pyrazin-8-yl)oxy)-1-cyanohexyl)carbamate (76 mg, 0.108 mmol) was dissolved in MeOH (1075 μl) and treated with 4 M HCl in dioxane (81 μl, 0.323 mmol) and stirred at ambient temperature for 30 min. This was concentrated to afford 4-nitrophenyl (1-cyano-6-((6-(2-((R)-1-(ethylamino)ethyl)-5-methoxypyridin-4-yl)imidazo[1,2-a]pyrazin-8-yl)oxy)hexyl)carbamate. LC-MS: 603.5 (M+1).

Step 8: (3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-carbonitrile (Example 224)

The 4-nitrophenyl (1-cyano-6-((6-(2-((R)-1-(ethylamino)ethyl)-5-methoxypyridin-4-yl)imidazo[1,2-a]pyrazin-8-yl)oxy)hexyl)carbamate (76 mg, 0.112 mmol) was dissolved in DMF (5625 μl) and treated with DIEA (98 μl, 0.562 mmol) and stirred at ambient temperature for 30 min. This was diluted with DMSO and purified via reverse phase chromatography (SunFire Prep C18 OBD column, 5 micron, 30×150 mm, 5-95% $CH_3CN$/Water/0.1% TFA, 25 min, 50 mL/min). The fractions containing the second eluting isomer were treated with saturated $NaHCO_3$, extracted with DCM and the organic portion was filtered through a hydrophobic frit and concentrated to give (3R,E)-4-ethyl-25-methoxy-3-methyl-5-oxo-13-oxa-4,6-diaza-1(6,8)-imidazo[1,2-a]pyrazina-2(4,2)-pyridinacyclotridecaphane-7-carbonitrile (Example 224). LC-MS: 464.4 (M+1).

Example 225

(3R,E)-4-ethyl-25-fluoro-3-methyl-5-oxo-13-oxa-4,6-diaza-1(6,8)-imidazo[1,2-a]pyrazina-2(4,2)-pyridinacyclotridecaphane-7-carboxamide

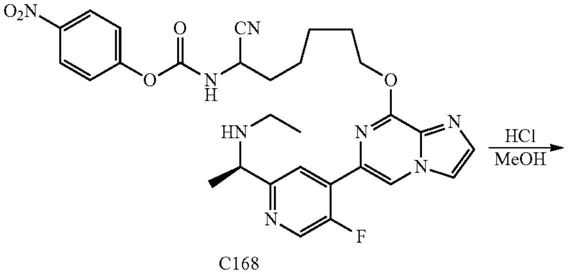

C168

-continued

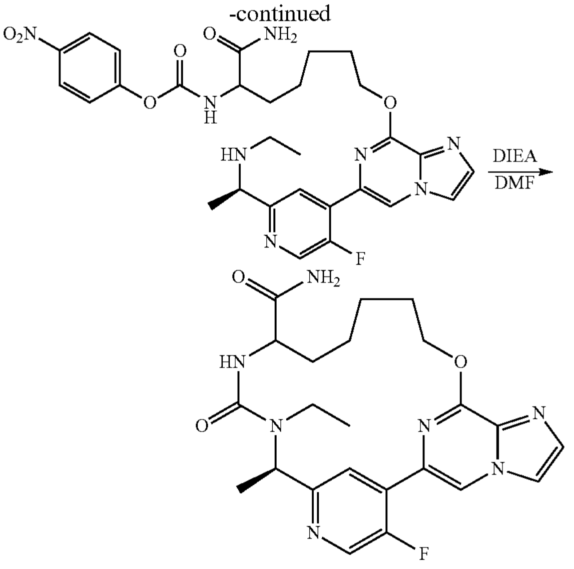

EXAMPLE 225

The tert-butyl ((1R)-1-(4-(8-((6-cyano-6-(((4-nitrophenoxy)carbonyl)amino)hexyl)oxy) imidazo[1,2-a]pyrazin-6-yl)-5-fluoropyridin-2-yl)ethyl)(ethyl)carbamate (C168, 49 mg, 0.071 mmol) was dissolved in MeOH (709 μl) and treated with 4 M HCl in dioxane (532 μl, 2.128 mmol) and stirred at ambient temperature for 2 h. This was concentrated under vacuum to afford an oil. This was purified via reverse phase chromatography (SunFire Prep C18 OBD column, 5 micron, 30×150 mm, 15-40% $CH_3CN$/Water/0.1% TFA, 25 min, 50 mL/min). The fractions containing product were treated with saturated $NaHCO_3$, extracted with DCM and the organic portion was filtered through a hydrophobic frit and concentrated to give 4-nitrophenyl (1-amino-7-((6-(2-((R)-1-(ethylamino)ethyl)-5-fluoropyridin-4-yl)imidazo[1,2-a]pyrazin-8-yl)oxy)-1-oxoheptan-2-yl)carbamate which was used directly in the next step. The 4-nitrophenyl (1-amino-7-((6-(2-((R)-1-(ethylamino)ethyl)-5-fluoropyridin-4-yl)imidazo[1,2-a]pyrazin-8-yl)oxy)-1-oxoheptan-2-yl)carbamate (15 mg, 0.018 mmol) was dissolved in DMF (896 μl) and treated with DIEA (15.66 μl, 0.090 mmol) and stirred at ambient temperature for 15 min. This was purified, via direct injection, using reverse phase chromatography (SunFire Prep C18 OBD column, 5 micron, 30×150 mm, 5-95% $CH_3CN$/water/0.1% TFA, 25 min, 50 mL/min). The fractions containing product were treated with saturated with $NaHCO_3$, extracted with DCM and the organic portion was filtered through a hydrophobic frit and concentrated to give the mixture of diastereomers as (3R,E)-4-ethyl-25-fluoro-3-methyl-5-oxo-13-oxa-4,6-diaza-1(6,8)-imidazo[1,2-a]pyrazina-2(4,2)-pyridinacyclotridecaphane-7-carboxamide (Example 225). LC-MS: 470.4 (M+1).

The following table shows representative data for the compounds of the Examples as orexin receptor agonists as determined by the assays described herein.

| Example Number | hOX2R_IPone EC50 (nM) | hOX2R_Ipone max %act |
|---|---|---|
| 1A | 1055 | 92.5 |
| 1B | 126.1 | 99.5 |
| 2 | 813.1 | 64.8 |
| 3 | 2501 | 88.8 |

-continued

| Example Number | hOX2R_IPone EC50 (nM) | hOX2R_Ipone max %act |
|---|---|---|
| 4 | 3840 | 79.4 |
| 5 | 1381 | 93.82 |
| 6A | 11.9 | 103.5 |
| 6B | 0.6 | 101.5 |
| 7 | 4.6 | 100.6 |
| 8 | 13.6 | 100.2 |
| 9A | 416.2 | 99.27 |
| 9B | 6.0 | 100.9 |
| 10 | 950.2 | 97.61 |
| 11 | 777.6 | 75.54 |
| 12 | 20.3 | 99.76 |
| 13 | 633.9 | 98.2 |
| 14 | 9.7 | 101 |
| 15 | 1177 | 96.2 |
| 16 | 3878 | 77.7 |
| 17 | 19.4 | 99.6 |
| 18 | 26.6 | 98.6 |
| 19A | 336.7 | 97.1 |
| 19B | 6.6 | 94.4 |
| 20 | 9.5 | 98.31 |
| 21A | 19.6 | 100.4 |
| 21B | 0.5 | 100.3 |
| 22 | 82.6 | 94.8 |
| 23 | 1013 | 64.2 |
| 24 | 813.9 | 61.5 |
| 25A | 249.5 | 96.6 |
| 25B | 172.8 | 97.81 |
| 26A | 13.9 | 99.4 |
| 26B | 12.0 | 98.8 |
| 27 | 1.4 | 101.1 |
| 28 | 0.9 | 102.2 |
| 29A | 42.9 | 99.5 |
| 29B | 4.5 | 99.7 |
| 30 | 51.1 | 98.5 |
| 31 | 8.0 | 100.5 |
| 32 | 2.8 | 101 |
| 33 | 335.1 | 98.8 |
| 34A | 540.9 | 99.9 |
| 34B | 16.4 | 101.1 |
| 35 | 4712 | 82.8 |
| 36A | 64 | 101 |
| 36B | 8.9 | 101.5 |
| 37 | 3013 | 77.3 |
| 38 | 2395 | 94.5 |
| 39A | 60.5 | 97.7 |
| 39B | 1059 | 97.5 |
| 40 | 1.2 | 101.2 |
| 41A | 114.7 | 100.9 |
| 41B | 21.3 | 100.4 |
| 41C | 23.4 | 98.9 |
| 42A | 6.6 | 100.6 |
| 42B | 155.7 | 99.1 |
| 42C | 8.6 | 99.7 |
| 42D | 3.6 | 98.8 |
| 43 | 49.9 | 97.6 |
| 44 | 1.0 | 100.4 |
| 45 | 14.1 | 100.1 |
| 46 | 9.9 | 99.9 |
| 47 | 4.3 | 100.5 |
| 48A | 4.1 | 99.4 |
| 48B | 88.8 | 99.9 |
| 49 | 42.0 | 74.7 |
| 50 | 0.8 | 98.7 |
| 51 | 0.6 | 99.5 |
| 52A | 548.4 | 97 |
| 52B | 4.9 | 99.5 |
| 53A | 55.7 | 101.5 |
| 53B | 0.9 | 102.3 |
| 54A | 142.6 | 102 |
| 54B | 1.0 | 100.7 |
| 55A | 78.9 | 99.2 |
| 55B | 0.6 | 101.2 |
| 56A | 32.0 | 101.7 |
| 56B | 1.0 | 101 |
| 57A | 119.1 | 100.7 |
| 57B | 1.2 | 101.6 |

-continued

| Example Number | hOX2R_IPone EC50 (nM) | hOX2R_Ipone max %act |
|---|---|---|
| 58A | 48.9 | 100.8 |
| 58B | 0.9 | 101.1 |
| 59A | 4.1 | 101.6 |
| 59B | 3.1 | 100.1 |
| 59C | 0.5 | 99.3 |
| 59D | 0.9 | 100.9 |
| 60A | 52.1 | 100.4 |
| 60B | 2.2 | 100.9 |
| 61A | 34.6 | 100.3 |
| 61B | 1.3 | 100.9 |
| 62A | 39.2 | 99.9 |
| 62B | 1.4 | 100.9 |
| 63A | 314.5 | 98.43 |
| 63B | 5.1 | 103.3 |
| 64A | 3.5 | 102.7 |
| 64B | 1.6 | 99.8 |
| 65A | 13.5 | 102.4 |
| 65B | 1.0 | 101.9 |
| 66A | 9.6 | 102.9 |
| 66B | 0.7 | 101.1 |
| 67A | 9.6 | 99.8 |
| 67B | 2.1 | 101 |
| 68A | 38.4 | 100.1 |
| 68B | 1.5 | 101.5 |
| 69A | 6.6 | 99.7 |
| 69B | 0.6 | 101.1 |
| 70A | 16.5 | 99.1 |
| 70B | 1.1 | 99.8 |
| 71A | 4.2 | 100.5 |
| 71B | 1.6 | 101.6 |
| 72A | 5.6 | 99.5 |
| 72B | 0.7 | 102.7 |
| 73A | 8.6 | 100.6 |
| 73B | 0.8 | 99.6 |
| 74A | 17.3 | 99.5 |
| 74B | 0.9 | 101.2 |
| 75A | 528.5 | 96.6 |
| 75B | 6.0 | 101.4 |
| 76A | 204.5 | 98.9 |
| 76B | 3.4 | 100.4 |
| 77 | 20.9 | 101.7 |
| 78 | 1.7 | 99.0 |
| 79 | 1.0 | 99.3 |
| 80A | 369.5 | 98.9 |
| 80B | 2.9 | 99.8 |
| 81 | 3.3 | 100.1 |
| 82 | 2.2 | 99.62 |
| 83 | 1.0 | 100.7 |
| 84 | 1.5 | 99.1 |
| 85 | 5.1 | 100.5 |
| 86 | 3.5 | 99.3 |
| 87 | 5.8 | 100.6 |
| 88A | 67.8 | 100.2 |
| 88B | 0.7 | 102.3 |
| 89 | 6.4 | 99.2 |
| 90 | 101.4 | 100.8 |
| 91 | 0.6 | 100.5 |
| 92A | 10130 | 67.1 |
| 92B | 24.2 | 99.1 |
| 93A | 167.4 | 100.8 |
| 93B | 1.8 | 100.6 |
| 94A | 167.4 | 97.9 |
| 94B | 54.4 | 100.3 |
| 95 | 25.4 | 99.78 |
| 96A | 11.9 | 100.3 |
| 96B | 2.9 | 100.5 |
| 97 | 0.6 | 102 |
| 98 | 8.6 | 101.2 |
| 99 | 48.8 | 95.9 |
| 100 | 10.0 | 102.2 |
| 101 | 247.5 | 97.69 |
| 102 | 14.9 | 101.4 |
| 103 | 13.1 | 100.8 |
| 104A | 4908 | 60.9 |
| 104B | 64.1 | 101.1 |
| 105A | 1362 | 73.0 |

-continued

| Example Number | hOX2R_IPone EC50 (nM) | hOX2R_Ipone max %act |
|---|---|---|
| 105B | 61.6 | 100 |
| 106 | 1.7 | 99.7 |
| 107A | 166.5 | 92.7 |
| 107B | 2.4 | 100.1 |
| 108 | 14.9 | 100.6 |
| 109 | 1.5 | 102.4 |
| 110 | 1.3 | 100.2 |
| 111 | 1.4 | 100.7 |
| 112A | 6.8 | 101.2 |
| 112B | 9.3 | 101.8 |
| 113A | 104.7 | 98.1 |
| 113B | 3.3 | 100.9 |
| 114 | 0.7 | 100.9 |
| 115 | 868 | 97.2 |
| 116 | 1.6 | 99.7 |
| 117A | 26.0 | 101.7 |
| 117B | 1.5 | 101.9 |
| 118A | 182.8 | 99.08 |
| 118B | 2.6 | 99.7 |
| 119A | 166.2 | 100.1 |
| 119B | 4.6 | 99.9 |
| 120 | 17.7 | 98.4 |
| 121A | 9.8 | 100.4 |
| 121B | 0.5 | 100.7 |
| 121C | 1.8 | 101.2 |
| 122 | 36.39 | 104.4 |
| 123 | 13.83 | 102.5 |
| 124 | 3.99 | 97.96 |
| 125 | 1.41 | 100.2 |
| 126 | 9.38 | 96.84 |
| 127 | 5.43 | 100.1 |
| 128 | 11.23 | 102.9 |
| 129 | 1.49 | 100.2 |
| 130 | 1.48 | 102 |
| 131 | 0.77 | 102.2 |
| 132 | 4.98 | 102.9 |
| 133 | 4.75 | 102.1 |
| 134 | 6.4 | 100.6 |
| 135 | 170.4 | 93.31 |
| 136 | 0.7243 | 101.7 |
| 137 | 4.66 | 100.7 |
| 138 | 8.48 | 100.1 |
| 139 | 1.08 | 97.88 |
| 140 | 1.4 | 101.9 |
| 141 | 8.35 | 99.01 |
| 142 | 4.705 | 100.3 |
| 143 | 270.7 | 89.95 |
| 144 | 6.09 | 101.4 |
| 145 | 4.4 | 103.8 |
| 146 | 14.67 | 100.8 |
| 147 | 3.69 | 102.4 |
| 148 | 1.7 | 101.7 |
| 149 | 1.11 | 109.6 |
| 150 | 2.43 | 103 |
| 151 | 0.51 | 108.6 |
| 152 | 4.17 | 106.5 |
| 153 | 2.2 | 107.8 |
| 154 | 1.05 | 106.1 |
| 155 | 0.74 | 96.86 |
| 156 | 1.319 | 100.3 |
| 157 | 2.681 | 99.72 |
| 158 | 3.87 | 102 |
| 159 | 541.3 | 72.77 |
| 160 | 0.7702 | 101.4 |
| 161 | 2.66 | 101.7 |
| 162 | 5.9 | 104.8 |
| 163 | 10.92 | 104.4 |
| 164 | 2.62 | 100.1 |
| 165 | 0.47 | 102.6 |
| 166 | 15.06 | 102 |
| 167 | 0.25 | 99.32 |
| 168 | 2.33 | 99.31 |
| 169 | 3.36 | 111.8 |
| 170 | 0.43 | 108.2 |
| 171 | 1.45 | 107.9 |
| 172 | 7.2 | 101 |

-continued

| Example Number | hOX2R_IPone EC50 (nM) | hOX2R_Ipone max %act |
|---|---|---|
| 173 | 3.71 | 103.9 |
| 174 | 3.08 | 103.8 |
| 175 | 9.06 | 93.8 |
| 176 | 2.97 | 99.6 |
| 177 | 62.54 | 100.5 |
| 178 | 324.9 | 88 |
| 179 | 8.24 | 100.8 |
| 180 | 4.147 | 100.8 |
| 181 | 0.2 | 99.3 |
| 182 | 0.85 | 98.9 |
| 183 | 1 | 100.2 |
| 184 | 0.78 | 101.1 |
| 185 | 2.03 | 102.1 |
| 186 | 1.02 | 102.3 |
| 187 | 0.62 | 104.1 |
| 188 | 0.74 | 100.6 |
| 189 | 0.69 | 99.85 |
| 190 | 0.61 | 101.7 |
| 191 | 1.73 | 102.3 |
| 192 | 0.46 | 100.9 |
| 193 | 1.21 | 100.7 |
| 194 | 1.2 | 102.2 |
| 195 | 0.84 | 101.4 |
| 196 | 0.44 | 101.6 |
| 197 | 1.3 | 105.4 |
| 198 | 0.58 | 103.1 |
| 199 | 4.25 | 100.6 |
| 200 | 0.53 | 99.5 |
| 201 | 3.68 | 101 |
| 202 | 1.7 | 99.8 |
| 203 | 11.44 | 100 |
| 204 | 2.11 | 100.5 |
| 205 | 2.39 | 104.8 |
| 206 | 2.07 | 107.8 |
| 207 | 4.29 | 104.7 |
| 208 | 0.29 | 101.8 |
| 209 | 1.1 | 99.62 |
| 210 | 5.24 | 102.8 |
| 211 | 1.13 | 99.83 |
| 212 | 2.79 | 99.48 |
| 213 | 6.44 | 101.8 |
| 214 | 3.43 | 102.9 |
| 215 | 3.56 | 104.9 |
| 216 | 0.37 | 102.1 |
| 217 | 0.98 | 100.1 |
| 218 | 0.9 | 102.4 |
| 219 | 37.47 | 102.6 |
| 220 | 12.12 | 108.5 |
| 221 | 408.5 | 90.75 |
| 222 | 759.5 | 61.55 |
| 223 | 0.29 | 102.6 |
| 224 | 71.22 | 99.26 |
| 225 | 285.9 | 78.64 |

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

What is claimed is:

1. A compound of the formula I:

I

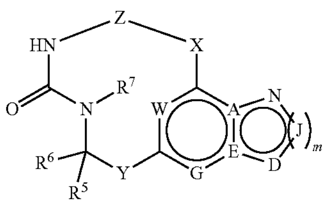

wherein:

A is N or $C(R^8)_n$;

D is N or $C(R^8)_n$;

E is N or $C(R^8)_n$;

G is N or $C(R^8)_n$;

J is Nor $C(R^8)_n$;

W is N or $C(R^8)_n$;

when J is N, m is 1 but when J is $C(R^8)_n$, m is 1 or 2;

n is 0 or 1;

X is —O— or —$CH_2$—;

Y is phenyl, pyridyl, pyrazinyl, pyrazolyl, pyridazinyl, pyrimidinyl, pyridofuranyl, oxazolyl, thiazolyl, which is unsubstituted or substituted with one to three groups selected from $R^4$;

Z is

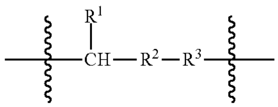

;

R is independently selected from H or $C_{1-6}$alkyl;

$R^1$ is selected from:

1) Hydrogen,

2) CN,

3) —C(O)$NR_2$—,

4) —$CH_2OCH_2CF_3$—,

5) —$CH_2OCH_2CHCF_2$—, and

6) $C_{1-6}$alkyl, which is substituted with 0, 1, or 3 independently selected from:

a) $C_{1-6}$alkyl, b) halogen, c) hydroxyl, d) —O—$C_{1-6}$alkyl which is substituted with 0, 1, or 3 substituents selected from halogen, or $C_{3-6}$cycloalkyl which is unsubstituted or substituted with halogen, $C_{1-6}$alkyl, or $C_{1-6}$alkylfluoro, e) $C_{3-6}$cycloalkyl, which is which is substituted with 0, 1, or 3 of $R^4$, f) Heteroaryl, which is substituted with 0, 1, or 3 of $R^4$, g) Heterocyclyl, which is substituted with 0, 1, or 3 $R^4$, h) CN, and i) $S(O)_2R$;

$R^2$ is selected from

1) Linear or branched $C_{1-10}$alkyl or $C_{4-8}$alkenyl, 2) —$(CR_2)_{1-6}$—O—$(CR_2)_{1-6}$—;

3) —$(CR_2)_{1-6}$—$N(R^9)$—$(CR_2)_{1-6}$—, wherein $R^9$ is hydrogen or —$C_{1-6}$alkyl, where the —$C_{1-6}$alkyl is unsubstituted or substituted with halogen, 4) —$(CR_2)_{1-6}C_{3-6}$cycloalkyl-$(CR_2)_{1-6}$—, where the —$C_{3-6}$cycloalkyl is unsubstituted or substituted with —$C_{1-6}$alkyl or halogen, and 5) Piperidinyl, pyrrolidinyl, oxaxolyl, oxadiazolyl or thiazolyl ring, which is unsubstituted or substituted with —$C_{1-6}$alkyl or halogen;

$R^3$ is selected from a direct bond, —S—, —NR—, —O—$C_{1-6}$alkyl-, —S—$C_{1-6}$alkyl-, and —$S(O)_2$—$C_{1-6}$alkyl-;

$R^4$ is selected from:

(1) hydrogen, (2) hydroxyl, (3) halogen, (4) —$C_{1-6}$alkyl, which is unsubstituted or substituted with one to six fluoro, (5) —O—$C_{1-6}$alkyl, which is unsubstituted or substituted with one to six fluoro, and (6) $C_{3-6}$cycloalkyl;

$R^5$ and $R^6$ are independently selected from:

(1) hydrogen, and (2) —$C_{1-6}$alkyl, where the alkyl is unsubstituted or substituted with one to six substituents independently selected from halogen, or $R^5$ and $R^6$ and the carbon atom to which they are attached may be joined together to form a —$C_{3-6}$cycloalkyl group;

$R^7$ is selected from:

(1) hydrogen, (2) —$C_{1-6}$alkyl, where the alkyl is unsubstituted or substituted with one to six substituents independently selected from halogen, and (3) —$C_{3-6}$cycloalkyl, where the —$C_{3-6}$cycloalkyl is unsubstituted or substituted with —$C_{1-6}$alkyl or halogen;

$R^8$ is selected from:

(1) hydrogen, (2) halogen, and (3) —$C_{1-6}$alkyl, where the alkyl is unsubstituted or substituted with one to six substituents independently selected from halogen;

or a pharmaceutically acceptable salt thereof.

2. The compound according to claim 1, having structure of Formula I':

I'

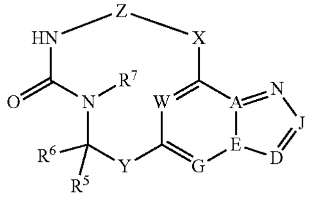

wherein:

A is C;

D is N or $C(R^8)_n$;

E is N or $C(R^8)_n$;

G is N or $C(R^8)_n$;

J is Nor $C(R^8)_n$;

W is N or $C(R^8)_n$;

with the proviso that one, two, three or four of D, E, G, J and W are N, and the remainder of D, E, G, J and W are other than N;

n is 0 or 1;

X is —O— or —$CH_2$—;

Y is phenyl, pyridyl, pyrazinyl, pyridazinyl, pyrimidinyl, pyridofuranyl, oxazolyl, thiazolyl, which is unsubstituted or substituted with one to three groups selected from $R^4$;

Z is

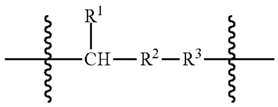

;

R is independently selected from H or $C_{1-6}$alkyl;

$R^1$ is selected from:

1) hydrogen,

2) CN,

3) —C(O)$NR_2$—,

4) —$CH_2OCH_2CF_3$—,

5) —$CH_2OCH_2CHCF_2$—, and

6) $C_{1-6}$alkyl, which is substituted with 0, 1, or 3 substituents independently selected from:

a) $C_{1-6}$alkyl, b) halogen, c) hydroxyl, d) —O—$C_{1-6}$alkyl which is substituted with 0, 1, or 3 substituents selected from halogen, or $C_{3-6}$cycloalkyl which is unsubstituted or substituted with halogen, $C_{1-6}$alkyl, or $C_{1-6}$alkylfluoro, e) $C_{3-6}$cycloalkyl, which is substituted with 0, 1, or 3 of $R^4$, f) Heteroaryl, which is substituted with 0, 1, or 3 of $R^4$, g) Heterocyclyl, which is substituted with 0, 1, or 3 of $R^4$, h) CN, and i) $S(O)_2R$;

$R^2$ is selected from

1) Linear or branched $C_{1-10}$alkyl or $C_{4-8}$alkenyl,

2) —$(CR_2)_{1-6}$—O—$(CR_2)_{1-6}$—,

3) —$(CR_2)_{1-6}$—N($R^9$)—$(CR_2)_{1-6}$—, wherein $R^9$ is hydrogen or —$C_{1-6}$alkyl, where the —$C_{1-6}$alkyl is unsubstituted or substituted with halogen, 4) —$(CR_2)_{1-6}C_{3-6}$cycloalkyl-$(CR_2)_{1-6}$, where the —$C_{3-6}$cycloalkyl is unsubstituted or substituted with —$C_{1-6}$alkyl or halogen, and 5) Piperidinyl, pyrrolidinyl, oxaxolyl, oxadiazolyl or thiazolyl ring, which is unsubstituted or substituted with —$C_{1-6}$alkyl or halogen;

$R^3$ is selected from a direct bond, —O—$C_{1-6}$alkyl-, —S—$C_{1-6}$alky-1, and —$S(O)_2$—$C_{1-6}$alkyl-;

$R^4$ is selected from:

(1) hydrogen, (2) hydroxyl, (3) fluoro, (4) —$C_{1-6}$alkyl, which is unsubstituted or substituted with one to six fluoro, and (5) —O—$C_{1-6}$alkyl, which is unsubstituted or substituted with one to six fluoro;

$R^5$ and $R^6$ are independently selected from:

(1) hydrogen, and (2) —$C_{1-6}$alkyl, where the alkyl is unsubstituted or substituted with one to six substituents independently selected from halogen, or $R^5$ and $R^6$ and the carbon atom to which they are attached may be joined together to form a —$C_{3-6}$cycloalkyl group;

$R^7$ is selected from:

(1) —$C_{1-6}$alkyl, where the alkyl is unsubstituted or substituted with one to six substituents independently selected from halogen, and (2) —$C_{3-6}$cycloalkyl, where the —$C_{3-6}$cycloalkyl is unsubstituted or substituted with —$C_{1-6}$alkyl or halogen;

$R^8$ is selected from:

(1) hydrogen, (2) halogen, and (3) —$C_{1-6}$alkyl, where the alkyl is unsubstituted or substituted with one to six substituents independently selected from halogen;

or a pharmaceutically acceptable salt thereof.

3. The compound of claim 1, or a pharmaceutically acceptable salt thereof, wherein the group:

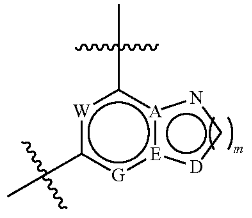

is selected from:

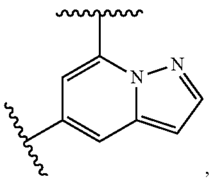
,
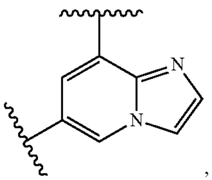
,
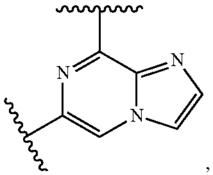
,
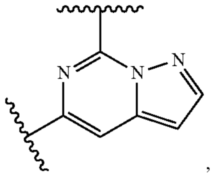
,
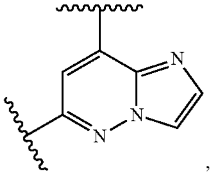
,
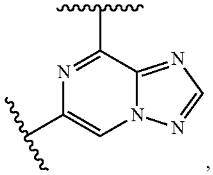
,
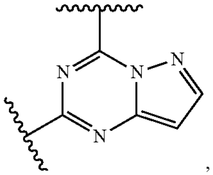
,
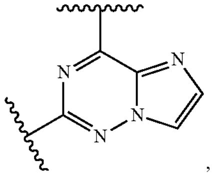
,
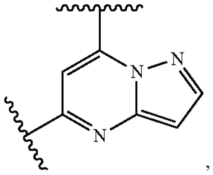
,
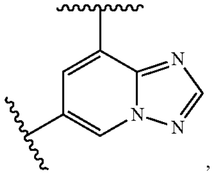
, -continued

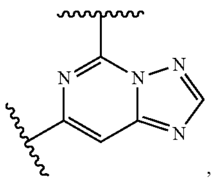

,

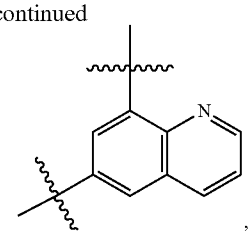

, and

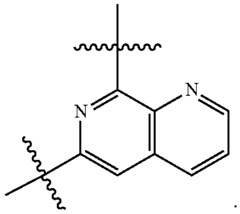

.

4. The compound of claim 1, or a pharmaceutically acceptable salt thereof, wherein the group:

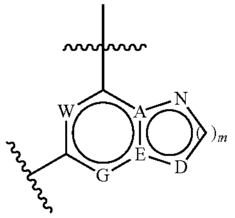

is:

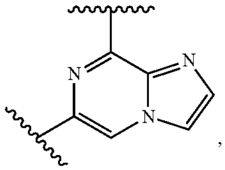

,

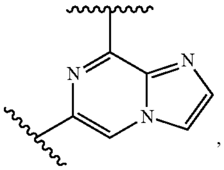

,

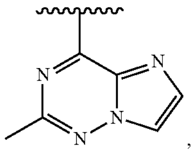

, and

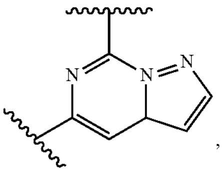

,

5. The compound of claim 1, or a pharmaceutically acceptable salt thereof, wherein X is —O—.

6. The compound of claim 1, or a pharmaceutically acceptable salt thereof, wherein Y is phenyl, pyridyl, pyridazinyl, pyrazinyl, or pyrimidinyl.

7. The compound of claim 1, or a pharmaceutically acceptable salt thereof, wherein Z is

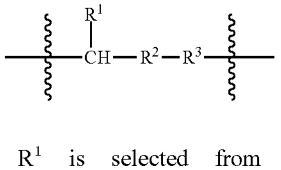

and $R^1$ is selected from hydrogen, —C(O)$NR_2$, $CH_2OCH_2CF_3$, $CH_2OCH_2CHF_2$, and —$C_{1-6}$alkyl, which is substituted with 0, 1, or 3 substituents independently selected from $C_{1-6}$alkyl, halogen, hydroxyl, CN, and $C_{3-6}$cycloalkyl, which is substituted with 0, 1, or 3 of $R^4$, and —O—$C_{1-6}$alkyl which is substituted with 0, 1, or 3 substituents selected from halogen, or $C_{3-6}$cycloalkyl which is unsubstituted or substituted with halogen, $C_{1-6}$alkyl, or $C_{1-6}$alkylfluoro;

$R^2$ is selected from

1) Linear or branched $C_{1-10}$alkyl or $C_{4-8}$alkenyl,
2) $(CR_2)_{1-6}$—O—$(CR_2)_{1-6}$—;
3) $(CR_2)_{1-6}$—N($R^9$)—$(CR_2)_{1-6}$—, wherein $R^9$ is hydrogen or —$C_{1-6}$alkyl, where the —$C_{1-6}$alkyl is unsubstituted or substituted with halogen,
4) —$(CR_2)_{1-6}C_{3-6}$cycloalkyl-$(CR_2)_{1-6}$, where the —$C_{3-6}$cycloalkyl is unsubstituted or substituted with —$C_{1-6}$alkyl or halogen, and
5) Piperidinyl, pyrrolidinyl, oxaxolyl, oxadiazolyl or thiazolyl ring, which is unsubstituted or substituted with —$C_{1-6}$alkyl or halogen; and $R^3$ is selected from a direct bond, —S—, —NR—, —O—$C_{1-6}$alkyl, —S—$C_{1-6}$alkyl, and —S(O)$_2$—$C_{1-6}$alkyl.

8. The compound of claim 1, or a pharmaceutically acceptable salt thereof, wherein $R^4$ is selected from:
(1) $C_{1-6}$alkyl, and
(2) —O—$C_{1-6}$alkyl.

9. The compound of claim 1, or a pharmaceutically acceptable salt thereof, wherein $R^5$ and $R^6$ are independently selected from:
(1) hydrogen, and
(2) —$C_{1-6}$alkyl, where the alkyl is unsubstituted or substituted with one to six substituents independently selected from fluoro.

10. The compound of claim 1, or a pharmaceutically acceptable salt thereof, wherein $R^7$ is selected from:
(1) hydrogen, and
(2) —$C_{1-6}$alkyl.

11. A compound which is selected from:
(10R,E)-9-ethyl-10-methyl-3-oxa-7,9-diaza-2(6,8)-imidazo[1,2-a]pyrazina-1(1,3)-benzena-4(1,3)-cyclopentanacyclodecaphan-8-one;
(12R)-13-ethyl-12-methyl-12,13,16,17,19,20-hexahydro-6,22-(azeno)-11,7-(metheno)imidazo[1,2-o][1,18,4,6,15]dioxatriazacycloicosin-14(15H)-one;
(12R)-13-ethyl-12-methyl-18-(propan-2-yl)-12,13,15,16,17,18,19,20-octahydro-14H-6,22-(azeno)-11,7-(metheno)imidazo[1,2-r][1,4,7,9,18]oxatetraazacycloicosin-14-one;
(12R)-13-ethyl-12-methyl-12,13,15,16,17,18,21,22,22a,23-decahydro-14H,20H-6,25-(azeno)-11,7-(metheno)imidazo[1,2-s]pyrrolo[2,1-c][1,4,8,10,19]oxatetraazacyclohenicosin-14-one;
(7R)-8-ethyl-7-methyl-18-oxa-8,10,13,21,24,26-hexaazapentacyclo-[17.6.1.1-2,6-1-13,17.0-20,24-]octacosa-1(25),2(28),3,5,19(26),20,22-heptaen-9-one;
(12R)-13-ethyl-8-methoxy-12-methyl-16-(3,3,3-trifluoropropyl)-12,13,15,16,17,18,20,21-octahydro-14H-6,23-(azeno)-11,7-(metheno)imidazo[2,1-f][1,4,7,13,16,18]dioxatetraazacyclohenicosin-14-one;
(12R)-13-ethyl-8-methoxy-12-methyl-12,13,15,16,17,18,20,21-octahydro-14H-6,23-(azeno)-11,7-(metheno)imidazo[2,1-f][1,4,7,13,16,18]dioxatetraazacyclohenicosin-14-one;
(12R)-13-ethyl-8-methoxy-12-methyl-12,13,16,17,20,21-hexahydro-19H-6,23-(azeno)-11,7-(metheno)imidazo[1,2-o][1,18,4,6,9,15]dioxatetraazacyclohenicosin-14(15H)-one;

(12R)-13-ethyl-8-methoxy-12,16-dimethyl-12,13,16,17,18,19,20,21-octahydro-6,23-(azeno)-11,7-(metheno)imidazo[2,1-c][1,4,10,13,15]oxatetraazacyclohenicosin-14(15H)-one;

(R,E)-4-ethyl-3-methyl-13-oxa-4,6,9-triaza-1(6,8)-imidazo[1,2-a]pyrazina-2(1,3)-benzenacyclotridecaphan-5-one;

(12R)-13-ethyl-12-methyl-12,13,16,17,18,19,20,21-octahydro-6,23-(azeno)-11,7-(metheno)imidazo[1,2-s][1,4,8,10,19]oxatetraazacyclohenicosin-14(15H)-one;

(12R)-13-ethyl-12-methyl-12,13,16,17,18,19,20,21-octahydro-6,23-(azeno)-11,7-(metheno)imidazo[2,1-c][1,4,13, 15]oxatriazacyclohenicosin-14(15H)-one;

(12R)-13-ethyl-12,19,19-trimethyl-12,13,15,16,17,18,19,20-octahydro-14H-6,22-(azeno)-11,7-(metheno)imidazo[2,1-c][1,4,13,15]oxatriazacycloicosin-14-one;

(12R)-13-ethyl-12-methyl-12,13,15,16,17,18,20,21-octahydro-14H-6,23-(azeno)-11,7-(metheno)imidazo[2,1-f][1,4,7,16,18]dioxatriazacyclohenicosin-14-one;

(12R)-13,18-diethyl-12-methyl-12,13,16,17,18,19,20,21-octahydro-6,23-(azeno)-11,7-(metheno)imidazo[2,1-c][1,4,13,15,18]oxatetraazacyclohenicosin-14(15H)-one;

(12R)-13-ethyl-12,18,21-trimethyl-12,13,16,17,18,19,20,21-octahydro-6,23-(azeno)-11,7-(metheno)imidazo[2,1-c][1,4,13,15,18]oxatetraazacyclohenicosin-14(15H)-one;

(12R)-13-ethyl-12-methyl-12,13,16,17,20,21-hexahydro-19H-6,23-(azeno)-11,7-(metheno)imidazo[1,2-o][1,18,4,6,15]dioxatriazacyclohenicosin-14(15H)-one;

(12R)-13-ethyl-12,16-dimethyl-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12-methyl-16-(1,3-thiazol-4-yl)-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-12-methyl-16-(1,2-oxazol-3-yl)-12,13,16,17,18,19,20,21-octahydro-6,23-(azeno)-11,7-(metheno)imidazo[2,1-c][1,4,13,15]oxatriazacyclohenicosin-14(15H)-one;

(12R)-13-ethyl-8-methoxy-12-methyl-16-(3,3,3-trifluoropropyl)-12,13,16,17,20,21-hexahydro-19H-6,23-(azeno)-11,7-(metheno)imidazo[1,2-o][1,18,4,6,9,15]dioxatetraazacyclohenicosin-14(15H)-one;

(R,$2^7$E,$6^2$Z)-10-ethyl-11-methyl-3-oxa-8,10-diaza-6(4,2)-thiazola-2(6,8)-imidazo[1,2-a]pyrazina-1(1,3)-benzenacycloundecaphan-9-one;

(R,$2^7$E,$5^4$Z)-10-ethyl-11-methyl-3-oxa-8,10-diaza-5(3,5)-oxadiazola-2(6,8)-imidazo[1,2-a]pyrazina-1(1,3)-benzenacycloundecaphan-9-one;

(3R,E)-4-ethyl-3,9-dimethyl-8-(trifluoromethyl)-12-oxa-4,6,9-triaza-1(6,8)-imidazo[1,2-a]pyrazina-2(1,3)-benzenacyclododecaphan-5-one;

(3R,E)-4-ethyl-3,9-dimethyl-8-(trifluoromethyl)-13-oxa-4,6,9-triaza-1(6,8)-imidazo[1,2-a]pyrazina-2(1,3)-benzenacyclotridecaphan-5-one;

(3R,7R,E)-4-ethyl-$2^2$-methoxy-3-methyl-7-(3,3,3-trifluoropropyl)-12-oxa-4,6-diaza-1(6,8)-imidazo[1,2-a]pyrazina-2(3,5)-pyridinacyclododecaphan-5-one;

(3R,7R,E)-4-ethyl-$2^2$-methoxy-3-methyl-7-(3,3,3-trifluoropropyl)-13-oxa-4,6-diaza-1(6,8)-imidazo[1,2-a]pyrazina-2(3,5)-pyridinacyclotridecaphan-5-one;

(12S,16R)-13-ethyl-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12R,16R)-13-ethyl-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12S,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

($1^7$E,3R,7S,9Z)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-9-en-5-one;

(3R,7R,E)-4-ethyl-3-methyl-7-(3,3,3-trifluoropropyl)-12-oxa-4,6-diaza-1(6,8)-imidazo[1,2-a]pyrazina-2(1,3)-benzenacyclododecaphan-5-one;

(16S,18Z)-13-ethyl-8-methoxy-12-(trifluoromethyl)-16-(3,3,3-trifluoropropyl)-12,13,15,16,17,20-hexahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-12-(trifluoromethyl)-16-(3,3,3-trifluoropropyl)-12,13,15,16,17,18,19,20-octahydro-14H-6,22-(azeno)-11,7-(metheno)[1,2,4]triazolo [5,1-c][1,4,10,13,15]oxatetraazacycloicosin-14-one;

(16R)-13-ethyl-8-methoxy-12-(trifluoromethyl)-16-(3,3,3-trifluoropropyl)-12,13,15,16,17,18,19,20-octahydro-14H-6,22-(azeno)-11,7-(metheno)[1,2,4]triazolo[5,1-c][1,4,10,13, 15]oxatetraazacycloicosin-14-one;

13-ethyl-8-methoxy-12-(trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-2-methyl-12-(trifluoromethyl)-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(16R)-13-ethyl-8-methoxy-12,16-bis (trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-16-(2,2,2-trifluoroethyl)-12-(trifluoromethyl)-12,13,15,16,17,18,19,20-octahydro-14H-6,22-(azeno)-11,7-(metheno)[1,2,4]triazolo[5,1-c][1,4,10,13,15]oxatetraazacycloicosin-14-one;

(16R)-13-ethyl-8-methoxy-12,16-bis (trifluoromethyl)-12,13,15,16,17,18,19,20-octahydro-14H-6,22-(azeno)-11,7-(metheno)imidazo[2,1-c][1,4,10,13,15]oxatetraazacycloicosin-14-one;

(12S,16R)-13-ethyl-8-methoxy-12-methyl-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(12R,18Z)-13-ethyl-12,17-dimethyl-16-(3,3,3-trifluoropropyl)-12,13,15,16,17,20-hexahydro-14H-6,22-(azeno)-11,7-(metheno)imidazo[2,1-c][1,4,13,15]oxatriazacycloicosin-14-one;

(12R)-13-ethyl-12,17-dimethyl-16-(3,3,3-trifluoropropyl)-12,13,15,16,17,18,19,20-octahydro-14H-6,22-(azeno)-11,7-(metheno)imidazo[2,1-c][1,4,13, 15]oxatriazacycloicosin-14-one;

(16R)-13-ethyl-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,13,15]oxatriazacycloicosin-14-one;

(16R)-13-ethyl-8-methoxy-16-(3,3,3-trifluoropropyl)-12,13,15,16,17,18,19,20-octahydro-14H-6,22-(azeno)-11,7-(metheno)imidazo[2,1-c][1,4,10,13,15]oxatetraazacycloicosin-14-one;

(3R,7R,E)-4-ethyl-$2^2$-methoxy-3-methyl-7-(3,3,3-trifluoropropyl)-12-oxa-4,6-diaza-1(2,4)-imidazo[2,1-f][1,2,4]triazina-2(3,5)-pyridinacyclododecaphan-5-one;

(3R,7R,E)-4-ethyl-$2^2$-methoxy-3-methyl-7-(3,3,3-trifluoropropyl)-13-oxa-4,6-diaza-1(2,4)-imidazo[2,1-f][1,2,4]triazina-2(3,5)-pyridinacyclotridecaphan-5-one;

(3R,E)-4-ethyl-3,9-dimethyl-7-(3,3,3-trifluoropropyl)-12-oxa-4,6-diaza-1(6,8)-imidazo[1,2-a]pyrazina-2(1,3)-benzenacyclododecaphan-5-one;

(12R)-13-ethyl-12-methyl-12,13,15,16,17,18,19,20-octahydro-14H-6,22-(azeno)-11,7-(metheno)imidazo[2,1-c][1,4,13,15]oxatriazacycloicosin-14-one;

(7R)-8-ethyl-14,14-difluoro-3-methoxy-7-methyl-11-(3,3,3-trifluoropropyl)-17-oxa-5,8,10,20,23,25-hexazatetracyclo(12R)[16.6.1.12,6.019,23]hexacosa-1(24),2(26),3,5,18(25), 19,21-heptaen-9-one;

(3R,7R,E)-4-ethyl-23-methoxy-3-methyl-7-(3,3,3-trifluoropropyl)-13-oxa-4,6-diaza-1(6,8)-imidazo[1,2-a]yridine-2(2,6)-pyridinacyclotridecaphan-5-one;

(16R)-13-ethyl-8-methoxy-16-(3,3,3-trifluoropropyl)-12,13,16,17,18,19,20,21-octahydro-6,23-(azeno)-11,7-(metheno)imidazo[2,1-c][1,4,9,13, 15]oxatetraazacyclohenicosin-14(15H)-one;

(12R)-13,16-diethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(2-methylpropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-propyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopropylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(2-methoxyethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-cyclopropyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-16-(methoxymethyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-[(2,2-difluorocyclopropyl) methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclo henicosin-14(15H)-one;

(12R)-13-ethyl-8-methoxy-16-(3-methoxypropyl)-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclobutylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(ethoxymethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-tert-butyl-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(2-ethylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-(cyclopentylmethyl)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-{[1-(trifluoromethyl)cyclopropyl]methyl}-12,13,16,17,18,19,20,21-octahydro-6,23-(azeno)-11,7-(metheno)imidazo[2,1c][1,4,10,13,15]oxatetraazacyclohenicosin-14(15H)-one;

(12R)-13-ethyl-8-methoxy-12-methyl-16-[(oxolan-3-yl)methyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-(oxan-4-yl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-[(3,3-difluorocyclobutyl) methyl]-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-16-{[1-(difluoromethyl)cyclopropyl]methyl}-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluoro-3-methylbutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-16-(3-fluorobutyl)-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-16-[2-(trifluoromethoxy)ethyl]-12,13,16,17,18,19,20,21-octahydro-6,23-(azeno)-11,7-(metheno)imidazo[2,1-c][1,4,10,13,15]oxatetraazacyclohenicosin-14(15H)-one;

(9R,E)-12-ethyl-13-methyl-9-(3,3,3-trifluoropropyl)-3-oxa-10,12-diaza-1(7,5)-furo[3,2-b]pyridina-2(6,8)-imidazo[1,2-a]pyrazinacyclotridecaphan-11-one;

(10R)-7-ethyl-6,19-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,19-dimethyl-10-(3,3,3-trifluoropropyl)-6,7,10,11,12,13,14, 15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,20-dimethyl-10-(3,3,3-trifluoropropyl)-6,7,10,11,12,13,14,15-octahydro-23,17-(azeno)-5,24-(metheno)furo[2,3-h]imidazo[2,1-c][1,4,10,13,15]oxatetraazacyclohenicosin-8(9H)-one;

(10R)-7-ethyl-6,20-dimethyl-10-(3,3,3-trifluoropropyl)-6,7,10,11,12,13,14,15-octahydro-23,17-(azeno)-5,24-

(metheno)furo[2,3-h]imidazo[2,1-c][1,4,10,13,15]oxatetraazacyclohenicosin-8(9H)-one;

(12R,16R)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-13-ethyl-8,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-7-methoxy-11-methyl-15-(3,3,3-trifluoropropyl)-11,12,15,16,17,18,19,20-octahydro-10,6-(azeno)-5,22-(metheno)pyrazolo[1,5-c][1,3,9,13,15]oxatetraazacyclohenicosin-13(14H)-one;

(12R,16R)-13-ethyl-8-methoxy-12-methyl-16-(3,3,3-trifluoropropyl)-12,13,15,16,17,18,19,20,21,22-decahydro-14H-6,23-(azeno)-11,7-(metheno)imidazo[1,2-1][1,3,6,12]tetraazacyclohenicosin-14-one;

(12R,16R)-13-ethyl-8-methoxy-12-methyl-16-(3,3,3-trifluoropropyl)-12,13,16,17,18,19,20,21-octahydro-6,23-(azeno)-11,7-(metheno)[1,2,4]triazolo[5,1-c][1,4,10,13,15]oxatetraazacyclohenicosin-14(15H)-one;

(12R,16R)-16-(3,3-difluorobutyl)-13-ethyl-8-methoxy-12-methyl-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-16-(3,3-difluorobutyl)-13-ethyl-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R)-13-ethyl-8-methoxy-12-methyl-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8-methoxy-5,12-dimethyl-16-(3,3,3-trifluoropropyl)-12,13,16,17,18,19,20,21-octahydro-6,23-(azeno)-11,7-(metheno)imidazo[2,1-c][1,4,9,13,15]oxatetraazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,13,15]oxatetraazacyclohenicosin-14(15H)-one;

(15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,10,13,15]oxatetraazacyclohenicosin-13(14H)-one;

(12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,5,9,13, 15]oxapentaazacyclohenicosin-14(15H)-one;

(16R)-13-ethyl-12-methyl-16-(3,3,3-trifluoropropyl)-12,13,16,17,18,19,20,21-octahydro-6,23:11,7-di(azeno)imidazo[2,1-c][1,4,13,15]oxatriazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(metheno)imidazo[2,1-c][1,4,9,13,15]oxatetraazacyclohenicosin-14(15H)-one;

(16R)-13-ethyl-10,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12S,16R)-13-ethyl-8,12-dimethyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(15R)-12-ethyl-11-methyl-15-(3,3,3-trifluoropropyl)-11,12,15,16,17,18,19,20-octahydro-6,22-(azeno)-7,10-epithioimidazo[2,1-c][1,4,8,12,14]oxatetraazacycloicosin-13(14H)-one;

(16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacyclohenicosin-14(15H)-one;

(16R)-13-ethyl-12-methyl-16-(3,3,3-trifluoropropyl)-12,13,16,17,18,19,20,21-octahydro-6,23:11,7-di(metheno)imidazo[2,1-c][1,4,8,10,13,15]oxapentaazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,13,15]oxatriazacyclohenicosin-14(15H)-one;

(11R,15R)-12-ethyl-7-methoxy-11-methyl-15-(3,3,3-trifluoropropyl)-11,12,15,16,17,18,19,20-octahydro-5,22-(azeno)-10,6-(metheno)pyrazolo[1,5-c][1,3,5,10,13,15]oxapentaazacyclohenicosin-13 (14H)-one;

(12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,5,9,13,15]oxapentaazacyclohenicosin-14(15H)-one;

(11R,15R)-12-ethyl-7-methoxy-11-methyl-15-(3,3,3-trifluoropropyl)-11,12,15,16,17,18,19,20-octahydro-5,22:10,6-di(metheno)pyrazolo[1,5-c][1,3,5,10,13,15]oxapentaazacyclohenicosin-13(14H)-one;

(12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,5,10,13,15]oxapentaazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,5,10,13,15]oxapentaazacyclohenicosin-14(15H)-one;

(12R,16R)-13-ethyl-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-11-methyl-15-(3,3,3-trifluoropropyl)-11,12,15,16,17,18,19,20-octahydro-6,22-(azeno)-7,10-epoxyimidazo[2,1-c][1,4,8,12,14]oxatetraazacycloicosin-13(14H)-one;

(15R)-12-ethyl-11-methyl-15-(3,3,3-trifluoropropyl)-11,12,15,16,17,18,19,20-octahydro-6,22:10,7-di(azeno)imidazo[2,1-c][1,8,4,12,14]dioxatriazacycloicosin-13(14H)-one;

(12R,16R)-13-ethyl-8-methoxy-12-methyl-16-(3,3,3-trifluoropropyl)-12,13,15,16,17,18,19,20,21,22-decahydro-14H-11,7-(azeno)-6,23-(metheno)imidazo[1,2-1][1,3,12]triazacyclohenicosin-14-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(15R)-12-ethyl-11-methyl-15-(3,3,3-trifluoropropyl)-11,12,15,16,17,18,19,20-octahydro-6,22-(azeno)-7,10-epoxyimidazo[2,1-c][1,4,9,12,14]oxatetraazacycloicosin-13(14H)-one;

(3R,7R,E)-4-ethyl-$2^5$-methoxy-3-methyl-7-(3,3,3-trifluoropropyl)-14-oxa-4,6-diaza-1(6,8)-imidazo[1,2-a]pyrazina-2(4,2)-pyridinacyclotetradecaphan-5-one;

(3R,7R,E)-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,7R,E)-4-ethyl-$2^5$-methoxy-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(12S,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-12-methyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-8-methoxy-12-methyl-16-(2,2,2-trifluoroethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16S)-13-ethyl-8-methoxy-12-methyl-16-(trifluoromethyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23-(azeno)-11,7-(metheno)imidazo[2,1-c][1,4,9,10,13,15]oxapentaazacyclohenicosin-14(15H)-one;

(12S,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(12R,16R)-13-ethyl-8-methoxy-12-methyl-16-(3,3,3-trifluoropropyl)-12,13,16,17,18,19,20,21-octahydro-6,23:11,7-di(azeno)imidazo[2,1-c][1,4,10,13,15]oxatetraazacyclohenicosin-14(15H)-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,13,15]oxatetraazacyclohenicosin-14(15H)-one;

(12S,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(12R,16R)-13-ethyl-9,12-dimethyl-16-(3,3,3-trifluoropropyl)-12,13,16,17,18,19,20,21-octahydro-6,23-(azeno)-11,7-(metheno)imidazo[2,1-c][1,4,8,10,13,15]oxapentaazacyclohenicosin-14(15H)-one;

(16R)-13-ethyl-16-(3,3,3-trifluoropropyl)-12,13,16,17,18,19,20,21-octahydro-6,23-(azeno)-11,7-(metheno)imidazo[2,1-c][1,4,10,13,15]oxatetraazacyclohenicosin-14(15H)-one;

(3R,E)-7-(2,2-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-16,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one;

(3R,7R,E)-4-ethyl-$2^5$-methoxy-17,3-dimethyl-7-(3,3,3-trifluoropropyl)-13-oxa-4,6-diaza-1(2,4)-imidazo[2,1-f][1,2,4]triazina-2(4,2)-pyridinacyclotridecaphan-5-one;

(R,E)-7-(3,3-difluorobutyl)-4-ethyl-$2^2$-methoxy-13-oxa-4,6-diaza-1(2,4)-imidazo[2,1-f][1,2,4]triazina-2(3,5)-pyridinacyclotridecaphan-5-one;

(3R,7R,E)-4-ethyl-7-(fluoromethyl)-$2^5$-methoxy-3-methyl-13-oxa-4,6-diaza-1(6,8)-imidazo[1,2-a]pyrazina-2(4,2)-pyridinacyclotridecaphan-5-one;

(3R,7S,E)-7-(3,3-difluoropropyl)-4-ethyl-$2^5$-fluoro-3-methyl-10,13-dioxa-4,6-diaza-1(2,4)-imidazo[2,1-f][1,2,4]triazina-2(4,2)-pyridinacyclotridecaphan-5-one;

(3R,7R,E)-$2^5$-chloro-7-(3,3-difluoropropyl)-4-ethyl-3-methyl-13-oxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-25,3-dimethyl-10,13-dioxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-3-methyl-7-((R)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-3-methyl-7-((S)-3,3,3-trifluoro-2-hydroxypropyl)-13-oxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-3-methyl-7-((R)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-3-methyl-7-((S)-3,3,3-trifluoro-1-hydroxypropyl)-13-oxa-4,6-diaza-1(6,8)-[1,2,4]triazolo[1,5-a]pyrazina-2(4,2)-pyridinacyclotridecaphan-5-one;

(3R,7S,E)-4-ethyl-$2^5$-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one;

(3R,7S,E)-4-ethyl-$2^5$-methoxy-3-methyl-7-(3,3,3-trifluoropropyl)-13-oxa-10-thia-4,6-diaza-1(6,8)-[1,2,4]triazolo[1,5-a]pyrazina-2(4,2)-pyridinacyclotridecaphan-5-one 10,10-dioxide;

(3R,7S,E)-4-ethyl-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;

(3R,7R,E)-4-ethyl-10-hydroxy-22,3-dimethyl-7-(3,3,3-trifluoropropyl)-13-oxa-4,6-diaza-1(6,8)-imidazo[1,2-a]pyrazina-2(3,5)-pyridinacyclotridecaphan-5-one;

(3R,7R,Z)-4-ethyl-23-methoxy-3-methyl-7-(3,3,3-trifluoropropyl)-4,6-diaza-1(6,8)-imidazo[1,2-a]pyridina-2(2,6)-pyridinacyclododecaphan-5-one;

(3R,7R,E)-4-ethyl-23-methoxy-3-methyl-7-(3,3,3-trifluoropropyl)-13-oxa-4,6-diaza-1(6,8)-imidazo[1,2-a]pyrazina-2(2,6)-pyrazinacyclotridecaphan-5-one;

(3R,7R,E)-4-ethyl-26-methoxy-3-methyl-7-(3,3,3-trifluoropropyl)-13-oxa-4,6-diaza-1(5,7)-pyrazolo[1,5-a]pyridina-2(5,3)-pyridazinacyclotridecaphan-5-one;

(3R,7S,E)-4-ethyl-8,8-difluoro-$2^5$-methoxy-3,7-dimethyl-13-oxa-4,6-diaza-1(6,8)-imidazo[1,2-a]pyrazina-2(4,2)-pyridinacyclotridecaphan-5-one;

(3R,7R,E)-4-ethyl-3-methyl-7-(3,3,3-trifluoropropyl)-13-oxa-4,6-diaza-1(6,8)-[1,2,4]triazolo[1,5-a]pyrazina-2(4,2)-pyridinacyclotridecaphan-5-one;

(R,E)-4-ethyl-3,3-dimethyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,7R,E)-4-ethyl-$2^5$-methoxy-3-methyl-7-(3,3,3-trifluoropropyl)-12-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-12-oxa-4,6-diaza-1(6,8)-imidazo[1,2-a]pyrazina-2(4,2)-pyridina-7(1,2)-cyclopropanacyclododecaphan-5-one;

(3R,7R,E)-7-(3,3-difluorobutyl)-4-ethyl-22,3-dimethyl-13-oxa-4,6-diaza-1(6,8)-[1,2,4]triazolo[1,5-a]pyrazina-2(3,5)-pyridinacyclotridecaphan-5-one;

(3R,7R,E)-4-ethyl-$2^5$-methoxy-3-methyl-7-(3,3,3-trifluoropropyl)-13-oxa-4,6-diaza-1(6,8)-[1,2,4]triazolo[1,5-a]pyrazina-2(4,2)-pyrimidinacyclotridecaphan-5-one;

(3R,7S,E)-7-(3,3-difluorobutyl)-4-ethyl-$2^2$-methoxy-3-methyl-10,13-dioxa-4,6-diaza-1(6,8)-[1,2,4]triazolo[1,5-a]pyrazina-2(3,5)-pyridinacyclotridecaphan-5-one;

(3R,7R,E)-4-ethyl-$2^5$-methoxy-3-methyl-7-(3,3,3-trifluoropropyl)-13-oxa-4,6-diaza-1(6,8)-imidazo[1,2-b]pyridazina-2(4,2)-pyridinacyclotridecaphan-5-one;

(3R,7S,E)-4-ethyl-$2^5$-methoxy-3-methyl-7-(3,3,3-trifluoropropyl)-10,13-dioxa-4,6-diaza-1(6,8)-[1,2,4]triazolo[1,5-a]pyridina-2(4,2)-pyridinacyclotridecaphan-5-one;

(3R,7R,E)-7-(2,2-difluoropropyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,7R,E)-4-ethyl-$2^5$-methoxy-3-methyl-7-(3-methylpyrazin-2-yl)-13-oxa-4,6-diaza-1(6,8)-imidazo[1,2-a]pyrazina-2(4,2)-pyridinacyclotridecaphan-5-one;

(3R,7S,E)-7-(3,3-difluorobutyl)-4-ethyl-25,3-dimethyl-9,13-dioxa-4,6-diaza-1(6,8)-[1,2,4]triazolo[1,5-a]pyrazina-2(4,2)-pyridinacyclotridecaphan-5-one;

(3R,7R,E)-4-ethyl-$2^5$-methoxy-3-methyl-7-(2-(methylsulfonyl) ethyl)-13-oxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-$2^5$-methoxy-3-methyl-10,13-dioxa-4,6-diaza-1(2,4)-imidazo[2,1-f][1,2,4]triazina-2(4,2)-pyridinacyclotridecaphan-5-one;

(3R,7R,E)-4-ethyl-3-methyl-7-(3,3,3-trifluoropropyl)-13-oxa-4,6-diaza-1(5,7)-pyrazolo[1,5-a]pyridina-2(4,2)-pyridinacyclotridecaphan-5-one;

(3R,7R)-4-ethyl-$2^5$-methoxy-3-methyl-7-(3,3,3-trifluoropropyl)-13-oxa-4,6-diaza-1(6,8)-quinolina-2(4,2)-pyridinacyclotridecaphan-5-one;

(3R,7R,E)-3,4-dimethyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,7R,E)-4-ethyl-3-methyl-7-(3,3,3-trifluoropropyl)-13-oxa-4,6-diaza-1(6,8)-imidazo[1,2-a]pyrazina-2(5,3)-pyridazinacyclotridecaphan-5-one;

(3R,7R,E)-7-(3,3-difluorobutyl)-4-ethyl-15,3-dimethyl-13-oxa-4,6-diaza-1(6,8)-imidazo[1,2-a]pyrazina-2(2,4)-pyridinacyclotridecaphan-5-one;

(3R,7S,E)-4-ethyl-3-methyl-7-(3,3,3-trifluoropropyl)-10,13-dioxa-4,6-diaza-1(6,8)-imidazo[1,2-a]pyrazina-2(2,4)-pyridinacyclotridecaphan-5-one;

(3R,7R)-4-ethyl-$2^5$-methoxy-3-methyl-7-(3,3,3-trifluoropropyl)-13-oxa-4,6-diaza-1(6,8)-naphthyridina-2(4,2)-pyridinacyclotridecaphan-5-one;

(3R,7S,E)-4-ethyl-$2^5$-methoxy-3-methyl-7-(3,3,3-trifluoropropyl)-13-oxa-4,6-diaza-1(6,8)-naphthyridina-2(4,2)-pyridinacyclotridecaphan-9-en-5-one;

(3R,7S,E)-4-ethyl-$2^5$-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;

(3R,7S,E)-4-ethyl-$2^5$-methoxy-3-methyl-7-(3,3,3-trifluoropropyl)-10,13-dioxa-4,6-diaza-1(5,7)-pyrazolo[1,5-c]pyrimidina-2(4,2)-pyridinacyclotridecaphan-5-one;

(3R,7R,E)-4-ethyl-$2^5$-methoxy-12,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one;

(3R,7S,E)-7-(3,3-difluorobutyl)-4-ethyl-$2^5$-methoxy-3-methyl-10,13-dioxa-4,6-diaza-1(5,7)-pyrazolo[1,5-c]pyrimidina-2(4,2)-pyridinacyclotridecaphan-5-one;

(3R,7R,E)-4-ethyl-$2^5$-methoxy-13,3-dimethyl-7-(3,3,3-trifluoropropyl)-13-oxa-4,6-diaza-1(6,8)-imidazo[1,2-b]pyridazina-2(4,2)-pyridinacyclotridecaphan-5-one;

(3R,E)-7-(3,3-difluorobutyl)-4-ethyl-$2^5$-methoxy-3-methyl-10,13-dioxa-4,6-diaza-1(7,5)-[1,2,4]triazolo[1,5-c]pyrimidina-2(4,2)-pyridinacyclotridecaphan-5-one;

(3R,7S,E)-7-(3,3-difluorobutyl)-4-ethyl-$2^5$-methoxy-3-methyl-9,13-dioxa-4,6-diaza-1(5,7)-pyrazolo[1,5-c]pyrimidina-2(4,2)-pyridinacyclotridecaphan-5-one;

(3R,7R,E)-7-(3,3-difluorobutyl)-4-ethyl-$2^5$-methoxy-15,3-dimethyl-13-oxa-4,6-diaza-1(6,8)-[1,2,4]triazolo[1,5-a]pyrazina-2(4,2)-pyridinacyclotridecaphan-5-one;

(3R,7S,E)-4-ethyl-$2^5$-methoxy-3-methyl-7-(3,3,3-trifluoropropyl)-9,13-dioxa-4,6-diaza-1(6,8)-[1,2,4]triazolo[1,5-a]pyrazina-2(4,2)-pyridinacyclotridecaphan-5-one;

(3R,7S,E)-4-ethyl-23-fluoro-3-methyl-7-(3,3,3-trifluoropropyl)-9,13-dioxa-4,6-diaza-1(6,8)-[1,2,4]triazolo[1,5-a]pyrazina-2(4,2)-pyridinacyclotridecaphan-5-one;

(3R,7R,E)-7-(3,3-difluorobutyl)-4-ethyl-$2^5$-methoxy-3-methyl-13-oxa-4,6-diaza-1(7,5)-[1,2,4]triazolo[1,5-c]pyrimidina-2(4,2)-pyridinacyclotridecaphan-5-one;

(R,E)-4-ethyl-$2^5$-methoxy-3-methyl-14-oxa-4,6-diaza-1(6,8)-imidazo[1,2-a]pyrazina-2(4,2)-pyridinacyclotetradecaphan-5-one;

(R,E)-4-ethyl-$2^5$-methoxy-3-methyl-11-oxa-4,6-diaza-1(6,8)-imidazo[1,2-a]pyrazina-2(4,2)-pyridinacycloundecaphan-5-one;

(7S,E)-4-ethyl-23-fluoro-$2^5$-methoxy-3-methyl-7-(3,3,3-trifluoropropyl)-10,13-dioxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-3-methyl-10,13-dioxa-4,6-diaza-1(6,8)-[1,2,4]triazolo[1,5-a]pyrazina-2(4,2)-pyridinacyclotridecaphan-5-one;

(3R,7S,E)-7-(3,3-difluorobutyl)-4-ethyl-3-methyl-10,13-dioxa-4,6-diaza-1(5,7)-pyrazolo[1,5-c]pyrimidina-2(4,2)-pyridinacyclotridecaphan-5-one;

(3R,E)-7-(2-(difluoromethoxy) ethyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-7-((1-fluorocyclopropyl) methyl)-$2^5$-methoxy-3-methyl-13-oxa-4,6-diaza-1(6,8)-imidazo[1,2-a]pyrazina-2(4,2)-pyridinacyclotridecaphan-5-one;

(3R,E)-7-(4,4-difluorobutyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-7-(isopropoxymethyl)-$2^5$-methoxy-3-methyl-13-oxa-4,6-diaza-1(6,8)-imidazo[1,2-a]pyrazina-2(4,2)-pyridinacyclotridecaphan-5-one;

(3R,E)-7-(2,2-difluoroethyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(2,2,3,3-tetrafluoropropyl)-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-((2,2,2-trifluoroethoxy) methyl)-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(tetrahydrofuran-3-yl)-13-oxa-4,6-diaza-1(6,8)-imidazo[1,2-a]pyrazina-2(4,2)-pyridinacyclotridecaphan-5-one;

(3R,E)-7-((2,2-difluoroethoxy) methyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-7-(1-methoxyethyl)-3-methyl-13-oxa-4,6-diaza-1(6,8)-imidazo[1,2-a]pyrazina-2(4,2)-pyridinacyclotridecaphan-5-one;

(3R,E)-7-(2,2-difluorocyclopropyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(tetrahydrofuran-2-yl)-13-oxa-4,6-diaza-1(6,8)-imidazo[1,2-a]pyrazina-2(4,2)-pyridinacyclotridecaphan-5-one;

2-((3R,E)-4-ethyl-$2^5$-methoxy-3-methyl-5-oxo-13-oxa-4,6-diaza-1(6,8)-imidazo[1,2-a]pyrazina-2(4,2)-pyridinacyclotridecaphane-7-yl)acetonitrile;

(3R,E)-7-(3,3-difluorocyclobutyl)-4-ethyl-$2^5$-methoxy-3-methyl-13-oxa-4,6-diaza-1(6,8)-imidazo[1,2-a]pyrazina-2(4,2)-pyridinacyclotridecaphan-5-one;

3-((3R,E)-4-ethyl-$2^5$-methoxy-3-methyl-5-oxo-13-oxa-4,6-diaza-1(6,8)-imidazo[1,2-a]pyrazina-2(4,2)-pyridinacyclotridecaphane-7-yl)propanenitrile;

(3R,E)-$2^5$-cyclopropyl-7-(3,3-difluoropropyl)-4-ethyl-3-methyl-13-oxa-4,6-diaza-1(6,8)-imidazo[1,2-a]pyrazina-2(4,2)-pyridinacyclotridecaphan-5-one;

(3R,E)-$2^5$-chloro-4-ethyl-3-methyl-7-(3,3,3-trifluoropropyl)-13-oxa-4,6-diaza-1(6,8)-imidazo[1,2-a]pyrazina-2(4,2)-pyridinacyclotridecaphan-5-one;

(3R,E)-4-ethyl-$2^5$-fluoro-7-(methoxymethyl)-3-methyl-13-oxa-4,6-diaza-1(6,8)-imidazo[1,2-a]pyrazina-2(4,2)-pyridinacyclotridecaphan-5-one;

(3R,E)-7-(3,3-difluorobutyl)-4-ethyl-$2^5$-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(3,3-difluoropropyl)-4-ethyl-25,3-dimethyl-13-oxa-4,6-diaza-1(6,8)-[1,2,4]triazolo[1,5-a]pyrazina-2(4,2)-pyridinacyclotridecaphan-5-one;

(3R,E)-7-(3,3-difluoropropyl)-4-ethyl-$2^5$-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(bicyclo[1.1.1]pentan-1-ylmethyl)-4-ethyl-$2^5$-methoxy-3-methyl-13-oxa-4,6-diaza-1(2,4)-imidazo[2,1-f][1,2,4]triazina-2(4,2)-pyridinacyclotridecaphan-5-one;

(3R,E)-7-(3,3-difluoropropyl)-4-ethyl-$2^5$-fluoro-3-methyl-13-oxa-4,6-diaza-1(6,8)-imidazo[1,2-b]pyridazina-2(4,2)-pyridinacyclotridecaphan-5-one;

(3R,E)-4-cyclopropyl-7-(3,3-difluoropropyl)-$2^5$-fluoro-3-methyl-13-oxa-4,6-diaza-1(2,4)-imidazo[2,1-f][1,2,4]triazina-2(4,2)-pyridinacyclotridecaphan-5-one;

(3R,E)-4-ethyl-$2^5$-methoxy-3-methyl-7-((1-methylcyclopropyl) methyl)-13-oxa-4,6-diaza-1(2,4)-imidazo[2,1-f][1,2,4]triazina-2(4,2)-pyridinacyclotridecaphan-5-one;

(3R,E)-7-(2,2-difluoropropyl)-4-ethyl-$2^5$-methoxy-3-methyl-13-oxa-4,6-diaza-1(2,4)-imidazo[2,1-f][1,2,4]triazina-2(4,2)-pyridinacyclotridecaphan-5-one;

(3S,E)-7-(3,3-difluoropropyl)-4-ethyl-$2^5$-methoxy-3-(trifluoromethyl)-13-oxa-4,6-diaza-1(6,8)-imidazo[1,2-a]pyrazina-2(4,2)-pyridinacyclotridecaphan-5-one;

(9R,13R,E)-14-Cyclopropyl-12-ethyl-13-methyl-9-(3,3,3-trifluoropropyl)-3-oxa-10,12-diaza-1(5,2)-thiazola-2(6,8)-imidazo[1,2-a]pyrazinacyclotridecaphan-11-one;

(16E,22E,7R)-$2^5$-cyclopropyl-4-ethyl-3-methyl-7-(3,3,3-trifluoropropyl)-21H-13-oxa-4,6-diaza-1(5,7)-pyrazolo[1,5-a]pyridina-2(1,3)-pyrazolacyclotridecaphan-5-one;

(9R,13R,E)-14-Cyclopropyl-12-ethyl-13-methyl-9-(3,3,3-trifluoropropyl)-3-oxa-10,12-diaza-1(5,2)-oxazola-2(6,8)-imidazo[1,2-a]pyrazinacyclotridecaphan-11-one;

(3R,E)-4-ethyl-$2^5$-methoxy-3-methyl-$7^4$-(trifluoromethyl)-11-oxa-4,6-diaza-1(6,8)-imidazo[1,2-a]pyrazina-2(4,2)-pyridina-7 (3,1)-pyrrolidinacycloundecaphan-5-one;

(3R,E)-4-ethyl-74,74-difluoro-3-methyl-11-oxa-4,6-diaza-1(6,8)-imidazo[1,2-a]pyrazina-7(3,1)-pyrrolidina-2(1,3)-benzenacycloundecaphan-5-one;

(3R,E)-4-ethyl-$2^5$-methoxy-3-methyl-$7^4$-(trifluoromethyl)-12-oxa-4,6-diaza-1(6,8)-imidazo[1,2-a]pyrazina-2(4,2)-pyridina-7(3,1)-pyrrolidinacyclododecaphan-5-one;

(3R,E)-4-ethyl-$2^2$-methoxy-3-methyl-7-(2-methylthiazol-4-yl)-13-oxa-4,6-diaza-1(6,8)-imidazo[1,2-a]pyrazina-2(3,5)-pyridinacyclotridecaphan-5-one;

(3R,E)-4-ethyl-$2^5$-methoxy-3-methyl-7-(2-methylthiazol-5-yl)-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(1-methyl-1H-tetrazol-5-yl)-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(4-methylthiazol-2-yl)-13-oxa-4,6-diaza-1(6,8)-imidazo[1,2-a]pyrazina-2(4,2)-pyridinacyclotridecaphan-5-one;

(3R,E)-4-ethyl-$2^5$-methoxy-3-methyl-7-(1-methyl-1H-1,2,4-triazol-5-yl)-13-oxa-4,6-diaza-1(6,8)-imidazo[1,2-a]pyrazina-2(4,2)-pyridinacyclotridecaphan-5-one;

($1^7$E,3R,8E)-4-ethyl-11,11-difluoro-$2^5$-methoxy-3,7-dimethyl-13-oxa-4,6-diaza-1(6,8)-imidazo[1,2-a]pyrazina-2(4,2)-pyridinacyclotridecaphan-8-en-5-one;

(3R,7S,E)-4-ethyl-11,11-difluoro-$2^5$-methoxy-3,7-dimethyl-13-oxa-4,6-diaza-1(6,8)-imidazo[1,2-a]pyrazina-2(4,2)-pyridinacyclotridecaphan-5-one;

(3'R,7'S,7'E,8'E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphanen]-8'-en-5'-one;

(3'R,7'S,E)-4'-ethyl-5'-methoxy-3',7'-dimethyl-2,3,5,6-tetrahydrospiro[pyran-4,11'-13-oxa-4,6-diaza-1(6,8)-imidazo[1,2-a]pyrazina-2(4,2)-pyridinacyclotridecaphan]-5'-one;

(3R,E)-4-ethyl-$2^5$-methoxy-3-methyl-5-oxo-13-oxa-4,6-diaza-1(6,8)-imidazo[1,2-a]pyrazina-2(4,2)-pyridinacyclotridecaphane-7-carbonitrile; and (3R,E)-4-ethyl-$2^5$-fluoro-3-methyl-5-oxo-13-oxa-4,6-diaza-1(6,8)-imidazo[1,2-a]pyrazina-2(4,2)-pyridinacyclotridecaphane-7-carboxamide;

or a pharmaceutically acceptable salt thereof.

12. A pharmaceutical composition which comprises an inert carrier and a compound of claim 1 or a pharmaceutically acceptable salt thereof.

13. A method for treating narcolepsy in a mammalian subject which comprises administering to the patient an effective amount of the compound of claim 1 or a pharmaceutically acceptable salt thereof.

14. A method for treating hypersomnia in a mammalian subject which comprises administering to the patient an effective amount of the compound of claim 1 or a pharmaceutically acceptable salt thereof.

* * * * *